US012780814B2

(12) United States Patent
Martinez Botella et al.

(10) Patent No.: US 12,780,814 B2
(45) Date of Patent: Nov. 3, 2026

(54) KCNT1 INHIBITORS AND METHODS OF USE

(71) Applicant: Praxis Precision Medicines, Inc., Boston, MA (US)

(72) Inventors: Gabriel Martinez Botella, Wayland, MA (US); Andrew Mark Griffin, L'lle Bizard (CA); Paul S. Charifson, Framingham, MA (US); Kiran Reddy, Boston, MA (US); Michael Kristopher Mathieu Kahlig, Redwood City, CA (US); Brian Edward Marron, Ada, MI (US)

(73) Assignee: PRAXIS PRECISION MEDICINES, INC., Boston, MA (US)

(*) Notice: Subject to any disclaimer, the term of this patent is extended or adjusted under 35 U.S.C. 154(b) by 939 days.

(21) Appl. No.: 17/607,802

(22) PCT Filed: May 1, 2020

(86) PCT No.: PCT/SU2020/031046

§ 371 (c)(1),
(2) Date: Oct. 29, 2021

(87) PCT Pub. No.: WO2020/227101

PCT Pub. Date: Nov. 12, 2020

(65) Prior Publication Data

US 2022/0259193 A1 Aug. 18, 2022

Related U.S. Application Data

(60) Provisional application No. 62/982,864, filed on Feb. 28, 2020, provisional application No. 62/842,849, filed on May 3, 2019.

(51) Int. Cl.
*C07D 413/12* (2006.01)
*C07D 413/14* (2006.01)

(52) U.S. Cl.
CPC ......... *C07D 413/12* (2013.01); *C07D 413/14* (2013.01)

(58) Field of Classification Search
CPC ............................ C07D 413/12; C07D 413/14
USPC ....................................................... 514/210.2
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,866,065 | A | 9/1989 | Watjen et al. |
| 4,873,244 | A | 10/1989 | Watjen et al. |
| 4,902,514 | A | 2/1990 | Barclay et al. |
| 4,968,682 | A | 11/1990 | Hansen et al. |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 6,221,866 | B1 | 4/2001 | Brendel et al. |
| 7,217,729 | B2 | 5/2007 | Sattleleger et al. |
| 7,300,939 | B2 | 11/2007 | Kuehnert et al. |
| 7,696,238 | B2 | 4/2010 | Merla et al. |
| 9,321,727 | B2 | 4/2016 | Bissantz et al. |
| 10,538,516 | B2 | 1/2020 | Yanagisawa et al. |
| 11,773,088 | B2 * | 10/2023 | Botella et al. |
| 2003/0055093 | A1 | 3/2003 | Strobel et al. |
| 2004/0266823 | A1 | 12/2004 | Cumming et al. |
| 2008/0021217 | A1 | 1/2008 | Borchardt et al. |
| 2008/0045571 | A1 | 2/2008 | Edwards et al. |
| 2008/0269241 | A1 | 10/2008 | Allen et al. |
| 2015/0105386 | A1 | 4/2015 | Mack et al. |
| 2018/0036295 | A1 | 2/2018 | Cheng et al. |
| 2018/0051015 | A1 | 2/2018 | Caferro et al. |
| 2018/0072708 | A1 | 3/2018 | Yanagisawa et al. |
| 2019/0022039 | A1 | 1/2019 | Fujii et al. |
| 2022/0135553 | A1 | 5/2022 | Martinez Botella et al. |
| 2023/0167102 | A1 * | 6/2023 | Botella et al. |
| 2023/0219921 | A1 * | 7/2023 | Botella et al. |
| 2023/0285377 | A1 * | 9/2023 | Botella et al. |
| 2024/0043415 | A1 * | 2/2024 | Botella et al. |
| 2024/0368142 | A1 * | 11/2024 | Botella et al. |

FOREIGN PATENT DOCUMENTS

| | | | |
|---|---|---|---|
| CL | 202102876 | A1 | 8/2022 |
| CL | 202102878 | A1 | 10/2022 |
| CN | 101096368 | A | 1/2008 |
| CN | 101790527 | A | 7/2010 |
| CN | 105263929 | A | 1/2016 |
| JP | 2005060255 | A * | 3/2005 |

(Continued)

OTHER PUBLICATIONS

STN Search Report for Registry Library Compounds (Year: 2025).*
Camci et al., Bioisosterism: 1,2,4-Oxadiazole Rings, ChemMedChem, vol. 18, Iss. 9, (Online May 2023; Received Nov. 23, 2022); https://doi.org/10.1002/cmdc.202200638 (Year: 2023).*
Patanti et al., Chem. Rev., 1996, 96, 3147-3176 (Year: 1996).*
Extended European Search Report issued in European Patent Application No. 20801870.5 dated Feb. 16, 2023, 15 pages.
Poulain, R. et al., "Parallel synthesis of 1,2,4-oxadiazoles from carboxylic acids using an improved, uronium-based, activation", Tetrahedron Letters, Dec. 11, 2000 vol. 42, No. 8, pp. 1495-1498, XP002427070.
Braga, A. et al., "'One-Pot' Synthesis of Chiral N-Protected alpha-Amino Acid-Derived 1,2,4-Oxadiazoles", Synthesis, Jan. 9, 2004, No. 10, pp. 1589-1594, XP002541366.

(Continued)

*Primary Examiner* — Kortney L. Klinkel
*Assistant Examiner* — Grace Ching Hsu
(74) *Attorney, Agent, or Firm* — MH2 Technology Law Group, LLP

(57) ABSTRACT

The present invention is directed to, in part, compounds and compositions useful for preventing and/or treating a neurological disease or disorder, a disease or condition relating to excessive neuronal excitability, and/or a gain-of-function mutation in a gene (e.g., KCNT1). Methods of treating a neurological disease or disorder, a disease or condition relating to excessive neuronal excitability, and/or a gain-of-function mutation in a gene such as KCNT1 are also provided herein.

22 Claims, No Drawings

(56) References Cited

FOREIGN PATENT DOCUMENTS

| | | | |
|---|---|---|---|
| WO | 2003037863 | A2 | 5/2003 |
| WO | 03059269 | A2 | 7/2003 |
| WO | 2006002981 | A1 | 1/2006 |
| WO | 2006014185 | A1 | 2/2006 |
| WO | 2006122799 | A1 | 11/2006 |
| WO | 2014141104 | A1 | 9/2014 |
| WO | 2015108861 | A1 | 7/2015 |
| WO | 2015162515 | A1 | 10/2015 |
| WO | 2018098491 | A1 | 5/2018 |
| WO | 2018187480 | A1 | 10/2018 |
| WO | 2019035951 | A1 | 2/2019 |
| WO | 2020225147 | A1 | 11/2020 |
| WO | 2020227097 | A1 | 11/2020 |
| WO | 2021173930 | A1 | 9/2021 |
| WO | 2021195066 | A2 | 9/2021 |
| WO | 2022010880 | A1 | 1/2022 |
| WO | 2023211850 | A1 | 11/2023 |
| WO | 2023239839 | A1 | 12/2023 |
| WO | 2025019407 | A1 | 1/2025 |

OTHER PUBLICATIONS

Braga, V. et al., "Synthesis of New 1,2,4-Oxadiazoles Carrying (I'S,2'S)-t-Butyloxycarbonyl-I-amino-2-met hyl-1-butyl and (l'S)-t-Butyloxycarbonyl-l'-amino-1'-ethyl Groups at C-5", J. Braz. Chem. Soc, May 17, 2004, vol. 15, No. 4, pp. 603-607, XP093021400.
Griffin, A. et al., "Discovery of the First Orally Available, Selective K Na 1.1 Inhibitor: In Vitro and In Vivo Activity of an Oxadiazole Series", ACS Medicinal Chemistry Letters, Mar. 9, 2021, vol. 12, No. 4, pp. 593-602, XP093003438.
Examination Report issued in Saudi Arabian Patent Application No. 521430751 dated Feb. 27, 2023, 10 pages, with English language translation.
Borlot, F. et al., "KCNT1-related epilepsy: An international multi-center cohort of 27 pediatric cases," Epilepsia, vol. 61, No. 4, Apr. 2020 (First published Mar. 13, 2020), pp. 679-692.
Ishii, A. et al., "A recurrent KCNT1 mutation in two sporadic cases with malignant migrating partial seizures in infancy," Gene, vol. 531, No. 2, Dec. 1, 2013 (Available online Sep. 10, 2013), pp. 467-471.
McTague, A. et al., "Clinical and molecular characterization of KCNT1-related severe early-onset epilepsy," Neurology, vol. 90, No. 1, Jan. 2, 2018 (Published online Dec. 1, 2017), pp. e55-e66.
Pubchem, Pubchem-SID: 260692697, ZINC35845049, Deposit/Available Dates: Dec. 10, 2015, 6 pages.
Pubchem, Pubchem-SID: 165919505, MCULE-4868029218, Deposit/Available Dates: Nov. 30, 2013, 7 pages.
Young, Lee (PCT Authorized Officer), International Search Report and Written Opinion of the International Searching Authority for International Application No. PCT/US2021/019814 dated Jul. 1, 2021, 11 pages.
Thomas, Shane (PCT Authorized Officer), International Search Report and Written Opinion of the International Searching Authority for International Application No. PCT/US2023/024794 dated Sep. 27, 2023, 9 pages.
Extended European Search Report for European Application No. 21760026.1 dated Jan. 30, 2024, 5 pages.
Rodriquez, Kari (PCT Authorized Officer), International Search Report and Written Opinion of the International Searching Authority for International Patent Application No. PCT/US2023/019648 dated Sep. 13, 2023, 11 pages.
Albrecht et al., "Discovery and optimization of substituted piperidines as potent, selective, CNS-penetrant $\alpha 4\beta 2$ nicotinic acetylcholine receptor potentiators", Bioorganic & Medicinal Chemistry Letters, vol. 18, 2008 (Available online Aug. 28, 2008), pp. 5209-5212.
Barcia et al., "De novo gain of function KCNT1 channel mutations cause malignant migrating partial seizures of infancy," Nat. Genet., vol. 44, No. 11, Nov. 2012, pp. 1255-1259 (14 pages provided).
Baumer et al. "Quinidine-associated skin discoloration in KCNT1-associated pediatric epilepsy," Neurology, vol. 89, 2017, p. 2212 (3 pages provided).
Berge et al., "Pharmaceutical Salts," Journal of Pharmaceutical Sciences, vol. 66, No. 1, Jan. 1977, pp. 1-19.
Dilena et al., "Early Treatment with Quinidine in 2 Patients with Epilepsy of Infancy with Migrating Focal Seizures (EIMFS) Due to Gain-of-Function KCNT1 Mutations: Functional Studies, Clinical Responses, and Critical Issues for Personalized Therapy," Neurotherapeutics, vol. 15, 2018 (Published online Aug. 15, 2018), pp. 1112-1126.
Epi4K Consortium & Epilepsy Phenome/Genome Project, "De novo mutations in the classic epileptic encephalopathies," Nature, vol. 501, No. 7466, Sep. 12, 2013, pp. 217-221 (16 pages provided).
Fukuoka et al., "Quinidine therapy for West syndrome with KCNTI mutation: A case report," Brain & Development, vol. 39, 2017, pp. 80-83.
Gould, "Salt selection for basic drugs," International Journal of Pharmaceutics, vol. 33, 1986, pp. 201-217.
Heron et al., "Missense mutations in the sodium-gated potassium channel gene KCNT1 cause severe autosomal dominant nocturnal frontal lobe epilepsy," Nature Genetics, vol. 44, No. 11, Nov. 2012 (Published online Oct. 21, 2012), pp. 1188-1190.
Kawasaki et al., "Three Cases of KCNT1 Mutations: Malignant Migrating Partial Seizures in Infancy with Massive Systemic to Pulmonary Collateral Arteries," The Journal of Pediatrics, vol. 191, Oct. 5, 2017, pp. 270-274.
Kim et al., "Human Slack Potassium Channel Mutations Increase Positive Cooperativity between Individual Channels," Cell Reports, vol. 9, Dec. 11, 2014, pp. 1661-1672.
Lim et al., "KCNT1 mutations in seizure disorders: the phenotypic spectrum and functional effects," J. Med. Genet., vol. 53, 2016 (Published online first Jan. 6, 2016), pp. 217-225.
Madaan et al., "A quinidine non responsive novel KCNT1 mutation in an Indian infant with epilepsy of infancy with migrating focal seizures," Brain & Development, vol. 40, No. 3, 2017, pp. 229-232.
Copenheaver, Blaine R. (PCT Authorized Officer), International Search Report and Written Opinion of the International Searching Authority for International Patent Application No. PCT/US2020/031039 dated Sep. 11, 2020, 14 pages.
Mikati et al., "Quinidine in the Treatment of KCNT1-Positive Epilepsies," Annals of Neurology, vol. 78, No. 6, Mar. 2015, pp. 995-999.
Milligan et al., "KCNT1 Gain of Function in 2 Epilepsy Phenotypes Is Reversed by Quinidine," Annals of Neurology, vol. 75, No. 4, Mar. 2014, pp. 581-590.
MØller et al., "Mutations in KCNT1 cause a spectrum of focal epilepsies," Epilepsia, vol. 56, No. 9, 2015 (Early View publication Jun. 30, 2015), pp. e114-e120.
Numis et al., "Lack of response to quinidine in KCNT1-related neonatal epilepsy," Epilepsia, vol. 59, Issue 10, Oct. 2018 (First published Sep. 4, 2018), pp. 1889-1898.
Ohba et al., "De novo KCNT1 mutations in early-onset epileptic encephalopathy," Epilepsia, vol. 56, No. 9, 2015 (Early View publication Jul. 3, 2015), pp. e121-e128.
Pubchem, "N,3-Dimethyl-N-[(pyridin-2-yl)methyl]-5-sulfamoylthiophene-2-carboxamide: CID 51106824," 2011 (Create Date: May 3, 2011), Available online at <https://pubchem.ncbi.nlm.nih.gov/compound/511 06824>, 7 pages.
Pubchem, "N-[[3-(dimethylamino)phenyl]methyl]-N-methyl-5-methylsulfonylthiophene-2-carboxamide: CID 136548438," 2019 (Create Date: Jan. 24, 2019), Available online at <https://pubchem.ncbi.nlm.nih.gov/compound/136548438>, 6 pages.
Pubchem, "N-Benzyl-5-sulfamoylthiophene-2-carboxamide: CID 22901904," 2007 (Create Date: Dec. 5, 2007), Available online at <https://pubchem.ncbi.nlm.nih.gov/compound/22901904>, 7 pages.
Pubchem, "N-methyl-N-[(3-methylphenyl)methyl]-5-methylsulfonylthiophene-2-carboxamide: CID 136548429," 2019 (Create Date: Jan. 24, 2019), Available online at <https://pubchem.ncbi.nlm.nih.gov/compound/136548429>,7 pages.
Pubchem, "Substance Record: SID 299402484," 2016 (Available/Deposit Dates: Jan. 28, 2016), Available online at <https://pubchem.ncbi.nlm.nih.gov/substance/299402484>, 4 pages.

(56) References Cited

OTHER PUBLICATIONS

Pubchem, "N-(3,4-dimethylphenyl)-2-(3-(4-fluorophenyl)-7-oxoisothiazolo[4,5-d]pyrimidin-6(7H)-yl]acetamide: CID 53124354," 2011 (Create Jun. 21, 2011), Available online at <https://pubchem.ncbi.nlm.nih .gov/compound/53124354)>, 7 pages.
Pubchem, "ZINC35845049: SID 260692697," 2015 (Available/Deposit Dates: Dec. 10, 2015), Available online at <https://pubchem.ncbi.nlm.nih.gov/substance/260692697>, 4 pages.
Rizzo et al., "Characterization of two de novo KCNT1 mutations in children with malignant migrating partial seizures in infancy," Molecular and Cellular Neuroscience, vol. 72, 2016 (Available online Jan. 16, 2016), pp. 54-63.
Rodriquez, Kari (PCT Authorized Officer), International Search Report and Written Opinion of the International Searching Authority for International Patent Application No. PCT/US2021/040486 dated Oct. 20, 2021, 9 pages.
Wilen et al., "Strategies in Optical Resolutions," Tetrahedron, vol. 33, Report No. 38, 1977, pp. 2725-2736.
Zhang et al., "Gene mutation analysis of 175 Chinese patients with early-onset epileptic encephalopathy," Clinical Genetics, vol. 91, No. 5, 2017, pp. 717-724.
Zhou et al., "Novel mutations and phenotypes of epilepsy-associated genes in epileptic encephalopathies," Genes, Brain and Behavior, vol. 17, e12456, 2018, 11 pages.
Rodriquez, Kari (PCT Authorized Officer), International Search Report and Written Opinion of the International Searching Authority for International Patent Application No. PCT/US2021/023653 dated Sep. 14, 2021, 10 pages.
STN Registry, "3-Furancarboxamide, N-[1-[3-[2-(trifluorornethyl)-4-pyridinyl]-1,2,4-oxadiazol-5-yl]ethyl]," May 2, 2017, 3 pages.
Purushotham, N. et al., "An Expeditious Synthesis of Chiral 1,2,4-Oxadiazole Peptidomimetics from Heteroaroyl Monopeptides," Organic and Supramolecular Chemistry, vol. 3, Oct. 22, 2018, pp. 10996-10998.
Pubchem, "N-{1-[3-(3-Chlorophenyl)-1,2,4-oxadiazol-5-YL]ethyl}benzamide," 2010 (Available/Deposit Date: Jun. 22, 2010), available online at <https://pubchem.ncbi.nlm.nih.gov/compound/46128945>, 4 pages.
Pubchem, "N-[(1R)-1-[3-(3-chlorophenyl)-1,2,4-oxadiazol-5-yl]ethyl]benzamide," 2015 (Available/Deposit Date: Dec. 10, 2015), available online at <https://pubchem.ncbi.nlm.nih.gov/compound/93117409>, 8 pages.
Copenheaver (Authorized officer); International Search Report and Written Opinion issued in International Patent Application No. PCT/US2020/031046 (13 pages).
STN Registry No. 1338698-26-2, "Carbamic acid, N-[1-[3-(3-methoxyphenyl)-1,2,4-oxadiazol-5-yl]ethyl]-, 1,1-dimethylethyl ester," Dec. 6, 2015, 1 page.
STN Registry No. 1823229-23-7, "Carbamic acid, N-[1-[3-(3-methoxyphenyl)-1,2,4-oxadiazol-5-yl]ethyl]-, 1,1-dimethylethyl ester," Dec. 6, 2015, 1 page.
STN Registry No. 1824064-84-7, "Carbamic acid, N-[1-[3-(3-fluorophenyl)-1,2,4-oxadiazol-5-yl]ethyl]-,1,1-dimethylethyl ester," Dec. 7, 2015, 1 page.
STN Registry Database CAS No. 2193413-67-9, "1H-Pyrazole-5-carboxamide, 3-(difluoromethyl)-1-methyl-N-[1-[3-(4-pyridinyl)-1,2,4-oxadiazol-5-yl]ethyl]-," Mar. 18, 2018, 13 pages.
Cas Registry No. 1832156-07-6,"N-[1-[3-(3-fluorophenyl)-1,2,4-oxadiazol-5-yl]ethyl]-4,5,6,7-tetrahydro-2H-Pyrazolo[4,3-c]pyridine-3-carboxamide," entered Dec. 18, 2015, 1 page.
Cas Registry No. 2395549-12-7, "1-Ethyl-N-[1-[3-(3-fluorophenyl)-1,2,4-oxadiazol-5-yl]ethyl]-5-methyl-1H-pyrazole-3-carboxamide" [1], entered Dec. 20, 2019, 1 page.
STN Registry Database No. 1783147-39-6 "1H-Pyrazole-5-carboxamide, 1-(2-ethoxyethyl)-3-methyl-N-[1-[3-(4-pyridinyl)-1,2,4-oxadiazol-5-yl]ethyl]-," Entered Jun. 18, 2015, 1 page.
STN Registry Database No. 1322538-98-6, "1H-Pyrazole-4-carboxamide, 5-methyl-N-[2-methyl-1-[3-(3-pyrdinyl)-1,2,4-oxadiazol-5-yl]propyl]-1-(2-pyridinyl)-" Entered Aug. 24, 2011, 1 page.
STN Registry Database No. 1422830-47-4, "1H-Pyrazole-4-carboxamide, N,1,3-trimethyl-N-[[3-(4-pyridinyl)-1,2,4-oxadiazol-5-yl]methyl]-" Entered Mar. 11, 2013, 1 page.
STN Registry Database No. 1625535-70-7, "1H-Pyrazole-4-carboxamide, 1-(2,4-difluorophenyl)-N,3,5-trimethyl-N-[[3-(3-pyridinyl)-1,2,4-oxadiazol-5-yl)methyl]-," Entered Sep. 24, 2014, 1 page.

* cited by examiner

KCNT1 INHIBITORS AND METHODS OF USE

CROSS REFERENCE TO RELATED APPLICATIONS

This application is a national stage application under 35 U.S.C. § 371 of International Application No. PCT/US2020/031046, filed internationally on May 1, 2020, which claims priority to and the benefit of U.S. Provisional Patent Application No. 62/842,849 filed May 3, 2019 and U.S. Provisional Patent Application No. 62/982,864 filed Feb. 28, 2020, the contents of each of which are incorporated herein by reference in their entirety.

BACKGROUND

KCNT1 encodes sodium-activated potassium channels known as Slack (Sequence like a calcium-activated $K^+$ channel). These channels are found in neurons throughout the brain and can mediate a sodium-activated potassium current $I_{KNa}$. This delayed outward current can regulate neuronal excitability and the rate of adaption in response to maintained stimulation. Abnormal Slack activity have been associated with development of early onset epilepsies and intellectual impairment. Accordingly, pharmaceutical compounds that selectively regulate sodium-activated potassium channels, e.g., abnormal KCNT1, abnormal $I_{KNa}$, are useful in treating a neurological disease or disorder or a disease or condition related to excessive neuronal excitability and/or KCNT1 gain-of-function mutations.

SUMMARY OF THE INVENTION

Described herein are compounds and compositions useful for preventing and/or treating a disease, disorder, or condition, e.g., a neurological disease or disorder, a disease, disorder, or condition associated with excessive neuronal excitability and/or a gain-of-function mutation in a gene, for example, KCNT1.

In one aspect, the present disclosure features a pharmaceutical composition comprising a compounds of Formula (I):

(I)

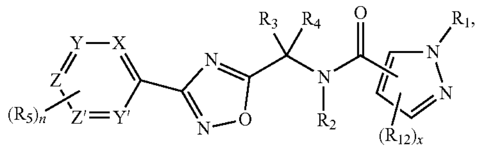

or a pharmaceutically acceptable salt thereof, wherein the variables are as defined herein, and a pharmaceutically acceptable excipient.

In another aspect, the present disclosure features a compound of Formula (II):

(II)

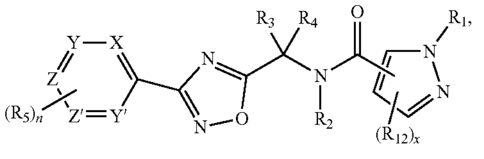

or a pharmaceutically acceptable salt thereof, wherein the variables are as defined herein.

In another aspect, the present disclosure features a compound of Formula (III):

(III)

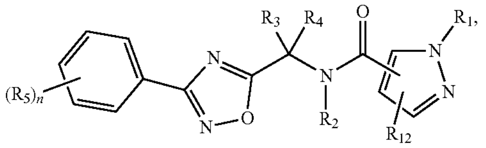

or a pharmaceutically acceptable salt thereof, wherein the variables are as defined herein.

In another aspect, the present disclosure features a compound of Formula (IV):

(IV)

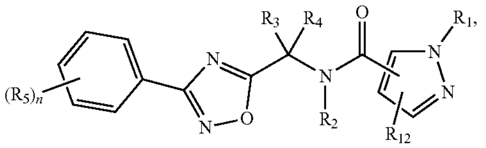

or a pharmaceutically acceptable salt thereof, wherein the variables are as defined herein.

In another aspect, the present disclosure features a compound of Formula (V):

(V)

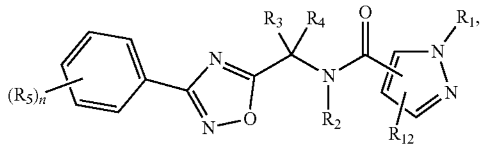

or a pharmaceutically acceptable salt thereof, wherein the variables are as defined herein.

In another aspect, the present disclosure features a compound of Formula (VI):

(VI)

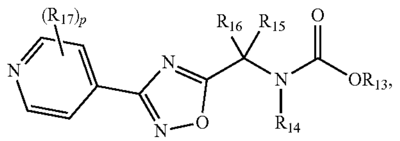

or a pharmaceutically acceptable salt thereof, wherein the variables are as defined herein.

In another aspect, the present disclosure features a pharmaceutical composition comprising a compound of Formula (VII):

(VII)

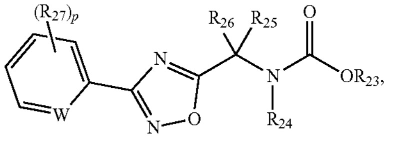

or a pharmaceutically acceptable salt thereof, wherein the variables are as defined herein, and a pharmaceutically acceptable excipient.

In another aspect, the present disclosure provides a pharmaceutical composition comprising a compound disclosed herein (e.g., a compound of formula (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a))) or a pharmaceutically acceptable salt thereof, and a pharmaceutically acceptable excipient.

In another aspect, the present disclosure provides a method of treating a neurological disease or disorder, wherein the method comprises administering to a subject in need thereof a compound disclosed herein (e.g., a compound of formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof) or a pharmaceutical composition disclosed herein (e.g., a pharmaceutical composition comprising a compound disclosed herein (e.g., a compound of formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof), and a pharmaceutically acceptable excipient).

In another aspect, the present disclosure provides a method of treating a disease or condition associated with excessive neuronal excitability, wherein the method comprises administering to a subject in need thereof a compound disclosed herein (e.g., a compound of formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof) or a pharmaceutical composition disclosed herein (e.g., a pharmaceutical composition comprising a compound disclosed herein (e.g., a compound of formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof), and a pharmaceutically acceptable excipient).

In another aspect, the present disclosure provides a method of treating a disease or condition associated with a gain-of-function mutation of a gene (e.g., KCNT1), wherein the method comprises administering to a subject in need thereof a compound disclosed herein (e.g., a compound of formula ((I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof) or a pharmaceutical composition disclosed herein (e.g., a pharmaceutical composition comprising a compound disclosed herein (e.g., a compound of formula ((I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof), and a pharmaceutically acceptable excipient).

In some embodiments, the neurological disease or disorder, the disease or condition associated with excessive neuronal excitability, or the disease or condition associated with a gain-of-function mutation of a gene (e.g., KCNT1) is epilepsy, an epilepsy syndrome, or an encephalopathy.

In some embodiments, the neurological disease or disorder, the disease or condition associated with excessive neuronal excitability, or the disease or condition associated with a gain-of-function mutation of a gene (e.g., KCNT1) is a genetic or pediatric epilepsy or a genetic or pediatric epilepsy syndrome.

In some embodiments, the neurological disease or disorder, the disease or condition associated with excessive neuronal excitability, or the disease or condition associated with a gain-of-function mutation of a gene (e.g., KCNT1) is a cardiac dysfunction.

In some embodiments, the neurological disease or disorder, the disease or condition associated with excessive neuronal excitability, or the disease or condition associated with a gain-of-function mutation of a gene (e.g., KCNT1) is selected from epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox Gastaut syndrome, seizures (e.g., Generalized tonic clonic seizures, Asymmetric Tonic Seizures), leukodystrophy, leukoencephalopathy, intellectual disability, Multifocal Epilepsy, Drug resistant epilepsy, Temporal lobe epilepsy, cerebellar ataxia).

In some embodiments, the neurological disease or disorder, the disease or condition associated with excessive neuronal excitability, or the disease or condition associated with a gain-of-function mutation of a gene (e.g., KCNT1) is selected from the group consisting of cardiac arrhythmia, sudden unexpected death in epilepsy, Brugada syndrome, and myocardial infarction.

In some embodiments, the neurological disease or disorder, the disease or condition associated with excessive neuronal excitability, or the disease or condition associated with a gain-of-function mutation of a gene (e.g., KCNT1) is selected from pain and related conditions (e.g. neuropathic pain, acute/chronic pain, migraine, etc).

In some embodiments, the neurological disease or disorder, the disease or condition associated with excessive neuronal excitability, or the disease or condition associated with a gain-of-function mutation of a gene (e.g., KCNT1) is a muscle disorder (e.g. myotonia, neuromyotonia, cramp muscle spasms, spasticity).

In some embodiments, the neurological disease or disorder, the disease or condition associated with excessive neuronal excitability, or the disease or condition associated with a gain-of-function mutation of a gene (e.g., KCNT1) is selected from itch and pruritis, ataxia and cerebellar ataxias.

In some embodiments, the neurological disease or disorder, the disease or condition associated with excessive neuronal excitability, or the disease or condition associated with a gain-of-function mutation of a gene (e.g., KCNT1) is selected from psychiatric disorders (e.g. major depression, anxiety, bipolar disorder, schizophrenia).

In some embodiments, the neurological disease or disorder or the disease or condition associated with excessive neuronal excitability and/or a gain-of-function mutation in a gene (e.g., KCNT1) is selected from the group consisting of learning disorders, Fragile X, neuronal plasticity, and autism spectrum disorders.

In some embodiments, the neurological disease or disorder, the disease or condition associated with excessive neuronal excitability, or the disease or condition associated with a gain-of-function mutation of a gene (e.g., KCNT1) is selected from the group consisting of epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

Other objects and advantages will become apparent to those skilled in the art from a consideration of the ensuing Detailed Description, Examples, and Claims.

DETAILED DESCRIPTION OF THE INVENTION

As generally described herein, the present invention provides compounds and compositions useful for preventing and/or treating a disease, disorder, or condition described herein, e.g., a disease, disorder, or condition associated with excessive neuronal excitability, and/or a disease, disorder, or condition associated with gain-of-function mutations in KCNT1. Exemplary diseases, disorders, or conditions include epilepsy and other encephalopathies (e.g., epilepsy of infancy with migrating focal seizures (MMF SI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures, leukodystrophy, leukoencephalopathy, intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritis, ataxia and cerebellar ataxias, psychiatric disorders (e.g. major depression, anxiety, bipolar disorder, schizophrenia), learning disorders, Fragile X, neuronal plasticity, and autism spectrum disorders.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$alkenyl groups include the aforementioned $C_{2-4}$alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. “Alkylene,” “alkenylene,” and “alkynylene,” groups may be substituted or unsubstituted with one or more substituents as described herein.

As used herein, “aryl” refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system (“$C_{6-14}$ aryl”). In some embodiments, an aryl group has six ring carbon atoms (“$C_6$ aryl”; e.g., phenyl). In some embodiments, an aryl group has ten ring carbon atoms (“$C_{10}$ aryl”; e.g., naphthyl such as 1-naphthyl and 2-naphthyl). In some embodiments, an aryl group has fourteen ring carbon atoms (“$C_{14}$ aryl”; e.g., anthracyl). “Aryl” also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, “heteroaryl” refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur (“5-10 membered heteroaryl”). In heteroaryl groups that contain one or more nitrogen atoms, the point of attachment can be a carbon or nitrogen atom, as valency permits. Heteroaryl bicyclic ring systems can include one or more heteroatoms in one or both rings. “Heteroaryl” includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. “Heteroaryl” also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur (“5-10 membered heteroaryl”). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur (“5-8 membered heteroaryl”). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur (“5-6 membered heteroaryl”). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

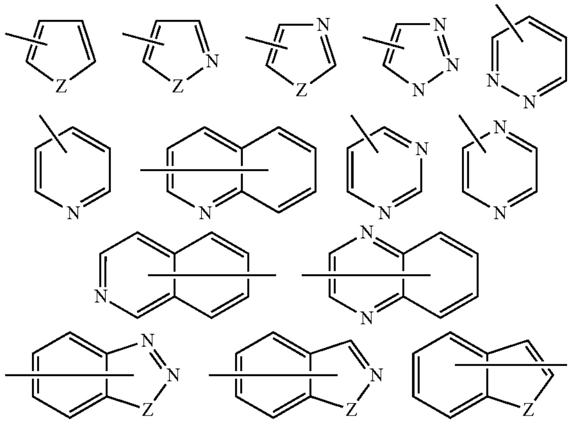

wherein each Z is selected from carbonyl, N, $NR^{65}$, O, and S; and $R^{65}$ is independently hydrogen, $C_1$-$C_8$alkyl, $C_3$-$C_{10}$ carbocyclyl, 4-10 membered heterocyclyl, $C_6$-$C_{10}$ aryl, and 5-10 membered heteroaryl.

As used herein, “carbocyclyl” or “carbocyclic” refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. Cycloalkyl groups can be fused to other cycloalkyl, aryl, or heterocyclyl groups. In certain embodiments, the cycloalkyl group is not substituted, i.e., it is unsubstituted.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

As used herein, "heterocyclene" refers to a divalent radical of a heterocycle.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

As used herein, "cyano" refers to —CN.

As used herein, "halo" or "halogen" refers to fluoro (F), chloro ($C_1$), bromo (Br) and iodo (I). In certain embodiments, the halo group is either fluoro or chloro.

As used herein, "haloalkyl" refers to an alkyl group substituted with one or more halogen atoms.

As used herein, "nitro" refers to $—NO_2$.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, $—OR^{aa}$, $—N(R^{aa})_2$, —CN, $—C(═O)R^{aa}$, $—C(═O)N(R^{aa})_2$, $—CO_2R^{aa}$, $—SO_2R^{aa}$, $—C(═NR^{bb})R^{aa}$, $C(═NR^{cc})OR^{aa}$, $—C(═NR^{aa})N(R^{aa})_2$, $—SO_2N(R^{aa})_2$, $—SO_2R^{aa}$, $—SO_2OR^{aa}$, $—SOR^{aa}$, $—C(═S)N(R^{aa})_2$, $—C(═O)SR^{aa}$, $—C(═S)SR^{aa}$, $—P(═O)_2R^{aa}$, $—P(═O)(R^{aa})_2$, $—P(═O)_2N(R^{aa})_2$, $—P(═O)(NR^{aa})_2$, $C_{1-10}$alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19, and Gould, Salt selection for basic drugs, International Journal of Pharmaceutics, 33 (1986) 201-217. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (also "therapeutic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternate embodiment, the present invention contemplates administration of the compounds of the present invention or a pharmaceutically acceptable salt or a pharmaceutically acceptable composition thereof, as a prophylactic before a subject begins to suffer from the specified disease, disorder or condition. As used herein, "prophylactic treatment" contemplates an action that occurs before a subject begins to suffer from the specified disease, disorder or condition. As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein, a "disease or condition associated with a gain-of-function mutation in KCNT1" refers to a disease or condition that is associated with, is partially or completely caused by, or has one or more symptoms that are partially or completely caused by, a mutation in KCNT1 that results in a gain-of-function phenotype, i.e. an increase in activity of the potassium channel encoded by KCNT1 resulting in an increase in whole cell current.

As used herein, a "gain-of-function mutation" is a mutation in KCNT1 that results in an increase in activity of the potassium channel encoded by KCNT1. Activity can be assessed by, for example, ion flux assay or electrophysiology (e.g. using the whole cell patch clamp technique). Typically, a gain-of-function mutation results in an increase of at least or about 20%, 30%, 40%, 50%, 60%, 70%, 80%, 90%, 100%, 125%, 150%, 175%, 200%, 225%, 250%, 275%, 300%, 325%, 350%, 375%, 400% or more compared to the activity of a potassium channel encoded by a wild-type KCNT1.

Compounds and Compositions

In one aspect, the present disclosure provides a compound of Formula I:

(I)

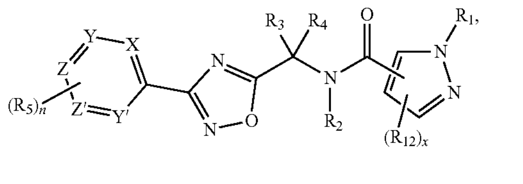

or a pharmaceutically acceptable salt thereof, wherein

X, Y, Z, Y', and Z' are each independently selected from CH and N, wherein the hydrogen of CH may be substituted with $R_5$, wherein at least 3 selected from X, Y, Z, Y', and Z' are CH;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, C(O)N$(R_9)_2$, N$(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$ alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of halogen, $C_{1-6}$alkyl, $C_{1-6}$haloalkyl, $C_{1-6}$alkylene-N$(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-6}$alkoxy, OH, N$(R_9)_2$, —C(O)O$R_8$, C(O)N$(R_9)_2$, $C_{1-6}$alkylene-CN, —CN, —S(O)$_2$—$C_{1-6}$alkyl, $C_{1-6}$alkylene-S(O)$_2$—$C_{1-6}$alkyl, —S(O)$_2$—N$(R_9)_2$, —OC(O)$C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 0, 1, 2, and 3;

$R_7$ is each independently selected from the group consisting of phenyl, $C_{1-6}$alkoxy, —OH, —N$(R_9)_2$, —N$R_9$—SO$_2$—$C_{1-6}$alkyl, —O—($C_{1-6}$alkylene)-phenyl, $C_{3-10}$cycloalkyl, —C(O)O$R_8$, —C(O)N$(R_9)_2$, —N$R_{10}$C(O)—$R_{11}$, —CN, —S(O)$_2$—$C_{1-6}$alkyl, —S(O)$_2$—N$(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —N$(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and when $R_3$ and $R_4$ are both hydrogen, at least one selected from X, Y, Z, Y', and Z' is N.

In another aspect, the present disclosure provides a pharmaceutical composition comprising a compound of Formula I:

(I)

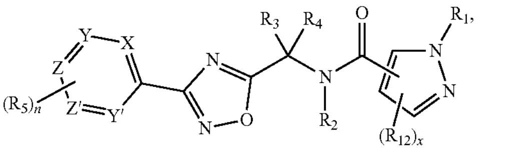

or a pharmaceutically acceptable salt thereof, wherein

X, Y, Z, Y', and Z' are each independently selected from CH and N, wherein the hydrogen of CH may be substituted with $R_5$, wherein at least 3 selected from X, Y, Z, Y', and Z' are CH;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, C(O)N$(R_9)_2$, $N(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of halogen, $C_{1-6}$alkyl, $C_{1-6}$haloalkyl, $C_{1-6}$alkylene-$N(R_9)_2$, $C_{1-6}$alkylene-O—$C_{3-10}$cycloalkyl, $C_{1-6}$alkoxy, $C_{1-6}$alkoxy substituted with $C_{3-10}$cycloalkyl optionally substituted with one or more halogens, $C_{1-6}$haloalkoxy, 3-10 membered heterocyclyl optionally substituted with one or more halogens or $C_{1-6}$alkoxy, 3-10 membered heteroaryl, $C_{1-6}$alkylene-OH, $C_{1-6}$alkylene-$C_{1-6}$alkoxy, OH, $N(R_9)_2$, —C(O)$OR_8$, C(O)$N(R_9)_2$, $C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 0, 1, 2, and 3;

$R_7$ is each independently selected from the group consisting of phenyl, $C_{1-6}$alkoxy, —OH, —$N(R_9)_2$, —$NR_9$—$SO_2$—$C_{1-6}$alkyl, —O—($C_{1-6}$alkylene)-phenyl, $C_{3-10}$cycloalkyl, —C(O)$OR_8$, —C(O)$N(R_9)_2$, —$NR_{10}$C(O)—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and when $R_3$ and $R_4$ are both hydrogen, at least one selected from X, Y, Z, Y', and Z' is N;

and a pharmaceutically acceptable excipient.

In some embodiments, the compound is a compound of Formula I-I or Formula I-II:

(I-I)

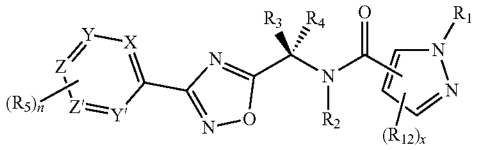

or (I-II)

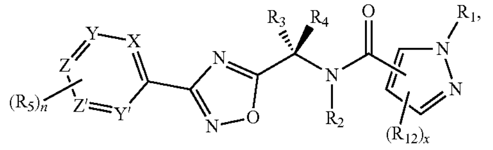

or a pharmaceutically acceptable salt thereof, wherein the variables are as defined above.

In some embodiments, one of X, Y, Z, Y', and Z' is N and the other four are CH.

In some embodiments, two of X, Y, Z, Y', and Z' are N and the other three are CH.

In some embodiments, the compound is a compound of Formula I-a:

(I-a)

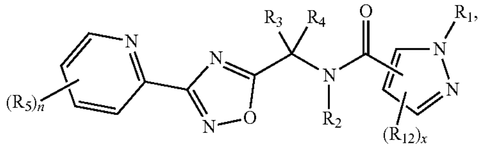

or a pharmaceutically acceptable salt thereof, wherein the variables are as defined above.

In some embodiments, the compound is a compound of Formula I-b:

(I-b)

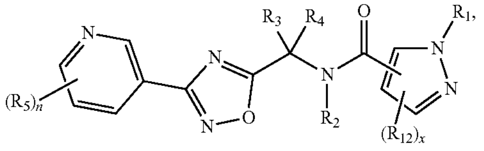

or a pharmaceutically acceptable salt thereof, wherein the variables are as defined above.

In some embodiments, the compound is a compound of Formula I-c:

(I-c)

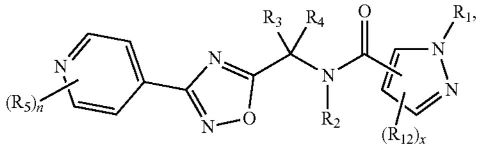

or a pharmaceutically acceptable salt thereof, wherein the variables are as defined above.

In some embodiments, the compound is a compound of Formula I-d:

(I-d)

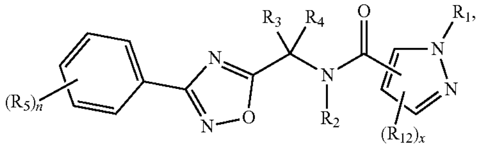

or a pharmaceutically acceptable salt thereof, wherein the variables are as defined above.

In some embodiments, the compound is a compound of Formula I-e:

(I-e)

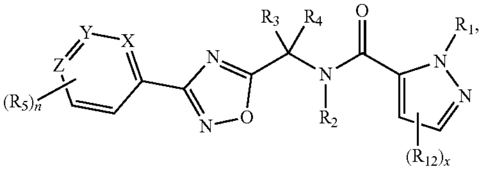

or a pharmaceutically acceptable salt thereof, wherein the variables are as defined above.

In some embodiments, the compound is a compound of Formula I-f:

(I-f)

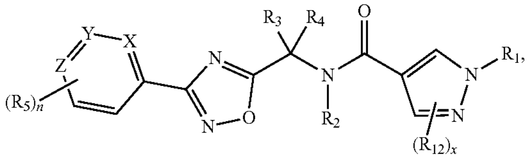

or a pharmaceutically acceptable salt thereof, wherein the variables are as defined above.

In some embodiments, the compound is a compound of Formula I-g:

(I-g)

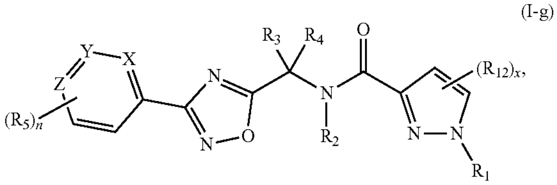

or a pharmaceutically acceptable salt thereof, wherein the variables are as defined above.

In some embodiments, the compound is a compound of Formula I-h:

(I-h)

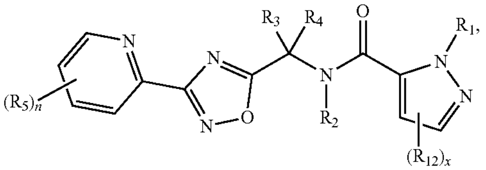

or a pharmaceutically acceptable salt thereof, wherein the variables are as defined above.

In some embodiments, the compound is a compound of Formula I-i:

(I-i)

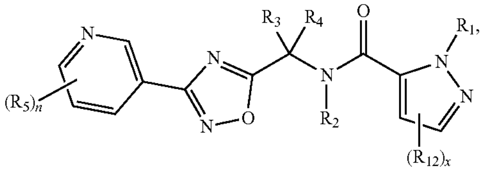

or a pharmaceutically acceptable salt thereof, wherein the variables are as defined above.

In some embodiments, the compound is a compound of Formula I-j:

(I-j)

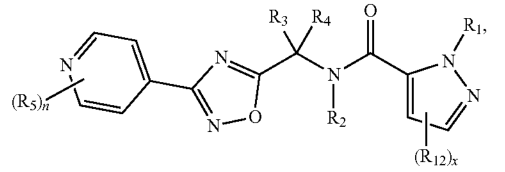

or a pharmaceutically acceptable salt thereof, wherein the variables are as defined above.

In some embodiments, the compound is a compound of Formula I-k:

(I-k)

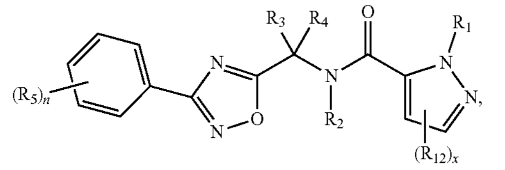

or a pharmaceutically acceptable salt thereof, wherein the variables are as defined above.

In some embodiments, the compound is a compound of Formula I-l:

(I-l)

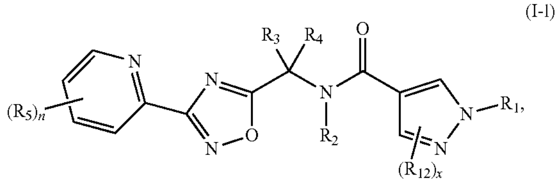

or a pharmaceutically acceptable salt thereof, wherein the variables are as defined above.

In some embodiments, the compound is a compound of Formula I-m:

(I-m)

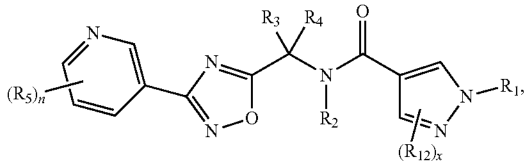

or a pharmaceutically acceptable salt thereof, wherein the variables are as defined above.

In some embodiments, the compound is a compound of Formula I-n:

(I-n)

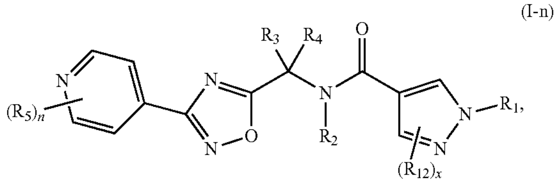

or a pharmaceutically acceptable salt thereof, wherein the variables are as defined above.

In some embodiments, the compound is a compound of Formula I-o:

(I-o)

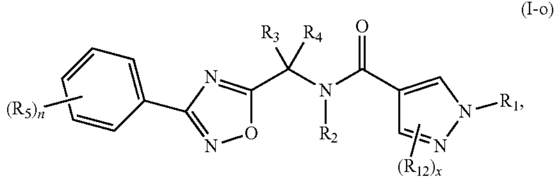

or a pharmaceutically acceptable salt thereof, wherein the variables are as defined above.

In some embodiments, the compound is a compound of Formula I-p:

(I-p)

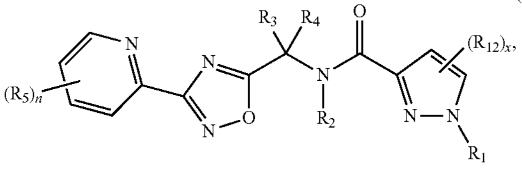

or a pharmaceutically acceptable salt thereof, wherein the variables are as defined above.

In some embodiments, the compound is a compound of Formula I-q:

(I-q)

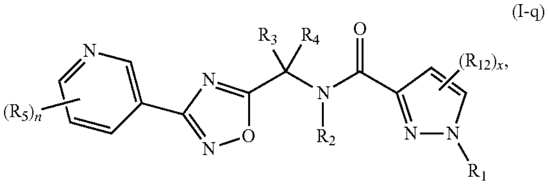

or a pharmaceutically acceptable salt thereof, wherein the variables are as defined above.

In some embodiments, the compound is a compound of Formula I-r:

(I-r)

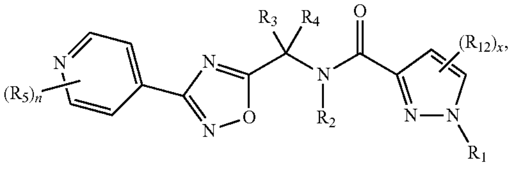

or a pharmaceutically acceptable salt thereof, wherein the variables are as defined above.

In some embodiments, the compound is a compound of Formula I-s:

(I-s)

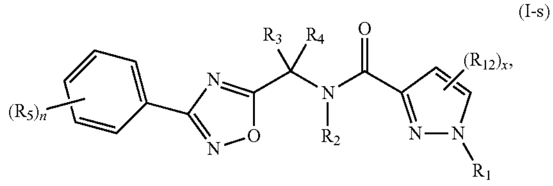

or a pharmaceutically acceptable salt thereof, wherein the variables are as defined above.

In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_2$ is hydrogen. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_2$ is methyl.

In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_3$ is hydrogen. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_3$ is $C_{1-6}$alkyl. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_3$ is selected from the group consisting of methyl, ethyl, and isopropyl. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_3$ is methyl. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_3$ is ethyl.

In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), $R_3$ is $C_{1-6}$alkyl substituted with $C_{1-6}$alkoxy, —OH, or —C(O)$OR_8$.

In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), $R_4$ is hydrogen.

In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), $R_3$ and $R_4$ are taken together with the carbon attached to $R_3$ and $R_4$ to form a $C_{3-7}$cycloalkylene or 3-7 membered heterocyclene. In some embodiments, the $C_{3-7}$cycloalkylene is selected from the group consisting of cyclopropyl, cyclobutyl, cyclopentyl, and cyclohexyl. In some embodiments, the 3-7 membered heterocyclene is selected from the group consisting of oxetanyl, tetrahydrofuranyl, and tetrahydropyranyl.

In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is independently selected from the group consisting of halogen, $C_{1-6}$alkyl, $C_{1-6}$haloalkyl, $C_{1-6}$alkoxy, $C_{1-6}$haloalkoxy, $C_{3-10}$cycloalkyl, O—$C_{3-10}$cycloalkyl, —OH, —CN, $N(R_9)_2$, and —C(O)$OR_8$.

In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is methyl. In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is halogen. In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is —F. In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is —Cl. In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is methoxy. In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is —$CF_3$. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), each $R_5$ is —$CHF_2$. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), each $R_5$ is —C(O)$OR_8$. In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), each $R_5$ is cyclopropyl, cyclobutyl, or cyclopentyl.

In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), $R_5$ is each independently selected from the group consisting of cyclopropyl, —$OCH_2CH_3$, —$OCH_2$—$CHF_2$, —O-cyclopropyl, —O-isopropyl, —$NHCH_3$, —$N(CH_3)_2$, and —$CH_2OCH_3$.

In some embodiments of formula (I) (e.g., (I-I), (I-II), (I-a), (I-b), (I-c), (I-d), (I-e), (I-g), (I-h), (I-i), (I-j), (I-k), (I-l), (I-m), (I-n), (I-o), (I-p), (I-q), (I-r), or (I-s)), n is 1. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), n is 2.

In some embodiments of formula (I) (e.g., (I-I), (I-II), (I-a), (I-b), (I-c), (I-d), (I-e), (I-g), (I-h), (I-i), (I j), (I-k), (I-l), (I-m), (I-n), (I-o), (I-p), (I-q), (I-r), or (I-s)), n is 1 and $R_5$ is at the meta-position. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), n is 2 and the two $R_5$ are at the ortho- and para-positions. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), n is 2 and the two $R_5$ are at the meta- and para-positions. In some embodiments of formula (I) (e.g., (I-I), (I-II), (I-a), (I-b), (I-c), (I-d), (I-e), (I-g), (I-h), (I-i), (I j), (I-k), (I-l), (I-m), (I-n), (I-o), (I-p), (I-q), (I-r), or (I-s)), n is 2 and the two $R_5$ are at the meta-positions.

In some embodiments of formula (I) (e.g., (I-I), (I-II), (I-a), (I-b), (I-c), (I-d), (I-e), (I-g), (I-h), (I-i), (I j), (I-k), (I-l), (I-m), (I-n), (I-o), (I-p), (I-q), (I-r), or (I-s)), $R_1$ is selected from the group consisting of $C_{1-6}$alkyl optionally substituted with $C_{1-6}$alkoxy, $N(R_9)_2$, $C(O)N(R_9)_2$, $C_{3-7}$cycloalkyl, pyridyl, tetrahydropyranyl, or phenyl, $C_{1-6}$haloalkyl, $C_{3-7}$cycloalkyl, phenyl optionally substituted with halogen, and pyridyl optionally substituted with halogen.

In some embodiments of formula (I) (e.g., (I-I), (I-II), (I-a), (I-b), (I-c), (I-d), (I-e), (I-g), (I-h), (I-i), (I j), (I-k), (I-l), (I-m), (I-n), (I-o), (I-p), (I-q), (I-r), or (I-s)), $R_1$ is $C_{1-6}$alkyl.

In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_1$ is methyl. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_1$ is ethyl.

In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_1$ is $C_{1-6}$haloalkyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is $—CH_2—CHF_2$. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is $—CHF_2$.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is $C_{3-7}$cycloalkyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is cyclopropyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is cyclobutyl.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is $C_{1-6}$alkyl substituted with $C_{1-6}$alkoxy. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is $C_{1-6}$alkyl substituted with methoxy.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is $C_{1-6}$alkyl substituted with $C_{3-7}$cycloalkyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is $C_{1-6}$alkyl substituted with cyclopropyl.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_1$ is phenyl substituted with halogen.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from halogen and $C_{1-6}$alkoxy.

In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_{12}$ is selected from the group consisting of $C_{1-6}$alkyl, $C_{1-6}$haloalkyl, $C_{3-7}$cycloalkyl, and phenyl optionally substituted with halogen.

In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_{12}$ is $C_{3-7}$cycloalkyl. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), $R_{11}$ is cyclopropyl.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{12}$ is $C_{1-6}$alkyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{12}$ is ethyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{11}$ is methyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{11}$ is t-butyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{11}$ is isopropyl.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{11}$ is $C_{1-6}$haloalkyl. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{12}$ is $—CF_3$. In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{11}$ is $—CHF_2$.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), $R_{11}$ is phenyl optionally substituted with —F.

In some embodiments of formula (I) (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), x is 1. In some embodiments of formula (I) (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), x is 2.

In another aspect, the present disclosure provides a compound of Formula II:

(II)

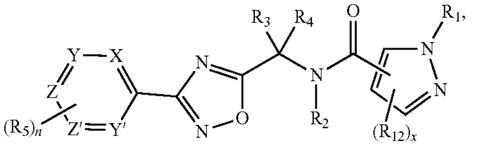

or a pharmaceutically acceptable salt thereof, wherein one or two selected from X, Y, Z, Y', and Z' are N, and the others are CH, wherein the hydrogen of CH may be substituted with $R_5$;

$R_1$ is selected from the group consisting of $C_{1-6}$alkyl, $C_{3-10}$cycloalkyl, 3-10 membered heterocyclyl, 3-10 membered heteroaryl, and phenyl, wherein $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, C(O)N$(R_9)_2$, N$(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons can be taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene may be optionally substituted with one or more $R_7$;

each $R_5$ is independently selected from the group consisting of halogen, $C_{1-6}$alkyl, $C_{1-6}$haloalkyl, $C_{1-6}$alkylene-$N(R_9)_2$, $C_{1-6}$alkylene-O—$C_{3-10}$cycloalkyl, $C_{1-6}$alkoxy optionally substituted with $C_{3-7}$cycloalkyl, $C_{1-6}$haloalkoxy, 3-10 membered heterocyclyl optionally substituted with one or more halogens or $C_{1-6}$alkoxy, 3-10 membered heteroaryl, —$C_{1-6}$alkylene-OH, $C_{1-6}$alkylene-$C_{1-6}$alkoxy, OH, —$N(R_9)_2$, —$C(O)OR_8$, —$C(O)N(R_9)_2$, —$C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —$OC(O)C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

n is selected from the group consisting of 1, 2, and 3;

$R_7$ is each independently selected from the group consisting of phenyl, $C_{1-6}$alkoxy, —OH, —$N(R_9)_2$, —$NR_9$—$SO_2$—$C_{1-6}$alkyl, —O—($C_{1-6}$alkylene)-phenyl, $C_{3-10}$cycloalkyl, —$C(O)OR_8$, —$C(O)N(R_9)_2$, —$NR_{10}C(O)$—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is selected from the group consisting of hydrogen, $C_{1-6}$alkyl, and $C_{3-10}$cycloalkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl; and $R_{11}$ is selected from the group consisting of $C_{1-6}$alkyl, $C_{1-6}$alkoxy, and —O—($C_{1-6}$alkylene)-phenyl.

In some embodiments, two of X, Y, Z, Y', and Z' are N and the other three are CH.

In some embodiments, the compound is a compound of Formula II-a:

(II-a)

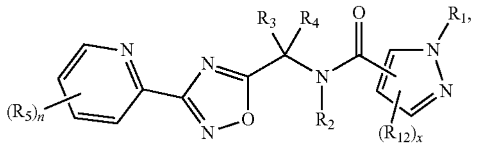

or a pharmaceutically acceptable salt thereof, wherein the variables are as defined above.

In some embodiments, the compound is a compound of Formula II-b:

(II-b)

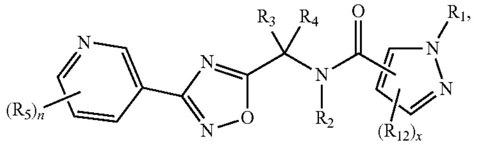

or a pharmaceutically acceptable salt thereof, wherein the variables are as defined above.

In some embodiments, the compound is a compound of Formula II-c:

(II-c)

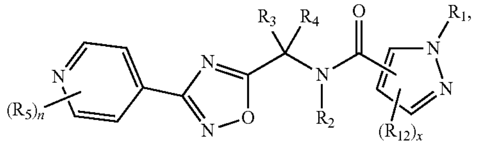

or a pharmaceutically acceptable salt thereof, wherein the variables are as defined above.

In some embodiments, the compound is a compound of Formula II-d:

(II-d)

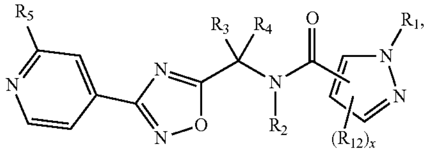

or a pharmaceutically acceptable salt thereof, wherein the variables are as defined above.

In some embodiments, the compound is a compound of Formula II-e:

(II-e)

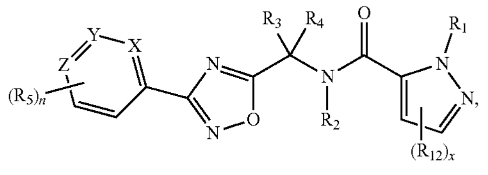

or a pharmaceutically acceptable salt thereof, wherein the variables are as defined above.

In some embodiments, the compound is a compound of Formula II-f:

(II-f)

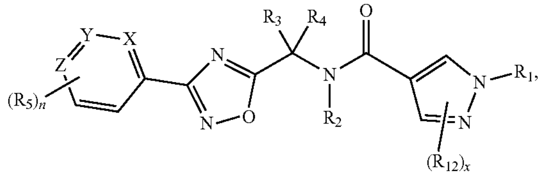

or a pharmaceutically acceptable salt thereof, wherein the variables are as defined above.

In some embodiments, the compound is a compound of Formula II-g:

(II-g)

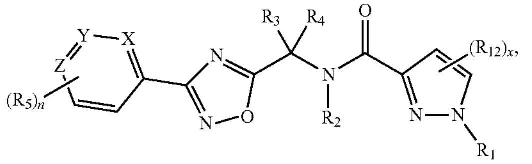

or a pharmaceutically acceptable salt thereof, wherein the variables are as defined above.

In some embodiments, the compound is a compound of Formula II-h:

(II-h)

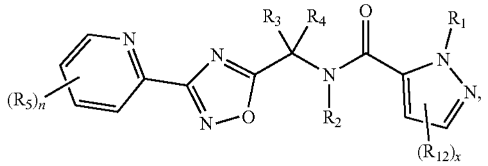

or a pharmaceutically acceptable salt thereof, wherein the variables are as defined above.

In some embodiments, the compound is a compound of Formula II-i:

(II-i)

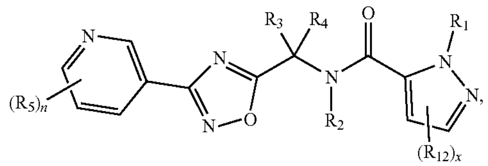

or a pharmaceutically acceptable salt thereof, wherein the variables are as defined above.

In some embodiments, the compound is a compound of Formula II-j:

(II-j)

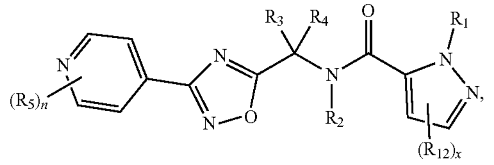

or a pharmaceutically acceptable salt thereof, wherein the variables are as defined above.

In some embodiments, the compound is a compound of Formula II-k:

(II-k)

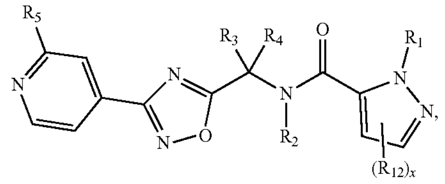

or a pharmaceutically acceptable salt thereof, wherein the variables are as defined above.

In some embodiments, the compound is a compound of Formula II-l:

(II-l)

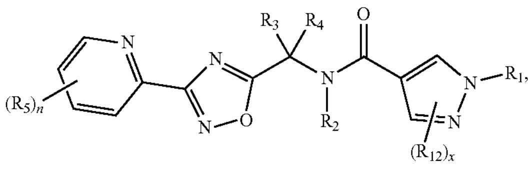

or a pharmaceutically acceptable salt thereof, wherein the variables are as defined above.

In some embodiments, the compound is a compound of Formula II-m:

(II-m)

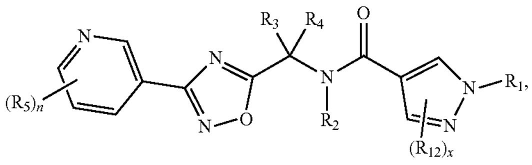

or a pharmaceutically acceptable salt thereof, wherein the variables are as defined above.

In some embodiments, the compound is a compound of Formula II-n:

(II-n)

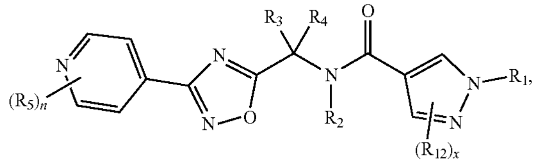

or a pharmaceutically acceptable salt thereof, wherein the variables are as defined above.

In some embodiments, the compound is a compound of Formula II-p:

(II-p)

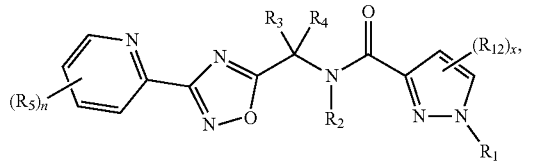

or a pharmaceutically acceptable salt thereof, wherein the variables are as defined above.

In some embodiments, the compound is a compound of Formula II-q:

(II-q)

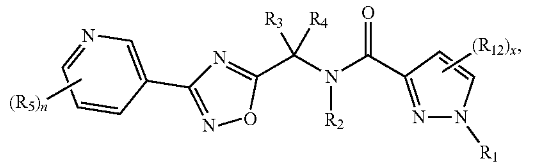

or a pharmaceutically acceptable salt thereof, wherein the variables are as defined above.

In some embodiments, the compound is a compound of Formula II-r:

(II-r)

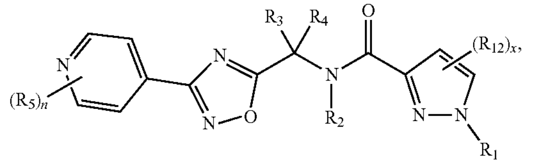

or a pharmaceutically acceptable salt thereof, wherein the variables are as defined above.

In some embodiments, the compound is a compound of Formula II-k1 or Formula II-k2:

(II-k1)

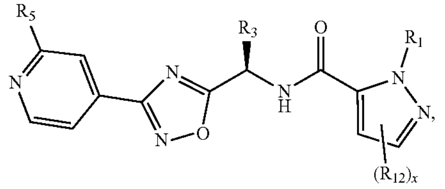

(II-k2)

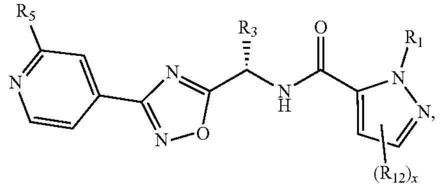

or a pharmaceutically acceptable salt thereof, wherein the variables are as defined as above.

In some embodiments of formula (II) (e.g., (II-a), (II-b), (II-c), (II-e), (II-g), (II-h), (II-i), (II-j), (II-l), (II-m), (II-n), (II-o), (II-p), (II-q), or (II-r)), n is 1. In some embodiments of formula (II) (e.g., (II-a), (II-b), (II-c), (II-e), (II-f), (II-g), (II-h), (II-i), (II j), (II-l), (II-m), (II-n), (II-o), (II-p), (II-q), or (II-r)), n is 2.

In some embodiments of formula (II) (e.g., (II-a), (II-b), (II-c), (II-e), (II-g), (II-h), (II-i), (II-j), (II-l), (II-m), (II-n), (II-o), (II-p), (II-q), or (II-r)), n is 1 and $R_5$ is at the meta-position. In some embodiments of formula (II) (e.g., (II-a), (II-b), (II-c), (II-e), (II-f), (II-g), (II-h), (II-i), (II-j), (II-l), (II-m), (II-n), (II-o), (II-p), (II-q), or (II-r)), n is 2 and the two $R_5$ are at the ortho- and para-positions. In some embodiments of formula (II) (e.g., (II-a), (II-b), (II-c), (II-e), (II-g), (II-h), (II-i), (II-j), (II-l), (II-m), (II-n), (II-o), (II-p), (II-q), or (II-r)), n is 2 and the two $R_5$ are at the meta- and para-positions. In some embodiments of formula (II) (e.g., (II-a), (II-b), (II-c), (II-e), (II-f), (II-g), (II-h), (II-i), (II j), (II-l), (II-m), (II-n), (II-o), (II-p), (II-q), or (II-r)), n is 2 and the two $R_5$ are at the meta-positions.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), or (II-r)), $R_3$ and $R_4$ are taken together with the carbon attached to $R_3$ and $R_4$ to form a $C_{3-7}$cycloalkylene or 3-7 membered heterocyclene. In some embodiments, the $C_{3-7}$cycloalkylene is selected from the group consisting of cyclopropyl, cyclobutyl, cyclopentyl, and cyclohexyl. In some embodiments, the 3-7 membered heterocyclene is selected from the group consisting of oxetanyl, tetrahydrofuranyl, and tetrahydropyranyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), or (II-r)), $R_4$ is hydrogen.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), or (II-r)), $R_2$ is hydrogen.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), or (II-r)), $R_2$ is methyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_3$ is $C_{1-6}$alkyl. In some embodiments of formula (II) (e.g., (II-a), (II-b), (II-c), (II-d), (II-e), (II-g), (II-h), (II-i), (II j), (II-k), (II-l), (II-m), (II-n), (II-o), (II-p), (II-q), (II-r), (II-k1), or (II-k2)), $R_3$ is methyl. In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_3$ is ethyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_3$ is $C_{1-6}$alkyl substituted with $C_{1-6}$alkoxy, —OH, or —C(O)$OR_8$.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_3$ is hydrogen.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), each $R_5$ is independently selected from the group consisting of $C_{1-6}$alkyl, $C_{1-6}$haloalkyl, $C_{1-6}$alkoxy, $C_{1-6}$haloalkoxy, $C_{3-10}$cycloalkyl, O—$C_{3-10}$cycloalkyl, —CN, $C_{1-6}$alkylene-$C_{1-6}$alkoxy, $C_{1-6}$alkylene-$(NR_9)_2$, $N(R_9)_2$, and —C(O)$OR_8$.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_5$ is $C_{1-6}$alkyl. In some embodiments of formula (II) (e.g., (II-a), (II-b), (II-c), (II-d), (II-e), (II-g), (II-h), (II-i), (II j), (II-k), (II-l), (II-m), (II-n), (II-o), (II-p), (II-q), (II-r), (II-k1), or (II-k2)), $R_5$ is methyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_5$ is halogen. In some embodiments of formula (II) (e.g., (II-a), (II-b), (II-c), (II-d), (II-e), (II-g), (II-h), (II-i), (II j), (II-k), (II-l), (II-m), (II-n), (II-o), (II-p), (II-q), (II-r), (II-k1), or (II-k2)), $R_5$ is —F. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_5$ is —Cl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_5$ is $C_{1-6}$haloalkyl. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_5$ is $CF_3$. In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_5$ is $CF_2H$.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_5$ is $C_{1-6}$alkoxy. In some embodiments of formula (II) (e.g., (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-k1), or (II-k2)), $R_5$ is methoxy.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_5$ is $C_{3-10}$cycloalkyl. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_5$ is cyclopropyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_5$ is —C(O)$OR_8$.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_1$ is selected from the group consisting of $C_{1-6}$alkyl optionally substituted with $C_{1-6}$alkoxy, $N(R_9)_2$, $C(O)N(R_9)_2$, $C_{3-7}$cycloalkyl, pyridyl, tetrahydropyranyl, or phenyl, $C_{1-6}$haloalkyl, $C_{3-7}$cycloalkyl, phenyl, and pyridyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_1$ is $C_{1-6}$alkyl. In some embodiments of formula (II) (e.g., (II-a), (II-b), (II-c), (II-d), (II-e), (II-g), (II-h), (II-i), (II j), (II-k), (II-l), (II-m), (II-n), (II-o), (II-p), (II-q), (II-r), (II-k1), or (II-k2)), $R_1$ is methyl. In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_1$ is ethyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_1$ is $C_{1-6}$haloalkyl. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_1$ is —$CH_2$—$CHF_2$. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_1$ is —$CHF_2$.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_1$ is $C_{3-7}$cycloalkyl. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_1$ is cyclopropyl, cyclobutyl, or cyclopentyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_1$ is phenyl substituted with halogen.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_1$ is $C_{1-6}$alkyl substituted with $C_{1-6}$alkoxy. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_1$ is $C_{1-6}$alkyl substituted with $N(R_9)_2$. In some embodiments of formula (II) (e.g., (II-a), (II-b), (II-c), (II-d), (II-e), (II-g), (II-h), (II-i), (II j), (II-k), (II-l), (II-m), (II-n), (II-o), (II-p), (II-q), (II-r), (II-k1), or (II-k2)), $R_1$ is $C_{1-6}$alkyl substituted with cyclopropyl, cyclobutyl, or cyclopentyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), x is 0 or 1.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), x is 1.

In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_{12}$ is selected from the group consisting of $C_{1-6}$alkyl, $C_{1-6}$haloalkyl, and phenyl optionally substituted with halogen.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_{12}$ is $C_{1-6}$alkyl. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_{12}$ is methyl. In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_{12}$ is ethyl. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_{12}$ is t-butyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_{11}$ is $C_{1-6}$haloalkyl. In some embodiments of formula (II) (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), $R_{11}$ is $CF_3$. In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_{11}$ is —$CHF_2$.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), $R_{11}$ is $C_{3-7}$cycloalkyl. In some embodiments of formula (II) (e.g., (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-k1), or (II-k2)), $R_{11}$ is cyclopropyl.

In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), In some embodiments of formula (II) (e.g., (II-a), (II-b), (II-c), (II-d), (II-e), (II-g), (II-h), (II-i), (II-j), (II-k), (II-l), (II-m), (II-n), (II-o), (II-p), (II-q), (II-r), (II-k1), or (II-k2)), x is 0.

In another aspect, the present disclosure provides a compound of Formula III:

(III)

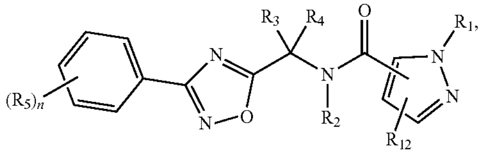

or a pharmaceutically acceptable salt thereof, wherein $R_1$ is $C_{1-6}$alkyl or $C_{3-7}$cycloalkyl, wherein the $C_{1-6}$alkyl or $C_{3-7}$cycloalkyl is optionally substituted with one or more halogen or $C_{1-6}$alkoxy;

$R_{11}$ is selected from the group consisting of $C_{3-10}$cycloalkyl, 3-10 membered saturated heterocyclyl, and phenyl, wherein the $C_{3-10}$cycloalkyl, 3-10 membered saturated heterocyclyl, or phenyl is optionally substituted with one or more substituents each independently selected from halogen and $C_{1-6}$alkoxy;

$R_2$ is hydrogen or $C_{1-4}$alkyl;

$R_3$ is selected from the group consisting of $C_{1-6}$alkyl, $C_{3-10}$cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$cycloalkyl, 3-10 membered heterocyclyl, 3-10 membered heteroaryl, phenyl, $C_{3-7}$cycloalkylene or 3-7 membered heterocyclene may be optionally substituted with one or more $R_7$;

$R_5$ is selected from the group consisting of halogen, $C_{1-6}$alkyl, $C_{1-6}$haloalkyl, $C_{1-6}$alkoxy, $C_{1-6}$haloalkoxy, 3-10 membered heterocyclyl, 3-10 membered heteroaryl, —$C_{1-6}$alkylene-OH, OH, —C(O)$OR_8$, —C(O)$N(R_9)_2$, —$C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, and —O—$C_{1-3}$cycloalkyl optionally substituted with one or more halogen;

$R_7$ is each independently selected from the group consisting of phenyl, $C_{1-6}$alkoxy, —OH, —O—($C_{1-6}$alkylene)-phenyl, $C_{3-10}$cycloalkyl, —C(O)$OR_8$, —C(O)$N(R_9)_2$, —$NR_{10}$C(O)—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and n is selected from the group consisting of 0, 1, 2, and 3;

wherein the compound is not:

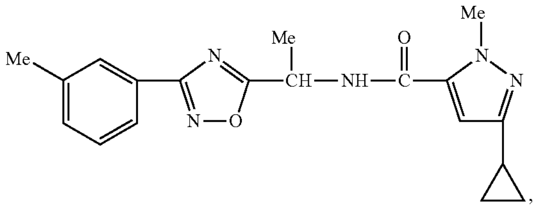

,

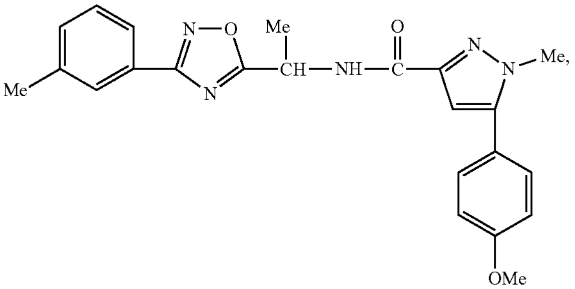

or a pharmaceutically acceptable salt thereof.

In another aspect, the present disclosure provides a compound of Formula IV:

(IV)

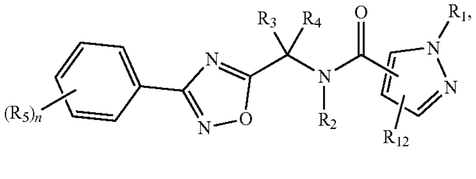

or a pharmaceutically acceptable salt thereof, wherein $R_1$ is selected from the group consisting of $C_{1-6}$alkyl, and $C_{3-7}$cycloalkyl, wherein the $C_{1-6}$alkyl or $C_{3-7}$cycloalkyl is optionally substituted with one or more substituents independently selected from halogen and $C_{1-6}$alkoxy;

$R_{12}$ is $C_{1-6}$alkyl optionally substituted with one or more halogen or $C_{1-6}$alkoxy;

$R_2$ is hydrogen or $C_{1-4}$alkyl;

$R_3$ is selected from the group consisting of $C_{1-6}$alkyl, $C_{3-10}$cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$cycloalkyl, 3-10 membered heterocyclyl, 3-10 membered heteroaryl, phenyl, $C_{3-7}$cycloalkylene or 3-7 membered heterocyclene may be optionally substituted with $R_7$;

$R_5$ is selected from the group consisting of halogen, $C_{1-6}$alkyl, $C_{1-6}$alkoxy, $C_{1-6}$haloalkyl, $C_{1-6}$haloalkoxy, 3-10 membered heterocyclyl, 3-10 membered heteroaryl, —$C_{1-6}$alkylene-OH, OH, —C(O)$OR_8$, —C(O)$N(R_9)_2$, —$C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, and —O—$C_{3-10}$cycloalkyl optionally substituted with one or more halogen;

$R_7$ is each independently selected from the group consisting of phenyl, $C_{1-6}$alkoxy, —OH, —O—($C_{1-6}$alkylene)-phenyl, $C_{3-10}$cycloalkyl, —C(O)$OR_8$, —C(O)$N(R_9)_2$, —$NR_{10}$C(O)—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and n is selected from the group consisting of 0, 1, 2, and 3;

wherein the compound is not:

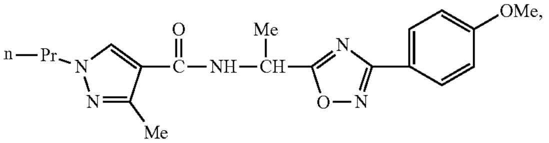

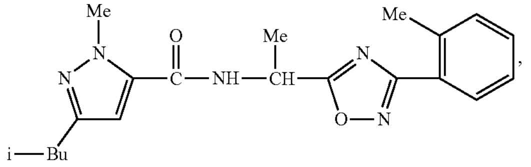

-continued

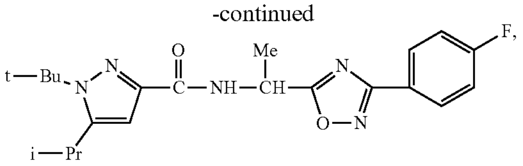

or a pharmaceutically acceptable salt thereof.

In another aspect, the present disclosure provides a compound of Formula V:

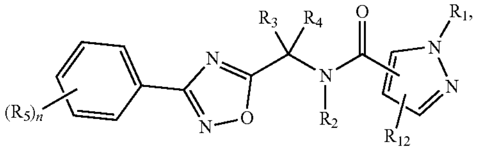

(V)

or a pharmaceutically acceptable salt thereof, wherein $R_1$ is phenyl or 3-10 membered heteroaryl, wherein the phenyl or 3-10 membered heteroaryl is optionally substituted with one or more substituents independently selected from halogen and $C_{1-6}$alkoxy, $R_{12}$ is selected from the group consisting of $C_{3-10}$cycloalkyl, 3-10 membered saturated heterocyclyl, 3-10 membered heteroaryl, and phenyl, wherein the $C_{3-10}$cycloalkyl, 3-10 membered saturated heterocyclyl, 3-10 membered heteroaryl, or phenyl is optionally substituted with one or more substituents each independently selected from halogen and $C_{1-6}$alkoxy;

$R_2$ is hydrogen or $C_{1-4}$alkyl;

$R_3$ is selected from the group consisting of $C_{1-6}$alkyl, $C_{3-10}$cycloalkyl, 3-10 membered heterocyclyl, 3-10 membered heteroaryl, and phenyl; and $R_4$ is selected from $C_{1-6}$alkyl and hydrogen; or $R_3$ and $R_4$ can be taken together with the carbon attached to $R_3$ and $R_4$ to form a $C_{3-7}$cycloalkylene or 3-7 membered heterocyclene; wherein the $C_{1-6}$alkyl, $C_{3-10}$cycloalkyl, 3-10 membered heterocyclyl, 3-10 membered heteroaryl, phenyl, $C_{3-7}$cycloalkylene or 3-7 membered heterocyclene may be optionally substituted with one or more $R_7$;

$R_5$ is selected from the group consisting of halogen, $C_{1-6}$alkyl, $C_{1-6}$haloalkyl, $C_{1-6}$alkoxy, $C_{1-6}$haloalkoxy, 3-10 membered heterocyclyl, 3-10 membered heteroaryl, —$C_{1-6}$alkylene-OH, OH, —C(O)$OR_8$, —C(O)$N(R_9)_2$, —$C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_9)_2$, —OC(O)$C_{1-6}$alkyl, and —O—$C_{3-10}$cycloalkyl;

$R_7$ is selected from the group consisting of phenyl, $C_{1-6}$alkoxy, —OH, —O—($C_{1-6}$alkylene)-phenyl, $C_{3-7}$cycloalkyl, —C(O)$OR_8$, —C(O)$N(R_9)_2$, —$NR_{10}$C(O)—$R_{11}$, —CN, —$S(O)_z$—$C_{1-6}$alkyl, —$S(O)_z$—$N(R_9)_2$, 3-7 membered heterocyclyl, and 3-10 membered heteroaryl, wherein the phenyl, $C_{3-10}$cycloalkyl, 3-10 membered heterocyclyl, or 3-10 membered heteroaryl is optionally substituted with one or more substituents each independently selected from the group consisting of $C_{1-6}$alkyl, halogen, —OH, $C_{1-6}$alkoxy, and —$N(R_9)_2$;

$R_8$ is hydrogen or $C_{1-6}$alkyl;

each $R_9$ is independently selected from the group consisting of hydrogen, $C_{1-6}$alkyl, and —($C_{1-6}$alkylene)-OH, or the two $R_9$ can be taken together with the nitrogen atom attached to the two $R_9$ to form a heterocycle optionally substituted with one or more substituents each independently selected from halogen and —OH;

each $R_{10}$ is independently hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and n is selected from the group consisting of 0, 1, 2, and 3; wherein the compound is not:

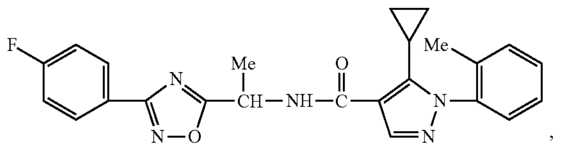

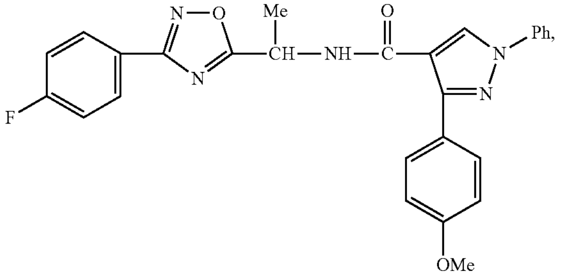

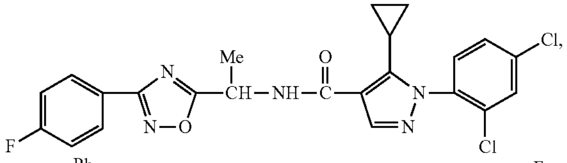

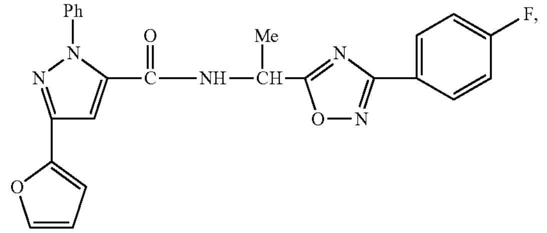

or a pharmaceutically acceptable salt thereof.

In some embodiments of formula (III), (IV), or (V), $R_2$ is hydrogen.

In some embodiments of formula (III), (IV), or (V), $R_3$ is $C_{1-6}$alkyl. In some embodiments of formula (III), (IV), or (V), $R_3$ is methyl. In some embodiments of formula (III), (IV), or (V), $R_3$ is ethyl.

In some embodiments of formula (III), (IV), or (V), $R_3$ is $C_{1-6}$alkyl substituted with $C_{1-6}$alkoxy, —OH, or —C(O)$OR_8$.

In some embodiments of formula (III), (IV), or (V), $R_4$ is hydrogen.

In some embodiments of formula (III), (IV), or (V), $R_3$ and $R_4$ are taken together with the carbon attached to $R_3$ and $R_4$ to form a $C_{3-7}$cycloalkylene or 3-7 membered heterocyclene.

In some embodiments of formula (III), (IV), or (V), $R_5$ is each independently selected from the group consisting of cyclopropyl, —$OCH_2CH_3$, —$OCH_2$—$CHF_2$, —O— cyclopropyl, —O-isopropyl, —$NHCH_3$, —$N(CH_3)_2$, and —$CH_2OCH_3$;

In some embodiments of formula (III), (IV), or (V), each $R_5$ is methyl.

In some embodiments of formula (III), (IV), or (V), each $R_5$ is halogen. In some embodiments of formula (III), (IV), or (V), each $R_5$ is —F. In some embodiments of formula (III), (IV), or (V), each $R_5$ is —Cl.

In some embodiments of formula (III), (IV), or (V), each $R_5$ is methoxy.

In some embodiments of formula (III), (IV), or (V), each $R_5$ is —$CF_3$.

In some embodiments of formula (III), (IV), or (V), each $R_5$ is —$CHF_2$.

In some embodiments of formula (III), (IV), or (V), each $R_5$ is —C(O)$OR_8$.

In some embodiments of formula (III), (IV), or (V), n is 1.

In some embodiments of formula (III), (IV), or (V), n is 2.

In some embodiments of formula (III), (IV), or (V), n is 1 and $R_5$ is at the meta-position. In some embodiments of formula (III), (IV), or (V), n is 2 and the two $R_5$ are at the ortho- and para-positions. In some embodiments of formula (III), (IV), or (V), n is 2 and the two $R_5$ are at the meta- and para-positions. In some embodiments of formula (III), (IV), or (V), n is 2 and the two $R_5$ are at the meta-positions.

In some embodiments of formula (III), (IV), or (V), $R_1$ is $C_{1-6}$alkyl. In some embodiments of formula (III), (IV), or (V), $R_1$ is methyl. In some embodiments of formula (III), (IV), or (V), $R_1$ is ethyl.

In some embodiments of formula (III), (IV), or (V), $R_1$ is $C_{1-6}$haloalkyl. In some embodiments of formula (III), (IV), or (V), $R_1$ is —$CH_2$—$CHF_2$. In some embodiments of formula (III), (IV), or (V), $R_1$ is —$CHF_2$.

In some embodiments of formula (III), (IV), or (V), $R_1$ is $C_{3-7}$cycloalkyl. In some embodiments of formula (III), (IV), or (V), $R_1$ is cyclopropyl.

In some embodiments of formula (III), (IV), or (V), $R_1$ is phenyl substituted with halogen.

In some embodiments of formula (III), (IV), or (V), $R_{12}$ is selected from the group consisting of $C_{1-6}$alkyl, $C_{3-10}$cycloalkyl, 3-10 membered heterocyclyl, 3-10 membered heteroaryl, and phenyl, wherein the $C_{1-6}$alkyl, $C_{3-10}$cycloalkyl, 3-10 membered heterocyclyl, 3-10 membered heteroaryl, or phenyl is optionally substituted with one or more substituents each independently selected from halogen and $C_{1-6}$alkoxy.

In some embodiments of formula (III), (IV), or (V), Rig is $C_{3-7}$cycloalkyl. In some embodiments of formula (III), (IV), or (V), $R_{12}$ is cyclopropyl.

In some embodiments of formula (III), (IV), or (V), $R_{12}$ is $C_{1-6}$alkyl. In some embodiments of formula (III), (IV), or (V), $R_{12}$ is ethyl. In some embodiments of formula (III), (IV), or (V), $R_{12}$ is methyl. In some embodiments of formula (III), (IV), or (V), $R_{12}$ is t-butyl.

In some embodiments of formula (III), (IV), or (V), $R_{12}$ is $C_{1-6}$haloalkyl. In some embodiments of formula (III), (IV), or (V), $R_{12}$ is —$CF_3$. In some embodiments of formula (III), (IV), or (V), $R_{12}$ is —$CHF_2$.

In another aspect, the present disclosure features a compound of Formula VI:

(VI)

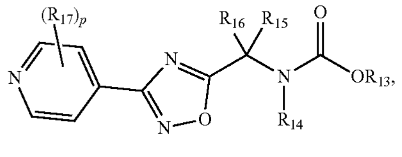

or a pharmaceutically acceptable salt thereof, wherein $R_{13}$ is $C_{1-6}$alkyl or $C_{3-10}$cycloalkyl, wherein the $C_{1-6}$alkyl or $C_{3-10}$cycloalkyl is optionally substituted with phenyl;

$R_{14}$ is hydrogen;

$R_{15}$ is $C_{1-6}$alkyl or hydrogen;

$R_{16}$ is $C_{1-6}$alkyl optionally substituted with one or more halogen, $C_{1-6}$alkoxy, $C_{3-10}$ cycloalkyl, or phenyl;

each $R_{17}$ is independently selected from the group consisting of halogen, $C_{1-6}$alkyl, $C_{1-6}$haloalkyl, $C_{1-6}$alkylene-$N(R_{20})_2$, $C_{1-6}$alkylene-O—$C_{3-10}$cycloalkyl, $C_{1-6}$alkoxy optionally substituted with $C_{3-7}$cycloalkyl, $C_{1-6}$haloalkoxy, 3-10 membered heterocyclyl optionally substituted with one or more halogens or $C_{1-6}$alkoxy, 3-10 membered heteroaryl, —$C_{1-6}$alkylene-OH, $C_{1-6}$alkylene-$C_{1-6}$alkoxy, OH, —$N(R_{20})_2$, —$C(O)OR_{19}$, —$C(O)N(R_{20})_2$, —$C_{1-6}$alkylene-CN, —CN, —$S(O)_2$—$C_{1-6}$alkyl, $C_{1-6}$alkylene-$S(O)_2$—$C_{1-6}$alkyl, —$S(O)_2$—$N(R_{20})_2$, —$OC(O)C_{1-6}$alkyl, —O—$C_{3-10}$cycloalkyl optionally substituted with one or more halogen or $C_{1-6}$alkyl, and $C_{3-10}$cycloalkyl optionally substituted with one or more substituents selected from halogen, $C_{1-6}$alkyl, and $C_{1-6}$alkoxy;

p is selected from the group consisting of 1, 2, and 3;

$R_{19}$ is selected from the group consisting of hydrogen, $C_{1-6}$alkyl, and $C_{3-10}$cycloalkyl;

each $R_{20}$ is independently hydrogen or $C_{1-6}$alkyl; and each $R_{21}$ is independently hydrogen or $C_{1-6}$alkyl.

In some embodiments of formula (VI), $R_{13}$ is selected from the group consisting of ethyl, tert-butyl, sec-butyl, iso-propyl, benzyl, and cyclopentyl.

In some embodiments of formula (VI), $R_{15}$ is hydrogen.

In some embodiments of formula (VI), $R_{16}$ is $C_{1-6}$alkyl.

In some embodiments of formula (VI), $R_{16}$ is methyl or ethyl.

In some embodiments of formula (VI), p is 1 or 2.

In some embodiments of formula (VI), the compound is a compound of Formula VI-a:

(VI-a)

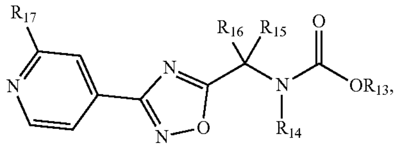

or a pharmaceutically acceptable salt thereof, wherein the variables are as defined above for Formula VI.

In some embodiments of formula (VI) (e.g., (VI-a)), $R_{17}$ is $C_{1-6}$alkyl, $C_{1-6}$haloalkyl, $C_{1-6}$alkoxy, $C_{1-6}$haloalkoxy, $C_{1-6}$alkylene-$C_{1-6}$alkoxy, —O—$C_{3-10}$cycloalkyl optionally substituted with one or more halogen, or $C_{3-10}$cycloalkyl optionally substituted with one or more substituents selected from halogen, $C_{1-6}$alkyl, and $C_{1-6}$alkoxy.

In some embodiments of formula (VI) (e.g., (VI-a)), $R_{17}$ is cyclopropyl optionally substituted with $C_{1-6}$alkyl or $C_{1-6}$alkoxy.

In some embodiments of formula (VI) (e.g., (VI-a)), $R_{17}$ is cyclopropyl optionally substituted with methyl or methoxy.

In some embodiments of formula (VI) (e.g., (VI-a)), $R_{17}$ is $C_{1-6}$alkyl.

In some embodiments of formula (VI) (e.g., (VI-a)), $R_{17}$ is methyl.

In some embodiments of formula (VI) (e.g., (VI-a)), $R_{17}$ is $C_{1-6}$alkoxy, $C_{1-6}$alkylene-$C_{1-6}$alkoxy, or $C_{1-6}$haloalkoxy.

In some embodiments of formula (VI) (e.g., (VI-a)), $R_{17}$ is —$OCH(CH_3)_2$, —$OCH_3$, —$OCH_2CH_3$, O—$CH_2CHF_2$, or —$CH_2OCH_3$.

In some embodiments of formula (VI) (e.g., (VI-a)), $R_{17}$ is $C_{1-6}$haloalkyl.

In some embodiments of formula (VI) (e.g., (VI-a)), $R_{17}$ is $CHF_2$ or $CF_3$.

In some embodiments of formula (VI) (e.g., (VI-a)), the compound is selected from the group consisting of Compound Nos. 272, 247, 262, 273, 274, 275, 276, 277, 284, 286, 287, 288, 289, 290, 291, 292, 293, 294, 295, and 296 in the Examples, or a pharmaceutically acceptable salt thereof.

In another aspect, the present disclosure features a compound of Formula VII:

(VII)

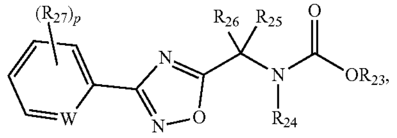

or a pharmaceutically acceptable salt thereof, wherein

W is N or CH;

$R_{23}$ is $C_{1-6}$alkyl;

$R_{24}$ is hydrogen;

$R_{25}$ is $C_{1-6}$alkyl or hydrogen;

$R_{26}$ is $C_{1-6}$alkyl optionally substituted with one or more halogen or $C_{1-6}$alkoxy;

each $R_{27}$ is independently selected from the group consisting of halogen, $C_{1-6}$alkyl, $C_{1-6}$haloalkyl, and $C_{1-6}$alkoxy; and p is selected from the group consisting of 1, 2, and 3.

In another aspect, the present disclosure features a pharmaceutical composition comprising a compound of Formula VII:

(VII)

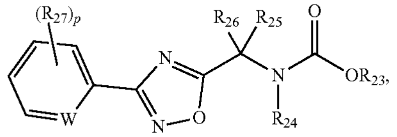

or a pharmaceutically acceptable salt thereof, wherein

W is N or CH;

$R_{23}$ is $C_{1-6}$alkyl;

$R_{24}$ is hydrogen;

$R_{25}$ is $C_{1-6}$alkyl or hydrogen;

$R_{26}$ is $C_{1-6}$alkyl optionally substituted with one or more halogen or $C_{1-6}$alkoxy;

each $R_{27}$ is independently selected from the group consisting of halogen, $C_{1-6}$alkyl, $C_{1-6}$haloalkyl, and $C_{1-6}$alkoxy; and p is selected from the group consisting of 1, 2, and 3;

and a pharmaceutically acceptable excipient.

In some embodiments of formula (VII), the compound is a compound of Formula VII-a or Formula VII-b:

(VII-a)

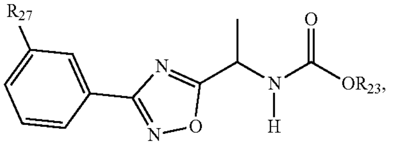

(VII-b)

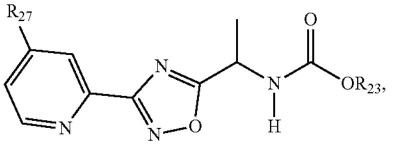

or a pharmaceutically acceptable salt thereof.

In some embodiments of formula (VII), p is 1.

In some embodiments of formula (VII) (e.g., (VII-a) or (VII-b)), $R_{23}$ is tert-butyl.

In some embodiments of formula (VII), $R_{25}$ is hydrogen.

In some embodiments of formula (VII), $R_{26}$ is methyl.

In some embodiments of formula (VII) (e.g., (VII-a) or (VII-b)), $R_{27}$ is halogen, $C_{1-6}$alkyl, or $C_{1-6}$alkoxy.

In some embodiments of formula (VII) (e.g., (VII-a) or (VII-b)), $R_{27}$ is fluoro.

In some embodiments of formula (VII) (e.g., (VII-a) or (VII-b)), $R_{27}$ is $OCH_3$.

In some embodiments of formula (VII) (e.g., (VII-a) or (VII-b)), $R_{27}$ is methyl.

In some embodiments of formula (VII) (e.g., (VII-a) or (VII-b)), the compound is selected from the group consisting of Compound Nos. 281, 282, 283, and 285 in the Examples, or a pharmaceutically acceptable salt thereof In typical embodiments, the present invention is intended to encompass the compounds disclosed herein, and the pharmaceutically acceptable salts, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, all polymorphs including polymorphs of hydrates and solvates, an enantiomer, a mixture of enantiomers, a diastereomer, a mixture of diastereomers, a stereoisomer or mixture of stereoisomers (pure or as a racemic or non-racemic mixture) of a compound described herein, e.g., a compound of formula (I), (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)).

In any and all aspects, in some embodiments, the compound of Formula (I), (II), (III), (IV), or (V) is selected from the group consisting of Compound Nos. 3, 4, 5, 6, 7, 8, 9, 10, 11, 12, 13, 14, 15, 16, 17, 19, 20, 21, 22, 23, 24, 25, 26, 29, 30, 31, 32, 33, 34, 35, 36, 37, 38, 39, 40, 41, 42, 43, 44, 45, 46, 47, 48, 49, 50, 51, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 238, 239, 240, 241, 242, 243, 244, 245, 246, 248, 249, 250, 251, 252, 253, 254, 255, 256, 257, 258, 259, 260, 261, 263, 264, 265, 266, 267, 268, 269, 270, 271, 278, 279, 280, 297, 299, 300, 301, 302, 303, 304, 305, 306, 307, 308, 309, and 310 in the Examples, or a pharmaceutically acceptable salt thereof.

General Synthetic Schemes

Exemplary methods for preparing compounds described herein are illustrated in the following synthetic schemes. These schemes are given for the purpose of illustrating the invention, and should not be regarded in any manner as limiting the scope or the spirit of the invention.

The synthetic route illustrated in Scheme 1 depicts an exemplary procedure for preparing carboxylic acid intermediates D and G. In the first step, compound A is reacted with hydrazine B to form ethyl pyrazole-5-carboxylate C. Then, hydrolysis of C provides carboxylic acid D. Carboxylic acid D may be coupled with amine E to form F, which is then hydrolyzed to yield carboxylic acid G.

SCHEME 1

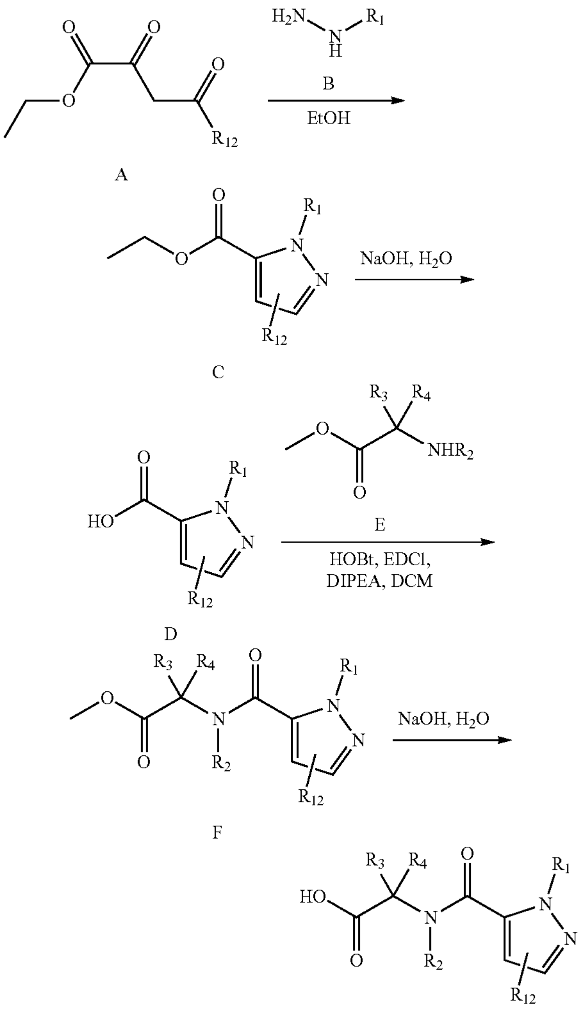

The synthetic route illustrated in Scheme 2 depicts an exemplary procedure for preparing amine-substituted oxadiazole intermediate L. In the first step, nitrile H is treated with hydroxylamine to provide N-hydroxyimidamide I. Then, cabonyldiimidazole (CDI)-mediated cyclization of I with glycine J affords oxadiazole K. Deprotection of K under acidic conditions provides amine-substituted oxadiazole intermediate L.

SCHEME 2

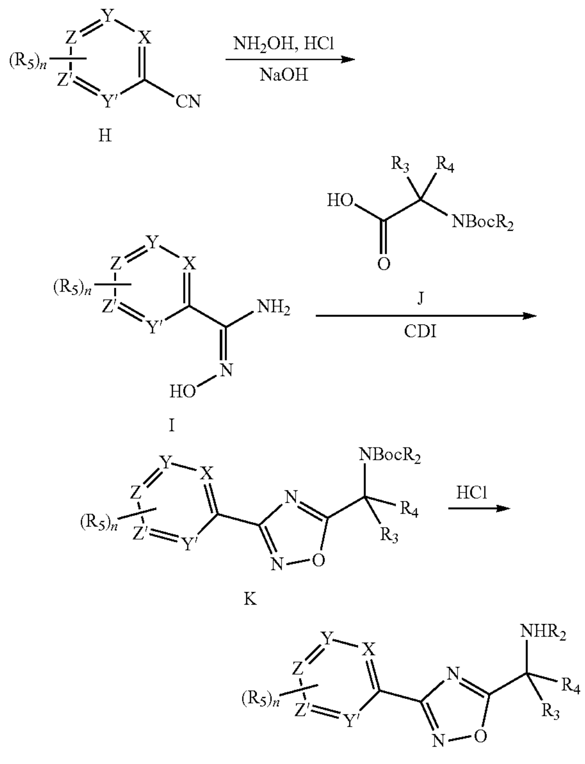

L

The synthetic route illustrated in Scheme 3 depicts an exemplary procedure for preparing M (a compound of formula I). Coupling of amine-substituted oxadiazole amine L with carboxylic acid D using standard peptide coupling procedures (e.g., HOBt, and EDCI in dichloromethane in the presence of DIPEA) provides compound M (a compound of formula I).

SCHEME 3

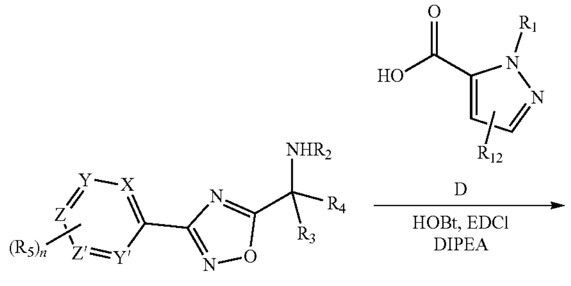

L

-continued

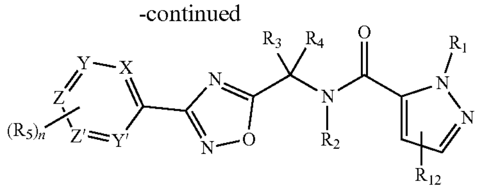

M

As illustrated in Scheme 4, N-hydroxyimidamide I may undergo CDI-mediated cyclization with carboxylic acid G to afford compound M (a compound of formula I).

SCHEME 4

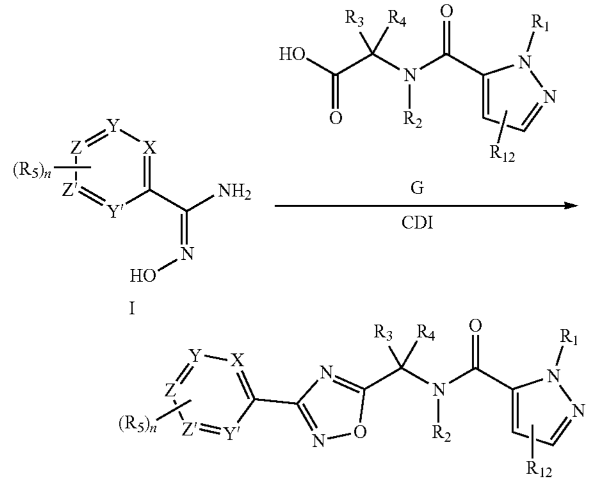

M

Methods of Treatment

The compounds and compositions described above and herein can be used to treat a neurological disease or disorder or a disease or condition associated with excessive neuronal excitability and/or a gain-of-function mutation in a gene (e.g., KCNT1). Exemplary diseases, disorders, or conditions include epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, developmental and epileptic encephalopathy (DEE), early infantile epileptic encephalopathy (EIEE), generalized epilepsy, focal epilepsy, multifocal epilepsy, temporal lobe epilepsy, Ohtahara syndrome, early myoclonic encephalopathy and Lennox Gastaut syndrome, drug resistant epilepsy, seizures (e.g., frontal lobe seizures, generalized tonic clonic seizures, asymmetric tonic seizures, focal seizures), leukodystrophy, hypomyelinating leukodystrophy, leukoencephalopathy, and sudden unexpected death in epilepsy, cardiac dysfunctions (e.g., cardiac arrhythmia, Brugada syndrome, myocardial infarction), pulmonary vasculopathy/hemorrhage, pain and related conditions (e.g. neuropathic pain, acute/chronic pain, migraine, etc), muscle disorders (e.g. myotonia, neuromyotonia, cramp muscle spasms, spasticity), itch and pruritis, movement disorders (e.g., ataxia and cerebellar ataxias), psychiatric disorders (e.g. major depression, anxiety, bipolar disorder, schizophrenia, attention-deficit hyperactivity disorder), neurodevelopmental disorder, learning disorders, intellectual disability, Fragile X, neuronal plasticity, and autism spectrum disorders.

In some embodiments, the neurological disease or disorder or the disease or condition associated with excessive neuronal excitability and/or a gain-of-function mutation in a gene (e.g., KCNT1) is selected from EIMFS, ADNFLE and West syndrome. In some embodiments, the neurological disease or disorder or the disease or condition associated with excessive neuronal excitability and/or a gain-of-function mutation in a gene (e.g., KCNT1) is selected from infantile spasms, epileptic encephalopathy, focal epilepsy, Ohtahara syndrome, developmental and epileptic encephalopathy and Lennox Gastaut syndrome. In some embodiments, the neurological disease or disorder or the disease or condition associated with excessive neuronal excitability and/or a gain-of-function mutation in a gene (e.g., KCNT1) is seizure. In some embodiments, the neurological disease or disorder or the disease or condition associated with excessive neuronal excitability and/or a gain-of-function mutation in a gene (e.g., KCNT1) is selected from cardiac arrhythmia, Brugada syndrome, and myocardial infarction.

In some embodiments, the neurological disease or disorder or the disease or condition associated with excessive neuronal excitability and/or a gain-of-function mutation in a gene (e.g., KCNT1) is selected from the group consisting of the learning disorders, Fragile X, intellectual function, neuronal plasticity, psychiatric disorders, and autism spectrum disorders.

Accordingly, the compounds and compositions thereof can be administered to a subject with a neurological disease or disorder or a disease or condition associated with excessive neuronal excitability and/or a gain-of-function mutation in a gene such as KCNT1 (e.g., EIMFS, ADNFLE, West syndrome, infantile spasms, epileptic encephalopathy, focal epilepsy, Ohtahara syndrome, developmental and epileptic encephalopathy, and Lennox Gastaut syndrome, seizures, cardiac arrhythmia, Brugada syndrome, and myocardial infarction).

EIMFS is a rare and debilitating genetic condition characterized by an early onset (before 6 months of age) of almost continuous heterogeneous focal seizures, where seizures appear to migrate from one brain region and hemisphere to another. Patients with EIMFS are generally intellectually impaired, non-verbal and non-ambulatory. While several genes have been implicated to date, the gene that is most commonly associated with EIMFS is KCNT1. Several de novo mutations in KCNT1 have been identified in patients with EIMFS, including V271F, G288S, R428Q, R474Q, R474H, R474C, I760M, A934T, P924L, G243S, H257D, A259D, R262Q, Q270E, L274I, F346L, $C_{377}S$, R398Q, P409S, A477T, F502V, M516V, Q550del, K629E, K629N, I760F, E893K, M896K, R933G, R950Q, K1154Q (Barcia et al. (2012) Nat Genet. 44: 1255-1260; Ishii et al. (2013) Gene 531:467-471; McTague et al. (2013) Brain. 136: 1578-1591; Epi4K Consortium & Epilepsy Phenome/Genome Project. (2013) Nature 501:217-221; Lim et al. (2016) Neurogenetics; Ohba et al. (2015) Epilepsia 56:e121-e128; Zhou et al. (2018) Genes Brain Behav. e12456; Moller et al. (2015) Epilepsia. e114-20; Numis et al. (2018) Epilepsia. 1889-1898; Madaan et al. Brain Dev. 40(3):229-232; McTague et al. (2018) Neurology. 90(1):e55-e66; Kawasaki et al. (2017) J Pediatr. 191:270-274; Kim et al. (2014) Cell Rep. 9(5):1661-1672; Ohba et al. (2015) Epilepsia. 56(9): e121-8; Rizzo et al. (2016) Mol Cell Neurosci. 72:54-63; Zhang et al. (2017) Clin Genet. 91(5):717-724; Mikati et al. (2015) Ann Neurol. 78(6):995-9; Baumer et al. (2017) Neurology. 89(21):2212; Dilena et al. (2018) Neurotherapeutics. 15(4):1112-1126). These mutations are gain-of-function, missense mutations that are dominant (i.e. present on only one allele) and result in change in function of the encoded potassium channel that causes a marked increase in whole cell current when tested in *Xenopus* oocyte or mammalian expression systems (see e.g. Milligan et al. (2015) Ann Neurol. 75(4): 581-590; Barcia et al. (2012) Nat Genet. 44(11): 1255-1259; and Mikati et al. (2015) Ann Neurol. 78(6): 995-999).

ADNFLE has a later onset than EIMFS, generally in mid-childhood, and is generally a less severe condition. It is characterized by nocturnal frontal lobe seizures and can result in psychiatric, behavioural and cognitive disabilities in patients with the condition. While ADNFLE is associated with genes encoding several neuronal nicotinic acetylcholine receptor subunits, mutations in the KCNT1 gene have been implicated in more severe cases of the disease (Heron et al. (2012) Nat Genet. 44: 1188-1190). Functional studies of the mutated KCNT1 genes associated with ADNFLE indicated that the underlying mutations (M896I, R398Q, Y796H and R928C) were dominant, gain-of-function mutations (Milligan et al. (2015) Ann Neurol. 75(4): 581-590; Mikati et al. (2015) Ann Neurol. 78(6): 995-999).

West syndrome is a severe form of epilepsy composed of a triad of infantile spasms, an interictal electroencephalogram (EEG) pattern termed hypsarrhythmia, and mental retardation, although a diagnosis can be made one of these elements is missing. Mutations in KCNT1, including G652V and R474H, have been associated with West syndrome (Fukuoka et al. (2017) Brain Dev 39:80-83 and Ohba et al. (2015) Epilepsia 56:e121-e128). Treatment targeting the KCNT1 channel suggests that these mutations are gain-of-function mutations (Fukuoka et al. (2017) Brain Dev 39:80-83).

In one aspect, the present invention features a method of treating treat a disease or condition associated with excessive neuronal excitability and/or a gain-of-function mutation in a gene such as KCNT1 (for example, epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy (DEE), and Lennox Gastaut syndrome, seizures, leukodystrophy, leukoencephalopathy, intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritis, ataxia and cerebellar ataxias, psychiatric disorders (e.g. major depression, anxiety, bipolar disorder, schizophrenia), learning disorders, Fragile X, neuronal plasticity, and autism spectrum disorders) comprising administering to a subject in need thereof a compound disclosed herein (e.g., a compound of Formula (I), (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof) or a pharmaceutical composition disclosed herein (e.g., a pharmaceutical composition comprising a compound disclosed herein (e.g., a compound of Formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof), and a pharmaceutically acceptable excipient).

In some examples, the subject presenting with a disease or condition that may be associated with a gain-of-function mutation in KCNT1 is genotyped to confirm the presence of a known gain-of-function mutation in KCNT1 prior to administration of the compounds and compositions thereof. For example, whole exome sequencing can be performed on the subject. Gain-of-function mutations associated with EIMFS may include, but are not limited to, V271F, G288S, R428Q, R474Q, R474H, R474C, I760M, A934T, P924L, G243S, H257D, A259D, R262Q, Q270E, L274I, F346L, $C_{377}S$, R398Q, P409S, A477T, F502V, M516V, Q550del, K629E, K629N, I760F, E893K, M896K, R933G, R950Q, and K1154Q. Gain-of-function mutations associated with ADNFLE may include, but are not limited to, M896I, R398Q, Y796H, R928C, and G288S. Gain-of-function mutations associated with West syndrome may include, but are not limited to, G652V and R474H. Gain-of-function mutations associated with temporal lobe epilepsy may include, but are not limited to, R133H and R565H. Gain-of-function mutations associated with Lennox-Gastaut may include, but are not limited to, R209C. Gain-of-function mutations associated with seizures may include, but are not limited to, A259D, G288S, R474C, R474H. Gain-of-function mutations associated with leukodystrophy may include, but are not limited to, G288S and Q906H. Gain-of-function mutations associated with Multifocal Epilepsy may include, but are not limited to, V340M. Gain-of-function mutations associated with EOE may include, but are not limited to, F346L and A934T. Gain-of-function mutations associated with Early-onset epileptic encephalopathies (EOEE) may include, but are not limited to, R428Q. Gain-of-function mutations associated with developmental and epileptic encephalopathies may include, but are not limited to, F346L, R474H, and A934T. Gain-of-function mutations associated with epileptic encephalopathies may include, but are not limited to, L437F, Y796H, P924L, R961H. Gain-of-function mutations associated with Early Infantile Epileptic Encephalopathy (EIEE) may include, but are not limited to, M896K. Gain-of-function mutations associated with drug resistant epilepsy and generalized tonic-clonic seizure may include, but are not limited to, F346L. Gain-of-function mutations associated with migrating partial seizures of infancy may include, but are not limited to, R428Q. Gain-of-function mutations associated with Leukoencephalopathy may include, but are not limited to, F932I. Gain-of-function mutations associated with NFLE may include, but are not limited to, A934T and R950Q. Gain-of-function mutations associated with Ohtahara syndrome may include, but are not limited to, A966T. Gain-of-function mutations associated with infantile spasms may include, but are not limited to, P924L. Gain-of-function mutations associated with Brugada Syndrome may include, but are not limited to, R1106Q. Gain-of-function mutations associated with Brugada Syndrome may include, but are not limited to, R474H.

In other examples, the subject is first genotyped to identify the presence of a mutation in KCNT1 and this mutation is then confirmed to be a gain-of-function mutation using standard in vitro assays, such as those described in Milligan et al. (2015) Ann Neurol. 75(4): 581-590. Typically, the presence of a gain-of-function mutation is confirmed when the expression of the mutated KCNT1 allele results an increase in whole cell current compared to the whole cell current resulting from expression of wild-type KCNT1 as assessed using whole-cell electrophysiology (such as described in Milligan et al. (2015) Ann Neurol. 75(4): 581-590; Barcia et al. (2012) Nat Genet. 44(11): 1255-1259; Mikati et al. (2015) Ann Neurol. 78(6): 995-999; or Rizzo et al. Mol Cell Neurosci. (2016) 72:54-63). This increase of whole cell current can be, for example, an increase of at least or about 50%, 100%, 150%, 200%, 250%, 300%, 350%, 400% or more. The subject can then be confirmed to have a disease or condition associated with a gain-of-function mutation in KCNT1.

In particular examples, the subject is confirmed as having a KCNT1 allele containing a gain-of-function mutation (e.g. V271F, G288S, R398Q, R428Q, R474Q, R474H, R474C, G652V, I760M, Y796H, M896I, P924L, R928C or A934T).

The compounds disclosed herein (e.g., a compound of Formula (I), (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II-j), (II-k) or a pharmaceutically acceptable salt thereof) or the pharmaceutical composition disclosed herein (e.g., a pharmaceutical composition comprising a compound disclosed herein (e.g., a compound of Formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof), and a pharmaceutically acceptable excipient) can also be used therapeutically for conditions associated with excessive neuronal excitability where the excessive neuronal excitability is not necessarily the result of a gain-of-function mutation in KCNT1. Even in instances where the disease is not the result of increased KCNT1 expression and/or activity, inhibition of KCNT1 expression and/or activity can nonetheless result in a reduction in neuronal excitability, thereby providing a therapeutic effect. Thus, the compounds disclosed herein (e.g., a compound of Formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof) or the pharmaceutical composition disclosed herein (e.g., a pharmaceutical composition comprising a compound disclosed herein (e.g., a compound of Formula (I), (e.g., (I-I), (I-II), (I-a), (I-b), (I-c), (I-d), (I-e), (I-f), (I-g), (I-h), (I-i), (I j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) or a pharmaceutically acceptable salt thereof), and a pharmaceutically acceptable excipient) can be used to treat a subject with conditions associated with excessive neuronal excitability, for example, epilepsy and other encephalopathies (e.g., epilepsy of infancy with migrating focal seizures (EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures) or cardiac dysfunctions (e.g., cardiac arrhythmia, Brugada syndrome, myocardial infarction), regardless of whether or not the disease or disorder is associated with a gain-of-function mutation in KCNT1.

Pharmaceutical Compositions and Routes of Administration

Compounds provided in accordance with the present invention, e.g., a compound of formula ((I), (e.g., (I-I), (I-II), (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), or (I-s)), (II), (e.g., (II-a), (II-b), (II-c), (II-d), (II-e), (II-f), (II-g), (II-h), (II-i), (II-j), (II-k), (II-l), (II-m), (II-n), (II-o), (II-p), (II-q), (II-r), (II-k1), or (II-k2)), (III), (IV), (V), (VI), (e.g., (VI-a)), or (VII), (e.g., (VII-a) or (VII-b)) are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprising a disclosed compound, or pharmaceutically acceptable salt thereof, and a pharmaceutically acceptable carrier.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

LIST OF ABBREVIATIONS

TEA triethylamine
NaH sodium hydride
THF tetrahydrofuran
DMF N,N-dimethylformamide
DCM dichloromethane
EtOH ethanol
ACN acetonitrile
MeCN acetonitrile
$CH_3CN$ acetonitrile
MeONa sodium methoxide
CbzCl benzyl chloroformate
MSCl methanesulfonyl chloride
AcOH acetic acid
TFA trifluoroacetic acid
TFAA trifluoroacetic anhydride
Py pyridine
MeI methyl iodide
LiOH lithium hydroxide
$MeNH_2$ methylamine
$Cu(OAc)_2$ copper(II)acetate
DCC N,N'-dicyclohexylcarbodiimide
DCE dichloroethane
i-PrOH isopropyl alcohol
EtOAc ethyl acetate
HOBt hydroxybenzotriazole
HATU hexafluorophosphate azabenzotriazole tetramethyl uranium
DEA diethanolamine
$MeNHNH_2$ methylhydrazine
EtONa sodium ethoxide
SFC supercritical fluid chemistry
DIPEA N,N-diisopropylethylamine
EDCI 1-ethyl-3-(3-dimethylaminopropyl)carbodiimide
Boc tert-butyloxycarbonyl
DMSO dimethylsulfoxide
Boc-L-Ala-OH N-(tert-butoxycarbonyl)-L-alanine
IPA isopropyl alcohol
$Ac_2O$ acetic anhydride
PTFE polytetrafluoroethylene Pd(dppf)$Cl_2$ [1,1'-bis(diphenylphosphino)ferrocene]dichloropalladium(II)
DMS dimethyl sulphate
$T_3P$ propylphosphonic anhydride solution
PE petroleum ether
LCMS liquid chromatography-mass spectrometry Example 1. Synthesis of 192 and 191 a) Synthesis of 191

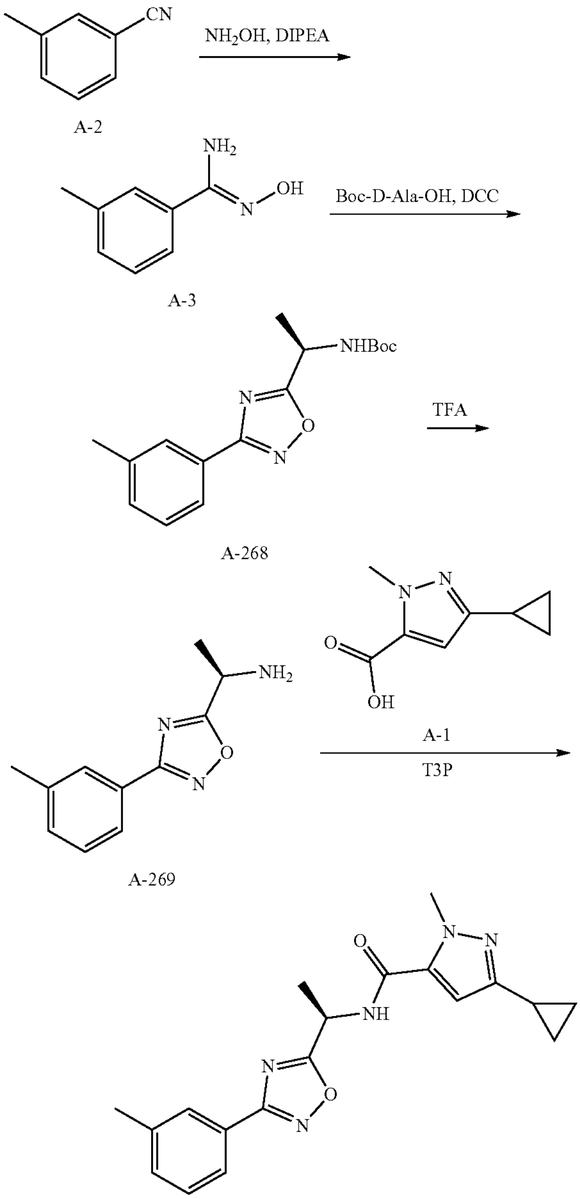

A-2

A-3

A-268

A-269

191

Synthesis of N'-hydroxy-3-methylbenzimidamide (A-3)

To a solution of 3-methylbenzonitrile (10 g, 85.36 mmol) in ethanol (200 mL) was added hydroxylamine hydrochloride (17.8 g, 256 mmol) and DIPEA (8.63 mL, 85.36 mmol). The reaction mixture was heated at 70° C. for 16 h. The reaction mixture was cooled to room temperature and concentrated. The mixture was treated with water (100 mL) and extracted with EtOAc (2×100 mL). The organic layer was washed with brine (50 mL), dried over anhydrous $Na_2SO_4$ and concentrated to afford compound A-3 (9.3 g).

Synthesis of tert-butyl (R)-(1-(3-(m-tolyl)-1,2,4-oxadiazol-5-yl)ethyl)carbamate (A-268)

To a solution of compound A-3 (2.0 g, 13.32 mmol) in 1,4-dioxane (60 mL) was added (2R)-2-(tert-butoxycarbonylamino)propanoic acid (2.52 g, 13.32 mmol) and DCC (3.02 g, 14.65 mmol). The reaction mixture heated at 100° C. for 16 h. The reaction mixture was cooled to room temperature and concentrated. The mixture was treated with water (30 mL) and extracted with EtOAc (2×40 mL). The organic layer was washed with brine (20 mL), dried over anhydrous $Na_2SO_4$ and concentrated. The crude was purified by column chromatography on silica gel with 10% EtOAc/PE to afford compound A-268 (1.1 g, 3.8 mmol, 28% yield). LCMS: 302.1 (M−H), Rt 2.57 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (R)-1-(3-(m-tolyl)-1,2,4-oxadiazol-5-yl)ethan-1-amine (A-269)

To a stirred solution of compound A-268 (500 mg, 1.65 mmol) in DCM (2.5 mL) was added TFA (1.5 mL) at 0° C. The reaction mixture was slowly warmed to room temperature and stirred for 8 h. The reaction mixture was concentrated and treated with saturated $NaHCO_3$ solution (10 mL). The mixture was extracted with EtOAc (2×20 mL) and washed with brine (20 mL). The organic layer was dried over anhydrous $Na_2SO_4$ and concentrated to afford compound A-269 (188 mg). The compound was used for the next step without further purification.

Synthesis of (R)-3-cyclopropyl-1-methyl-N-(1-(3-(m-tolyl)-1,2,4-oxadiazol-5-yl)ethyl)-1H-pyrazole-5-carboxamide (191)

To a stirred solution of compound A-269 (188 mg, 0.92 mmol) in THF (5.0 mL) was added 3-cyclopropyl-1-methyl-1H-pyrazole-5-carboxylic acid (179 mg, 1.08 mmol) followed by T3P (1.17 mL, 1.97 mmol) and TEA (0.41 mL, 2.95 mmol). The reaction mixture was stirred at room temperature for 16 h. The reaction mixture was treated with water (20 mL) and extracted with EtOAc (2×20 mL). The organic layer was washed with brine (20 mL), dried over anhydrous $Na_2SO_4$ and concentrated. The crude was purified by column chromatography on silica gel with 30% EtOAc/PE to afford 191 (105 mg, 0.29 mmol, 30% yield) as a solid. HPLC: Rt 4.71 min, 99.2%; Column: XBridge C8 (50×4.6) mm, 3.5 μm; Mobile phase: A: 0.1% TFA in water, B: 0.1% TFA in ACN; Flow Rate: 2.0 mL/min. LCMS: 352.1 (M+H), Rt 2.36 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.79 min, SFC column: LUX A1; mobile phase: 60:40 (A:B), A=liquid $CO_2$, B=0.5% isopropyl amine in methanol; flow rate: 4.0 mL/min; wave length: 210 nm. $^1H$ NMR (400 MHz, $CDCl_3$): δ 7.91-7.88 (m, 2H), 7.42-7.34 (m, 2H), 6.59

(d, 1H), 6.32 (s, 1H), 5.64-5.57 (m, 1H), 4.12 (s, 3H), 2.45 (s, 3H), 1.97-1.92 (m, 1H), 1.75 (d, 3H), 0.99-0.94 (m, 2H), 0.78-0.74 (m, 2H).

b) Synthesis of 192

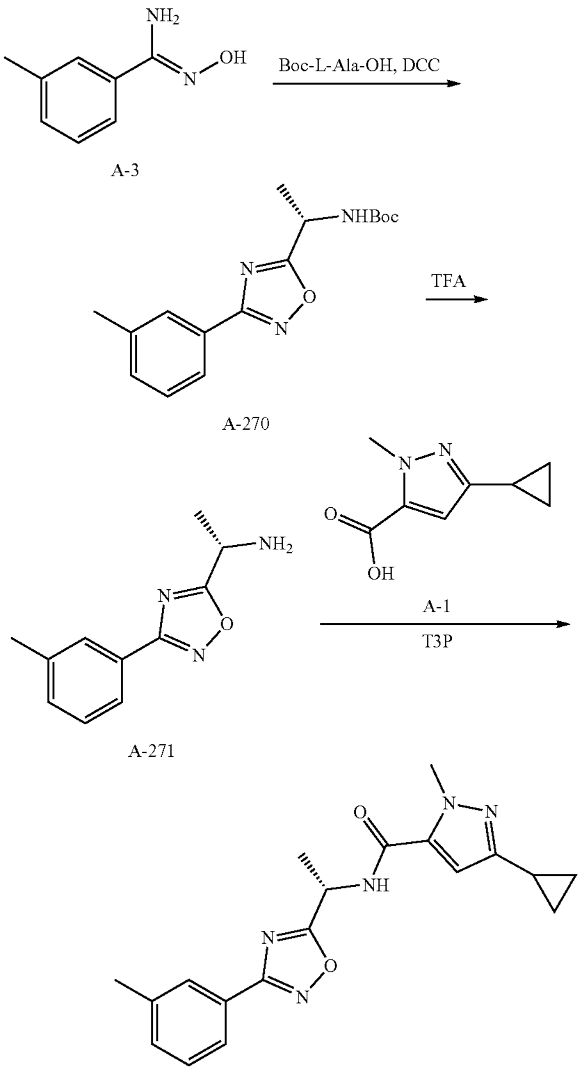

A-3, A-270, A-271, 192

Synthesis of tert-butyl (S)-(1-(3-(m-tolyl)-1,2,4-oxadiazol-5-yl)ethyl)carbamate (A-270)

To a solution of compound A-3 (1.0 g, 6.66 mmol) in 1,4-dioxane (60 mL) was added (2S)-2-(tert-butoxycarbonylamino)propanoic acid (1.37 g, 7.22 mmol) and DCC (1.51 g, 7.32 mmol). The reaction mixture was heated at 100° C. for 16 h. The reaction mixture was cooled to room temperature and concentrated. The mixture was treated with water (20 mL) and extracted with EtOAc (2×30 mL). The organic layer was washed with brine (20 mL), dried over anhydrous $Na_2SO_4$ and concentrated. The crude was purified by column chromatography on silica gel with 10% EtOAc/PE to afford compound A-270 (0.80 g, 2.62 mmol, 39% yield).

LCMS: 302.1 (M−H), Rt 2.56 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, DMSO-$d_6$): δ 7.82-7.78 (m, 2H), 7.47-7.40 (m, 2H), 5.00-4.93 (m, 1H), 2.40 (s, 3H), 1.51 (d, 3H), 1.40 (s, 9H).

Synthesis of (S)-1-(3-(m-tolyl)-1,2,4-oxadiazol-5-yl)ethan-1-amine (A-271)

To a stirred solution of compound A-270 (400 mg, 1.32 mmol) in DCM (2.4 mL) was added TFA (2.1 mL) at 0° C. The reaction mixture was slowly warmed to room temperature and stirred for 8 h. The reaction mixture was concentrated and treated with saturated $NaHCO_3$ solution (10 mL). The mixture was extracted with EtOAc (2×20 mL) and washed with brine (20 mL). The organic layer was dried over anhydrous $Na_2SO_4$ and concentrated to afford compound A-271 (200 mg). The compound was used for the next step without further purification.

Synthesis of (S)-3-cyclopropyl-1-methyl-N-(1-(3-(m-tolyl)-1,2,4-oxadiazol-5-yl)ethyl)-1H-pyrazole-5-carboxamide (192)

To a stirred solution of A-271 (200 mg, 0.98 mmol) in THF (10.0 mL) was added 3-cyclopropyl-1-methyl-1H-pyrazole-5-carboxylic acid (179 mg, 1.08 mmol) followed by T3P (1.17 mL, 1.97 mmol) and TEA (0.41 mL, 20.52 mmol). The reaction mixture was stirred at room temperature for 16 h. The reaction mixture was treated with water (20 mL) and extracted with EtOAc (2×20 mL). The organic layer was washed with brine (20 mL), dried over anhydrous $Na_2SO_4$ and concentrated. The crude was purified by column chromatography on silica gel with 30% EtOAc/PE to afford 192 (80 mg, 0.22 mmol, 23% yield) as a solid. HPLC: Rt 4.68 min, 99.7%; Column: XBridge C8 (50×4.6) mm, 3.5 μm; Mobile phase: A: 0.1% TFA in water, B: 0.1% TFA in ACN; Flow Rate: 2.0 mL/min. LCMS: 352.3 (M+H), Rt 2.37 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.56 min, SFC column: LUX A1; mobile phase: 60:40 (A:B), A=liquid $CO_2$, B=0.5% isopropyl amine in methanol; flow rate: 4.0 mL/min; wave length: 210 nm. $^1H$ NMR (400 MHz, $CDCl_3$): δ 7.91-7.88 (m, 2H), 7.42-7.34 (m, 2H), 6.58 (d, 1H), 6.32 (s, 1H), 5.62-5.58 (m, 1H), 4.12 (s, 3H), 2.45 (s, 3H), 1.97-1.93 (m, 1H), 1.75 (d, 3H), 0.99-0.94 (m, 2H), 0.78-0.74 (m, 2H).

Example 2. Synthesis of 3 and 4

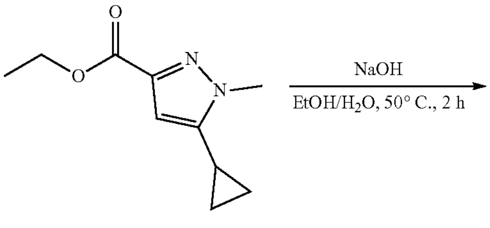

A-4

-continued

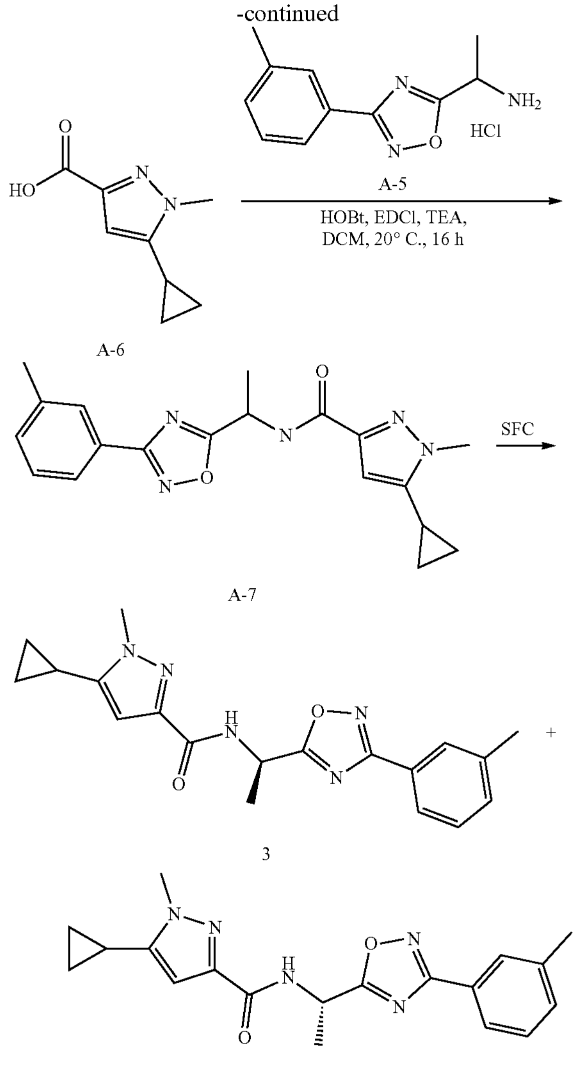

A-6:

A mixture of ethyl 5-cyclopropyl-1-methyl-pyrazole-3-carboxylate (1.4 g, 7.21 mmol) and NaOH (576.64 mg, 14.42 mmol) in ethanol (20 mL) and water (10 mL) was stirred at 50° C. for 2 hours. After cooling to room temperature, the reaction mixture was concentrated. Then the residue was diluted with $H_2O$ (20 mL) and acidified with HCl (1M) to pH~6, and the mixture was extracted with EtOAc (50 mL×2). The combined organic phase was washed with brine (30 mL), dried over $Na_2SO_4$, filtered and concentrated to give the crude product (2000 mg) as a solid. LCMS $R_t$=0.46 min in 1.5 min chromatography, 5-95AB, MS ESI calcd. for $C_8H_{11}N_2O_2$ $[M+H]^+$ 167.1, found 167.0.

A-7:

A mixture of 5-cyclopropyl-1-methyl-pyrazole-3-carboxylic acid (300 mg, 1.81 mmol), 1-[3-(m-tolyl)-1,2,4-oxadiazol-5-yl]ethanamine hydrochloride (432.72 mg, 1.81 mmol), TEA (913.38 mg, 9.03 mmol), EDCI (1038.21 mg, 5.42 mmol) and HOBt (731.84 mg, 5.42 mmol) in DCM (20 mL) was stirred at 20° C. for 16 hours. The reaction was quenched with the addition of sat. $NH4C_1$ (30 mL), and the mixture was extracted with DCM (20 mL×2). The combined organic phase was washed with brine (10 mL), dried over $Na_2SO_4$, filtered and concentrated to give the crude product.

The crude product was purified by prep-HPLC (Boston Prime C18 (150×30 mm, 5 μm), A=$H_2O$ (0.05% $NH_4OH$) and B=$CH_3CN$; 55-85% B over 7 min) to give the product (300 mg, 0.85 mmol, 47% yield) as a solid. LCMS $R_t$=1.11 min in 2.0 min chromatography, 5-95AB, MS ESI calcd. for $C_{19}H_{22}N_5O_2$ $[M+H]^+$ 352.2, found 352.1.

3 & 4:

Analytical SFC (Daicel CHIRALPAK AD-3 (50 mm×3 mm, 3 μm), mobile phase: A: $CO_2$ B: ethanol (0.05% DEA), gradient: from 5% to 40% of B in 2.5 min and hold 40% for 0.35 min, then from 40% to 5% of B for 0.15 min, flow rate: 2.5 mL/min, column temp: 35° C.) showed two peaks at 1.37 min and 1.61 min. The product was purified by SFC (Daicel CHIRALPAK AD-3 (50 mm×3 mm, 5 μm); A=$CO_2$ and B=EtOH (0.1% $NH_3H_2O$); 38° C.; 60 mL/min; 25% B; 12 min run; 7 injections, Rt of peak 1=5.74 min, Rt of peak 2=10.1 min) to give the enantiomer 1, randomly assigned as 3 (73.33 mg, 0.21 mmol, 24% yield) (Rt=1.37 min in analytical SFC) as a solid and enantiomer 2, randomly assigned as 4 (77.03 mg, 0.22 mmol, 26% yield) (Rt=1.61 min in analytical SFC) as a solid.

3:

$^1H$ NMR (400 MHz, $CDCl_3$) $\delta_H$=7.95-7.83 (m, 2H), 7.43-7.29 (m, 3H), 6.41 (s, 1H), 5.71-5.60 (m, 1H), 3.94 (s, 3H), 2.43 (s, 3H), 1.78-1.67 (m, 4H), 1.07-0.96 (m, 2H), 0.75-0.65 (m, 2H). LCMS $R_t$=1.14 min in 2.0 min chromatography, 10-80AB, MS ESI calcd. for $C_{19}H_{22}N_5O_2$ $[M+H]^+$ 352.2, found 352.1.

4:

$^1H$ NMR (400 MHz, $CDCl_3$) $\delta_H$=7.94-7.84 (m, 2H), 7.44-7.29 (m, 3H), 6.41 (s, 1H), 5.73-5.59 (m, 1H), 3.94 (s, 3H), 2.43 (s, 3H), 1.79-1.67 (m, 4H), 1.07-0.97 (m, 2H), 0.74-0.66 (m, 2H). LCMS $R_t$=1.12 min in 2.0 min chromatography, 10-80AB, MS ESI calcd. for $C_{19}H_{22}N_5O_2$ $[M+H]^+$ 352.2, found 352.1.

Example 3. Synthesis of 5

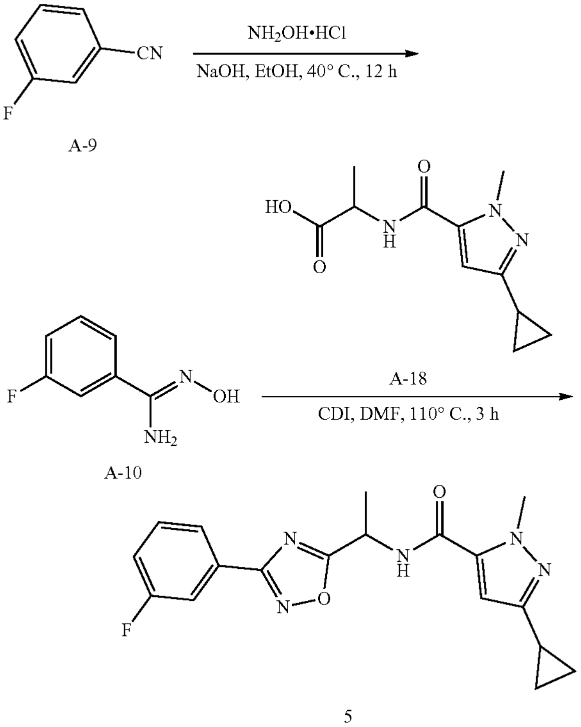

A-10:

A mixture of 3-fluorobenzonitrile (500 mg, 4.13 mmol), hydroxylamine hydrochloride (860.66 mg, 12.39 mmol) and NaOH (495.42 mg, 12.39 mmol) in ethanol (6 mL) and water (2 mL) was stirred at 40° C. for 12 hours to give a mixture. After cooling to room temperature, the reaction mixture was concentrated to remove most of EtOH, then diluted with $H_2O$ (20 mL). The mixture was extracted with EtOAc (30 mL×2). The combined organic phase was washed with brine (30 mL), dried over $Na_2SO_4$, filtered and concentrated to give the crude product (600 mg) as a solid. LCMS $R_t$=0.46 min in 1.5 min chromatography, 5-95AB, MS ESI calcd. for $C_7H_8FN_2O$ $[M+H]^+$ 155.1, found 154.8.

5:

A mixture of 2-[(5-cyclopropyl-2-methyl-pyrazole-3-carbonyl)amino]propanoic acid (170 mg, 0.72 mmol) and CDI (127.8 mg, 0.79 mmol) in DMF (3 mL) was stirred at 15° C. for 1 hour and then 3-fluoro-N'-hydroxy-benzamidine (110.44 mg, 0.72 mmol) was added. The reaction mixture was then stirred at 110° C. for 2 hours. After cooling to room temperature, the mixture was diluted with water (20 mL) and extracted with EtOAc (30 mL×2). The combined organic phase was washed with brine (20 mL), dried over $Na_2SO_4$, filtered and concentrated to give the crude product. The crude product was purified by Prep-HPLC (Boston Prime C18 (150 mm×30 mm, 5 μm), A=water (0.05% $NH_4OH$) and B=$CH_3CN$; 49-79% B over 8 min) to give the product (23.03 mg, 64.8 μmol, 9% yield) as a solid. $^1H$ NMR (400 MHz, $CDCl_3$) $\delta_H$=7.88 (dd, 1H), 7.81-7.76 (m, 1H), 7.52-7.46 (m, 1H), 7.26-7.19 (m, 1H), 6.52 (d, 1H), 6.31 (s, 1H), 5.64-5.54 (m, 1H), 4.10 (s, 3H), 1.98-1.87 (m, 1H), 1.75 (d, 3H), 1.00-0.91 (m, 2H), 0.78-0.72 (m, 2H). LCMS $R_t$=1.26 min in 2.0 min chromatography, 10-80AB, MS ESI calcd. for $C_{18}H_{19}FN_5O_2$ $[M+H]^+$ 356.1, found 356.0.

Example 4. Synthesis of 6

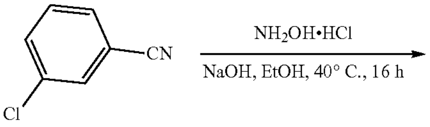

A-11

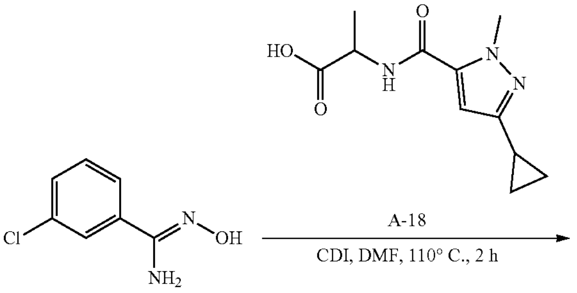

A-12

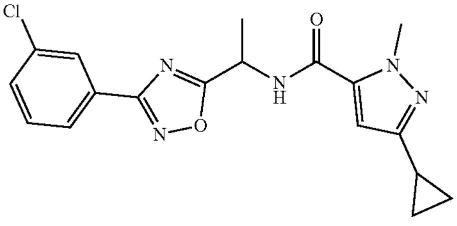

6

A-12:

A mixture of 3-chlorobenzonitrile (500 mg, 3.63 mmol), hydroxylamine hydrochloride (757.69 mg, 10.9 mmol) and NaOH (436.14 mg, 10.9 mmol) in ethanol (6 mL) and water (2 mL) was stirred at 40° C. for 16 hours. After cooling to room temperature, the reaction mixture was concentrated to remove most of EtOH, then diluted with $H_2O$ (20 mL). The mixture was extracted with EtOAc (30 mL×2). The combined organic phase was washed with brine (30 mL), dried over $Na_2SO_4$, filtered and concentrated to give the crude. The crude product was purified by silica gel column (EtOAc in PE=0% to 60%) to give the product (70 mg, 410.3 μmol, 11% yield) as a solid. LCMS $R_t$=0.15 min in 1.5 min chromatography, 5-95AB, MS ESI calcd. for $C_7H_8ClN_2O$ $[M+H]^+$ 171.0, found 170.9.

6:

A mixture of 2-[(5-cyclopropyl-2-methyl-pyrazole-3-carbonyl)amino]propanoic acid (105 mg, 0.44 mmol) and CDI (78.94 mg, 0.49 mmol) in DMF (3 mL) was stirred at 15° C. for 1 hour and then 3-chloro-N'-hydroxy-benzamidine (67.95 mg, 0.40 mmol) was added. The reaction mixture was stirred at 110° C. for 2 hours. After cooling to room temperature, the mixture was diluted with water (20 mL), extracted with EtOAc (30 mL×2). The combined organic phase was washed with brine (20 mL), dried over $Na_2SO_4$, filtered. The filtrate was concentrated to give the crude product. The crude product was purified by prep-HPLC (Waters Xbridge (150 mm×25 mm, 5 μm), A=$H_2O$ (0.05% $NH_4OH$) and B=$CH_3CN$; 53-83% B over 8 min) to give the product (21.27 mg, 56.9 μmol, 13% yield) as a solid. $^1H$ NMR (400 MHz, $CDCl_3$) $\delta_H$=8.09 (t, 1H), 8.05-7.92 (m, 1H), 7.53-7.48 (m, 1H), 7.47-7.41 (m, 1H), 6.51 (d, 1H), 6.31 (s, 1H), 5.63-5.52 (m, 1H), 4.10 (s, 3H), 1.98-1.89 (m, 1H), 1.75 (d, 3H), 0.99-0.92 (m, 2H), 0.78-0.71 (m, 2H). LCMS $R_t$=1.31 min in 2.0 min chromatography, 10-80AB, MS ESI calcd. for $C_{18}H_{19}ClN_5O_2$ $[M+H]^+$ 372.1, found 372.0.

Example 5. Synthesis of 7

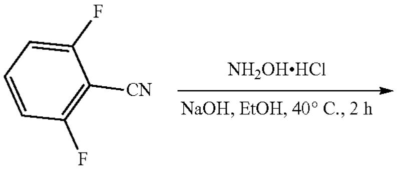

A-13

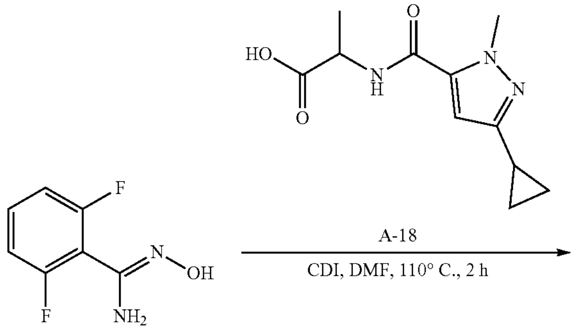

A-14

-continued

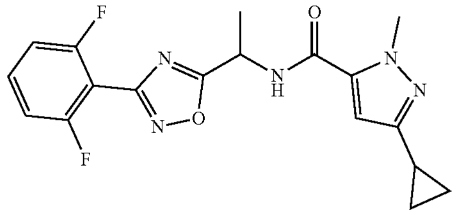

7

A-14:

A mixture of 2,6-difluorobenzonitrile (500 mg, 3.59 mmol), hydroxylamine hydrochloride (749.35 mg, 10.78 mmol) and NaOH (431.34 mg, 10.78 mmol) in ethanol (6 mL) and water (2 mL) was stirred at 40° C. for 2 hours. After cooling to room temperature, the reaction mixture was concentrated to remove most of EtOH and then diluted with $H_2O$ (20 mL). The mixture was extracted with EtOAc (30 mL×2). The combined organic phase was washed with brine (30 mL), dried over $Na_2SO_4$, filtered and concentrated to give the crude product (600 mg) as a solid. LCMS $R_t$=0.26 min in 1.5 min chromatography, 5-95AB, MS ESI calcd. for $C_7H_7F_2N_2O$ $[M+H]^+$ 173.0, found 172.8

7:

A mixture of 2-[(5-cyclopropyl-2-methyl-pyrazole-3-carbonyl)amino]propanoic acid (150 mg, 0.63 mmol) and CDI (112.77 mg, 0.70 mmol) in DMF (3 mL) was stirred at 15° C. for 1 hour and then 2,6-difluoro-N'-hydroxy-benzamidine (119.71 mg, 0.70 mmol) was added. The reaction was then stirred at 110° C. for 2 hours. After cooling to room temperature, the mixture was diluted with water (20 mL) and extracted with EtOAc (30 mL×2). The combined organic phase was washed with brine (20 mL), dried over $Na_2SO_4$, filtered. The filtrate was concentrated to give the crude product. The crude product was purified by prep-HPLC (Waters Xbridge (150 mm×25 mm, 5 μm), A=$H_2O$ (0.05% $NH_4OH$ v/v) and B=$CH_3CN$; 41-71% B over 8 min) to give the product (52.31 mg, 140.1 μmol, 22% yield) as a solid. $^1H$ NMR (400 MHz, $CDCl_3$) $\delta_H$=7.55-7.45 (m, 1H), 7.07 (t, 2H), 6.60 (d, 1H), 6.27 (s, 1H), 5.69-5.60 (m, 1H), 4.09 (s, 3H), 1.96-1.86 (m, 1H), 1.76 (d, 3H), 0.96-0.88 (m, 2H), 0.74-0.66 (m, 2H). LCMS $R_t$=1.12 min in 2.0 min chromatography, 10-80AB, MS ESI calcd. for $C_{18}H_{18}F_2N50$ $[M+H]^+$ 374.1, found 374.0.

Example 6. Synthesis of 8

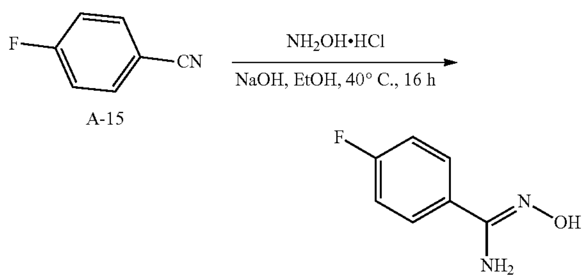

A-15

A-16

-continued

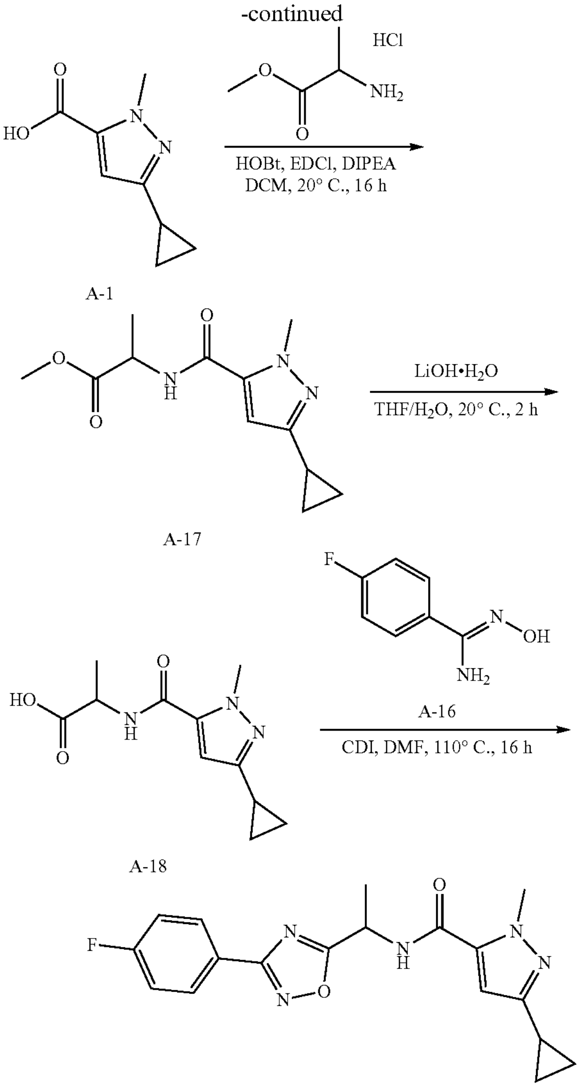

A-1

A-17

A-16

A-18

8

A-16:

A mixture of 4-fluorobenzonitrile (500 mg, 4.13 mmol), hydroxylamine hydrochloride (860.66 mg, 12.39 mmol) and NaOH (495.42 mg, 12.39 mmol) in ethanol (6 mL) and water (2 mL) was stirred at 40° C. for 16 hours. After cooling to room temperature, the reaction mixture was concentrated to remove most of EtOH, then diluted with $H_2O$ (15 mL). The mixture was extracted with EtOAc (20 mL×2). The combined organic phase was washed with brine (10 mL), dried over $Na_2SO_4$, filtered and concentrated to give the crude product (300 mg) as a solid. $^1H$ NMR (400 MHz, $CDCl_3$) $\delta_H$=8.70 (s, 1H), 7.74-7.56 (m, 2H), 7.19-6.98 (m, 2H), 4.88 (s, 2H).

A-17:

A mixture of 5-cyclopropyl-2-methyl-pyrazole-3-carboxylic acid (500 mg, 3.01 mmol), DIPEA (2.63 mL, 15.04 mmol), EDCI (865.18 mg, 4.51 mmol), HOBt (813.15 mg, 6.02 mmol) and methyl 2-aminopropanoate hydrochloride (419.97 mg, 3.01 mmol) in DCM (15 mL) was stirred 20° C. at for 16 hours. The reaction mixture was diluted with sat. $NH_4Cl$ (20 mL). The mixture was extracted with DCM (20 mL×2). The combined organic phase was washed with brine (10 mL), dried over $Na_2SO_4$, filtered and concentrated to give the crude product (500 mg) as an oil. LCMS $R_t$=0.72 min in 1.5 min chromatography, 5-95AB, MS ESI calcd. for $C_{12}H_{18}N_3O_3$ $[M+H]^+$ 252.1, found 252.0.

A-18:

To a solution of methyl 2-[(5-cyclopropyl-2-methyl-pyrazole-3-carbonyl)amino]propanoate (500 mg, 1.99 mmol) in THF (4 mL) was slowly added a solution of $LiOH.H_2O$ (166.99 mg, 3.98 mmol) in water (4 mL). The resulting mixture was stirred at 20° C. for 2 hours. The mixture was concentrated to remove THF. To the residue was added 1N HCl to adjust the pH=2, and the mixture was extracted with EtOAc (20 mL×2). The combined organic phase was washed with brine (10 mL), dried over $Na_2SO_4$, filtered and concentrated to give the crude product (350 mg) as oil. LCMS $R_t$=0.67 min in 1.5 min chromatography, 5-95AB, MS ESI calcd. for $C_{11}H_{16}N_3O_3$ $[M+H]^+$ 238.1, found 238.0.

8:

A mixture of 2-[(5-cyclopropyl-2-methyl-pyrazole-3-carbonyl)amino]propanoic acid (150 mg, 0.63 mmol) and CDI (112.77 mg, 0.70 mmol) in DMF (10 mL) was stirred at 15° C. for 1 hour and then 4-fluoro-N'-hydroxy-benzamidine (97.45 mg, 0.63 mmol) was added. The reaction mixture was then stirred at 110° C. for 16 hours. After cooling to room temperature, the mixture was diluted with $H_2O$ (20 mL) and the mixture was extracted with EtOAc (20 mL×2). The combined organic phase was washed with brine (10 mL), dried over $Na_2SO_4$, filtered and concentrated to give the crude product. The crude product was purified by prep-HPLC (Agela DuraShell (150 mm×25 mm, 5 μm), A=$H_2O$ (10 mM $NH_4HCO_3$) and B=$CH_3CN$; 40-80% B over 8.5 minutes) to give the product (40.74 mg, 114.60 μmol, 18% yield) as an oil. $^1H$ NMR (400 MHz, $CDCl_3$) $\delta_H$=8.15-8.00 (m, 2H), 7.23-7.13 (m, 2H), 6.53 (d, 1H), 6.30 (s, 1H), 5.65-5.51 (m, 1H), 4.10 (s, 3H), 1.98-1.87 (m, 1H), 1.74 (d, 3H), 1.03-0.88 (m, 2H), 0.81-0.68 (m, 2H). LCMS $R_t$=1.15 min in 2 min chromatography, 10-80AB, MS ESI calcd. for $C_{18}H_{19}FN_5O_2$ $[M+H]^+$ 356.1, found 356.0.

Example 7. Synthesis of 9

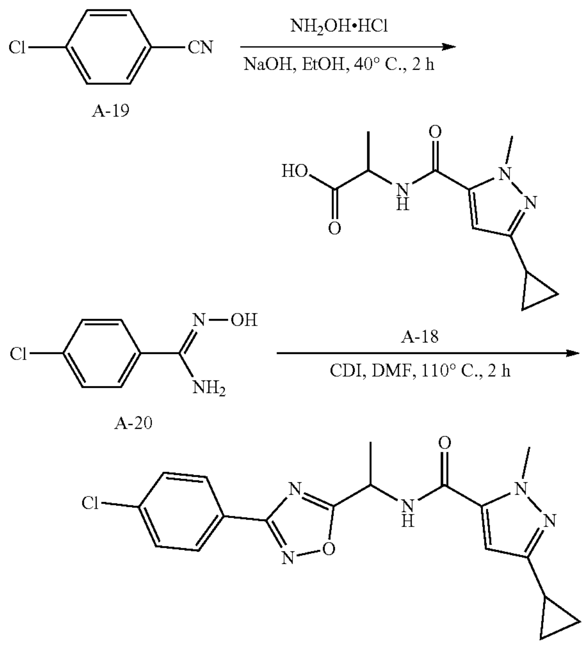

9

A-20:

A mixture of 4-chlorobenzonitrile (494.5 mg, 3.59 mmol), hydroxylamine hydrochloride (749.35 mg, 10.78 mmol) and NaOH (431.34 mg, 10.78 mmol) in ethanol (6 mL) and water (2 mL) was stirred at 40° C. for 2 hours. After cooling to room temperature, the reaction mixture was concentrated to remove most of EtOH, then diluted with $H_2O$ (20 mL). The mixture was extracted with EtOAc (30 mL×2). The combined organic phase was washed with brine (30 mL), dried over $Na_2SO_4$, filtered and concentrated to give the crude product (600 mg) as a solid. LCMS $R_t$=0.43 min in 1.5 min chromatography, 5-95AB, MS ESI calcd. for $C_7H_8ClN_2O$ $[M+H]^+$ 171.0, found 170.8.

9:

A mixture of 2-[(5-cyclopropyl-2-methyl-pyrazole-3-carbonyl)amino]propanoic acid (150 mg, 0.63 mmol) and CDI (112.77 mg, 0.70 mmol) in DMF (3 mL) was stirred at 15° C. for 1 hour and then 4-chloro-N'-hydroxy-benzamidine (118.64 mg, 0.70 mmol) was added. The reaction mixture was stirred at 110° C. for 2 hours. After cooling to room temperature, the mixture was diluted with water (20 mL), extracted with EtOAc (30 mL×2). The combined organic phase was washed with brine (20 mL), dried over $Na_2SO_4$ and filtered. The filtrate was concentrated to give the crude product. The crude product was purified by prep-HPLC (Waters)(Bridge (150 mm×25 mm, 5 μm), A=water (0.05% $NH_4OH$) and B=$CH_3CN$; 49-79% B over 8 min) to give the product (53.21 mg, 143.1 μmol, 23% yield) as a solid. $^1H$ NMR (400 MHz, $CDCl_3$) $\delta_H$=8.06-7.97 (m, 2H), 7.50-7.44 (m, 2H), 6.52 (d, 1H), 6.30 (s, 1H), 5.58 (quin, 1H), 4.09 (s, 3H), 1.98-1.60 (m, 1H), 1.74 (d, 3H), 1.00-0.91 (m, 2H), 0.78-0.70 (m, 2H). LCMS $R_t$=1.20 min in 2.0 min chromatography, 10-80AB, MS ESI calcd. for $C_{18}H_{19}ClN_5O_2$ $[M+H]^+$ 372.1, found 372.0.

Example 8. Synthesis of 10

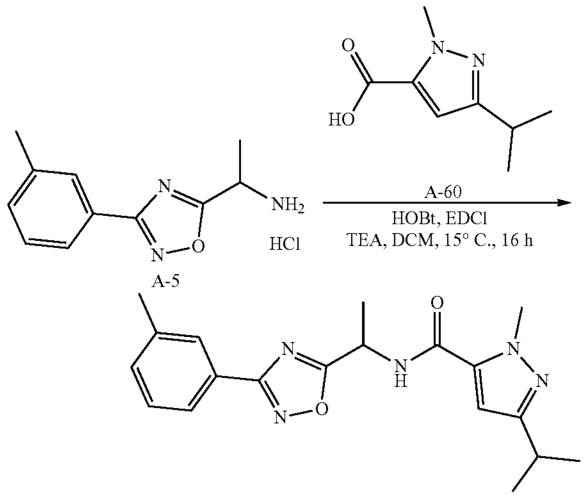

10

A mixture of 1-[3-(m-tolyl)-1,2,4-oxadiazol-5-yl]ethanamine hydrochloride (100 mg, 0.42 mmol), 5-isopropyl-2-methyl-pyrazole-3-carboxylic acid (70.17 mg, 0.42 mmol), HOBt (112.75 mg, 0.83 mmol), EDCI (119.96 mg, 0.63 mmol) and TEA (0.29 mL, 2.09 mmol) in DCM (20 mL) was stirred at 20° C. for 16 hours. The mixture was concentrated, diluted with $H_2O$ (10 mL) and then extracted with EtOAc (20 mL×2). The combined organic phase was washed with brine (10 mL), dried over $Na_2SO_4$, filtered and concentrated to give the crude product. The crude product was purified by prep-HPLC (Kromasil (150 mm×30 mm, 5 μm), A=$H_2O$ (0.05% $NH_4OH$) and B=$CH_3CN$; 55-85% B over 8 min) to give the product (44.51 mg, 0.13 mmol, 30% yield) as a solid. $^1H$ NMR (400 MHz, $CDCl_3$) $\delta_H$=7.92-7.84 (m, 2H), 7.42-7.30 (m, 2H), 6.63 (d, 1H), 6.46 (s, 1H), 5.66-5.56 (m, 1H), 4.12 (s, 3H), 3.05-2.94 (m, 1H), 2.43 (s, 3H), 1.75 (d, 3H), 1.28 (d, 6H). LCMS $R_t$=1.30 min in 2.0 min chromatography, 10-80AB, MS ESI calcd. for $C_{19}H_{24}N_5O_2$ [M+H]$^+$ 354.19, found 354.1.

Example 9. Synthesis of 11

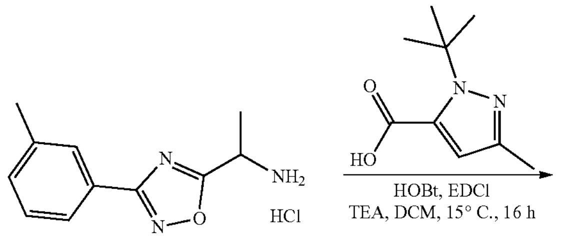

A-5

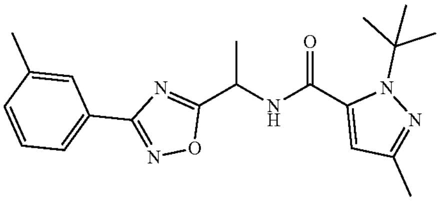

11

A mixture of 1-[3-(m-tolyl)-1,2,4-oxadiazol-5-yl] ethanamine hydrochloride (100 mg, 0.42 mmol), 2-tert-butyl-5-methyl-pyrazole-3-carboxylic acid (76.02 mg, 0.42 mmol), HOBt (112.75 mg, 0.83 mmol), EDCI (119.96 mg, 0.63 mmol) and TEA (0.29 mL, 2.09 mmol) in DCM (20 mL) was stirred at 20° C. for 16 hours. The mixture was concentrated, diluted with $H_2O$ (10 mL) and then extracted with EtOAc (20 mL×2). The combined organic phase was washed with brine (10 mL), dried over $Na_2SO_4$, filtered and concentrated to give the crude product. The crude product was purified by prep-HPLC (Kromasil (150 mm×30 mm, 5 μm), A=$H_2O$ (0.05% $NH_4OH$) and B=$CH_3CN$; 55-85% B over 8 min) to give the product (30.81 mg, 0.08 mmol, 20% yield) as a solid. $^1H$ NMR (400 MHz, $CDCl_3$) $\delta_H$=7.96-7.83 (m, 2H), 7.44 (d, 1H), 7.39-7.29 (m, 2H), 6.58 (s, 1H), 5.71-5.60 (m, 1H), 2.48 (s, 3H), 2.47 (s, 3H), 1.76 (d, 3H), 1.67 (s, 9H). LCMS $R_t$=1.36 min in 2.0 min chromatography, 10-80AB, MS ESI calcd. for $C_{20}H_{26}N_5O_2$ [M+H]$^+$ 368.20, found 368.2.

Example 10. Synthesis of 12

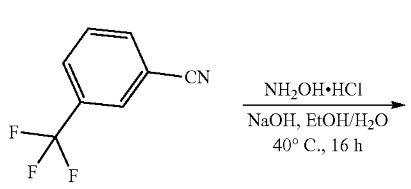

A-19b

-continued

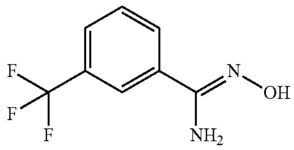

A-19c

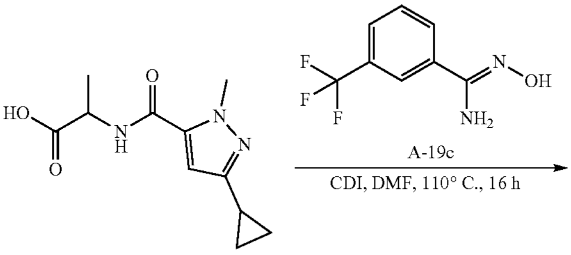

A-18

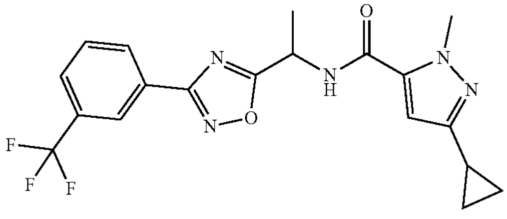

12

A-19c:

A mixture of 3-(trifluoromethyl)benzonitrile (500 mg, 2.92 mmol), hydroxylamine hydrochloride (609.13 mg, 8.77 mmol) and NaOH (350.63 mg, 8.77 mmol) in ethanol (6 mL) and water (2 mL) was stirred at 40° C. for 16 hours. After cooling to room temperature, the reaction mixture was diluted with $H_2O$ (20 mL). The mixture was extracted with EtOAc (20 mL×2). The combined organic phase was washed with brine (10 mL), dried over $Na_2SO_4$, filtered and concentrated to give the crude product (300 mg) as a solid. $^1H$ NMR (400 MHz, $CDCl_3$) $\delta_H$=7.91 (s, 1H), 7.83 (d, 1H), 7.70 (d, 1H), 7.59-7.50 (m, 1H), 4.93 (br s, 2H).

12:

A mixture of 2-[(5-cyclopropyl-2-methyl-pyrazole-3-carbonyl)amino]propanoic acid (150 mg, 0.63 mmol) and CDI (112.77 mg, 0.70 mmol) in DMF (10 mL) was stirred at 15° C. for 1 hour and then N'-hydroxy-3-(trifluoromethyl)benzamidine (129.07 mg, 0.63 mmol) was added. The reaction mixture was then stirred at 110° C. for 16 hours. After cooling to room temperature, the mixture was diluted with $NH_4Cl$ (20 mL), and the mixture was extracted with EtOAc (20 mL×2). The combined organic phase was washed with brine (10 mL), dried over $Na_2SO_4$, filtered and concentrated to give the crude product. The crude product was purified by prep-HPLC (Welch Xtimate C18 (150 mm×25 mm, 5 μm), A=$H_2O$ (10 mM $NH_4HCO_3$) and B=$CH_3CN$; 20-50% B over 9 min) to give the product (26.89 mg, 65.60 mmol, 10% yield) as an oil. $^1H$ NMR (400 MHz, $CDCl_3$) $\delta_H$=8.36 (s, 1H), 8.28 (d, 1H), 7.79 (d, 1H), 7.68-7.61 (m, 1H), 6.52 (d, 1H), 6.32 (s, 1H), 5.67-5.54 (m, 1H), 4.10 (s, 3H), 1.99-1.88 (m, 1H), 1.76 (d, 3H), 1.00-0.90 (m, 2H), 0.81-0.68 (m, 2H). LCMS $R_t$=1.23 min in 2 min chromatography, 10-80AB, MS ESI calcd. for $C_{19}H_{19}F_3N_5O_2$ [M+H]$^+$ 406.1, found 406.0.

Example 11. Synthesis of 13

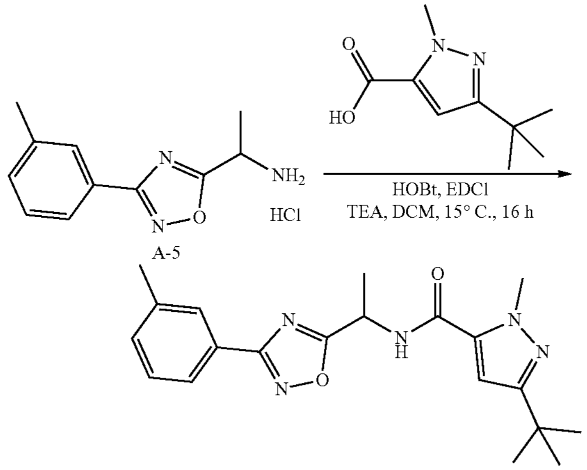

A-5

13

A mixture of 1-[3-(m-tolyl)-1,2,4-oxadiazol-5-yl]ethanamine hydrochloride (100 mg, 0.42 mmol), 5-tert-butyl-2-methyl-pyrazole-3-carboxylic acid (76.02 mg, 0.42 mmol), HOBt (112.75 mg, 0.83 mmol), EDCI (119.96 mg, 0.63 mmol) and TEA (0.29 mL, 2.09 mmol) in DCM (20 mL) was stirred at 15° C. for 16 hours. The mixture was concentrated, diluted with $H_2O$ (10 mL) and then extracted with EtOAc (20 mL×2). The combined organic phase was washed with brine (10 mL), dried over $Na_2SO_4$, filtered and concentrated to give the crude product. The crude product was purified by prep-HPLC (Kromasil (150 mm×30 mm, 5 μm), A=$H_2O$ (0.05% $NH_4OH$) and B=$CH_3CN$; 60-90% B over 8 min) to give the product (61 mg, 0.17 mmol, 39% yield) as a solid. $^1H$ NMR (400 MHz, $CDCl_3$) $\delta_H$=7.94-7.84 (m, 2H), 7.41-7.31 (m, 2H), 6.60-6.54 (m, 1H), 6.48 (s, 1H), 5.65-5.57 (m, 1H), 4.13 (s, 3H), 2.43 (s, 3H), 1.76 (d, 3H), 1.33 (s, 9H). LCMS $R_t$=1.37 min in 2.0 min chromatography, 10-80AB, MS ESI calcd. for $C_{20}H_{26}N_5O_2$ $[M+H]^+$ 368.20, found 368.1.

Example 12. Synthesis of 14 and 15

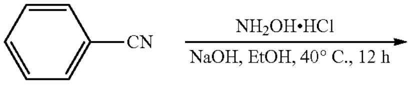

A-20a

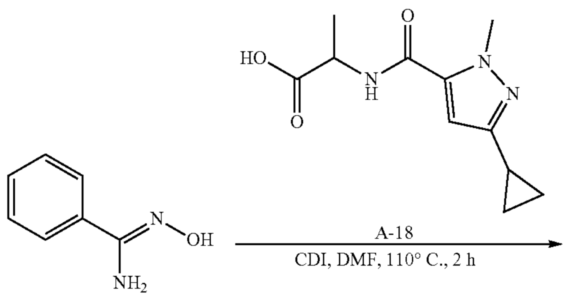

A-21a

-continued

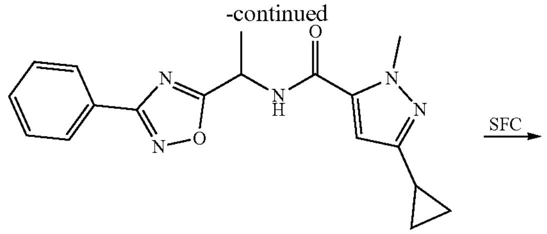

A-22

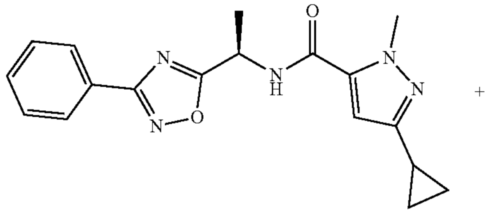

+

14

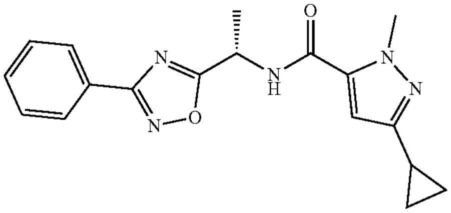

15

A-21a:

A mixture of benzonitrile (370.67 mg, 3.59 mmol), hydroxylamine hydrochloride (749.35 mg, 10.78 mmol) and NaOH (431.34 mg, 10.78 mmol) in ethanol (6 mL) and water (2 mL) was stirred at 40° C. for 12 hours. After cooling to room temperature, the reaction mixture was concentrated to remove most of EtOH, then diluted with $H_2O$ (20 mL). The mixture was extracted with EtOAc (30 mL×2). The combined organic phase was washed with brine (30 mL), dried over $Na_2SO_4$, filtered and concentrated to give the crude product (500 mg, 3.43 mmol, 95% yield) as a solid. LCMS $R_t$=0.29 min in 1.5 min chromatography, 5-95AB, MS ESI calcd. for $C_7H_9N_2O$ $[M+H]^+$ 137.0, found 136.8.

A-22:

A mixture of 2-[(5-cyclopropyl-2-methyl-pyrazole-3-carbonyl)amino]propanoic acid (200 mg, 0.84 mmol) and CDI (150.35 mg, 0.93 mmol) in DMF (3 mL) was stirred at 15° C. for 1 hour. Then N'-hydroxybenzamidine (126.25 mg, 0.93 mmol) was added and then the reaction mixture was then stirred at 110° C. for 2 hours to give a mixture. After cooling to room temperature, the mixture was diluted with water (20 mL) and extracted with EtOAc (30 mL×2). The combined organic phase was washed with brine (20 mL), dried over $Na_2SO_4$, filtered and concentrated to give the crude product. The crude product was purified by prep-HPLC (Boston Prime C18 (150 mm×30 mm, 5 μm), A=water (0.05% $NH_4OH$ v/v) and B=$CH_3CN$; 45-75% B over 8 min) to give the product (170 mg, 495.1 μmol, 59% yield) as a solid. LCMS $R_t$=0.87 min in 1.5 min chromatography, 5-95AB, MS ESI calcd. for $C_{18}H_{20}N_5O_2$ $[M+H]^+$ 338.2, found 338.1.

14 & 15:

Analytical SFC (Daicel CHIRACEL OJ-H (150 mm×4.6 mm, 5 μm), mobile phase: A: $CO_2$ B: methanol (0.05% DEA,) gradient: hold 5% for 0.5 min, then from 5% to 40% of B in 3.5 min and hold 40% for 2.5 min, then 5% of B for 1.5 min, flow rate: 3 mL/min, column temp: 40° C.) showed two peaks at 3.40 min and 3.73 min. The product was separated by SFC (Daicel CHIRALPAK AS (250 mm×30 mm, 5 μm); A=$CO_2$ and B=MeOH (0.1% $NH_3H_2O$); 35° C.; 50 mL/min; 20% B; 9 min run; 7 injections, Rt of peak 1=5.87 min, Rt of peak 2=7.39 min) to give the enantiomer 1, randomly assigned as 14 (11.44 mg, 33.9 μmol, 7% yield) (Rt=3.40 min in analytical SFC) as a solid and enantiomer 2, randomly assigned as 15 (31.75 mg, 94.1 μmol, 19% yield) (Rt=3.73 min in analytical SFC) as a solid.

14:

$^1$H NMR (400 MHz, $CDCl_3$) $\delta_H$=8.08 (dd, 2H), 7.56-7.46 (m, 3H), 6.56 (d, 1H), 6.31 (s, 1H), 5.59 (quin, 1H), 4.10 (s, 3H), 1.98-1.87 (m, 1H), 1.75 (d, 3H), 0.99-0.90 (m, 2H), 0.77-0.68 (m, 2H). LCMS $R_t$=1.21 min in 2.0 min chromatography, 10-80AB, MS ESI calcd. for $C_{18}H_{20}N_5O_2$ $[M+H]^+$ 338.2, found 338.0.

15:

$^1$H NMR (400 MHz, $CDCl_3$) $\delta_H$=8.08 (dd, 2H), 7.57-7.45 (m, 3H), 6.56 (d, 1H), 6.31 (s, 1H), 5.59 (quin, 1H), 4.10 (s, 3H), 1.99-1.88 (m, 1H), 1.75 (d, 3H), 1.00-0.91 (m, 2H), 0.79-0.69 (m, 2H). LCMS $R_t$=1.21 min in 2.0 min chromatography, 10-80AB, MS ESI calcd. for $C_{18}H_{20}N_5O_2$ $[M+H]^+$ 338.2, found 338.0.

Example 13. Synthesis of 16 and 17

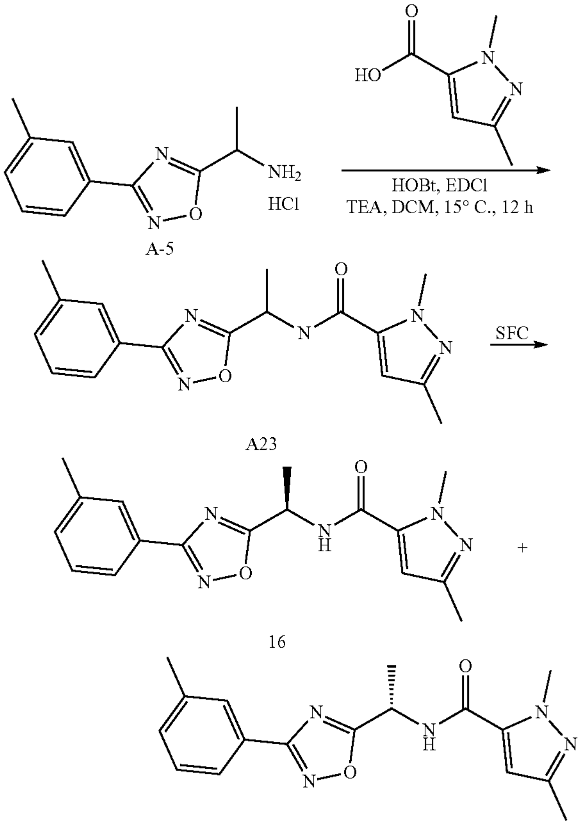

A-5
A23
16
17

To a mixture of 2,5-dimethylpyrazole-3-carboxylic acid (58.46 mg, 420 μmol), EDCI (119.96 mg, 630 μmol), TEA (0.29 mL, 2.09 mmol) and HOBt (112.75 mg, 830 μmol) in DCM (20 mL) was added 1-[3-(m-tolyl)-1,2,4-oxadiazol-5-yl]ethanamine hydrochloride (100 mg, 420 μmol), and the mixture was stirred at 15° C. for 16 hours. The mixture was concentrated and diluted with $H_2O$ (10 mL) and then extracted with EtOAc (20 mL×2). The organic layer was washed brine (10 mL) and dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 37-67% B over 8 min) to give A-23 (65 mg, 195.7 μmol, 47% yield) as an oil. LCMS $R_t$=0.78 min in 1.5 min chromatography, 5-95AB, MS ESI calcd. for $C_{17}H_{20}N_5O_2$ $[M+H]^+$ 326.15, found 326.7. Analytical SFC (Daicel CHIRALPAK IC-3 (150×4.6 mm, 3 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 3.61 min and 4.64 min. The product was separated by SFC (Daicel CHIRALPAK IC (250 mm×30 mm, 5 μm); A=$CO_2$ and B=EtOH (0.1% $NH_3H_2O$); 38° C.; 65 mL/min; 30% B; 7 min run; 4 injections, Rt of peak 1=3.75 min, Rt of peak 2=5.50 min) to give enantiomer 1, randomly assigned as 16 (12.35 mg, 38 μmol, 19% yield) (Rt=3.61 min in analytical SFC) as a solid and enantiomer 2, randomly assigned as 17 (11.51 mg, 35.4 μmol, 18% yield) (Rt=4.64 min in analytical SFC) as a solid.

16:

$^1$H NMR (400 MHz, $CDCl_3$) $\delta_H$=7.97-7.83 (m, 2H), 7.44-7.31 (m, 2H), 6.60 (d, 1H), 6.44 (s, 1H), 5.60 (quin, 1H), 4.12 (s, 3H), 2.44 (s, 3H), 2.30 (s, 3H), 1.75 (d, 3H). LCMS $R_t$=1.18 min in 2.0 min chromatography, 10-80AB, MS ESI calcd. for $C_{17}H_{20}N_5O_2$ $[M+H]^+$ 326.15, found 325.9.

17:

$^1$H NMR (400 MHz, $CDCl_3$) $\delta_H$=7.93-7.85 (m, 2H), 7.43-7.31 (m, 2H), 6.59 (d, 1H), 6.44 (s, 1H), 5.60 (quin, 1H), 4.12 (s, 3H), 2.44 (s, 3H), 2.30 (s, 3H), 1.75 (d, 3H). LCMS $R_t$=1.17 min in 2.0 min chromatography, 10-80AB, MS ESI calcd. for $C_{17}H_{20}N_5O_2$ $[M+H]^+$ 326.15, found 326.0.

Example 14. Synthesis of 19 and 20

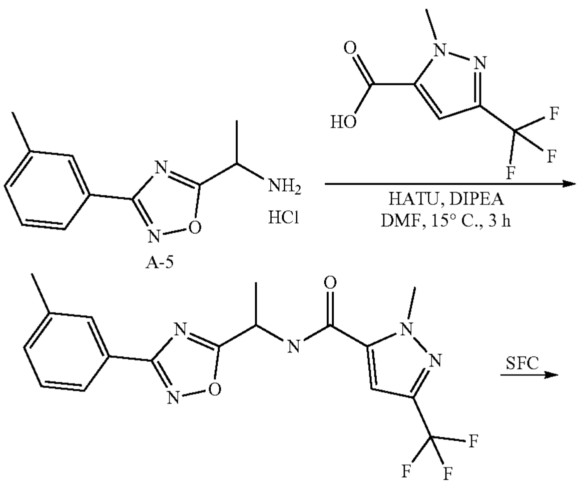

A-5
A-27

-continued

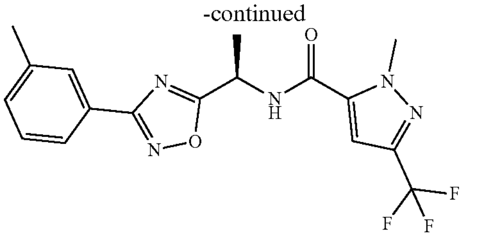

+

19

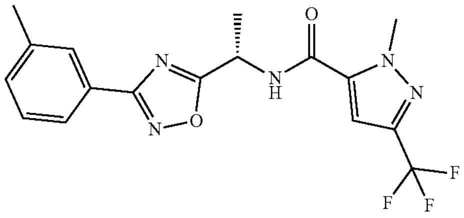

20

A-27:

To a solution of 1-[3-(m-tolyl)-1,2,4-oxadiazol-5-yl] ethanamine hydrochloride (150 mg, 630 μmol) and 2-methyl-5-(trifluoromethyl)pyrazole-3-carboxylic acid (242.94 mg, 1.25 mmol), HATU (475.88 mg, 1.25 mmol) in DMF (10 mL) was added DIPEA (0.44 mL, 2.5 mmol) and the reaction mixture was stirred at 15° C. for 3 hours. The mixture was diluted with $H_2O$ (40 mL) and then extracted with EtOAc (40 mL×3). The combined organic layer was washed brine (40 mL) and dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 65-75% B over 8 min) to give the product (200 mg, 527.2 mol, 84% yield) as an oil. LCMS $R_t$=3.97 min in 7.0 min chromatography, 10-80AB, MS ESI calcd. for $C_{17}H_{17}F_3N_5O_2$ $[M+H]^+$ 380.13, found 380.0.

19 & 20:

Analytical SFC (Daicel CHIRALCEL OJ-3 (150 mm×4.6 mm, 3 μm), mobile phase: A: $CO_2$ B: ethanol (0.05% DEA), gradient: from 5% to 40% of B in 5 min and hold 40% for 0.5 min, then 5% of B for 1.5 min, flow rate: 2.5 mL/min, column temp: 35° C.) showed two peaks at 2.53 min and 3.11 min. The product was separated by SFC (Daicel CHIRALCEL OJ-H (250 mm×30 mm, 5 μm); A=$CO_2$ and B=EtOH (0.1% $NH_3H_2O$); 35° C.; 50 mL/min; 25% B; 7 min run; 6 injections, Rt of peak 1=3.45 min, Rt of peak 2=4.40 min) to give the enantiomer 1, randomly assigned as 19 (55.59 mg, 146.5 mol, 28% yield) (Rt=2.53 min in analytical SFC) as a solid and the enantiomer 2, randomly assigned as 20 (61.98 mg, 163 mol, 31% yield) (Rt=3.11 min in analytical SFC) as a solid.

19:

$^1H$ NMR (400 MHz, $CDCl_3$) $\delta_H$=7.91-7.85 (m, 2H), 7.42-7.30 (m, 2H), 6.93 (s, 1H), 6.71 (br d, 1H), 5.60 (quin, 1H), 4.24 (s, 3H), 2.44 (s, 3H), 1.77 (d, 3H). LCMS $R_t$=1.33 min in 2.0 min chromatography, 10-80AB, MS ESI calcd. for $C_{17}H_{17}F_3N_5O_2$ $[M+H]^+$ 380.13, found 379.9.

20:

$^1H$ NMR (400 MHz, $CDCl_3$) $\delta_H$=7.92-7.84 (m, 2H), 7.43-7.32 (m, 2H), 6.93 (s, 1H), 6.71 (br d, 1H), 5.60 (quin, 1H), 4.24 (s, 3H), 2.44 (s, 3H), 1.77 (d, 3H). LCMS $R_t$=1.34 min in 2.0 min chromatography, 10-80AB, MS ESI calcd. for $C_{17}H_{17}F_3N_5O_2$ $[M+H]^+$ 380.13, found 379.9.

Example 15. Synthesis of 21

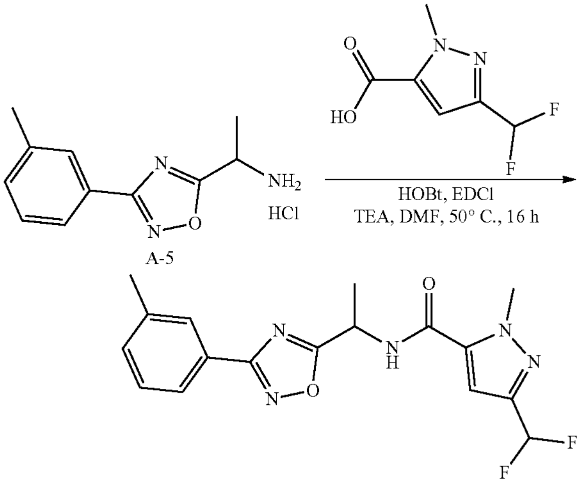

A-5

21

A mixture of 1-[3-(m-tolyl)-1,2,4-oxadiazol-5-yl] ethanamine hydrochloride (100 mg, 0.42 mmol), 5-(difluoromethyl)-2-methyl-pyrazole-3-carboxylic acid (73.48 mg, 0.42 mmol), HOBt (112.75 mg, 0.83 mmol), EDCI (119.96 mg, 0.63 mmol) and TEA (0.29 mL, 2.09 mmol) in DCM (20 mL) was stirred at 15° C. for 16 hours. The mixture was concentrated, diluted with $H_2O$ (10 mL) and extracted with EtOAc (20 mL×2). The combined organic phase was washed with brine (10 mL), dried over $Na_2SO_4$, filtered and concentrated to give the crude product. The crude product was purified by prep-HPLC (Kromasil (150 mm×30 mm, 5 μm), A=$H_2O$ (0.05% $NH_4OH$) and B=$CH_3CN$; 53-83% B over 8 min) to give the product (96 mg, 0.26 mmol, 63% yield) as a solid. $^1H$ NMR (400 MHz, DMSO-$d_6$) $\delta_H$=9.40 (d, 1H), 7.87-7.76 (m, 2H), 7.51-7.37 (m, 2H), 7.28 (s, 1H), 7.06 (t, 1H), 5.49-5.40 (m, 1H), 4.09 (s, 3H), 2.39 (s, 3H), 1.67 (d, 3H). LCMS $R_t$=1.24 min in 2.0 min chromatography, 10-80AB, MS ESI calcd. for $C_{17}H_{18}F_2N_5O_2$ $[M+H]^+$ 362.14, found 362.1.

Example 16. Synthesis of 22

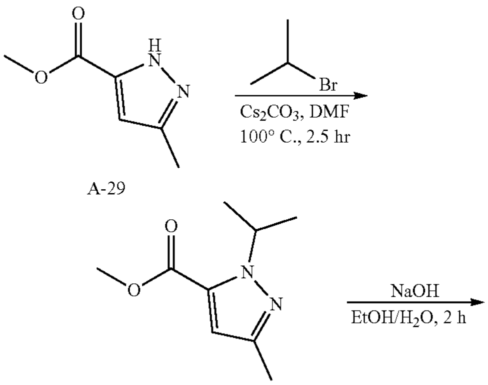

A-29

A-29b

-continued

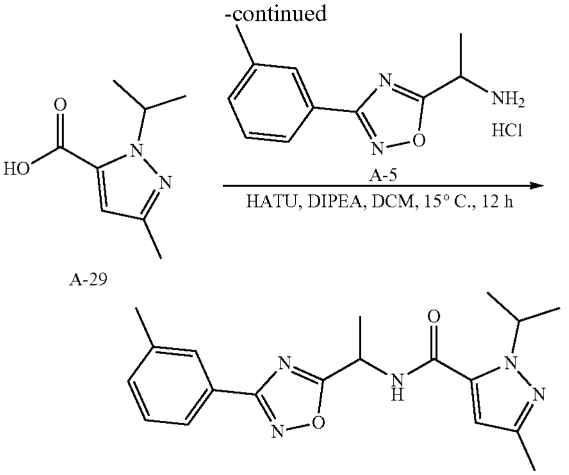

A-29

22

A-29b:

To a mixture of $Cs_2CO_3$ (4649.64 mg, 14.27 mmol) and 2-bromopropane (1755.24 mg, 14.27 mmol) in DMF (15 mL) was added methyl 3-methyl-1H-pyrazole-5-carboxylate (1000 mg, 7.14 mmol), and then the reaction mixture was stirred at 100° C. for 2.5 hours. After cooling to room temperature, the reaction mixture was diluted with $H_2O$ (100 mL) and then extracted with EtOAc (150 mL×2). The combined organic layer was washed with brine (150 mL), dried over $Na_2SO_4$, filtered and concentrated to give the crude product. The crude product was purified by flash chromatography on silica gel (EtOAc in PE=0% to 5%) to give the product (620 mg, 3.24 mmol, 45% yield) as a solid. $^1H$ NMR (400 MHz, $CDCl_3$) $\delta_H$=6.58 (s, 1H), 5.46 (spt, 1H), 3.86 (s, 3H), 2.29 (s, 3H), 1.48 (d, 6H). LCMS $R_t$=3.60 min in 7.0 min chromatography, 0-60AB, MS ESI calcd. for $C_9H_{15}N_2O_2$ $[M+1-1]^+$183.11, found 182.9.

A-29:

To a solution of methyl 2-isopropyl-5-methyl-pyrazole-3-carboxylate (300 mg, 1.65 mmol) in ethanol (5 mL) was added a solution of NaOH (65.85 mg, 1.65 mmol) in water (5 mL). The mixture was stirred at 15° C. for 2 hours. The reaction mixture was concentrated to give a residue. The residue was diluted with $H_2O$ (20 mL) and washed with EtOAc (20 mL×1). The aqueous phase was acidified with 1N HCl (20 mL) to pH=1. The mixture was extracted with EtOAc (50 mL×2). The combined organic phase was washed with brine (70 mL), dried over $Na_2SO_4$, filtered and concentrated to give the crude product (200 mg) as a solid. $^1H$ NMR (400 MHz, $CDCl_3$) $\delta_H$=6.72 (s, 1H), 5.50-5.40 (m, 1H), 2.37-2.26 (m, 3H), 1.50 (d, 6H).

22:

To a mixture of 2-isopropyl-5-methyl-pyrazole-3-carboxylic acid (140.33 mg, 0.83 mmol), HATU (317.25 mg, 0.83 mmol), DIPEA (0.29 mL, 1.67 mmol) in DCM (8 mL) was added 1-[3-(m-tolyl)-1,2,4-oxadiazol-5-yl]ethanamine hydrochloride (100 mg, 0.42 mmol) and the mixture was stirred at 15° C. for 12 hours. The mixture was concentrated and diluted with $H_2O$ (10 mL) and then extracted with EtOAc (20 mL×2). The organic layer was washed brine (30 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 37-67% B over 8 min) to give the product (35.39 mg, 99.7 μmol, 24% yield) as a solid. $^1H$ NMR (400 MHz, $CDCl_3$) $\delta_H$=7.93-7.82 (m, 2H), 7.42-7.33 (m, 2H), 6.59 (br d, 1H), 6.39 (s, 1H), 5.58 (quin, 1H), 5.40 (spt, 1H), 2.43 (s, 3H), 2.32 (s, 3H), 1.75 (d, 3H), 1.48 (dd, 6H). LCMS $R_t$=1.28 min in 2.0 min chromatography, 10-80AB, MS ESI calcd. $C_{19}H_{24}N_5O_2$ $[M+H]^+$ 354.19, found 354.2.

Example 17. Synthesis of 23 and 24

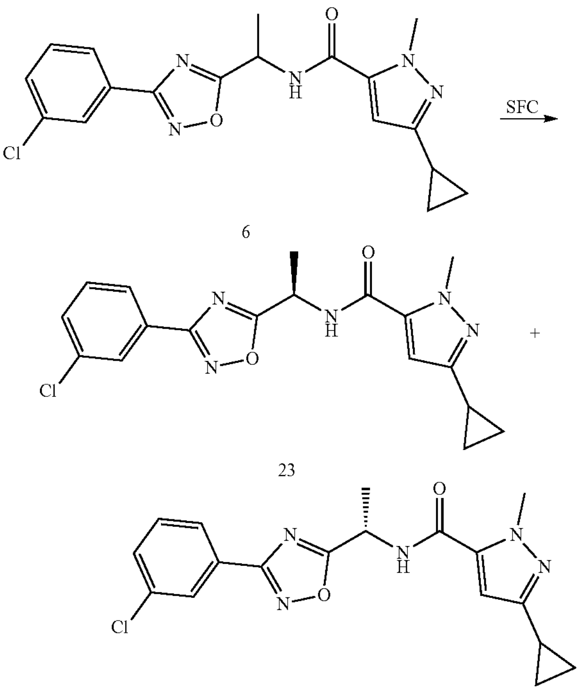

6

23

24

Analytical SFC (Daicel CHIRALPAK AD-3 (150 mm×4.6 mm, 3 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 3.76 min and 4.09 min. The product was separated by SFC (Daicel CHIRALPAK AS (250 mm×30 mm, 5 μm); A=$CO_2$ and B=MeOH (0.1% $NH_3H_2O$); 38° C.; 50 mL/min; 20% B; 10 min run; 8 injections, Rt of peak 1=7.2 min, Rt of peak 2=8.5 min) to give the enantiomer 1, randomly assigned as 23 (2.31 mg, 6.2 μmol, 13% yield) (Rt=3.76 min in analytical SFC) as a solid and enantiomer 2, randomly assigned as 24 (2.02 mg, 5.4 μmol, 11% yield) (Rt=4.09 min in analytical SFC) as a solid.

23:

$^1H$ NMR (400 MHz, $CD_3CN$) $\delta_H$=8.10-8.00 (m, 1H), 8.00-7.94 (m, 1H), 7.61-7.40 (m, 3H), 6.46 (s, 1H), 5.43 (quin, 1H), 3.96 (s, 3H), 1.90-1.84 (m, 1H), 1.69 (d, 3H), 0.91-0.86 (m, 2H), 0.68-0.63 (m, 2H). LCMS $R_t$=1.28 min in 2.0 min chromatography, 10-80AB, MS ESI calcd. for $C_{18}H_{19}ClN_5O_2$ $[M+H]^+$ 372.1, found 372.0.

24:

$^1H$ NMR (400 MHz, $CD_3CN$) $\delta_H$=8.09-8.01 (m, 1H), 8.00-7.95 (m, 1H), 7.62-7.43 (m, 3H), 6.46 (s, 1H), 5.43 (quin, 1H), 3.96 (s, 3H), 1.91-1.83 (m, 1H), 1.69 (d, 3H), 0.92-0.86 (m, 2H), 0.69-0.62 (m, 2H). LCMS $R_t$=1.29 min in 2.0 min chromatography, 10-80AB, MS ESI calcd. for $C_{18}H_{19}ClN_5O_2$ $[M+H]^+$ 372.1, found 371.9.

Example 18. Synthesis of 25 and 26

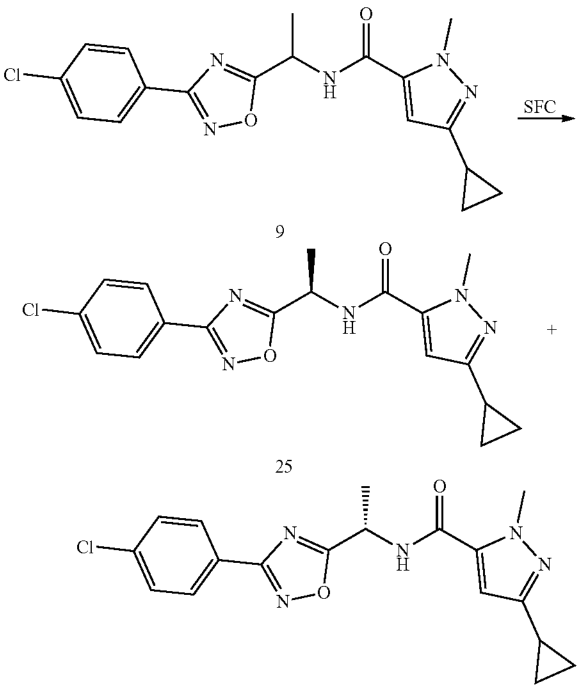

9

25

26

Analytical SFC (Regis, (S,S) Whelk-O1 (250 mm×4.6 mm, 5 μm), mobile phase: A: $CO_2$ B: methanol (0.05% DEA), gradient: hold 5% for 0.5 min, then from 5% to 40% of B in 3.5 min and hold 40% for 2.5 min, then 5% of B for 1.5 min, flow rate: 3 mL/min, column temp: 35° C.) showed two peaks at 3.51 min and 4.72 min. The product was separated by SFC (Daicel CHIRALPAK AS (250 mm×30 mm, 5 μm); A=$CO_2$ and B=MeOH (0.1% $NH_3H_2O$); 38° C.; 50 mL/min; 20% B; 9 min run; 5 injections, Rt of peak 1=5.9 min, Rt of peak 2=7.5 min) to give the enantiomer 1, randomly assigned as 25 (8.68 mg, 23.3 μmol, 17% yield) (Rt=3.51 min in analytical SFC) as a solid and enantiomer 2, randomly assigned as 26 (7.31 mg, 19.7 μmol, 15% yield) (Rt=4.72 min in analytical SFC) as a solid.

25:

$^1$H NMR (400 MHz, $CDCl_3$) $\delta_H$=8.06-7.99 (m, 2H), 7.51-7.44 (m, 2H), 6.53 (d, 1H), 6.30 (s, 1H), 5.59 (quin, 1H), 4.09 (s, 3H), 2.00-1.89 (m, 1H), 1.74 (d, 3H), 0.99-0.92 (m, 2H), 0.78-0.71 (m, 2H). LCMS $R_t$=1.29 min in 2.0 min chromatography, 10-80AB, MS ESI calcd. for $C_{18}H_{19}ClN_5O_2$ $[M+1-1]^+$372.1, found 372.0.

26:

$^1$H NMR (400 MHz, $CDCl_3$) $\delta_H$=8.08-7.97 (m, 2H), 7.51-7.43 (m, 2H), 6.52 (d, 1H), 6.30 (s, 1H), 5.58 (quin, 1H), 4.10 (s, 3H), 1.99-1.87 (m, 1H), 1.74 (d, 3H), 1.00-0.91 (m, 2H), 0.78-0.70 (m, 2H). LCMS $R_t$=1.27 min in 2.0 min chromatography, 10-80AB, MS ESI calcd. for $C_{18}H_{19}ClN_5O_2$ $[M+1-1]^+$372.1, found 372.1.

Example 19. Synthesis of 29 and 30

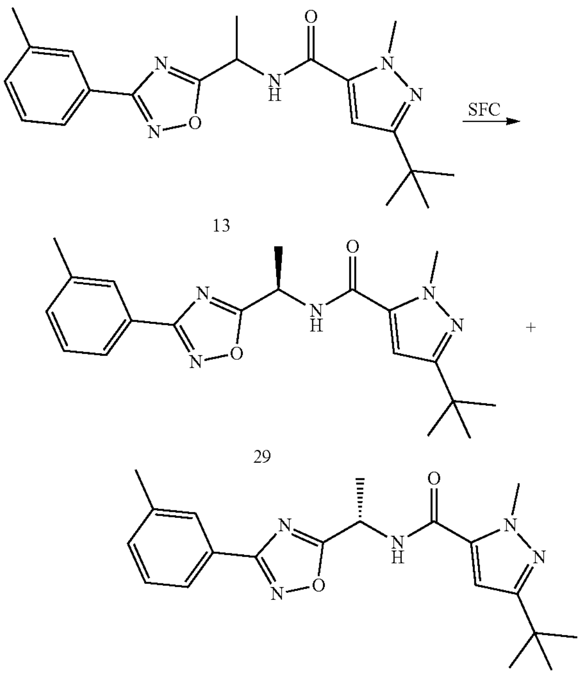

13

29

30

The product was analyzed by SFC (Daicel CHIRALCEL OJ-3 (100 mm×4.6 mm, 3 μm), mobile phase: A: $CO_2$ B: ethanol (0.05% DEA), gradient: from 5% to 40% of B in 4.5 min and hold 40% for 0.5 min, then 5% of B for 1 min, flow rate: 2.8 mL/min, column temp: 40° C.) showed two peaks at 1.91 min and 2.22 min. The product was separated by SFC (Daicel CHIRALCEL OJ-H (250 mm×30 mm, 5 μm); A=$CO_2$ and B=0.1% $NH_3.H_2O$-EtOH; 35° C.; 60 mL/min; 25% B; 8 min run; 10 injections, Rt of peak 1=5.38 min, Rt of peak 2=6.62 min) to give the enantiomer 1, randomly assigned as 29 (12.72 mg, 0.03 mmol, 22% yield) (Rt=1.91 min in analytical SFC) as a solid and the enantiomer 2, randomly assigned 30 (15.52 mg, 0.04 mmol, 27% yield) (Rt=2.22 min in analytical SFC) as a solid.

29:

$^1$H NMR (400 MHz, $CDCl_3$) $\delta_H$=7.93-7.84 (m, 2H), 7.43-7.30 (m, 2H), 6.57 (d, 1H), 6.48 (s, 1H), 5.61 (quin, 1H), 4.13 (s, 3H), 2.44 (s, 3H), 1.76 (d, 3H), 1.33 (s, 9H). LCMS $R_t$=1.33 min in 2.0 min chromatography, 10-80AB, MS ESI calcd. for $C_{20}H_{26}N_5O_2$ $[M+H]^+$ 368.20, found 368.2.

30:

$^1$H NMR (400 MHz, $CDCl_3$) $\delta_H$=7.93-7.85 (m, 2H), 7.42-7.31 (m, 2H), 6.56 (d, 1H), 6.47 (s, 1H), 5.61 (quin, 1H), 4.13 (s, 3H), 2.44 (s, 3H), 1.76 (d, 3H), 1.33 (s, 9H). LCMS $R_t$=1.32 min in 2.0 min chromatography, 10-80AB, MS ESI calcd. for $C_{20}H_{26}N_5O_2$ $[M+H]^+$ 368.20, found 368.2.

Example 20. Synthesis of 31 and 32

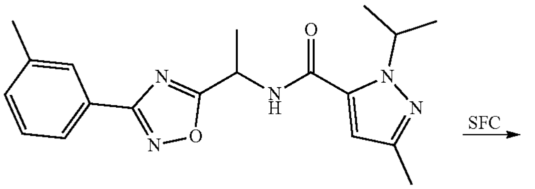

22

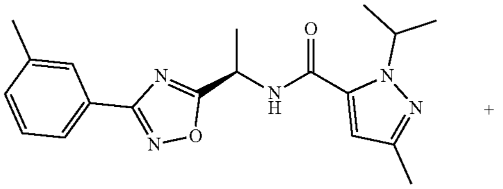

31

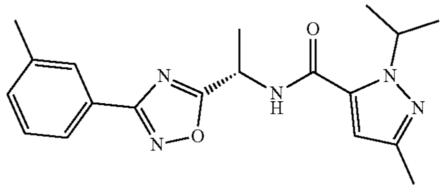

32

Analytical SFC (Regis (R,R) Whelk-01 (100 mm×4.6 mm, 5 μm), mobile phase: A: $CO_2$ B: ethanol (0.05% DEA), gradient: from 5% to 40% of B in 5.5 min and hold 40% for 3 min, then 5% of B for 1.5 min, flow rate: 2.5 mL/min, column temp: 40° C.) showed two peaks at 3.68 min and 4.40 min.

The product was separated by SFC (Regis (S,S) Whelk-O1 (250 mm×30 mm, 5 μm); A=$CO_2$ and B=ethanol (0.1% $NH_3H_2O$); 38° C.; 60 mL/min; 60% B; 10 min run; 3 injections, Rt of peak 1=7.9 min, Rt of peak 2=5.5 min) to give the enantiomer 1, randomly assigned as 31 (9.92 mg, 28.1 μmol, 33% yield) (Rt=3.68 min in analytical SFC) as oil and the enantiomer 2, randomly assigned as 32 (9.16 mg, 25.9 μmol, 30% yield) (Rt=4.40 min in analytical SFC) as oil.

31

$^1$H NMR (400 MHz, DMSO-$d_6$) $\delta_H$=9.12 (d, 1H), 7.85-7.74 (m, 2H), 7.48-7.36 (m, 2H), 6.66 (s, 1H), 5.43-5.27 (m, 2H), 2.38 (s, 3H), 2.18 (s, 3H), 1.63 (d, 3H), 1.36-1.27 (m, 6H). LCMS $R_t$=1.28 min in 2.0 min chromatography, 10-80AB, MS ESI calcd. for $C_{19}H_{24}N_5O_2$ $[M+H]^+$ 354.19, found 354.1.

32

$^1$H NMR (400 MHz, DMSO-$d_6$) $\delta_H$=9.13 (d, 1H), 7.85-7.76 (m, 2H), 7.49-7.37 (m, 2H), 6.66 (s, 1H), 5.45-5.26 (m, 2H), 2.39 (s, 3H), 2.19 (s, 3H), 1.64 (d, 3H), 1.37-1.28 (m, 6H). LCMS $R_t$=1.27 min in 2.0 min chromatography, 10-80AB, MS ESI calcd. for $C_{19}H_{24}N_5O_2$ $[M+H]^+$ 354.19, found 354.0.

Example 21. Synthesis of 33

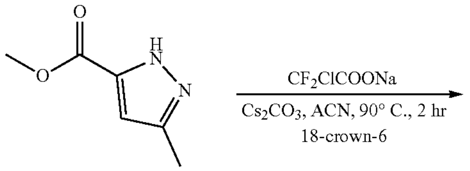

A-29a

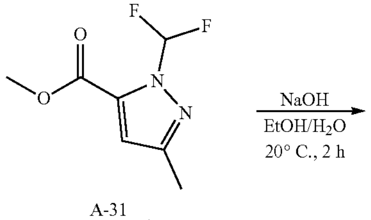

A-31

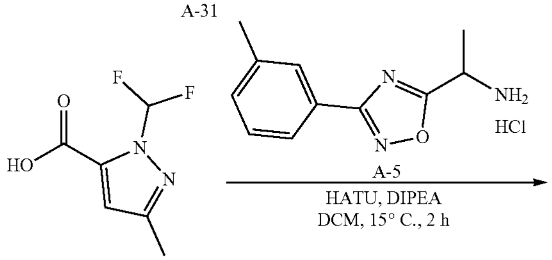

A-32

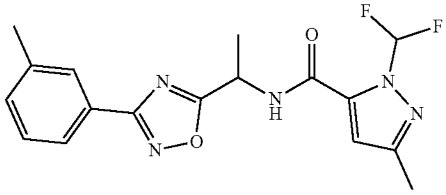

33

A-31:

To a solution of methyl 3-methyl-1H-pyrazole-5-carboxylate (800 mg, 5.71 mmol) in MeCN (20 mL) was added $Cs_2CO_3$ (3719.71 mg, 11.42 mmol), sodium 2-chloro-2,2-difluoro-acetate (1740.66 mg, 11.42 mmol) and 18-crown-6 (301.77 mg, 1.14 mmol) and the reaction mixture was stirred at 90° C. for 2 hours under $N_2$. After cooling to room temperature, the mixture was filtered, and the filtrate was concentrated to give a residue. The residue was diluted with $H_2O$ (50 mL) and extracted with EtOAc (40 mL×2). The combined organic phase was washed with brine (60 mL), dried over $Na_2SO_4$, filtered and concentrated to give the crude product. The crude product was purified by flash chromatography on silica gel (EtOAc in PE=0% to 5.5% to 40%) to give the product (120 mg, 631.1 μmol, 11% yield) as a solid. $^1$H NMR (400 MHz, $CDCl_3$) $\delta_H$=8.03 (t, 1H), 6.77 (s, 1H), 3.92 (s, 3H), 2.36 (s, 3H).

A-32:

To a solution of methyl 2-(difluoromethyl)-5-methyl-pyrazole-3-carboxylate (120 mg, 631.1 μmol) in ethanol (2 mL) was added a solution of NaOH (25.24 mg, 631.1 μmol) in water (2 mL). The mixture was stirred at 20° C. for 2 hours. The reaction mixture was then diluted with $H_2O$ (15 mL) and washed with EtOAc (20 mL, discarded). The aqueous phase was acidified with 1N HCl (20 mL) to adjust the pH=1 and extracted with EtOAc (50 mL×2). The combined organic phase was washed with brine (70 mL), dried over $Na_2SO_4$, filtered and concentrated to give the product (100 mg, 567.8 μmol, 90% yield) as a solid. $^1H$ NMR (400 MHz, DMSO-$d_6$) $\delta_H$=14.15 (br s, 1H), 8.13 (t, 1H), 6.86 (s, 1H), 2.26 (s, 3H).

33:

To a mixture of 2-(difluoromethyl)-5-methyl-pyrazole-3-carboxylic acid (100 mg, 570 μmol), HATU (380.71 mg, 1 mmol), DIPEA (0.35 mL, 2 mmol) in DCM (8 mL) was added 1-[3-(m-tolyl)-1,2,4-oxadiazol-5-yl]ethanamine hydrochloride (120.mg, 500 mol) and the mixture was stirred at 15° C. for 2 hours. The mixture was concentrated and diluted with $H_2O$ (10 mL) and then extracted with EtOAc (20 mL×2). The combined organic layer was washed brine (30 mL) and dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 53-83% B over 8 min) to give the product (109.62 mg, 303.4 μmol, 61% yield) as an oil. $^1H$ NMR (400 MHz, DMSO-$d_6$) $\delta_H$=9.55 (d, 1H), 8.19 (t, 1H), 7.85-7.75 (m, 2H), 7.49-7.37 (m, 2H), 7.02 (s, 1H), 5.44 (quin, 1H), 2.39 (s, 3H), 2.28 (s, 3H), 1.66 (d, 3H). LCMS $R_t$=1.24 min in 2.0 min chromatography, 10-80AB, MS ESI calcd. $C_{17}H_{18}F_2N_5O_2$ $[M+H]^+$ 362.14, found 362.0.

Example 22. Synthesis of 34 and 35

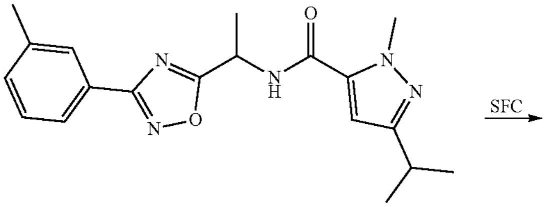

10

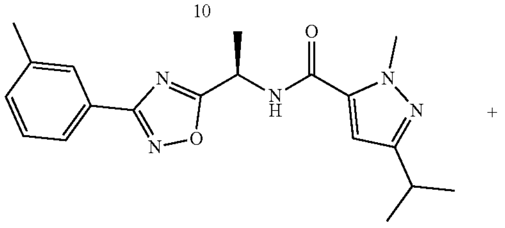

34

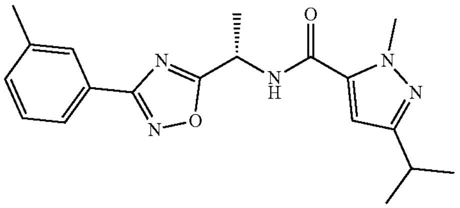

35

Analytical SFC (CHIRALCEL OJ-3 (100 mm×4.6 mm, 3 μm), mobile phase: A: $CO_2$ B: ethanol (0.05% DEA), gradient: from 5% to 40% of B in 4.5 min and hold 40% for 0.5 min, then 5% of B for 1 min, flow rate: 2.8 mL/min, column temp: 40° C.) showed two peaks at 2.01 min and 2.31 min. The product was separated by SFC (Daicel CHIRALCEL OJ-H (250 mm×30 mm, 5 μm); A=$CO_2$ and B=0.1% $NH_3.H_2O$-EtOH; 35° C.; 60 mL/min; 25% B; 8 min run; 10 injections, Rt of peak 1=5.37 min, Rt of peak 2=6.75 min) to give the enantiomer 1, randomly assigned as (5.56 mg, 0.02 mmol, 13% yield) (Rt=2.01 min in analytical SFC) as a solid and the enantiomer 2, randomly assigned as (10.86 mg, 0.03 mmol, 26% yield) (Rt=2.31 min in analytical SFC) as a solid.

34:

$^1H$ NMR (400 MHz, $CDCl_3$) $\delta_H$=7.92-7.86 (m, 2H), 7.41-7.32 (m, 2H), 6.60 (d, 1H), 6.46 (s, 1H), 5.61 (quin, 1H), 4.13 (s, 3H), 3.04-2.95 (m, 1H), 2.44 (s, 3H), 1.76 (d, 3H), 1.29 (d, 6H). LCMS $R_t$=1.29 min in 2.0 min chromatography, 10-80AB, MS ESI calcd. for $C_{19}H_{24}N_5O_2$ $[M+H]^+$ 354.19, found 354.1.

35:

$^1H$ NMR (400 MHz, $CDCl_3$) $\delta_H$=7.93-7.85 (m, 2H), 7.42-7.31 (m, 2H), 6.58 (d, 1H), 6.45 (s, 1H), 5.61 (quin, 1H), 4.13 (s, 3H), 3.05-2.94 (m, 1H), 2.44 (s, 3H), 1.76 (d, 3H), 1.29 (d, 6H). LCMS $R_t$=1.27 min in 2.0 min chromatography, 10-80AB, MS ESI calcd. for $C_{19}H_{24}N_5O_2$ $[M+H]^+$ 354.19, found 354.1.

Example 23. Synthesis of 36 and 37

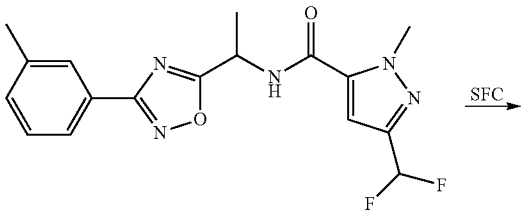

21

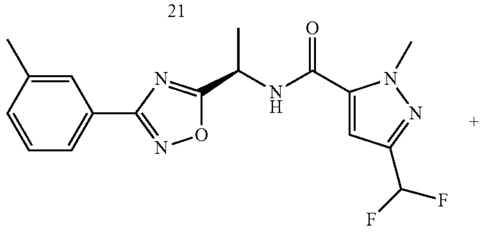

36

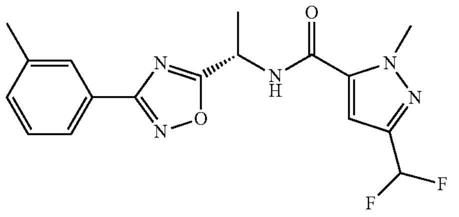

37

Analytical SFC (Daicel CHIRALCEL OJ-3 (100 mm×4.6 mm, 3 μm), mobile phase: A: $CO_2$ B: ethanol (0.05% DEA), gradient: from 5% to 40% of B in 4.5 min and hold 40% for 2.5 min, then 5% of B for 1 min, flow rate: 2.8 mL/min, column temp: 40° C.) showed two peaks at 1.94 min and Rt=2.38 min. The product was separated by SFC (Daicel CHIRALCEL OJ-H (250 mm×30 mm, 5 μm); A=$CO_2$ and B=EtOH (0.1% $NH_3H_2O$); 38° C.; 50 mL/min; 20% B; 9 min run; 11 injections, Rt of peak 1=5.5 min, Rt of peak 2=7.6 min) to give the enantiomer 1, randomly assigned as 36 (16.17 mg, 44.4 mol, 17% yield) (Rt=1.94 min in analytical SFC) as a solid and the enantiomer 2, randomly assigned as 37 (28.82 mg, 79.5 mol, 30% yield) (Rt=2.38 min in analytical SFC) as a solid.

36:

$^1$H NMR (400 MHz, DMSO-$d_6$) $\delta_H$=9.38 (d, 1H), 7.85-7.77 (m, 2H), 7.48-7.39 (m, 2H), 7.27 (s, 1H), 7.06 (t, 1H), 5.44 (quin, 1H), 4.09 (s, 3H), 2.40 (s, 3H), 1.66 (d, 3H). LCMS $R_t$=1.29 min in 2.0 min chromatography, 10-80AB, MS ESI calcd. for $C_{17}H_{18}F_2N_5O_2$ $[M+H]^+$ 362.1, found 362.3.

37:

$^1$H NMR (400 MHz, DMSO-$d_6$) $\delta_H$=9.39 (d, 1H), 7.84-7.78 (m, 2H), 7.48-7.39 (m, 2H), 7.27 (s, 1H), 7.06 (t, 1H), 5.44 (quin, 1H), 4.09 (s, 3H), 2.39 (s, 3H), 1.66 (d, 3H). LCMS $R_t$=1.23 min in 2.0 min chromatography, 10-80AB, MS ESI calcd. for $C_{17}H_{18}F_2N_5O_2$ $[M+H]^+$ 362.1, found 362.1.

Example 24. Synthesis of 38 and 39

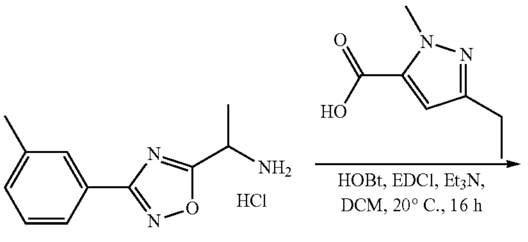

A-5

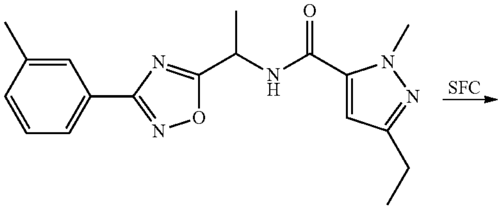

A-34

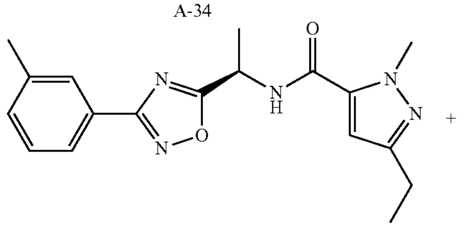

38

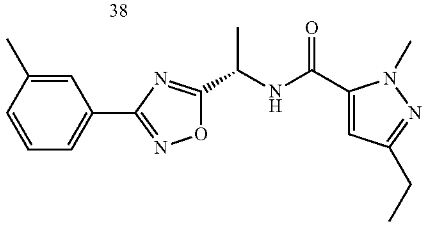

39

A-34:

A mixture of 5-ethyl-2-methyl-pyrazole-3-carboxylic acid (69.46 mg, 0.45 mmol), HOBt (135.3 mg, 1 mmol), $Et_3N$ (0.35 mL, 2.5 mmol), EDCI (143.95 mg, 0.75 mmol) and 1-[3-(m-tolyl)-1,2,4-oxadiazol-5-yl]ethanamine hydrochloride (120 mg, 0.5 mmol) in DCM (20 mL) was stirred at 20° C. for 16 hours under $N_2$. The reaction was quenched with the addition of sat. $NH_4Cl$ (20 mL), and the mixture was extracted with DCM (20 mL×2). The combined organic phase was washed with brine (20 mL), dried over $Na_2SO_4$, filtered and concentrated to give the crude product. The crude product was purified by prep-HPLC (Agela DuraShell (150 mm×25 mm, 5 μm), A=$H_2O$ (0.05% $NH_4OH$) and B=$CH_3CN$; 34-74% B over 8 min) to give the product (88 mg, 0.26 mmol, 52% yield) as a solid.

38 & 39:

Analytical SFC (Column: Daicel CHIRALCEL IC-3 (150 mm×4.6 mm, 3 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 3.42 min and Rt=4.26 min. The product was separated by SFC (Daicel CHIRALCEL (250 mm×30 mm, 5 μm); A=$CO_2$ and B=EtOH; 38° C.; 50 mL/min; 30% B; 7 min run; 4 injections, Rt of peak 1=3.75 min, Rt of peak 2=5.4 min) to give the enantiomer 1, randomly assigned as 38 (24.43 mg, 0.07 mmol, 41% yield) (Rt=3.42 min in analytical SFC) as oil and the enantiomer 2, randomly assigned as 39 (27.23 mg, 0.08 mmol, 45% yield) (Rt=4.26 min in analytical SFC) as an oil.

38:

$^1$H NMR (400 MHz, $CD_3CN$) $\delta_H$=7.87 (s, 1H), 7.83 (d, 1H), 7.49 (br d, 1H), 7.44-7.37 (m, 2H), 6.61 (s, 1H), 5.50-5.37 (m, 1H), 3.99 (s, 3H), 2.60 (q, 2H), 2.41 (s, 3H), 1.69 (d, 3H), 1.21 (t, 3H). LCMS $R_t$=1.25 min in 2.0 min chromatography, 10-80AB, MS ESI calcd. for $C_{18}H_{22}N_5O_2$ $[M+H]^+$ 340.2, found 340.1.

39:

$^1$H NMR (400 MHz, $CD_3CN$) $\delta_H$=7.87 (s, 1H), 7.83 (d, 1H), 7.48 (br d, 1H), 7.44-7.37 (m, 2H), 6.61 (s, 1H), 5.49-5.39 (m, 1H), 3.99 (s, 3H), 2.60 (q, 2H), 2.41 (s, 3H), 1.69 (d, 3H), 1.21 (t, 3H). LCMS $R_t$=1.25 min in 2.0 min chromatography, 10-80AB, MS ESI calcd. for C t8$H_{22}N_5O_2$ $[M+H]^+$ 340.2, found 340.1.

Example 25. Synthesis of 40 and 41

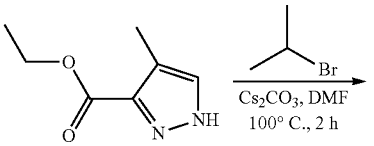

A-35

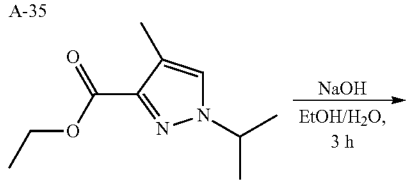

A-36

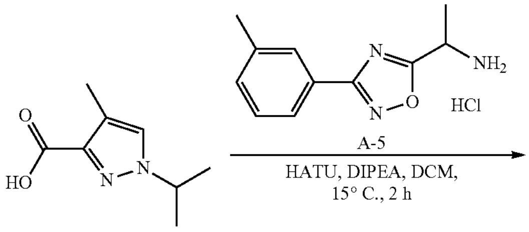

A-37

-continued

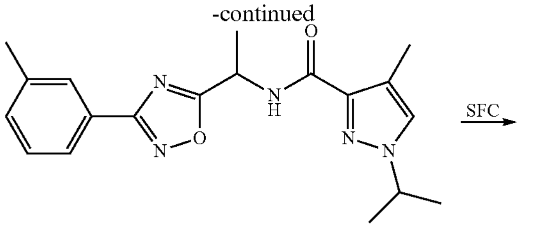

A-38

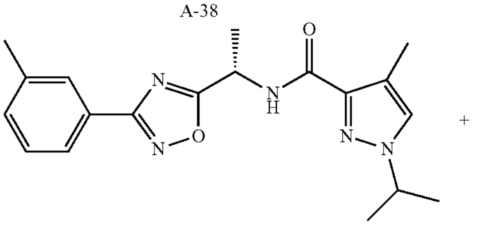

+

40

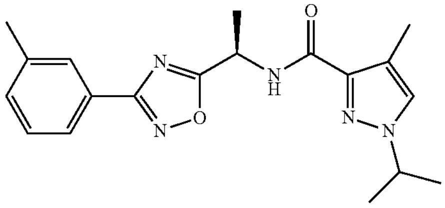

41

A-36:

To a mixture of $Cs_2CO_3$ (1310 mg, 4.02 mmol) and 2-bromopropane (494.61 mg, 4.02 mmol) in DMF (6 mL) was added ethyl 4-methyl-1H-pyrazole-5-carboxylate (310 mg, 2.01 mmol), and then the reaction mixture was stirred at 100° C. for 2 hours. After cooling to room temperature, the reaction mixture was diluted with $H_2O$ (40 mL) and then extracted with EtOAc (30 mL×2). The combined organic layer was washed with brine (50 mL), dried over $Na_2SO_4$, filtered and concentrated to give the crude product. The crude product was purified by flash chromatography on silica gel (EtOAc in PE=0% to 5% to 20%) to give the product (190 mg, 0.97 mmol, 48% yield) as an oil. $^1$H NMR (400 MHz, $CDCl_3$) $\delta_H$=7.26 (s, 1H), 4.65-4.50 (m, 1H), 4.40 (q, 2H), 2.28 (s, 3H), 1.50 (d, 6H), 1.40 (t, 3H).

A-37:

To a solution of ethyl 1-isopropyl-4-methyl-pyrazole-3-carboxylate (190 mg, 0.97 mmol) in ethanol (9 mL) was added a solution of NaOH (116.18 mg, 2.9 mmol) in water (9 mL) and the mixture was stirred at 50° C. for 3 hours. After cooling to room temperature, the reaction mixture was concentrated to give a residue. The residue was diluted with $H_2O$ (30 mL) and washed with EtOAc (20 mL×1). The aqueous phase was acidified with 1N HCl (20 mL) to adjust the pH=1 and extracted with EtOAc (50 mL×2). The combined organic phase was washed with brine (70 mL), dried over $Na_2SO_4$, filtered and concentrated to give the product (130 mg, 0.76 mmol, 78% yield) as a solid. LCMS $R_t$=0.65 min in 1.5 min chromatography, 5-95AB, MS ESI calcd. $C_8H_{13}N_2O_2$ $[M+H]^+$ 169.09, found 168.9.

A-38:

To a mixture of 1-isopropyl-4-methyl-pyrazole-3-carboxylic acid (130 mg, 0.77 mmol), HATU (317.25 mg, 0.83 mmol), DIPEA (0.29 mL, 1.67 mmol) in DCM (8 mL) was added 1-[3-(m-tolyl)-1,2,4-oxadiazol-5-yl]ethanamine (100 mg, 0.42 mmol) and the mixture was stirred at 15° C. for 2 hours. The mixture was concentrated and diluted with $H_2O$ (10 mL), then extracted with EtOAc (20 mL×2). The combined organic layer was washed brine (30 mL) and dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 59-89% B over 8 min) to give the product (150 mg, 412.9 μmol, 99% yield) as an oil. LCMS $R_t$=0.93 min in 1.5 min chromatography, 5-95AB, MS ESI calcd. $C_{19}H_{24}N_5O_2$ $[M+H]^+$ 354.19, found 354.2.

40 & 41:

Analytical SFC (Regis (S,S) Whelk-O1 (250 mm×4.6 mm, 5 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 3.46 min and 5.05 min. The product was separated by SFC (Regis (S,S) Whelk-O1 (250 mm×30 mm, 5 μm); A=$CO_2$ and B=methanol (0.1% DEA); 38° C.; 60 mL/min; 40% B; 12 min run; 4 injections, Rt of peak 1=6.2 min, Rt of peak 2=9.0 min) to give the enantiomer 1, randomly assigned as 41 (47.98 mg, 135.8 mol, 32% yield) (Rt=3.46 min in analytical SFC) as oil and enantiomer 2, randomly assigned as 40 (51.51 mg, 145.7 mol, 34% yield) (Rt=5.05 min in analytical SFC) as a solid.

41:

$^1$H NMR (400 MHz, DMSO-$d_6$) $\delta_H$=8.66 (d, 1H), 7.84-7.75 (m, 2H), 7.68 (s, 1H), 7.47-7.37 (m, 2H), 5.39 (quin, 1H), 4.55-4.42 (m, 1H), 2.39 (s, 3H), 2.17 (s, 3H), 1.66 (d, 3H), 1.43 (d, 6H). LCMS $R_t$=1.36 min in 2.0 min chromatography, 10-80AB, MS ESI calcd. for $C_{19}H_{24}N_5O_2$ $[M+H]^+$ 354.19, found 354.0.

40:

$^1$H NMR (400 MHz, DMSO-$d_6$) $\delta_H$=8.66 (d, 1H), 7.85-7.76 (m, 2H), 7.68 (s, 1H), 7.48-7.37 (m, 2H), 5.39 (quin, 1H), 4.55-4.43 (m, 1H), 2.39 (s, 3H), 2.17 (s, 3H), 1.66 (d, 3H), 1.43 (d, 6H). LCMS $R_t$=1.33 min in 2.0 min chromatography, 10-80AB, MS ESI calcd. for $C_{19}H_{24}N_5O_2$ $[M+H]^+$ 354.19, found 354.0.

Example 26. Synthesis of 42 and 43

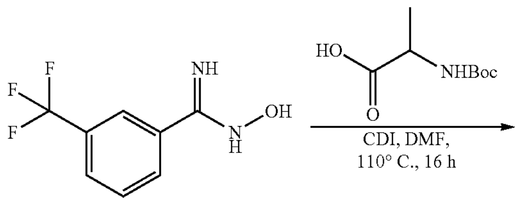

A-39

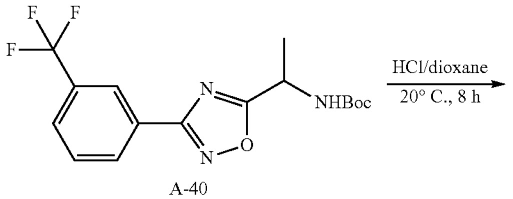

A-40

-continued

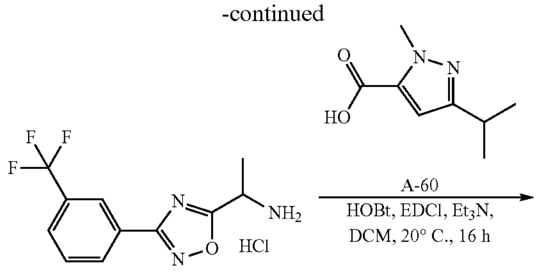

A-41

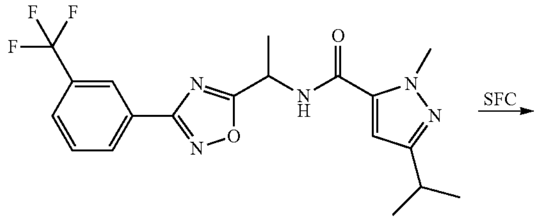

A-42

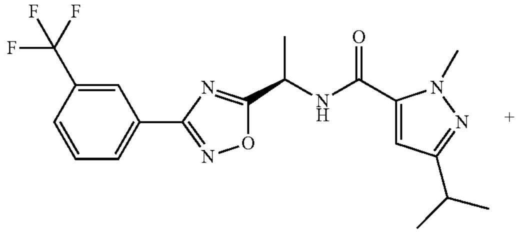

42

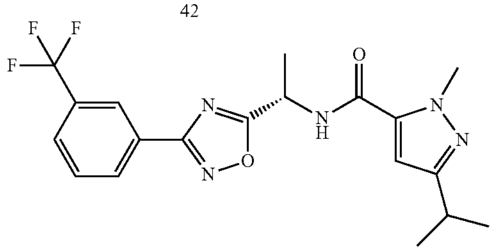

43

A-40:

A mixture of 2-(tert-butoxycarbonylamino)propanoic acid (296.58 mg, 1.57 mmol) and CDI (279.58 mg, 1.72 mmol) in DMF (30 mL) was stirred at 15° C. for 1 hour and then N'-hydroxy-3-(trifluoromethyl)benzamidine (320 mg, 1.57 mmol) was added. The reaction mixture was stirred at 110° C. for 16 hours. After cooling to room temperature, the mixture was diluted with $NH_4Cl$ (30 mL) and extracted with EtOAc (30 mL×2). The combined organic phase was washed with brine (30 mL), dried over $Na_2SO_4$, filtered and concentrated to give the crude product. The crude product was purified by flash column chromatography on silica gel (EtOAc in PE=10% to 30% to 50%) to give the product (500 mg, 1.24 mmol, 79% yield) as an oil. LCMS $R_t$=0.95 min in 1.5 min chromatography, 5-95AB, MS ESI calcd. for $C_{12}H_{11}F_3N_3O_3$[M−tBu+H]$^+$ 302.1, found 302.1.

A-41:

To a solution of tert-butyl N-[1-[3-[3-(trifluoromethyl) phenyl]-1,2,4-oxadiazol-5-yl]ethyl]carbamate (240 mg, 0.67 mmol) in 1,4-dioxane (3 mL) was added 4M HCl/1,4-dioxane (20 mL) and the mixture was stirred at 20° C. for 8 hours. The mixture was concentrated to give the crude product (180 mg, 0.61 mmol, 79% yield) as a solid. LCMS $R_t$=0.69 min in 1.5 min chromatography, 5-95AB, MS ESI calcd. for $C_{11}H_{11}F_3N_3O$ [M+H]$^+$ 258.1, found 258.0.

A-42:

A mixture of 5-isopropyl-2-methyl-pyrazole-3-carboxylic acid (54.41 mg, 0.32 mmol), HOBt (92.03 mg, 0.68 mmol), $Et_3N$ (0.24 mL, 1.7 mmol), EDCI (97.92 mg, 0.51 mmol) and 1-[3-[3-(trifluoromethyl)phenyl]-1,2,4-oxadiazol-5-yl] ethanamine hydrochloride (100 mg, 0.34 mmol) in DCM (20 mL) was stirred at 20° C. for 16 hours under N2. The reaction mixture was quenched with sat. $NH_4Cl$ (20 mL), and the mixture was extracted with DCM (20 mL×2). The combined organic phase was washed with brine (20 mL), dried over $Na_2SO_4$, filtered and concentrated to give the crude product. The crude product was purified by prep-HPLC (Boston Prime (150 mm×30 mm, 5 μm), A=$H_2O$ (0.05% $NH_4OH$) and B=$CH_3CN$; 20-80% B over 8 min) to give the product (85 mg, 0.21 mmol, 61% yield) as a an oil. LCMS $R_t$=0.93 min in 1.5 min chromatography, 5-95AB, MS ESI calcd. for $C_{19}H_{21}F_3N_5O_2$ [M+H]$^+$ 408.2, found 408.1.

42 & 43:

Analytical SFC (Regis (R,R) Whelk-O1 (100 mm×4.6 mm, 5 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 3.15 min and Rt=3.68 min. The product was separated by SFC (Regis (S,S) Whelk-O1 (250 mm×30 mm, 5 μm); A=$CO_2$ and B=EtOH; 38° C.; 65 mL/min; 30% B; 7 min run; 6 injections, Rt of peak 1=4.43 min, Rt of peak 2=5.72 min) to give the enantiomer 1, randomly assigned as 42 (25.66 mg, 0.06 mmol, 31% yield) (Rt=3.15 min in analytical SFC) as oil and enantiomer 2, randomly assigned as 43 (25.41 mg, 0.06 mmol, 32% yield) (Rt=3.68 min in analytical SFC) as an oil.

42:

$^1$H NMR (400 MHz, $CD_3CN$) $\delta_H$=8.36-8.23 (m, 2H), 7.88 (d, 1H), 7.74 (t, 1H), 7.50 (d, 1H), 6.64 (s, 1H), 5.46 (quin, 1H), 3.99 (s, 3H), 3.00-2.85 (m, 1H), 1.71 (d, 3H), 1.23 (d, 6H). LCMS $R_t$=1.36 min in 2.0 min chromatography, 10-80AB, MS ESI calcd. for $C_{19}H_{21}F_3N_5O_2$ [M+H]$^+$ 408.2, found 408.1.

43:

$^1$H NMR (400 MHz, $CD_3CN$) $\delta_H$=8.34-8.25 (m, 2H), 7.88 (d, 1H), 7.74 (t, H), 7.50 (d1H), 6.65 (s, 1H), 5.46 (quin, 1H), 3.99 (s, 3H), 2.99-2.86 (m, 1H), 1.71 (d, 3H), 1.23 (d, 6H). LCMS $R_t$=1.35 min in 2.0 min chromatography, 10-80AB, MS ESI calcd. for $C_{19}H_{21}F_3N_5O_2$ [M+H]$^+$ 408.2, found 408.1.

Example 27. Synthesis of 44

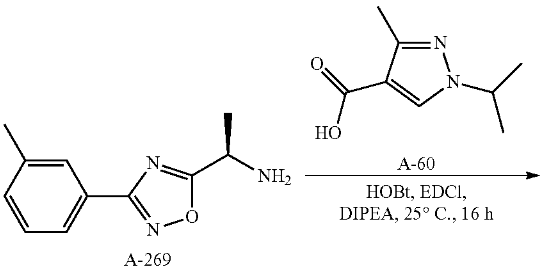

A-269

-continued

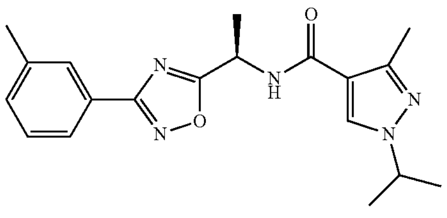

44

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1R)-1-[3-(m-tolyl)-1,2,4-oxadiazol-5-yl]ethanamine (120.84 mg, 0.59 mmol) and the reaction mixture was stirred at 25° C. for 16 hours. The reaction was quenched with $H_2O$ (10 mL), then extracted with DCM (20 mL×3). The combined organic phase was washed with brine (30 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 17-47% B over 8 min) to give the product as an oil. Analytical SFC (Daicel CHIRALPAK AS-3 (150 mm×4.6 mm, 3 μm), mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C., ABPR: 1500 psi) showed 2.39 min (main peak, 91.6%) and 2.55 min (8.4%). Note: the condensation reaction leads to some racemization. Then the product was purified by SFC (Daicel CHIRALPAK AS-H (250 mm×30 mm, 5 μm); A=$CO_2$ and B=EtOH (0.1% $NH_3H_2O$); 38° C.; 65 mL/min; 20% B; 8.60 min run; 50 injections, Rt of peak 1=5.57 min, Rt of peak 2=6.60 min) to give the product (66.75 mg, 0.19 mmol, 32% yield) as an oil. $^1H$ NMR (400 MHz, $CD_3CN$) δ=8.00 (s, 1H), 7.89 (s, 1H), 7.86 (d, 1H), 7.48-7.38 (m, 2H), 7.06 (br d, 1H), 5.50-5.40 (m, 1H), 4.46 (quin, 1H), 2.44 (s, 3H), 2.39 (s, 3H), 1.69 (d, 3H), 1.48 (d, 6H). LCMS $R_t$=1.13 min in in 2.0 min chromatography, 10-80AB, MS ESI calcd. for $C_{19}H_{24}N_5O_2$ $[M+H]^+$ 354.2, found 354.0.

Example 28. Synthesis of 45

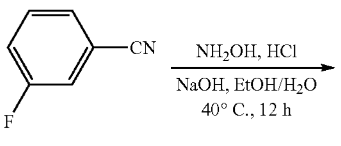

A-9

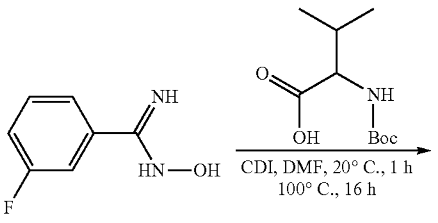

A-10

-continued

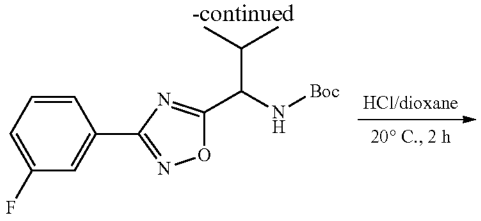

A-45

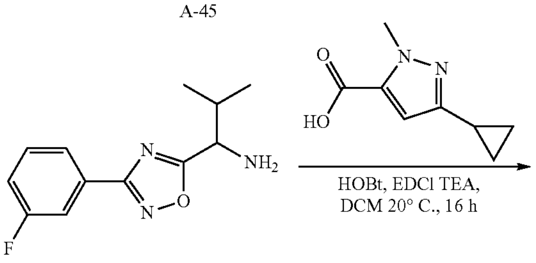

A-46

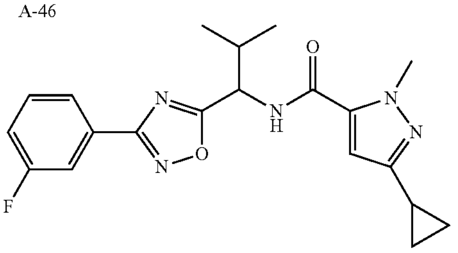

45

A-10:

A mixture of 3-fluorobenzonitrile (2.2 g, 18.17 mmol), hydroxylamine hydrochloride (3.79 g, 54.5 mmol) and NaOH (2.18 g, 54.5 mmol) in ethanol (24 mL) and water (8 mL) was stirred at 40° C. for 12 hours to give a mixture. After cooling to room temperature, the reaction mixture was concentrated to remove most of the EtOH and then diluted with $H_2O$ (20 mL). The mixture was extracted with EtOAc (30 mL×2). The combined organic phase was washed with brine (15 mL), dried over $Na_2SO_4$, filtered and concentrated to give the crude product (3200 mg) as a solid. LCMS $R_t$=0.16 min in 1.5 min chromatography, 5-95AB, MS ESI calcd. for $C_7H_8FN_2O$ $[M+1H]^+$155.05, found 155.1.

A-45:

To a mixture of 2-(tert-butoxycarbonylamino)-3-methyl-butanoic acid (400 mg, 1.84 mmol) and CDI (328.39 mg, 2.03 mmol) in DMF (20 mL) was stirred at 20° C. for 1 h before 3-fluoro-N-hydroxy-benzamidine (283.79 mg, 1.84 mmol) was added. The reaction mixture was stirred at 100° C. for 16 hours. After cooling to room temperature, the mixture was diluted with $H_2O$ (10 mL) and extracted with EtOAc (20 mL×2). The combined organic phase was washed with brine (10 mL), dried over $Na_2SO_4$, filtered and concentrated to give the crude product. The crude product was purified by flash chromatography on silica gel (EtOAc in PE=0% to 20% to 50%) to give the product (150 mg, 0.45 mmol, 24% yield) as an oil. LCMS $R_t$=0.96 min in 1.5 min chromatography, 5-95AB, MS ESI calcd. for $C_{17}H_{23}FN_3O_3$ $[M+H-Boc]^+$280.1, found 280.1.

A-46:

To a solution of tert-butyl N-[1-[3-(3-fluorophenyl)-1,2,4-oxadiazol-5-yl]-2-methyl-propyl]carbamate (200 mg, 0.60 mmol) in 1,4-dioxane (10 mL) was added 4M HCl/1,4-dioxane (10 mL, 40 mmol) and the reaction mixture was stirred at 20° C. for 2 hours. The mixture was concentrated, and the pH was adjusted with the addition of sat. $NaHCO_3$ to pH~9. The mixture was extracted with EtOAc (40 mL×2) and the combined organic phase was washed with brine (10 mL), dried over $Na_2SO_4$, filtered and concentrated to give the crude product (150 mg) as an oil. LCMS $R_t$=0.696 min in 1.5 min chromatography, 5-95AB, MS ESI calcd. for $C_{12}H_{14}FN_3O$ $[M+H]^+$ 236.11, found 236.1.

45:

A mixture of 1-[3-(3-fluorophenyl)-1,2,4-oxadiazol-5-yl]-2-methyl-propan-1-amine (150 mg, 0.64 mmol), HOBt (172.32 mg, 1.28 mmol), EDCI (183.34 mg, 0.96 mmol), TEA (0.44 mL, 3.19 mmol) and 5-cyclopropyl-2-methyl-pyrazole-3-carboxylic acid (105.96 mg, 0.64 mmol) in DCM (20 mL) was stirred at 20° C. for 16 hours. The mixture was diluted with $H_2O$ (20 mL) and extracted with EtOAc (20 mL×2). The combined organic phase was washed with brine (10 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 59-89% B over 8 min) to give the product (75.38 mg, 0.20 mmol, 31% yield) as an oil. $^1H$ NMR (400 MHz, $CDCl_3$) $\delta_H$=7.89 (d, 1H), 7.79 (td, 1H), 7.52-7.42 (m, 1H), 7.23 (dt, 1H), 6.53 (br d, 1H), 6.33 (s, 1H), 5.44 (dd, 1H), 4.09 (s, 3H), 2.45-2.36 (m, 1H), 1.98-1.90 (m, 1H), 1.10-1.01 (m, 6H), 0.98-0.92 (m, 2H), 0.79-0.74 (m, 2H). LCMS $R_t$=1.35 min in 2.0 min chromatography, 5-95AB, MS ESI calcd. for $C_{20}H_{22}FN_5O_2$ $[M+H]^+$ 384.2, found 384.2.

Example 29. Synthesis of 46 and 47

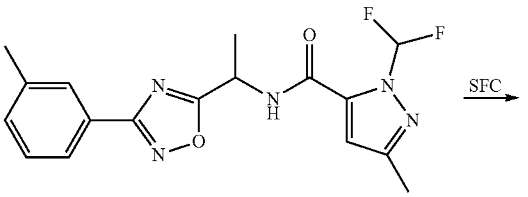

33

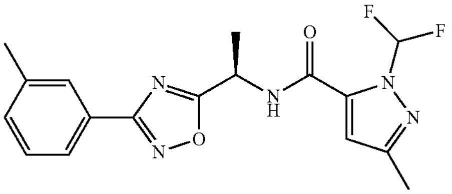

+

46

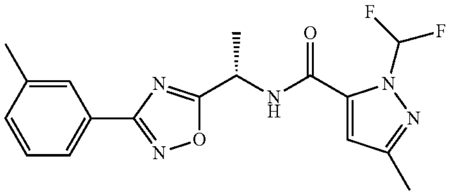

47

Analytical SFC (Regis (S,S) Whelk-O1 (250 mm×4.6 mm, 5 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 5.34 min and 6.12 min. The product was separated by SFC (Regis (S,S) Whelk-O1 (250 mm×30 mm, 5 μm); A=$CO_2$ and B=ethanol (0.1% DEA); 38° C.; 60 mL/min; 40% B; 8 min run; 5 injections, Rt of peak 1=4.6 min, Rt of peak 2=5.8 min to give the enantiomer 1, randomly assigned as 46 (25.02 mg, 69.2 μmol, 25% yield) (Rt=5.34 min in analytical SFC) as an oil and the enantiomer 2, randomly assigned as 47 (28.95 mg, 80.1 μmol, 29% yield) (Rt=6.12 min in analytical SFC) as an oil.

46:

$^1H$ NMR (400 MHz, DMSO-$d_6$) $\delta_H$=9.55 (d, 1H), 8.18 (t, 1H), 7.85-7.74 (m, 2H), 7.50-7.36 (m, 2H), 7.02 (s, 1H), 5.44 (quin, 1H), 2.39 (s, 3H), 2.28 (s, 3H), 1.66 (d, 3H). LCMS $R_t$=1.29 min in 2.0 min chromatography, 10-80AB, MS ESI calcd. for $C_{17}H_{18}F_2N_5O_2$ $[M+H]^+$ 362.14, found 362.1.

47:

$^1H$ NMR (400 MHz, DMSO-$d_6$) $\delta_H$=9.56 (d, 1H), 8.19 (t, 1H), 7.88-7.71 (m, 2H), 7.53-7.35 (m, 2H), 7.03 (s, 1H), 5.45 (quin, 1H), 2.40 (s, 3H), 2.29 (s, 3H), 1.67 (d, 3H). LCMS $R_t$=1.26 min in 2.0 min chromatography, 10-80AB, MS ESI calcd. for $C_{17}H_{18}F_2N_5O_2$ $[M+H]^+$ 362.14, found 362.0.

Example 30. Synthesis of 48

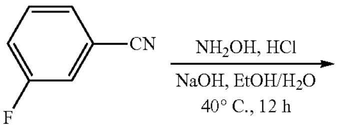

A-9

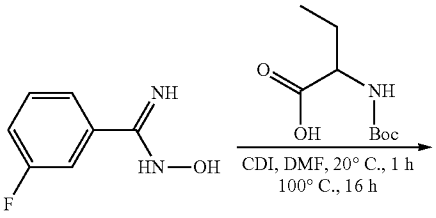

A-10

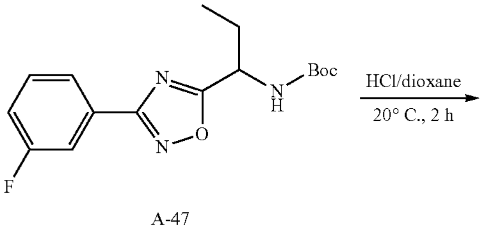

A-47

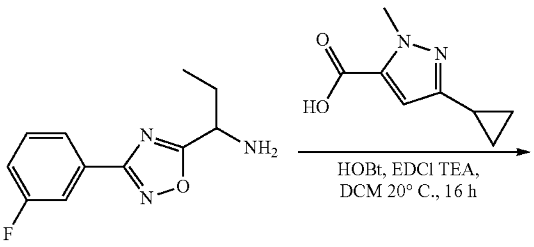

A-48

-continued

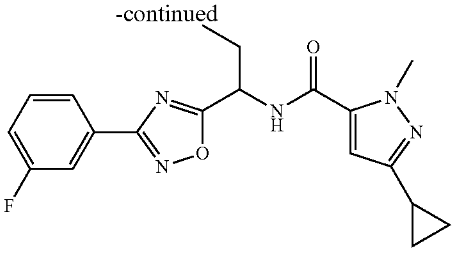

48

A-10:

A mixture of 3-fluorobenzonitrile (2.2 g, 18.17 mmol), hydroxylamine hydrochloride (3.79 g, 54.5 mmol) and NaOH (2.18 g, 54.5 mmol) in ethanol (24 mL) and water (8 mL) was stirred at 40° C. for 12 hours to give a mixture. After cooling to room temperature, the reaction mixture was concentrated to remove most of the EtOH, then diluted with $H_2O$ (20 mL). The mixture was extracted with EtOAc (30 mL×2). The combined organic phase was washed with brine (15 mL), dried over $Na_2SO_4$, filtered and concentrated to give the crude product (3200 mg) as a solid. LCMS $R_t$=0.16 min in 1.5 min chromatography, 5-95AB, MS ESI calcd. for $C_7H_8FN_2O$ $[M+1H]^+$155.05, found 155.1.

A-47:

A mixture of 2-(tert-butoxycarbonylamino)butanoic acid (400 mg, 1.97 mmol) and CDI (351.04 mg, 2.16 mmol) in DMF (20 mL) was stirred at 20° C. for 1 hour before 3-fluoro-N-hydroxy-benzamidine (303.37 mg, 1.97 mmol) was added. The mixture was stirred at 100° C. for 16 hours. The mixture was cooled then diluted with $H_2O$ (10 mL) and extracted with EtOAc (20 mL×2). The combined organic phase was washed with brine (10 mL), dried over $Na_2SO_4$, filtered and concentrated to give the crude product. The crude product was purified by flash chromatography on silica gel (EtOAc in PE=0% to 20% to 50%) to give the product (150 mg, 0.45 mmol, 23% yield) as an oil. LCMS $R_t$=0.94 min in 1.5 min chromatography, 5-95AB, MS ESI calcd. for $C_{16}H_{21}FN_3O_3$ $[M+H-Boc]^+$266.1, found 266.1.

A-48:

To a solution of tert-butyl N-[1-[3-(3-fluorophenyl)-1,2,4-oxadiazol-5-yl]propyl]carbamate (200 mg, 0.62 mmol) in 1,4-dioxane (10 mL) was added 4M HCl/1,4-dioxane (10 mL, 40 mmol) and the reaction mixture was stirred at 20° C. for 2 hours. The mixture was concentrated, and the pH was adjusted with the addition of sat. $NaHCO_3$ to pH 9. The mixture was extracted with EtOAc (40 mL×2) and the combined organic phase was washed with brine (10 mL), dried over $Na_2SO_4$, filtered and concentrated to give the crude product (150 mg) as an oil. LCMS $R_t$=0.66 min in 1.5 min chromatography, 5-95AB, MS ESI calcd. for $C_{11}H_{14}ClFN_3O$ $[M+H]^+$ 222.0, found 222.0.

48:

A mixture of 1-[3-(3-fluorophenyl)-1,2,4-oxadiazol-5-yl]propan-1-amine (150 mg, 0.68 mmol), HOBt (183.24 mg, 1.36 mmol), EDCI (194.97 mg, 1.02 mmol), TEA (0.47 mL, 3.39 mmol) and 5-cyclopropyl-2-methyl-pyrazole-3-carboxylic acid (112.67 mg, 0.68 mmol) in DCM (20 mL) was stirred at 20° C. for 16 hours. The mixture was diluted with sat. $NH_4Cl$ (10 mL) and extracted with DCM (20 mL×2). The combined organic phase was washed with brine (10 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 55-85% B over 8 min) to give the product (77.37 mg, 0.21 mmol, 31% yield) as a solid. $^1H$ NMR (400 MHz, $CDCl_3$) $\delta_H$=7.88 (dd, 1H), 7.82-7.76 (m, 1H), 7.51-7.44 (m, 1H), 7.26-7.19 (m, 1H), 6.50 (br d, 1H), 6.32 (s, 1H), 5.53-5.45 (m, 1H), 4.09 (s, 3H), 2.23-2.11 (m, 1H), 2.10-1.98 (m, 1H), 1.98-1.88 (m, 1H), 1.06 (t, 3H), 0.98-0.91 (m, 2H), 0.78-0.72 (m, 2H). LCMS $R_t$=1.28 min in 2.0 min chromatography, 5-95AB, MS ESI calcd. for $C_{19}H_{21}FN_5O_2$ $[M+H]^+$ 370.2, found 370.1.

Example 31. Synthesis of 49

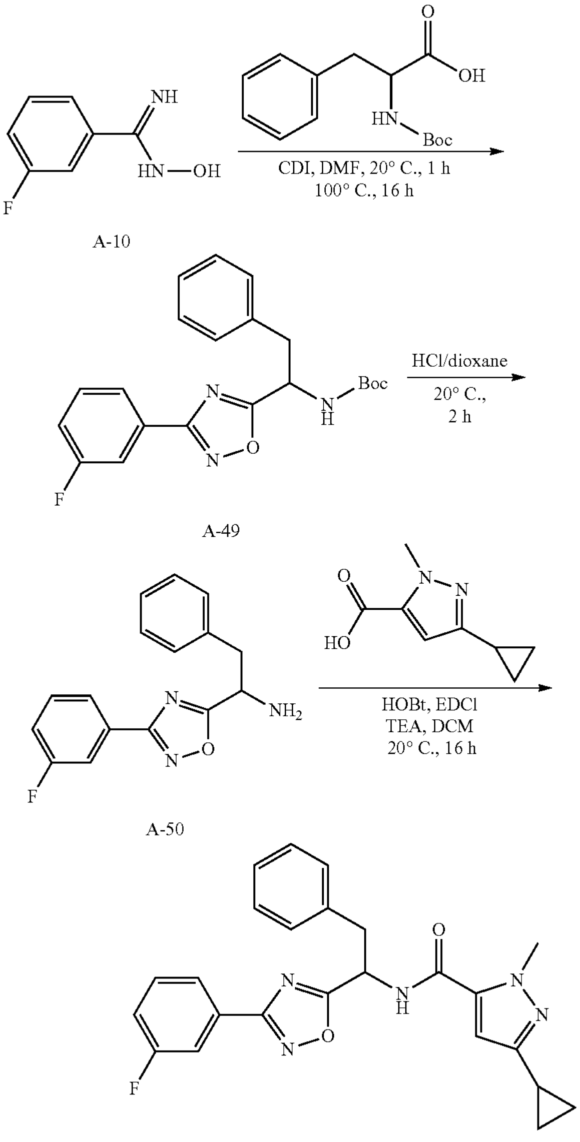

A-10

A-49

A-50

49

A-49:

A mixture of 2-(tert-butoxycarbonylamino)-3-phenylpropanoic acid (400 mg, 1.51 mmol) and CDI (268.93 mg, 1.66 mmol) in DMF (20 mL) was stirred at 20° C. for 1 hour before 3-fluoro-N-hydroxy-benzamidine (232.4 mg, 1.51 mmol) was added. The mixture was stirred at 100° C. for 16 hours. The mixture was cooled then diluted with $H_2O$ (10 mL) and extracted with EtOAc (20 mL×2). The combined organic phase was washed with brine (10 mL), dried over $Na_2SO_4$, filtered and concentrated to give the crude product. The crude product was purified by flash chromatography on silica gel (EtOAc in PE=0% to 20% to 50%) to give the product (150 mg, 0.39 mmol, 26% yield,) as an oil. LCMS $R_t$=0.98 min in 1.5 min chromatography, 5-95AB, MS ESI calcd. for $C_{21}H_{23}FN_3O_3$ $[M+2H-Boc]^+$ 328.1, found 328.1.

A-50:

To tert-butyl N-[1-[3-(3-fluorophenyl)-1,2,4-oxadiazol-5-yl]-2-phenyl-ethyl]carbamate (200 mg, 0.52 mmol) in 1,4-dioxane (10 mL) was added 4M HCl/1,4-dioxane (10 mL, 40 mmol) add the reaction mixture was stirred at 20° C. for 2 hours. The mixture was concentrated, and the pH was adjusted with the addition of sat. $NaHCO_3$ to pH 9. The mixture was extracted with EtOAc (40 mL×2), and the combined organic phase was washed with brine (10 mL), dried over $Na_2SO_4$, filtered and concentrated to give the crude product (150 mg, 0.46 mmol, 88% yield) as oil. LCMS $R_t$=0.73 min in 1.5 min chromatography, 5-95AB, MS ESI calcd. for $C_{16}H_{16}ClFN_3O$ $[M+H]^+$ 284.1, found 284.1.

49:

A mixture of 1-[3-(3-fluorophenyl)-1,2,4-oxadiazol-5-yl]-2-phenyl-ethanamine (150 mg, 0.53 mmol), HOBt (143.1 mg, 1.06 mmol), EDCI (152.25 mg, 0.79 mmol), TEA (0.37 mL, 2.65 mmol) and 5-cyclopropyl-2-methyl-pyrazole-3-carboxylic acid (87.99 mg, 0.53 mmol) in DCM (20 mL) was stirred at 20° C. for 16 hours. The mixture was diluted with $H_2O$ (20 mL) and extracted with EtOAc (20 mL×2). The combined organic phase was washed with brine (10 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 62-92% B over 8 min) to give the product (42.55 mg, 0.10 mmol, 18% yield) as a solid. $^1H$ NMR (400 MHz, DMSO-$d_6$) $\delta_H$=9.17 (d, 1H), 7.86 (d, 1H), 7.77-7.70 (m, 1H), 7.68-7.60 (m, 1H), 7.48 (dt, 1H), 7.35-7.26 (m, 4H), 7.24-7.18 (m, 1H), 6.60 (s, 1H), 5.62-5.50 (m, 1H), 3.84 (s, 3H), 3.49-3.42 (m, 1H), 3.38-3.34 (m, 1H), 1.90-1.81 (m, 1H), 0.90-0.84 (m, 2H), 0.64-0.58 (m, 2H). LCMS $R_t$=1.37 min in 2.0 min chromatography, 5-95AB, MS ESI calcd. for $C_{24}H_{23}FN_5O_2$ $[M+H]^+$ 432.2, found 432.1.

Example 32. Synthesis of 50

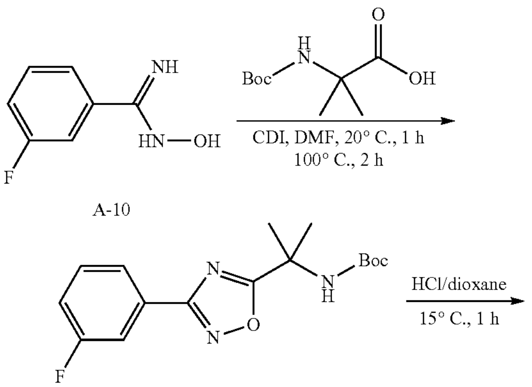

A-10

A-51

-continued

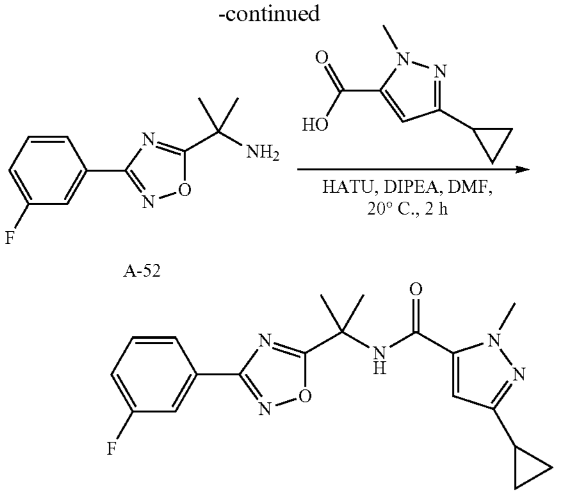

A-52

50

A-51:

A mixture of 2-(tert-butoxycarbonylamino)-2-methyl-propanoic acid (580.16 mg, 2.85 mmol) and CDI (462.86 mg, 2.85 mmol) in DMF (6 mL) was stirred at 15° C. for 1 hour and then 3-fluoro-N-hydroxy-benzamidine (400 mg, 2.6 mmol) was added. The reaction mixture was then stirred at 100° C. for 2 hours. After cooling to room temperature, the mixture was diluted with water (20 mL) and extracted with EtOAc (30 mL×2). The combined organic phase was washed with brine (20 mL), dried over $Na_2SO_4$, filtered and concentrated to give the crude product. The crude product was purified by flash chromatography on silica gel (EtOAc in PE=0% to 30% to 60%) to give the product (140 mg, 344.1 μmol, 13% yield) as a solid. LCMS Rt=0.91 min in 1.5 min chromatography, 5-95AB, MS ESI calcd. for $C_{12}H_{13}FN_3O_3$ $[M+H-t-Bu]^+$ 266.1, found 266.0.

A-52:

To tert-butyl N-[1-[3-(3-fluorophenyl)-1,2,4-oxadiazol-5-yl]-1-methyl-ethyl]carbamate (140 mg, 0.44 mmol) in 1,4-dioxane (2 mL) was added 4M HCl in 1,4-dioxane (3 mL, 12 mmol) and the mixture was stirred at 15° C. for 1 hour. The mixture was concentrated to give the product of 2-[3-(3-fluorophenyl)-1,2,4-oxadiazol-5-yl]propan-2-amine hydrochloride (110 mg, 417. 8 μmol, 96% yield) as a solid. LCMS Rt=0.64 min in 1.5 min chromatography, 5-95AB, MS ESI calcd. for $C_{15}H_{13}FN_3O$ $[M+H]^+$ 222.1, found 222.0.

50:

To a mixture of 5-cyclopropyl-2-methyl-pyrazole-3-carboxylic acid (77.39 mg, 0.47 mmol), HATU (177.06 mg, 0.47 mmol) and 2-[3-(3-fluorophenyl)-1,2,4-oxadiazol-5-yl] propan-2-amine hydrochloride (100 mg, 0.39 mmol) in DMF (6 mL) was added DIPEA (0.2 mL, 1.16 mmol) and the mixture was stirred at 20° C. for 2 hours. The mixture was diluted with water (20 mL) and extracted with EtOAc (20 mL×2). The combined organic phase was washed with water (20 mL×2) and brine (20 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 52-82% B over 8 min) to give the product (116.91 mg, 0.32 mmol, 81% yield) as a solid. $^1H$ NMR (400 MHz, DMSO-$d_6$) $\delta_H$=8.93 (s, 1H), 7.85 (d, 1H), 7.73 (d, 1H), 7.67-7.59 (m, 1H), 7.50-7.40 (m, 1H), 6.72 (s, 1H), 3.83 (s, 3H), 1.93-1.84 (m, 1H), 1.75 (s, 6H), 0.92-0.86 (m, 2H), 0.68-0.60 (m, 2H). LCMS $R_t$=1.32 min in 2.0 min chromatography, 10-80AB, MS ESI calcd. for $C_{19}H_{21}FN_5O_2$ $[M+H]^+$ 370.2, found 369.9.

Example 33. Synthesis of 51

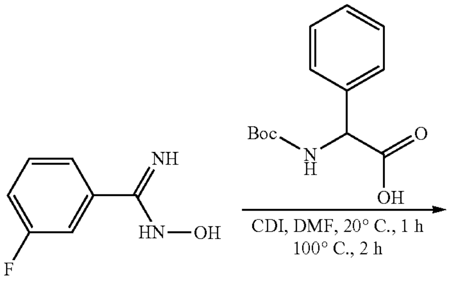

A-10

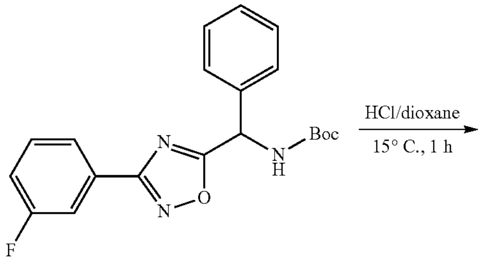

A-53

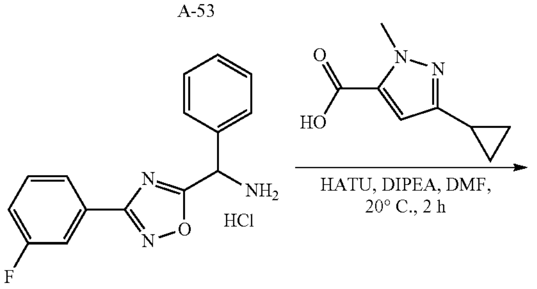

A-54

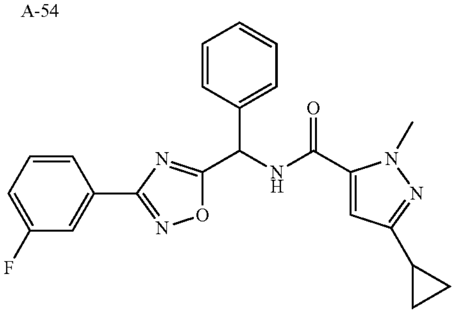

51

A-53:

A mixture of 2-(tert-butoxycarbonylamino)-2-phenyl-acetic acid (717.29 mg, 2.85 mmol) and CDI (462.86 mg, 2.85 mmol) in DMF (6 mL) was stirred at 15° C. for 1 hour and then 3-fluoro-N-hydroxy-benzamidine (400 mg, 2.6 mmol) was added. The reaction was then stirred at 100° C. for 2 hours to give a mixture. After cooling to room temperature, the mixture was diluted with water (20 mL) and extracted with EtOAc (30 mL×2). The combined organic phase was washed with brine (20 mL), dried over $Na_2SO_4$, filtered and concentrated to give the crude product. The crude product was purified by flash chromatography on silica gel (EtOAc in PE=0% to 30% to 60%) to give the product (140 mg, 209.0 μmol, 8% yield) as a solid. LCMS Rt=0.96 min in 1.5 min chromatography, 5-95AB, MS ESI calcd. for $C_{16}H_{13}FN_3O_3$ $[M+H-t-Bu]^+$ 314.1, found 314.1.

A-54:

To tert-butyl N-[[3-(3-fluorophenyl)-1,2,4-oxadiazol-5-yl]-phenyl-methyl]carbamate (140 mg, 0.38 mmol) in 1,4-dioxane (6 mL) was added 4M HCl in 1,4-dioxane (3 mL, 12 mmole) and the mixture was stirred at 15° C. for 1 hour. The mixture was concentrated to give the product (110 mg, 351.4 μmol, 93% yield) as a solid. LCMS Rt=0.71 min in 1.5 min chromatography, 5-95AB, MS ESI calcd. for $C_{15}H_DFN_3O$ $[M+H]^+$ 270.1, found 270.0.

51:

To a mixture of 5-cyclopropyl-2-methyl-pyrazole-3-carboxylic acid (91.32 mg, 0.55 mmol), HATU (208.94 mg, 0.55 mmol) and [3-(3-fluorophenyl)-1,2,4-oxadiazol-5-yl]-phenyl-methanamine hydrochloride (140 mg, 0.46 mmol) in DMF (3 mL) was added DIPEA (0.24 mL, 1.37 mmol) and the mixture was stirred at 20° C. for 2 hours. The mixture was diluted with water (20 mL) and extracted with EtOAc (20 mL×2). The combined organic phase was washed with water (20 mL×2) and brine (20 mL), dried over $Na_2SO_4$, filtered and concentrated to give the crude product. The crude product was purified by rep-HPLC (Boston Prime C18 (150 mm×30 mm, 5 μm), A=$H_2O$ (0.05% $NH_4OH$) and B=$CH_3CN$; 60-90% B over 8 min) to give the product (88.39 mg, 0.21 mmol, 46% yield) as a solid. $^1$H NMR (400 MHz, DMSO-$d_6$) $\delta_H$=9.61 (d, 1H), 7.84 (d, 1H), 7.77-7.70 (m, 1H), 7.67-7.58 (m, 1H), 7.56-7.50 (m, 2H), 7.49-7.38 (m, 4H), 6.78 (s, 1H), 6.64 (d, 1H), 3.94 (s, 3H), 1.92-1.82 (m, 1H), 0.91-0.82 (m, 2H), 0.66-0.56 (m, 2H). LCMS $R_t$=1.41 min in 2.0 min chromatography, 10-80AB, MS ESI calcd. for $C_{23}H_{21}FN_5O_2$ $[M+H]^+$ 418.2, found 418.0.

Example 34. Synthesis of 52

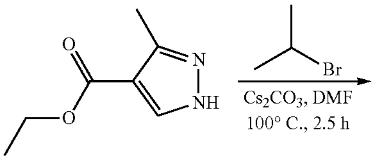

A-57a

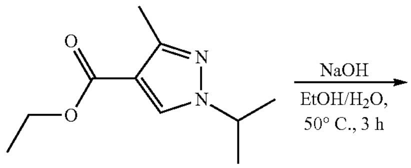

A-57b

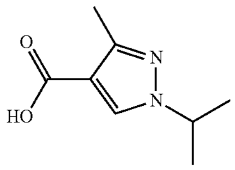

A-57

-continued

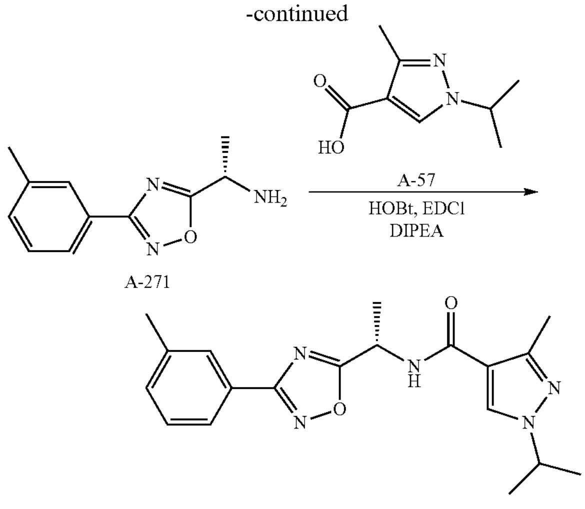

A-271

52

A-57b:

To a mixture of $Cs_2CO_3$ (8.45 g, 25.95 mmol) and 2-bromopropane (3.19 g, 25.95 mmol) in DMF (30 mL) was added ethyl 3-methyl-1H-pyrazole-4-carboxylate (2 g, 12.97 mmol) and the reaction mixture was stirred at 100° C. for 2.5 hours. After cooling to room temperature, the reaction mixture was diluted with sat. $NH_4Cl$ (50 mL), then extracted with EtOAc (50 mL×2), the organic layer was washed with brine (50 mL), dried over $Na_2SO_4$, filtered and concentrated to give the crude product. The product was purified by flash chromatography on silica gel (EtOAc in PE=0% to 30%) to give the product (300 mg, 1.53 mmol, 12% yield) as a solid. $^1H$ NMR (400 MHz, $CDCl_3$) $\delta_H$=7.85 (s, 1H), 4.51-4.34 (m, 1H), 4.28 (q, 2H), 2.46 (s, 3H), 1.50 (d, 6H), 1.34 (t, 3H). LCMS Rt=3.25 min in 7.0 min chromatography, 0-60AB, MS ESI calcd. $C_{10}H_{17}N_2O_2$ $[M+H]^+$ 197.1, found 197.0.

A-57:

To a solution of ethyl 1-isopropyl-3-methyl-pyrazole-4-carboxylate (300 mg, 1.53 mmol) in ethanol (5 mL) was slowly added a solution of NaOH (122.29 mg, 3.06 mmol) in water (5 mL). The resulting mixture was stirred at 25° C. for 2 hours. The mixture was concentrated under reduced pressure to remove the EtOH. To the aqueous phase was added 1N HCl (30 mL) to adjust the pH=2 and the mixture was diluted with EtOAc (10 mL). The phases were separated, and the organic phase was washed with brine (10 mL), dried over $Na_2SO_4$ then concentrated to give the crude product (210 mg, 1.22 mmol, 80% yield) as a solid. LCMS Rt=0.61 min in 2.0 min chromatography, 10-80AB, MS ESI calcd. $C_8H_{13}N_2O_2$ $[M+H]^+$ 169.1, found 168.8.

52:

A mixture of 1-isopropyl-3-methyl-pyrazole-4-carboxylic acid (100 mg, 0.59 mmol), HOBt (160.69 mg, 1.19 mmol), EDCI (227.96 mg, 1.19 mmol), DIPEA (0.33 mL, 2.38 mmol) and (1S)-1-[3-(m-tolyl)-1,2,4-oxadiazol-5-yl] ethanamine (120.84 mg, 0.59 mmol) in DCM (10 mL) was stirred at 25° C. for 16 hours. The mixture was concentrated, and the residue was diluted with $H_2O$ (20 mL) and then extracted with EtOAc (20 mL×2). The combined organic phase was washed with water (20 mL) and brine (20 mL), dried over $Na_2SO_4$, filtered and concentrated to give the crude product. The crude product was purified by prep-HPLC (Boston Prime (150 mm×30 mm, 5 μm), A=$H_2O$ (0.05% $NH_4OH$) and B=$CH_3CN$; 40-60% B over 9 min) to give the product. Analytical SFC (Column: Daicel CHIRALPAK AS-3 150 mm×4.6 mm I.D., 3 μm, mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C., ABPR: 1500 psi) showed two peaks at 2.52 min (11.1%) and 2.73 min (main peak, 88.9%). Note: the condensation reaction leads to some racemization. The product was separated by SFC (Daicel CHIRALPAK AS-H (250 mm×30 mm, 5 μm); A=$CO_2$ and B=EtOH (0.1% $NH_3H_2O$); 38° C.; 60 mL/min; 20% B; 8 min run; 10 injections, Rt of peak 1=4.8 min, Rt of peak 2=6 min) to give the product (50.77 mg, 0.14 mmol, 24% yield) (Rt=2.55 min in analytical SFC) as a solid. $^1H$ NMR (400 MHz, $CD_3CN$) $\delta_H$=7.96 (s, 1H), 7.86 (s, 1H), 7.83 (br d, 1H), 7.44-7.36 (m, 2H), 7.04 (br d, 1H), 5.46-5.37 (m, 1H), 4.47-4.36 (m, 1H), 2.41 (s, 3H), 2.36 (s, 3H), 1.66 (d, 3H), 1.44 (d, 6H). LCMS Rt=1.20 min in 2.0 min chromatography, 10-80AB, MS ESI calcd. $C_{19}H_{24}N_5O_2$ $[M+H]^+$ 354.2, found 354.1.

Example 35. Synthesis of 55

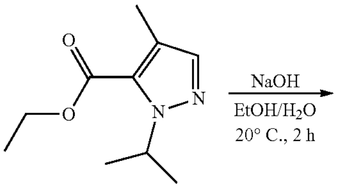

A-58

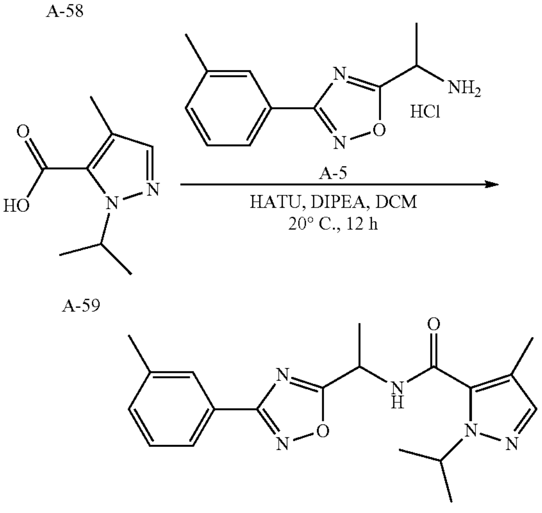

A-5

A-59

55

A-59:

To a solution of ethyl 2-isopropyl-4-methyl-pyrazole-3-carboxylate (220 mg, 1.12 mmol) in ethanol (5 mL) was added a solution of NaOH (134.52 mg, 3.36 mmol) in water (5 mL). The mixture was stirred at 20° C. for 2 hours. The reaction mixture was concentrated to give a residue and the residue was diluted with $H_2O$ (30 mL) and extracted with EtOAc (20 mL×1). To the aqueous phase was added 1N HCl (20 mL) to adjust pH=1 and it was diluted with $H_2O$ (10 mL). The mixture was extracted with EtOAc (50 mL×2). The combined organic phase was washed with brine (70 mL), dried over $Na_2SO_4$, filtered and concentrated to give the product (130 mg) as a solid. LCMS $R_t$=0.70 min in 2.0 min chromatography, 5-95AB, MS ESI calcd. for $C_8H_{13}N_2O_2$ $[M+H]^+$ 169.09, found 169.0.

55:

To a mixture of 2-isopropyl-4-methyl-pyrazole-3-carboxylic acid (129.45 mg, 0.77 mmol), HATU (315.92 mg, 0.83 mmol), DIPEA (0.29 mL, 1.66 mmol) in DCM (8 mL) was added 1-[3-(m-tolyl)-1,2,4-oxadiazol-5-yl]ethanamine hydrochloride (100 mg, 0.42 mmol) and the reaction mixture was stirred at 20° C. for 12 hours. The mixture was concentrated and diluted with $H_2O$ (10 mL) then extracted with EtOAc (20 mL×2). The combined organic layer was washed with brine (30 mL) and dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 44-74% B over 9 min) to give the product (75.42 mg, 213.4 μmol, 51% yield) as an oil. $^1H$ NMR (400 MHz, DMSO-$d_6$) $\delta_H$=9.17 (d, 1H), 7.85-7.76 (m, 2H), 7.49-7.39 (m, 2H), 7.33 (s, 1H), 5.42 (quin, 1H), 4.80 (spt, 1H), 2.39 (s, 3H), 2.15 (s, 3H), 1.65 (d, 3H), 1.36 (d, 6H). LCMS $R_t$=1.24 min in 2.0 min chromatography, 10-80AB, MS ESI calcd. $C_{19}H_{24}N_5O_2$ $[M+H]^+$ 354.19, found 354.0.

Example 36. Synthesis of 56 and 57

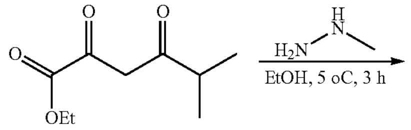

A-60a

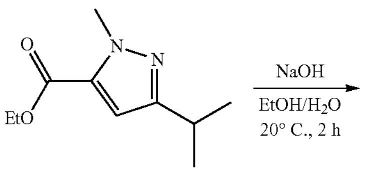

A-60b

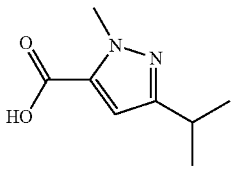

A-60

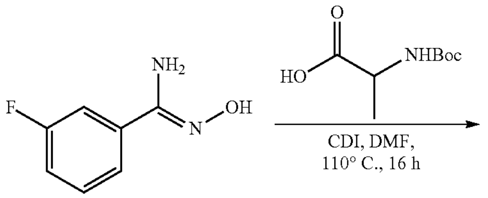

A-10

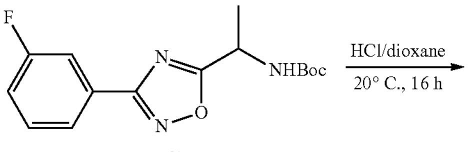

A-61

-continued

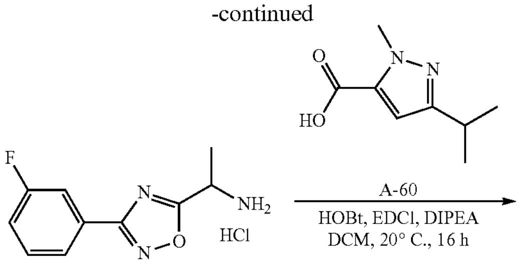

A-62

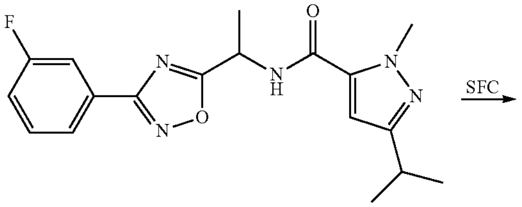

A-63

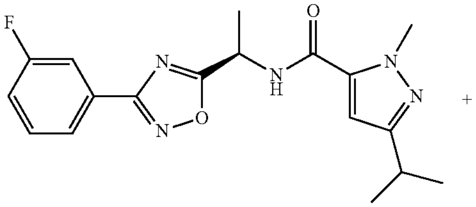

56

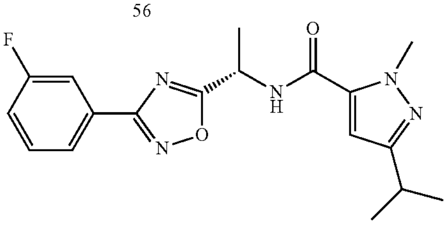

57

A-60b:

To a solution of ethyl 5-methyl-2,4-dioxo-hexanoate (2 g, 10.74 mmol) in ethanol (20 mL) at 5° C. was added methylhydrazine (1.36 g, 11.81 mmol, 40% in $H_2O$) in a dropwise manner. The reaction mixture was stirred at 5° C. for 3 hours and then was concentrated. The residue was purified by flash chromatography on silica gel (EtOAc in PE=0% to 10% to 50%) to give the product (700 mg, 3.57 mmol, 33% yield) as an oil. $^1H$ NMR (400 MHz, $CDCl_3$) $\delta_H$=6.70-6.59 (m, 1H), 4.43-4.24 (m, 2H), 4.12 (s, 3H), 3.07-2.77 (m, 1H), 1.38 (t, 3H), 1.26 (d, 6H).

A-60:

A mixture of ethyl 5-isopropyl-2-methyl-pyrazole-3-carboxylate (700 mg, 3.57 mmol) and NaOH (428.03 mg, 10.70 mmol) in ethanol (10 mL) and water (10 mL) was stirred at 20° C. for 2 hours. The reaction mixture was concentrated under reduced pressure to remove the EtOH and then extracted with EtOAc (10 mL). The aqueous phase was acidified with HCl (1N) to pH~2 and extracted with EtOAc (20 mL×2). The combined organic phase was washed with brine (15 mL), dried over $Na_2SO_4$, filtered and concentrated to give the crude product (400 mg) as an oil. $^1H$ NMR (400 MHz, DMSO-$d_6$) $\delta_H$=13.17 (br s, 1H), 6.62 (s, 1H), 3.99 (s, 3H), 2.91-2.80 (m, 1H), 1.17 (d, 6H).

A-61:

A mixture of 2-(tert-butoxycarbonylamino)propanoic acid (1227.52 mg, 6.49 mmol) and CDI (1157.16 mg, 7.14 mmol) in DMF (20 mL) was stirred at 15° C. for 1 hour and then 3-fluoro-N'-hydroxy-benzamidine (1000 mg, 6.49 mmol) was added. The reaction mixture was then stirred at 110° C. for 16 hours. The mixture was cooled then diluted with $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by flash chromatography on silica gel (EtOAc in PE=0% to 30% to 50%) to give the product (600 mg, 1.95 mmol, 30% yield) as a solid. $^1H$ NMR (400 MHz, $CDCl_3$) $\delta_H$=7.89-7.78 (m, 2H), 7.76-7.70 (m, 1H), 7.68-7.60 (m, 1H), 7.50-7.43 (m, 1H), 5.02-4.93 (m, 1H), 1.51 (d, 3H), 1.40 (s, 9H).

A-62:

To a mixture of tert-butyl N-[1-[3-(3-fluorophenyl)-1,2,4-oxadiazol-5-yl]ethyl]carbamate (200 mg, 0.65 mmol) in 1,4-dioxane (5 mL) was added 4M HCl in 1,4-dioxane (10 mL, 40 mmol). The reaction mixture was stirred at 20° C. for 16 hours. The reaction mixture was concentrated to give the crude product (200 mg) as a an oil. LCMS $R_t$=0.61 min in 1.5 min chromatography, 5-95AB, MS ESI calcd. for $C_{10}H_NFN_3O$ [M+H] 208.1, found 207.7.

A-63:

A mixture of 5-isopropyl-2-methyl-pyrazole-3-carboxylic acid (120 mg, 0.71 mmol), DIPEA (0.62 mL, 3.57 mmol), HOBt (192.82 mg, 1.43 mmol) EDCI (205.16 mg, 1.07 mmol) and 1-[3-(3-fluorophenyl)-1,2,4-oxadiazol-5-yl] ethanamine hydrochloride (173.85 mg, 0.71 mmol) in DCM (15 mL) was stirred at 20° C. for 16 hours. The mixture was diluted with $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by prep-HPLC (Waters)(Bridge (150 mm×25 mm, 5 μm), A=$H_2O$ (10 mM $NH_4HCO_3$) and B=$CH_3CN$; 24-54% B over 8 min) to give the product (180 mg, 0.50 mmol, 70% yield) as an oil. LCMS $R_t$=0.88 min in 1.5 min chromatography, 5-95AB, MS ESI calcd. for $C_{18}H_{21}FN_5O_2$ $[M+H]^+$ 358.2, found 358.1.

56 & 57:

Analytical SFC (Daicel CHIRALPAK IC-3 (150 mm×4.6 mm, 3 μm), mobile phase: A: $CO_2$ B: IPA (0.05% DEA), gradient: from 5% to 40% of B in 5.5 min and hold 40% for 3 min, then 5% of B for 1.5 min, flow rate: 2.5 mL/min, column temp: 40° C.) showed two peaks at 3.55 min and 4.32 min. The product was separated by SFC (Daicel CHIRALPAK IC (250 mm×30 mm, 5 μm); A=$CO_2$ and B=i-PrOH; 38° C.; 65 mL/min; 30% B; 7 min run; 7 injections, Rt of peak 1=3.5 min, Rt of peak 2=4.7 min) to give the enantiomer 1, randomly assigned as 56 (75.09 mg, 0.21 mmol, 41% yield) (Rt=3.55 min in analytical SFC) as an oil and enantiomer 2, randomly assigned as 57 (73.93 mg, 0.21 mmol, 41% yield) (Rt=4.32 min in analytical SFC) as an oil.

56:

$^1H$ NMR (400 MHz, $CDCl_3$) $\delta_H$=7.91-7.86 (m, 1H), 7.82-7.76 (m, 1H), 7.51-7.44 (m, 1H), 7.26-7.19 (m, 1H), 6.56 (br d, 1H), 6.45 (s, 1H), 5.65-5.56 (m, 1H), 4.12 (s, 3H), 3.06-2.94 (m, 1H), 1.76 (d, 3H), 1.29 (d, 6H). LCMS $R_t$=1.26 min in 2 min chromatography, 10-80AB, MS ESI calcd. for $C_{18}H_{21}FN_5O_2$ $[M+H]^+$ 358.2, found 358.1.

57:

$^1H$ NMR (400 MHz, $CDCl_3$) $\delta_H$=7.91-7.86 (m, 1H), 7.82-7.75 (m, 1H), 7.52-7.44 (m, 1H), 7.26-7.19 (m, 1H), 6.56 (br d, 1H), 6.45 (s, 1H), 5.66-5.56 (m, 1H), 4.12 (s, 3H), 3.05-2.95 (m, 1H), 1.76 (d, 3H), 1.29 (d, 6H). LCMS $R_t$=1.26 min in 2 min chromatography, 10-80AB, MS ESI calcd. for $C_{18}H_{21}FN_5O_2$ $[M+H]^+$358.2, found 358.1.

Example 37. Synthesis of 58

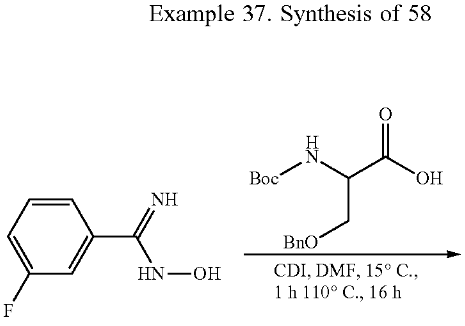

A-10

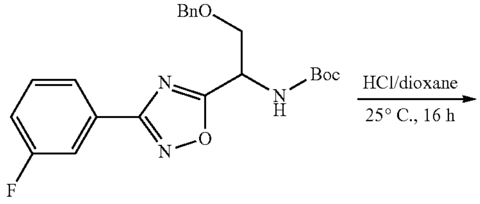

A-64

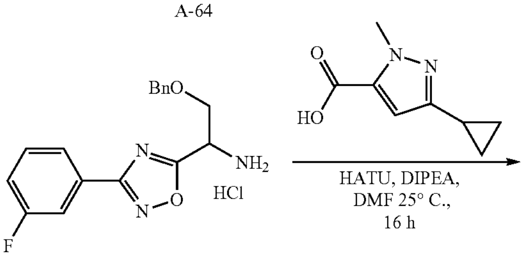

A-65

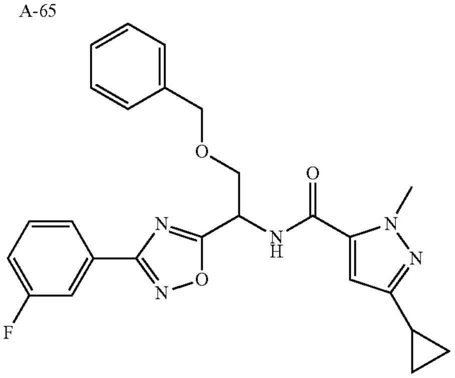

58

A-64:

A mixture of 3-benzyloxy-2-(tert-butoxycarbonylamino) propanoic acid (843.03 mg, 2.85 mmol) and CDI (462.86 mg, 2.85 mmol) in DMF (6 mL) was stirred at 15° C. for 1 hour and then 3-fluoro-N-hydroxy-benzamidine (400 mg, 2.6 mmol) was added. The reaction mixture was stirred at 110° C. for 16 hours. After cooling to room temperature, the mixture was diluted with water (20 mL) and extracted with EtOAc (30 mL×2). The combined organic phase was washed with brine (20 mL), dried over $Na_2SO_4$, filtered and concentrated to give the crude product. The crude product was purified by flash chromatography on silica gel (EtOAc in PE=0% to 60%) to give the product (260 mg, 0.58 mmol, 22% yield) as an oil. LCMS $R_t$=1.45 min in in 2.0 min chromatography, 10-80AB, MS ESI calcd. for $C_{22}H_{25}FN_3O_4$ $[M+H-tBu]^+$ 358.1, found 358.1.

A-65:

A mixture of tert-butyl N-[2-benzyloxy-1-[3-(3-fluorophenyl)-1,2,4-oxadiazol-5-yl] ethyl]carbamate (260 mg, 0.63 mmol) and 4M HCl in 1,4-dioxane (5 mL, 20 mmol) was stirred at 25° C. for 16 hours. The mixture was concentrated to give the product (300 mg, 0.59 mmol, 94% yield) as a solid. LCMS $R_t$=0.99 min in in 2.0 min chromatography, 10-80AB, MS ESI calcd. for $C_{17}H_{17}FN_3O_2$ $[M+H]^+$314.1, found 314.0.

58:

To a mixture of 5-cyclopropyl-2-methyl-pyrazole-3-carboxylic acid (171.03 mg, 1.03 mmol), HATU (391.33 mg, 1.03 mmol) and DIPEA (0.45 mL, 2.57 mmol) in DMF (3 mL) was added 2-benzyloxy-1-[3-(3-fluorophenyl)-1,2,4-oxadiazol-5-yl]ethanamine hydrochloride (300 mg, 0.86 mmol) and the mixture was stirred at 25° C. for 16 hours. The mixture was diluted with water (20 mL) and extracted with EtOAc (20 mL×3). The combined organic phase was washed with water (20 mL×2) and brine (20 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 55-85% B over 9 min) to give the product (49.27 mg, 0.11 mmol, 12% yield) as an oil. $^1H$ NMR (400 MHz, DMSO-$d_6$) δ=9.16 (d, 1H), 7.86 (d, 1H), 7.74 (m, 1H), 7.64 (m, 1H), 7.48 (m, 1H), 7.37-7.21 (m, 5H), 6.69 (s, 1H), 5.61 (q, 1H), 4.59 (s, 2H), 4.02 (m, 2H), 3.93 (s, 3H), 1.97-1.76 (m, 1H), 0.95-0.84 (m, 2H), 0.69-0.56 (m, 2H). LCMS $R_t$=1.31 min in in 2.0 min chromatography, 10-80AB, MS ESI calcd. for $C_{25}H_{25}FN_5O_3$ $[M+H]^+$ 462.1, found 462.1.

Example 38. Synthesis of 54

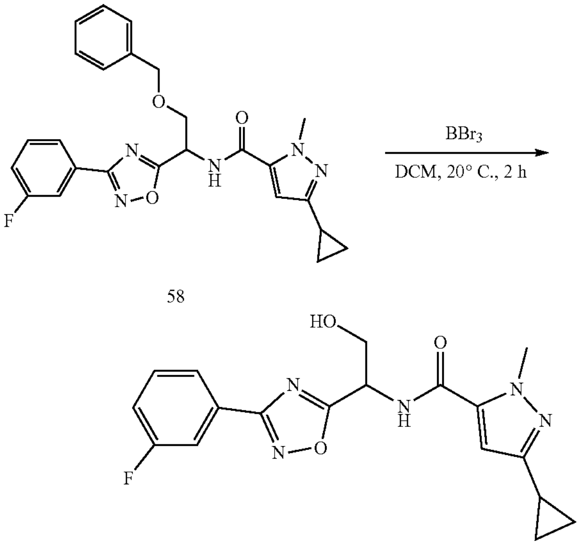

58

54

To a mixture of N-[2-benzyloxy-1-[3-(3-fluorophenyl)-1,2,4-oxadiazol-5-yl]ethyl]-5-cyclopropyl-2-methyl-pyrazole-3-carboxamide (70 mg, 0.15 mmol) in DCM (3 mL) was added $BBr_3$ (0.03 mL, 0.30 mmol) and the mixture was stirred at 20° C. for 2 hours. The reaction mixture was diluted with $H_2O$ (5 mL) and extracted with DCM (5 mL×2). The combined organic phase was washed with brine (10 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 39-69% B over 9 min) to give the product (21.67 mg, 0.06 mmol, 38% yield) as a solid. $^1H$ NMR (400 MHz, $CDCl_3$) $\delta_H$=9.01 (d, 1H), 7.87 (d, 1H), 7.80-7.73 (m, 1H), 7.65 (m, 1H), 7.48 (m, 1H), 6.73 (s, 1H), 5.26-5.44 (m, 2H), 3.88-4.05 (m, 5H), 1.81-1.99 (m, 1H), 0.79-0.99 (m, 2H), 0.53-0.74 (m, 2H). LCMS $R_t$=1.12 min in 2.0 min chromatography, 10-80AB, MS ESI calcd. for $C_{18}H_{19}FN_5O_3$ $[M+H]^+$ 372.1, found 372.1.

Example 39. Synthesis of 59

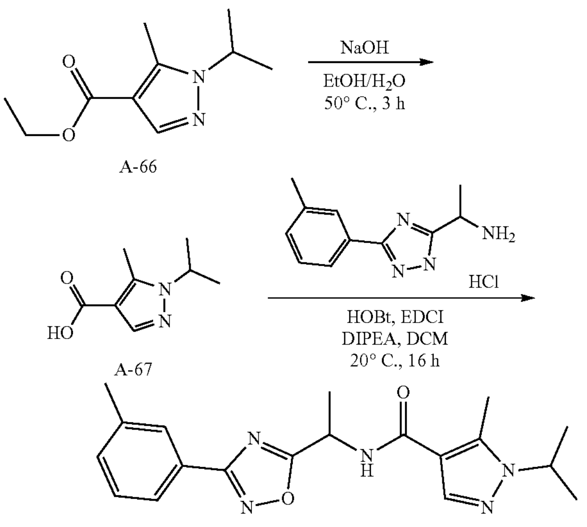

59

A-67:

To a mixture of ethyl 1-isopropyl-5-methyl-pyrazole-4-carboxylate (650 mg, 3.31 mmol) in ethanol (5 mL) and water (5 mL) was added NaOH (264.97 mg, 6.62 mmol), and the mixture was stirred at 50° C. for 3 hours. After cooling to room temperature, the reaction mixture was concentrated under reduced pressure to remove most of the ethanol then the residue was diluted with $H_2O$ (10 mL) and the mixture was washed with EtOAc (5 mL×2). The pH of the aqueous phase was adjusted to pH~2 with 1N HCl, then extracted with EtOAc (20 mL×2). The combined organic phase was washed with $H_2O$ (10 mL) and brine (10 mL), dried over $Na_2SO_4$, filtered and concentrated to give the product (520 mg, 3.09 mmol, 93% yield) as a solid. LCMS $R_t$=0.63 min in 1.5 min chromatography, 10-80AB, MS ESI calcd. for $C_8H_{13}N_2O_2$ $[M+H]^+$ 169.1, found 169.0.

59:

A mixture of 1-[3-(m-tolyl)-1,2,4-oxadiazol-5-yl]ethanamine (241.68 mg, 1.19 mmol), HOBt (321.37 mg, 2.38 mmol), DIPEA (0.62 mL, 3.57 mmol), EDCI (455.91 mg, 2.38 mmol) and 1-isopropyl-5-methyl-pyrazole-4-carboxylic acid (200 mg, 1.19 mmol) in DCM (10 mL) was stirred at 20° C. for 16 hours The mixture was concentrated to give a residue. The residue was dissolved in EtOAc (20 mL) and washed with sat. $NH_4Cl$ (10 mL), water (10 mL) and brine (10 mL), dried over $Na_2SO_4$, filtered and concentrated to give the crude product. The crude product was partially purified by flash chromatography on silica gel (EtOAc in PE=0% to 40% to 100%) to give the impure product. The impure product was purified by prep-HPLC (Boston Prime C18 (150 mm×30 mm, 5 μm), A=$H_2O$ (0.05% $NH_4OH$) and B=$CH_3CN$; 50-70% B over 9 min) to give the product (17.06 mg, 48.1 mol, 4% yield) as a solid. $^1$H NMR (400 MHz, $CDCl_3$) $\delta_H$=7.93-7.85 (m, 2H), 7.77 (s, 1H), 7.41-7.30 (m, 2H), 6.38 (br d, 1H), 5.64 (quin, 1H), 4.50 (spt, 1H), 2.59 (s, 3H), 2.43 (s, 3H), 1.74 (d, 3H), 1.50 (d, 6H). LCMS $R_t$=1.24 min in 2.0 min chromatography, 10-80AB, MS ESI calcd. for $C_{19}H_{24}N_5O_2$ [M+H]$^+$ 354.2, found 354.2.

Example 40. Synthesis of 60 and 61

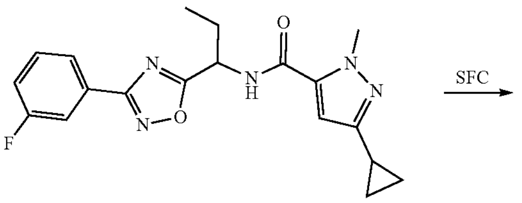

48

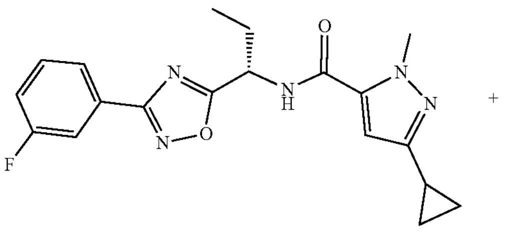

60

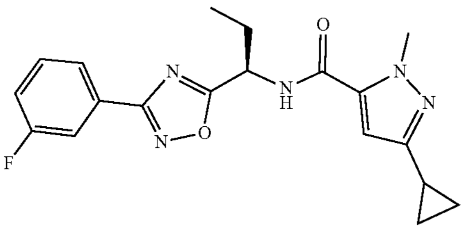

61

Analytical SFC (Daicel CHIRALCEL OJ-3 (150 mm×4.6 mm, 3 μm), mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C.) showed two peaks at 3.00 min and Rt=3.93 min). The product was separated by SFC (Daicel CHIRALCEL OJ-H (250 mm×30 mm, 5 μm); A=$CO_2$ and B=ethanol (0.1% DEA); 38° C.; 60 mL/min; 20% B; 7 min run; 5 injections, Rt of peak 1=5.2 min, Rt of peak 2=5.4 min) to give the enantiomer 1, randomly assigned as 60 (16.59 mg, 44.9 μmol, 24% yield) (Rt=3.00 min in analytical SFC) as oil and the enantiomer 2, randomly assigned as 61 (26.44 mg, 71.6 μmol, 38% yield) (Rt=3.93 min in analytical SFC) as an oil.

60:

$^1$H NMR (400 MHz, $CDCl_3$) $\delta_H$=7.88 (d, 1H), 7.84-7.75 (m, 1H), 7.50-7.42 (m, 1H), 7.26-7.20 (m, 1H), 6.50 (br d, 1H), 6.32 (s, 1H), 5.53-5.46 (m, 1H), 4.09 (s, 3H), 2.23-2.11 (m, 1H), 2.10-1.98 (m, 1H), 1.98-1.89 (m, 1H), 1.06 (t, 3H), 0.99-0.92 (m, 2H), 0.78-0.73 (m, 2H). LCMS $R_t$=1.23 min in 2.0 min chromatography, 10-80AB, MS ESI calcd. for $C_{19}H_{21}FN_5O_2$ [M+H]$^+$ 369.16, found 370.0.

61:

$^1$H NMR (400 MHz, $CDCl_3$) $\delta_H$=7.88 (d, 1H), 7.83-7.74 (m, 1H), 7.51-7.41 (m, 1H), 7.27-7.20 (m, 1H), 6.50 (br d, 1H), 6.32 (s, 1H), 5.53-5.45 (m, 1H), 4.09 (s, 3H), 2.22-2.11 (m, 1H), 2.11-1.98 (m, 1H), 1.98-1.87 (m, 1H), 1.06 (t, 3H), 0.98-0.91 (m, 2H), 0.78-0.73 (m, 2H). LCMS $R_t$=1.27 min in 2.0 min chromatography, 10-80AB, MS ESI calcd. for $C_{19}H_{21}FN_5O_2$ [M+H]$^+$ 369.16, found 370.1.

Example 41. Synthesis of 62 and 63

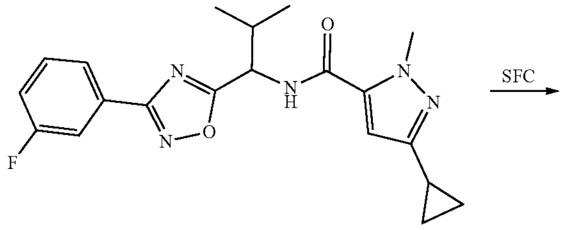

45

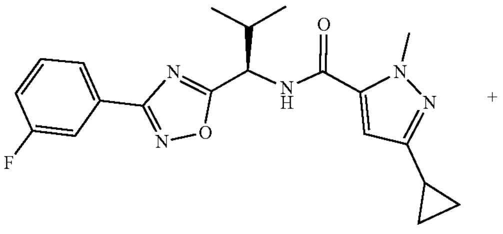

62

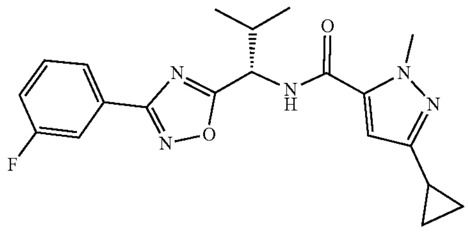

63

Analytical SFC (Daicel CHIRALCEL OJ-3 (150 mm×4.6 mm, 3 μm), mobile phase: A: $CO_2$ B: ethanol (0.05% DEA) gradient: from 5% to 40% of B in 5 min and hold 40% for 2.5 min, then 5% of B for 2.5 min, flow rate: 2.5 mL/min, column temp: 35° C. ABPR: 1500 psi) showed two peaks at 2.60 min and Rt=3.27 min. The product was purified by SFC (Daicel CHIRALCEL OJ-H (250 mm×30 mm, 5 μm); A=$CO_2$ and B=EtOH (0.1% $NH_3H_2O$); 38° C.; 60 mL/min; 15% B; 10 min run; 5 injections, Rt of peak 1=5.7 min, Rt of peak 2=8.5 min) to give the enantiomer 1, randomly assigned as 62 (22.57 mg, 58.9 μmol, 33% yield) (Rt=2.60 min in analytical SFC) as a solid and the enantiomer 2, randomly assigned as 63 (25.47 mg, 66.2 μmol, 37% yield) (Rt=3.27 min in analytical SFC) as a solid.

62:

$^1$H NMR (400 MHz, DMSO-$d_6$) $\delta_H$=9.02 (d, 1H), 7.86 (d, 1H), 7.74 (br d, 1H), 7.69-7.60 (m, 1H), 7.47 (dt, 1H), 6.75 (s, 1H), 5.13 (t, 1H), 3.91 (s, 3H), 2.46-2.36 (m, 1H), 1.92-1.84 (m, 1H), 1.05 (d, 3H), 0.95-0.85 (m, 5H), 0.66-0.60 (m, 2H). LCMS $R_t$=1.33 min in 2.0 min chromatography, 10-80AB, MS ESI calcd. for $C_{20}H_{23}FN_5O_2$ [M+H]$^+$ 384.2, found 384.2.

63:

$^1$H NMR (400 MHz, DMSO-$d_6$) $\delta_H$=9.02 (d, 1H), 7.86 (d, 1H), 7.74 (br d, 1H), 7.70-7.60 (m, 1H), 7.47 (dt, 1H), 6.75 (s, 1H), 5.13 (t, 1H), 3.91 (s, 3H), 2.46-2.36 (m, 1H), 1.92-1.84 (m, 1H), 1.05 (d, 3H), 0.96-0.85 (m, 5H), 0.66-0.59 (m, 2H). LCMS $R_t$=1.33 min in 2.0 min chromatography, 10-80AB, MS ESI calcd. for $C_{20}H_{23}FN_5O_2$ $[M+H]^+$ 384.2, found 384.2.

Example 42. Synthesis of 64 and 65

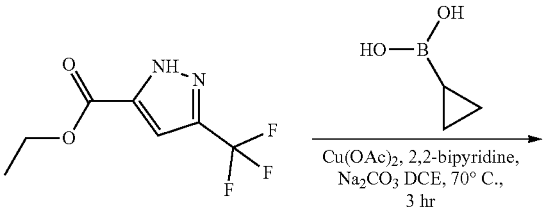

A-71a

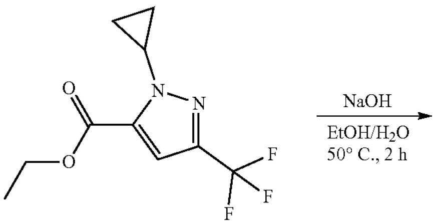

A-71b

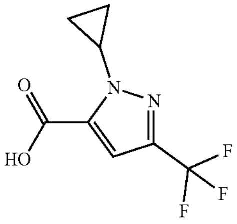

A-71

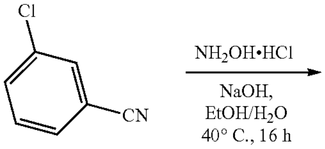

A-11

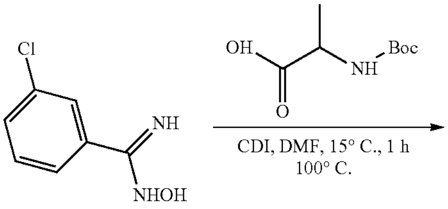

A-12

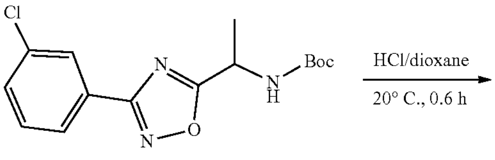

A-68

-continued

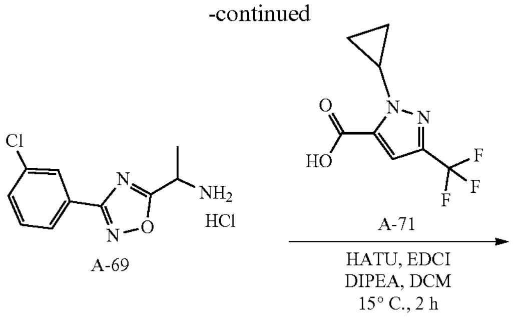

A-69 A-71

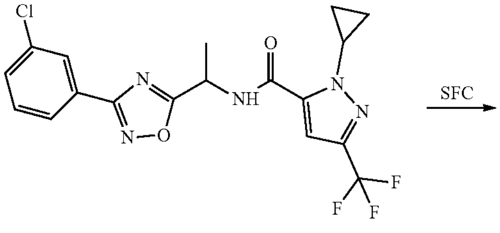

A-70

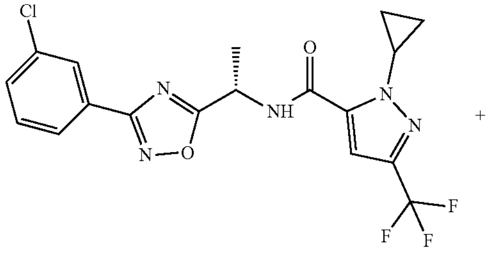

64

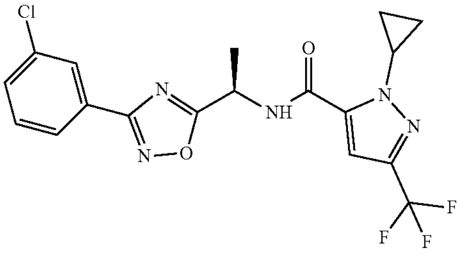

65

A-71b:

To a solution of ethyl 3-(trifluoromethyl)-1H-pyrazole-5-carboxylate (500 mg, 2.4 mmol), cyclopropylboronic acid (412.7 mg, 4.8 mmol) and $Na_2CO_3$ (509.22 mg, 4.8 mmol) in DCE (7 mL) was added a solution of $Cu(OAc)_2$ (436.32 mg, 2.4 mmol) and 2,2-bipyridine (450.25 mg, 2.88 mmol) in DCE (14 mL). The reaction mixture was stirred at 70° C. for 4 hours. After cooling to room temperature, the mixture was diluted with sat. $NH_4C_1$ (20 mL) and then extracted with EtOAc (20 mL×2). The combined organic phase was washed with brine (40 mL), dried over $Na_2SO_4$, filtered and concentrated to give the crude product. The crude product was purified by flash chromatography on silica gel (EtOAc in PE=0% to 5% to 50%) to give the product (180 mg, 0.73 mmol, 30% yield) as an oil. $^1$H NMR (400 MHz, $CDCl_3$) $\delta_H$=7.07 (s, 1H), 4.43-4.36 (m, 3H), 1.41 (t, 3H), 1.36-1.30 (m, 2H), 1.14-1.07 (m, 2H).

A-71:

To a solution of ethyl 2-cyclopropyl-5-(trifluoromethyl) pyrazole-3-carboxylate (180 mg, 0.73 mmol) in ethanol (3 mL) was added a solution of NaOH (87.03 mg, 2.18 mmol) in water (3 mL). The reaction mixture was stirred at 50° C.

for 2 hours. After cooling to room temperature, the reaction mixture was diluted with $H_2O$ (20 mL) and washed with EtOAc (20 mL×1). The pH of the aqueous phase was adjusted to pH=1 by adding 1N HCl (20 mL) and then diluted with $H_2O$ (10 mL). The mixture was extracted with EtOAc (50 mL×2). The combined organic phase was washed with brine (70 mL), dried over $Na_2SO_4$, filtered and concentrated to give the product (160 mg, 661.7 μmol, 84% yield) as an oil. LCMS $R_t$=0.79 min in 1.5 min chromatography, 5-95AB, MS ESI calcd. $C_8H_8F_3N_2O_2$ $[M+H]^+$ 221.05, found 221.1.

A-12:

A mixture of 3-chlorobenzonitrile (1.2 g, 8.72 mmol), $NH_2OH$ HCl (1818.45 mg, 26.17 mmol) and NaOH (1046.74 mg, 26.17 mmol) in ethanol (9 mL) and water (3 mL) was stirred at 40° C. for 16 hours. After cooling to room temperature, the reaction mixture was concentrated under reduced pressure to remove most of the EtOH and then diluted with $H_2O$ (100 mL). The mixture was extracted with EtOAc (150 mL×2). The combined organic phase was washed with brine (100 mL), dried over $Na_2SO_4$, filtered and concentrated to give the crude product (1760 mg, 6.62 mmol, 76% yield) as a solid. LCMS $R_t$=0.21 min in 1.5 min chromatography, 5-95AB, MS ESI calcd. for $C_7H_8ClN_2O$ $[M+H]^+$ 171.02, found 170.9.

A-68:

A mixture of 2-(tert-butoxycarbonylamino)propanoic acid (1.24 g, 6.54 mmol) and CDI (1.17 g, 7.19 mmol) in DMF (60 mL) was stirred at 15° C. for 1 hour and then 3-chloro-N'-hydroxy-benzamidine (1.74 g, 6.54 mmol) was added. The reaction mixture was then stirred at 100° C. for 16 hours. After cooling to room temperature, the mixture was diluted with $NH_4Cl$ (100 mL) and extracted with EtOAc (50 mL×3). The combined organic phase was washed with brine (100 mL), dried over $Na_2SO_4$, filtered and concentrated to give the crude product. The crude product was purified by chromatography flash column on silica gel (EtOAc in PE=0% to 30% to 50%) to give the product (1480 mg, 4.29 mmol, 66% yield) as an oil. $^1H$ NMR (400 MHz, $CDCl_3$) $\delta_H$=8.09 (s, 1H), 7.97 (d, 1H), 7.52-7.46 (m, 1H), 7.45-7.39 (m, 1H), 5.26-5.05 (m, 2H), 1.64 (br d, 3H), 1.47 (s, 9H). LCMS $R_t$=0.94 min in 1.5 min chromatography, 5-95AB, MS ESI calcd. for $C_{15}H_{19}ClN_3O_3$ $[M+H-t-Bu]^+$ 268.1, found 268.1.

A-69:

To tert-butyl N-[1-[3-(3-chlorophenyl)-1,2,4-oxadiazol-5-yl]ethyl]carbamate (1480 mg, 4.57 mmol) was added 4 N HCl/1,4-dioxane (10 mL, 40 mmol) and the reaction mixture was stirred at 20° C. for 0.5 hours. The mixture was concentrated to give the crude product (1160 mg, 4.30 mmol, 94% yield) as a solid. LCMS $R_t$=0.66 min in 1.5 min chromatography, 5-95AB, MS ESI calcd. $C_{10}H_{11}ClN_3O$ $[M+H]^+$ 224.05, found 224.0.

A-70:

To a mixture of 2-cyclopropyl-5-(trifluoromethyl)pyrazole-3-carboxylic acid (160 mg, 0.73 mmol), HATU (292.35 mg, 0.77 mmol), DIPEA (0.27 mL, 1.54 mmol) in DCM (8 mL) was added 1-[3-(3-chlorophenyl)-1,2,4-oxadiazol-5-yl]ethanamine hydrochloride (100 mg, 0.38 mmol) and the mixture was stirred at 15° C. for 2 hours. The mixture was concentrated and diluted with $H_2O$ (10 mL) and then extracted with EtOAc (20 mL×2). The organic layer was washed brine (30 mL) and dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 59-89% B over 8 min) to give the product (140 mg, 322.6 μmol, 84% yield) as a solid. LCMS $R_t$=0.98 min in 1.5 min chromatography, 5-95AB, MS ESI calcd. $C_{18}H_{16}ClF_3N_5O_2$ $[M+H]^+$ 426.19, found 426.1.

64 & 65:

Analytical SFC (column: Regis (S,S) Whelk-O1 (100 mm×4.6 mm I.D., 5.0 μm), mobile phase: A: $CO_2$ B: IPA (0.05% DEA), gradient: from 5% to 40% of B in 5.5 min and then 5% of B for 1.5 min, flow rate: 2.5 mL/min, column tem: 35° C.) showed two peaks at 3.78 min and 4.30 min. The product was purified by SFC (Regis (S,S) Whelk-01 (250 mm×30 mm, 5 μm); A=$CO_2$ and B=IPA (0.1% DEA); 38° C.; 60 mL/min; 35% B; 9 min run; 8 injections, Rt of peak 1=4.7 min, Rt of peak 2=6.8 min) to give the enantiomer 1, randomly assigned as (54.51 mg, 128 μmol, 39% yield) (Rt=3.78 min in analytical SFC) as a solid and the enantiomer 2, randomly assigned as (55.53 mg, 130.4 μmol, 39% yield) (Rt=4.30 min in analytical SFC) as a solid.

65:

$^1H$ NMR (400 MHz, $CDCl_3$) $\delta_H$=8.08 (t, 1H), 7.97 (td, 1H), 7.54-7.48 (m, 1H), 7.48-7.41 (m, 1H), 6.91 (s, 1H), 6.69 (br d, 1H), 5.63 (quin, 1H), 4.39 (tt, 1H), 1.79 (d, 3H), 1.40-1.28 (m, 2H), 1.16-1.05 (m, 2H). LCMS Rt=1.43 min in 2.0 min chromatography, 10-80AB, MS ESI calcd. for $C_{18}H_{16}ClF_3N_5O_2$ $[M+H]^+$ 426.09, found 426.0.

64:

$^1H$ NMR (400 MHz, $CDCl_3$) $\delta_H$=8.08 (t, 1H), 7.97 (td, 1H), 7.54-7.49 (m, 1H), 7.47-7.41 (m, 1H), 6.91 (s, 1H), 6.70 (br d, 1H), 5.63 (quin, 1H), 4.39 (tt, 1H), 1.79 (d, 3H), 1.39-1.29 (m, 2H), 1.16-1.05 (m, 2H). LCMS Rt=1.41 min in 2.0 min chromatography, 10-80AB, MS ESI calcd. for $C_{18}H_{16}ClF_3N_5O_2$ $[M+H]^+$ 426.09, found 426.0.

Example 43. Synthesis of 66

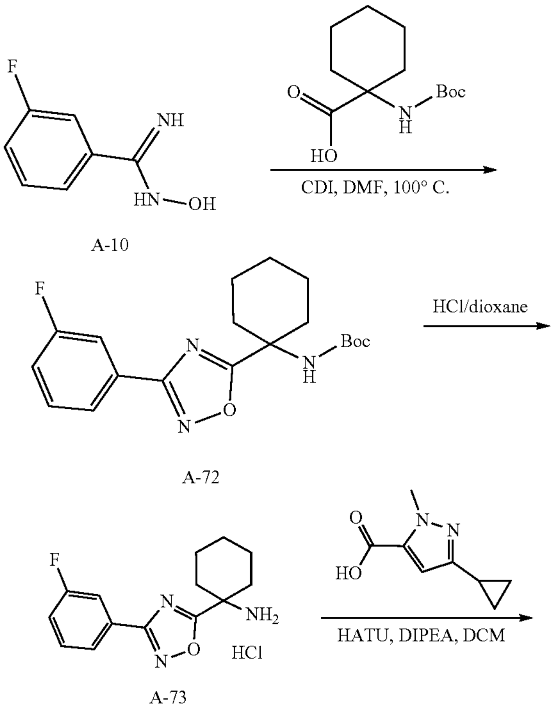

A-10

A-72

A-73

-continued

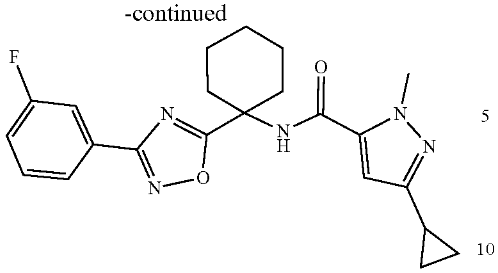

66

A-72:

A mixture of 1-(tert-butoxycarbonylamino)cyclohexanecarboxylic acid (0.79 g, 3.24 mmol) and CDI (0.58 g, 3.57 mmol) in DMF (10 mL) was stirred at 15° C. for 1 hour and then 3-fluoro-N-hydroxy-benzamidine (0.5 g, 3.24 mmol) was added. The reaction mixture was then stirred at 100° C. for 16 hours. After cooling to room temperature, the mixture was diluted with sat. $NH_4Cl$ (30 mL) and the mixture was extracted with EtOAc (20 mL×3). The combined organic phase was washed with brine (50 mL), dried over $Na_2SO_4$, filtered and concentrated to give the crude product. The crude product was purified by flash column chromatography on silica gel (EtOAc in PE=0% to 20% to 50%) to give the product (260 mg, 0.66 mmol, 20% yield) as a solid. LCMS $R_t$=0.98 min in 1.5 min chromatography, 5-95AB, MS ESI calcd. for $C_{19}H_{25}FN_3O_3$ $[M+H-t-Bu]^+$306.2, found 306.2.

A-73:

To tert-butyl N-[1-[3-(3-fluorophenyl)-1,2,4-oxadiazol-5-yl]cyclohexyl]carbamate (260 mg, 0.72 mmol) was added 4 M HCl in 1,4-dioxane (3 mL, 12 mmol) and the reaction mixture was stirred at 20° C. for 0.5 hours. The mixture was concentrated to give the crude product (210 mg, 705.3 μmol, 98% yield) as a solid. LCMS $R_t$=0.71 min in 1.5 min chromatography, 5-95AB, MS ESI calcd. for $C_{14}H_{17}FN_3O$ $[M+H]^+$ 262.13, found 262.2.

66:

To a mixture of HATU (254.54 mg, 0.67 mmol), 5-cyclopropyl-2-methyl-pyrazole-3-carboxylic acid (55.62 mg, 0.33 mmol), 1-[3-(3-fluorophenyl)-1,2,4-oxadiazol-5-yl]cyclohexanamine hydrochloride (100 mg, 0.33 mmol) in DCM (8 mL) was added DIPEA (0.23 mL, 1.34 mmol) and the mixture was stirred at 25° C. for 3.5 hours. The mixture was diluted with $H_2O$ (20 mL) and extracted with EtOAc (15 mL×2). The combined organic phase was washed with brine (20 mL) and dried over $Na_2SO_4$, filtered and concentrated to give the crude product. The crude product was purified by prep-HPLC (Welch Xtimate C18 (150×25 mm, 5 μm), A=$H_2O$ (0.04% $NH_4OH$+10 mM $NH_4HCO_3$) and B=$CH_3CN$; 60-90% B over 7.5 min) to give the product (26.87 mg, 65.6 μmol, 20% yield) as a solid. $^1H$ NMR (400 MHz, DMSO-$d_6$) $\delta_H$=8.68 (s, 1H), 7.85 (d, 1H), 7.76-7.70 (m, 1H), 7.67-7.58 (m, 1H), 7.50-7.41 (m, 1H), 6.73 (s, 1H), 3.81 (s, 3H), 2.33 (br d, 2H), 2.15-2.01 (m, 2H), 1.94-1.80 (m, 1H), 1.74-1.51 (m, 5H), 1.49-1.35 (m, 1H), 0.93-0.83 (m, 2H), 0.71-0.58 (m, 2H). LCMS $R_t$=1.32 min in 2.0 min chromatography, 10-80AB, MS ESI calcd. $C_{22}H_{25}FN_5O_2$ $[M+H]^+$ 410.19, found 410.0.

Example 44. Synthesis of 67

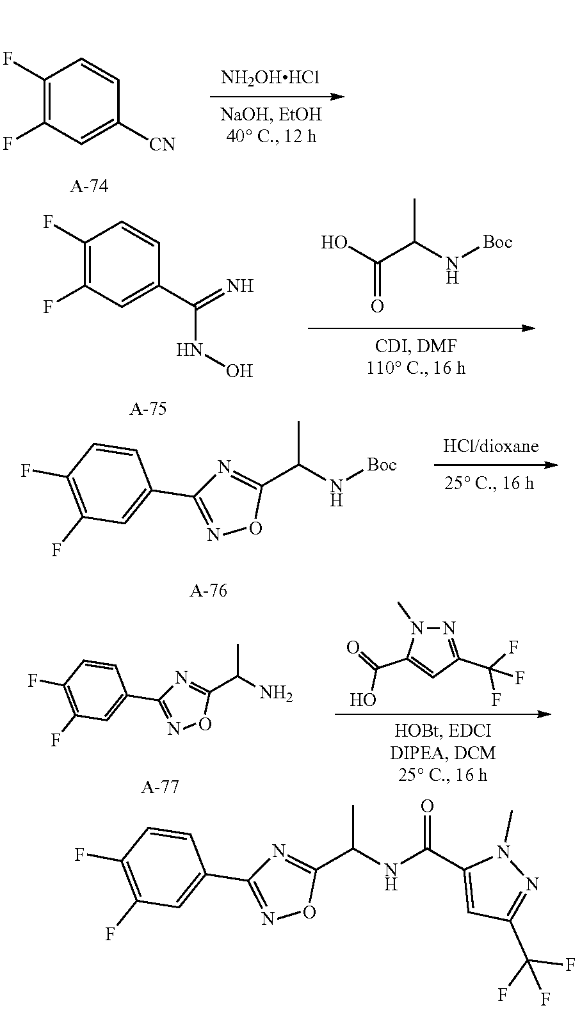

A-74

A-75

A-76

A-77

67

A-75:

A mixture of 3,4-difluorobenzonitrile (2 g, 14.38 mmol), hydroxylamine hydrochloride (3 g, 43.13 mmol) and NaOH (1.73 g, 43.13 mmol) in ethanol (24 mL) and water (8 mL) was stirred at 40° C. for 12 hours. After cooling to room temperature, the reaction mixture was concentrated under reduced pressure to remove most of the ethanol and then it was diluted with $H_2O$ (20 mL). The mixture was extracted with EtOAc (30 mL×2). The combined organic phase was washed with brine (15 mL), dried over $Na_2SO_4$, filtered and concentrated to give the crude product (1.5 g, 7.20 mmol, 50% yield) as a solid. LCMS $R_t$=0.8 min in in 1.5 min chromatography, 5-95AB, MS ESI calcd. for $C_7H_7F_2N_2O$ $[M+H]^+$ 173.0, found 173.0.

A-76:

A mixture of 2-(tert-butoxycarbonylamino) propanoic acid (549.61 mg, 2.9 mmol) and CDI (518.11 mg, 3.2 mmol) in DMF (10 mL) was stirred at 15° C. for 1 hour and then 3,4-difluoro-N'-hydroxy-benzamidine (500 mg, 2.9 mmol) was added. The reaction mixture was then stirred at 110° C. for 16 hours. After cooling to room temperature, the mixture was diluted with $NH_4Cl$ (10 mL) and extracted with EtOAc (10 mL×3). The combined organic phase was washed with brine (10 mL), dried over $Na_2SO_4$, filtered and concentrated to give the crude product. The crude product was purified by flash chromatography on silica gel (EtOAc in PE=0% to 50%) to give the product (230 mg, 0.58 mmol, 20% yield) as an oil. LCMS $R_t$=0.94 min in in 2.0 min chromatography, 10-80AB, MS ESI calcd. for $C_{11}H_{10}F_2N_3O_3$ $[M+H-tBu]^+$ 270.1, found 270.0.

A-77:

To tert-butyl N-[1-[3-(3,4-difluorophenyl)-1,2,4-oxadiazol-5-yl]ethyl]carbamate (230 mg, 0.71 mmol) was added 4M HCl in 1,4-dioxane (6.91 mL, 27.63 mmol) and the reaction mixture was stirred at 25° C. for 16 hours. The mixture was concentrated, diluted with $H_2O$ (20 mL) and the pH adjusted with addition of solid $NaHCO_3$ to pH~9. The solution was extracted with EtOAc (20 mL×3). The combined organic phase was concentrated to give the crude product (300 mg, 0.99 mmol) as a solid.

67:

A mixture of 2-methyl-5-(trifluoromethyl)pyrazole-3-carboxylic acid (300 mg, 1.55 mmol) in DCM (15 mL), DIPEA (0.86 mL, 6.18 mmol), HOBt (417.69 mg, 3.09 mmol) and EDCI (592.55 mg, 3.09 mmol) was stirred at 25° C. for 30 minutes and then 1-[3-(3,4-difluorophenyl)-1,2,4-oxadiazol-5-yl]ethanamine (348.03 mg, 1.55 mmol) was added, and the mixture was stirred at 25° C. for 16 hours. The reaction mixture was washed with $H_2O$ (20 mL), then extracted with EtOAc (30 mL×3). The combined organic phase was washed with brine (40 mL), dried over $Na_2SO_4$, filtered and concentrated to give the crude product. The crude product was purified by prep-HPLC (Column (Boston Prime C18 (150 mm×30 mm, 5 μm), A=$H_2O$ (0.05% $NH_4OH$) and B=$CH_3CN$; 63-75% B over 9 min) to give the product (15.72 mg, 39.2 μmol, 3% yield) as a solid. $^1H$ NMR (400 MHz, DMSO-$d_6$) δ=9.45 (d, 1H), 8.12-7.94 (m, 1H), 7.88 (m, 1H), 7.72-7.60 (m, 1H), 7.44 (s, 1H), 5.45 (quin, 1H), 4.13 (s, 3H), 1.67 (d, 3H). LCMS $R_t$=1.32 min in in 2.0 min chromatography, 10-80AB, MS ESI calcd. for $C_{16}H_{12}F_5N_5O_2$ $[M+H]^+$ 402.1, found 402.0.

Example 45. Synthesis of 68

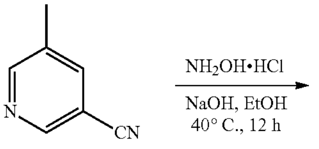

A-78

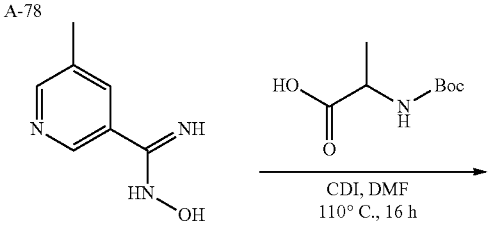

A-79

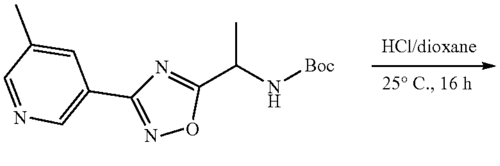

A-80

-continued

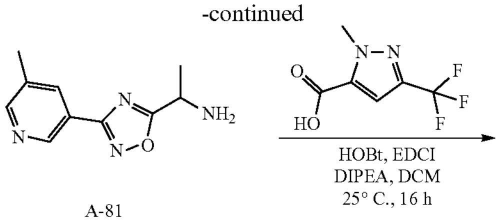

A-81

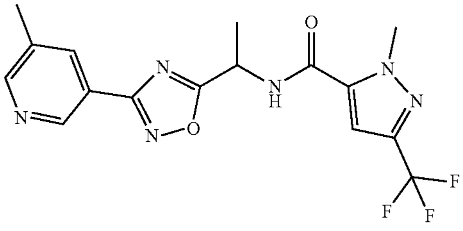

68

A-79:

A mixture of 5-methylpyridine-3-carbonitrile (1.9 g, 16.08 mmol), hydroxylamine hydrochloride (3.35 g, 48.25 mmol) and NaOH (1.93 g, 48.25 mmol) in ethanol (5 mL) and water (0.50 mL) was stirred at 40° C. for 12 hours. After cooling to room temperature, the reaction mixture was concentrated under reduced pressure to remove most of the EtOH and then diluted with $H_2O$ (40 mL). The mixture was extracted with EtOAc (50 mL×2). The combined organic phase was washed with brine (30 mL), dried over $Na_2SO_4$, filtered and concentrated to give the crude product (2.1 g, 12.79 mmol, 79% yield) as a solid. LCMS $R_t$=1.02 min in in 1.5 min chromatography, 5-95AB, MS ESI calcd. for $C_7H_9N_3O$ $[M+H]^+$ 152.1, found 152.0.

A-80:

A mixture of 2-(tert-butoxycarbonylamino) propanoic acid (1251.64 mg, 6.62 mmol) and CDI (1179.9 mg, 7.28 mmol) in DMF (10 mL) was stirred at 15° C. for 1 hour and then N'-hydroxy-5-methyl-pyridine-3-carboxamidine (1 g, 6.62 mmol) was added. The reaction mixture was stirred at 110° C. for 16 hours. The mixture was diluted with $H_2O$ (50 mL) and extracted with EtOAc (30 mL×3). The combined organic phase was washed with brine (30 mL), dried over $Na_2SO_4$, filtered and concentrated to give the crude product. The crude product was purified by flash chromatography on silica gel (EtOAc in PE=0% to 50%) to give the product (300 mg, 0.55 mmol, 8% yield) as a solid. LCMS $R_t$=0.79 min in in 2.0 min chromatography, 10-80AB, MS ESI calcd. for $C_{15}H_{20}N_4O_3$ $[M+H]^+$ 305.2, found 304.9.

A-81:

A mixture of tert-butyl N-[1-[3-(5-methyl-3-pyridyl)-1,2,4-oxadiazol-5-yl]ethyl]carbamate (300 mg, 0.99 mmol) and 4M HCl in 1,4-dioxane (9.63 mL, 38.52 mmol) was stirred at 25° C. for 16 hours. The mixture was concentrated and diluted with $H_2O$ (20 mL) and the pH adjusted with addition of $NaHCO_3$ (solid) to pH~9. The mixture was extracted with EtOAc (20 mL×3). The combined organic phase was concentrated to give the crude product (150 mg, 0.11 mmol, 11% yield) as an oil. LCMS $R_t$=0.39 min in in 2.0 min chromatography, 10-80AB, MS ESI calcd. for $C_{10}H_{13}N_4O$ $[M+H]^+$ 205.1, found 204.9.

68:

To a solution of 2-methyl-5-(trifluoromethyl)pyrazole-3-carboxylic acid (140 mg, 0.72 mmol) in DCM (20 mL) was added DIPEA (0.4 mL, 2.88 mmol), HOBt (194.92 mg, 1.44 mmol) and EDCI (276.52 mg, 1.44 mmol) and the mixture was stirred at 25° C. for 30 minutes. Then 1-[3-(5-methyl- 3-pyridyl)-1,2,4-oxadiazol-5-yl]ethanamine (147.3 mg, 0.72 mmol) was added and the mixture was stirred at 25° C. for 16 hours. The reaction mixture was washed with $H_2O$ (20 mL) and then the aqueous phase was extracted with DCM (20 mL×2). The combined organic phase was concentrated to give the crude product. The crude product was purified by prep-HPLC (Boston Prime C18 (150 mm×30 mm, 5 μm), A=$H_2O$ (0.05% $NH_4OH$) and B=$CH_3CN$; 17-47% B over 8 min) to give the product (91.9 mg, 0.24 mmol, 33% yield) as a solid. $^1H$ NMR (400 MHz, DMSO-$d_6$) δ=9.12 (d, 1H), 8.59 (d, 1H), 8.17 (s, 1H), 6.94 (s, 1H), 6.89 (br d, 1H), 5.63 (quin, 1H), 4.24 (s, 3H), 2.44 (s, 3H), 1.78 (d, 3H). LCMS $R_t$=1.02 min in in 2.0 min chromatography, 10-80AB, MS ESI calcd. for $C_{16}H_{16}F_3N_6O_2$ [M+H]$^+$ 381.1, found 380.9.

Example 46. Synthesis of 69 and 70

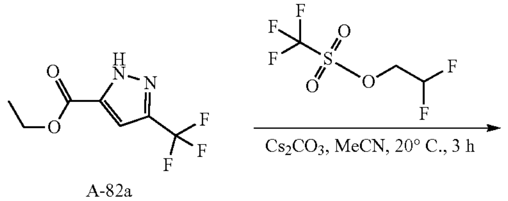

A-82a

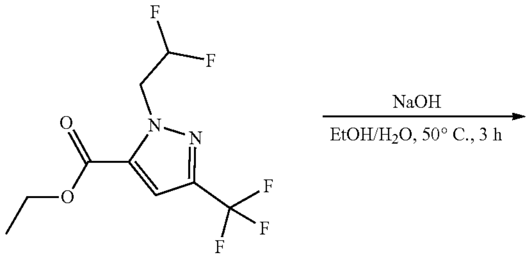

A-82b

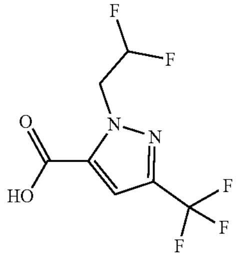

A-82

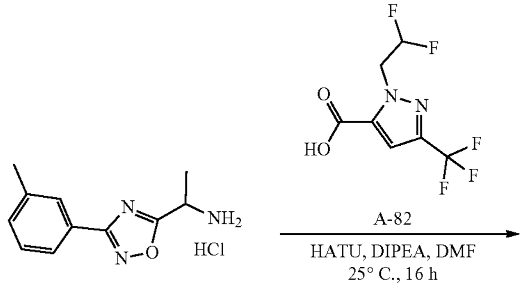

A-5

A-82

-continued

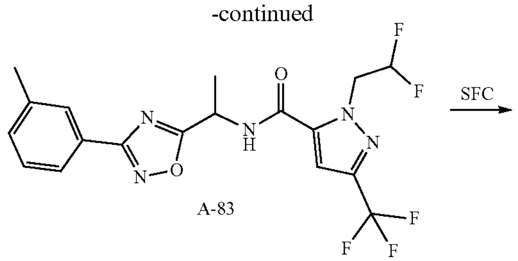

A-83

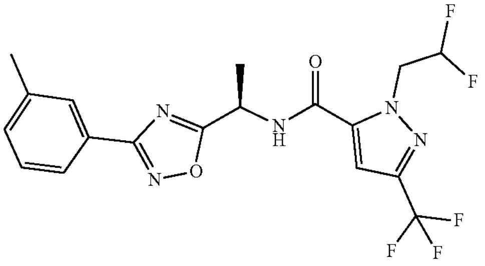

69

+

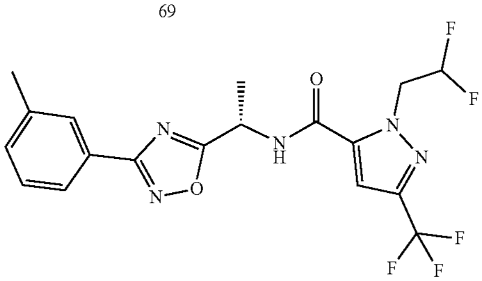

70

A-82b:

To a solution of $Cs_2CO_3$ (1.57 g, 4.8 mmol) and 2,2-difluoroethyl trifluoromethanesulfonate (1.03 g, 4.8 mmol) in $CH_3CN$ (15 mL) was added ethyl 3-(trifluoromethyl)-1H-pyrazole-5-carboxylate (500 mg, 2.4 mmol). The reaction mixture was stirred at 20° C. for 3 hours. The mixture was concentrated to give a residue. The residue was diluted with sat. $NH_4Cl$ (30 mL), and the mixture was extracted with EtOAc (30 mL×2). The combined organic phase was washed with water (30 mL) and brine (30 mL), dried over $Na_2SO_4$, filtered and concentrated to give the crude product. The crude product was purified by flash chromatography on silica gel (EtOAc in PE=0% to 15%) to give the product (400 mg, 1.44 mmol, 60% yield) as a solid. LCMS $R_t$=4.52 min in 7.0 min chromatography, 0-60AB, MS ESI calcd. for $C_9H_{10}F_5N_2O_2$ [M+H]$^+$ 273.1, found 272.9.

A-82:

To a mixture of ethyl 2-(2,2-difluoroethyl)-5-(trifluoromethyl)pyrazole-3-carboxylate (400 mg, 1.47 mmol) in ethanol (5 mL) and water (5 mL) was added NaOH (117.57 mg, 2.94 mmol), and the mixture was stirred at 50° C. for 3 hours. After cooling to room temperature, the reaction mixture was concentrated under reduced pressure to remove most of the ethanol and then diluted with $H_2O$ (10 mL) and the mixture was washed with EtOAc (10 mL×2, discarded). The pH of the aqueous phase was adjusted to pH~2 with 1N HCl, then extracted with EtOAc (20 mL×2). The combined organic phase was washed with $H_2O$ (10 mL) and brine (10 mL), dried over $Na_2SO_4$, filtered and concentrated to give the crude product (450 mg) as a solid. $^1H$ NMR (400 MHz, DMSO-$d_6$) $\delta_H$=7.36 (s, 1H), 6.62-6.31 (m, 1H), 5.10 (dt, 2H).

A-83:

To a mixture of 2-(2,2-difluoroethyl)-5-(trifluoromethyl) pyrazole-3-carboxylic acid (224.06 mg, 0.92 mmol), HATU (634.51 mg, 1.67 mmol) and DIPEA (0.44 mL, 2.5 mmol) in DMF (10 mL) was added 1-[3-(m-tolyl)-1,2,4-oxadiazol-5-yl]ethanamine hydrochloride (200 mg, 0.83 mmol) and the mixture was stirred at 25° C. for 16 hours. The reaction was quenched with sat. $NH_4Cl$ (20 mL) and the mixture was extracted with EtOAc (20 mL×2). The combined organic phase was washed with water (20 mL) and brine (20 mL), dried over $Na_2SO_4$, filtered and concentrated to give the crude product. The crude product was purified by prep-HPLC (Boston Prime C18 (150 mm×30 mm 5 μm), A=$H_2O$ (0.05% $NH_4OH$) and B=$CH_3CN$; 57-77% B over 9 min) to give the product (140 mg, 0.32 mmol, 39% yield) as a solid. LCMS $R_t$=0.94 min in 1.5 min chromatography, 10-80AB, MS ESI calcd. for $C_{18}H_{17}F_5N_5O_2$ $[M+H]^+$ 430.1, found 430.2.

69 & 70:

The product was analyzed by SFC (Daicel CHIRALCEL OJ-3 (150 mm×4.6 mm, 3 μm), mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C., ABPR: 1500 psi) showed two peaks 2.18 min and 2.59 min. The product was separated by SFC (Daicel CHIRALCEL OJ-H (250 mm×30 mm, 5 μm); A=$CO_2$ and B=EtOH (0.1% $NH_3H_2O$); 38° C.; 60 mL/min; 15% B; 7 min run; 6 injections, Rt of peak 1=4.55 min, Rt of peak 2=5.55 min) to give the enantiomer 1, randomly assigned as 69 (37.48 mg, 87.3 mmol, 27% yield) (Rt=2.18 min in analytical SFC) as a solid and the enantiomer 2, randomly assigned as 70 (48.34 mg, 112.6 mmol, 34% yield) (Rt=2.59 min in analytical SFC) as a solid.

69:

$^1H$ NMR (400 MHz, DMSO-$d_6$) $\delta_H$=9.59 (d, 1H), 7.85-7.75 (m, 2H), 7.54 (s, 1H), 7.48-7.38 (m, 2H), 6.57-6.25 (m, 1H), 5.46 (quin, 1H), 5.10 (dt, 2H), 2.39 (s, 3H), 1.67 (d, 3H). LCMS $R_t$=1.38 min in 2.0 min chromatography, 10-80AB, MS ESI calcd. for $C_{18}H_{17}F_5N_5O_2$ $[M+H]^+$ 430.1, found 430.0.

70:

$^1H$ NMR (400 MHz, DMSO-$d_6$) $\delta_H$=9.60 (d, 1H), 7.86-7.77 (m, 2H), 7.54 (s, 1H), 7.49-7.39 (m, 2H), 6.57-6.26 (m, 1H), 5.47 (quin, 1H), 5.10 (dt, 2H), 2.40 (s, 3H), 1.68 (d, 3H). LCMS $R_t$=1.37 min in 2.0 min chromatography, 10-80AB, MS ESI calcd. for $C_{18}H_{17}F_5N_5O_2$ $[M+H]^+$ 430.1, found 430.1.

Example 47. Synthesis of 71

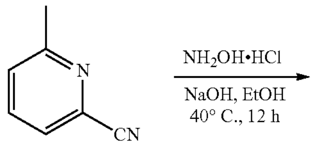

A-83

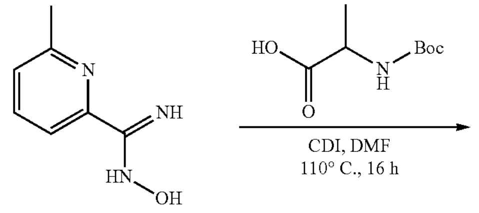

A-84

-continued

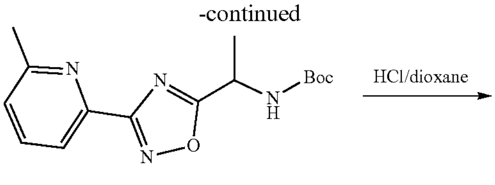

A-85

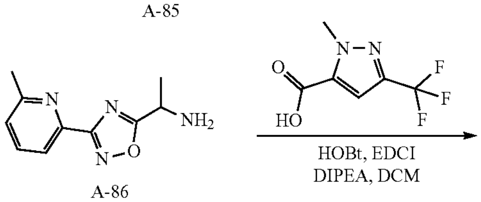

A-86

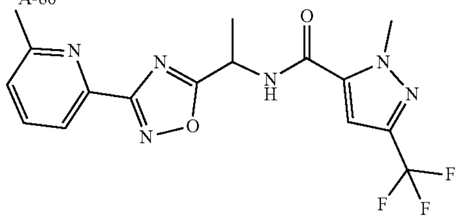

71

A-84:

A mixture of 6-methylpyridine-2-carbonitrile (10 g, 84.65 mmol), hydroxylamine hydrochloride (17.65 g, 253.94 mmol) in ethanol (24 mL) and NaOH (10.16 g, 253.94 mmol) in water (8 mL) was stirred at 40° C. for 12 hours. After cooling to room temperature the mixture was concentrated to give a residue. The residue was diluted with $H_2O$ (20 mL). The mixture was extracted with EtOAc (30 mL×2). The combined organic phase was washed with brine (15 mL), dried over $Na_2SO_4$, filtered and concentrated to give the crude product (8.2 g, 52.96 mmol, 62% yield) as a solid. LCMS Rt=0.153 min in 1.5 min chromatography, 5-95AB, MS ESI calcd. $C_7H_{10}N30$ $[M+H]^+$ 152.07, found 152.0.

A-85:

A mixture of 2-(tert-butoxycarbonylamino)propanoic acid (3754.91 mg, 19.85 mmol) and CDI (3539.69 mg, 21.83 mmol) in DMF (30 mL) was stirred at 15° C. for 1 hour. N-hydroxy-6-methyl-pyridine-2-carboxamidine (3 g, 19.85 mmol) was added and the reaction mixture was stirred at 110° C. for 16 hours. The mixture was diluted with $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by flash chromatography on silica gel (EtOAc in PE=0% to 30% to 50%) to give the product (1800 mg, 3.82 mmol, 19% yield) as a solid. LCMS Rt=0.805 min in 1.5 min chromatography, 5-95AB, MS ESI calcd. $C_{15}H_{21}N_4O_3$ $[M+H]^+$ 305.15, found 305.2.

A-86:

To tert-butyl N-[1-[3-(6-methyl-2-pyridyl)-1,2,4-oxadiazol-5-yl]ethyl]carbamate (500 mg, 1.64 mmol) in 1,4-dioxane (10 mL) was added 4M HCl in 1,4-dioxane (10 mL, 40 mmol) and the reaction mixture was stirred at 40° C. under $N_2$ for 5 hours. After cooling to room temperature, the mixture was concentrated to give a residue. The residue was poured into ice-water (20 mL) and the pH of mixture was adjusted with the addition of $Na_2CO_3$ (solid) to pH~9 and then extracted with EtOAc (20 mL×2). The organic phase was washed with brine (50 mL), dried over anhydrous $Na_2SO_4$, filtered and concentrated to give the crude product (300 mg, 0.78 mmol, 69% yield) as a solid. LCMS Rt=0.278 min in 1.5 min chromatography, 5-95AB, MS ESI calcd. $C_{10}H_{13}N_4O$ $[M+H]^+$ 205.1, found 205.1.

71:

A mixture of 1-[3-(6-methyl-2-pyridyl)-1,2,4-oxadiazol-5-yl]ethanamine (200 mg, 0.98 mmol), HOBt (264.66 mg, 1.96 mmol), EDCI (375.46 mg, 1.96 mmol), DIPEA (0.54 mL, 3.92 mmol) and 2-methyl-5-(trifluoromethyl)pyrazole-3-carboxylic acid (190.09 mg, 0.98 mmol) in DCM (10 mL) was stirred at 25° C. for 16 hours. The mixture was partially concentrated under reduced pressure to give a residue. The residue was diluted with $H_2O$ (30 mL), and the mixture was extracted with EtOAc (50 mL×2). The combined organic phase was washed with water (20 mL) and brine (20 mL), dried over $Na_2SO_4$, filtered and concentrated to give the crude product. The crude product was purified by prep-HPLC (Boston Prime (150 mm×30 mm, 5 μm), A=$H_2O$ (0.05% $NH_4OH$) and B=$CH_3CN$; 30-60% B over 9 min) to give the product (78.77 mg, 0.20 mmol, 21% yield) as a solid. $^1H$ NMR (400 MHz, $CDCl_3$) $\delta_H$=7.94 (d, 1H), 7.76 (t, 1H), 7.33 (d, 1H), 7.03-6.91 (m, 2H), 5.73-5.57 (m, 1H), 4.22 (s, 3H), 2.68 (s, 3H), 1.77 (d, 3H). LCMS $R_t$=1.16 min in 2.0 min chromatography, 10-80AB, MS ESI calcd. for $C_{16}H_{16}F_3N_6O_2$ $[M+1-1]^+$381.12, found 381.1.

Example 48. Synthesis of 72

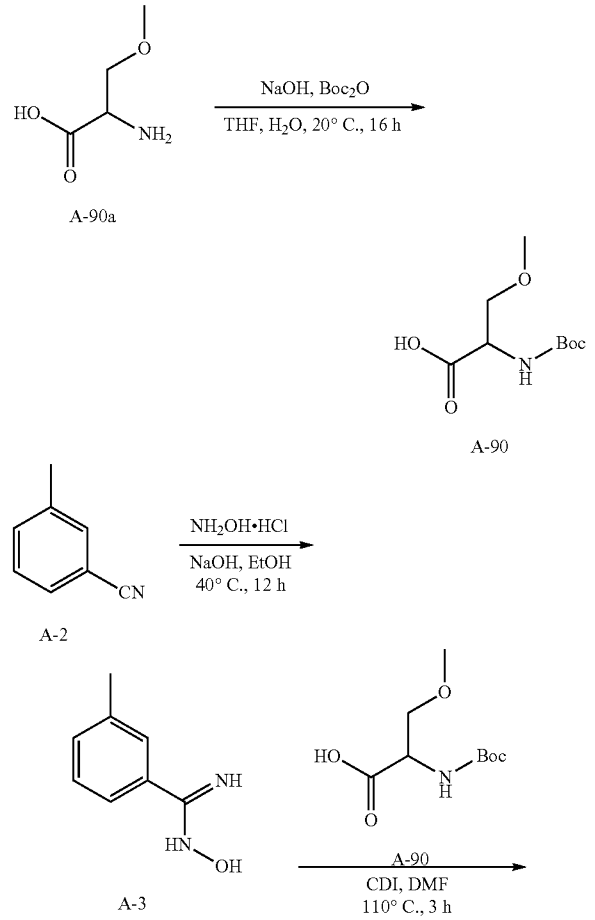

A-90a
A-90
A-2
A-3

-continued

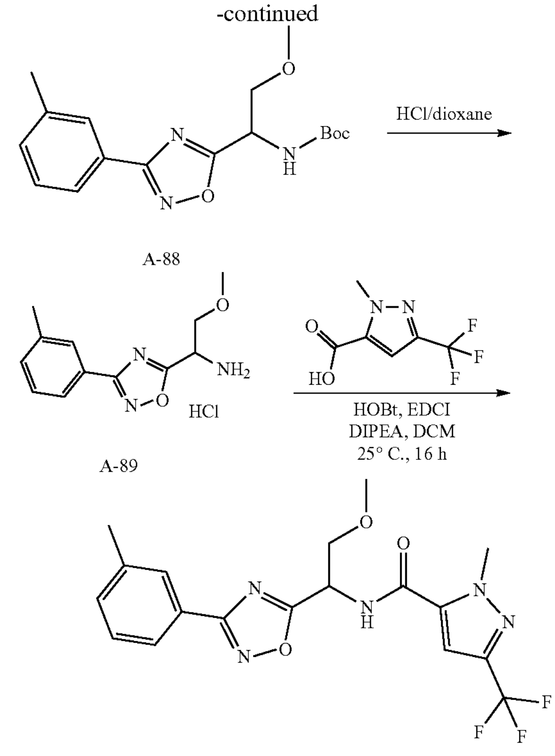

A-88
A-89
72

A-90:

To a solution of tert-butoxycarbonyl tert-butyl carbonate (2.02 g, 9.23 mmol) in THF (8 mL) was added 2-amino-3-methoxy-propanoic acid (1 g, 8.39 mmol) in THF (18 mL) and NaOH (671.59 mg, 16.79 mmol) in water (18 mL) and the mixture was stirred at 20° C. for 16 hours. The mixture was partially concentrated to give a residue. The residue was diluted with $H_2O$ (30 mL) and extracted with EtOAc (30 mL×2), the organic phase was discarded. The aqueous phase was acidified with 10% aqueous acetic acid to pH 4, and the mixture was extracted with EtOAc (50 mL×2). The combined organic phase was washed with brine (20 mL), dried over $Na_2SO_4$, filtered and concentrated to give the product (1650 mg, 7.53 mmol, 89% yield) as an oil. $^1H$ NMR (400 MHz, $CDCl_3$) $\delta_H$=8.05-7.75 (m, 1H), 5.41 (br s, 1H), 4.52-4.37 (m, 1H), 3.86 (br d, 1H), 3.63 (dd, 1H), 3.38 (d, 3H), 1.46 (d, 9H).

A-3:

A mixture of 3-methylbenzonitrile (10 g, 85.36 mmol), hydroxylamine hydrochloride (17795.13 mg, 256.08 mmol) in ethanol (12 mL) and NaOH (10.24 g, 256.08 mmol) in water (4 mL) was stirred at 40° C. for 12 hours. After cooling to room temperature, the reaction mixture was partially concentrated under reduced pressure to remove most of the EtOH then diluted with $H_2O$ (20 mL). The mixture was extracted with EtOAc (30 mL×2). The combined organic phase was washed with brine (15 mL), dried over $Na_2SO_4$, filtered and concentrated to give the crude product (12500 mg, 66.38 mmol, 77% yield) as a solid. LCMS Rt=0.178 min in 1.5 min chromatography, 5-95AB, MS ESI calcd. $C_8H_{11}N2O$ $[M+H]^+$ 151.1, found 151.1.

A-88:

A mixture of N-hydroxy-3-methyl-benzamidine (650.78 mg, 4.33 mmol) and CDI (772.92 mg, 4.77 mmol) in DMF (20 mL) was stirred at 15° C. for 1 hour and then 2-(tert-butoxycarbonylamino)-3-methoxy-propanoic acid (950 mg, 4.33 mmol) was added. The reaction mixture was stirred at 110° C. for 16 hours. The mixture was diluted with sat. $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by flash chromatography on silica gel (EtOAc in PE=0% to 30% to 50%) to give the product (290 mg, 0.86 mmol, 20% yield) as a solid. LCMS Rt=0.92 min in 1.5 min chromatography, 5-95AB, MS ESI calcd. $C_{17}H_{24}N_3O_4$ $[M+H-Boc]^+$278.1, found 334.2.

A-89:

To tert-butyl N-[2-methoxy-1-[3-(m-tolyl)-1,2,4-oxadiazol-5-yl]ethyl]carbamate (290 mg, 0.87 mmol) in 1,4-dioxane (10 mL) was added 4M HCl in 1,4-dioxane (10 mL, 40 mmol) and the mixture was stirred at 40° C. under $N_2$ for 5 hours. After cooling to room temperature, the mixture was concentrated under partial pressure to give a residue. The residue was poured into ice-water (20 mL) and the pH of the mixture was adjusted with $Na_2CO_3$ (solid) to pH~9 and then extracted with EtOAc (20 mL×2). The combined organic phase was washed with brine (50 mL), dried over anhydrous $Na_2SO_4$, filtered and concentrated to give the crude product (180 mg, 0.63 mmol, 69% yield) as a solid. LCMS $R_t$=0.678 min in 1.5 min chromatography, 5-95AB, MS ESI calcd. for $C_{12}H_{16}N_3O_2$ $[M+H]^+$ 234.1, found 234.12.

72:

A mixture of 2-methoxy-1-[3-(m-tolyl)-1,2,4-oxadiazol-5-yl]ethanamine (180 mg, 0.77 mmol), HOBt (208.54 mg, 1.54 mmol), EDCI (295.85 mg, 1.54 mmol), DIPEA (0.43 mL, 3.09 mmol) and 2-methyl-5-(trifluoromethyl)pyrazole-3-carboxylic acid (149.78 mg, 0.77 mmol) in DCM (10 mL) was stirred at 25° C. for 16 hours. The mixture was partially concentrated to give a residue. The residue was diluted with $H_2O$ (20 mL), and the mixture was extracted with EtOAc (20 mL×2). The combined organic phase was washed with brine (20 mL), dried over $Na_2SO_4$, filtered and concentrated to give the crude product. The crude product was purified by prep-HPLC (Boston Prime (150 mm×30 mm, 5 μm), A=$H_2O$ (0.05% $NH_4OH$) and B=$CH_3CN$; 50-80% B over 9 min) to give the product (77.3 mg, 0.19 mmol, 24% yield) as a solid. $^1H$ NMR (400 MHz, $CDCl_3$) $\delta_H$=7.91-7.85 (m, 2H), 7.41-7.31 (m, 2H), 7.05-7.00 (m, 1H), 6.99 (s, 1H), 5.70-5.64 (m, 1H), 4.25 (s, 3H), 4.09-4.03 (m, 1H), 3.93-3.88 (m, 1H), 3.41 (s, 3H), 2.43 (s, 3H). LCMS $R_t$=1.33 min in 2.0 min chromatography, 10-80AB, MS ESI calcd. for $C_{18}H_{19}F_3N_5O_3$ $[M+H]^+$ 410.2, found 410.14.

Example 49. Synthesis of 73

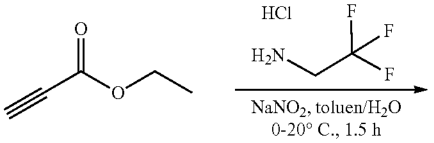

A-91

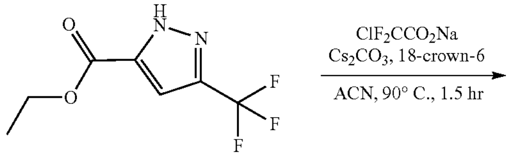

A-92

-continued

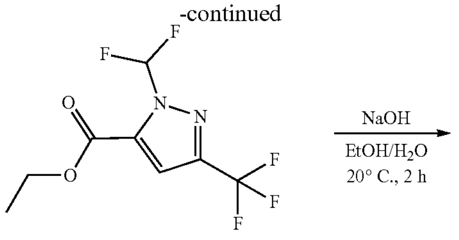

A-93

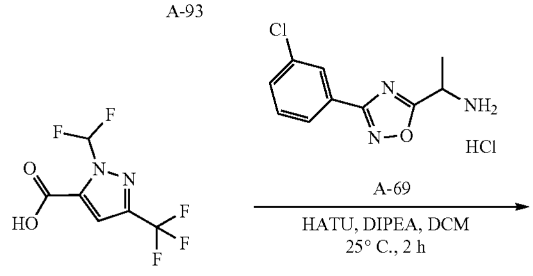

A-69

A-94

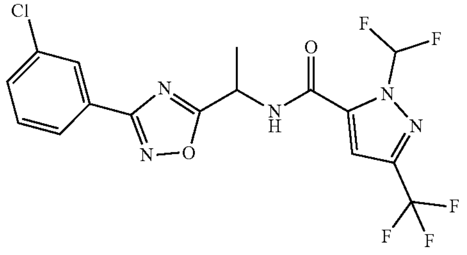

73

A-92:

To a solution of 2,2,2-trifluoroethanamine hydrochloride (4144.34 mg, 30.58 mmol) in toluene (50 mL) was added $NaNO_2$ (2109.94 mg, 30.58 mmol) in water (2.5 mL) and the reaction mixture was stirred at 0° C. for 0.5 hour. Then to the mixture was added ethyl prop-2-ynoate (1000 mg, 10.19 mmol) and the mixture was stirred at 20° C. for 1 hour. The mixture was diluted with $H_2O$ (30 mL) and extracted with EtOAc (50 mL×2). The combined organic phase was washed with water (50 mL×1) and brine (60 mL), dried over $Na_2SO_4$, filtered and concentrated to give the crude product. The crude product was purified by flash chromatography on silica gel (EtOAc in PE=0% to 20%) to give the product (2000 mg, 9.61 mmol, 94% yield) as a solid. $^1H$ NMR (400 MHz, $CDCl_3$) $\delta_H$=11.84 (br s, 1H), 7.11 (s, 1H), 4.45 (q, 2H), 1.42 (t, 3H).

A-93:

To a solution of ethyl 3-(trifluoromethyl)-1H-pyrazole-5-carboxylate (1000 mg, 4.8 mmol) in MeCN (20 mL) was added $Cs_2CO_3$ (3130.59 mg, 9.61 mmol) followed by sodium 2-chloro-2,2-difluoro-acetate (1464.98 mg, 9.61 mmol) and 18-crown-6 (253.98 mg, 0.96 mmol). The reaction mixture was stirred at 90° C. for 1.5 hours under $N_2$. After cooling to room temperature, the mixture was diluted with $H_2O$ (30 mL) and then extracted with EtOAc (30 mL×2). The combined organic phase was washed with brine (50 mL), dried over $Na_2SO_4$, filtered and concentrated to give the crude product. The crude product was purified by flash chromatography on silica gel (EtOAc in PE=0% to 5% to 10%) to give the product (100 mg, 387.4 μmol, 8.06% yield) as an oil. $^1H$ NMR (400 MHz, $CDCl_3$) $\delta_H$=8.26-7.85 (m, 1H), 7.21 (s, 1H), 4.45 (q, 2H), 1.43 (t, 3H).

A-94:

To a solution of ethyl 2-(difluoromethyl)-5-(trifluoromethyl)pyrazole-3-carboxylate (70 mg, 0.27 mmol) in ethanol (3 mL) was added a solution of NaOH (32.54 mg, 0.81 mmol) in water (3 mL). The mixture was stirred at 20° C. for 2 hours. The reaction mixture was quenched by addition of 1N HCl (1 mL) and diluted with $H_2O$ (10 mL) and extracted with EtOAc (15 mL×2). The combined organic phase was washed with brine (20 mL), dried over $Na_2SO_4$, filtered and concentrated to give the product (60 mg, 260.8 μmol, 96% yield) as a solid. $^1H$ NMR (400 MHz, $CDCl_3$) $\delta_H$=8.21-7.81 (m, 1H), 7.30 (s, 1H).

73:

To a mixture of 2-(difluoromethyl)-5-(trifluoromethyl) pyrazole-3-carboxylic acid (60 mg, 0.26 mmol), HATU (292.35 mg, 0.77 mmol) and DIPEA (0.27 mL, 1.54 mmol) in DCM (8 mL) was added 1-[3-(3-chlorophenyl)-1,2,4-oxadiazol-5-yl]ethanamine hydrochloride (100 mg, 0.38 mmol) and the mixture was stirred at 25° C. for 2 hours. The mixture was diluted with $H_2O$ (10 mL) and then extracted with EtOAc (20 mL×2). The organic layer was washed brine (30 mL), dried over $Na_2SO_4$, filtered and concentrated to give the crude product. The crude product was purified by flash chromatography on silica gel (EtOAc in PE=0% to 24%) to give the product (26.79 mg, 61.5 μmol, 16% yield) as an oil. $^1H$ NMR (400 MHz, $CDCl_3$) $\delta_H$=8.31-7.99 (m, 2H), 7.99-7.95 (m, 1H), 7.55-7.49 (m, 1H), 7.48-7.42 (m, 1H), 7.10 (s, 1H), 6.95 (br d, 1H), 5.62 (quin, 1H), 1.80 (d, 3H). LCMS $R_t$=1.35 min in 2.0 min chromatography, 10-80AB, MS ESI calcd. $C_{16}H_{12}ClF_5N_5O_2$ $[M+H]^+$ 436.1, found 435.9.

Example 50. Synthesis of 74 and 75

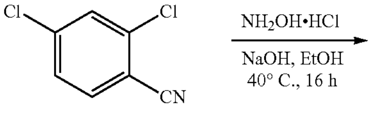

A-95

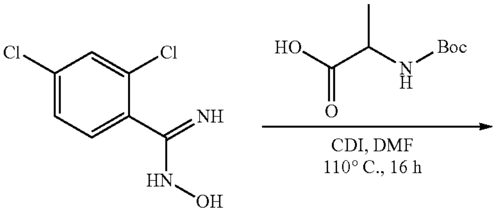

A-96

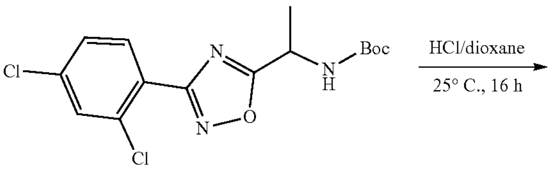

A-97

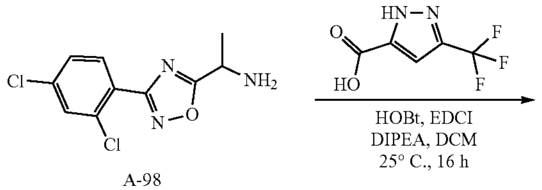

A-98

-continued

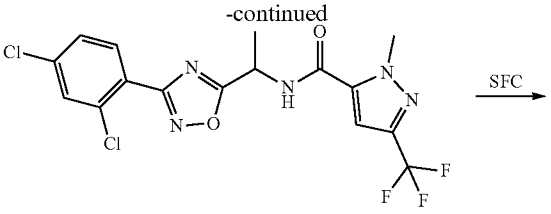

A-99

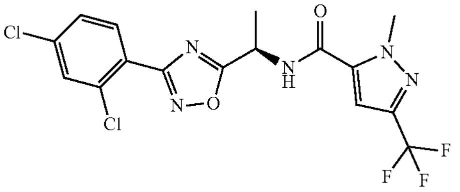

+

74

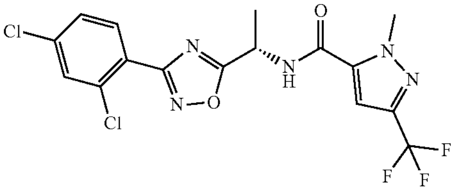

75

A-96:

A mixture of 2,4-dichlorobenzonitrile (3 g, 17.44 mmol), hydroxylamine hydrochloride (3.64 g, 52.32 mmol) and NaOH (2.09 g, 52.32 mmol) in ethanol (24 mL) and water (8 mL) was stirred at 40° C. for 16 hours to give a suspension. After cooling to room temperature, the reaction mixture was partially concentrated under vacuum to remove most of the EtOH and then diluted with $H_2O$ (50 mL). The mixture was extracted with EtOAc (50 mL×3). The combined organic phase was washed with brine (50 mL), dried over $Na_2SO_4$, filtered and concentrated to give the product (2 g, 7.72 mmol, 44% yield) as a solid. LCMS $R_t$=0.232 min in in 2.0 min chromatography, 10-80AB, MS ESI calcd. for $C_7H_7Cl_2N_2O$ $[M+H]^+$ 205.1, found 204.8.

A-97:

A mixture of 2-(tert-butoxycarbonylamino) propanoic acid (1.38 g, 7.32 mmol) and CDI (1.3 g, 8.05 mmol) in DMF (10 mL) was stirred at 15° C. for 1 hour and then 2,4-dichloro-N'-hydroxy-benzamidine (1.5 g, 7.32 mmol) was added. The reaction mixture was then stirred at 110° C. for 16 hours. After cooling to room temperature the mixture was diluted with $H_2O$ (100 mL) and extracted with EtOAc (30 mL×3). The combined organic phase was washed with brine (40 mL), dried over $Na_2SO_4$, filtered and concentrated to give the crude product. The crude product was purified by flash chromatography on silica gel (EtOAc in PE=0% to 10%) to give the product (600 mg, 1.62 mmol, 22% yield) as a solid. LCMS $R_t$=1.380 min in in 2.0 min chromatography, 10-80AB, MS ESI calcd. for $C_{11}H_9Cl_2N_3O_3$ $[M+H-tBu]^+$ 302.0, found 301.9.

A-98:

To tert-butyl N-[1-[3-(2,4-dichlorophenyl)-1,2,4-oxadiazol-5-yl]ethyl]carbamate (600 mg, 1.67 mmol) was added 4M HCl in 1,4-dioxane (16.36 mL, 65.45 mmol) and the mixture was stirred at 25° C. for 16 hours. The mixture was concentrated, diluted with $H_2O$ (20 mL) and the pH was adjusted with $NaHCO_3$ (solid) to pH~9. The mixture was extracted with EtOAc (20 mL×3). The combined organic phase was concentrated to give the crude product (500 mg, 0.92 mmol, 55% yield) as an oil. LCMS $R_t$=0.906 min in in 2.0 min chromatography, 10-80AB, MS ESI calcd. for $C_{10}H_{10}Cl_2N_3O$ [M+H–tBu]$^+$ 258.0, found 257.8.

A-99:

To a mixture of 2-methyl-5-(trifluoromethyl) pyrazole-3-carboxylic acid (280 mg, 1.44 mmol) in DCM (25 mL) was added DIPEA (0.8 mL, 5.77 mmol), HOBt (389.84 mg, 2.88 mmol), EDCI (553.05 mg, 2.88 mmol) and the mixture was stirred at 25° C. for 30 min. Then 1-[3-(2,4-dichlorophenyl)-1,2,4-oxadiazol-5-yl]ethanamine (372.3 mg, 1.44 mmol) was added and the reaction mixture was stirred at 25° C. for 16 hours. The reaction mixture was washed with $H_2O$ (30 mL) and the mixture was extracted with DCM (30 mL×2). The combined organic phase was washed with brine (30 mL), dried over $Na_2SO_4$, filtered and concentrated to give the crude product. The crude product was purified from prep-HPLC (Boston Prime C18 (150 mm×30 mm, 5 μm), A=$H_2O$ (0.05% $NH_4OH$) and B=$CH_3CN$; 56-76% B over 9 min) to give the product (450 mg, 1.04 mmol, 72% yield) as oil. LCMS $R_t$=1.318 min in in 2.0 min chromatography, 10-80AB, MS ESI calcd. For C16H13C12F3N5O2 [M+H]$^+$ 434.0, found 433.9.

74 & 75:

Analytical SFC (Daicel CHIRALCEL OJ-H (150 mm×4.6 mm, 5 μm), mobile phase: A: $CO_2$, B: ethanol (0.05% DEA), gradient: from 5% to 40% of B in 4.5 min and hold 40% for 5.5 min, then 5% of B for 1.5 min, flow rate: 2.5 mL/min, column temp: 40° C.) showed two peaks at 2.94 min and 3.79 min. The product was purified by SFC (Daicel CHIRALCEL OJ-H (250 mm×30 mm, 5 μm); A=$CO_2$ and B=EtOH (0.1% $NH_3H_2O$); 38° C.; 60 mL/min; 25% B; 7.76 min run; 45 injections, Rt of peak 1=4.39 min, Rt of peak 2=5.76 min) to give the enantiomer 1, randomly assigned as 74 (176.6 mg, 0.41 mmol, 44% yield) (Rt=2.943 min in analytical SFC) as a solid and the enantiomer 2, randomly assigned as 75 (211.15 mg, 0.49 mmol, 53% yield) (Rt=3.79 min in analytical SFC) as a solid.

74:

$^1$H NMR (400 Mhz, DMSO-$d_6$) δ=9.47 (d, 1H), 7.96 (d, 1H), 7.91 (d, 1H), 7.66 (dd, 1H), 7.45 (s, 1H), 5.49 (quin, 1H), 4.14 (s, 3H), 1.68 (d, 3H). LCMS $R_t$=1.38 min in 2.0 min chromatography, 10-80AB, MS ESI calcd. for $C_{16}H_{13}Cl_2F_3N_5O_2$ [M+H]$^+$ 434.0, found 434.0.

75:

$^1$H NMR (400 MHz, DMSO-$d_6$) δ=9.46 (d, 1H), 7.96 (d, 1H), 7.91 (d, 1H), 7.66 (dd, 1H), 7.45 (s, 1H), 5.49 (quin, 1H), 4.14 (s, 3H), 1.68 (d, 3H). LCMS $R_t$=1.38 min in 2.0 min chromatography, 10-80AB, MS ESI calcd. for $C_{16}H_{13}Cl_2F_3N_5O_2$ [M+H]$^+$ 434.0, found 434.0.

Example 51. Synthesis of 76 and 77

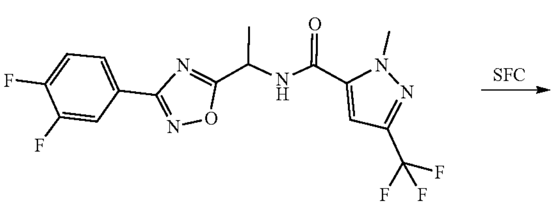

67

-continued

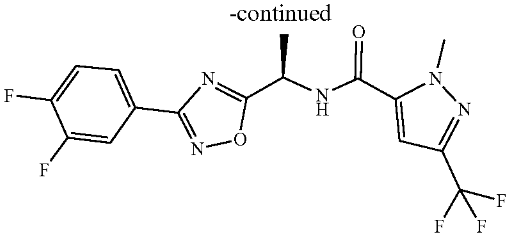

+

76

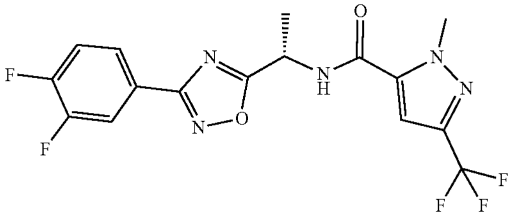

77

Analytical SFC (Daicel CHIRALCEL OJ-H (150 mm×4.6 mm, 5 μm), mobile phase: A: $CO_2$, B: ethanol (0.05% DEA), Gradient: from 5% to 40% of B in 4.5 min and hold 40% for 5.5 min, then 5% of B for 1.5 min, flow rate: 2.5 mL/min, column temp: 40° C.) showed two peaks at 2.18 min and 2.40 min. The product was separated by SFC (Daicel CHIRALCEL OJ-H (250 mm×30 mm, 5 μm); A=$CO_2$ and B=EtOH (0.1% $NH_3H_2O$); 38° C.; 60 mL/min; 10% B; 8.74 min run; 120 injections, Rt of peak 1=5.95 min, Rt of peak 2=6.74 min) to give the enantiomer 1, randomly assigned as 76 (178.71 mg, 0.44 mmol) (Rt=2.18 min in analytical SFC) as a solid and the enantiomer 2 randomly assigned as 77 (138.05 mg, 0.34 mmol, 37% yield) (Rt=2.40 min in analytical SFC) as a solid.

76:

$^1$H NMR (400 MHz, DMSO-$d_6$) 400 MHz δ=9.46 (d, 1H), 8.05-7.96 (m, 1H), 7.94-7.83 (m, 1H), 7.74-7.59 (m, 1H), 7.45 (s, 1H), 5.46 (quin, 1H), 4.14 (s, 3H), 1.68 (d, 3H). LCMS $R_t$=1.33 min in 2.0 min chromatography, 10-80AB, MS ESI calcd. for $C_{16}H_{13}F_5N_5O_2$ [M+H]$^+$ 402.1, found 402.0.

77:

$^1$H NMR (400 MHz, DMSO-$d_6$) 400 MHz δ=9.46 (d, 1H), 8.10-7.95 (m, 1H), 7.93-7.82 (m, 1H), 7.67 (m, 1H), 7.45 (s, 1H), 5.46 (quin, 1H), 4.13 (s, 3H), 1.68 (d, 3H). LCMS $R_t$=1.32 min in 2.0 min chromatography, 10-80AB, MS ESI calcd. for $C_{16}H_{13}F_5N_5O_2$ [M+H]$^+$ 402.1, found 402.0.

Example 52. Synthesis of 78 and 79

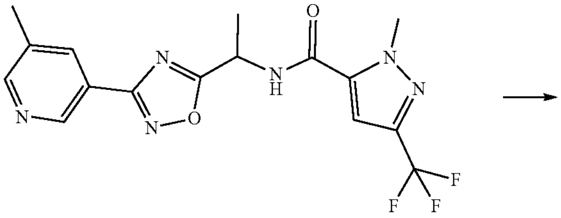

68

-continued

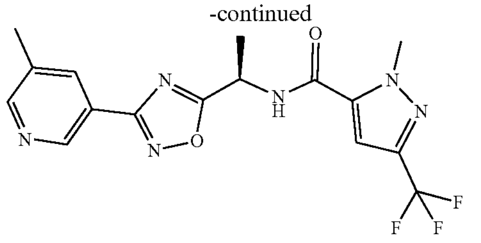

+

78

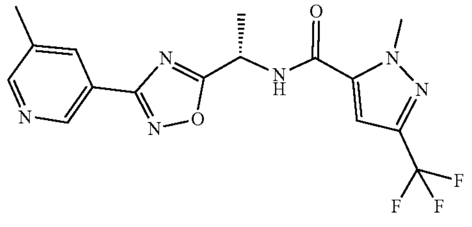

79

Analytical SFC (Regis (S,S) Whelk-O1 (100 mm×4.6 mm I.D., 5.0 μm), mobile phase: A: $CO_2$ B: ethanol (0.05% DEA), gradient: from 5% to 40% of B in 5.5 min and hold 40% for 3 min, then 5% of B for 1.5 min, flow rate: 2.5 mL/min, column temp: 35° C.) showed 2 peaks at 3.78 min and 4.09 min. The product was separated by SFC (Regis (S,S) Whelk-O1 (250 mm×30 mm, 5 μm); A=$CO_2$ and B=i-PrOH (0.1% DEA); 38° C.; 60 mL/min; 35% B; 9 min run; 6 injections, Rt of peak 1=6.3 min, Rt of peak 2=7.3 min) to give the enantiomer 1, randomly assigned as 78 (35.11 mg, 92.3 mol, 41% yield)(Rt=3.78 min in analytical SFC) as an oil and enantiomer 2, randomly assigned as 79 (28.13 mg, 74 mol, 33% yield) (Rt=4.09 min in analytical SFC) as an oil.

78:

$^1$H NMR (400 MHz, $CDCl_3$) $\delta_H$=9.13 (s, 1H), 8.60 (s, 1H), 8.22 (s, 1H), 6.96 (s, 1H), 6.90 (br d, 1H), 5.68-5.57 (m, 1H), 4.24 (s, 3H), 2.46 (s, 3H), 1.79 (d, 3H). LCMS $R_t$=1.05 min in 2.0 min chromatography, 10-80AB, MS ESI calcd. for $C_{16}H_{16}F_3N_6O_2$ $[M+H]^+$ 381.12, found 381.1.

79:

$^1$H NMR (400 MHz, $CDCl_3$) $\delta_H$=9.13 (s, 1H), 8.64-8.54 (m, 1H), 8.23-8.16 (m, 1H), 6.95 (s, 1H), 6.85-6.75 (m, 1H), 5.69-5.55 (m, 1H), 4.24 (s, 3H), 2.46 (s, 3H), 1.79 (d, 3H). LCMS $R_t$=1.05 min in 2.0 min chromatography, 10-80AB, MS ESI calcd. for $C_{16}H_{16}F_3N_6O_2$ $[M+H]^+$ 381.12, found 381.1.

Example 53. Synthesis of 80 and 81

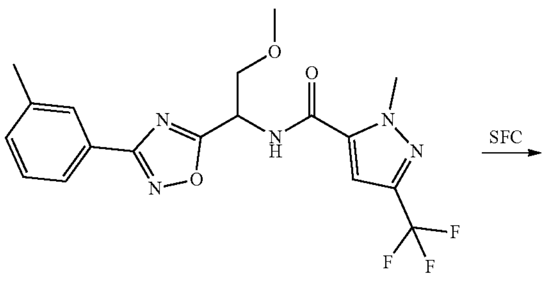

72

-continued

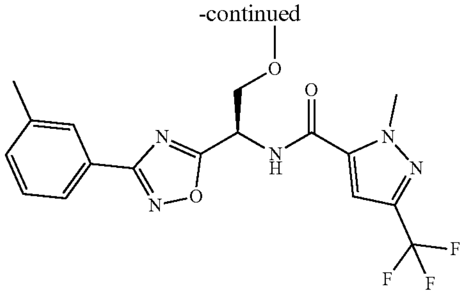

+

80

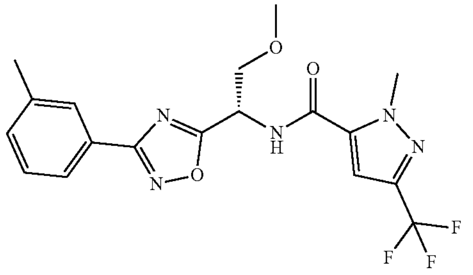

81

Analytical SFC (Daicel CHIRALPAK IC-3 (150 mm×4.6 mm I.D., 3 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C., ABPR: 1500 psi) showed two peaks at 2.00 min and 2.57 min. The product was separated by SFC (Daicel CHIRALPAK IC (250 mm×30 mm, 5 μm); A=$CO_2$ and B=EtOH (0.1% $NH_3H_2O$); 38° C.; 60 mL/min; 15% B; 7 min run; 6 injections, Rt of peak 1=4.4 min, Rt of peak 2=5.5 min) to give the enantiomer 1, randomly assigned as 80 (18.41 mg, 45.0 μmol, 26% yield) (Rt=2.00 min in analytical SFC) as a oil and enantiomer 2, randomly assigned as 81 (19.73 mg, 48.2 μmol, 28% yield) (Rt=2.57 min in analytical SFC) as an oil.

80:

$^1$H NMR (400 MHz, $CDCl_3$) $\delta_H$=7.92-7.85 (m, 2H), 7.40-7.31 (m, 2H), 7.07-6.97 (m, 2H), 5.70-5.64 (m, 1H), 4.25 (s, 3H), 4.06 (dd, 1H), 3.90 (dd, 1H), 3.41 (s, 3H), 2.43 (s, 3H). LCMS $R_t$=1.31 min in 2.0 min chromatography, 10-80AB, MS ESI calcd. for $C_{18}H_{19}F_3N_5O_3$ $[M+H]^+$ 410.1, found 410.1.

81:

$^1$H NMR (400 MHz, $CDCl_3$) $\delta_H$=7.92-7.85 (m, 2H), 7.40-7.32 (m, 2H), 7.06-6.98 (m, 2H), 5.70-5.65 (m, 1H), 4.25 (s, 3H), 4.06 (dd, 1H), 3.90 (dd, 1H), 3.41 (s, 3H), 2.43 (s, 3H). LCMS $R_t$=1.31 min in 2.0 min chromatography, 10-80AB, MS ESI calcd. for $C_{18}H_{19}F_3N_5O_3$ $[M+H]^+$ 410.1, found 410.1.

Example 54. Synthesis of 82 and 83

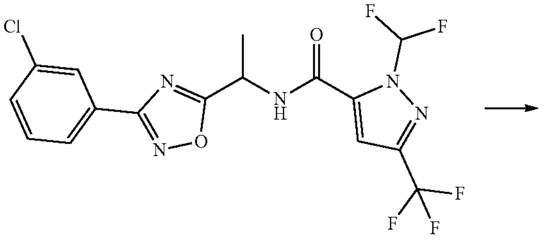

73

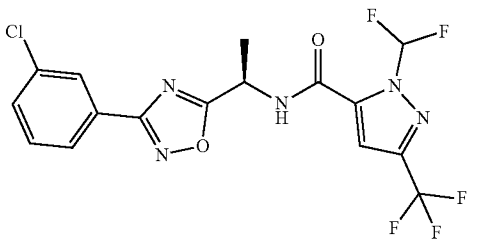

+

82

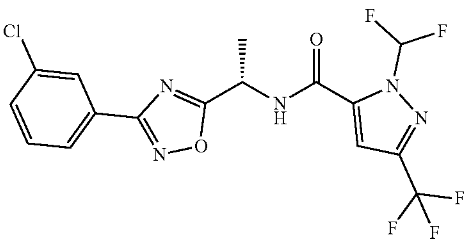

83

Analytical SFC (Daicel CHIRALCEL OJ-3 (150 mm×4.6 mm, 3 μm), mobile phase: A: $CO_2$ B: methanol (0.05% DEA), gradient: from 5% to 40% of B in 5 min and from 40% to 5% of B in 0.5 min, hold 5% for 1.5 min, flow rate: 2.5 mL/min, column temp: 35° C.) showed two peaks at 2.16 min and 2.44 min. The product was separated by SFC (Regis (S,S) Whelk-O1 (250 mm×30 mm, 5 μm); A=$CO_2$ and B=IPA (0.1% DEA); 38° C.; 60 mL/min; 35% B; 8 min run; 5 injections, Rt of peak 1=4.46 min, Rt of peak 2=5.3 min) to give the enantiomer 1, randomly assigned as 82 (3.68 mg, 8.4 μmol, 14% yield) (Rt=2.16 min in analytical SFC) as an oil and enantiomer 2, randomly assigned as 83 (7.25 mg, 16.6 μmol, 27% yield) (Rt=2.44 min in analytical SFC) as an oil.

82:

$^1$H NMR (400 MHz, $CDCl_3$) $\delta_H$=8.31-7.99 (m, 2H), 7.99-7.94 (m, 1H), 7.54-7.50 (m, 1H), 7.46 (d, 1H), 7.10 (s, 1H), 6.99-6.91 (m, 1H), 5.68-5.57 (m, 1H), 1.80 (d, 3H). LCMS $R_t$=1.39 min in 2.0 min chromatography, 10-80AB, MS ESI calcd. for $C_{16}H_{12}ClF_5N_5O_2$ $[M+H]^+$ 436.05, found 436.0.

83:

$^1$H NMR (400 MHz, $CDCl_3$) $\delta_H$=8.30-7.99 (m, 2H), 7.99-7.95 (m, 1H), 7.54-7.49 (m, 1H), 7.48-7.42 (m, 1H), 7.09 (s, 1H), 6.96-6.88 (m, 1H), 5.68-5.57 (m, 1H), 1.82-1.78 (m, 3H). LCMS $R_t$=1.37 min in 2.0 min chromatography, 10-80AB, MS ESI calcd. for $C_{16}H_{12}ClF_5N_5O_2$ $[M+H]^+$ 436.05, found 436.1.

Example 55. Synthesis of 84

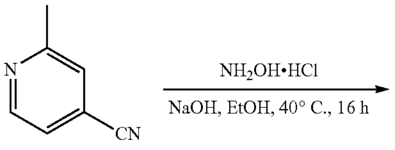

A-100

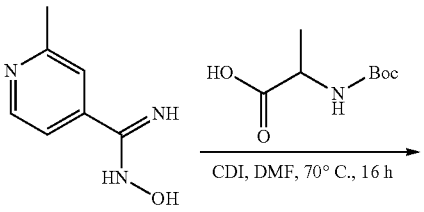

A-101

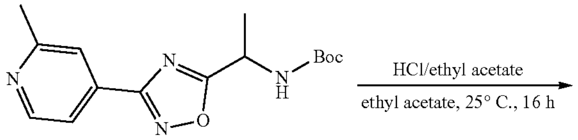

A-102

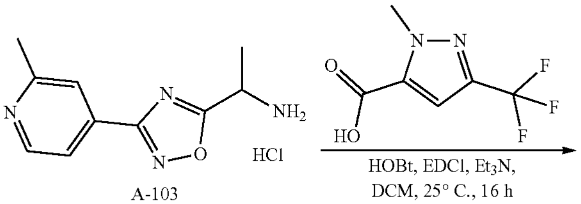

A-103

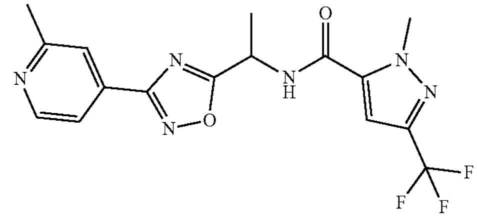

84

A-101:

A mixture of hydroxylamine hydrochloride (3.53 g, 50.79 mmol), 2-methylpyridine-4-carbonitrile (2 g, 16.93 mmol) and NaOH (2.03 g, 50.79 mmol) in ethanol (24 mL) was stirred at 40° C. for 16 hours. After cooling to room temperature, the reaction mixture was concentrated under vacuum to remove most of EtOH and then diluted with $H_2O$ (30 mL). The mixture was extracted with EtOAc (30 mL×2), and the combined organic phase was washed with brine (20 mL), dried over $Na_2SO_4$, filtered and concentrated to give the crude product (1.45 g, 9.59 mmol, 56% yield) as a solid. LCMS $R_t$=0.11 min in 1.5 min chromatography, 5-95AB, MS ESI calcd. for $C_7H_{10}N30$ $[M+H]^+$ 152.1, found 152.0.

A-102:

A mixture of 2-(tert-butoxycarbonylamino)propanoic acid (1.22 g, 6.48 mmol) and CDI (1.16 g, 7.13 mmol) in DMF (20 mL) was stirred at 25° C. for 1 hour and then N'-hydroxy-2-methyl-pyridine-4-carboxamidine (980 mg, 6.48 mmol) was added. The reaction mixture was then stirred at 70° C. for 16 hours. After cooling to room temperature, the mixture was diluted with sat NaCl (30 mL), and the mixture was extracted with EtOAc (30 mL×3). The combined organic phase was washed with brine (30 mL), dried over $Na_2SO_4$, filtered and concentrated to give the crude product. The crude product was purified by flash column chromatography on silica gel (EtOAc in PE=0% to 20% to 50%) to give the product (220 mg, 0.66 mmol, 10% yield) as an oil. LCMS $R_t$=0.70 min in 1.5 min chromatography, 5-95AB, MS ESI calcd. for $C_{15}H_{21}N_4O_3$ $[M+H]^+$ 305.2, found 305.7.

A-103:

To a mixture of tert-butyl N-[1-[3-(2-methyl-4-pyridyl)-1,2,4-oxadiazol-5-yl]ethyl]carbamate (220 mg, 0.72 mmol) in ethyl acetate (3 mL) was added ethyl acetate/HCl (15 mL, 60 mmol), and the mixture was stirred at 25° C. for 3 hours. The reaction mixture was concentrated to give the crude product (180 mg, 0.74 mmol) as a solid. LCMS $R_t$=0.12 min in 1.5 min chromatography, 5-95AB, MS ESI calcd. for $C_{10}H_{13}N_4O$ $[M+H]^+$205.1, found 205.2.

84:

A mixture of 2-methyl-5-(trifluoromethyl)pyrazole-3-carboxylic acid (77.58 mg, 0.4 mmol), HOBt (120.01 mg, 0.89 mmol), $Et_3N$ (0.31 mL, 2.22 mmol) and EDCI (127.69 mg, 0.67 mmol) in DCM (7 mL) was stirred at 25° C. for 1 hour. Then to the mixture was added 1-(3-(2-methylpyridin-4-yl)-1,2,4-oxadiazol-5-yl)ethanamine hydrochloride (100 mg, 0.44 mmol) and it was stirred at 25° C. for 16 hours. The reaction mixture was quenched with sat. $NH_4Cl$ (20 mL), and the mixture was extracted with DCM (20 mL×2). The combined organic phase was washed with brine (20 mL), dried over $Na_2SO_4$, filtered and concentrated to give the crude product. The crude product was purified by flash chromatography on silica gel (EtOAc in PE=0 to 10% to 25% to 50%) to give the product (63.51 mg, 0.17 mmol, 38% yield) as a solid. $^1H$ NMR (400 MHz, $CD_3CN$) $\delta_H$=8.67 (d, 1H), 7.81 (s, 1H), 7.74 (d, 1H), 6.95 (s, 1H), 6.75 (d, 1H), 5.62 (q, 1H), 4.24 (s, 3H), 2.67 (s, 3H), 1.79 (d, 3H). LCMS $R_t$=0.90 min in 2.0 min chromatography, 10-80AB, MS ESI calcd. for $C_{16}H_{16}F_3N_6O_2$ $[M+H]^+$ 381.1, found 380.9.

Example 56. Synthesis of 85

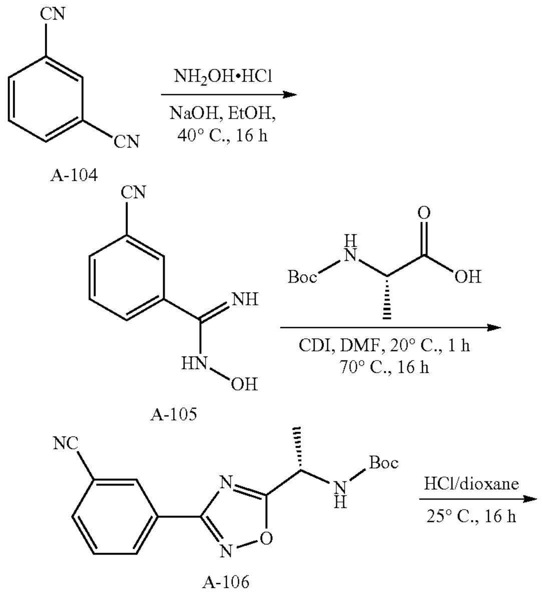

-continued

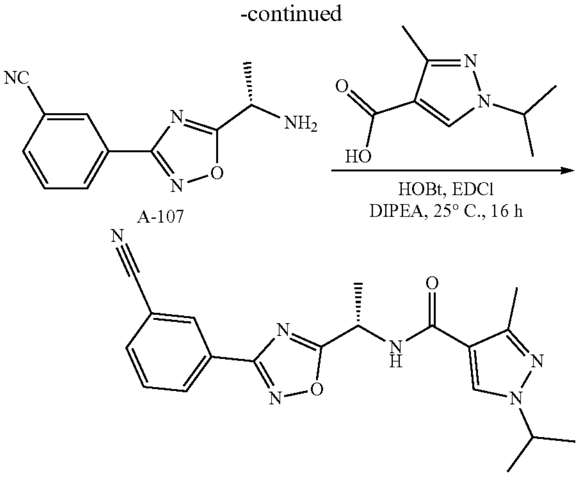

A-105:

A mixture of hydroxylamine hydrochloride (0.54 g, 7.8 mmol), benzene-1,3-dicarbonitrile (1 g, 7.8 mmol) and NaOH (0.31 g, 7.8 mmol) in ethanol (20 mL) was stirred at 40° C. for 16 hours. After cooling to room temperature, the reaction mixture was partially concentrated under reduced pressure to remove most of EtOH and then it was diluted with $H_2O$ (20 mL). The mixture was extracted with EtOAc (30 mL×3). The combined organic phase was washed with brine (30 mL), dried over $Na_2SO_4$, filtered and concentrated to give the crude product (1.4 g, 6.06 mmol, 77% yield) as a solid. LCMS $R_t$=0.14 min in in 1.5 min chromatography, 5-95AB, MS ESI calcd. for $C_8H_8N_3O$ $[M+H]^+$ 162.1, found 162.0.

A-106:

A mixture of (2S)-2-(tert-butoxycarbonylamino)propanoic acid (821.84 mg, 4.34 mmol) and CDI (774.73 mg, 4.78 mmol) in DMF (15 mL) was stirred at 25° C. for 1 hour and then 3-cyano-N'-hydroxy-benzamidine (700 mg, 4.34 mmol) was added. The reaction mixture was then stirred at 70° C. for 16 hours. After cooling to room temperature, the mixture was diluted with water (60 mL) and extracted with EtOAc (50 mL×2). The combined organic phase was washed with brine (30 mL), dried over $Na_2SO_4$, filtered and concentrated to give the crude product. The crude product was purified by chromatography flash column on silica gel (EtOAc in PE=0% to 30%) to give the product (400 mg, 0.77 mmol) as a solid. LCMS $R_t$=1.15 min in in 2.0 min chromatography, 10-80AB, MS ESI calcd. for $C_{12}H_{10}N_4O_3$ $[M+H-tBu]^+$ 259.1, found 258.9.

A-107:

A mixture of tert-butyl N-[(1S)-1-[3-(3-cyanophenyl)-1,2,4-oxadiazol-5-yl]ethyl]carbamate (400 mg, 1.27 mmol) and 4M HCl in 1,4-dioxane (15 mL, 60 mmol) was stirred at 25° C. for 16 hours. The mixture was concentrated, diluted with $H_2O$ (20 mL) and basified with $NaHCO_3$ (solid) to pH~8. The mixture was extracted with EtOAc (30 mL×3), and the combined organic phase was washed with brine (30 mL), dried over $Na_2SO_4$, filtered and concentrated to give the crude product (410 mg, 1.60 mmol, 29% yield) as an oil.

85:

To a mixture of 1-isopropyl-3-methyl-pyrazole-4-carboxylic acid (100 mg, 0.59 mmol) in DCM (10 mL) was added HOBt (160 mg, 1.19 mmol), EDCI (228 mg, 1.19 mmol), DIPEA (0.33 mL, 2.38 mmol) and 3-[5-[(1S)-1-aminoethyl]-1,2,4-oxadiazol-3-yl]benzonitrile (152.84 mg, 0.71 mmol) and the mixture was stirred at 25° C. for 16 hours. The reaction was quenched with $H_2O$ (10 mL), then extracted with DCM (20 mL×3). The combined organic phase was washed with brine (30 mL), dried over $Na_2SO_4$, filtered and concentrated to give the crude product. The crude product was purified with flash chromatography on silica gel (EtOAc in PE=0% to 20%) to give the product (66 mg, 0.18 mmol, 30% yield) as a solid. $^1H$ NMR (400 MHz, $CDCl_3$) δ=8.40 (s, 1H), 8.34 (d, 1H), 7.86 (s, 1H), 7.82 (d, 1H), 7.64 (t, 1H), 6.27 (br d, 1H), 5.70-5.57 (m, 1H), 4.53-4.40 (m, 1H), 2.56 (s, 3H), 1.76 (d, 3H), 1.54 (d, 6H). LCMS $R_t$=1.10 min in in 2.0 min chromatography, 10-80AB, MS ESI calcd. for $C_{19}H_{20}N_6O_2$ $[M+H]^+$ 365.2, found 365.2.

Example 57. Synthesis of 86

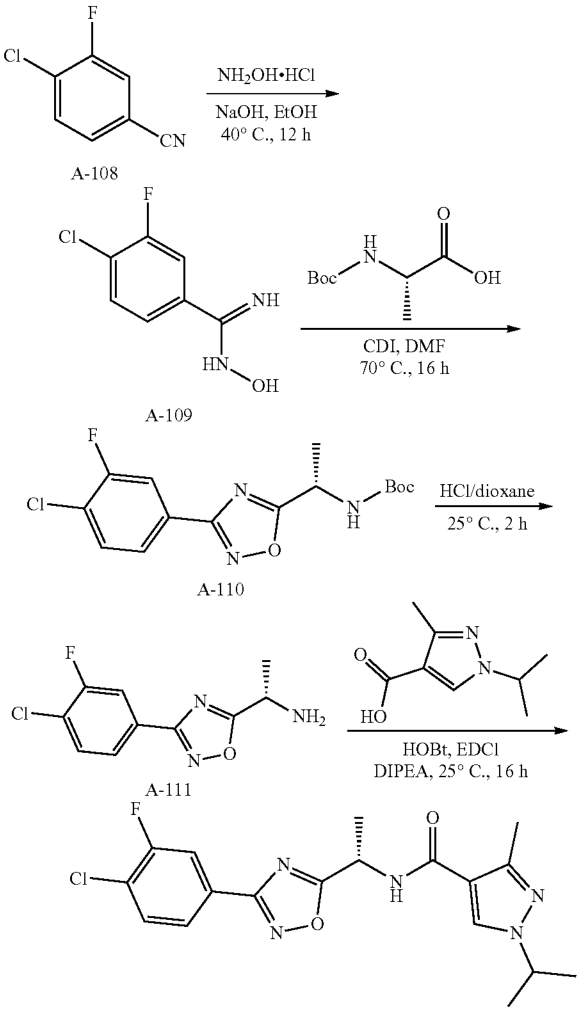

A-108

A-109

A-110

A-111

86

A-109:

A mixture of 4-chloro-3-fluoro-benzonitrile (1 g, 6.43 mmol), hydroxylamine hydrochloride (1.34 g, 19.29 mmol), NaOH (0.77 g, 19.29 mmol) in ethanol (24 mL) and water (8 mL) was stirred at 40° C. for 12 hours. After cooling to room temperature, the mixture was partially concentrated under reduced pressure to give a residue. The residue was diluted with $H_2O$ (20 mL) and extracted with EtOAc (30 mL×2). The combined organic phase was washed with brine (15 mL), dried over $Na_2SO_4$, filtered and concentrated to give the crude product (1 g, 2.74 mmol, 43% yield) as a solid. LCMS Rt=0.33 min in 1.5 min chromatography, 5-95AB, MS ESI calcd. $C_7H_7ClFN_2O$ $[M+H]^+$ 189.02, found 188.7.

A-110:

To a mixture of 4-chloro-3-fluoro-N-hydroxy-benzamidine (1 g, 5.3 mmol) and CDI (945.78 mg, 5.83 mmol) in DMF (30 mL) was stirred at 25° C. for 1 hour before (25)-2-(tert-butoxycarbonylamino)propanoic acid (1 g, 5.3 mmol) was added. The reaction mixture was then stirred at 80° C. for 16 hours. After cooling to room temperature, the mixture was diluted with $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by flash chromatography on silica gel (EtOAc in PE=0% to 30% to 50%) to give the product (350 mg, 0.99 mmol, 19% yield) as a solid. LCMS Rt=0.96 min in 1.5 min chromatography, 5-95AB, MS ESI calcd. $C_{15}H_{18}ClFN_3O_3$ $[M+H-BOC]^+$ 286.09, found 286.1.

A-111:

To tert-butyl N-[(1S)-1-[3-(4-chloro-3-fluoro-phenyl)-1,2,4-oxadiazol-5-yl]ethyl]carbamate (350 mg, 1.02 mmol) in 1,4-dioxane (10 mL) was added 4M HCl in 1,4-dioxane (10 mL, 40 mmol) and the reaction mixture was stirred at 30° C. under $N_2$ for 5 hours. After cooling to room temperature, the mixture was concentrated under reduced pressure to give a residue. The residue was poured into ice-water (20 mL) and the mixture was basified with $Na_2CO_3$ (solid) to pH~9, and extracted with EtOAc (20 mL×2), the organic phase was washed with brine (20 mL), dried over anhydrous $Na_2SO_4$, filtered and concentrated to give the crude product (250 mg, 0.99 mmol, 69% yield) as an oil. LCMS Rt=0.68 min in 1.5 min chromatography, 5-95AB, MS ESI calcd. $C_{10}H_{10}ClFN_3O$ $[M+H]^+$ 242.04, found 241.8.

86:

A mixture of 1-isopropyl-3-methyl-pyrazole-4-carboxylic acid (100 mg, 0.59 mmol), HOBt (160.69 mg, 1.19 mmol), EDCI (227.96 mg, 1.19 mmol), DIPEA (0.33 mL, 2.38 mmol) and (1S)-1-[3-(4-chloro-3-fluoro-phenyl)-1,2,4-oxadiazol-5-yl]ethanamine (172.41 mg, 0.71 mmol) in DCM (10 mL) was stirred at 25° C. for 16 hours. The mixture was concentrated to give a residue. The residue was diluted with $H_2O$ (30 mL), and the mixture was extracted with EtOAc (50 mL×2). The combined organic phase was washed with water (20 mL) and brine (20 mL), dried over $Na_2SO_4$, filtered and concentrated to give the crude product. The crude product was purified by flash chromatography on silica gel (EtOAc in PE=0% to 50%) to give the product.

Analytical SFC (Regis (S,S) Whelk-01 (100 mm×4.6 mm I.D., 5.0 μm), mobile phase: A: $CO_2$ B: ethanol (0.05% DEA), gradient: from 5% to 40% of B in 5.5 min and hold 40% for 3 min, then 5% of B for 1.5 min, flow rate: 2.5 mL/min) showed two peaks at 4.41 (12.4%) min and 5.48 min (87.6%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 40% B; 10 min run; 5 injections, Rt of peak 1=5.6 min, Rt of peak 2=8.2 min) to give the product (100.73 mg, 0.26 mmol, 43% yield) (Rt=5.48 min in analytical SFC) as a solid. $^1H$ NMR (400 MHz, $CDCl_3$) $\delta_H$=7.91-7.80 (m, 3H), 7.53 (t, 1H), 6.26 (br d, 1H), 5.74-5.53 (m, 1H), 4.52-4.38 (m, 1H), 2.54 (s, 3H), 1.74 (d, 3H), 1.52 (d, 6H). LCMS Rt=1.18 min in 2.0 min chromatography, 10-80AB, MS ESI calcd. $C_{18}H_{20}ClFN_5O_2$ $[M+H]^+$ 392.12, found 391.9.

Example 58. Synthesis of 87

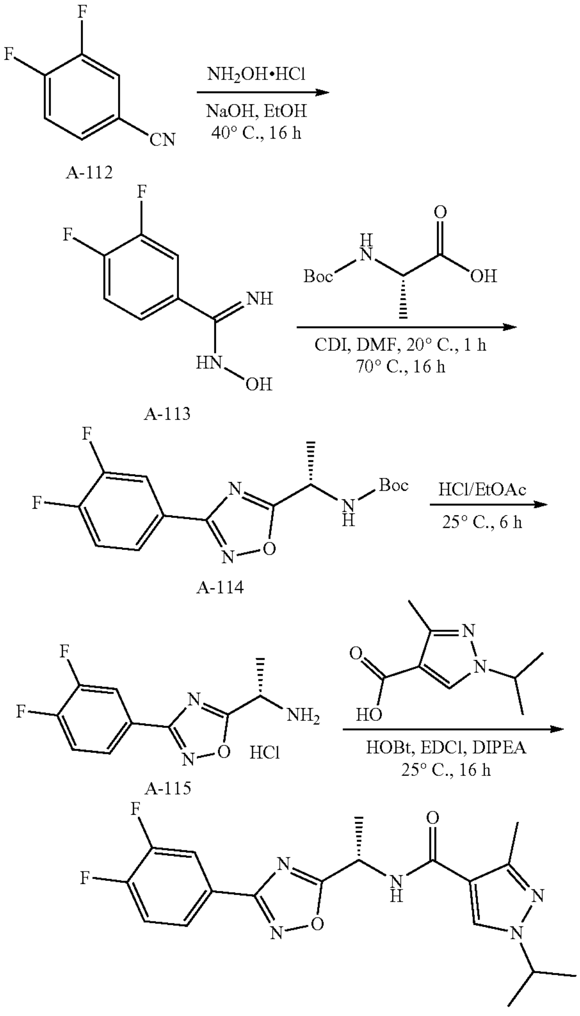

A-112

A-113

A-114

A-115

87

A-113:

To a mixture of 3,4-difluorobenzonitrile (2 g, 14.38 mmol) and hydroxylamine hydrochloride (3 g, 43.13 mmol) in ethanol (24 mL) was added NaOH (1.73 g, 43.13 mmol). The mixture was stirred at 40° C. for 16 hours. The mixture was diluted with $H_2O$ (30 mL) and extracted with EtOAc (30 mL×2). The combined organic phase was washed with brine (20 mL), dried over $Na_2SO_4$, filtered and concentrated to give the crude product (3 g, 16.11 mmol) as a solid. LCMS $R_t$=0.13 min in 1.5 min chromatography, 5-95AB, MS ESI calcd. for $C_7H_7F_2N_2O$ $[M+H]^+$ 173.0, found 173.1.

A-114:

A mixture of (2S)-2-(tert-butoxycarbonylamino)propanoic acid (1099.23 mg, 5.81 mmol) and CDI (1036.22 mg, 6.39 mmol) in DMF (15 mL) was stirred at 25° C. for 1 hour and then 3,4-difluoro-N'-hydroxy-benzamidine (1000 mg, 5.81 mmol) was added. The reaction mixture was then stirred at 70° C. for 16 hours. After cooling to room temperature, the mixture was diluted with bine (20 mL) and extracted with EtOAc (30 mL×2). The combined organic phase was washed with brine (30 mL), dried over $Na_2SO_4$, filtered and concentrated to give the crude product. The crude product was purified by flash column chromatography on silica gel (EtOAc in PE=0% to 20%) to give the product (700 mg, 2.15 mmol, 37% yield) as a solid. $^1$H NMR (400 MHz, $CDCl_3$) $\delta_H$=7.96-7.88 (m, 1H), 7.88-7.83 (m, 1H), 7.32-7.28 (m, 1H), 5.16 (s, 2H), 1.63 (d, 3H), 1.47 (s, 9H).

A-115:

A colorless mixture of tert-butyl N-[(1S)-1-[3-(3,5-difluorophenyl)-1,2,4-oxadiazol-5-yl]ethyl]carbamate (700 mg, 2.15 mmol) and HCl/EtOAc (10 mL, 4M) was stirred at 25° C. for 6 hours. The mixture was concentrated to give the crude product as a solid, which was used directly without any further purification. LCMS $R_t$=0.61 min in 2 min chromatography, 10-80AB, MS ESI calcd. for $C_{10}H_{10}F_2N30$ $[M+H]^+$ 226.1, found 225.8.

87:

To a mixture of 1-isopropyl-3-methyl-pyrazole-4-carboxylic acid (100 mg, 0.59 mmol) in DCM (15 mL) was added HOBt (160.69 mg, 1.19 mmol), EDCI (227.96 mg, 1.19 mmol), DIPEA (0.33 mL, 2.38 mmol) and (I S)-1-[3-(3,5-difluorophenyl)-1,2,4-oxadiazol-5-yl]ethanamine hydrochloride (171.13 mg, 0.65 mmol) and the mixture was stirred at 25° C. for 16 hours. The reaction mixture was quenched with saturated $NH_4Cl$ (15 mL), then extracted with DCM (20 mL×2). The combined organic phase was washed with brine (30 mL), dried over $Na_2SO_4$, filtered and concentrated to give the crude product. The crude product was purified by flash chromatography on silica gel (EtOAc in PE=0% to 30% to 50%) to give the impure product, the impure product was purified by prep-TLC (silica gel, PE:EtOAc=5:2) to give the product. The product was triturated from DCM (1 mL) and n-hexane (5 mL) to give the product (160.64 mg, 0.43 mmol, 72% yield) as a solid. $^1$H NMR (400 MHz, DMSO-$d_6$) $\delta_H$=8.55 (d, 1H), 8.27 (s, 1H), 8.02-7.94 (m, 1H), 7.90-7.83 (m, 1H), 7.70-7.60 (m, 1H), 5.41-5.30 (m, 1H), 4.48-4.33 (m, 1H), 2.29 (s, 3H), 1.61 (d, 3H), 1.40 (d, 6H). LCMS $R_t$=1.13 min in 2 min chromatography, 10-80AB, MS ESI calcd. for $C_{18}H_{20}F_2N_5O_2$ $[M+H]^+$ 376.2, found 376.0.

Example 59. Synthesis of 88

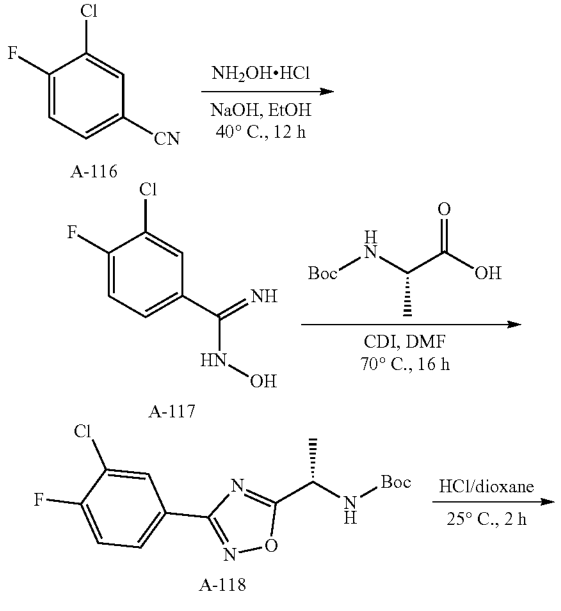

A-116

A-117

A-118

-continued

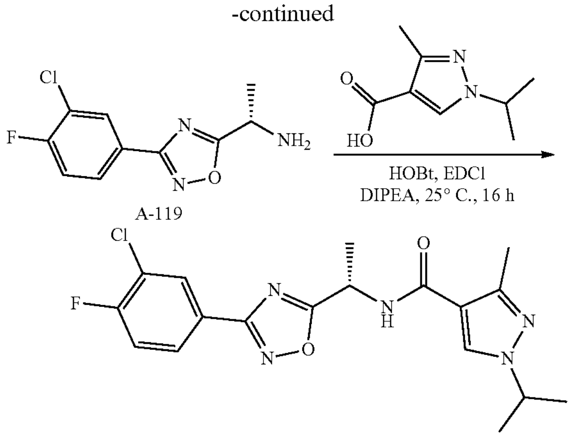

A-119

88

A-117:

A mixture of 3-chloro-4-fluoro-benzonitrile (1 g, 6.43 mmol), hydroxylamine hydrochloride (1.34 g, 19.29 mmol), NaOH (0.77 g, 19.29 mmol) in ethanol (24 mL) and water (8 mL) was stirred at 40° C. for 12 hours. After cooling to room temperature, the mixture was partially concentrated under reduced pressure to give the residue and the residue was diluted with $H_2O$ (20 mL). The mixture was extracted with EtOAc (30 mL×2). The combined organic phase was washed with brine (15 mL), dried over $Na_2SO_4$, filtered and concentrated to give the crude product (1 g, 3.35 mmol, 52% yield) as a solid. LCMS Rt=0.29 min in 1.5 min chromatography, 5-95AB, MS ESI calcd. $C_7H_7ClFN_2O$ $[M+H]^+$ 189.0, found 188.8.

A-118:

A mixture of 3-chloro-4-fluoro-N-hydroxy-benzamidine (1 g, 5.3 mmol) and CDI (945.78 mg, 5.83 mmol) in DMF (15 mL) was stirred at 25° C. for 1 hour before (25)-2-(tert-butoxycarbonylamino)propanoic acid (1 g, 5.3 mmol) was added. The reaction mixture was then stirred at 70° C. for 16 hours. After cooling to room temperature, the mixture was diluted with $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by flash column chromatography on silica gel (EtOAc in PE=0% to 30% to 50%) to give the product (350 mg, 1.00 mmol, 19% yield) as a solid. LCMS Rt=0.96 min in 1.5 min chromatography, 5-95AB, MS ESI calcd. $C_{15}H_{18}ClFN_3O_3$ $[M+H-Boc]^+$286.1, found 286.0.

A-119:

To tert-butyl N-[(1S)-1-[3-(3-chloro-4-fluoro-phenyl)-1,2,4-oxadiazol-5-yl]ethyl]carbamate (350 mg, 1.02 mmol) in 1,4-dioxane (10 mL) was added 4M HCl in 1,4-dioxane (10 mL, 40 mmol) and the mixture was stirred at 30° C. under $N_2$ for 5 hours. After cooling to room temperature, the mixture was concentrated to give a residue. The residue was poured into ice-water (20 mL) and the pH of the mixture was basified with $Na_2CO_3$ (solid) to pH~9, and then extracted with EtOAc (20 mL×2). The organic phase was washed with brine (20 mL), dried over anhydrous $Na_2SO_4$, filtered and concentrated to give the crude product (250 mg, 0.99 mmol, 69% yield) as an oil. LCMS Rt=0.67 min in 1.5 min chromatography, 5-95AB, MS ESI calcd. $C_{10}H_{10}ClFN_3O$ $[M+H]^+$ 242.0, found 241.8.

88:

A mixture of 1-isopropyl-3-methyl-pyrazole-4-carboxylic acid (100 mg, 0.59 mmol), HOBt (160.69 mg, 1.19 mmol), EDCI (227.96 mg, 1.19 mmol), DIPEA (0.33 mL, 2.38 mmol) and (I S)-1-[3-(3-chloro-4-fluoro-phenyl)-1,2,4-oxadiazol-5-yl]ethanamine (172.41 mg, 0.71 mmol) in DCM (10 mL) was stirred at 25° C. for 16 hours. The mixture was concentrated to give a residue. The residue was diluted with $H_2O$ (30 mL), and the mixture was extracted with EtOAc (50 mL×2). The combined organic phase was washed with water (20 mL) and brine (20 mL), dried over $Na_2SO_4$, filtered and concentrated to give the crude product. The crude product was purified by flash chromatography on silica gel (EtOAc in PE=0% to 50%) to give the product.

Analytical SFC (Regis (S,S) Whelk-O1 (100 mm×4.6 mm, 5.0 μm), mobile phase: A: $CO_2$ B: ethanol (0.05% DEA), gradient: from 5% to 40% of B in 5.5 min and hold 40% for 3 min, then 5% of B for 1.5 min, flow rate: 2.5 mL/min.) showed two peaks at 4.45 (17.1%) and 5.55 min (main peak, 82.9%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 50% B; 8 min run; 4 injections, Rt of peak 1=4.4 min, Rt of peak 2=6.5 min) to give the product (80.08 mg, 0.20 mmol, 34% yield) (Rt=5.55 min in analytical SFC) as a solid. $^1H$ NMR (400 MHz, $CD_3CN$) $\delta_H$=8.14 (dd, 1H), 8.03-7.97 (m, 1H), 7.96 (s, 1H), 7.40 (t, 1H), 7.02 (br d, 1H), 5.54-5.30 (m, 1H), 4.53-4.31 (m, 1H), 2.35 (s, 3H), 1.66 (d, 3H), 1.44 (d, 6H). LCMS Rt=1.18 min in 2.0 min chromatography, 10-80AB, MS ESI calcd. $C_{18}H_{20}ClFN_5O_2$ $[M+H]^+$ 392.12, found 391.9.

Example 60. Synthesis of 89

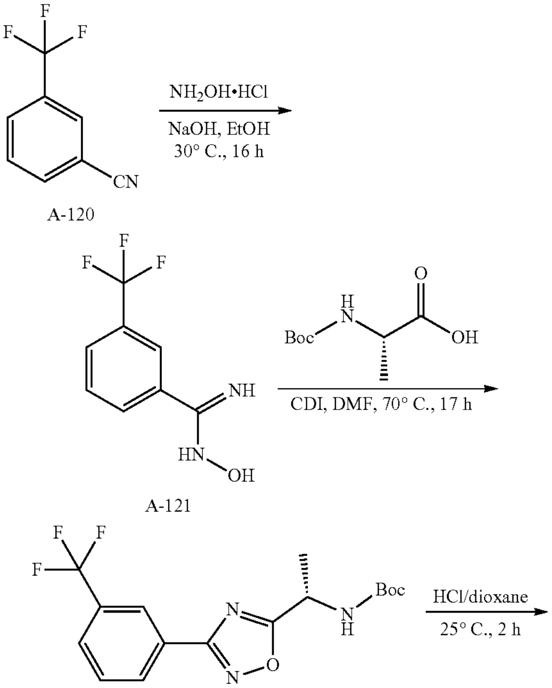

A-120

A-121

A-122

-continued

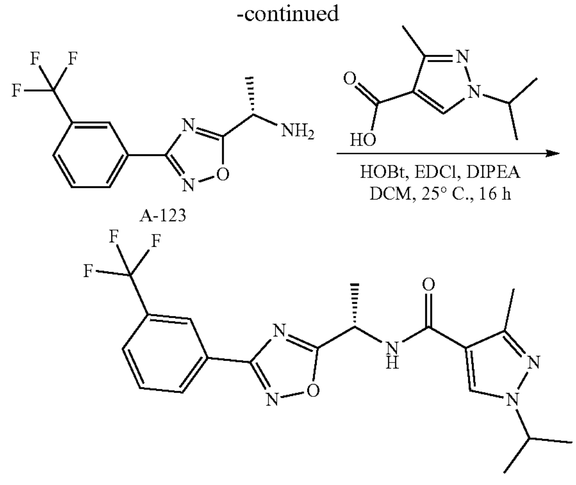

A-123

89

A-121:

A mixture of 3-(trifluoromethyl)benzonitrile (2 g, 11.69 mmol), $NH_2OH.HCl$ (2.44 g, 35.06 mmol) and NaOH (1.4 g, 35.06 mmol) in ethanol (30 mL) was stirred at 30° C. for 16 hours. The reaction mixture was partially concentrated under reduced pressure to remove the EtOH and then diluted with $H_2O$ (20 mL). The mixture was extracted with EtOAc (15 mL×2). The combined organic phase was washed with brine (30 mL), dried over $Na_2SO_4$, filtered and concentrated to give the crude product (2.2 g, 9.36 mmol, 80% yield) as a solid. LCMS $R_t$=0.33 min in 1.5 min chromatography, 5-95AB, MS ESI calcd. for $C_8H_8F_3N_2O$ $[M+H]^+$ 205.1, found 205.1.

A-122:

A mixture of (2S)-2-(tert-butoxycarbonylamino)propanoic acid (648.78 mg, 3.43 mmol) and CDI (611.59 mg, 3.77 mmol) in DMF (10 mL) was stirred at 25° C. for 1 hour and then N'-hydroxy-3-(trifluoromethyl)benzamidine (700 mg, 3.43 mmol) was added. The reaction mixture was then stirred at 70° C. for 16 hours. After cooling to room temperature, the mixture was diluted with water (30 mL), and the mixture was extracted with EtOAc (30 mL×2). The combined organic phase was washed with brine (50 mL), dried over $Na_2SO_4$, filtered and concentrated to give the crude product. The crude product was purified by flash column chromatography on silica gel (EtOAc in PE=0% to 20%) to give the product (250 mg, 0.65 mmol, 19% yield) as a solid. LCMS $R_t$=0.96 min in 1.5 min chromatography, 5-95AB, MS ESI calcd. for $C_{12}H_{11}F_3N_3O_3$ [M+H−t-Bu]$^+$ 302.1, found 302.1.

A-123:

To tert-butyl N-[(1S)-1-[3-[3-(trifluoromethyl)phenyl]-1,2,4-oxadiazol-5-yl]ethyl]carbamate (250 mg, 0.70 mmol) was added 4N HCl in 1,4-dioxane (20 mL, 0.70 mmol) and the mixture was stirred at 25° C. for 2 hours. The mixture was concentrated, diluted with water (20 mL) and basified with $Na_2CO_3$ (solid) to pH ~9. The mixture was extracted with EtOAc (20 mL×2). The combined organic phase was washed with brine (30 mL), dried over $Na_2SO_4$, filtered and concentrated to give the product (160 mg, 0.57 mmol, 82% yield) as a solid. LCMS $R_t$=0.71 min in 1.5 min chromatography, 5-95AB, MS ESI calcd. for $C_{11}H_{11}F_3N_3O$ $[M+H]^+$ 258.1, found 258.1.

89:

A mixture of 1-isopropyl-3-methyl-pyrazole-4-carboxylic acid (100 mg, 0.59 mmol), HOBt (160.69 mg, 1.19 mmol), EDCI (227.96 mg, 1.19 mmol), DIPEA (0.33 mL, 2.38 mmol) and (I S)-1-[3-[3-(trifluoromethyl)phenyl]-1,2,4-oxadiazol-5-yl]ethanamine (152.93 mg, 0.59 mmol) in $CH_2Cl_2$ (10 mL) was stirred at 25° C. for 16 hours. The reaction was quenched with $H_2O$ (20 mL) and extracted with $CH_2Cl_2$ (20 mL×2). The combined organic phase was washed with brine (40 mL), dried over $Na_2SO_4$, filtered and concentrated to give the crude product. The crude product was purified by flash chromatography on silica gel (EtOAc in PE=0% to 40%), then triturated from n-hexane/DCM (2:1, 3 mL) to give the product. Analytical SFC (Regis (S,S) Whelk-O1 (100 mm×4.6 mm, 5.0 μm), mobile phase: A: $CO_2$ B: ethanol (0.05% DEA) gradient: from 5% to 40% of B in 5.5 min and hold 40% for 3 min, then 5% of B for 1.5 min, flow rate: 2.5 mL/min) showed two peaks at 3.79 (38.1%) min and 4.80 min (main peak, 61.9%).

The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 35% B; 10 min run; 7 injections, Rt of peak 1=5 min, Rt of peak 2=8 min) to give the product (152.93 mg, 0.59 mmol) (Rt=4.80 min in analytical SFC) as a solid. $^1H$ NMR (400 MHz, $CDCl_3$) $\delta_H$=8.36 (s, 1H), 8.27 (d, 1H), 7.85 (s, 1H), 7.78 (d, 1H), 7.66-7.60 (m, 1H), 6.31 (br d, 1H), 5.66 (quin, 1H), 4.50-4.39 (m, 1H), 2.55 (s, 3H), 1.75 (d, 3H), 1.52 (d, 6H). LCMS $R_t$=1.18 min in 2.0 min chromatography, 10-80AB, MS ESI calcd. for $C_{19}H_{21}F_3N_5O_2$ $[M+H]^+$ 408.2, found 408.0.

Example 61. Synthesis of 90

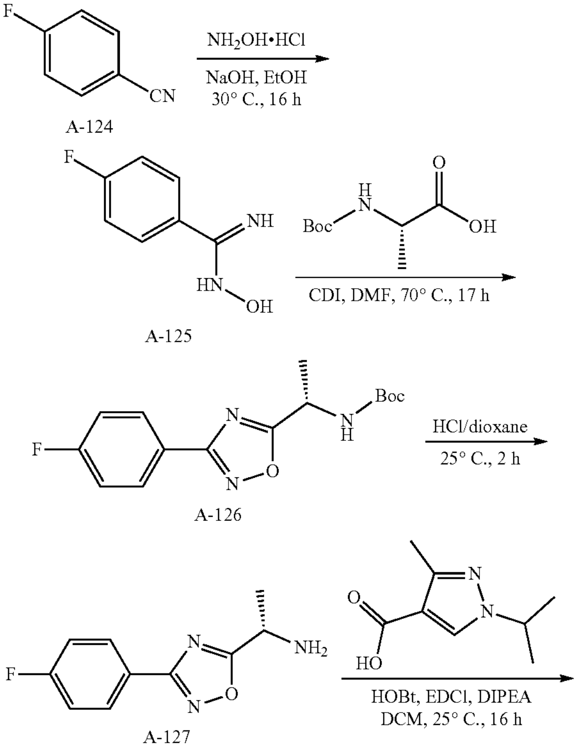

A-124

A-125

A-126

A-127

-continued

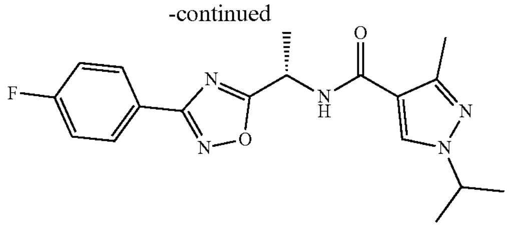

90

A-125:

A mixture of 4-fluorobenzonitrile (2 g, 16.51 mmol), $NH_2OH.HCl$ (3.44 g, 49.54 mmol) and NaOH (1.98 g, 49.54 mmol) in ethanol (30 mL) and was stirred at 30° C. for 16 hours. The reaction mixture was partially concentrated under reduced pressure to remove most of the EtOH, then diluted with $H_2O$ (20 mL). The mixture was extracted with EtOAc (15 mL×2). The combined organic phase was washed with brine (30 mL), dried over $Na_2SO_4$, filtered and concentrated to give the crude product (2.2 g, 11.03 mmol, 67% yield) as a solid. LCMS $R_t$=0.15 min in 1.5 min chromatography, 5-95AB, MS ESI calcd. for $C_7H_8FN_2O$ $[M+H]^+$ 155.1, found 155.0.

A-126:

A mixture of (2S)-2-(tert-butoxycarbonylamino)propanoic acid (736.52 mg, 3.89 mmol) and CDI (694.3 mg, 4.28 mmol) in DMF (10 mL) was stirred at 25° C. for 1 hour and then 4-fluoro-N'-hydroxy-benzamidine (600 mg, 3.89 mmol) was added. The reaction mixture was then stirred at 70° C. for 16 hours. After cooling to room temperature, the mixture was diluted with water (30 mL) and extracted with EtOAc (30 mL×2). The combined organic phase was washed with brine (30 mL), dried over $Na_2SO_4$, filtered and concentrated to give the crude product. The crude product was purified by chromatography flash column on silica gel (EtOAc in PE=0% to 40%) to give the product (257 mg, 0.80 mmol, 21% yield) as a solid. LCMS $R_t$=0.90 min in 1.5 min chromatography, 5-95AB, MS ESI calcd. for $C_{11}H_{11}FN_3O_3$ $[M+H-t-Bu]^+$252.1, found 252.1.

A-127:

To tert-butyl N-[(1S)-1-[3-(4-fluorophenyl)-1,2,4-oxadiazol-5-yl]ethyl]carbamate (257 mg, 0.84 mmol) was added 4M HCl in 1,4-dioxane (30 mL, 0.84 mmol) and the reaction mixture was stirred at 25° C. for 2 hours. The mixture was concentrated, diluted with water (30 mL), and basified with $Na_2CO_3$ (solid) to pH ~9. and the mixture was extracted with EtOAc (30 mL×2). The combined organic phase was washed with brine (50 mL), dried over $Na_2SO_4$, filtered and concentrated to give the product (180 mg, 0.77 mmol, 92% yield) as a solid. LCMS $R_t$=0.61 min in 1.5 min chromatography, 5-95AB, MS ESI calcd. for $C_{10}H_{11}FN_3O$ $[M+H]^+$ 208.1, found 208.1.

90:

A mixture of 1-isopropyl-3-methyl-pyrazole-4-carboxylic acid (100 mg, 0.59 mmol), HOBt (160.69 mg, 1.19 mmol), EDCI (227.96 mg, 1.19 mmol), DIPEA (0.33 mL, 2.38 mmol) and (I S)-1-[3-(4-fluorophenyl)-1,2,4-oxadiazol-5-yl]ethanamine (147.83 mg, 0.71 mmol) in $CH_2Cl_2$ (6 mL) was stirred at 25° C. for 16 hours. The reaction mixture was quenched with $H_2O$ (10 mL) and then extracted with $CH_2Cl_2$ (10 mL×2). The combined organic phase was washed with brine (20 mL), dried over $Na_2SO_4$, filtered and concentrated to give the crude product. The crude product was purified by flash chromatography on silica gel (EtOAc in PE=0% to 40%), then triturated from n-hexane/DCM (2:1, 3 mL) to give the product.

analytical SFC (Regis (S,S) Whelk-O1 (100 mm×4.6 mm, 5.0 μm), mobile phase: A: $CO_2$ B: ethanol (0.05% DEA) gradient: from 5% to 40% of B in 5.5 min and hold 40% for 3 min, then 5% of B for 1.5 min, flow rate: 2.5 mL/min) showed two peaks at 4.28 (7.2%) min and 5.36 min (main peak, 92.8%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 40% B; 10 min run; 5 injections, Rt of peak 1=5.4 min, Rt of peak 2=8.1 min) to give the product (84.82 mg, 0.24 mmol, 40% yield) (Rt=5.36 min in analytical SFC) as a solid. $^1H$ NMR (400 MHz, $CDCl_3$) $\delta_H$=8.12-8.04 (m, 2H), 7.85 (s, 1H), 7.21-7.15 (m, 2H), 6.34 (br d, 1H), 5.64 (quin, 1H), 4.44 (spt, 1H), 2.55 (s, 3H), 1.73 (d, 3H), 1.51 (d, 6H). LCMS $R_t$=1.10 min in 2.0 min chromatography, 10-80AB, MS ESI calcd. for $C_{18}H_{21}FN_5O_2$ $[M+H]^+$ 358.2, found 358.0.

Example 62. Synthesis of 91

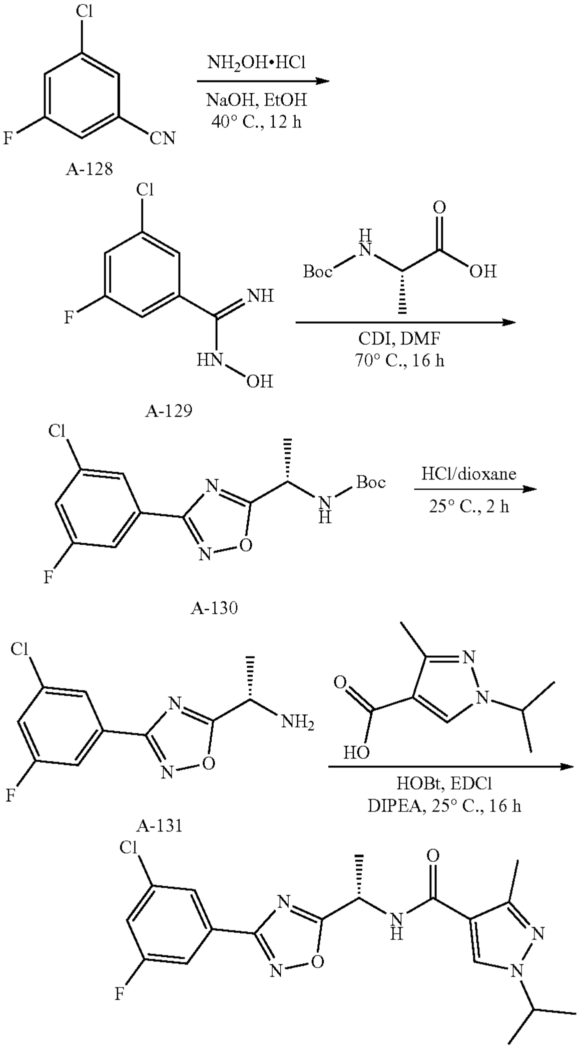

91

A-129:

A mixture of 3-chloro-5-fluoro-benzonitrile (1 g, 6.43 mmol), hydroxylamine hydrochloride (1.34 g, 19.29 mmol), and NaOH (0.77 g, 19.29 mmol) in ethanol (24 mL) and water (8 mL) was stirred at 40° C. for 12 hours. After cooling to room temperature, the mixture was partially concentrated under reduced pressure to give a residue. The residue was diluted with $H_2O$ (20 mL) and extracted with EtOAc (30 mL×2). The combined organic phase was washed with brine (15 mL), dried over $Na_2SO_4$, filtered and concentrated to give the crude product (1 g, 5.27 mmol, 82% yield) as a solid. LCMS Rt=0.313 min in 1.5 min chromatography, 5-95AB, MS ESI calcd. $C_7H_7ClFN_2O$ $[M+H]^+$ 189.0, found 188.8.

A-130:

To a mixture of 3-chloro-5-fluoro-N-hydroxy-benzamidine (500 mg, 2.65 mmol) and CDI (472.89 mg, 2.92 mmol) in DMF (15 mL) was stirred at 25° C. for 1 hour before (25)-2-(tert-butoxycarbonylamino)propanoic acid (501.64 mg, 2.65 mmol) was added. The reaction was then stirred at 70° C. for 16 hours. After cooling to room temperature, the mixture was diluted with saturated $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by flash column chromatography on silica gel (EtOAc in PE=0% to 30% to 50%) to give the product (250 mg, 0.72 mmol, 27% yield) as a solid. LCMS Rt=0.97 min in 1.5 min chromatography, 5-95AB, MS ESI calcd. $C_{15}H_{18}ClFN_3O_3$ $[M+H-Boc]^+$286.1, found 286.0.

A-131:

To tert-butyl N-[(1S)-1-[3-(3-chloro-5-fluoro-phenyl)-1,2,4-oxadiazol-5-yl]ethyl]carbamate (250 mg, 0.73 mmol) in 1,4-dioxane (10 mL) was added 4M HCl in 1,4-dioxane (10 mL, 40 mmol) and the reaction mixture was stirred at 40° C. under $N_2$ for 5 hours. After cooling to room temperature, the mixture was concentrated to give a residue. The residue was poured into ice-water (20 mL) and the pH of the mixture was basified with $Na_2CO_3$ (solid) to pH~9, and then extracted with EtOAc (20 mL×2). The organic phase was washed with brine (20 mL), dried over anhydrous $Na_2SO_4$, filtered and concentrated to give the crude product (180 mg, 0.69 mmol, 69% yield) as an oil. LCMS Rt=0.69 min in 1.5 min chromatography, 5-95AB, MS ESI calcd. $C_{10}H_{10}ClFN_3O$ $[M+H]^+$ 242.0, found 242.0.

91:

A mixture of 1-isopropyl-3-methyl-pyrazole-4-carboxylic acid (100 mg, 0.59 mmol), HOBt (160.69 mg, 1.19 mmol), EDCI (227.96 mg, 1.19 mmol), DIPEA (0.33 mL, 2.38 mmol) and (I S)-1-[3-(3-chloro-5-fluoro-phenyl)-1,2,4-oxadiazol-5-yl]ethanamine (172.41 mg, 0.71 mmol) in DCM (10 mL) was stirred at 25° C. for 16 hours. The mixture was concentrated under reduced to give a residue. The residue was diluted with $H_2O$ (30 mL) and extracted with EtOAc (50 mL×2). The combined organic phase was washed with water (20 mL) and brine (20 mL), dried over $Na_2SO_4$, filtered and concentrated to give the crude product. The crude product was purified by flash chromatography on silica gel (EtOAc in PE=0% to 50%) to give the product.

Analytical SFC (Regis (S,S) Whelk-O1 (100 mm×4.6 mm I.D., 5.0 μm), mobile phase: A: $CO_2$ B: ethanol (0.05% DEA), gradient: from 5% to 40% of B in 5.5 min and hold 40% for 3 min, then 5% of B for 1.5 min, flow rate: 2.5 mL/min) showed two peaks at 4.23 (12.8%) min and 5.29 min (main peak, 87.2%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 50% B; 8 min run; 4 injections, Rt of peak 1=4.2 min, Rt of peak 2=6.0 min) to give the product (63.77 mg, 0.16 mmol, 27% yield) (Rt=5.29 min in analytical SFC) as a solid. $^1$H NMR (400 MHz, $CD_3CN$) $\delta_H$=7.96 (s, 1H), 7.88 (s, 1H), 7.73 (br d, 1H), 7.42 (br d, 1H), 7.04 (br s, 1H), 5.46-5.35 (m, 1H), 4.47-4.36 (m, 1H), 2.35 (s, 3H), 1.67 (d, 3H), 1.45 (d, 6H). LCMS Rt=1.19 min in 2.0 min chromatography, 10-80AB, MS ESI calcd. $C_{18}H_{20}ClFN_5O_2$ $[M+H]^+$ 392.12, found 391.9.

Example 63. Synthesis of 92

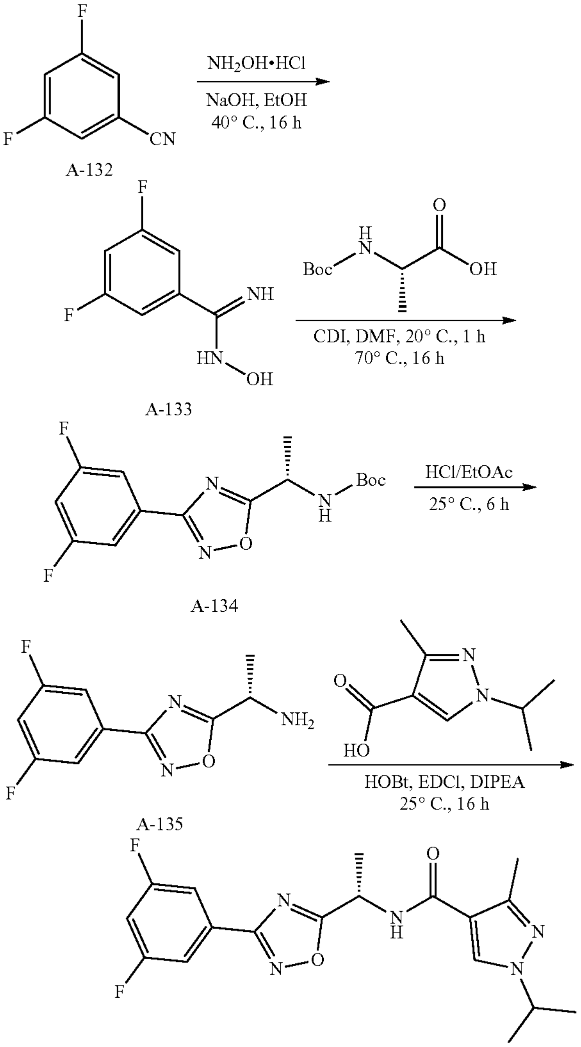

92

A-133:

A mixture of hydroxylamine hydrochloride (1.5 g, 21.57 mmol), 3,5-difluorobenzonitrile (1 g, 7.19 mmol) and NaOH (0.86 g, 21.57 mmol) in ethanol (24 mL) was stirred at 40° C. for 16 hours. After cooling to room temperature, the reaction mixture was partially concentrated under reduced pressure to remove most of the EtOH, diluted with $H_2O$ (20 mL) and extracted with EtOAc (30 mL×2). The combined organic phase was washed with brine (15 mL), dried over $Na_2SO_4$, filtered and concentrated to give the crude product (1.28 g, 4.19 mmol, 58% yield) as a solid. LCMS $R_t$=0.18 min in 1.5 min chromatography, 5-95AB, MS ESI calcd. for $C_7H_7F_2N_2O$ [M+H]$^+$ 173.0, found 173.0.

A-134:

A mixture of (25)-2-(tert-butoxycarbonylamino)propanoic acid (1.41 g, 7.44 mmol) and CDI (1.33 g, 8.18 mmol) in DMF (15 mL) was stirred at 25° C. for 1 hour and then 3,5-difluoro-N'-hydroxy-benzamidine (1.28 g, 7.44 mmol) was added. The reaction mixture was stirred at 70° C. for 16 hours then cooled to room temperature. The residue was diluted with $H_2O$ (20 mL), and the mixture was extracted with EtOAc (20 mL×2). The combined organic phase was washed with and brine (20 mL×2), dried over $Na_2SO_4$, filtered and concentrated to give the crude product. The crude product was purified by flash chromatography on silica gel (EtOAc in PE=0% to 10% to 15%) to give the product (660 mg, 2.03 mmol, 27% yield) as an oil. $^1H$ NMR (400 MHz, $CDCl_3$) $\delta_H$=7.68-7.54 (m, 2H), 7.02-6.91 (m, 1H), 5.17 (s, 2H), 1.64 (d, 3H), 1.47 (s, 9H).

A-135:

A mixture of tert-butyl N-[(1S)-1-[3-(3,5-difluorophenyl)-1,2,4-oxadiazol-5-yl]ethyl]carbamate (660 mg, 2.03 mmol) and HCl/EtOAc (10.mL, 4M) was stirred at 25° C. for 6 hours. The mixture was concentrated under reduced pressure to give the crude product as a solid. The mixture was used directly without any further purification. LCMS $R_t$=0.63 min in 2 min chromatography, 10-80AB, MS ESI calcd. for $C_{10}H_{10}F_2N30$ [M+H]$^+$ 226.1, found 226.1.

92:

To a mixture of 1-isopropyl-3-methyl-pyrazole-4-carboxylic acid (100 mg, 0.59 mmol) in DCM (15 mL) was added HOBt (160.69 mg, 1.19 mmol), EDCI (227.96 mg, 1.19 mmol), DIPEA (0.33 mL, 2.38 mmol) and (1S)-1-[3-(3,5-difluorophenyl)-1,2,4-oxadiazol-5-yl]ethanamine hydrochloride (186.69 mg, 0.71 mmol) and the mixture was stirred at 25° C. for 16 hours. The reaction mixture was quenched with saturated $NH_4Cl$ (15 mL), then extracted with DCM (20 mL×2). The combined organic phase was washed with brine (30 mL), dried over $Na_2SO_4$, filtered and concentrated to give the crude product. The crude product was partially purified by prep-TLC (silica gel, PE:EtOAc=5:2) to give the impure product. The impure product was triturated from DCM (1 mL) and n-hexane (5 mL) to give the product (120.53 mg, 0.32 mmol, 53% yield) as a solid. $^1H$ NMR (400 MHz, $CDCl_3$) $\delta_H$=7.84 (s, 1H), 7.66-7.58 (m, 2H), 7.01-6.92 (m, 1H), 6.28 (d, 1H), 5.70-5.57 (m, 1H), 4.50-4.40 (m, 1H), 2.54 (s, 3H), 1.74 (d, 3H), 1.52 (d, 6H). LCMS $R_t$=1.15 min in 2 min chromatography, 10-80AB, MS ESI calcd. for $C_{18}H_{20}F_2N_5O_2$ [M+H]$^+$ 376.2, found 375.9.

Example 64. Synthesis of 93 and 94

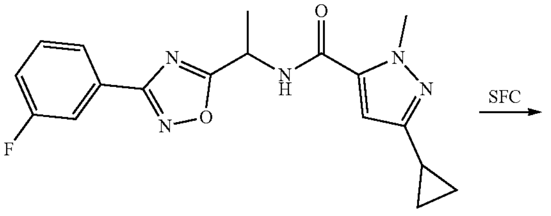

5

-continued

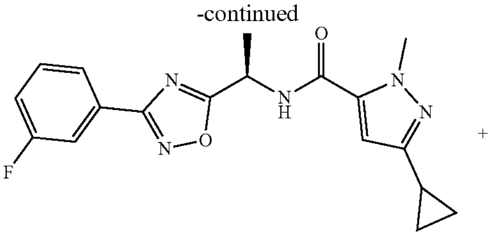

93

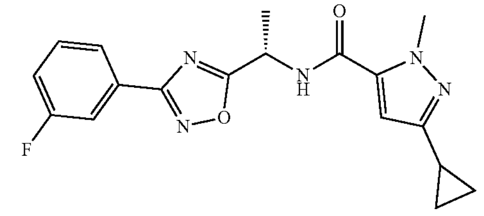

94

Analytical SFC (Daicel CHIRALCEL OJ-3 (100×4.6 mm, 3 μm), mobile phase: A: $CO_2$ B: ethanol (0.05% DEA). gradient: from 5% to 40% of B in 4 min and hold 40% for 2.5 min, then 5% of B for 1.5 min, flow rate: 2.8 mL/min, column temp: 35° C., ABPR: 1500 psi) showed two peaks at 2.29 min and 2.50 min. The product was purified by SFC (Daicel CHIRALCEL OJ-H (250 mm×30 mm, 5 μm); A=$CO_2$ and B=EtOH (0.1% $NH_3H_2O$); 38° C.; 60 mL/min; 15% B; 13 min run; 6 injections, Rt of peak 1=8.7 min, Rt of Peak 2=11.2 min) to give the enantiomer 1, randomly assigned as 93 (4.23 mg, 12 μmol, 22% yield) (Rt=2.29 min in analytical SFC) as a solid and enantiomer 2, randomly assigned as 94 (5.91 mg, 17 μmol, 30% yield) (Rt=2.50 min in analytical SFC) as a solid.

93:

$^1H$ NMR (400 MHz, $CDCl_3$) $\delta_H$=7.88 (d, 1H), 7.79 (td, 1H), 7.47 (dt, 1H), 7.25-7.15 (m, 1H), 6.53 (br d, 1H), 6.31 (s, 1H), 5.59 (quin, 1H), 4.10 (s, 3H), 1.98-1.88 (m, 1H), 1.75 (d, 3H), 0.99-0.91 (m, 2H), 0.78-0.71 (m, 2H). LCMS $R_t$=1.16 min in 2.0 min chromatography, 10-80AB, MS ESI calcd. for $C_{18}H_{19}FN_5O_2$ [M+H]$^+$ 356.1, found 355.9.

94:

$^1H$ NMR (400 MHz, $CDCl_3$) $\delta_H$=7.88 (d, 1H), 7.79 (td, 1H), 7.47 (dt, 1H), 7.26-7.15 (m, 1H), 6.55 (br d, 1H), 6.31 (s, 1H), 5.59 (quin, 1H), 4.10 (s, 3H), 1.99-1.87 (m, 1H), 1.75 (d, 3H), 0.99-0.91 (m, 2H), 0.78-0.71 (m, 2H). LCMS $R_t$=1.22 min in 2.0 min chromatography, 10-80AB, MS ESI calcd. for $C_{18}H_{19}FN_5O_2$ [M+H]$^+$ 356.1, found 356.1.

Example 65. Synthesis of 281 & 95

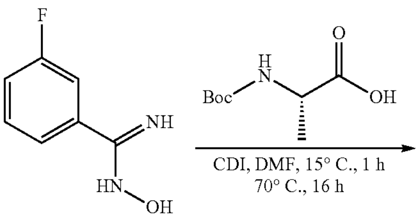

A-10

-continued

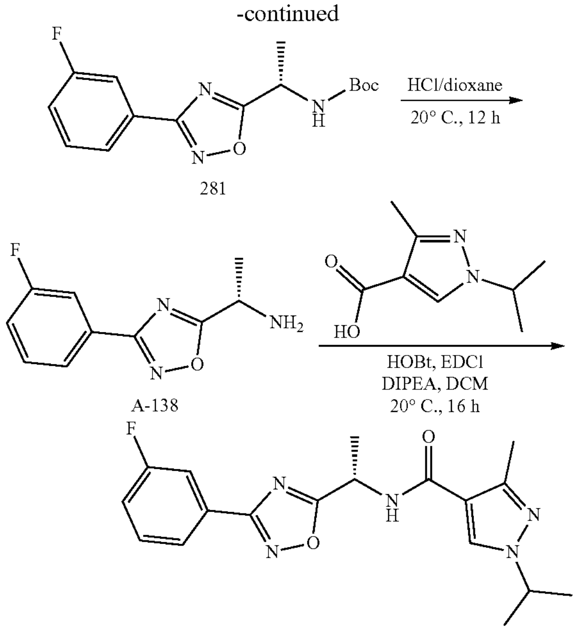

281

A-138

95

281:

A mixture of (25)-2-(tert-butoxycarbonylamino)propanoic acid (0.74 g, 3.89 mmol) and CDI (0.69 g, 4.28 mmol) in DMF (18 mL) was stirred at 15° C. for 1 hour and then 3-fluoro-N'-hydroxy-benzamidine (0.6 g, 3.89 mmol) was added. The reaction mixture was stirred at 70° C. for 16 hours. After cooling to room temperature, the mixture was diluted with $H_2O$ (30 mL) and extracted with EtOAc (30 mL×3). The combined organic phase was washed with brine (50 mL), dried over $Na_2SO_4$, filtered and concentrated to give the crude product. The crude product was purified by flash column chromatography on silica gel (EtOAc in PE=0% to 15% to 40%) to give the product (420 mg, 1.37 mmol, 35% yield) as an oil. LCMS $R_t$=0.91 min in 1.5 min chromatography, 5-95AB, MS ESI calcd. for $C_{11}H_{11}FN_3O_3$ $[M+H-t-Bu]^+$ 252.07, found 252.1.

A-138:

To tert-butyl N-[(1S)-1-[3-(3-fluorophenyl)-1,2,4-oxadiazol-5-yl]ethyl]carbamate (420 mg, 1.37 mmol) was added 4M HCl in 1,4-dioxane (10 mL, 40 mmol) and the reaction mixture was stirred at 20° C. for 12 hours. The mixture was concentrated under reduced pressure and diluted with $H_2O$ (20 mL) and basified with $NaHCO_3$ (solid) to a pH~8. The mixture was extracted with EtOAc (20 mL×2), and the combined organic phase was washed with brine (30 mL), dried over $Na_2SO_4$, filtered and concentrated to give the crude product (270 mg, 1.30 mmol, 95% yield) as an oil. LCMS $R_t$=0.41 min in 2.0 min chromatography, 10-80AB, MS ESI calcd. for $C_{10}H_{11}FN_3O$ $[M+H]^+$ 208.08, found 207.9.

95:

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1S)-1-[3-(3-fluorophenyl)-1,2,4-oxadiazol-5-yl]ethanamine (147.83 mg, 0.71 mmol) and the reaction mixture was stirred at 25° C. for 16 hours. The reaction was quenched with $H_2O$ (30 mL) and brine (5 mL) and then extracted with EtOAc (20 mL×2). The combined organic phase was washed with brine (30 mL), dried over $Na_2SO_4$, filtered and concentrated to give the crude product. The crude product was purified by flash chromatography on silica gel (EtOAc in PE=0% to 15% to 40%) to give the product (150 mg) as a solid. Analytical SFC analysis (Regis (S,S) Whelk-O1 (100×4.6 mm, 5 μm), mobile phase: A: $CO_2$ B: ethanol (0.05% DEA), gradient: from 5% to 40% of B in 5.5 min and hold 40% for 3 min, then 5% of B in 1.5 min, flow rate: 2.5 mL/min, column temp: 35° C.) showed 2 peaks at 4.27 min (8.1%), and 5.32 min (main peak, 91.9%) The product was purified by SFC (Regis (S,S) Whelk-O1 (250 mm×30 mm, 5 μm); A=$CO_2$ and B=ethanol (0.1% $NH_4OH$); 38° C.; 60 mL/min; 50% B; 8 min run; 8 injections, Rt of peak 1=4.1 min, Rt of peak 2=6 min) to give the product (105.13 mg, 294.2 μmol, 70% yield) (Rt=5.32 min in analysis analytical SFC) as a solid. $^1H$ NMR (400 MHz, $CDCl_3$) $\delta_H$=7.88 (d, 1H), 7.85 (s, 1H), 7.81-7.76 (m, 1H), 7.51-7.43 (m, 1H), 7.25-7.19 (m, 1H), 6.43-6.21 (m, 1H), 5.76-5.55 (m, 1H), 4.50-4.87 (m, 1H), 2.55 (s, 3H), 1.74 (d, 3H), 1.52 (d, 6H). LCMS $R_t$=1.16 min in 2.0 min chromatography, 10-80AB, MS ESI calcd. $C_{18}H_{21}FN_5O_2$ $[M+H]^+$ 358.16, found 358.1.

Example 66. Synthesis of 96

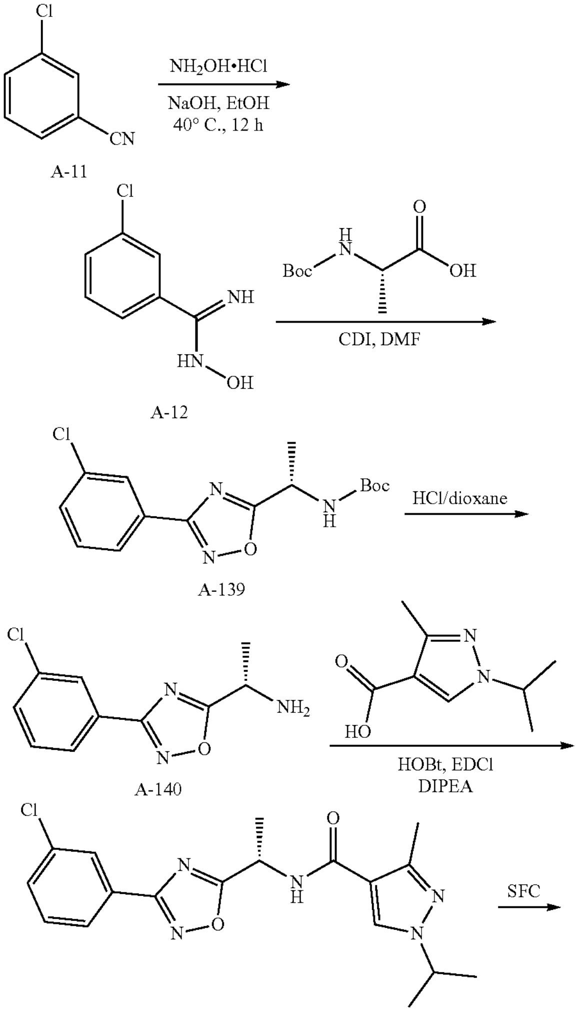

A-11

A-12

A-139

A-140

A-141

-continued

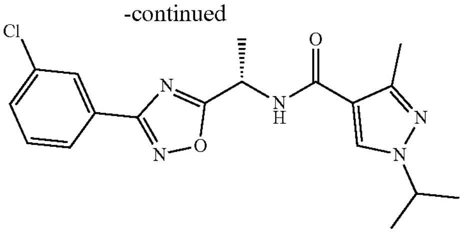

96

A-12:

A mixture of 3-chlorobenzonitrile (2 g, 14.54 mmol), $NH_2OH$.HCl (3.03 g, 43.61 mmol) and NaOH (1.74 g, 43.61 mmol) in ethanol (18 mL) and water (6 mL) was stirred at 40° C. for 16 hours. After cooling to room temperature, the reaction mixture was partially concentrated under reduced pressure to remove most of EtOH and then diluted with $H_2O$ (30 mL). The mixture was extracted with EtOAc (30 mL×2). The combined organic phase was washed with brine (30 mL), dried over $Na_2SO_4$, filtered and concentrated to give the crude product as a solid. LCMS $R_t$=0.2 min in 1.5 min chromatography, 5-95AB, MS ESI calcd. for $C_7H_8ClN_2O$ $[M+H]^+$ 171.0, found 171.0.

A-139:

A mixture of (2S)-2-(tert-butoxycarbonylamino)propanoic acid (0.43 g, 2.26 mmol) and CDI (0.4 g, 2.48 mmol) in DMF (18 mL) was stirred at 15° C. for 1 hour and then 3-chloro-N'-hydroxy-benzamidine (0.6 g, 2.26 mmol) was added. The reaction mixture was then stirred at 70° C. for 16 hours. After cooling to room temperature, the mixture was diluted with saturated $NH_4Cl$ (30 mL), and the mixture was extracted with EtOAc (30 mL×3). The combined organic phase was washed with brine (50 mL), dried over $Na_2SO_4$, filtered and concentrated to give the crude product. The crude product was purified by flash column chromatography on silica gel (EtOAc in PE=0% to 20% to 50%) to give the product (370 mg, 1.14 mmol, 50% yield) as an oil. $^1H$ NMR (400 MHz, $CDCl_3$) $\delta_H$=8.09 (t, 1H), 7.97 (td, 1H), 7.52-7.46 (m, 1H), 7.45-7.40 (m, 1H), 5.18 (br s, 2H), 1.66-1.62 (m, 3H), 1.47 (s, 9H). LCMS $R_t$=0.94 min in 1.5 min chromatography, 5-95AB, MS ESI calcd. for $C_{11}H_{11}ClN_3O_3$ $[M+H-t-Bu]^+$ 268.04, found 268.0.

A-140:

To tert-butyl N-[(1S)-1-[3-(3-chlorophenyl)-1,2,4-oxadiazol-5-yl]ethyl]carbamate (370 mg, 1.14 mmol) was added 4M HCl in 1,4-dioxane (5 mL, 20 mmol) and the reaction mixture was stirred at 20° C. for 1.5 hours. The mixture was concentrated under reduced pressure and diluted with $H_2O$ (20 mL) and basified with $NaHCO_3$ (solid) to pH~8. The mixture was extracted with EtOAc (20 mL×2), and the combined organic phase was washed with brine (30 mL), dried over $Na_2SO_4$, filtered and concentrated to give the crude product (250 mg, 1.07 mmol, 94% yield) as an oil. LCMS $R_t$=0.67 min in 1.5 min chromatography, 5-95AB, MS ESI calcd. for $C_{10}H_{11}ClN_3O$ $[M+H]^+$ 224.05, found 224.0.

A-141:

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1S)-1-[3-(3-chlorophenyl)-1,2,4-oxadiazol-5-yl]ethanamine (159.58 mg, 0.71 mmol) and the mixture was stirred at 25° C. for 16 hours. The reaction was quenched with sat. $NH_4Cl$ (30 mL) and brine (5 mL), extracted with EtOAc (20 mL×2). The combined organic phase was washed with brine (30 mL), dried over $Na_2SO_4$, filtered and concentrated to give the crude product. The crude product was purified by flash chromatography on silica gel (EtOAc in PE=0% to 15% to 40%) to give the product (150 mg) as a solid.

96:

Analytical SFC (Regis (S,S) Whelk-O1 (100 mm×4.6 mm, 5 μm), mobile phase: A: $CO_2$ B: ethanol (0.05% DEA), gradient: from 5% to 40% of B in 5.5 min and hold 40% for 3 min, then 5% of B in 1.5 min, flow rate: 2.5 mL/min, column temp: 35° C.) showed 2 peaks at 4.74 min (6.9%), and 5.89 min (93.1%). The product was purified by SFC (Regis (S,S) Whelk-O1 (250 mm×30 mm, 5 μm); A=$CO_2$ and B=ethanol (0.1% $NH_4OH$); 38° C.; 60 mL/min; 50% B; 9 min run; 6 injections, Rt of peak 1=4.8 min, Rt of peak 2=7 min) to give the product (84.2 mg, 225.2 μmol, 56% yield) (Rt=5.89 min in analytical SFC) as a solid. $^1H$ NMR (400 MHz, $CDCl_3$) $\delta_H$=8.08 (t, 1H), 7.97 (td, 1H), 7.85 (s, 1H), 7.52-7.47 (m, 1H), 7.45-7.39 (m, 1H), 6.37-6.23 (m, 1H), 5.71-5.59 (m, 1H), 4.51-4.39 (m, 1H), 2.55 (s, 3H), 1.74 (d, 3H), 1.52 (d, 6H). LCMS $R_t$=1.22 min in 2.0 min chromatography, 10-80AB, MS ESI calcd. $C_{18}H_{21}ClN_5O_2$ $[M+H]^+$ 374.1, found 374.1.

Example 67. Synthesis of 97

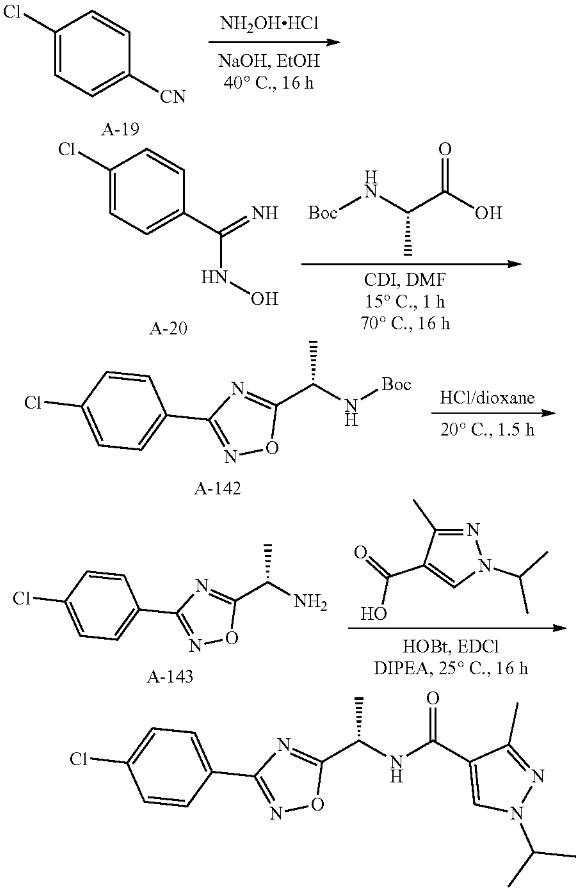

97

A-20:

A mixture of 4-chlorobenzonitrile (2 g, 14.54 mmol), $NH_2OH$.HCl (3.03 g, 43.61 mmol) and NaOH (1.74 g, 43.61 mmol) in ethanol (18 mL) and water (6 mL) was stirred at 40° C. for 16 hours. After cooling to room temperature, the reaction mixture was partially concentrated under reduced pressure to remove most of the EtOH and then diluted with $H_2O$ (30 mL). The mixture was extracted with EtOAc (30 mL×2). The combined organic phase was washed with brine (50 mL), dried over $Na_2SO_4$, filtered and concentrated to give the crude product (2.1 g, 11.81 mmol, 81% yield) as a solid. LCMS $R_t$=0.18 min in 1.5 min chromatography, 5-95AB, MS ESI calcd. for $C_7H_8ClN_2O$ $[M+H]^+$ 171.02, found 171.0.

A-142:

A mixture of (2S)-2-(tert-butoxycarbonylamino)propanoic acid (0.67 g, 3.52 mmol) and CDI (0.63 g, 3.87 mmol) in DMF (18 mL) was stirred at 15° C. for 1 hour and then 4-chloro-N'-hydroxy-benzamidine (0.6 g, 3.52 mmol) was added. The reaction mixture was then stirred at 70° C. for 16 hours. After cooling to room temperature, the mixture was diluted with saturated $NH_4Cl$ (30 mL), and the mixture was extracted with EtOAc (30 mL×3). The combined organic phase was washed with brine (50 mL), dried over $Na_2SO_4$, filtered and concentrated to give the crude product. The crude product was purified by chromatography flash column on silica gel (EtOAc in PE=0% to 15% to 40%) to give the product (580 mg, 1.79 mmol, 51% yield) as a solid. $^1H$ NMR (400 MHz, $CDCl_3$) $\delta_H$=8.05-8.03 (m, 1H), 8.02-8.01 (m, 1H), 7.49-7.46 (m, 1H), 7.46-7.44 (m, 1H), 5.17 (br s, 2H), 1.65-1.62 (m, 3H), 1.47 (s, 9H).

A-143:

To tert-butyl N-[(1S)-1-[3-(4-chlorophenyl)-1,2,4-oxadiazol-5-yl]ethyl]carbamate (580 mg, 1.79 mmol) was added 4M HCl in 1,4-dioxane (10 mL, 40 mmol) and the reaction mixture was stirred at 20° C. for 1.5 hours. The mixture was concentrated under reduced pressure and diluted with $H_2O$ (20 mL) and basified with $NaHCO_3$ (solid) to pH~8. The mixture was extracted with EtOAc (20 mL×2), and the combined organic phase was washed with brine (30 mL), dried over $Na_2SO_4$, filtered and concentrated to give the crude product (320 mg, 1.42 mmol, 79% yield) as an oil. LCMS $R_t$=0.85 min in 2.0 min chromatography, 10-80AB, MS ESI calcd. for $C_{10}H_{11}ClN_3O$ $[M+H]^+$ 224.05, found 223.9.

97:

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (I S)-1-[3-(4-chlorophenyl)-1,2,4-oxadiazol-5-yl]ethanamine (159.58 mg, 0.71 mmol) and it was stirred at 25° C. for 16 hours. The reaction mixture was quenched with sat. $NH_4Cl$ (30 mL) and brine (5 mL) and then extracted with EtOAc (20 mL×2). The combined organic phase was washed with brine (30 mL), dried over $Na_2SO_4$, filtered and concentrated to give the crude product. The crude product was purified by flash chromatography on silica gel (EtOAc in PE=0% to 15% to 40%) to give the product (100 mg, 267.5 μmol, 45% yield) as a solid. Analytical SFC (Regis (S,S) Whelk-01 (150 mm×4.6 mm, 5 μm), mobile phase: A: $CO_2$ B: ethanol (0.05% DEA), gradient: from 5% to 40% of B in 5.5 min and hold 40% for 3 min, then 5% of B in 1.5 min, flow rate: 2.5 mL/min, column temp: 35° C.) showed 2 peaks at 4.70 min (10.2%) and 5.82 min (89.8%). The product was purified by SFC (Regis (S,S) Whelk-O1 (250 mm×30 mm, 5 μm); A=$CO_2$ and B=ethanol (0.1% $NH_4OH$); 38° C.; 60 mL/min; 50% B; 9 min run; 6 injections, Rt of peak 1=4.8 min, Rt of peak 2=7 min) to give the product (91.16 mg, 243.8 μmol, 61% yield) (Rt=5.82 in analytical SFC) as a solid. $^1H$ NMR (400 MHz, $CDCl_3$) $\delta_H$=8.05-7.99 (m, 2H), 7.84 (s, 1H), 7.50-7.44 (m, 2H), 6.39-6.23 (m, 1H), 5.72-5.53 (m, 1H), 4.51-4.38 (m, 1H), 2.55 (s, 3H), 1.73 (d, 3H), 1.52 (d, 6H). LCMS $R_t$=1.16 min in 2.0 min chromatography, 10-80AB, MS ESI calcd. $C_{18}H_{21}ClN_5O_2$ $[M+H]^+$ 374.1, found 374.0.

Example 68. Synthesis of 98

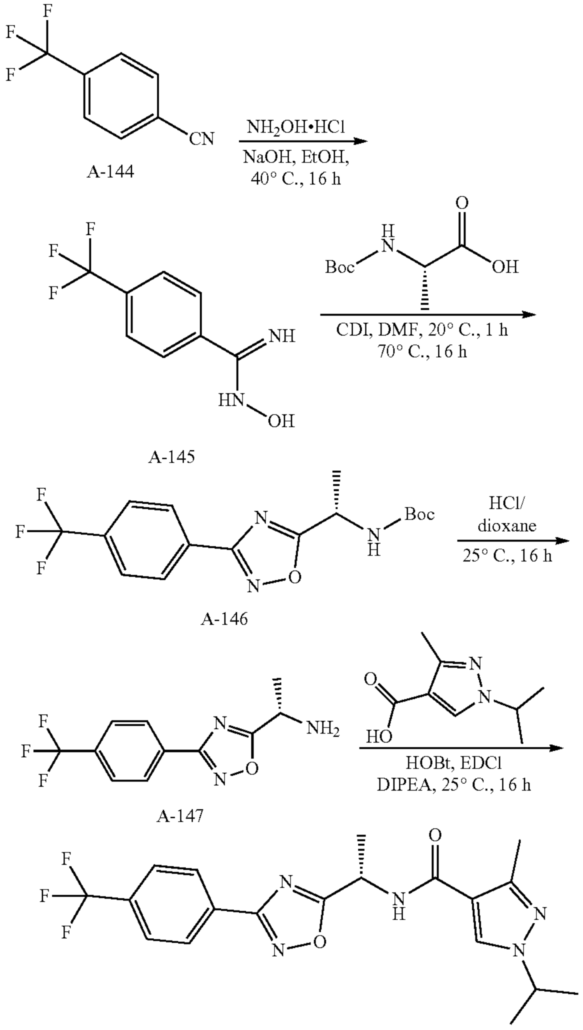

A-144

A-145

A-146

A-147

98

A-145:

A mixture of 4-(trifluoromethyl)benzonitrile (1 g, 5.84 mmol), hydroxylamine hydrochloride (1.22 g, 17.53 mmol) and NaOH (0.7 g, 17.53 mmol) in ethanol (20 mL) as stirred at 40° C. for 16 hours. After cooling to room temperature, the reaction mixture was partially concentrated under reduce pressure to remove most of the EtOH and then diluted with $H_2O$ (20 mL). The mixture was extracted with EtOAc (30 mL×2). The combined organic phase was washed with brine (15 mL), dried over $Na_2SO_4$, filtered and concentrated to give the crude product (1.46 g, 6.96 mmol) as a solid. LCMS $R_t$=0.41 min in in 1.5 min chromatography, 5-95AB, MS ESI calcd. for $C_8H_8F_3N_2O$ $[M+H]^+$ 205.1, found 205.0.

A-146:

A mixture of (2S)-2-(tert-butoxycarbonylamino)propanoic acid (463.41 mg, 2.45 mmol) and CDI (436.85 mg, 2.69 mmol) in DMF (15 mL) was stirred at 25° C. for 1 hour and then N'-hydroxy-4-(trifluoromethyl)benzamidine (500 mg, 2.45 mmol) was added. The reaction mixture was then stirred at 70° C. for 16 hours. After cooling to room temperature, the mixture was diluted with water (60 mL), and the mixture was extracted with EtOAc (50 mL×2). The combined organic phase was washed with brine (30 mL), dried over $Na_2SO_4$, filtered and concentrated to give the crude product. The crude product was purified by chromatography flash column on silica gel (EtOAc in PE=0% to 30%) to give the product (550 mg, 1.54 mmol, 63% yield) as a solid. LCMS $R_t$=1.34 min in in 2.0 min chromatography, 10-80AB, MS ESI calcd. for $C_{12}H_{10}F_3N_3O_3$ $[M+H-tBu]^+$ 302.1, found 301.9.

A-147:

To tert-butyl N-[(1S)-1-[3-[4-(trifluoromethyl)phenyl]-1,2,4-oxadiazol-5-yl]ethyl]carbamate (550 mg, 1.54 mmol) was added 4M HCl in 1,4-dioxane (15 mL) and the reaction mixture was stirred at 25° C. for 16 hours. The mixture was concentrated under reduced pressure and diluted with $H_2O$ (20 mL) and basified with $NaHCO_3$ (solid) to pH~8. The mixture was extracted with EtOAc (30 mL×3), and the combined organic phase was washed with brine (30 mL), dried over $Na_2SO_4$, filtered and concentrated to give the crude product (440 mg, 1.71 mmol) as an oil.

98:

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1S)-1-[3-[4-(trifluoromethyl)phenyl]-1,2,4-oxadiazol-5-yl]ethanamine (183.51 mg, 0.71 mmol) and the resultant mixture was stirred at 25° C. for 16 hours. The reaction was quenched with $H_2O$ (10 mL), then extracted with DCM (20 mL×3). The combined organic phase was washed with brine (30 mL), dried over $Na_2SO_4$, filtered and concentrated to give the crude product. The crude product was purified with flash chromatography on silica gel (EA in PE=0/1 to 1/5) to give the product. Analytical SFC (Regis (S,S) Whelk-O1 (100 mm×4.6 mm, 5.0 μm), mobile phase: A: $CO_2$ B: ethanol (0.05% DEA), gradient: from 5% to 40% of B in 5.5 min and hold 40%, for 3 min, then 5% of B for 1.5 min, flow rate: 2.5 mL/min) showed two peaks at 3.78 min (6.7%) and 4.74 min (main peak, 93.3%).

Then the product was purified by SFC (Regis (S,S) Whelk-O1 (250 mm×30 mm, 5 μm); A=$CO_2$ and B=EtOH (0.1% $NH_3H_2O$); 38° C.; 60 mL/min; 40% B; 7.80 min run; 4 injections, Rt of peak 1=4.00 min, Rt of peak 2=5.80 min) to give the product (58.15 mg, 0.14 mmol) (Rt=4.74 min in analytical SFC) as a solid. $^1H$ NMR (400 MHz, $CDCl_3$) δ=8.21 (d, 2H), 7.85 (s, 1H), 7.76 (d, 2H), 6.30 (br d, 1H), 5.66 (quin, 1H), 4.50-4.36 (m, 1H), 2.55 (s, 3H), 1.75 (d, 3H), 1.52 (d, 6H). LCMS $R_t$=1.24 min in in 2.0 min chromatography, 10-80AB, MS ESI calcd. for $C_{19}H_{21}F_3N_5O_2$ $[M+H]^+$ 408.2, found 408.1.

Example 69. Synthesis of 99

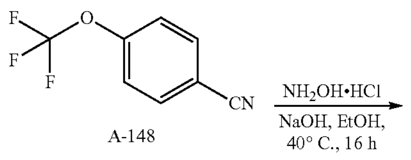

A-148

-continued

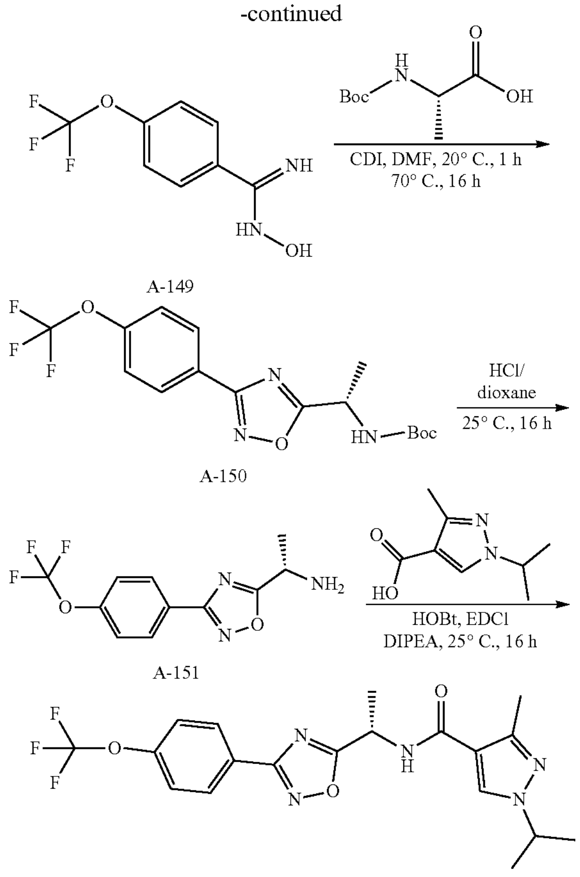

A-149

A-150

A-151

99

A-149:

A mixture of hydroxylamine hydrochloride (1.11 g, 16.03 mmol), 4-(trifluoromethoxy)benzonitrile (1 g, 5.34 mmol) and NaOH (0.64 g, 16.03 mmol) in ethanol (24 mL) was stirred at 40° C. for 16 hours. After cooling to room temperature, the reaction mixture was partially concentrated under reduced pressure to remove most of the EtOH and then it was diluted with $H_2O$ (20 mL). The mixture was extracted with EtOAc (30 mL×2). The combined organic phase was washed with brine (15 mL), dried over $Na_2SO_4$, filtered and concentrated to give the crude product (1.48 g, 6.24 mmol) as a solid. LCMS $R_t$=0.59 min in in 1.5 min chromatography, 5-95AB, MS ESI calcd. for $C_8H_8F_3N_2O_2$ $[M+H]^+$ 221.0, found 221.0.

A-150:

A mixture of (2S)-2-(tert-butoxycarbonylamino)propanoic acid (429.73 mg, 2.27 mmol) and CDI (405.1 mg, 2.5 mmol) in DMF (15 mL) was stirred at 25° C. for 1 hour and then N'-hydroxy-4-(trifluoromethoxy)benzamidine (500 mg, 2.27 mmol) was added. The reaction mixture was then stirred at 70° C. for 16 hours. After cooling to room temperature, the mixture was diluted with water (60 mL) and extracted with EtOAc (50 mL×2). The combined organic phase was washed with brine (30 mL), dried over $Na_2SO_4$, filtered and concentrated to give the crude product. The crude product was purified by flash column chromatography on silica gel (EtOAc in PE=0% to 50%) to give the product (610 mg, 1.63 mmol, 72% yield) as a solid. LCMS $R_t$=1.38 min in in 2.0 min chromatography, 10-80AB, MS ESI calcd. for $C_{12}H_{10}F_3N_3O_4$ $[M+H-tBu]^+$ 318.1, found 318.0.

A-151:

To tert-butyl N-[(1S)-1-[3-[4-(trifluoromethoxy)phenyl]-1,2,4-oxadiazol-5-yl]ethyl]carbamate (610 mg, 1.63 mmol) was added 4M HCl in 1,4-dioxane (15 mL) and the reaction mixture was stirred at 25° C. for 16 hours. The mixture was concentrated under reduced pressure and diluted with $H_2O$ (20 mL) and basified with $NaHCO_3$(s) to pH~8. The mixture was extracted with EtOAc (30 mL×2), and the combined organic phase was washed with brine (30 mL), dried over $Na_2SO_4$, filtered and concentrated to give the crude product (510 mg, 1.87 mmol) as an oil.

99:

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1S)-1-[3-[4-(trifluoromethoxy)phenyl]-1,2,4-oxadiazol-5-yl]ethanamine (194.93 mg, 0.71 mmol) and the reaction mixture was stirred at 25° C. for 16 hours. The reaction was quenched with $H_2O$ (10 mL), then extracted with DCM (20 mL×3). The combined organic phase was washed with brine (30 mL), dried over $Na_2SO_4$, filtered and concentrated to give the crude product. The crude product was purified with flash chromatography on silica gel (0% to 20% EtOAc in PE) to give the product. Analytical SFC (Regis (S,S) Whelk-O1 (100×4.6 mm, 5.0 μm), mobile phase: A: $CO_2$ B: ethanol (0.05% DEA), gradient: from 5% to 40% of B in 5.5 min and hold 40%, for 3 min, then 5% of B for 1.5 min, flow rate: 2.5 mL/min) showed two peaks at 3.75 min (18.7%) and 4.71 min (main peak, 81.3%).

The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 45% B; 7.50 min run; 4 injections, Rt of peak 1=4.00 min, Rt of peak 2=5.50 min) to give the product (53.39 mg, 0.13 mmol, 21% yield) (Rt=4.71 min in analytical SFC) as a solid. $^1H$ NMR (400 MHz, $CDCl_3$) 400 MHz δ=8.20-8.07 (m, 2H), 7.85 (s, 1H), 7.34 (d, 2H), 6.32 (br d, 1H), 5.70-5.57 (m, 1H), 4.50-4.40 (m, 1H), 2.55 (s, 3H), 1.74 (d, 3H), 1.52 (d, 6H). LCMS $R_t$=1.26 min in in 2.0 min chromatography, 10-80AB, MS ESI calcd. for $C_{19}H_{20}F_3N_5O_3$ $[M+H]^+$ 424.2, found 424.1.

Example 70. Synthesis of 100

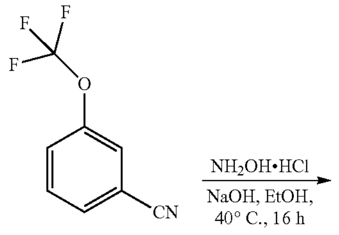

A-152

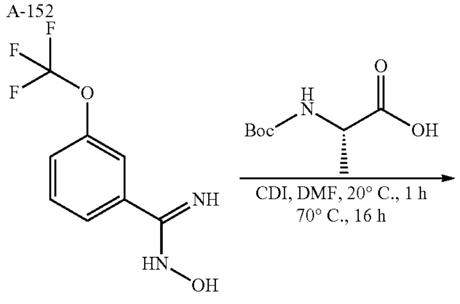

A-153

-continued

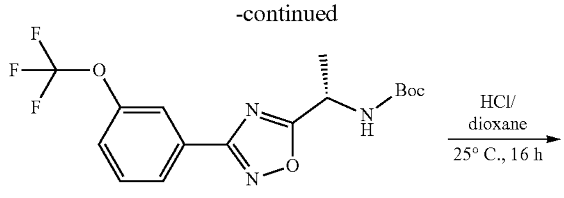

A-154

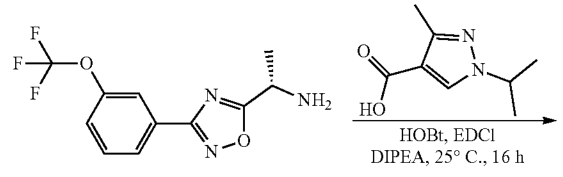

A-155

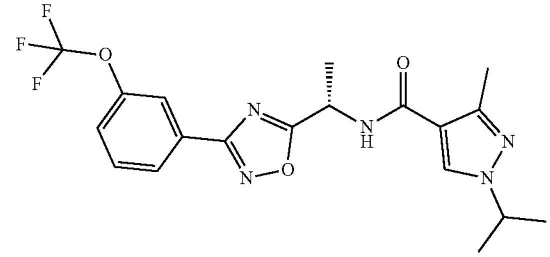

100

A-153:

A mixture of hydroxylamine hydrochloride (1.11 g, 16.03 mmol), 3-(trifluoromethoxy)benzonitrile (1 g, 5.34 mmol) and NaOH (0.64 g, 16.03 mmol) in ethanol (24 mL) was stirred at 40° C. for 16 hours. After cooling to room temperature, the reaction mixture was partially concentrated under reduced pressure to remove most of the EtOH and then diluted with $H_2O$ (20 mL). The mixture was extracted with EtOAc (30 mL×2). The combined organic phase was washed with brine (15 mL), dried over $Na_2SO_4$, filtered and concentrated to give the crude product (1.2 g, 3.07 mmol, 57% yield) as an oil. LCMS $R_t$=0.59 min in in 1.5 min chromatography, 5-95AB, MS ESI calcd. for $C_8H_8F_3N_2O_2$ $[M+H]^+$ 221.0, found 221.0.

A-154:

A mixture of (2S)-2-(tert-butoxycarbonylamino)propanoic acid (429.73 mg, 2.27 mmol) and CDI (405.1 mg, 2.5 mmol) in DMF (15 mL) was stirred at 25° C. for 1 hour and then N'-hydroxy-3-(trifluoromethoxy)benzamidine (500 mg, 2.27 mmol) was added. The reaction mixture was then stirred at 70° C. for 16 hours. After cooling to room temperature, the mixture was diluted with water (60 mL) and extracted with EtOAc (50 mL×2). The combined organic phase was washed with brine (30 mL), dried over $Na_2SO_4$, filtered and concentrated to give the crude product. The crude product was purified by flash column chromatography on silica gel (EtOAc in PE=0% to 30%) to give the product (640 mg, 1.71 mmol, 75% yield) as a solid. LCMS $R_t$=1.38 min in in 2.0 min chromatography, 10-80AB, MS ESI calcd. for $C_{12}H_{10}F_3N_3O_4$ $[M+H-tBu]^+$ 318.1, found 317.9.

A-155:

To tert-butyl N-[(1S)-1-[3-[3-(trifluoromethoxy)phenyl]-1,2,4-oxadiazol-5-yl]ethyl]carbamate (640 mg, 1.71 mmol) was added 4M HCl in 1,4-dioxane (15 mL) and the reaction mixture was stirred at 25° C. for 16 hours. The mixture was concentrated under reduced pressure and diluted with $H_2O$ (20 mL) and basified with $NaHCO_3$ (solid) to pH~8. The mixture was extracted with EtOAc (30 mL×2), and the combined organic phase was washed with brine (30 mL), dried over $Na_2SO_4$, filtered and concentrated to give the crude product (500 mg, 1.83 mmol) as an oil.

100:

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1S)-1-[3-[3-(trifluoromethoxy)phenyl]-1,2,4-oxadiazol-5-yl]ethanamine (194.93 mg, 0.71 mmol) and the resultant reaction mixture was stirred at 25° C. for 16 hours. The reaction was quenched with $H_2O$ (10 mL), then extracted with DCM (20 mL×3). The combined organic phase was washed with brine (30 mL), dried over $Na_2SO_4$, filtered and concentrated to give the crude product. The crude product was purified with flash chromatography on silica gel (EtOAc in PE=0% to 20%) to give the product. Analytical SFC (Regis (S,S) Whelk-O1 (100 mm×4.6 mm, 5.0 μm), mobile phase: A: $CO_2$ B: ethanol (0.05% DEA), gradient: from 5% to 40% of B in 5.5 min and hold 40%, for 3 min, then 5% of B for 1.5 min, flow rate: 2.5 mL/min) showed two peaks at 3.71 min (12.9%) and 4.67 min (87.1%). The product as purified by SFC (Regis (S,S) Whelk-O1 (250 mm×30 mm, 5 μm); A=$CO_2$ and B=EtOH (0.1% $NH_3H_2O$); 38° C.; 60 mL/min; 50% B; 7.50 min run; 4 injections, Rt of peak 1=3.71 min, Rt of peak 2=4.67 min) to give the product (64.7 mg, 0.16 mmol, 25% yield) (Rt=4.67 min in analytical SFC) as a solid. $^1H$ NMR (400 MHz, $CDCl_3$) δ=8.12 (d, 2H), 7.85 (s, 1H), 7.33 (d, 2H), 6.33 (br d, 1H), 5.65 (quin, 1H), 4.55-4.33 (m, 1H), 2.55 (s, 3H), 1.74 (d, 3H), 1.52 (d, 6H). LCMS $R_t$=1.26 min in in 2.0 min chromatography, 10-80AB, MS ESI calcd. for $C_{19}H_{21}F_3N_5O_3$ $[M+H]^+$ 424.2, found 424.1.

Example 71. Synthesis of 101

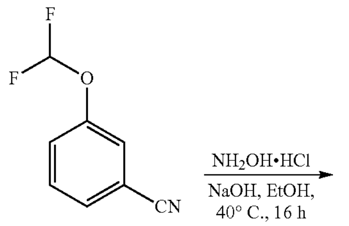

A-156

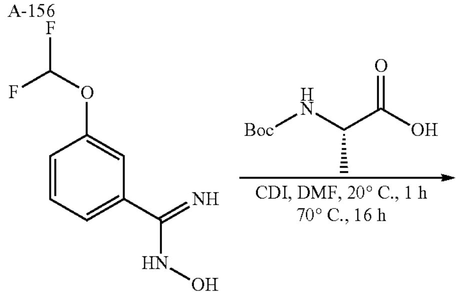

A-157

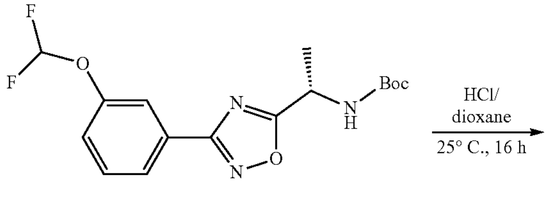

A-158

-continued

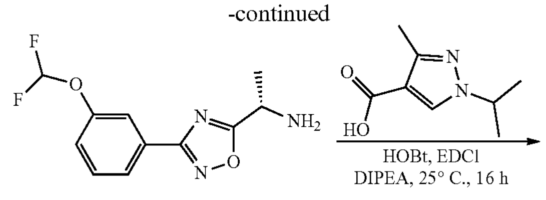

A-160

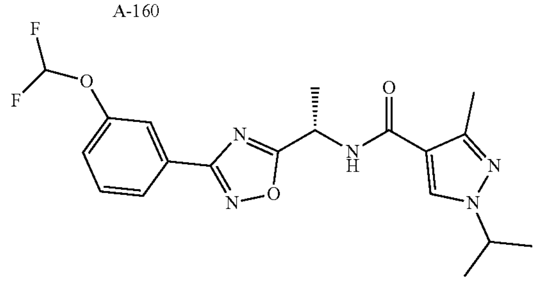

101

A-157:

A mixture of hydroxylamine hydrochloride (0.49 g, 7.1 mmol), 3-(difluoromethoxy)benzonitrile (0.4 g, 2.37 mmol) and NaOH (0.28 g, 7.1 mmol) in ethanol (24 mL) was stirred at 40° C. for 16 hours. After cooling to room temperature, the reaction mixture was partially concentrated under reduced pressure to remove most of EtOH and then diluted with $H_2O$ (20 mL). The mixture was extracted with EtOAc (30 mL×2). The combined organic phase was washed with brine (15 mL), dried over $Na_2SO_4$, filtered and concentrated to give the crude product (0.52 g, 2.43 mmol) as a solid. LCMS $R_t$=0.23 min in in 1.5 min chromatography, 5-95AB, MS ESI calcd. for $C_8H_9F_2N_2O_2$ $[M+H]^+$203.1, found 203.1.

A-158:

A mixture of (2S)-2-(tert-butoxycarbonylamino)propanoic acid (486.69 mg, 2.57 mmol) and CDI (458.79 mg, 2.83 mmol) in DMF (15 mL) was stirred at 25° C. for 1 hour and then 3-(difluoromethoxy)-N'-hydroxy-benzamidine (520 mg, 2.57 mmol) was added. The reaction mixture was then stirred at 70° C. for 16 hours. After cooling to room temperature, the mixture was diluted with water (60 mL) and extracted with EtOAc (30 mL×3). The combined organic phase was washed with brine (30 mL), dried over $Na_2SO_4$, filtered and concentrated to give the crude product. The crude product was purified by chromatography flash column on silica gel (EtOAc in PE=0% to 30%) to give the product (440 mg, 1.23 mmol, 48% yield) as a solid. LCMS $R_t$=1.38 min in in 2.0 min chromatography, 10-80AB, MS ESI calcd. for $C_{12}H_{12}F_2N_3O_4$ $[M+H-tBu]^+$ 300.1, found 299.9.

A-160:

To tert-butyl N-[(1S)-1-[3-[3-(difluoromethoxy)phenyl]-1,2,4-oxadiazol-5-yl]ethyl]carbamate (440 mg, 1.24 mmol) was added 4M HCl in 1,4-dioxane (15 mL, 60 mmol) was stirred at 25° C. for 16 hours. The mixture was concentrated under reduced pressure, diluted with $H_2O$ (20 mL) and basified with $NaHCO_3$ (solid) to pH~8. The mixture was extracted with EtOAc (30 mL×3), and the combined organic phase was washed with brine (30 mL), dried over $Na_2SO_4$, filtered and concentrated to give the crude product (220 mg, 0.86 mmol) as an oil.

101:

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1S)-1-[3-[3-(difluoromethoxy)phenyl]-1,2,4-oxadiazol-5-yl]ethanamine (182.09 mg, 0.71 mmol) and the reaction mixture was stirred at 25° C. for 16 hours. The reaction was quenched with $H_2O$ (10 mL), then extracted with DCM (20 mL×3). The combined organic phase was washed with brine (30 mL), dried over $Na_2SO_4$, filtered and concentrated to give the crude product. The crude product was purified with flash chromatography on silica gel (EtOAc in PE=0% to 20%) to give the product. Analytical SFC (Regis (S,S) Whelk-O1 (100 mm×4.6 mm, 5.0 μm); mobile phase: A: $CO_2$ B: ethanol (0.05% DEA), gradient: from 5% to 40% of B in 5.5 min and hold 40%, for 3 min, then 5% of B for 1.5 min, flow rate: 2.5 mL/min) showed two peaks at 4.29 min (13.4%) and 5.43 min (main peak, 86.6%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 50% B; 8.00 min run; 5 injections, Rt of peak 1=4.00 min, Rt of peak 2=6.00 min) to give the product (51.8 mg, 0.13 mmol, 21% yield) (Rt=5.43 min in analytical SFC) as a solid. $^1$H NMR (400 MHz, $CDCl_3$) δ=7.96 (s, 1H), 7.92 (d, 1H), 7.78 (s, 1H), 7.58 (t, 1H), 7.34 (dd, 1H), 7.08-6.61 (m, 2H), 5.42 (quin, 1H), 4.48-4.36 (m, 1H), 2.35 (s, 3H), 1.67 (d, 3H), 1.45 (d, 6H). LCMS $R_t$=1.13 min in in 2.0 min chromatography, 10-80AB, MS ESI calcd. for $C_{19}H_{22}F_2N_5O_3$ [M+H]$^+$ 406.2, found 406.0.

Example 72. Synthesis of 102

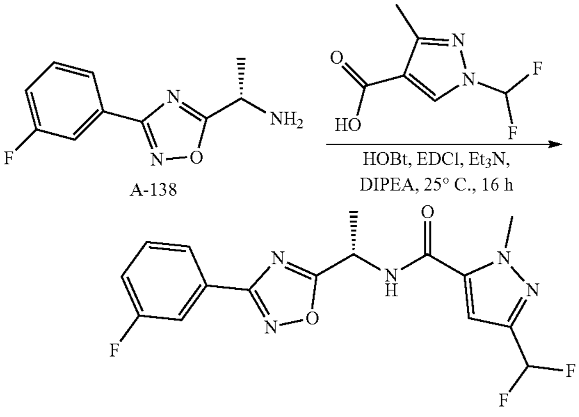

A-138

102

A mixture of 1-(difluoromethyl)-3-methyl-pyrazole-4-carboxylic acid (91.8 mg, 0.52 mmol), HOBt (156.52 mg, 1.16 mmol), $Et_3N$ (0.4 mL, 2.9 mmol) and EDCI (166.53 mg, 0.87 mmol) in DMF (20 mL) was stirred at 25° C. for 1 hour and then (1S)-1-[3-(3-fluorophenyl)-1,2,4-oxadiazol-5-yl]ethanamine (120 mg, 0.58 mmol) was added and the mixture was stirred at 25° C. for 16 hours. The reaction was quenched with sat. $NH_4Cl$ (20 mL), and the mixture was extracted with DCM (20 mL×2). The combined organic phase was washed with brine (20 mL), dried over $Na_2SO_4$, filtered and concentrated to give the crude product. The crude product was purified by flash chromatography on silica gel (EtOAc in PE=0 to 10% to 25% to 50%) to give the product. Analytical SFC (Regis (S,S) Whelk-01 (100 mm×4.6 mm, 3 μm); mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 2.93 min (9.1%) and 3.38 min (main peak, 90.9%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 25% B; 9 min run; 4 injections, Rt of peak 1=6 min, Rt of peak 2=7.5 min) to give the product (68.18 mg, 0.18 mmol, 32% yield) (Rt=3.38 min in analytical SFC) as a solid. $^1$H NMR (400 MHz, $CDCl_3$) $\delta_H$=7.88 (d, 1H), 7.82-7.75 (m, 1H), 7.52-7.44 (m, 1H), 7.26-7.19 (m, 1H), 6.89 (s, 1H), 6.86-6.55 (m, 2H), 5.65-5.50 (m, 1H), 4.20 (s, 3H), 1.77 (d, 3H). LCMS $R_t$=1.24 min in 2.0 min chromatography, 10-80AB, MS ESI calcd. for $C_{16}H_{15}F_3N_5O_2$ [M+H]$^+$ 366.1, found 366.1.

Example 73. Synthesis of 103

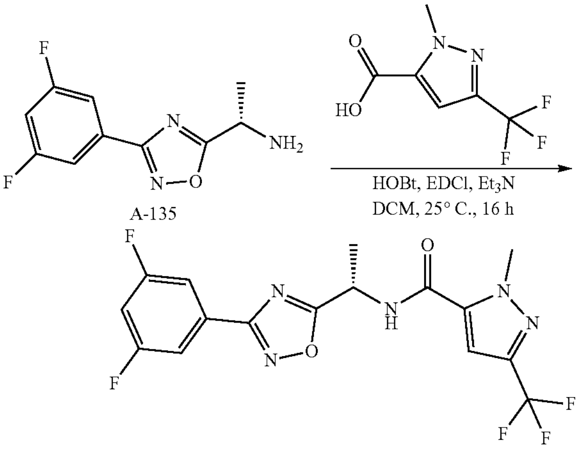

A-135

103

A mixture of 2-methyl-5-(trifluoromethyl)pyrazole-3-carboxylic acid (77.58 mg, 0.4 mmol), HOBt (120.01 mg, 0.89 mmol), $Et_3N$ (0.31 mL, 2.22 mmol) and EDCI (127.69 mg, 0.67 mmol) in DCM (15 mL) was stirred at 25° C. for 1 hours and to the mixture was added (I S)-1-[3-(3,5-difluorophenyl)-1,2,4-oxadiazol-5-yl]ethanamine (100 mg, 0.44 mmol) with additional stirring at 25° C. for 16 hours to give a solution. The reaction was quenched with sat. $NH_4Cl$ (20 mL), and the mixture was extracted with DCM (20 mL×2). The combined organic phase was washed with brine (20 mL), dried over $Na_2SO_4$, filtered and concentrated to give the crude product. The crude product was purified by flash chromatography on silica gel (EtOAc in PE=0 to 10% to 25% to 50%) to give the product. Analytical SFC (Regis (S,S) Whelk-O1 (100 mm×4.6 mm, 3 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 2.37 min (18.1%) and 2.66 min (main peak, 81.9%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 20% B; 8 min run; 5 injections, Rt of peak 1=5.5 min, Rt of peak 2=6.5 min) to give the product (41.14 mg, 0.1 mmol, 23% yield) (Rt=2.66 min in analytical SFC) as a solid. $^1$H NMR (400 MHz, $CDCl_3$) $\delta_H$=7.68-7.56 (m, 2H), 7.04-6.95 (m, 1H), 6.93 (s, 1H), 6.67 (d, 1H), 5.61 (q, 1H), 4.24 (s, 3H), 1.78 (d, 3H). LCMS $R_t$=1.31 min in 2.0 min chromatography, 10-80AB, MS ESI calcd. for $C_{16}H_{13}F_5N_5O_2$ [M+H]$^+$ 402.1, found 402.0.

Example 74. Synthesis of 104

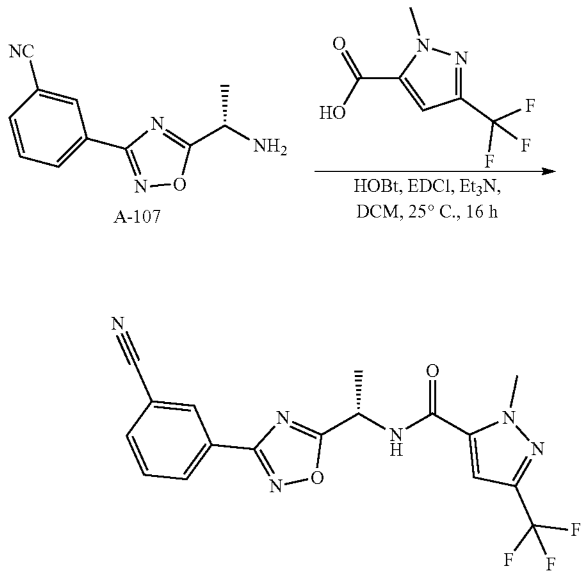

A-107

104

A mixture of 2-methyl-5-(trifluoromethyl)pyrazole-3-carboxylic acid (97.86 mg, 0.5 mmol), HOBt (151.39 mg, 1.12 mmol), $Et_3N$ (0.39 mL, 2.8 mmol) and EDCI (161.08 mg, 0.84 mmol) in DCM (15 mL) was stirred at 25° C. for 1 hour and then to the mixture was added 3-[5-[(1S)-1-aminoethyl]-1,2,4-oxadiazol-3-yl]benzonitrile (120 mg, 0.56 mmol) and the mixture was stirred at 25° C. for 16 hours. The reaction was quenched with sat. $NH_4C_1$ (20 mL), and the mixture was extracted with DCM (20 mL×2). The combined organic phase was washed with brine (20 mL), dried over $Na_2SO_4$, filtered and concentrated to give the crude product. The crude product was purified by flash chromatography on silica gel (EtOAc in PE=0 to 10% to 25% to 50%) to give the product. Analytical SFC (Regis (S,S) Whelk-O1 (100 mm×4.6 mm, 3 μm), mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 3.38 min (5.6%) and 3.76 min (main peak, 94.4%). Note: the condensation reaction might lead to some racemization. The analogue have the risk of racemization under basic condition.

The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 30% B; 8 min run; 5 injections, Rt of peak 1=5.2 min, Rt of peak 2=6.5 min) to give the product (50.78 mg, 0.13 mmol, 23% yield) (Rt=3.76 min in analytical SFC) as a solid. $^1H$ NMR (400 MHz, $CDCl_3$) $\delta_H$=8.39 (s, 1H), 8.32 (d, 1H), 7.82 (d, 1H), 7.64 (t, 1H), 6.94 (s, 1H), 6.69 (d, 1H), 5.62 (quin, 1H), 4.24 (s, 3H), 1.79 (d, 3H). LCMS $R_t$=1.23 min in 2.0 min chromatography, 10-80AB, MS ESI calcd. for $C_{17}H_{14}F_3N_6O_2$ $[M+H]^+$ 391.1, found 391.3.

Example 75. Synthesis of 105

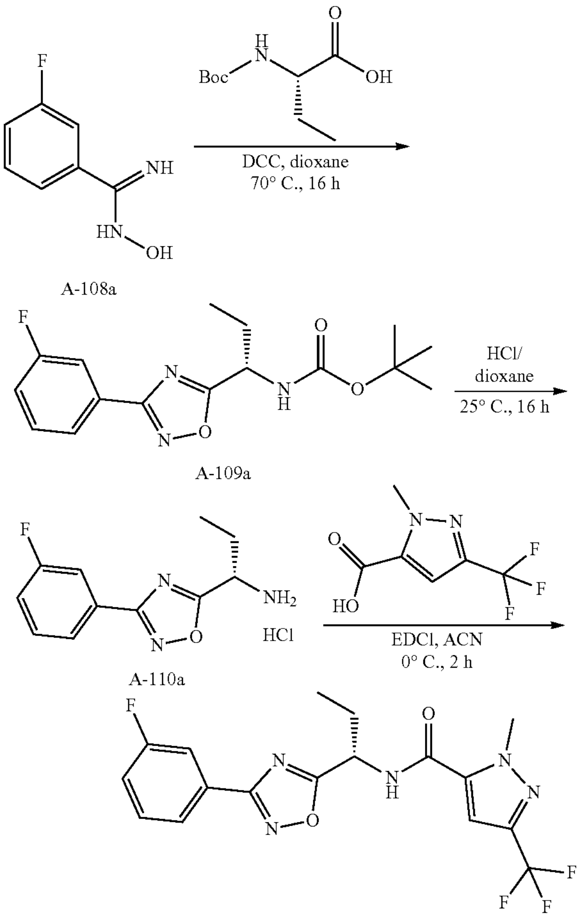

A-108a

A-109a

A-110a

105

A-109a:

A mixture of (2S)-2-(tert-butoxycarbonylamino)butanoic acid (263.71 mg, 1.3 mmol), DCC (534.58 mg, 2.6 mmol), 3-fluoro-N-hydroxy-benzamidine (200 mg, 1.3 mmol) in 1,4-dioxane (6 mL) was stirred at 70° C. for 16 hours. After cooling to room temperature, the mixture was diluted with saturated $NH_4Cl$ (30 mL), and the mixture was extracted with EtOAc (30 mL×3). The combined organic phase was washed with brine (50 mL), dried over $Na_2SO_4$, filtered and concentrated to give the crude product. The crude product was purified by flash column chromatography on silica gel (EtOAc in PE=0% to 10%) to give the product (290 mg, 0.89 mmol, 68% yield) as a solid. LCMS $R_t$=0.94 min in 1.5 min chromatography, 5-95AB, MS ESI calcd. for $C_{12}H_{13}FN_3O_3$ $[MH-tBu+H]^+$ 266.09, found 266.1.

A-110a:

To tert-butyl (1S)-1-[3-(3-fluorophenyl)-1,2,4-oxadiazol-5-yl]propyl]carbamate (290.mg, 0.9000 mmol) was added 4M HCl in 1,4-dioxane (10 mL, 40 mmol) and the reaction mixture was stirred at 25° C. for 16 hours. The mixture was concentrated to give the crude product as a solid. LCMS $R_t$=0.68 min in 1.5 min chromatography, 5-95AB, MS ESI calcd. for $C_{11}H_{13}FN_3O$ $[M+H]^+$ 222.10, found 222.1.

105:

To a mixture of 2-methyl-5-(trifluoromethyl)pyrazole-3-carboxylic acid (105.46 mg, 0.54 mmol), EDCI (104.15 mg, 0.54 mmol) in MeCN (4 mL) was added (1S)-1-[3-(3-fluorophenyl)-1,2,4-oxadiazol-5-yl]propan-1-amine hydrochloride (140 mg, 0.54 mmol) and the reaction mixture was stirred at 0° C. for 2 hours. The reaction was quenched with 1N HCl (10 mL) and then extracted with EtOAc (10 mL×2). The combined organic phase was washed with brine (15 mL), dried over $Na_2SO_4$, filtered and concentrated to give the crude product. The crude product was purified by flash chromatography on silica gel (EtOAc in PE=0% to 10% to 20%) to give the crude product. The crude product was purified by prep-TLC (silica gel, PE:EtOAc=3:1) to give the product (25.53 mg, 64.3 μmol, 12% yield) as a solid. $^1H$ NMR (400 MHz, $CDCl_3$) $\delta_H$=7.91-7.86 (m, 1H), 7.81-7.76 (m, 1H), 7.52-7.44 (m, 1H), 7.26-7.20 (m, 1H), 6.94 (s, 1H), 6.66 (br d, 1H), 5.56-5.38 (m, 1H), 4.23 (s, 3H), 2.24-2.14 (m, 1H), 2.13-2.03 (m, 1H), 1.08 (t, 3H). LCMS $R_t$=1.35 min in 2.0 min chromatography, 10-80AB, MS ESI calcd. $C_{17}H_{16}F_4N_5O_2$ $[M+H]^+$398.12, found 398.1.

Example 76. Synthesis of 106 and 107 a) Synthesis of 107

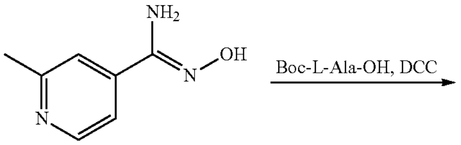

A-336

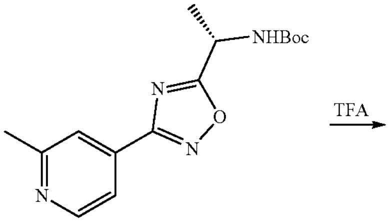

A-337

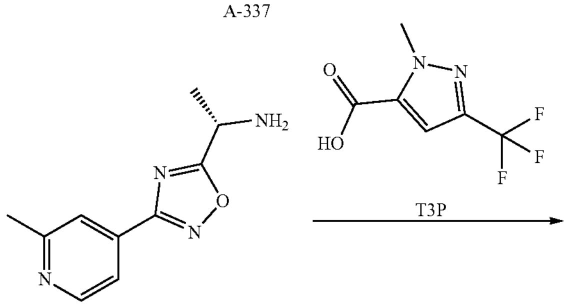

A-338

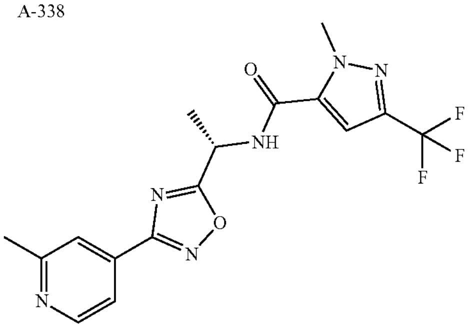

107

Synthesis of tert-butyl N-[(1S)-1-[3-(2-methyl-4-pyridyl)-1,2,4-oxadiazol-5-yl]ethyl]carbamate (A-337)

To a stirred solution of compound A-336 (300 mg, 1.98 mmol) in 1,4-dioxane (20 mL) was added (25)-2-(tert-butoxycarbonylamino)propanoic acid (375 mg, 1.98 mmol) and DCC (449 mg, 2.18 mmol) at room temperature. The reaction mixture was heated at 100° C. for 16 h. The reaction mixture was cooled to room temperature and concentrated. The mixture was treated with water (30 mL) and extracted with EtOAc (2×30 mL). The organic layer was washed with brine (20 mL), dried over anhydrous $Na_2SO_4$ and concentrated. The crude was purified by column chromatography on silica gel with 20% EtOAc/PE to afford compound A-337 (390 mg, 1.27 mmol, 64% yield). LCMS: 305.1 (M+H), Rt 1.66 min (Column: ZORBAX XDB C-18 (50×4.6 mm), 3.5 μm; Mobile Phase: A: 0.1% HCOOH in water:ACN (95:5), B: ACN; Flow Rate: 1.5 mL/min)

Synthesis of (1S)-1-[3-(2-methyl-4-pyridyl)-1,2,4-oxadiazol-5-yl]ethanamine (A-338)

To a stirred solution of compound A-337 (390 mg, 1.27 mmol) in DCM (10.0 mL) was added TFA (1.47 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (5 mL) and extracted with EtOAc (2×30 mL). The organic layer was washed with brine (20 mL), dried over anhydrous $Na_2SO_4$ and concentrated to afford compound A-338 (230 mg). The compound was used for the next step without further purification.

Synthesis of 2-methyl-N-[(1S)-1-[3-(2-methyl-4-pyridyl)-1,2,4-oxadiazol-5-yl]ethyl]-5-(trifluoromethyl)pyrazole-3-carboxamide (107)

To a stirred solution of compound A-338 (230 mg, 1.13 mmol) in THF (10.0 mL) was added 2-methyl-5-(trifluoromethyl)pyrazole-3-carboxylic acid (218 mg, 1.13 mmol) followed by T3P (2.01 mL, 3.38 mmol) and $Et_3N$ (0.47 mL, 3.38 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude compound was purified by preparative HPLC to afford 107 (140 mg, 0.36 mmol, 32% yield) as a solid. Prep. HPLC method: Rt 8.86; Column: Atlantis C18 (150×19 mm), 5.0 μm; Mobile phase: 0.1% TFA in water/acetonitrile; Flow Rate: 15.0 mL/min. HPLC: Rt 3.1 min, 99.4% Column: XBridge C8 (50×4.6) mm, 3.5 μm; Mobile phase: A: 0.1% TFA in water, B: 0.1% TFA in ACN; Flow Rate: 2.0 mL/min. LCMS: 381.2 (M+H), Rt 1.82 min, Column: ZORBAX XDB C-18 (50×4.6 mm), 3.5 μm; Mobile Phase: A: 0.1% HCOOH in water, B: ACN; Flow Rate: 1.5 mL/min. Chiral method: Rt 1.87 min, SFC column: (R,R)-Whelk-01 (250 mm×4.6 mm, 5 μm); mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.61 (d, 1H), 7.95 (s, 1H), 7.86 (d, 1H), 7.26 (s, 1H), 5.54 (q, 1H), 4.19 (s, 3H), 2.64 (s, 3H), 1.77 (d, 3H).

b) Synthesis of 106

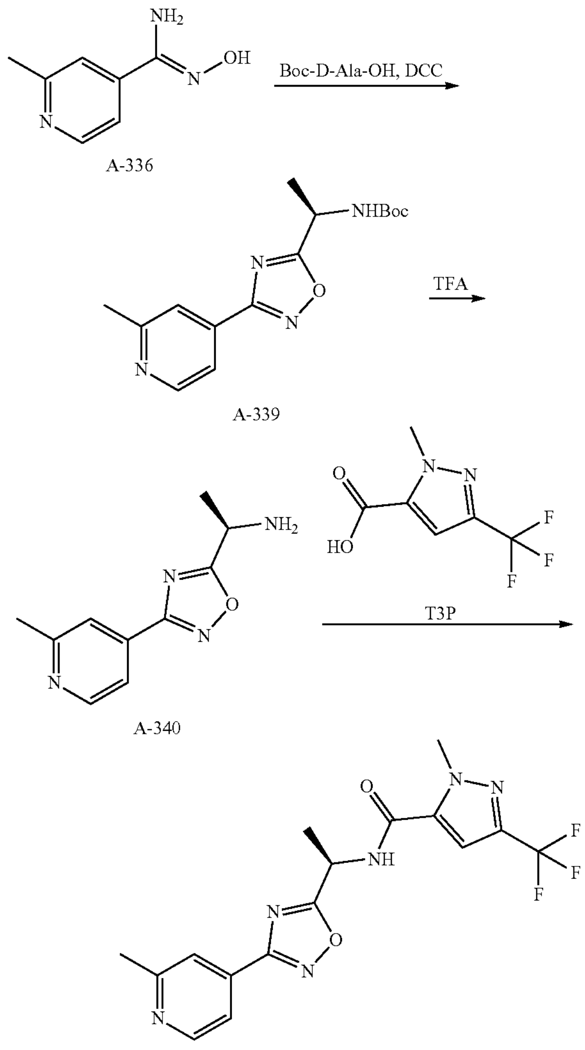

A-336

A-339

A-340

106

Synthesis of tert-butyl N-[(1R)-1-[3-(2-methyl-4-pyridyl)-1,2,4-oxadiazol-5-yl]ethyl]carbamate (A-339)

To a stirred solution of compound A-336 (400 mg, 2.65 mmol) in 1,4-dioxane (10.0 mL) at room temperature was added Boc-D-alanine (600 mg, 3.18 mmol) and DCC (817 mg, 3.97 mmol) and the reaction mixture was heated at 100° C. for 16 h. The reaction mixture was cooled to room temperature and concentrated. The mixture was treated with water (30 mL) and extracted with EtOAc (2x30 mL). The organic layer was washed with brine (20 mL), dried over anhydrous $Na_2SO_4$ and concentrated. The crude was purified by column chromatography on silica gel with 24% EtOAc/PE to afford compound A-339 (600 mg, 1.9 mmol, 73% yield). LCMS: 305.2 (M+H), Rt 1.65 min; Column: ZORBAX XDB C-18 (50x4.6 mm), 3.5 μm; Mobile Phase: A: 0.1% HCOOH in water:ACN (95:5), B: ACN; Flow Rate: 1.5 mL/min Synthesis of (1R)-1-[3-(2-methyl-4-pyridyl)-1,2,4-oxadiazol-5-yl]ethanamine (A-340)

To a stirred solution of compound A-339 (600.mg, 1.97 mmol) in DCM (7.0 mL) was added TFA (1.51 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (5 mL) and extracted with EtOAc (2x30 mL). The organic layer was washed with brine (20 mL), dried over anhydrous $Na_2SO_4$ and concentrated to afford compound A-340 (280 mg). The compound was used for the next step without further purification.

Synthesis of 2-methyl-N-[(1R)-1-[3-(2-methyl-4-pyridyl)-1,2,4-oxadiazol-5-yl]ethyl]-5-(trifluoromethyl)pyrazole-3-carboxamide (106)

To a stirred solution of compound A-340 (280 mg, 1.37 mmol) in THF (10.0 mL) was added 2-methyl-5-(trifluoromethyl)pyrazole-3-carboxylic acid (266 mg, 1.37 mmol) followed by T3P (2.44 mL, 4.11 mmol) and $Et_3N$ (0.57 mL, 4.11 mmol). The reaction mixture was stirred at room temperature for 16 h. The reaction mixture was treated with water (30 mL) and extracted with ethyl acetate (2x30 mL). The organic layer was washed with saturated sodium bicarbonate solution (20 mL), washed with brine (20 mL), dried over $Na_2SO_4$ and concentrated. The crude compound was purified by preparative HPLC to afford 106 (272 mg, 0.70 mmol, 51% yield) as a solid. Prep. HPLC method: Rt 11.1; Column: X-Bridge C8 (150x19 mm), 5.0 μm; Mobile phase: 0.1% TFA in water/acetonitrile; Flow Rate: 15.0 mL/min. HPLC: Rt 3.09 min, 99.2% Column: XBridge C8 (50x4.6 mm, 3.5 μm); Mobile phase: A: 0.1% TFA in water, B: 0.1% TFA in ACN; Flow Rate: 2.0 mL/min; LCMS: 381.1 (M+H), Rt 1.79 min, Column: ZORBAX XDB C-18 (50x4.6 mm, 3.5 μm); Mobile Phase: A: 0.1% HCOOH in water:ACN (95:5), B: ACN; Flow Rate: 1.5 mL/min. Chiral method: Rt 2.14 min, SFC column: Regis (R,R)-Whelk-O1 (250 mmx4.6 mm, 5 μm); mobile phase: 60:40 (A:B), A=liquid $CO_2$, B=0.5% isopropyl amine in methanol; flow rate: 3.0 mL/min; wave length: 210 nm. $^1H$ NMR (400 MHz, DMSO-$d_6$): δ 9.47 (d, 1H), 8.66 (d, 1H), 7.81 (s, 1H), 7.74-7.73 (dd, 1H), 7.45 (s, 1H), 5.50-5.46 (m, 1H), 4.13 (s, 3H), 2.58 (s, 3H), 1.68 (d, 3H).

Example 77. Synthesis of 108 and 109

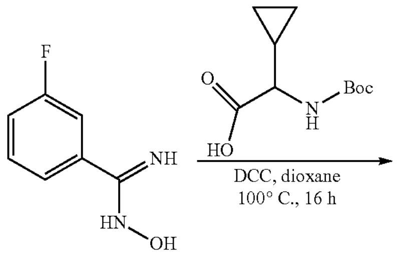

A-108a

-continued

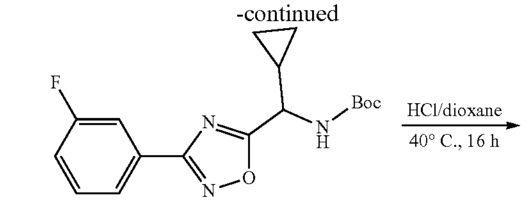

A-110b

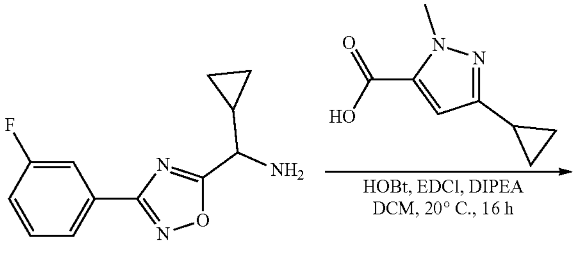

A-111c

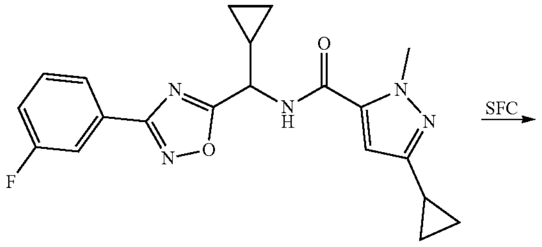

A-112c

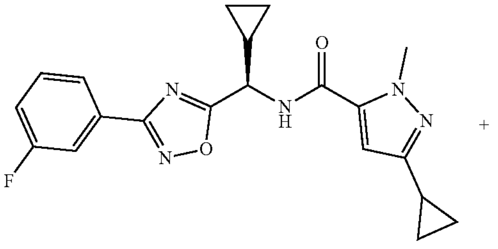

108

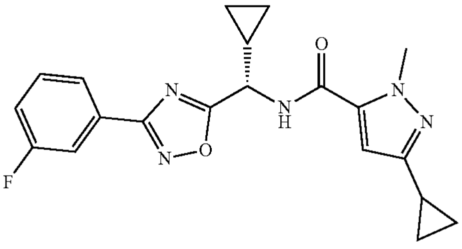

109

A-110b:

A mixture of 3-fluoro-N-hydroxy-benzamidine (500 mg, 3.24 mmol) 2-(tert-butoxycarbonylamino)-2-cyclopropyl-acetic acid (698.23 mg, 3.24 mmol) and DCC (1336.45 mg, 6.49 mmol) in 1,4-dioxane (10 mL) was stirred at 100° C. for 16 hours. After cooling to room temperature, the mixture was concentrated under reduced pressure to give a residue. The residue was diluted with $H_2O$ (20 mL) and the mixture was extracted with EtOAc (20 mL×2). The combined organic phase was washed with brine (20 mL), dried over $Na_2SO_4$, filtered and concentrated to give the crude product. The crude product was purified by flash chromatography on silica gel (EtOAc in PE=0% to 30%) to give the product (800 mg, 2.39 mmol, 74% yield) as an oil. LCMS $R_t$=0.94 min in 1.5 min chromatography, 5-95AB, MS ESI calcd. for $C_{12}H_{13}FN_3O$ [M+H−tBu] 278.1, found 278.1.

A-111c:

To tert-butyl N-[cyclopropyl-[3-(3-fluorophenyl)-1,2,4-oxadiazol-5-yl]methyl]carbamate (800 mg, 2.4 mmol) was added 4M HCl in 1,4-dioxane (8 mL, 32 mmol) an the reaction mixture was stirred 40° C. at for 16 hours. The reaction mixture was concentrated under reduced pressure and diluted with EtOAc (20 mL) and $H_2O$ (20 mL). The EtOAc phase was discarded and the pH of the aqueous phase was basified with NaOH (solid) to pH=9 and then extracted with EtOAc (20 mL×2). The combined organic phase was washed with brine (15 mL), dried over anhydrous $Na_2SO_4$ to give the crude product (500 mg, 1.90 mmol, 79% yield) as an oil. LCMS $R_t$=0.64 min in 1.5 min chromatography, 5-95AB, MS ESI calcd. for $C_{12}H_{13}FN_3O$ [M+H] 234.1, found 233.8.

A-112c:

A mixture of 1-cyclopropyl-3-methyl-pyrazole-4-carboxylic acid (150 mg, 0.90 mmol), EDCI (346.07 mg, 1.81 mmol), DIPEA (0.47 mL, 2.71 mmol), HOBt (243.95 mg, 1.81 mmol) and cyclopropyl-[3-(3-fluorophenyl)-1,2,4-oxadiazol-5-yl]methanamine (210.53 mg, 0.90 mmol) in DCM (2 mL) was stirred at 20° C. for 16 hours. The residue was diluted with sat. $NH_4Cl$ (20 mL) and extracted with DCM (20 mL×2). The combined organic phase was washed with brine (15 mL), dried over anhydrous $Na_2SO_4$, filtered and concentrated to give the crude product. The crude product was purified by flash chromatography on silica gel (EtOAc in PE=0% to 5% to 60%) to give the product (400 mg, 0.95 mmol) as a solid. LCMS $R_t$=0.88 min in 1.5 min chromatography, 5-95AB, MS ESI calcd. for $C_{20}H_{21}FN_5O_2$ $[M+H]^+$ 382.2, found 382.0.

108 & 109:

The product was analyzed by SFC (Diacel CHIRALPAK AD-3 (50 mm×4.6 mm, 3 μm), mobile phase: A: $CO_2$ B: ethanol (0.05% DEA), gradient: from 5% to 40% of B in 2 min and hold 40% for 1.2 min, then 5% of B for 0.8 min, flow rate: 4 mL/min, column temp: 35° C.) to show two peaks at 0.98 min and 1.31 min. The product was separated by SFC (Daicel CHIRALPAK AD-H (250 mm×30 mm, 5 μm); A=$CO_2$ and B=EtOH (0.1% $NH_3H_2O$); 35° C.; 30 mL/min; 30% B; 10 min run; 9 injections, Rt of peak 1=7.5 min, Rt of peak 2=8.44 min) to give the enantiomer 1, randomly assigned as 108 (104.77 mg, 0.3 mmol, 26% yield) (Rt=0.98 min in analytica SFC) as an oil, and the enantiomer 2, randomly assigned as 109 (103.84 mg, 0.3 mmol, 25% yield) (Rt=1.30 min in analytical SFC) as an oil.

108:

$^1H$ NMR (400 MHz, $CDCl_3$) $\delta_H$=7.92-7.85 (m, 1H), 7.82-7.75 (m, 1H), 7.51-7.42 (m, 1H), 7.26-7.18 (m, 1H), 6.64 (d, 1H), 6.35 (s, 1H), 4.96-4.86 (m, 1H), 4.07 (s, 3H), 1.98-1.89 (m, 1H), 1.42-1.32 (m, 1H), 0.99-0.92 (m, 2H), 0.82-0.58 (m, 6H). LCMS $R_t$=1.26 min in 2 min chromatography, 10-80AB, MS ESI calcd. for $C_{24121}FN_5O_2$ $[M+H]^+$ 382.2, found 382.1.

109:

$^1H$ NMR (400 MHz, $CDCl_3$) $\delta_H$=7.92-7.85 (m, 1H), 7.82-7.76 (m, 1H), 7.52-7.42 (m, 1H), 7.26-7.18 (m, 1H), 6.65 (d, 1H), 6.35 (s, 1H), 4.96-4.85 (m, 1H), 4.07 (s, 3H), 1.99-1.88 (m, 1H), 1.43-1.32 (m, 1H), 0.99-0.91 (m, 2H), 0.79-0.58 (m, 6H). LCMS $R_t$=1.25 min in 2 min chromatography, 10-80AB, MS ESI calcd. for $C_{20}H_{21}FN_5O_2$ $[M+H]^+$ 382.2, found 382.1.

Example 78. Synthesis of 110

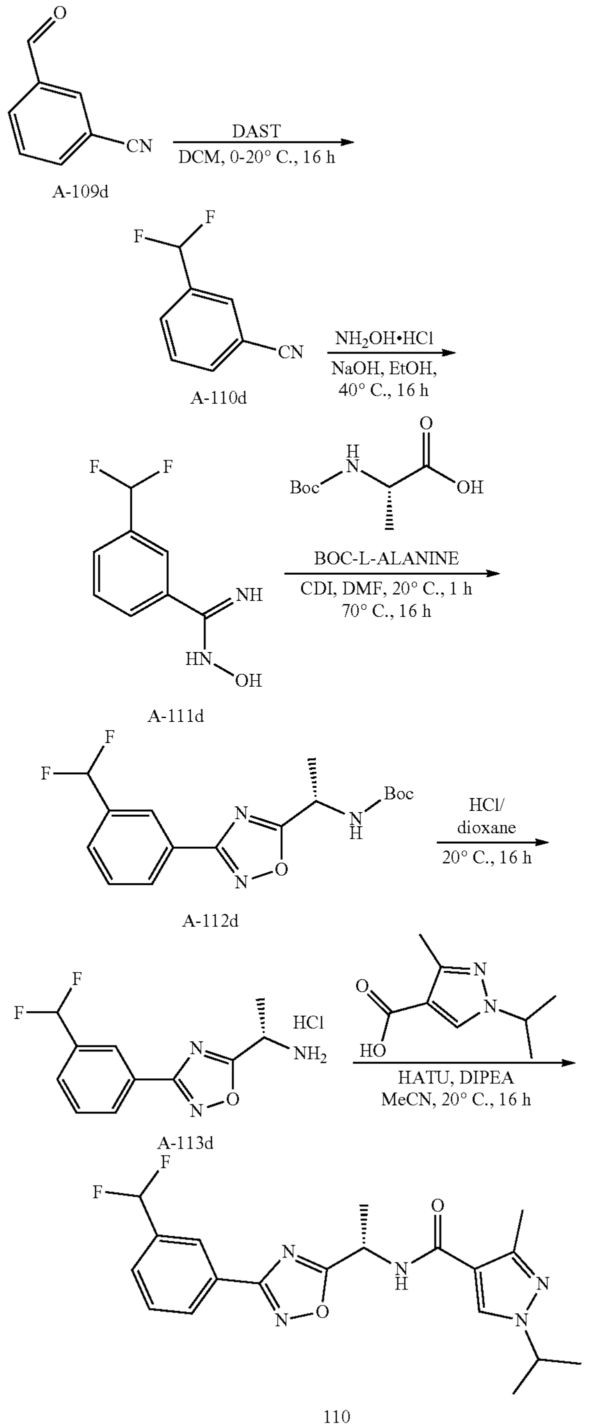

A-109d

A-110d

A-111d

A-112d

A-113d

110

A-110d:

DAST (8 mL, 60.05 mmol) was added dropwise to a solution of 3-formylbenzonitrile (3 g, 22.88 mmol) in DCM (30 mL). The resulting mixture was stirred at 20° C. for 16 hours to give a solution. The reaction mixture was added dropwise into saturated $NaHCO_3$ aqueous (200 mL) and then extracted with DCM (100 mL×2). The organic phase was washed with brine (100 mL), dried over anhydrous $Na_2SO_4$, filtered and concentrated to give the crude product. The crude product was purified by flash chromatography on silica gel (DCM in PE=0% to 2%) to give the product (2.4 g, 15.67 mmol, 68% yield) as an oil. $^1H$ NMR (400 MHz, $CDCl_3$) $\delta_H$=7.84-7.73 (m, 3H), 7.65-7.57 (m, 1H), 6.85-6.51 (m, 1H).

A-111d:

A mixture of 3-fluorobenzonitrile (2.4 g, 19.82 mmol), hydroxylamine hydrochloride (4.13 g, 59.45 mmol) and NaOH (2.38 g, 59.45 mmol) in ethanol (45 mL) and water (15 mL) was stirred at 40° C. for 16 hours to give a mixture. After cooling to room temperature, it was concentrated under reduced pressure and then water (50 mL) and EtOAc (50 mL) were added. The phases were separated, and the organic phase was washed with brine (50 mL), dried over anhydrous $Na_2SO_4$, filtered and concentrated to give the crude product as an oil. $^1H$ NMR (400 MHz, $CDCl_3$) $\delta_H$=7.79 (s, 1H), 7.76 (d, 1H), 7.61-7.55 (m, 1H), 7.54-7.47 (m, 1H), 6.83-6.50 (m, 1H), 4.95 (s, 2H).

A-112d:

A mixture of (2S)-2-(tert-butoxycarbonylamino)propanoic acid (3.05 g, 16.12 mmol) and CDI (2.87 g, 17.73 mmol) in DMF (30 mL) was stirred at 25° C. for 1 hour. To the mixture was added 3-(difluoromethyl)-N-hydroxy-benzamidine (3 g, 16.1 2 mmol) and the resulting mixture was stirred at 70° C. for 16 hours. After cooling to room temperature, water (50 mL) was added and the mixture was extracted with EtOAc (50 mL×2). The combined organic phase was washed with brine (50 mL), dried over anhydrous $Na_2SO_4$, filtered and concentrated to give the crude product. The crude product was purified by flash column chromatography on silica gel (EtOAc in PE=0% to 10% to 20%) to give the product (1.8 g, 5.30 mmol, 33% yield) as an oil. $^1H$ NMR (400 MHz, $CDCl_3$) $\delta_H$=8.26-8.18 (m, 2H), 7.71-7.65 (m, 1H), 7.63-7.57 (m, 1H), 6.87-6.56 (m, 1H), 5.19 (s, 2H), 1.68-1.63 (m, 3H), 1.48 (s, 9H).

A-113d:

To tert-butyl N-[(1S)-1-[3-[3-(difluoromethyl)phenyl]-1,2,4-oxadiazol-5-yl]ethyl]carbamate (1.8 g, 5.3 mmol) was added 4M HCl in 1,4-dioxane (20 mL, 5.3 mmol) and the reaction mixture was stirred at 25° C. for 16 hours. The mixture was concentrated under reduced pressure to give the crude product (1.4 g) as a solid. LCMS $R_t$=0.39 min in 1.5 min chromatography, 5-95AB, MS ESI calcd. for $C_{11}H_{12}F_2N_3O$ [M−NH2]$^+$ 240.1, found 239.9.

110:

A mixture of 1-isopropyl-3-methyl-pyrazole-4-carboxylic acid (152.52 mg, 0.91 mmol), HATU (689.62 mg, 1.81 mmol), DIPEA (0.38 mL, 2.72 mmol) and then (1S)-1-[3-[3-(difluoromethyl)phenyl]-1,2,4-oxadiazol-5-yl] ethanamine hydrochloride (250 mg, 0.91 mmol) in MeCN (15 mL) was stirred at 25° C. for 16 hours. The reaction mixture was concentrated under reduced pressure and water (20 mL) was added to the residue and the mixture was extracted with EtOAc (20 mL×2). The combined organic phase was washed with brine (20 mL), dried over anhydrous $Na_2SO_4$, filtered and concentrated to give the crude product. The crude product was purified by flash column chromatography on silica gel (EtOAc in PE=0% to 30% to 50%) to give the product. Analytical SFC (Regis (S,S) Whelk-O1 (100 mm×4.6 mm, 5.0 μm), mobile phase: A: $CO_2$ B: ethanol (0.05% DEA), gradient: from 5% to 40% of B in 5.5 min, then 5% of B, for 1.5 min, flow rate: 2.5 mL/min, column temp: 40° C., ABPR: 100 bar) showed two peaks at 4.36 min (8.8%) and 5.50 min (91.2%). The impure product was purified by SFC (Regis (S,S) Whelk-O1 (250 mm×30 mm, 5 μm); A=$CO_2$ and B=0.1% $NH_3$.$H_2O$-EtOH; 38° C.; 50 mL/min; 45% B; 8 min run; 10 injections, Rt of peak 2=7.2 min) to give the product (93.5 mg, 240.1 μmol, 26% yield) as a solid. $^1$H NMR (400 MHz, DMSO-$d_6$) 400 MHz $\delta_H$=8.58 (d, 1H), 8.29 (s, 1H), 8.21-8.14 (m, 2H), 7.84-7.78 (m, 1H), 7.77-7.70 (m, 1H), 7.18 (t, 1H), 5.43-5.33 (m, 1H), 4.47-4.36 (m, 1H), 2.30 (s, 3H), 1.63 (d, 3H), 1.41 (d, 6H). LCMS $R_t$=1.18 min in 2.0 min chromatography, 10-80AB, MS ESI calcd. for $C_{19}H_{22}F_2N_5O_2$ [M+H]$^+$ 390.2, found 390.1.

Example 79. Synthesis of 111

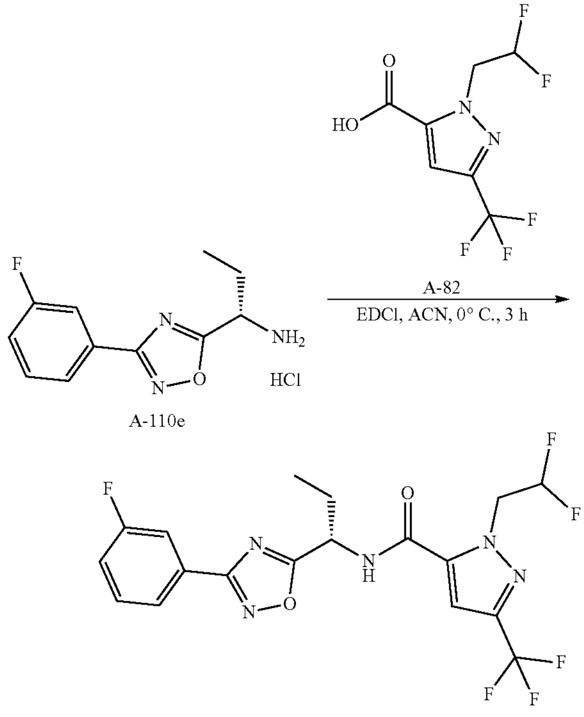

A-110e

111

To a mixture of 2-(2,2-difluoroethyl)-5-(trifluoromethyl) pyrazole-3-carboxylic acid (210 mg, 0.86 mmol), EDCI (164.91 mg, 0.86 mmol) in $CH_3CN$ (3 mL) was added (1S)-1-[3-(3-fluorophenyl)-1,2,4-oxadiazol-5-yl]propan-1-amine hydrochloride (221.67 mg, 0.86 mmol) and the mixture was stirred at 0° C. for 3 hours. The reaction was quenched with 1N HCl (10 mL) and then extracted with EtOAc (10 mL×2). The combined organic phase was washed with water (15 mL) and brine (15 mL), dried over $Na_2SO_4$, filtered and concentrated to give the crude product. The crude product was partially purified by prep-TLC (silica gel, PE:EtOAc=5:1) to give the impure product. The impure product was triturated from n-hexane/DCM (10:1, 10 mL) to give the product (98.1 mg, 0.22 mmol, 25% yield) as a solid. $^1$H NMR (400 MHz, DMSO-$d_6$) 400 MHz $\delta_H$=9.54 (d, 1H), 7.86 (d, 1H), 7.74 (d, 1H), 7.68-7.60 (m, 1H), 7.56 (s, 1H), 7.47 (dt, 1H), 6.40 (tt, 1H), 5.35-5.25 (m, 1H), 5.09 (dt, 2H), 2.19-1.98 (m, 2H), 1.02 (t, 3H). LCMS $R_t$=1.28 min in 2.0 min chromatography, 10-80AB, MS ESI calcd. for $C_{18}H_{16}F_6N_5O_2$ [M+H]$^+$ 448.1, found 448.1.

Example 80. Synthesis of 112

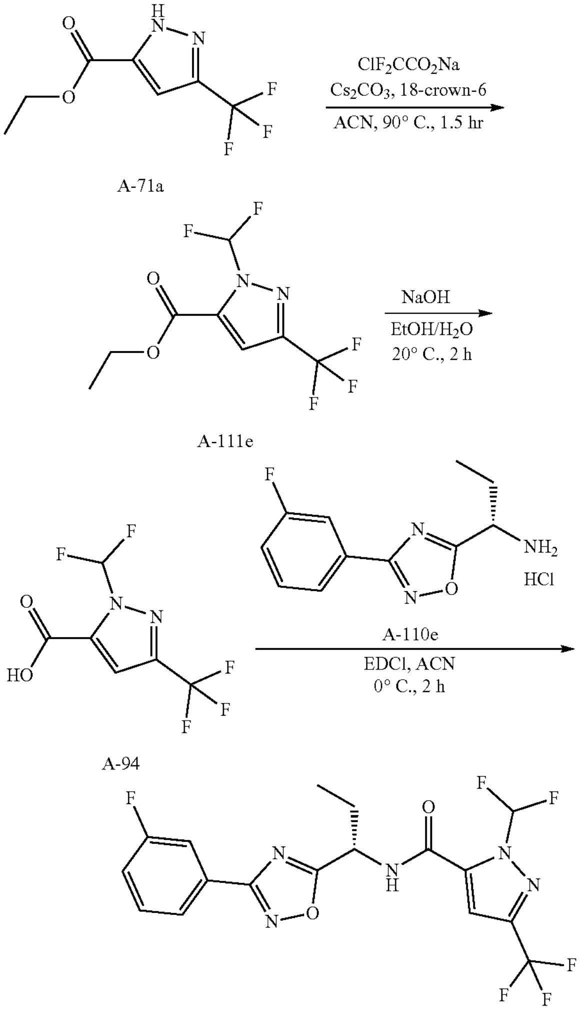

A-71a

A-111e

A-94

112

A-111e:

To a solution of ethyl 3-(trifluoromethyl)-1H-pyrazole-5-carboxylate (1000 mg, 4.8 mmol) in MeCN (20 mL) was added $Cs_2CO_3$ (3130.59 mg, 9.61 mmol), sodium 2-chloro-2,2-difluoro-acetate (1464.98 mg, 9.61 mmol) and 18-crown-6 (253.98 mg, 0.96 mmol). The reaction mixture was stirred at 90° C. for 1.5 hours. After cooling to room temperature, the mixture was diluted with $H_2O$ (30 mL), and then extracted with EtOAc (30 mL×2). The combined organic phase was washed with brine (50 mL), dried over $Na_2SO_4$, filtered and concentrated to give the crude product. The crude product was purified by flash chromatography on silica gel (EtOAc in PE=0% to 15%) to give the product (140 mg, 437.4 μmol, 10% yield) as an oil. $^1$H NMR (400 MHz, $CDCl_3$) $\delta_H$=8.29-7.89 (m, 1H), 7.21 (s, 1H), 4.44 (q, H), 1.43 (t, 3H). LCMS $R_t$=4.45 min in 7.0 min chromatography, 0-60AB, MS ESI calcd. for $C_8H_8F_5N_2O_2$ [M+H]$^+$ 259.04, found 258.9.

A-94:

To a solution of ethyl 2-(difluoromethyl)-5-(trifluoromethyl)pyrazole-3-carboxylate (140 mg, 0.54 mmol) in ethanol (4 mL) was added a solution of NaOH (65.08 mg, 1.63 mmol) in water (4 mL). The mixture was stirred at 20° C. for 2 hours. The reaction mixture was quenched by addition of 1N HCl (15 mL) and diluted with $H_2O$ (15 mL) and then extracted with EtOAc (20 mL×2). The combined organic phase was washed with brine (30 mL) and dried over $Na_2SO_4$, filtered and concentrated to give the product (100 mg) as an oil. $^1H$ NMR (400 MHz, $CDCl_3$) $\delta_H$=8.39 (t, 1H), 7.45 (s, 1H).

112:

To a mixture of 2-(difluoromethyl)-5-(trifluoromethyl) pyrazole-3-carboxylic acid (100 mg, 0.43 mmol), EDCI (104.15 mg, 0.54 mmol) in MeCN (4 mL) was added (1S)-1-[3-(3-fluorophenyl)-1,2,4-oxadiazol-5-yl]propan-1-amine hydrochloride (167.99 mg, 0.65 mmol) and the mixture was stirred at 0° C. for 2 hours. The reaction was quenched with 1N HCl (10 mL) and then extracted with EtOAc (10 mL×2). The combined organic phase was washed with brine (15 mL), dried over $Na_2SO_4$, filtered and concentrated to give the crude product. The crude product was purified by flash chromatography on silica gel (EtOAc in PE=0% to 10% to 20%) to give the impure product. The impure product was purified by prep-TLC (silica gel, PE:EtOAc=3:1) to give the product (4.5 mg, 10 μmol, 2% yield) as an oil. $^1H$ NMR (400 MHz, $CDCl_3$) $\delta_H$=8.13 (t, 1H), 7.88 (d, 1H), 7.78 (d, 1H), 7.54-7.44 (m, 1H), 7.25-7.19 (m, 1H), 7.09 (s, 1H), 6.86-6.75 (m, 1H), 5.63-5.41 (m, 1H), 2.28-2.16 (m, 1H), 2.15-2.03 (m, 1H), 1.09 (t, 3H). LCMS $R_t$=1.35 min in 2.0 min chromatography, 10-80AB, MS ESI calcd. $C_{17}H_{14}F_6N_5O_2$ $[M+H]^+$ 434.10, found 433.9.

Example 81. Synthesis of 113

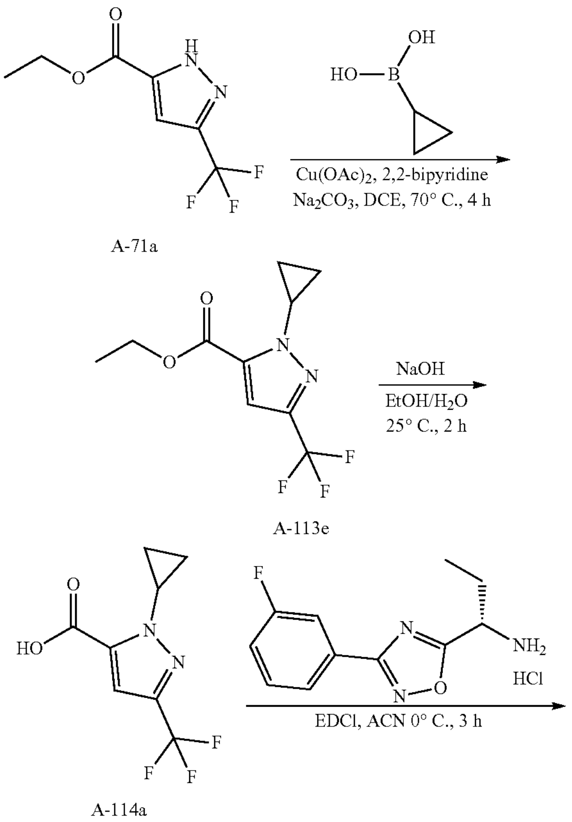

-continued

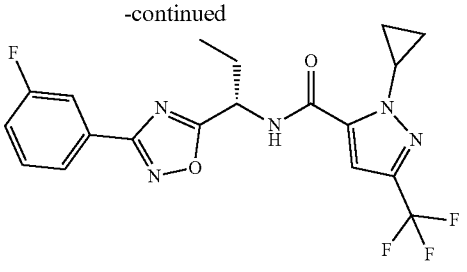

113

A-113e:

To a solution of ethyl 3-(trifluoromethyl)-1H-pyrazole-5-carboxylate (600 mg, 2.88 mmol), cyclopropylboronic acid (495.24 mg, 5.77 mmol) and $Na_2CO_3$ (611.07 mg, 5.77 mmol) in DCE (7 mL) was added a solution of $Cu(OAc)_2$ (523.58 mg, 2.88 mmol) and 2,2-bipyridine (540.29 mg, 3.46 mmol) in DCE (14 mL). The reaction mixture was stirred at 70° C. for 4 hours. After cooling to room temperature, the mixture was diluted with sat. $NH_4Cl$ (20 mL) and extracted with EtOAc (20 mL×2). The combined organic phase was washed with water (40 mL) and brine (40 mL), dried over $Na_2SO_4$, filtered and concentrated to give the crude product. The crude product was purified by flash chromatography on silica gel (EtOAc in PE=0% to 5% to 50%) to give the product (180 mg, 0.73 mmol, 25% yield) as an oil. $^1H$ NMR (400 MHz, $CDCl_3$) $\delta_H$=7.07 (s, 1H), 4.40 (q, 3H), 1.41 (t, 3H), 1.36-1.30 (m, 2H), 1.14-1.07 (m, 2H). LCMS $R_t$=0.94 min in 1.5 min chromatography, 5-95AB, MS ESI calcd. for $C_{10}H_{12}F_3N_2O_2$ $[M+1-1]^+$249.1, found 249.1.

A-114a:

To a solution of ethyl 2-cyclopropyl-5-(trifluoromethyl) pyrazole-3-carboxylate (180 mg, 0.73 mmol) in ethanol (3 mL) was added a solution of NaOH (87.03 mg, 2.18 mmol) in water (3 mL). The reaction mixture was stirred at 50° C. for 2 hours. After cooling to room temperature, the reaction mixture was diluted with $H_2O$ (20 mL) and extracted with EtOAc (20 mL). The pH of the aqueous phase was adjusted with the addition of 1 N HCl to pH~2, and it was then extracted with EtOAc (30 mL×2). The combined organic phase was washed with water (50 mL) and brine (50 mL), dried over $Na_2SO_4$, filtered and concentrated to give the product (140 mg) as a solid. LCMS $R_t$=0.81 min in 1.5 min chromatography, 5-95AB, MS ESI calcd. for $C_8H_8F_3N_2O_2$ $[M+H]^+$221.0, found 221.1.

113:

To a mixture of 2-cyclopropyl-5-(trifluoromethyl)pyrazole-3-carboxylic acid (140 mg, 0.64 mmol), EDCI (121.91 mg, 0.64 mmol) in $CH_3CN$ (3 mL) was added (1S)-1-[3-(3-fluorophenyl)-1,2,4-oxadiazol-5-yl]propan-1-amine hydrochloride (163.87 mg, 0.64 mmol), the mixture was stirred at 0° C. for 3 hours. The reaction was quenched with 1 N HCl (10 mL) and extracted with EtOAc (10 mL×2). The combined organic phase was washed with water (15 mL) and brine (15 mL), dried over $Na_2SO_4$, filtered and concentrated to give the crude product. The crude product was partially purified by prep-TLC (silica gel, PE:EtOAc=5:1) to give the impure product. The impure product was triturated from n-hexane:DCM (10:1, 6 mL) to give the product (34 mg, 80.3 μmol, 13% yield) as a solid. $^1H$ NMR (400 MHz, DMSO-$d_6$) $\delta_H$=9.43 (d, 1H), 7.87 (d, 1H), 7.78-7.71 (m, 1H), 7.64 (dt, 1H), 7.48 (dt, 1H), 7.41 (s, 1H), 5.34-5.26 (m, 1H), 4.45-4.34 (m, 1H), 2.19-1.98 (m, 2H), 1.16-0.97 (m, 7H). LCMS $R_t$=1.40 min in 2.0 min chromatography, 10-80AB, MS ESI calcd. for $C_{19}H_{18}F_4N_5O_2$ $[M+H]^+$ 424.1, found 424.1.

Example 82. Synthesis of 116

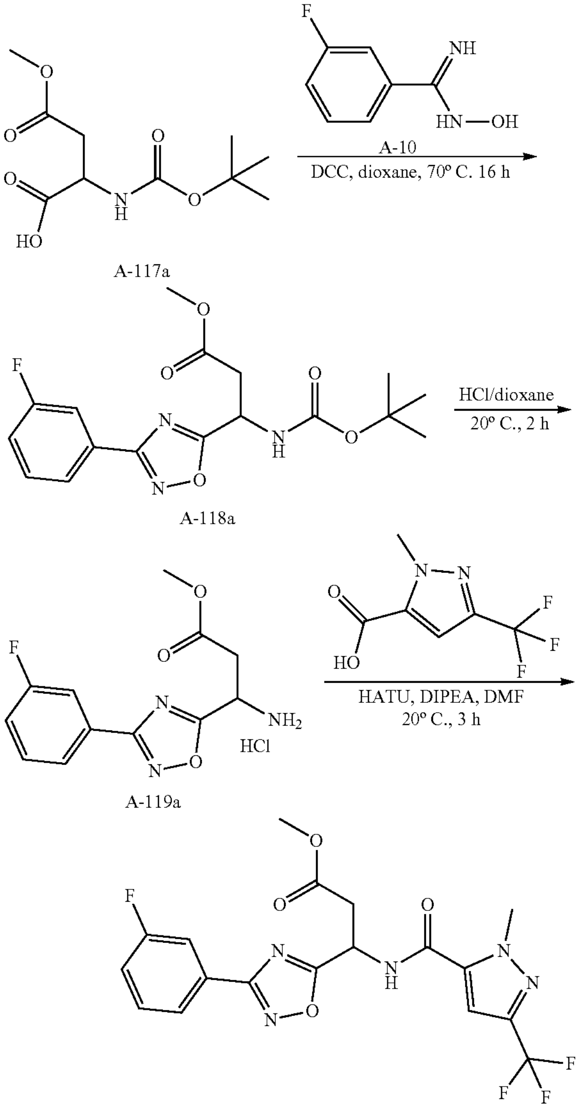

A-117a

A-118a

A-119a

116

A-118a:

A mixture of 3-fluoro-N-hydroxy-benzamidine (5 g, 32.44 mmol), 2-(tert-butoxycarbonylamino)-4-methoxy-4-oxo-butanoic acid (8.02 g, 32.44 mmol) and DCC (13.36 g, 64.88 mmol) in 1,4-dioxane (150 mL) was stirred at 70° C. for 16 hours. The mixture was cooled to room temperature and concentrated under reduced pressure and then EtOAc (250 mL) and water (150 mL) were added to the residue and the mixture was filtered. After the phases were separated, the organic phase was washed with brine (150 mL), dried over anhydrous $Na_2SO_4$, filtered and concentrated to give the crude product. The crude product was purified by flash column chromatography on silica gel (EtOAc in PE=0% to 10% to 20%) to give the product (9 g, 24.63 mmol, 75% yield) as an oil. $^1H$ NMR (400 MHz, $CDCl_3$) $\delta_H$=7.86 (d, 1H), 7.79-7.72 (m, 1H), 7.48-7.40 (m, 1H), 7.23-7.16 (m, 1H), 5.82 (d, 1H), 5.45-5.36 (m, 1H), 3.70 (s, 3H), 3.29-3.18 (m, 1H), 3.12-3.03 (m, 1H), 1.48 (s, 9H).

A-119a:

To methyl 3-(tert-butoxycarbonylamino)-3-[3-(3-fluorophenyl)-1,2,4-oxadiazol-5-yl]propanoate (9 g, 24.63 mmol) was added 4M HCl in 1,4-dioxane (50 mL, 24.63 mmol) and the reaction mixture was stirred at 20° C. for 2 hour to give a solution. The solution was concentrated under reduced pressure to give the crude product (7.4 g) as a solid. LCMS $R_t$=0.65 min in 1.5 min chromatography, 5-95AB, MS ESI calcd. for $C_{12}H_{13}FN_3O_3$ $[M+H]^+$ 332.2, found 266.1.

116:

A mixture of 2-methyl-5-(trifluoromethyl)pyrazole-3-carboxylic acid (4.76 g, 24.53 mmol), HATU (13.99 g, 36.79 mmol), DIPEA (6.82 mL, 49.06 mmol) and methyl 3-amino-3-[3-(3-fluorophenyl)-1,2,4-oxadiazol-5-yl]propanoate hydrochloride (7.4 g, 24.53 mmol) in DMF (30 mL) was stirred at 20° C. for 3 hours to give a solution. To the mixture was added water (100 mL) and the mixture was extracted with EtOAc (80 mL×2). The combined organic phase was washed with brine (50 mL), dried over anhydrous $Na_2SO_4$, filtered and concentrated to give the crude product. The crude product was purified by flash chromatography on silica gel (EtOAc in PE=0% to 10% to 30%) to give the product (7.7 g, 17.44 mmol) as a solid. The crude product (300 mg) was triturated from DCM (10 mL) and n-hexane (10 mL) at 65° C. to give the product (238.05 mg, 534.6 μmol, 78% yield) as a solid. $^1H$ NMR (400 MHz, $CDCl_3$) $\delta_H$=7.87 (d, 1H), 7.78-7.75 (m, 1H), 7.55 (d, 1H), 7.49-7.44 (m, 1H), 7.25-7.20 (m, 1H), 6.94 (s, 1H), 5.86-5.81 (m, 1H), 4.26 (s, 3H), 3.76 (s, 3H), 3.40 (dd, 1H), 3.14 (dd, 1H). LCMS $R_t$=1.26 min in 2.0 min chromatography, 10-80AB, MS ESI calcd. for $C_{18}H_{16}F_4N_5O_4$ $[M+H]^+$ 442.1, found 442.1.

Example 83. Synthesis of 114 and 115

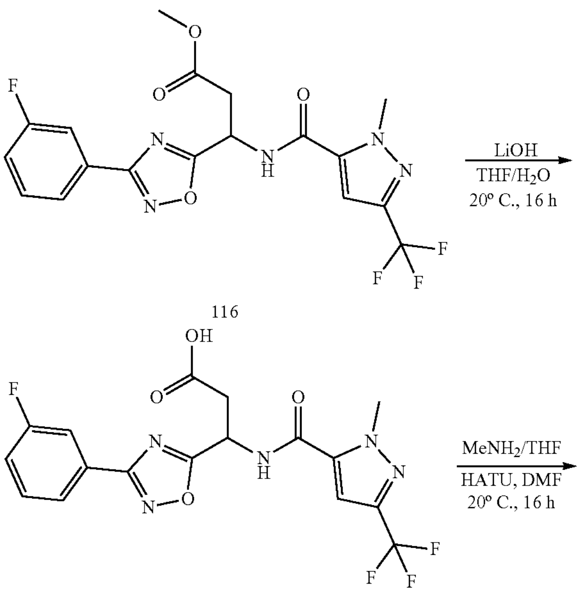

116

A-115

-continued

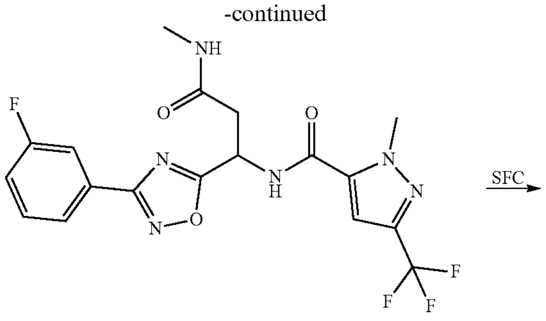

A-116

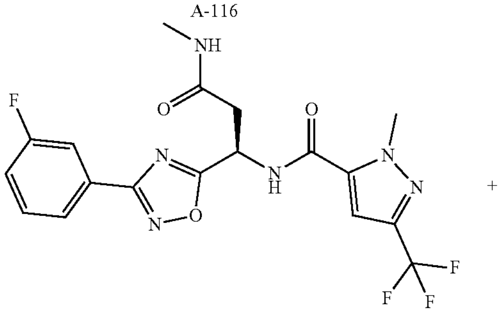

+

114

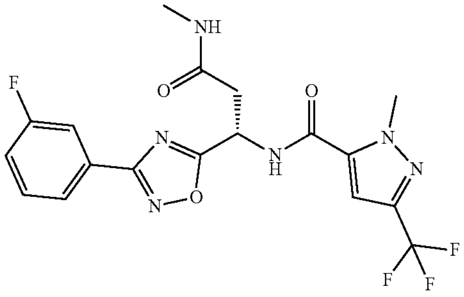

115

A-115:

A mixture of methyl 3-[3-(3-fluorophenyl)-1,2,4-oxadiazol-5-yl]-3-[[2-methyl-5-(trifluoromethyl)pyrazole-3-carbonyl]amino]propanoate (3 g, 6.8 mmol) and $LiOH.H_2O$ (570.44 mg, 13.59 mmol) in THF (10 mL) and water (5 mL) was stirred at 20° C. for 16 hours. To the mixture was added 1N HCl (50 mL) to adjust the pH=2 and then extracted with EtOAc (50 mL×2). The combined organic phase was washed with brine (50 mL), dried over anhydrous $Na_2SO_4$, filtered and concentrated to give the crude product as an oil. $^1$H NMR (400 MHz, $CDCl_3$) $\delta_H$=12.59 (br s, 1H), 9.51 (d, 1H), 7.86 (d, 1H), 7.78-7.71 (m, 1H), 7.64 (dt, 1H), 7.53-7.43 (m, 1H), 7.40 (s, 1H), 5.67 (q, 1H), 4.13 (s, 3H), 3.23 (dd, 1H), 3.11 (dd, 1H).

A-116:

To a solution of 3-[3-(3-fluorophenyl)-1,2,4-oxadiazol-5-yl]-3-[[2-methyl-5-(trifluoromethyl)pyrazole-3-carbonyl]amino]propanoic acid (500 mg, 1.17 mmol) and HATU (667.37 mg, 1.7 6 mmol) in DMF (10 mL) was added $MeNH_2$/THF (2M, 0.59 mL, 1.17 mmol) and DIPEA (0.49 mL, 3.51 mmol). The mixture was stirred at 20° C. for 16 hours. The reaction was quenched with $H_2O$ (20 mL) and then extracted with EtOAc (20 mL×2). The combined organic phase was washed with brine (30 mL), dried over $Na_2SO_4$, filtered and concentrated to give the crude product. The crude product was purified by flash chromatography on silica gel (EtOAc in PE=0% to 20% to 60%) to give the product (200 mg, 425.7 μmol, 36% yield) as a solid. LCMS $R_t$=0.85 min in 1.5 min chromatography, 5-95AB, MS ESI calcd. for $C_{18}H_{17}F_4N_6O_3$ $[M+H]^+$ 441.12, found 441.2.

114 & 115:

Analytical SFC (Daicel CHIRALPAK AD-3 (150 mm×4.6 mm I.D., 3 μm), mobile phase: A: $CO_2$ B: methanol (0.05% DEA), gradient: from 5% to 40% of B in 5 min and hold 40% for 2.5 min, then 5% of B for 2.5 min, flow rate: 2.5 mL/min, column temp: 35° C., ABPR: 1500 psi) showed two peaks at 3.45 min and 4.34 min. The product was separated by SFC (Daicel CHIRALPAK AD-H (250 mm×30 mm, 5 μm); A=$CO_2$ and B=EtOH (0.1% DEA); 38° C.; 50 mL/min; 30% B; 8 min run; 11 injections, Rt of peak 1=4.1 min, Rt of peak 2=5.3 min) to give the enantiomer 1, randomly assigned as 114 (50.1 mg, 113.8 mol, 25% yield) (Rt=3.45 min in analytical SFC) as a solid, and the enantiomer 2, randomly assigned as 115 (51.5 mg, 117 mol, 25% yield) (Rt=4.34 min in analytical SFC) as a solid.

114:

$^1$H NMR (400 Mhz $CDCl_3$) $\delta_H$=8.46 (br d, 1H), 7.90-7.82 (m, 1H), 7.78-7.72 (m, 1H), 7.50-7.41 (m, 1H), 7.25-7.16 (m, 1H), 7.00 (s, 1H), 5.87-5.77 (m, 1H), 5.71 (br d, 1H), 4.26 (s, 3H), 3.19 (dd, 1H), 3.03-2.95 (m, 1H), 2.83 (d, 3H). LCMS Rt=1.15 min in 2.0 min chromatography, 10-80AB, MS ESI calcd. for $C_{18}H_{17}F_4N_6O_3$ $[M+H]^+$ 441.1, found 441.1.

115:

$^1$H NMR (400 Mhz $CDCl_3$) $\delta_H$=8.46 (br d, 1H), 7.90-7.81 (m, 1H), 7.77-7.72 (m, 1H), 7.49-7.41 (m, 1H), 7.24-7.16 (m, 1H), 7.00 (s, 1H), 5.87-5.77 (m, 1H), 5.71 (br d, 1H), 4.26 (s, 3H), 3.19 (dd, 1H), 3.03-2.95 (m, 1H), 2.83 (d, 3H). LCMS Rt=1.16 min in 2.0 min chromatography, 10-80AB, MS ESI calcd. for $C_{18}H_{17}F_4N_6O_3$ $[M+H]^+$ 441.1, found 441.1.

Example 84. Synthesis of 117

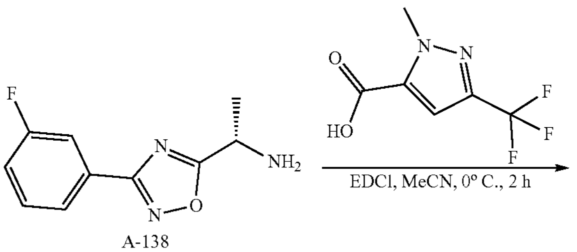

A-138

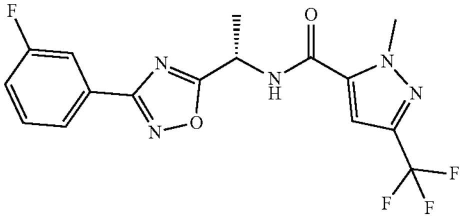

117

To a mixture of 2-methyl-5-(trifluoromethyl)pyrazole-3-carboxylic acid (159.32 mg, 0.82 mmol), EDCI (157.34 mg, 0.82 mmol) in $CH_3CN$ (3 mL) was added (1S)-1-[3-(3-fluorophenyl)-1,2,4-oxadiazol-5-yl]ethanamine hydrochloride (200 mg, 0.82 mmol) and the reaction mixture was stirred at 0° C. for 2 hours. The reaction was quenched with 1N HCl (10 mL) and extracted with EtOAc (10 mL×2). The combined organic phase was washed with water (15 mL) and brine (15 mL), dried over $Na_2SO_4$, filtered and concentrated to give the crude product. The crude product was purified by prep-TLC (silica gel, PE:EtOAc=3:1) after flash chromatography on silica gel (EtOAc in PE=0% to 40%) to give the impure product.

Analytical SFC (Daicel CHIRALCEL OJ-3 (150 mm×4.6 mm I.D., 3 μm), mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C.) showed two peaks at 2.25 min (96.2%) and 2.70 min (3.8%). The impure product was purified by SFC (Daicel CHIRALCEL OJ-H (250 mm×30 mm, 5 μm); A=$CO_2$ and B=EtOH (0.1% $NH_3H_2O$); 38° C.; 60 mL/min; 15% B; 8 min run; 6 injections, Rt of peak 1=4.2 min, Rt of peak 2=6.5 min) to give the product (59.08 mg, 0.15 mmol, 67% yield) (Rt=2.25 min in analytical SFC) as a solid. $^1H$ NMR (400 MHz, DMSO-$d_6$) $\delta_H$=9.46 (d, 1H), 7.86 (d, 1H), 7.79-7.72 (m, 1H), 7.67-7.58 (m, 1H), 7.51-7.43 (m, 2H), 5.46 (quin, 1H), 4.13 (s, 3H), 1.67 (d, 3H). LCMS $R_t$=1.21 min in 2.0 min chromatography, 10-80AB, MS ESI calcd. for $C_{16}H_{14}F_4N_5O_2$ $[M+H]^+$ 384.1, found 383.9.

Example 85. Synthesis of 118

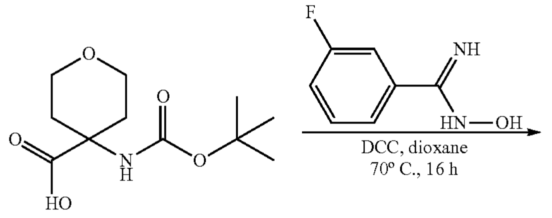

A-139a

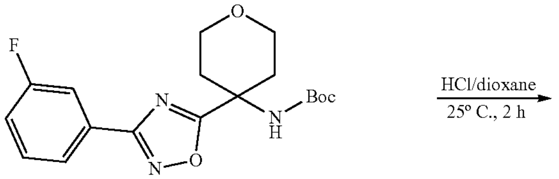

A-140a

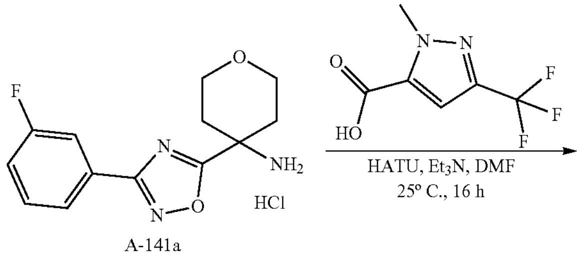

A-141a

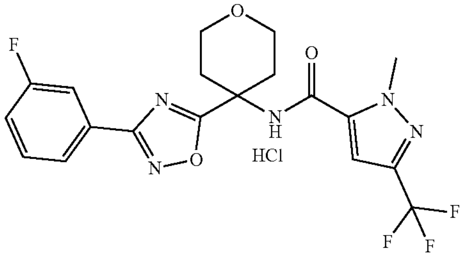
118

A-140a:

A mixture of 3-fluoro-N-hydroxy-benzamidine (251.38 mg, 1.63 mmol) and DCC (671.91 mg, 3.26 mmol), 4-(tert-butoxycarbonylamino)tetrahydropyran-4-carboxylic acid (400 mg, 1.63 mmol) in 1,4-dioxane (5 mL) was stirred at 70° C. for 16 hours. After cooling to room temperature, the mixture was filtered and diluted with EtOAc (10 mL). To the combined organic layer was added saturated $NH_4Cl$ (30 mL) and it was extracted with EtOAc (30 mL×2). The combined organic phase was washed with brine (50 mL), dried over $Na_2SO_4$, filtered and concentrated to give the crude product. The crude product was purified by flash column chromatography on silica gel (EtOAc in PE=0% to 10%) to give the product (400 mg, 1.09 mmol, 66% yield) as a solid. LCMS $R_t$=0.9 min in 1.5 min chromatography, 5-95AB, MS ESI calcd. for $C_{18}H_{23}FN_3O_4$ $[M+H-56]^+$364.16, found 308.1.

A-141a:

To tert-butyl N-[4-[3-(3-fluorophenyl)-1,2,4-oxadiazol-5-yl]tetrahydropyran-4-yl]carbamate (200 mg, 0.54 mmol) was added 4M HCl in 1,4-dioxane (10 mL, 0.54 mmol) and the reaction mixture was stirred at 25° C. for 2 hours. The mixture was concerned under reduced pressure to give the crude product (130 mg, 0.49 mmol,) as a solid. LCMS $R_t$=0.65 min in 1.5 min chromatography, 5-95AB, MS ESI calcd. for $C_{13}H_{15}FN_3O_2$ $[M+H]^F$264.1, found 264.1.

118:

To a solution of 4-[3-(3-fluorophenyl)-1,2,4-oxadiazol-5-yl]tetrahydropyran-4-amine hydrochloride (130 mg, 0.49 mmol), 2-methyl-5-(trifluoromethyl)pyrazole-3-carboxylic acid (105.43 mg, 0.54 mmol) and HATU (375.51 mg, 0.99 mmol) in DMF (2 mL) was added TEA (0.21 mL, 1.48 mmol). The mixture was stirred at 25° C. for 16 hours. The mixture was diluted with $H_2O$ (10 mL) and extracted with DCM (20 mL×2). The combined organic phase was washed with brine (10 mL), dried over $Na_2SO_4$, filtered and concentrated to give the crude product. The crude product was purified by purified by prep-HPLC (Boston Prime C18 (150 mm×30 mm, 5 μm), A=$H_2O$ (0.05% $NH_3.H_2O$) and B=$CH_3CN$; 50-80% B over 9 min) to give the product (159.97 mg, 0.36 mmol, 73% yield) as a solid. $^1H$ NMR (400 MHz, $CDCl_3$) $\delta_H$=7.89 (d, 1H), 7.80 (td, 1H), 7.47 (dt, 1H), 7.22 (dt, 1H), 6.92 (s, 1H), 6.38 (s, 1H), 4.12 (s, 3H), 4.01-3.81 (m, 4H), 2.72-2.53 (m, 2H), 2.43-2.25 (m, 2H). LCMS $R_t$=1.3 min in 2.0 min chromatography, 10-80AB, MS ESI calcd. for $C_{19}H_{18}F_4N_5O_3$ $[M+H]^+$ 440.1, found 440.2.

Example 86. Synthesis of 119

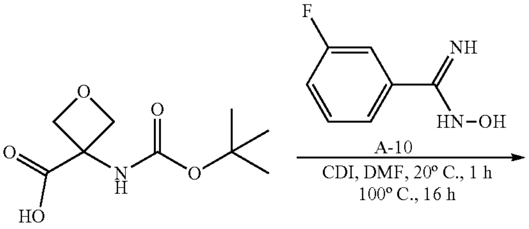

A-142a

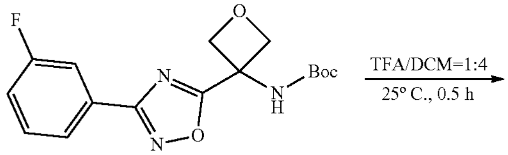

A-143a

-continued

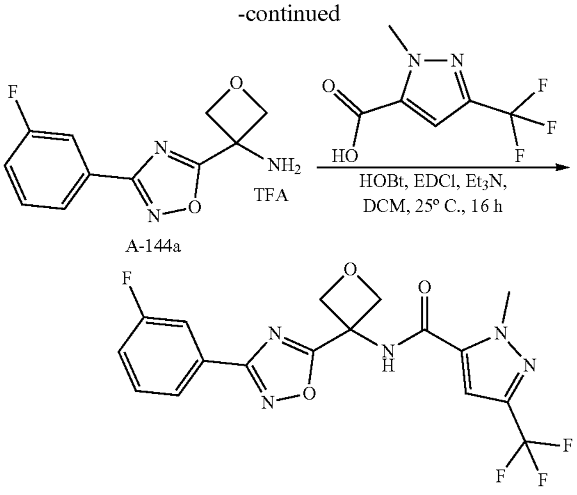

A-144a

119

A-143a:

CDI (298.59 mg, 1.84 mmol) was added to a stirred solution of 3-(tert-butoxycarbonylamino)oxetane-3-carboxylic acid (200 mg, 0.92 mmol) in DMF (10 mL). After 40 min, 3-fluoro-N-hydroxy-benzamidine (283.84 mg, 1.84 mmol) was added in one portion and the resulting solution was stirred for 30 min before it was heated to 100° C. and stirred for 16 hours. After cooling to room temperature, the reaction was diluted with $H_2O$ (40 mL), then extracted with EtOAc (30 mL×2). The combined organic phase was washed with brine (30 mL), dried over $Na_2SO_4$, filtered and concentrated to give the crude product. The crude product was purified with flash chromatography on silica gel (EtOAc in PE=0% to 5%) to give the product (180 mg, 0.54 mmol, 58% yield) as an oil. LCMS $R_t$=0.88 min in 1.5 min chromatography, 5-95% AB, MS ESI calcd. for $C_{16}H_{19}FN_3O_4$ $[M+H-tBu]^+$ 280.1, found 279.7.

A-144a:

To the solution of tert-butyl N-[3-[3-(3-fluorophenyl)-1,2,4-oxadiazol-5-yl]oxetan-3-yl]carbamate (120 mg, 0.36 mmol) in DCM (2 mL) was added TFA (0.5 mL, 6.83 mmol) and the resulting solution was stirred at 25° C. for 30 min. The reaction mixture was concentrated under reduced pressure to give the crude product (150 mg, 0.40 mmol) as an oil. LCMS $R_t$=0.87 min in 2.0 min chromatography, 10-80% AB, MS ESI calcd. for $C_{13}H_{12}F_4N_3O_4$ $[M+H]^+$ 236.1, found 235.9.

119:

A mixture of 2-methyl-5-(trifluoromethyl)pyrazole-3-carboxylic acid (100 mg, 0.52 mmol), HOBt (139.23 mg, 1.03 mmol), EDCI (197.52 mg, 1.03 mmol), $Et_3N$ (0.29 mL, 2.06 mmol), 3-[3-(3-fluorophenyl)-1,2,4-oxadiazol-5-yl]oxetan-3-amine 2,2,2-trifluoroacetic acid (150 mg, 0.43 mmol) in DCM (10 mL) was stirred at 25° C. for 16 hours. The reaction mixture was concentrated and then diluted with $H_2O$ (20 mL) and extracted with DCM (30 mL×2). The combined organic phase was washed with brine (30 mL), dried over $Na_2SO_4$, filtered and concentrated to give the crude product. The crude product was purified with prep-HPLC (Boston Prime C18 (150 mm×30 mm, 5 μm), A=$H_2O$ (0.05% $NH_4OH$) and B=$CH_3CN$; 45-75% B over 9 min) to give the product (62.95 mg, 0.15 mmol, 30% yield) as a solid. $^1H$ NMR (400 MHz, DMSO-$d_6$) δ=10.25 (s, 1H), 7.90 (d, 1H), 7.84-7.75 (m, 1H), 7.66 (dt, 1H), 7.58-7.44 (m, 2H), 5.17 (d, 2H), 5.00 (d, 2H), 4.09 (s, 3H). LCMS: $R_t$=1.22 min in 2.0 min chromatography, 10-80AB, MS ESI calcd. for $C_{17}H_{14}F_4N_5O_3$ $[M+H]^+$ 421.1, found 411.6.

Example 87. Synthesis of 120

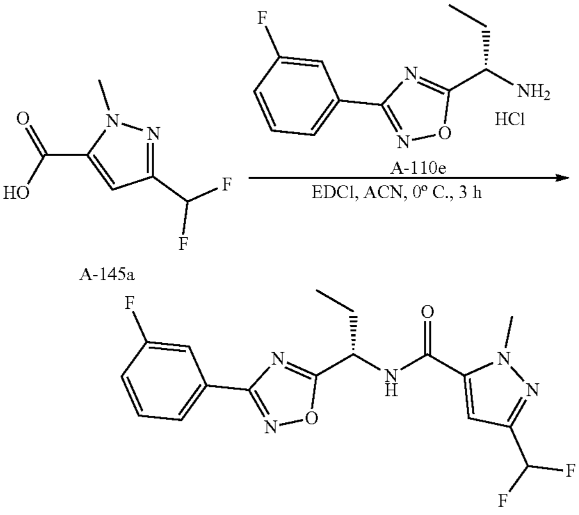

A-145a

120

To a mixture of 5-(difluoromethyl)-2-methyl-pyrazole-3-carboxylic acid (150.65 mg, 0.86 mmol), EDCI (148.78 mg, 0.78 mmol) in MeCN (4 mL) was added (1S)-1-[3-(3-fluorophenyl)-1,2,4-oxadiazol-5-yl]propan-1-amine hydrochloride (200 mg, 0.78 mmol), and the mixture was stirred at 0° C. for 2 hours. The reaction was quenched with 1N HCl (10 mL) and extracted with EtOAc (10 mL×2). The combined organic phase was washed with brine (15 mL), dried over $Na_2SO_4$, filtered and concentrated to give the crude product. The crude product was partially purified by flash chromatography on silica gel (EtOAc in PE=0% to 10% to 20%) to give an impure product. The impure product was purified by prep-TLC (silica gel, PE:EtOAc=3:1) to give the product (32.2 mg, 84.9 μmol, 10% yield) as an oil. $^1H$ NMR (400 MHz, $CDCl_3$) $\delta_H$=7.89 (d, 1H), 7.82-7.77 (m, 1H), 7.52-7.43 (m, 1H), 7.26-7.20 (m, 1H), 6.90 (s, 1H), 6.86-6.55 (m, 2H), 5.58-5.41 (m, 1H), 4.20 (s, 3H), 2.25-2.13 (m, 1H), 2.09 (s, 1H), 1.08 (t, 3H). LCMS $R_t$=1.19 min in 2.0 min chromatography, 10-80AB, MS ESI calcd. $C_{17}H_{17}F_3N_5O_2$ $[M+H]^+$ 380.13, found 379.9.

Example 88. Synthesis of 121 and 122

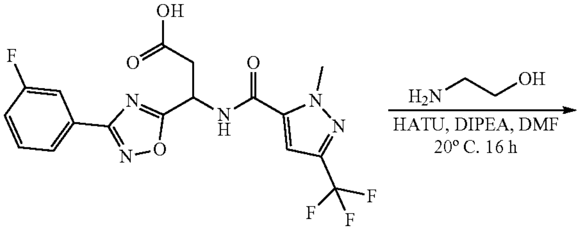

A-115a

-continued

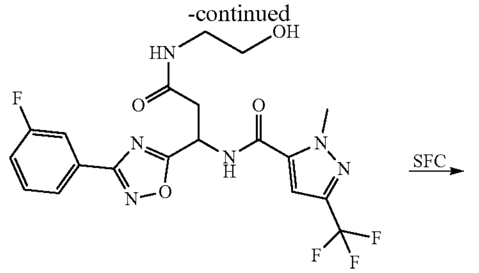

A-146a

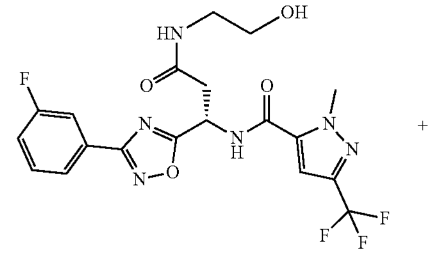

121

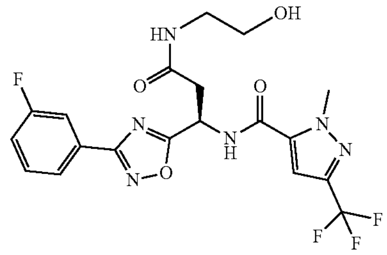

122

A-146a:

A mixture of 3-[3-(3-fluorophenyl)-1,2,4-oxadiazol-5-yl]-3-[[2-methyl-5-(trifluoromethyl)pyrazole-3-carbonyl]amino]propanoic acid (300 mg, 0.70 mmol), HATU (400.42 mg, 1.05 mmol), DIPEA (0.29 mL, 2.11 mmol), and 2-aminoethanol (57.25 mg, 0.94 mmol) in DMF (10 mL) was stirred at 20° C. for 16 hours. The residue was diluted with sat. $NH_4Cl$ (20 mL) and extracted with EtOAc (20 mL). The combined organic phase was washed with brine (15 mL×2), dried over anhydrous $Na_2SO_4$, filtered and concentrated to give the crude product. The crude product was purified by flash chromatography on silica gel (EtOAc in PE=0% to 50% to 90%) to give the product (120 mg, 0.25 mmol, 36% yield) as a solid. LCMS $R_t$=0.81 min in 1.5 min chromatography, 5-95AB, MS ESI calcd. for $C_{19}H_{19}F_4N_6O_4$ [M+H] 471.1, found 471.0.

121 & 122:

Analytical SFC (Daicel CHIRALPAK AS-3 (150 mm×4.6 mm, 3 μm), mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C.) showed two peaks at 2.49 min and 2.93 min. The product was separated by SFC (Daicel CHIRALPAK AS-H (250 mm×30 mm, 5 μm); A=$CO_2$ and B=ETOH (0.1% $NH_3H_2O$); 38° C.; 70 mL/min; 30% B; 5 min run; 14 injections, Rt of peak 1=2.4 min, Rt of peak 2=3.0 min) to give the enantiomer 1, randomly assigned as 120 (10.72 mg, 0.02 mmol, 8% yield) (Rt=2.49 min in analytical SFC) as a solid, and the enantiomer 2, randomly assigned as 121 (11.6 mg, 0.02 mmol, 9% yield) (Rt=2.93 min in analytical SFC) as a solid.

121:

$^1$H NMR (400 MHz, DMSO-$d_6$) $\delta_H$=9.49 (d, 1H), 8.20-8.12 (m, 1H), 7.85 (d, 1H), 7.77-7.70 (m, 1H), 7.68-7.60 (m, 1H), 7.52-7.43 (m, 1H), 7.41 (s, 1H), 5.77-5.61 (m, 1H), 4.66 (t, 1H), 4.12 (s, 3H), 3.42-3.35 (m, 2H), 3.17-3.05 (m, 3H), 2.98-2.88 (m, 1H). LCMS $R_t$=1.08 min in 2 min chromatography, 10-80AB, MS ESI calcd. for $C_{19}H_{19}F_4N_6O_4$ [M+II]$^+$471.1, found 471.0.

122:

$^1$H NMR (400 MHz, DMSO-$d_6$) $\delta_H$=9.48 (d, 1H), 8.19-8.11 (m, 1H), 7.85 (d, H), 7.76-7.70 (m, 1H), 7.68-7.59 (m, 1H), 7.51-7.43 (m, 1H), 7.40 (s, 1H), 5.72-5.64 (m, 1H), 4.65 (t, 1H), 4.12 (s, 3H), 3.40-3.34 (m, 2H), 3.15-3.05 (m, 3H), 2.97-2.89 (m, 1H). LCMS $R_t$=1.07 min in 2 min chromatography, 10-80AB, MS ESI calcd. for $C_{19}H_{19}F_4N_6O_4$ [M+II]$^+$471.1, found 471.0.

Example 89. Synthesis of 123 and 124

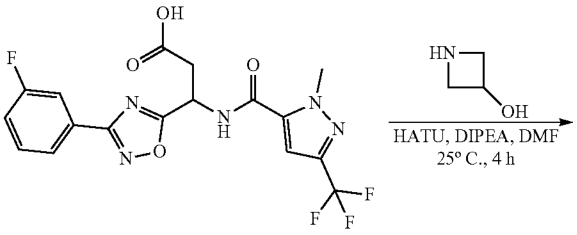

A-115a

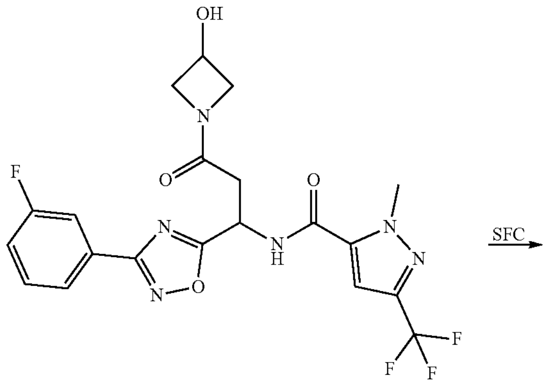

A-147a

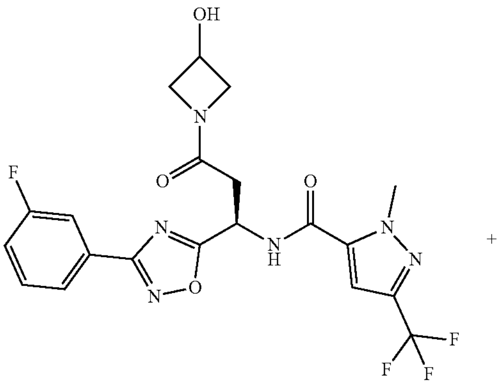

123

-continued

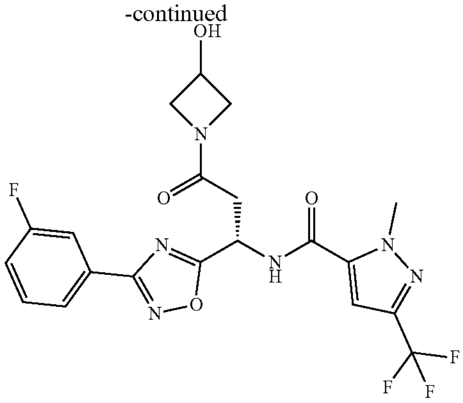

124

A-147a:

A mixture of 3-[3-(3-fluorophenyl)-1,2,4-oxadiazol-5-yl]-3-[[2-methyl-5-(trifluoromethyl)pyrazole-3-carbonyl]amino]propanoic acid (600 mg, 1.4 mmol), HATU (800.84 mg, 2.11 mmol), DIPEA (0.59 mL, 4.21 mmol) and azetidin-3-ol hydrochloride (461.47 mg, 4.21 mmol) in DMF (5 mL) was stirred at 25° C. for 4 hours. The reaction was quenched with sat. $NH_4Cl$ (20 mL) and extracted with EtOAc (20 mL×2). The combined organic phase was washed with water (30 mL) and brine (30 mL), dried over $Na_2SO_4$, filtered and concentrated to give the crude product. The crude product was purified by prep-TLC (silica gel, PE:EtOAc=3:1) to give an impure product. The impure product was triturated from n-hexane/DCM (10:1, 11 mL) to give the product (210 mg, 0.42 mmol, 30% yield) as a solid. LCMS $R_t$=0.82 min in 1.5 min chromatography, 5-95AB, MS ESI calcd. for $C_{20}H_{19}F_4N_6O_4$ $[M+H]^+$ 483.1, found 483.0.

123 & 124:

Analytical SFC (Daicel CHIRALPAK AS-3 (150 mm×4.6 mm, 3 μm), mobile phase: A: $CO_2$ B: ethanol (0.05% DEA) gradient: from 5% to 40% of B in 5 min and from 40% to 5% of B in 0.5 min hold 5% of B for 1.5 min, flow rate: 2.5 mL/min, column temp: 35° C.) showed two peaks at 2.42 min and 3.82 min. The product was separated by SFC (Daicel CHIRALPAK AS-H (250 mm×30 mm, 5 μm); A=$CO_2$ and B=EtOH (0.1% $NH_3H_2O$); 38° C.; 60 mL/min; 35% B; 8 min run; 4 injections, Rt of peak 1=2.52 min, Rt of peak 2=6.45 min) to give the enantiomer 1, randomly assigned as 123 (57.28 mg, 118.7 μmol, 27% yield) (Rt=2.42 min in analytical SFC) as a solid, and the enantiomer 2, randomly assigned as 124 (81.28 mg, 164.8 μmol, 37% yield) (Rt=3.82 min in analytical SFC) as a solid.

123:

$^1$H NMR (400 MHz, $CDCl_3$) $\delta_H$=8.47 (br t, 1H), 7.91-7.84 (m, 1H), 7.83-7.72 (m, 1H), 7.50-7.43 (m, 1H), 7.25-7.18 (m, 1H), 6.97 (d, 1H), 5.82-5.75 (m, 1H), 4.78-4.70 (m, 1H), 4.52-4.40 (m, 1H), 4.30-4.24 (m, 4H), 4.22-4.07 (m, 1H), 3.95-3.84 (m, 1H), 3.27-3.18 (m, 1H), 2.86-2.74 (m, 1H), 2.34 (m, 1H). LCMS $R_t$=1.15 min in 2.0 min chromatography, 10-80AB, MS ESI calcd. for $C_{20}H_{19}F_4N_6O_4$ $[M+H]^+$ 483.1.1, found 483.1.

124:

$^1$H NMR (400 MHz, $CDCl_3$) $\delta_H$=8.47 (br t, 1H), 7.91-7.84 (m, 1H), 7.83-7.73 (m, 1H), 7.50-7.42 (m, 1H), 7.25-7.19 (m, 1H), 6.97 (d, 1H), 5.82-5.76 (m, 1H), 4.78-4.70 (m, 1H), 4.52-4.41 (m, 1H), 4.30-4.24 (m, 4H), 4.22-4.07 (m, 1H), 3.94-3.83 (m, 1H), 3.26-3.18 (m, 1H), 2.86-2.74 (m, 1H), 2.31-2.25 (m, 1H). LCMS $R_t$=1.13 min in 2.0 min chromatography, 10-80AB, MS ESI calcd. for $C_{20}H_{19}F_4N_6O_4$ $[M+H]^+$ 483.1.1, found 483.1.

Example 90. Synthesis of 125 and 126

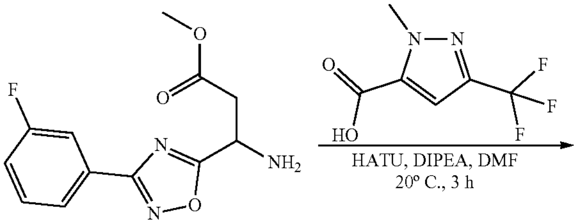

A-119b

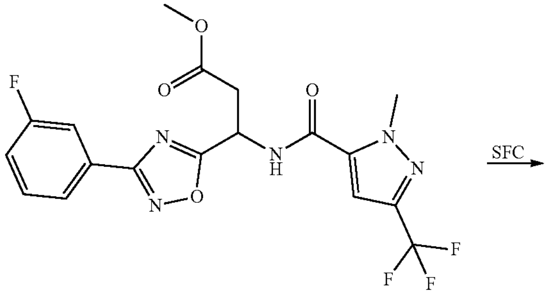

A-119c

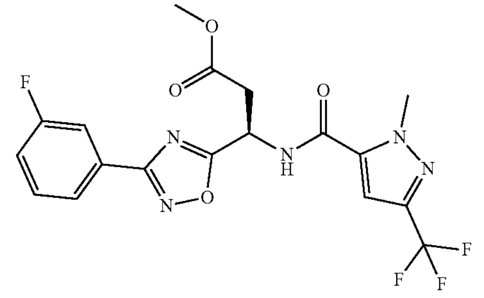

125

&

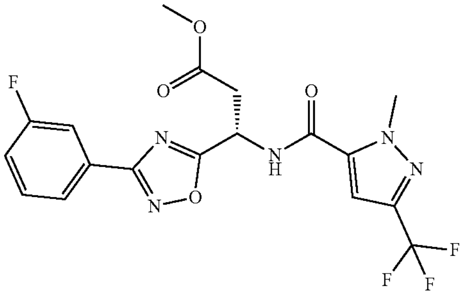

126

A-119c:

A mixture of 2-methyl-5-(trifluoromethyl)pyrazole-3-carboxylic acid (315.26 mg, 1.62 mmol), HATU (926.34 mg, 2.44 mmol), DIPEA (0.45 mL, 3.25 mmol) and methyl 3-amino-3-[3-(3-fluorophenyl)-1,2,4-oxadiazol-5-yl]propanoate hydrochloride (490 mg, 1.62 mmol) in DMF (30 mL) was stirred at 20° C. for 3 hours. To the mixture was added water (50 mL) and then it was extracted with EtOAc (80 mL×2). The combined organic phase was washed with brine (50 mL), dried over anhydrous $Na_2SO_4$, filtered and concentrated to give the crude product. The crude product was purified by flash column chromatography on silica gel (EtOAc in PE=0% to 10% to 30%) to give the product. Analytical SFC (Daicel CHIRALCEL OJ-H (150 mm×4.6 mm, 5 μm), mobile phase: A: $CO_2$ B: ethanol (0.05% DEA), gradient: from 5% to 40% of B in 5.5 min and hold 5% of B for 1.5 min, flow rate: 2.5 mL/min, column temp: 40° C.) showed two peaks at 2.65 min and 2.78 min. The product was separated by SFC (Daicel CHIRALCEL OJ-H (250 mm×30 mm, 5 μm); A=$CO_2$ and B=0.1% $NH_3.H_2O$-EtOH; 35° C.; 60 mL/min; 15% B; 8 min run; 41 injections, Rt of peak 1=5.21 min, Rt of peak 2=5.69 min) to give the enantiomer 1 (Rt=2.65 min in analytical SFC, 87% ee) and the enantiomer 2 (Rt=2.78 min in analytical SFC, 65% ee). The impure enantiomer 1 was purified again by SFC (Daicel CHIRALCEL OJ-H (250 mm×30 mm, 5 μm); A=$CO_2$ and B=0.1% $NH_3.H_2O$-EtOH; 35° C.; 60 mL/min; 15% B; 8 min run; 22 injections, Rt of Peak 1=5.38 min) to give the enantiomer 1, randomly assigned as 125 (15.5 mg, 34.6 mol, 2% yield) (Rt=2.65 min in analytical SFC) as a solid. The impure enantiomer 2 was purified again by SFC two times (Daicel CHIRALCEL OJ-H (250 mm×30 mm, 5 μm); A=$CO_2$ and B=0.1% $NH_3.H_2O$-EtOH; 35° C.; 60 mL/min; 15% B; 8 min run; 20 injections, Rt of peak 2=5.71 min. Daicel CHIRALCEL OJ-H (250 mm×30 mm, 5 μm); A=$CO_2$ and B=0.1% $NH_3.H_2O$-EtOH; 35° C.; 60 mL/min; 15% B; 8 min run; 10 injections, Rt of peak 2=6.14 min) to give the enantiomer 2, randomly assigned as 126 (31.41 mg, 68.8 mol, 4% yield) (Rt=2.78 min in analytical SFC) as a solid.

125:

$^1$H NMR (400 MHz, $CDCl_3$) $\delta_H$=7.87 (d, 1H), 7.81-7.74 (m, 1H), 7.55 (d, 1H), 7.50-7.44 (m, 1H), 7.26-7.20 (m, 1H), 6.94 (s, 1H), 5.86-5.81 (m, 1H), 4.27 (s, 3H), 3.76 (s, 3H), 3.40 (dd, 1H), 3.14 (dd, 1H). LCMS $R_t$=1.28 min in 2.0 min chromatography, 10-80AB, MS ESI calcd. for $C_{18}H_{16}F_4N_5O_4$ $[M+H]^+$ 442.1, found 442.2.

126:

$^1$H NMR (400 MHz, $CDCl_3$) $\delta_H$=7.87 (d, 1H), 7.79-7.75 (m, 1H), 7.55 (d, 1H), 7.49-7.44 (m, 1H), 7.26-7.20 (m, 1H), 6.94 (s, 1H), 5.86-5.81 (m, 1H), 4.26 (s, 3H), 3.76 (s, 3H), 3.40 (dd, 1H), 3.14 (dd, 1H). LCMS $R_t$=1.26 min in 2.0 min chromatography, 10-80AB, MS ESI calcd. for $C_{18}H_{16}F_4N_5O_4$ $[M+H]^+$ 442.1, found 442.1.

Example 91. Synthesis of 127

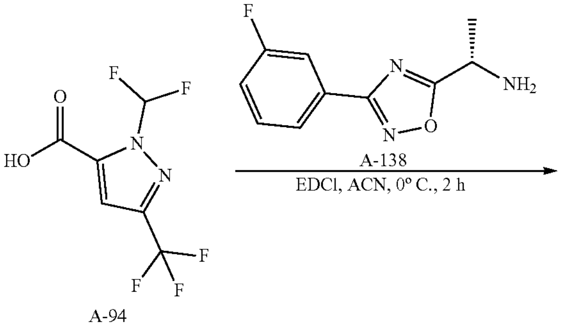

A-138

A-94

-continued

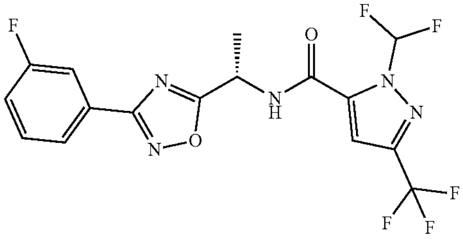

127

To a mixture of 2-(difluoromethyl)-5-(trifluoromethyl) pyrazole-3-carboxylic acid (120 mg, 0.52 mmol), EDCI (99.98 mg, 0.52 mmol) in $CH_3CN$ (3 mL) was added (1S)-1-[3-(3-fluorophenyl)-1,2,4-oxadiazol-5-yl] ethanamine hydrochloride (134.39 mg, 0.55 mmol) and the mixture was stirred at 0° C. for 2 hours. The reaction was quenched with 1N HCl (10 mL) and then extracted with EtOAc (10 mL×2). The combined organic phase was washed with water (15 mL) and brine (15 mL), dried over $Na_2SO_4$, filtered and concentrated to give the crude product. The crude product was purified by flash column chromatography on silica gel (EtOAc in PE=0% to 30%) to give an impure product. The impure product was triturated with n-hexane/DCM (10:1, 5 mL) to give the product (44.1 mg, 0.1 mmol, 20% yield) as a solid. $^1$H NMR (400 MHz, DMSO-$d_6$) $\delta_H$=9.81 (d, 1H), 8.51-8.17 (m, 1H), 7.87 (d, 1H), 7.78-7.72 (m, 1H), 7.70-7.61 (m, 2H), 7.48 (dt, 1H), 5.54-5.45 (m, 1H), 1.69 (d, 3H). LCMS $R_t$=1.29 min in 2.0 min chromatography, 10-80AB, MS ESI calcd. for $C_{16}H_{12}F_6N_5O_2$ $[M+H]^+$ 420.1, found 420.1.

Example 92. Synthesis of 128 and 129

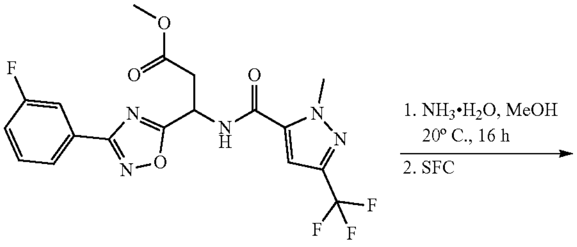

116

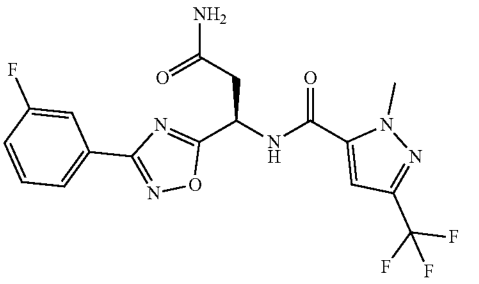

+

128

-continued

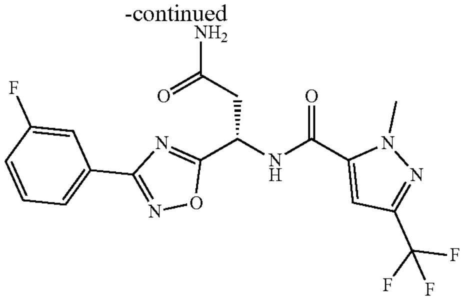

129

A solution of methyl 3-[3-(3-fluorophenyl)-1,2,4-oxadiazol-5-yl]-3-[[2-methyl-5-(trifluoromethyl)pyrazole-3-carbonyl]amino]propanoate (500 mg, 1.13 mmol) and $NH_3.H_2O$ (5 mL, 1.13 mmol) in methanol (5 mL) was stirred at 20° C. for 16 hours. To the mixture was added water (20 mL) and it was then extracted with EtOAc (20 mL×2). The combined organic phase was washed with brine (20 mL), dried over anhydrous $Na_2SO_4$, filtered and concentrated to give the crude product. The crude product was purified by flash column chromatography on silica gel (EtOAc in PE=0% to 30% to 50%) to give the product.

Analytical SFC (Daicel CHIRALPAK AS-3 (150 mm×4.6 mm, 3 μm), mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C.) showed two peaks at 2.66 min and 3.38 min. The product was separated by SFC (Daicel CHIRALPAK AS-H (250 mm×30 mm, 5 μm); $A=CO_2$ and B=0.1% $NH_3.H_2O$-EtOH; 35° C.; 60 mL/min; 35% B; 8 min run; 6 injections, Rt of peak 1=2.88 min, Rt of peak 2=4.66 min) to give the enantiomer 1, randomly assigned as 128 (74.06 mg, 171.7 μmol, 15% yield) (Rt=2.66 min in analytical SFC) as a solid, and the enantiomer 2 (Rt=3.38 min in analytical SFC, 93.1% ee).

The impure enantiomer 2 was purified again by SFC (Daicel CHIRALPAK AS-H (250 mm×30 mm, 5 μm); $A=CO_2$ and B=EtOH; 35° C.; 60 mL/min; 25% B; 8 min run; 6 injections, Rt of Peak 2=4.6 min) to give the enantiomer 2, randomly assigned as 129 (62.93 mg, 147.6 μmol, 13% yield) (Rt=3.38 min in analytical SFC) as a solid.

128:

$^1H$ NMR (400 MHz, DMSO-$d_6$) $\delta_H$=9.49 (d, 1H), 7.85 (d, 1H), 7.74 (d, 1H), 7.68-7.57 (m, 2H), 7.51-7.44 (m, 1H), 7.41 (s, 1H), 7.09 (s, 1H), 5.67 (q, 1H), 4.13 (s, 3H), 3.11-3.05 (m, 1H), 2.97-2.90 (m, 1H). LCMS $R_t$=1.11 min in 2.0 min chromatography, 10-80AB, MS ESI calcd. for $C_{17}H_{15}F_4N_6O_3$ $[M+H]^+$ 427.1, found 427.1.

129:

$^1H$ NMR (400 MHz, DMSO-$d_6$) $\delta_H$=9.49 (d, 1H), 7.85 (d, 1H), 7.74 (d, 1H), 7.68-7.57 (m, 2H), 7.51-7.44 (m, 1H), 7.41 (s, 1H), 7.09 (s, 1H), 5.67 (q, 1H), 4.13 (s, 3H), 3.13-3.03 (m, 1H), 2.99-2.88 (m, 1H). LCMS $R_t$=1.12 min in 2.0 min chromatography, 10-80AB, MS ESI calcd. for $C_{17}H_{15}F_4N_6O_3$ $[M+H]^+$ 427.1, found 427.1.

Example 93. Synthesis of 130

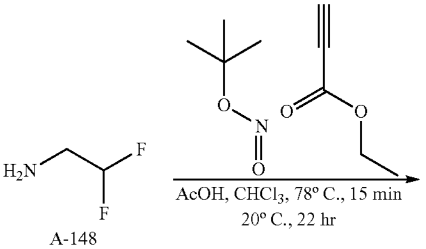

A-148

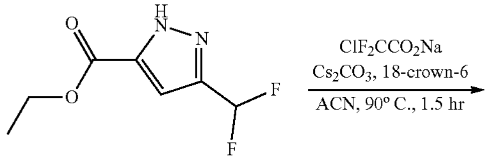

A-149a

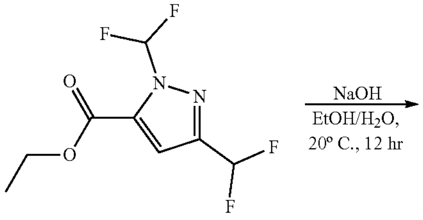

A-150a

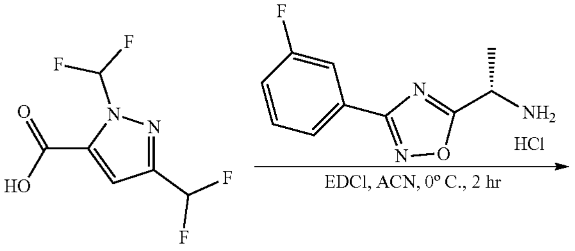

A-151a

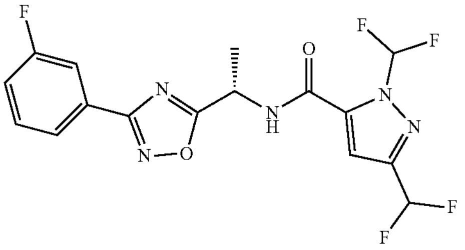

130

A-149a:

To a solution of 2,2-difluoroethanamine (1.65 g, 20.39 mmol) in chloroform (300 mL) was added tert-butyl nitrite (2.5 g, 24.46 mmol) and AcOH (0.23 mL, 4.08 mmol). The reaction mixture was stirred at 78° C. for 15 mins then cooled to room temperature. Ethyl prop-2-ynoate (1 g, 10.19 mmol) was then added to the reaction mixture and the mixture was stirred at 20° C. for 22 hours. The mixture was concentrated under reduced pressure. The residue was diluted with $H_2O$ (50 mL), and the mixture was extracted with DCM (40 mL×2). The combined organic phase was washed with water (60 mL) and brine (60 mL), dried over $Na_2SO_4$, filtered and concentrated to give the crude product. The crude product was purified by flash column chromatography on silica gel (EtOAc in PE=0% to 10% to 15%) to give the product (1.7 g, 8.94 mmol, 62% yield) as an oil. $^1$H NMR (400 MHz, $CDCl_3$) $\delta_H$=11.63-10.72 (m, 1H), 7.11-7.03 (m, 1H), 6.75 (s, 1H), 4.48-4.35 (m, 2H), 1.41 (t, 3H).

A-150a:

To a solution of ethyl 3-(difluoromethyl)-1H-pyrazole-5-carboxylate (900 mg, 4.73 mmol) in MeCN (10 mL) was added $Cs_2CO_3$ (3.08 g, 9.47 mmol) and sodium 2-chloro-2,2-difluoro-acetate (1.44 g, 9.47 mmol) and 18-crown-6 (250.21 mg, 0.95 mmol). The reaction mixture was stirred at 90° C. for 1.5 hours. After cooling to room temperature, the mixture was diluted with $H_2O$ (50 mL), and then extracted with EtOAc (30 mL×2). The combined organic phase was washed with brine (60 mL), dried over $Na_2SO_4$, filtered and concentrated to give the crude product. The crude product was purified by flash column chromatography on silica gel (EtOAc in PE=0% to 7%) to give the product (100 mg, 416.4 μmol, 8% yield) as an oil. $^1$H NMR (400 MHz, $CDCl_3$) $\delta_H$=8.27-7.85 (m, 1H), 7.20 (s, 1H), 6.94-6.47 (m, 1H), 4.43 (q, 2H), 1.42 (t, 3H).

A-151a:

To a solution of ethyl 2,5-bis(difluoromethyl)pyrazole-3-carboxylate (100 mg, 0.42 mmol) in ethanol (8 mL) was added a solution of NaOH (49.97 mg, 1.25 mmol) in water (8 mL) and the mixture was stirred at 20° C. for 12 hours. The reaction mixture was quenched by addition of 1N HCl (15 mL) and diluted with $H_2O$ (15 mL) and extracted with EtOAc (20 mL×2). The combined organic phase was washed with brine (30 mL) and dried over $Na_2SO_4$, filtered and concentrated to give the product (50 mg) as an oil. $^1$H NMR (400 MHz, $CDCl_3$) $\delta_H$=8.46-8.04 (m, 1H), 7.31-6.97 (m, 2H).

130:

To a mixture of 2,5-bis(difluoromethyl)pyrazole-3-carboxylic acid (69.72 mg, 0.33 mmol), EDCI (70.02 mg, 0.37 mmol) in MeCN (2 mL) was added (1S)-1-[3-(3-fluorophenyl)-1,2,4-oxadiazol-5-yl]ethanamine hydrochloride (89 mg, 0.37 mmol) and the reaction mixture was stirred at 0° C. for 2 hours. The reaction was quenched with 1N HCl (10 mL) and then extracted with EtOAc (10 mL×2). The combined organic phase was washed with brine (15 mL), dried over $Na_2SO_4$, filtered and concentrated to give the crude product. The crude product was partially purified by flash chromatography on silica gel (EtOAc in PE=0% to 10% to 20%) to give an impure product. The impure product was purified by prep-TLC (silica gel, PE:EtOAc=3:1) to give the product (17.27 mg, 43 mol, 11% yield) as a solid. $^1$H NMR (400 MHz, $CDCl_3$) $\delta_H$=8.31-7.99 (m, 1H), 7.89 (d, 1H), 7.82-7.76 (m, 1H), 7.49 (d, 1H), 7.27-7.20 (m, 1H), 7.06 (s, 1H), 6.93-6.62 (m, 2H), 5.66-5.56 (m, 1H), 1.80 (d, 3H). LCMS $R_t$=1.32 min in 2.0 min chromatography, 10-80AB, MS ESI calcd. for $C_{16}H_{13}F_5N_5O_2$ $[M+H]^+$ 402.0, found 402.09.

Example 94. Synthesis of 131

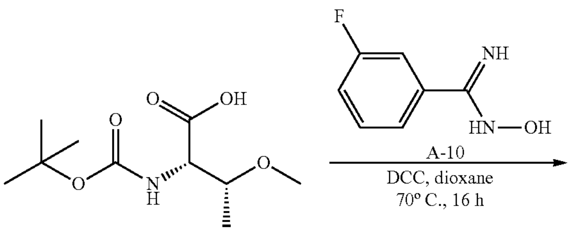

A-152a

-continued

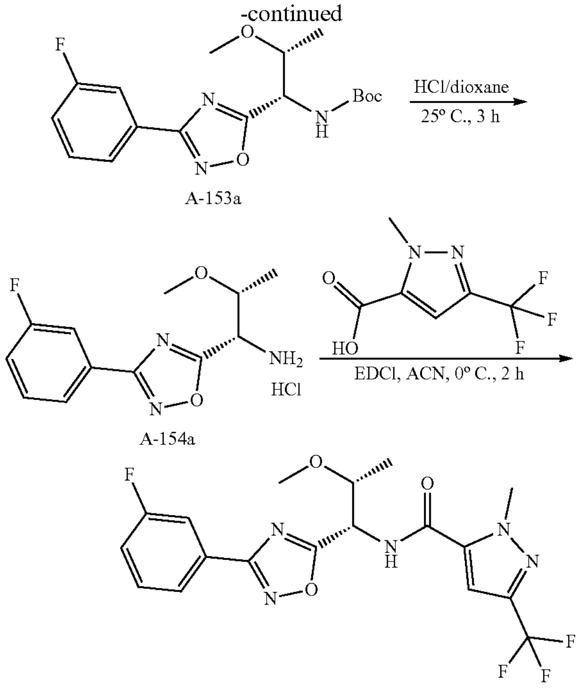

A-153a

A-154a

131

A-153a:

A mixture of (2S,3R)-2-(tert-butoxycarbonylamino)-3-methoxy-butanoic acid (1 g, 4.29 mmol) and DCC (1.77 g, 8.57 mmol), 3-fluoro-N-hydroxy-benzamidine (660.81 mg, 4.29 mmol) in 1,4-dioxane (15 mL) was stirred at 70° C. for 16 hours. After cooling to room temperature, the mixture was diluted with saturated aqueous $NH_4Cl$ (30 mL) and the mixture was extracted with EtOAc (30 mL×2). The combined organic phase was washed with water (50 mL) and brine (50 mL), dried over $Na_2SO_4$, filtered and concentrated to give the crude product. The crude product was purified by flash column chromatography on silica gel (EtOAc in PE=0% to 30%) to give the product (780 mg, 2.1 mmol, 48% yield) as an oil. LCMS $R_t$=0.93 min in 1.5 min chromatography, 5-95AB, MS ESI calcd. for $C_{13}H_{15}FN_3O_4$ $[M+H-t-Bu]^+$ 296.1, found 296.1.

A-154a:

To tert-butyl N-[(1S,2R)-1-[3-(3-fluorophenyl)-1,2,4-oxadiazol-5-yl]-2-methoxy-propyl]carbamate (780 mg, 2.22 mmol) was added 4M HCl in 1,4-dioxane (20 mL, 2.22 mmol) and the reaction mixture was stirred at 25° C. for 3 hours. The mixture was concentrated under reduced pressure to give the product (700 mg) as a solid. LCMS $R_t$=0.68 min in 1.5 min chromatography, 5-95AB, MS ESI calcd. for $C_{12}H_{15}FN_3O_2$ $[M+H]^+$ 252.1, found 252.1.

131:

To a mixture of 2-methyl-5-(trifluoromethyl)pyrazole-3-carboxylic acid (202.39 mg, 1.04 mmol), EDCI (199.88 mg, 1.04 mmol) in $CH_3CN$ (4 mL) was added (1S,2R)-1-[3-(3-fluorophenyl)-1,2,4-oxadiazol-5-yl]-2-methoxy-propan-1-amine hydrochloride (300 mg, 1.04 mmol) and the reaction mixture was stirred at 0° C. for 2 hours. The reaction was quenched with 1N HCl (20 mL) and then extracted with EtOAc (20 mL×2). The combined organic phase was washed with water (30 mL) and brine (30 mL), dried over $Na_2SO_4$, filtered and concentrated to give the crude product. The crude product was purified by flash chromatography on silica gel (EtOAc in PE=0% to 40%) to give an impure product. The impure product was purified by prep-TLC (silica gel, PE:EtOAc=3:1) to give the product (91.9 mg, 0.2 mmol, 20% yield) as an oil. $^1$H NMR (400 MHz, DMSO-$d_6$) $\delta_H$=9.45 (d, 1H), 7.87 (d, 1H), 7.80-7.72 (m, 1H), 7.69-7.61 (m, 2H), 7.53-7.43 (m, 1H), 5.58 (dd, 1H), 4.15-4.06 (m, 4H), 3.31 (s, 3H), 1.22 (d, 3H). LCMS $R_t$=1.30 min in 2.0 min chromatography, 10-80AB, MS ESI calcd. for $C_{18}H_{18}F_4N_5O_3$ $[M+1-1]^+$428.1, found 428.0.

Example 95. Synthesis of 132

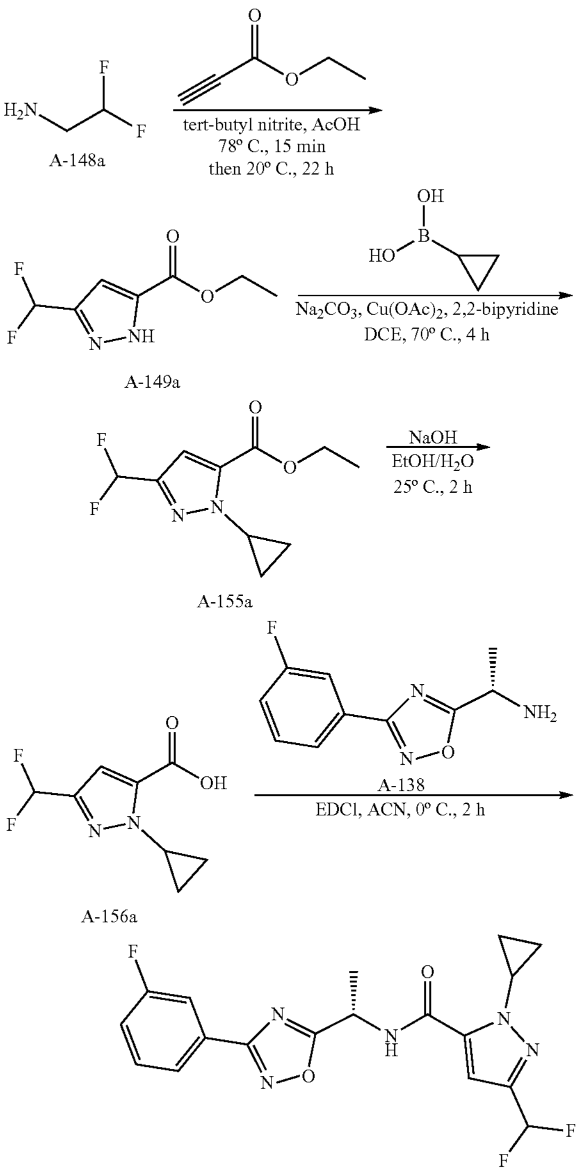

132

A-149a:

To a solution of 2,2-difluoroethanamine (1.65 g, 20.39 mmol) in chloroform (300 mL) was added tert-butyl nitrite (2.52 g, 24.46 mmol) and AcOH (0.23 mL, 4.08 mmol and the reaction mixture was stirred at 78° C. for 15 minutes. The mixture was cooled to room temperature and then ethyl prop-2-ynoate (1 g, 10.19 mmol) was added. The mixture was stirred at 20° C. for 22 hours. The mixture was concentrated under reduced pressure to give the crude product (1.6 g) as an oil. A second batch was obtained of the crude product (600 mg) from 500 mg of 1, and the combined crude product was purified by flash chromatography on silica gel (EtOAc in PE=0% to 10% to 15%) to give the product (1.7 g, 8.9 mmol) as an oil. $^1$H NMR (400 MHz, $CDCl_3$) $\delta_H$=11.63-10.72 (m, 1H), 7.11-7.03 (m, 1H), 6.75 (s, 1H), 4.48-4.35 (m, 2H), 1.41 (t, 3H).

A-155a:

To a solution of ethyl 3-(difluoromethyl)-1H-pyrazole-5-carboxylate (300 mg, 1.44 mmol), cyclopropylboronic acid (247.62 mg, 2.88 mmol) and $Na_2CO_3$ (305.53 mg, 2.88 mmol) in DCE (3 mL) was added a solution of $Cu(OAc)_2$ (261.79 mg, 1.44 mmol) and 2,2-bipyridine (270.15 mg, 1.73 mmol) in DCE (6 mL). The reaction mixture was stirred at 70° C. for 4 hours. After cooling to room temperature, the mixture was diluted with sat. $NH_4Cl$ (20 mL) and then the mixture was extracted with EtOAc (20 mL×2). The combined organic phase was washed with water (40 mL) and brine (40 mL), dried over $Na_2SO_4$, filtered and concentrated to give the crude product. The crude product was purified by flash chromatography on silica gel (EtOAc in PE=0% to 5% to 50%) to give the product (210 mg, 0.9 mmol, 63% yield) as an oil. $^1$H NMR (400 MHz, $CDCl_3$) $\delta_H$=7.04 (s, 1H), 6.79-6.48 (m, 1H), 4.42-4.30 (m, 3H), 1.44-1.37 (m, 3H), 1.31-1.26 (m, 2H), 1.12-1.05 (m, 2H). LCMS $R_t$=0.88 min in 1.5 min chromatography, 5-95AB, MS ESI calcd. for $C_{10}H_{13}F_2N_2O_2$ $[M+H]^+$ 231.1, found 231.1.

A-156a:

A mixture of ethyl 2-cyclopropyl-5-(difluoromethyl)pyrazole-3-carboxylate (210 mg, 0.91 mmol) and NaOH (109.47 mg, 2.74 mmol) in ethanol (4 mL) and water (4 mL) was stirred at 25° C. for 2 hours. The reaction mixture was quenched by addition of 1N HCl (15 mL) and diluted with $H_2O$ (15 mL) and then extracted with EtOAc (20 mL×2). The combined organic phase was washed with brine (30 mL) and dried over $Na_2SO_4$, filtered and concentrated to give the product (150 mg, 0.7 mmol, 79% yield) as a solid. LCMS $R_t$=0.73 min in 1.5 min chromatography, 5-95AB, MS ESI calcd. for $C_8H_9F_2N_2O_2$ $[M+1-1]^+$203.1, found 203.1.

132:

To a mixture of 2-cyclopropyl-5-(difluoromethyl)pyrazole-3-carboxylic acid (150 mg, 0.74 mmol) and EDCI (142.24 mg, 0.74 mmol) in $CH_3CN$ (3 mL) was added (I S)-1-[3-(3-fluorophenyl)-1,2,4-oxadiazol-5-yl]ethanamine hydrochloride (180.8 mg, 0.74 mmol) and the mixture was stirred at 0° C. for 2 hours. The reaction was quenched with 1N HCl (10 mL) and extracted with EtOAc (10 mL×2). The combined organic phase was washed with water (15 mL) and brine (15 mL), dried over $Na_2SO_4$, filtered and concentrated to give the crude product. The crude product was purified by flash chromatography on silica gel (EtOAc in PE=0% to 30%) to give the impure product. The impure product was purified by prep-HPLC (Waters)(Bridge (150 mm×25 mm, 5 μm), A=$H_2O$ (10 mM $NH_4HCO_3$) and B=$CH_3CN$; 45-75% B over 8 min) to give the product (35.8 mg, 91.6 μmol, 12% yield) as a solid. $^1$H NMR (400 MHz, DMSO-$d_6$) $\delta_H$=9.41 (d, 1H), 7.87 (td, 1H), 7.78-7.72 (m, 1H), 7.68-7.61 (m, 1H), 7.51-7.44 (m, 1H), 7.20 (s, 1H), 7.17-6.87 (m, 1H), 5.50-5.41 (m, 1H), 4.47-4.39 (m, 1H), 1.68 (d, 3H), 1.13-1.07 (m, 2H), 1.02-0.94 (m, 2H). LCMS $R_t$=1.24 min in 2.0 min chromatography, 10-80AB, MS ESI calcd. for $C_{18}H_{17}F_3N_5O_2$ $[M+H]^+$ 392.1, found 392.0.

Example 96. Synthesis of 133

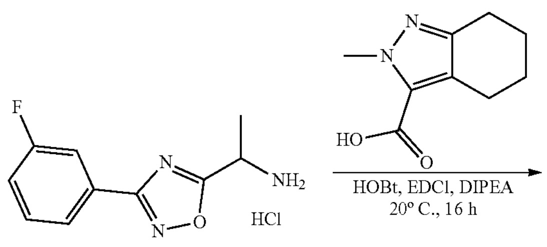

A-62

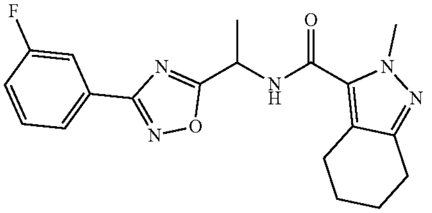

133

A mixture of 2-methyl-4,5,6,7-tetrahydroindazole-3-carboxylic acid (100 mg, 0.55 mmol), EDCI (212.76 mg, 1.11 mmol), DIPEA (0.29 mL, 1.66 mmol), HOBt (149.98 mg, 1.11 mmol) and 1-[3-(3-fluorophenyl)-1,2,4-oxadiazol-5-yl] ethanamine hydrochloride (148.74 mg, 0.61 mmol) in DCM (5 mL) was stirred at 20° C. for 16 hours. The reaction was concentrated and the residue was diluted with water (20 mL) and extracted with DCM (20 mL×2). The combined organic phase was washed with brine (15 mL), dried over anhydrous $Na_2SO_4$, filtered and concentrated to give the crude product. The crude product was purified by prep-HPLC (Waters XBridge (150 mm×25 mm, 5 μm), A=$H_2O$ (10 mM $NH_4HCO_3$) and B=$CH_3CN$; 40-70% B over 10 min) to give the impure product. Further purification by prep-HPLC (Waters)(Bridge (150 mm×25 mm, 5 μm), A=$H_2O$ (10 mM $NH_4HCO_3$) and B=$CH_3CN$; 40-70% B over 10 min gave the product (26.88 mg, 0.07 mmol, 13% yield) as a solid. $^1$H NMR (400 MHz $CDCl_3$) $\delta_H$=7.87 (d, 1H), 7.82-7.74 (m, 1H), 7.52-7.42 (m, 1H), 7.26-7.19 (m, 1H), 6.46 (br d, 1H), 5.68-5.58 (m, 1H), 4.12 (s, 3H), 2.90-2.74 (m, 2H), 2.71 (t, 2H), 1.94-1.82 (m, 4H), 1.76 (d, 3H). LCMS $R_t$=1.15 min in 2 min chromatography, 10-80AB, MS ESI calcd. for $C_{19}H_{21}FN_5O_2$[M+H]$^+$370.2, found 370.2.

Example 97. Synthesis of 134

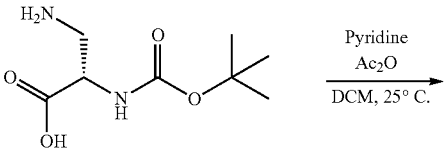

A-157a

-continued

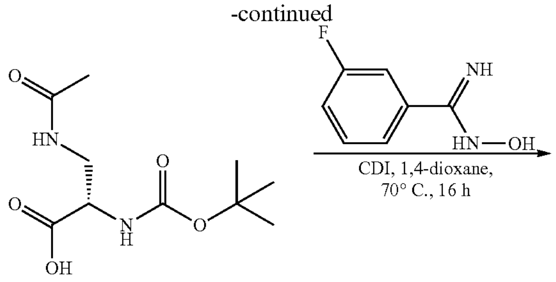

A-158a

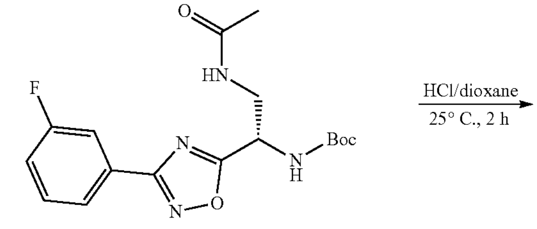

A-159a

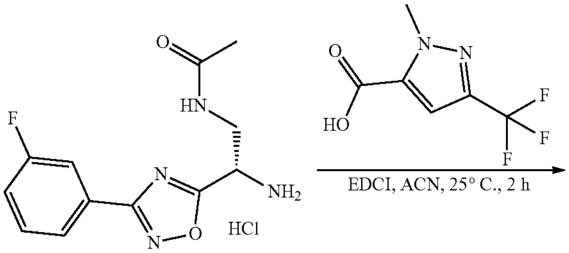

A-160a

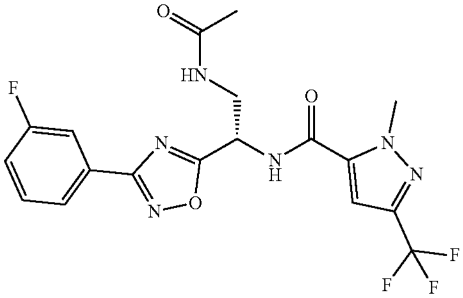

134

A-158a:

A mixture of (2S)-3-amino-2-(tert-butoxycarbonylamino) propanoic acid (15 g, 73.45 mmol), pyridine (6.52 mL, 80.8 mmol) and $Ac_2O$ (9 g, 88.14 mmol) in DCM (30 mL) was stirred at 25° C. for 16 under $N_2$. The mixture was acidified with 10% aqueous acetic acid to pH ~4, extracted with EtOAc (50 mL×2). The combined organic phase was washed with water (20 mL×2) and brine (20 mL), dried over $Na_2SO_4$, filtered and concentrated to give the crude product (10.5 g, 13.51 mmol, 18% yield) as an oil. LCMS Rt=0.56 min in 1.5 min chromatography, 5-95AB, MS ESI calcd. $C_{10}H_{19}N_2O_5$ [M+H-BOC]$^+$ 147.1, found 147.0.

A-159a:

A mixture of rac-(2S)-3-acetamido-2-(tert-butoxycarbonylamino)propanoic acid (10 g, 40.61 mmol), CDI (7.24 g, 44.67 mmol), 3-fluoro-N-hydroxy-benzamidine (6.26 g, 40.61 mmol) in 1,4-dioxane (100 mL) was stirred at 70° C. for 16 hours. After cooling to room temperature, the mixture was diluted with saturated aqueous $NH_4Cl$ (20 mL) and extracted with EtOAc (20 mL×2). The combined organic phase was washed with brine (15 mL), dried over $Na_2SO_4$, filtered and concentrated to give the crude product. The crude product was purified by flash chromatography on silica gel (EtOAc in PE=0% to 50% to 100%) to give the product (1.8 g, 1.42 mmol, 3% yield) as a solid. $^1H$ NMR (400 MHz $CDCl_3$) $\delta_H$=7.92-7.82 (m, 1H), 7.81-7.70 (m, 1H), 7.50-7.41 (m, 1H), 7.27 (s, 1H), 7.26-7.17 (m, 1H), 6.25-6.05 (m, 1H), 5.84 (br s, 1H), 5.24-5.11 (m, 1H), 3.98-3.70 (m, 2H), 2.02 (s, 3H), 1.47 (s, 9H). LCMS Rt=0.83 min in 1.5 min chromatography, 5-95AB, MS ESI calcd. $C_{17}H_{22}FN_4O_4$ [M+H-BOC]$^+$ 265.15, found 265.2.

A-160a:

To a mixture of tert-butyl N-[(1S)-2-acetamido-1-[3-(3-fluorophenyl)-1,2,4-oxadiazol-5-yl]ethyl]carbamate (800 mg, 2.2 mmol) in 1,4-dioxane (5 mL) and 4M HCl in 1,4-dioxane (10 mL, 40 mmol) was stirred at 25° C. for 16 hours. The mixture was filtered and concentrated to give the crude product (500 mg) as a solid. LCMS Rt=0.56 min in 1.5 min chromatography, 5-95AB, MS ESI calcd. $C_{12}H_{15}ClFN_4O_2$ [M+H-HCl]$^+$265.08, found 265.1.

134:

To a mixture of 2-methyl-5-(trifluoromethyl)pyrazole-3-carboxylic acid (322.74 mg, 1.66 mmol), EDCI (318.74 mg, 1.66 mmol) in MeCN (10 mL) was added N-[(2S)-2-amino-2-[3-(3-fluorophenyl)-1,2,4-oxadiazol-5-yl]ethyl]acetamide hydrochloride (500 mg, 1.66 mmol) and the mixture was stirred at 25° C. for 2 hours. The reaction was quenched with 1N HCl (10 mL), then extracted with EtOAc (10 mL×2). The combined organic phase was washed with brine (15 mL), dried over $Na_2SO_4$, filtered and concentrated to give the crude product. The crude product was purified by flash chromatography on silica gel (EtOAc in PE=0% to 10% to 20%) to give the impure product. The impure product was purified by prep-TLC (silica gel, PE:EtOAc=3:1) to give the product as a solid. Analytical SFC (Regis (S,S) Whelk-O1 (100 mm×4.6 mm I.D., 5.0 μm), mobile phase: A: $CO_2$ B: IPA (0.05% DEA), gradient: from 5% to 40% of B in 5.5 min, then 5% of B for 1.5 min, flow rate: 2.5 mL/min, column temp: 40° C., ABPR: 100 bar.) showed two peaks at 3.57 min (8%) and 4.13 min (92%). The product was purified by SFC (Regis (S,S) Whelk-O1 (250 mm×30 mm, 5 μm); A=$CO_2$ and B=EtOH (0.1% DEA); 35° C.; 60 mL/min; 30% B; 9 min run; 7 injections, Rt of peak 1=4.4 min, Rt of peak 2=7.9 min) to give the product (36.7 mg, 0.8 mmol) (Rt=4.13 min in analytical SFC) as a solid. $^1H$ NMR (400 MHz, DMSO-$d_6$) $\delta_H$=9.48 (d, 1H), 8.23 (br t, 1H), 7.88 (d, 1H), 7.77 (d, 1H), 7.69-7.61 (m, 1H), 7.48 (dt, 1H), 7.43 (s, 1H), 5.41 (d, 1H), 4.12 (s, 3H), 3.94-3.81 (m, 1H), 3.66-3.54 (m, 1H), 1.82 (s, 3H). LCMS Rt=1.19 min in 2.0 min chromatography, 10-80AB, MS ESI calcd. $C_{18}H_{17}F_4N_6O_3$ [M+H]$^+$ 341.12, found 441.1.

Example 98. Synthesis of 135 and 136

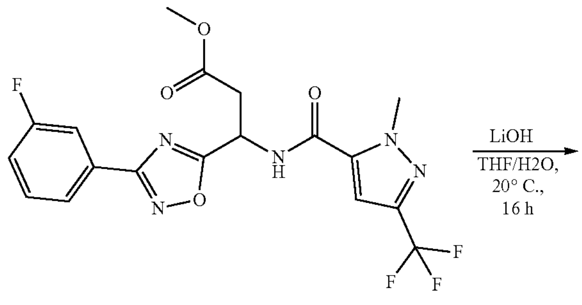

116

-continued

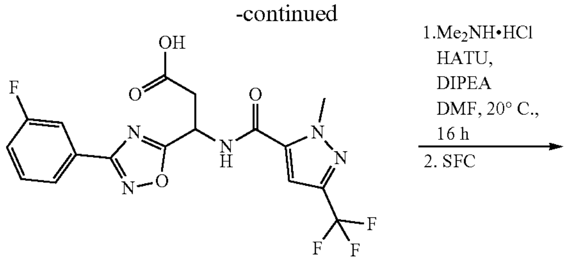

A-161

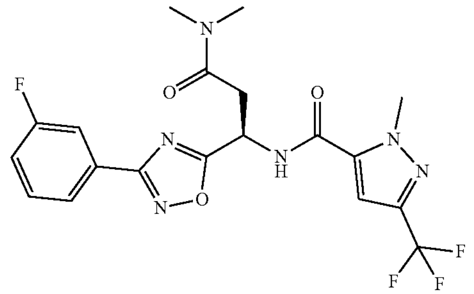

+

135

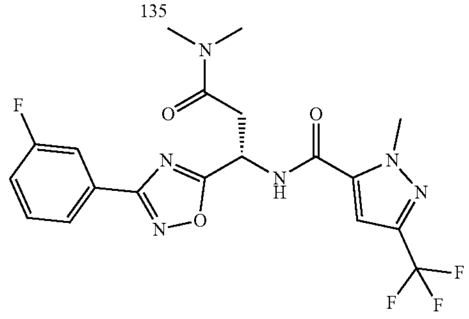

136

A-161:

A mixture of methyl 3-[3-(3-fluorophenyl)-1,2,4-oxadiazol-5-yl]-3-[[2-methyl-5-(trifluoromethyl)pyrazole-3-carbonyl]amino]propanoate (3 g, 6.8 mmol) and $LiOH.H_2O$ (570.44 mg, 13.59 mmol) in THF (10 mL) and water (5 mL) was stirred at 20° C. for 16 hours. To the mixture was added 1N HCl aqueous (50 mL) to adjust the pH=2 and then the mixture was extracted with EtOAc (50 mL×2). The combined organic phase was washed with brine (50 mL), dried over anhydrous $Na_2SO_4$, filtered and concentrated to give the crude product (2.5 g, 5.85 mmol, 86% yield) as an oil. $^1H$ NMR (400 MHz, DMSO-$d_6$) $\delta_H$=12.59 (br s, 1H), 9.51 (d, 1H), 7.86 (d, 1H), 7.78-7.71 (m, 1H), 7.66-7.61 (m, 1H), 7.52-7.44 (m, 1H), 7.40 (s, 1H), 5.67 (q, 1H), 4.13 (s, 3H), 3.15-3.05 (m, 2H).

135 & 136:

A mixture of 3-[3-(3-fluorophenyl)-1,2,4-oxadiazol-5-yl]-3-[[2-methyl-5-(trifluoromethyl)pyrazole-3-carbonyl]amino]propanoic acid (300 mg, 0.70 mmol), HATU (400.42 mg, 1.05 mmol), DIPEA (0.29 mL, 2.11 mmol) and N-dimethylamine hydrochloride (57.25 mg, 0.70 mmol) in DMF (5 mL) was stirred at 20° C. for 16 hours. To the mixture was added water (20 mL) and it was then extracted with EtOAc (30 mL×2). The combined organic phase was washed with brine (30 mL), dried over anhydrous $Na_2SO_4$, filtered and concentrated to give the crude product. The crude product was purified by chromatography flash column on silica gel (EtOAc in PE=0% to 10% to 20%) to give the product. Analytical SFC (Daicel CHIRALPAK AD-3 (150 mm×4.6 mm, 3 μm), mobile phase: A: $CO_2$ B: ethanol (0.05% DEA), gradient: from 5% to 40% of B in 5 min and hold 40% of B for 2.5 min, then hold 5% of B for 2.5 min, flow rate: 2.5 mL/min, column temp: 40° C.) showed two peaks at 2.59 min and 2.92 min. The product was separated by SFC (Phenomenex-Amylose-1 (250 mm×30 mm, 5 μm); A=$CO_2$ and B=0.1% $NH_3.H_2O$-EtOH; 38° C.; 55 mL/min; 15% B; 8 min run; 8 injections, Rt of peak 1=5.5 min, Rt of peak 2=7.5 min) to give the enantiomer 1, randomly assigned as 135 (23.42 mg, 51.5 μmol, 7% yield) (Rt=2.59 min in analytical SFC) as a solid and the enantiomer 2, randomly assigned as 136 (29.42 mg, 64.1 μmol, 9% yield) (Rt=2.92 min in analytical SFC) as a solid.

135:

$^1H$ NMR ($CDCl_3$ 400 MHz) $\delta_H$=8.20 (d, 1H), 7.86 (d, 1H), 7.80-7.73 (m, 1H), 7.47-7.42 (m, 1H), 7.23-7.18 (m, 1H), 6.96 (s, 1H), 5.86-5.77 (m, 1H), 4.27 (s, 3H), 3.56 (dd, 1H), 3.10 (s, 3H), 3.03 (dd, 1H), 2.95 (s, 3H). LCMS $R_t$=1.21 min in 2.0 min chromatography, 10-80AB, MS ESI calcd. for $C_{19}H_{19}F_4N_6O_3$ $[M+H]^+$ 455.1, found 455.1.

136:

$^1H$ NMR ($CDCl_3$ 400 MHz) $\delta_H$=8.20 (d, 1H), 7.86 (d, 1H), 7.77-7.74 (m, 1H), 7.47-7.42 (m, 1H), 7.23-7.18 (m, 1H), 6.96 (s, 1H), 5.87-5.78 (m, 1H), 4.27 (s, 3H), 3.56 (dd, 1H), 3.10 (s, 3H), 3.03 (dd, 1H), 2.95 (s, 3H). LCMS $R_t$=1.20 min in 2.0 min chromatography, 10-80AB, MS ESI calcd. for $C_{19}H_{19}F_4N_6O_3$ $[M+H]^+$ 455.1, found 455.1.

Example 99. Synthesis of 137

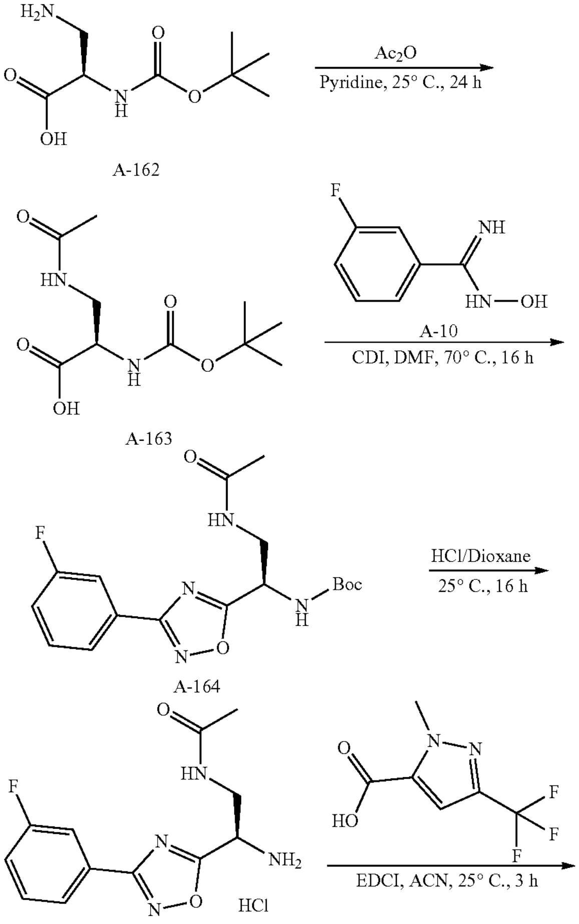

A-162

A-163

A-164

A-165

-continued

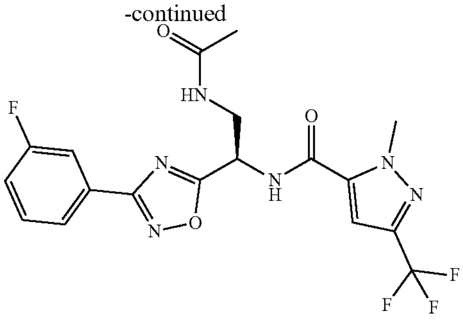

137

A-163:

A mixture of (2R)-3-amino-2-(tert-butoxycarbonylamino) propanoic acid (10.00 g, 48.97 mmol), pyridine (4.35 mL, 53.86 mmol) and $Ac_2O$ (6 g, 58.76 mmol) in DCM (30.00 mL) was stirred at 25° C. for 24 under $N_2$. The mixture was concentrated and diluted with sat. citric acid (40 mL) and then the mixture was extracted with EtOAc (40 mL×2). The combined organic phase was washed with brine (40 mL), dried over $Na_2SO_4$, filtered and concentrated to give the product (5.00 g) as a solid.

A-164:

A mixture of (2R)-3-acetamido-2-(tert-butoxycarbonylamino)propanoic acid (4.35 g, 17.66 mmol), CDI (3.15 g, 19.43 mmol) and 3-fluoro-N-hydroxy-benzamidine (2.72 g, 17.66 mmol) in DMF (30.00 mL) was stirred at 70° C. for 16 hours. The mixture was cooled to room temperature, filtered and solid washed with EtOAc (30 mL). The filtrate was diluted with saturated aqueous $NH_4Cl$ (30 mL) and extracted with EtOAc (30 mL×2). The combined organic phase was washed with brine (30 mL), dried over $Na_2SO_4$, filtered and concentrated to give the crude product. The crude product was purified by chromatography flash column on silica gel (EtOAc in PE=0% to 10% to 30% to 50% to 100%) to give the product (800 mg, 2.20 mmol, 12% yield) as a solid. $^1H$ NMR (400 MHz $CDCl_3$) $\delta_H$=7.92-7.83 (m, 1H), 7.81-7.71 (m, 1H), 7.51-7.42 (m, 1H), 7.27 (s, 1H), 7.26-7.17 (m, 1H), 6.09 (br s, 1H), 5.84 (br s, 1H), 5.25-5.07 (s, 1H), 3.98-3.70 (m, 2H), 2.02 (s, 3H), 1.47 (s, 9H).

A-165:

To a mixture of tert-butyl N-[(1R)-2-acetamido-1-[3-(3-fluorophenyl)-1,2,4-oxadiazol-5-yl]ethyl]carbamate (300.0 mg, 0.82 mmol) in 1,4-dioxane (1.00 mL) was added 4M HCl in 1,4-dioxane (3.00 mL) and the reaction mixture was stirred at 25° C. for 16 hours. The mixture was concentrated to give the crude product (240.0 mg) as a solid. LCMS $R_t$=0.35 min in 2 min chromatography, 10-80AB, MS ESI calcd. for $C_{12}H_{14}FN_4O_2$ $[M+H]^+$ 265.1, found 264.9.

137:

To a mixture of 2-methyl-5-(trifluoromethyl)pyrazole-3-carboxylic acid (154.9 mg, 0.80 mmol), EDCI (153.0 mg, 0.80 mmol) in MeCN (10.00 mL) was added N-[(2R)-2-amino-2-[3-(3-fluorophenyl)-1,2,4-oxadiazol-5-yl]ethyl]acetamide hydrochloride (240.0 mg, 0.80 mmol) and the reaction mixture was stirred at 25° C. for 3 hours. The reaction was quenched with the addition of 1 N HCl (15 mL) and then extracted with EtOAc (15 mL×2). The combined organic phase was washed with brine (15 mL), dried over $Na_2SO_4$, filtered and concentrated to give the crude product. The crude product was purified by flash chromatography on silica gel (EtOAc in PE=0% to 30% to 50% to 100%) to give the product (70.0 mg, 0.16 mmol) as a solid. Analytical SFC (Regis (S,S) Whelk-01 (150 mm×4.6 mm, 5 μm), mobile phase: A: $CO_2$ B: methanol (0.05% DEA), gradient: from 5% to 40% of B in 5 min and hold 40% for 2.5 min, then 5% of B for 2.5 min, flow rate: 2.5 mL/min, column temp: 35° C.) showed two peaks at 3.57 min (70.5%) and 4.13 min (29.5%). The product was purified by SFC (Regis (S,S) Whelk-O1 (250 mm×30 mm, 5 μm); A=$CO_2$ and B=IPA (0.1% $NH_4OH$); 38° C.; 60 mL/min; 30% B; 10 min run; 3 injections, Rt of peak 1=5.7 min, Rt of peak 2=8.0 min) to give the product (22.47 mg, 51 μmol, 45% yield) (Rt=3.57 min in analytical SFC) as a solid. $^1H$ NMR (400 MHz $CDCl_3$) $\delta_H$=8.78 (d, 1H), 7.87 (d, 1H), 7.82-7.73 (m, 1H), 7.52-7.41 (m, 1H), 7.26-7.19 (m, 1H), 7.04 (s, 1H), 6.12-5.96 (m, 1H), 5.52-5.38 (m, 1H), 4.23 (s, 3H), 4.08-3.82 (m, 2H), 2.09 (s, 3H). LCMS Rt=1.21 min in 2.0 min chromatography, 10-80AB, MS ESI calcd. for $C_{18}H_{17}F_4N_6O_3$ $[M+H]^+$ 441.1, found 441.1.

Example 100 Synthesis of 138

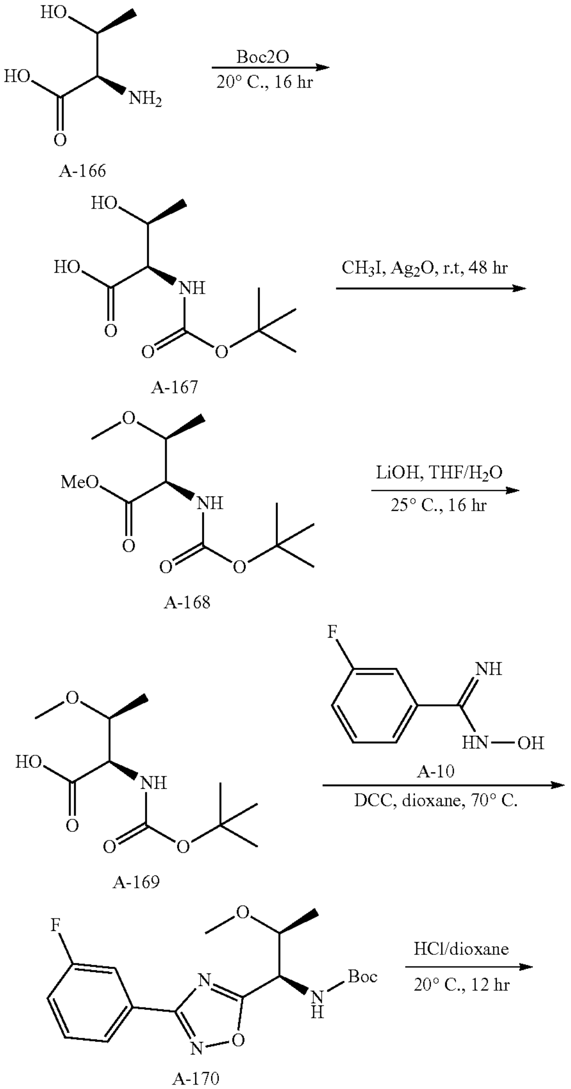

A-166

A-167

A-168

A-169

A-170

-continued

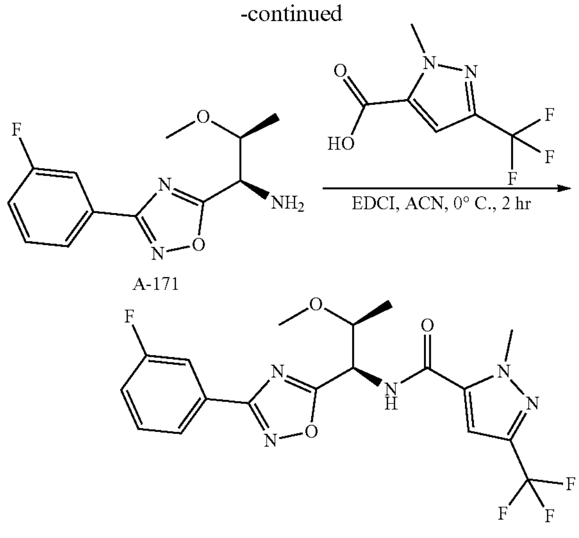

A-171

138

A-167:

To a solution of (2R,3S)-2-amino-3-hydroxy-butanoic acid (1 g, 8.39 mmol) and $NaHCO_3$ (1.0 g, 12.59 mmol) in water (18 mL) and methanol (18 mL) was added $Boc_2O$ (2.75 g, 12.59 mmol). The reaction mixture was stirred at 20° C. for 16 hours. The mixture was concentrated, and the residue was partitioned between 1% HCl (1%, 40 mL) and EtOAc (30 mL). The aqueous layer was extracted with EtOAc (30 mL×2). The combined organic phase was dried over $Na_2SO_4$, filtered and concentrated to give the crude product (1.8 g, 8.2 mmol, 97% yield) as an oil. $^1H$ NMR (400 MHz, DMSO-$d_6$) $\delta_H$=12.48 (br s, 1H), 6.31 (d, 1H), 4.67 (br s, 1H), 3.91-3.83 (m, 1H), 1.38 (s, 9H), 1.07 (d, 3H).

A-168:

To a solution of (2R,3S)-2-(tert-butoxycarbonylamino)-3-hydroxy-butanoic acid (1.6 g, 7.3 mmol) in MeCN (140 mL) was added $Ag_2O$ (8.45 g, 36.49 mmol) followed by $CH_3I$ (6.8 mL, 109.2 mmol) at 0° C. The reaction mixture was warmed and stirred at 20° C. for 48 hours. The reaction mixture was filtered through Celite, eluted with EtOAc (30 mL×2) and the filtrate was concentrated to give the product. The crude product was purified by flash chromatography on silica gel (EtOAc in PE=0% to 12% to 30%) to give the product (490 mg, 1.9 mmol, 27% yield) as an oil. $^1H$ NMR (400 MHz CDCl3) $\delta_H$=5.22 (br d, 1H), 4.32-4.24 (m, 1H), 3.97-3.86 (m, 1H), 3.77 (s, 3H), 3.29 (s, 3H), 1.46 (s, 9H), 1.21 (d, 3H).

A-169:

To a solution of methyl (2R,3S)-2-(tert-butoxycarbonylamino)-3-methoxy-butanoate (390 mg, 1.58 mmol) in THF (8 mL) was added $LiOH.H_2O$ (397.05 mg, 9.46 mmol) in water (4 mL). The mixture was stirred at 25° C. for 16 hours. The reaction mixture was quenched by the addition of 1N HCl (20 mL), diluted with $H_2O$ (15 mL) and then extracted with EtOAc (20 mL×2). The combined organic phase was washed with brine (30 mL) and dried over $Na_2SO_4$, filtered and concentrated to give the product (300 mg, 1.2 mmol, 81% yield) as an oil. $^1H$ NMR (400 MHz $CDCl_3$) $\delta_H$=5.30 (br d, 1H), 4.35 (br d, 1H), 4.04-3.94 (m, 1H), 3.39 (s, 3H), 1.46 (s, 9H), 1.22 (d, 3H).

A-170:

A mixture of 3-fluoro-N-hydroxy-benzamidine (198 mg, 1.28 mmol) and (2R,3S)-2-(tert-butoxycarbonylamino)-3-methoxy-butanoic acid (299.63 mg, 1.28 mmol), DCC (529.23 mg, 2.57 mmol) in 1,4-dioxane (5 mL) was stirred at 70° C. for 16 hours. After cooling to room temperature, the mixture was filtered and the solid washed with EtOAc (10 mL). The combined organic layer was diluted with saturated aqueous $NH_4Cl$ (30 mL) and extracted with EtOAc (20 mL×2). The combined organic phase was washed with brine (50 mL), dried over $Na_2SO_4$, filtered and concentrated to give the crude product. The crude product was purified by flash column chromatography on silica gel (EtOAc in PE=0% to 15%) to give the product (400 mg, 1.1 mmol, 88% yield) as an oil. LCMS $R_t$=1.0 min in 1.5 min chromatography, 5-95AB, MS ESI calcd. $C_{13}H_{15}FN_3O_4$ $[M+H-t-Bu]^+$ 296.10, found 295.8.

A-171:

To tert-butyl N-[(1R,2S)-1-[3-(3-fluorophenyl)-1,2,4-oxadiazol-5-yl]-2-methoxy-propyl]carbamate (400 mg, 1.14 mmol) was added 4M HCl in 1,4-dioxane (20 mL, 80 mmol) and the reaction mixture was stirred at 20° C. for 12 hours. The mixture was concentrated to give the crude product (370 mg, 371.3 μmol, 32% yield) as an oil. LCMS $R_t$=0.69 min in 1.5 min chromatography, 5-95AB, MS ESI calcd. $C_{12}H_{15}FN_3O_2$ $[M+H]^+$ 252.11, found 252.1.

138:

To a mixture of 2-methyl-5-(trifluoromethyl)pyrazole-3-carboxylic acid (249.62 mg, 1.29 mmol), EDCI (246.52 mg, 1.29 mmol) in MeCN (8 mL) was added (1R,2S)-1-[3-(3-fluorophenyl)-1,2,4-oxadiazol-5-yl]-2-methoxy-propan-1-amine hydrochloride (370 mg, 1.29 mmol) and the mixture was stirred at 0° C. for 2 hours. The reaction was quenched with the addition of 1N HCl (20 mL) and then extracted with EtOAc (15 mL×2). The combined organic phase was washed with brine (20 mL), dried over $Na_2SO_4$, filtered and concentrated to give the crude product. The crude product was purified by flash chromatography on silica gel (EtOAc in PE=0% to 10% to 20%) to give the impure product. The impure product was purified by prep-TLC (silica gel, PE:EtOAc=3:1) to give the impure product (60 mg) as a solid. Analytical SFC (Regis (S,S) Whelk-O1 (100 mm×4.6 mm I.D., 5 μm), mobile phase: A: $CO_2$ B: methanol (0.05% DEA), gradient: from 5% to 40% of B in 5.5 min, then 5% of B for 1.5 min, flow rate: 2.5 mL/min, column temp: 35° C., ABPR: 100 bar) showed two peaks at 2.52 min (main peak, 88.7%) and 2.93 min (11.3%). The product was purified by SFC (Regis (S,S) Whelk-O1 (250 mm×30 mm, 5 μm); A=$CO_2$ and B=EtOH (0.1% $NH_3H_2O$); 38° C.; 60 mL/min; 25% B; 8 min run; 7 injections, Rt of peak 1=4.7 min, Rt of peak 2=5.1 min) to give the product (37.97 mg, 88.2 μmol, 47% yield) (Rt=2.52 min in analytical SFC) as an oil. $^1H$ NMR (400 MHz DMSO-$d_6$) $\delta_H$=9.49-9.35 (m, 1H), 7.87 (d, 1H), 7.79-7.73 (m, 1H), 7.68-7.61 (m, 2H), 7.48 (dt, 1H), 5.58 (dd, 1H), 4.13 (s, 3H), 4.12-4.07 (m, 1H), 3.31 (s, 3H), 1.22 (d, 3H). LCMS Rt=1.40 min in 2.0 min chromatography, 10-80AB, MS ESI calcd. for $C_{18}H_{18}F_4N_5O_3$ $[M+H]^+$ 428.13, found 428.1.

Example 101. Synthesis of 139

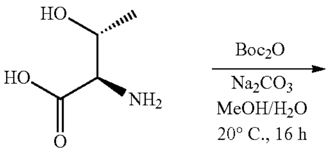

A-172

-continued

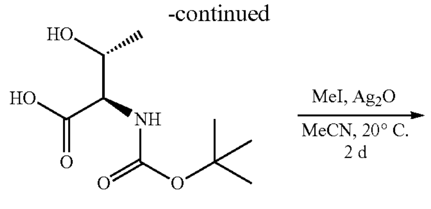

A-173

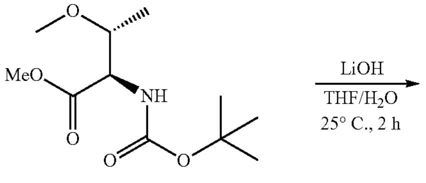

A-174

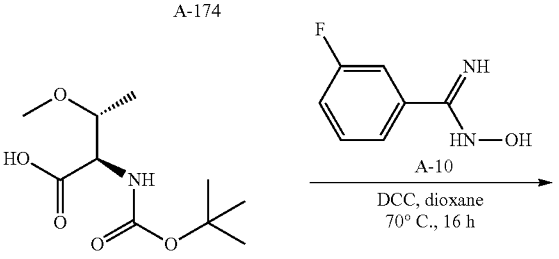

A-175

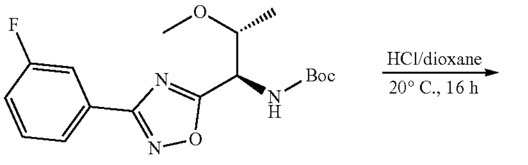

A-176

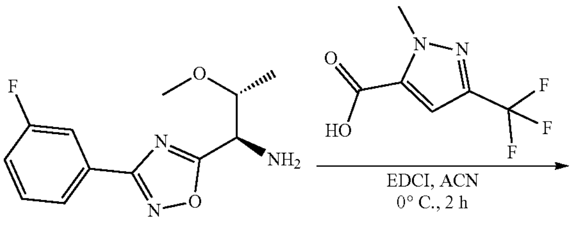

A-177

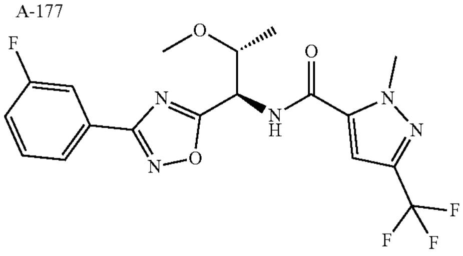

139

A-173:

To a mixture of (2R,3R)-2-amino-3-hydroxy-butanoic acid (2 g, 16.79 mmol) in methanol (18 mL) and water (18 mL) at 0° C. was added $NaHCO_3$ (2.12 g, 25.18 mmol) and $Boc_2O$ (5.5 g, 25.18 mmol) and it was stirred at 20° C. for 16 hours. The mixture was partially concentrated under reduced pressure to remove the MeOH. The residue was diluted with $H_2O$ (20 mL), and the mixture was extracted with EtOAc (30 mL×2). The combined organic phase was washed with brine (20 mL), dried over $Na_2SO_4$, filtered and concentrated to give the crude product (1.8 g, 6.93 mmol, 41% yield) as an oil. LCMS $R_t$=0.60 min in 1.5 min chromatography, 5-95AB, MS ESI calcd. for $C_9H_{18}NO_5$ [M+H−tBu] 164.1, found 163.8.

A-174:

To a mixture of (2R,3R)-2-(tert-butoxycarbonylamino)-3-hydroxy-butanoic acid (4 g, 18.25 mmol) in MeCN (100 mL) at 0° C. was added $Ag_2O$ (21.14 g, 91.23 mmol) and iodomethane (38.85 g, 273.69 mmol) and the mixture was stirred at 20° C. for 2 days. The mixture was filtered through Celite, eluted with EtOAc (20 mL) and the filtrate was concentrated to give the crude product. The crude product was purified by flash chromatography on silica gel (EtOAc in PE=0% to 30% to 50%) to give the product of (900 mg, 3.64 mmol, 19% yield) as an oil. $^1H$ NMR $CDCl_3$ $\delta_H$=5.34-5.19 (m, 1H), 4.50-4.39 (m, 1H), 3.77 (s, 3H), 3.68-3.59 (m, 1H), 3.37 (s, 3H), 1.46 (s, 9H), 1.21 (d, 3H).

A-175:

To a solution of methyl (2R,3R)-2-(tert-butoxycarbonylamino)-3-methoxy-butanoate (500 mg, 2.02 mmol) in THF (5 mL) was added $LiOH.H_2O$ (509.04 mg, 12.13 mmol) in water (5 mL) and the mixture was stirred at 25° C. for 2 hours. The mixture was partially concentrated under reduced pressure to give remove the THF. The mixture was washed with EtOAc (5 mL), and the water phase was acidified with 1N HCl solution to pH=4. The mixture was extracted with EtOAc (15 mL×2). The combined organic phase was washed brine (10 mL), dried over $Na_2SO_4$, filtered and concentrated to give the crude product (400 mg, 0.94 mmol, 46% yield) as an oil. LCMS $R_t$=0.83 min in 1.5 min chromatography, 5-95AB, MS ESI calcd. for $C_{10}H_{20}NO_5$ [M+H−Boc] 134.1, found 133.8.

A-176:

A mixture of 3-fluoro-N-hydroxy-benzamidine (264 mg, 1.71 mmol), (2R,3R)-2-(tert-butoxycarbonylamino)-3-methoxy-butanoic acid (399.51 mg, 1.71 mmol) and DCC (705.64 mg, 3.43 mmol) in 1,4-dioxane (10 mL) was stirred at 70° C. for 16 hours. After cooling to room temperature, the mixture was filtered and the solid washed with EtOAc (10 mL). The filtrate was diluted with saturated aqueous $NH_4Cl$ (30 mL) and extracted with EtOAc (30 mL×2). The combined organic phase was washed with brine (20 mL), dried over $Na_2SO_4$, filtered and concentrated to give the crude product. The crude product was purified by flash column chromatography on silica gel (EtOAc in PE=0% to 10%) to give the product (200 mg, 0.33 mmol, 19% yield) as a solid. LCMS $R_t$=0.92 min in 1.5 min chromatography, 5-95AB, MS ESI calcd. for $C_{17}H_{23}FN_3O_4$ [M+H−tBu] 296.2, found 296.1.

A-177:

A mixture of tert-butyl N-[(1R,2R)-1-[3-(3-fluorophenyl)-1,2,4-oxadiazol-5-yl]-2-methoxy-propyl]carbamate (230 mg, 0.65 mmol) and 4M HCl in 1,4-dioxane (10 mL, 40 mmol) was stirred at 20° C. for 16 hours. The mixture was concentrated under reduced pressure to give the crude product (200 mg) as an oil. LCMS $R_t$=0.68 min in 1.5 min chromatography, 5-95AB, MS ESI calcd. for $C_{12}H_{15}FN_3O_2$ [M+H] 252.1, found 252.0.

139:

To a mixture of 2-methyl-5-(trifluoromethyl)pyrazole-3-carboxylic acid (134.93 mg, 0.70 mmol), EDCI (133.25 mg, 0.70 mmol) in MeCN (4 mL) was added (1R,2R)-1-[3-(3-fluorophenyl)-1,2,4-oxadiazol-5-yl]-2-methoxy-propan-1-amine hydrochloride (200 mg, 0.70 mmol) and the reaction mixture was stirred at 0° C. for 2 hours. The reaction was quenched with the addition of 1N HCl (15 mL) and then extracted with EtOAc (20 mL×2). The combined organic phase was washed brine (15 mL), dried over $Na_2SO_4$, filtered and concentrated to give the crude product. The crude product was partially purified by flash chromatography on silica gel (EtOAc in PE=0% to 40%) to give the impure product. The impure product was purified by prep-TLC (silica gel, PE:EtOAc=3:1) (twice) to give the product. The product was triturated from DCM/n-hexane (1:20, 3 mL) to give the product (18.8 mg, 0.04 mmol, 6% yield) as an oil. $^1H$ NMR (400 MHz, DMSO-$d_6$) $\delta_H$=9.46 (d, 1H), 7.87 (d, 1H), 7.79-7.73 (m, 1H), 7.69-7.61 (m, 1H), 7.53 (s, 1H), 7.51-7.44 (m, 1H), 5.40 (t, 1H), 4.11 (s, 3H), 4.05-3.94 (m, 1H), 3.27 (s, 3H), 1.29 (d, 3H). LCMS $R_t$=1.37 min in 2 min chromatography, 10-80AB, MS ESI calcd. for $C_{18}H_{18}F_4N_5O_3$ $[M+H]^+$ 428.1, found 428.1.

Example 102. Synthesis of 140 and 141

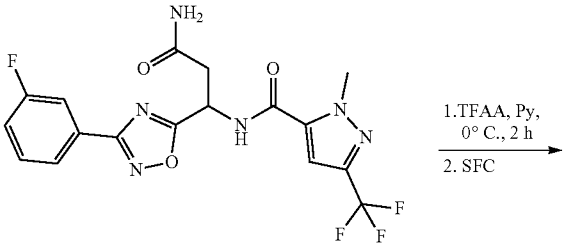

A-178
(128 and 129)

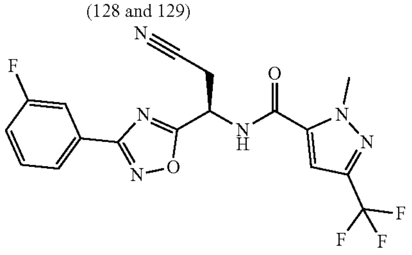

+

140

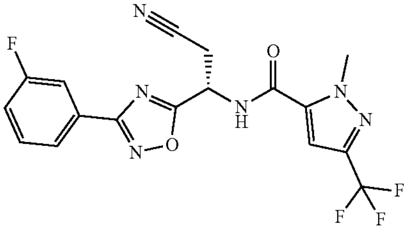

141

A mixture of N-[3-amino-1-[3-(3-fluorophenyl)-1,2,4-oxadiazol-5-yl]-3-oxo-propyl]-2-methyl-5-(trifluoromethyl) pyrazole-3-carboxamide (180 mg, 0.42 mmol), pyridine (0.14 mL, 1.69 mmol) and TFAA (0.12 mL, 0.84 mmol) in THF (5 mL) was stirred at 0° C. for 16 hours. The reaction mixture was warmed to room temperature and the pH of the mixture was adjusted pH=2 with 1N HCl aqueous (20 mL) and then extracted with EtOAc (20 mL×2). The combined organic phase was washed with water (20 mL), saturated $NaHCO_3$ aqueous (20 mL) and brine (20 mL), dried over anhydrous $Na_2SO_4$, filtered and concentrated to give the crude product. The crude product was purified by prep-HPLC (Waters)(Bridge (150 mm×25 mm, 5 μm) A=$H_2O$ (10 mM $NH_4HCO_3$) and B=$CH_3CN$; 45-73% B over 8 min) to give the product. Analytical SFC (Daicel CHIRALPAK AD-3 (150 mm×4.6 mm, 3 μm), mobile phase: A: $CO_2$ B: ethanol (0.05% DEA), gradient: from 5% to 40% of B in 5 min and hold 40% of B for 2.5 min, then hold 5% of B for 2.5 min, flow rate: 2.5 mL/min, column temp: 35° C.) showed two peaks at 2.40 min and 2.80 min. The product was separated by SFC (Daicel CHIRALPAK AD-H (250 mm×30 mm, 5 μm); A=$CO_2$ and B=EtOH; 38° C.; 50 mL/min; 20% B; 8 min run; 22 injections, Rt of peak 1=4.25 min, Rt of peak 2=5.25 min) to give the enantiomer 1 (Rt=2.40 min in analytical SFC, 65% ee) and the enantiomer 2 (Rt=2.80 min in analytical SFC, 71% ee). The impure enantiomer 1 was purified by SFC (Phenomenex-Amylose-1 (250 mm×30 mm, 5 μm); A=$CO_2$ and B=0.1% $NH_3.H_2O$-EtOH; 38° C.; 50 mL/min; 20% B; 8 min run; 16 injections, Rt of peak 1=4.4 min) to give the enantiomer 1, randomly assigned as 140 (21.11 mg, 51.7 mol, 12% yield) (Rt=2.40 min in analytical SFC) as a solid. The impure enantiomer 2 was purified by SFC (Phenomenex-Amylose-1 (250 mm×30 mm, 5 μm); A=$CO_2$ and B=0.1% $NH_3.H_2O$-EtOH; 38° C.; 50 mL/min; 20% B; 8 min run; 11 injections, Rt of peak 2=5.4 min) to give the enantiomer 2, randomly assigned as 141 (19.51 mg, 47.8 mol, 11% yield) (Rt=2.80 min in analytical SFC) as a solid.

140:

$^1$H NMR (DMSO-$d_6$ 400 MHz) $\delta_H$=(d, 1H), 7.88 (d, 1H), 7.77 (d, 1H), 7.70-7.62 (m, 1H), 7.54-7.46 (m, 1H), 7.43 (s, 1H), 5.89-5.77 (m, 1H), 4.15 (s, 3H), 3.52-3.38 (m, 2H). LCMS $R_t$=1.07 min in 2.0 min chromatography, 10-80AB, MS ESI calcd. for $C_{17}H_{13}F_4N_6O_2$ $[M+H]^+$ 409.1, found 409.1.

141:

$^1$H NMR (DMSO-$d_6$ 400 MHz) $\delta_H$=9.82 (d, 1H), 7.88 (d, 1H), 7.77 (d, 1H), 7.70-7.62 (m, 1H), 7.54-7.46 (m, 1H), 7.43 (s, 1H), 5.88-5.79 (m, 1H), 4.15 (s, 3H), 3.52-3.37 (m, 2H). LCMS $R_t$=1.28 min in 2.0 min chromatography, 10-80AB, MS ESI calcd. for $C_{17}H_{13}F_4N_6O_2$ $[M+H]^+$ 409.1, found 409.1.

Example 103. Synthesis of 142

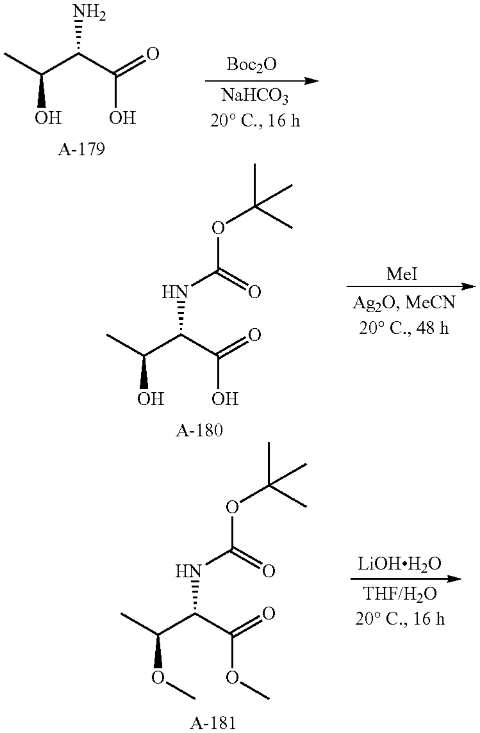

A-179
A-180
A-181

-continued

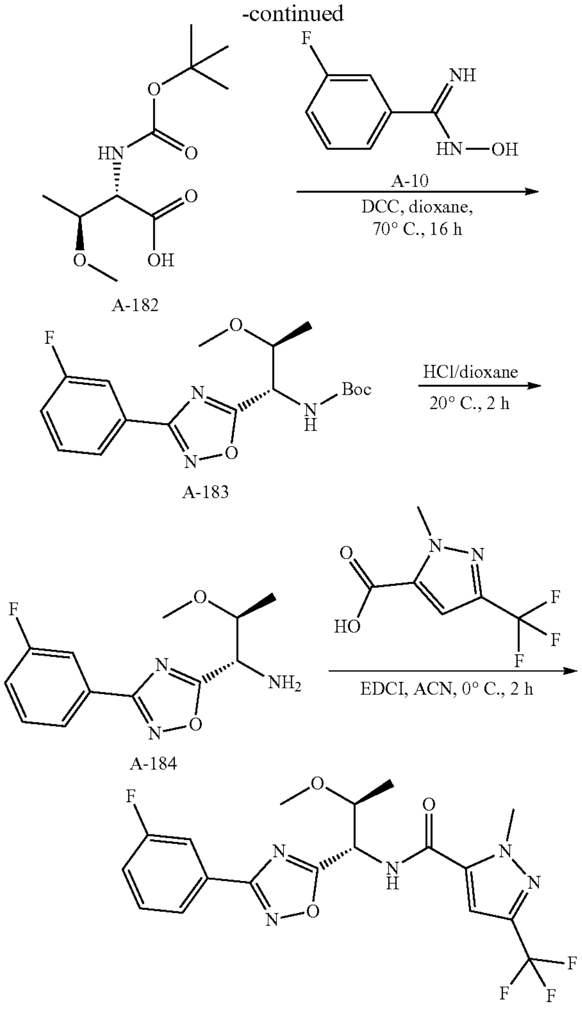

A-182
A-183
A-184
142

A-180:

To a solution of (2S,3S)-2-amino-3-hydroxy-butanoic acid (3 g, 25.18 mmol) and $NaHCO_3$ (3.17 g, 37.78 mmol) dissolved in water (18 mL) and methanol (25 mL) was added $Boc_2O$ (8.24 g, 37.78 mmol) and the reaction mixture was stirred at 20° C. for 16 hours. The mixture was partially concentrated, and the residue was partitioned between 1% HCl (80 mL) and EtOAc (80 mL). The aqueous layer was extracted with EtOAc (50 mL). The combined organic phase was dried over $Na_2SO_4$, filtered and concentrated to give the crude product (2 g, 9.12 mmol, 36% yield) as an oil. $^1$H NMR (400 MHz, DMSO-$d_6$) $\delta_H$=6.80 (d, 1H), 4.10 (s, 1H), 3.85 (d, 1H), 3.16 (s, 2H), 1.38 (s, 9H), 1.08 (d, 3H).

A-181:

To a mixture of (2S,3S)-2-(tert-butoxycarbonylamino)-3-hydroxy-butanoic acid (4 g, 18.25 mmol) in MeCN (20 mL) was added $Ag_2O$ (21.14 g, 91.23 mmol) and iodomethane (41.12 g, 289.7 mmol) at 0° C. The resulting mixture was then stirred at 20° C. for 48 hours. The reaction mixture was filtered through Celite, eluted with EtOAc (30 mL×2) and the filtrate was concentrated to give the product. The crude product was purified by flash chromatography on silica gel (EtOAc in PE=0% to 12% to 30%) to give the product (1.6 g, 6.47 mmol, 35% yield) as an oil. $^1$H NMR (400 MHz, $CDCl_3$) $\delta_H$=5.28 (br d, 1H), 4.43 (dd, 1H), 3.76 (s, 3H), 3.67-3.59 (m, 1H), 3.36 (s, 3H), 1.45 (s, 9H), 1.20 (d, 3H).

A-182:

To a solution of methyl (2S,3S)-2-(tert-butoxycarbonylamino)-3-methoxy-butanoate (1.6 g, 6.47 mmol) in THF (12 mL) and water (6 mL) was added $LiOH.H_2O$ (1.63 g, 38.82 mmol) and the resulting mixture was stirred at 20° C. for 4 hours. The mixture was partially concentrated under reduced pressure. The residue was partitioned between 1% HCl (40 mL) and EtOAc (30 mL). The aqueous layer was extracted with EtOAc (30 mL×2). The combined organic phase was dried over $Na_2SO_4$, filtered and concentrated to give the crude product (1.5 g, 6.43 mmol, 99% yield) as an oil. $^1H$ NMR (400 MHz, $CDCl_3$) $\delta_H$=5.40-5.21 (m, 1H), 4.50-4.40 (m, 1H), 3.75-3.67 (m, 1H), 3.38 (s, 3H), 1.45 (s, 9H), 1.27-1.25 (m, 3H).

A-183:

To a mixture of (2S,3S)-2-(tert-butoxycarbonylamino)-3-methoxy-butanoic acid (1.5 g, 6.43 mmol) and 3-fluoro-N-hydroxy-benzamidine (991.21 mg, 6.43 mmol) in 1,4-dioxane (20 mL) was added DCC (2.65 g, 12.86 mmol) and the mixture was stirred at 70° C. for 16 hours. The mixture was cooled to room temperature and filtered through Celite. The filtrate was concentrated to give the crude product. The crude product was purified by flash column chromatography on silica gel (EtOAc in PE=0% to 15% to 30%) to give the product (1.4 g, 3.72 mmol, 57% yield) as an oil. LCMS $R_t$=0.93 min in 1.5 min chromatography, 5-95AB, MS ESI calcd. for $C_{13}H_{15}FN_3O_4$ [M+H−t−Bu]$^+$ 296.1, found 296.1.

A-184:

A solution of tert-butyl N-[(1S,2S)-1-[3-(3-fluorophenyl)-1,2,4-oxadiazol-5-yl]-2-methoxy-propyl]carbamate (300 mg, 0.85 mmol) in 4M HCl in 1,4-dioxane (10 mL, 0.85 mmol) was stirred at 20° C. for 2 hours. The solution was concentrated to give the crude product (245 mg) as an oil. LCMS $R_t$=0.72 min in 1.5 min chromatography, 5-95AB, MS ESI calcd. for $C_{12}H_{15}FN_3O_2$ [M+H]$^+$ 252.1, found 251.6.

142:

To a mixture of 2-methyl-5-(trifluoromethyl)pyrazole-3-carboxylic acid (165.29 mg, 0.85 mmol), EDCI (163.24 mg, 0.85 mmol) in MeCN (8 mL) was added (1S,2S)-1-[3-(3-fluorophenyl)-1,2,4-oxadiazol-5-yl]-2-methoxy-propan-1-amine hydrochloride (245 mg, 0.85 mmol), the resulting mixture was stirred at 0° C. for 2 hours. The reaction was quenched with 1N HCl (20 mL), then extracted with EtOAc (15 mL×2). The combined organic phase was washed with brine (20 mL), dried over $Na_2SO_4$, filtered and concentrated to give the crude product. The crude product was partially purified by flash chromatography on silica gel (EtOAc in PE=0% to 10% to 20%) to give the impure product. The impure product was purified by prep-TLC (silica gel, PE:EtOAc=3:1) to give the product (112.34 mg, 262.9 μmol, 30% yield) as a an oil. $^1H$ NMR (DMSO-$d_6$ 400 MHz) $\delta_H$=9.46 (d, 1H), 7.87 (d, 1H), 7.79-7.73 (m, 1H), 7.67-7.61 (m, 1H), 7.52 (s, 1H), 7.50-7.45 (m, 1H), 5.40 (t, 1H), 4.11 (s, 3H), 4.05-3.94 (m, 1H), 3.27 (s, 3H), 1.29 (d, 3H). LCMS $R_t$=1.36 min in 2.0 min chromatography, 10-80AB, MS ESI calcd. for $C_{18}H_{18}F_4N_5O_3$ [M+H]$^+$ 428.1, found 428.2.

Example 104. Synthesis of 143 and 144

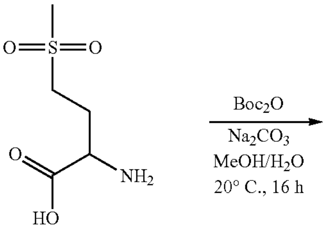

A-185

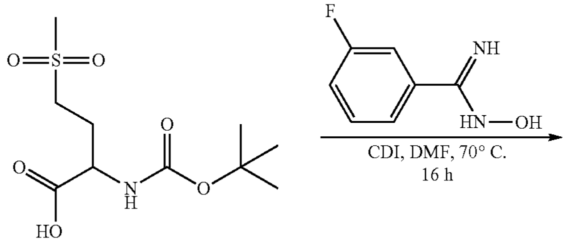

A-186

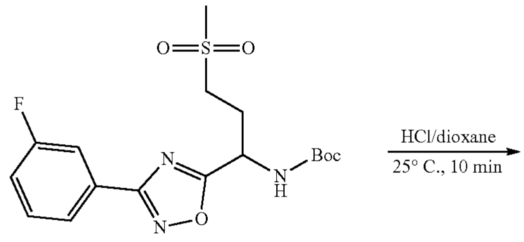

A-187

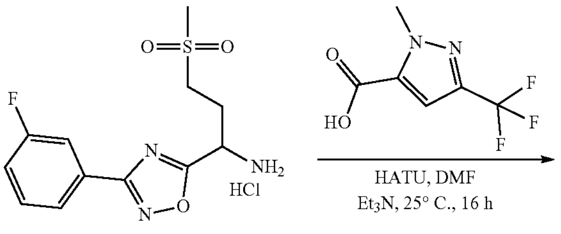

A-188

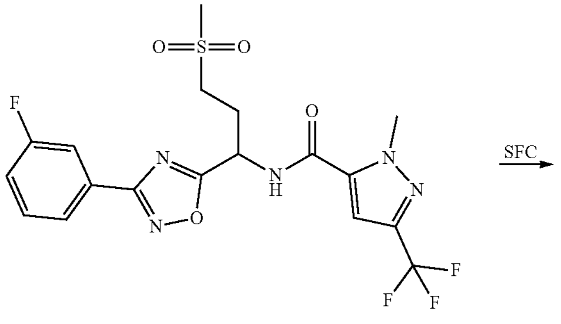

A-189

-continued

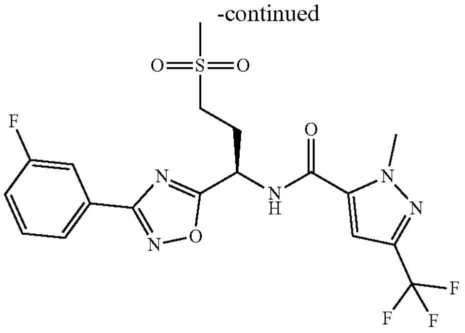

+

143

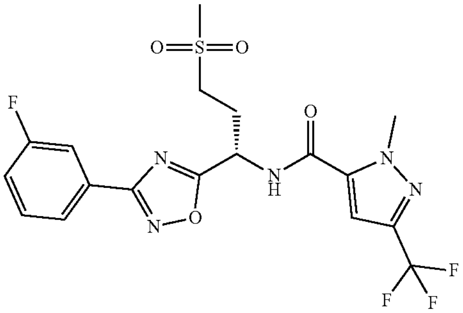

144

A-186:

To a solution of 2-amino-4-methylsulfonyl-butanoic acid (2 g, 11.04 mmol) and $Boc_2O$ (3.61 g, 16.56 mmol) in methanol (20 mL) and water (20 mL) was added $NaHCO_3$ (1.39 g, 16.56 mmol) and the mixture was stirred at 20° C. for 16 hours. The mixture was partially concentrated, and the residue was partitioned between sat. citric acid (20 mL) and EtOAc (15 mL). The organic layer was separated, and the aqueous layer was extracted with EtOAc (15 mL×2). The combined organic phase was dried over $Na_2SO_4$, filtered and concentrated to give the crude product (2.9 g) as a solid.

A-187:

A mixture of 2-(tert-butoxycarbonylamino)-4-methylsulfonyl-butanoic acid (1.5 g, 5.33 mmol), 3-fluoro-N-hydroxy-benzamidine (0.82 g, 5.33 mmol) and DCC (2.2 g, 10.66 mmol) in 1,4-dioxane (15 mL) was stirred at 70° C. for 16 hours. The mixture was diluted with $H_2O$ (100 mL) and extracted with EtOAc (20 mL×2). The combined organic phase was washed with brine (50 mL), dried over $Na_2SO_4$, filtered and concentrated to give the crude product. The crude product was purified by flash chromatography on silica gel (EtOAc in PE=0% to 50%) to give the product (1.5 g, 2.87 mmol, 54% yield) as a solid. LCMS $R_t$=0.86 min in 1.5 min chromatography, 5-95AB, MS ESI calcd. for $C_{17}H_{23}FN_3O_5S$ $[M+H-tBu]^+$344.13, found 344.1.

A-188:

To tert-butyl N-[1-[3-(3-fluorophenyl)-1,2,4-oxadiazol-5-yl]-3-methylsulfonyl-propyl]carbamate (1.5 g, 3.76 mmol) was added 4M HCl in 1,4-dioxane (25 mL, 3.76 mmol) and the mixture was stirred at 25° C. for 10 mins. The mixture was concentrated to give the crude product (1.5 g) as a solid.

A-189:

To a solution of 1-[3-(3-fluorophenyl)-1,2,4-oxadiazol-5-yl]-3-methylsulfonyl-propan-1-amine hydrochloride (400 mg, 1.34 mmol), 2-methyl-5-(trifluoromethyl)pyrazole-3-carboxylic acid (285.34 mg, 1.47 mmol) and HATU (1.02 g, 2.67 mmol) in DMF (5 mL) was added $Et_3N$ (0.92 mL, 6.68 mmol) and mixture was stirred at 25° C. for 16 hours. The mixture was diluted with $H_2O$ (20 mL) and extracted with EtOAc (20 mL×2). The combined organic phase was washed with brine (10 mL), dried over $Na_2SO_4$, filtered and concentrated to give the crude product. The crude product was purified by prep-HPLC (Boston Prime C18 (150 mm×30 mm, 5 μm), A=$H_2O$ (0.05% $NH_4OH$) and B=$CH_3CN$; 46-66% B over 9 min) to give the product (280 mg, 0.58 mmol, 44% yield) as a solid. LCMS $R_t$=1.19 min in 2 min chromatography, 10-80AB, MS ESI calcd. for $C_{18}H_{18}F_4N_5O_4S$ $[M+H]^+$ 476.1, found 476.1.

143 & 144:

Analytical SFC (Daicel CHIRALPAK AD-3 (150 mm×4.6 mm, 3 μm), mobile phase: A: $CO_2$ B: ethanol (0.05% DEA), gradient: from 5% to 40% of B in 5.5 min and hold 40% for 3 min, then 5% of B for 1.5 min, flow rate: 2.5 mL/min, column temp: 40° C. ABPR: 100 bar) showed two peaks at 2.97 min and 3.71 min. The product was separated by SFC (Phenomenex-Amylose-1 (250 mm×30 mm, 5 μm); A=$CO_2$ and B=EtOH (0.1% $NH_3H_2O$ ETOH); 38° C.; 50 mL/min; 30% B; 8 min run; 15 injections, Rt of peak 1=5.2 min, Rt of peak 2=8.3 min) to give enantiomer 1 (100 mg, Rt=2.97 min in analytical SFC, ee %=92.34%) and enantiomer 2 (100 mg, Rt=3.71 min in analytical SFC, ee %=93.37%). The impure enantiomer 1 was purified by SFC (Daicel CHIRALPAK AD-H (250 mm×30 mm, 5 μm); A=$CO_2$ and B=EtOH (0.1% $NH_3H_2O$); 38° C.; 50 mL/min; 30% B; 10 min run; 7 injections, Rt of peak 1=5.2 min, Rt of peak 2=8.3 min) to give the enantiomer 1, randomly assigned as 143 (70.77 mg, 0.15 mmol, 71% yield) (Rt=2.97 min in analytical SFC) as a solid. The impure enantiomer 2 was purified by SFC (Daicel CHIRALPAK AD-H (250 mm×30 mm, 5 μm); A=$CO_2$ and B=EtOH (0.1% $NH_3H_2O$); 38° C.; 50 mL/min; 30% B; 10 min run; 6 injections, Rt of peak 1=5.2 min, Rt of peak 2=8.3 min) to give the enantiomer 2, randomly assigned as 144 (40.42 mg, 85 μmol, 40% yield) (Rt=3.71 min in analytical SFC) as a solid.

143:

$^1H$ NMR (400 MHz, $CDCl_3$) $\delta_H$=7.88 (d, 1H), 7.82-7.75 (m, 1H), 7.65 (br d, 1H), 7.53-7.44 (m, 1H), 7.26-7.21 (m, 1H), 7.05 (s, 1H), 5.69 (dt, 1H), 4.24 (s, 3H), 3.43-3.34 (m, 1H), 3.32-3.22 (m, 1H), 3.05 (s, 3H), 2.86-2.63 (m, 2H). LCMS $R_t$=1.25 min in 2 min chromatography, 10-80AB, MS ESI calcd. for $C_{18}H_{18}F_4N_5O_4S$ $[M+H]^+$ 476.1, found 476.0.

144:

$^1H$ NMR (400 MHz, $CDCl_3$) $\delta_H$=7.88 (d, 1H), 7.81-7.75 (m, 1H), 7.65 (br d, 1H), 7.54-7.42 (m, 1H), 7.25-7.20 (m, 1H), 7.04 (s, 1H), 5.69 (dt, 1H), 4.24 (s, 3H), 3.44-3.34 (m, 1H), 3.32-3.22 (m, 1H), 3.06 (s, 3H), 2.88-2.63 (m, 2H). LCMS $R_t$=1.26 min in 2 min chromatography, 10-80AB, MS ESI calcd. for $C_{18}H_{18}F_4N_5O_4S$ $[M+H]^+$ 476.1, found 476.0.

Example 105. Synthesis of 147

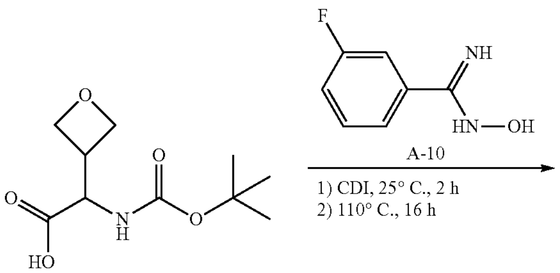

A-191

-continued

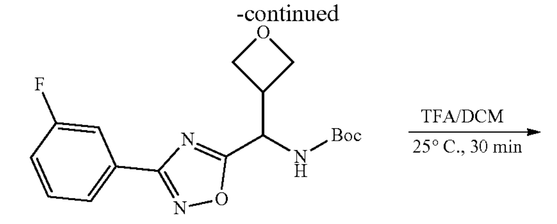

A-192

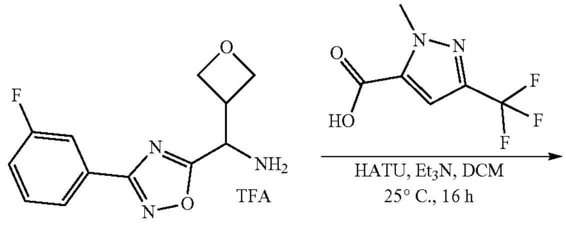

A-193

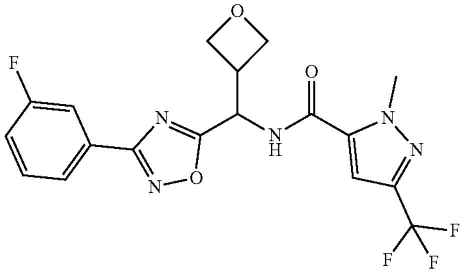

147

A-192:

To a solution of 2-(tert-butoxycarbonylamino)-2-(oxetan-3-yl)acetic acid (500 mg, 2.16 mmol) in DMF (5 mL) was added CDI (525.89 mg, 3.24 mmol) at 25° C. and the mixture was stirred at 25° C. for 30 min. Then 3-fluoro-N-hydroxy-benzamidine (399.93 mg, 2.59 mmol) was added to the solution and the mixture was stirred at 25° C. for 2 hours then heated to 110° C. and stirred for 16 hours. The reaction was cooled and was poured into water (30 mL) and extracted with EtOAc (20 mL×2). The combined organic phase was washed with brine (30 mL), dried over $Na_2SO_4$ filtered and concentrated. The crude was purified by flash chromatography on silica gel (EtOAc in PE=0% to 20%) to give the product (360 mg, 1.03 mmol, 48% yield) as a solid. $^1H$ NMR (400 MHz, CDCl3) $\delta_H$=7.86 (d, 1H), 7.76 (d, 1H), 7.50-7.44 (m, 1H), 7.26-7.19 (m, 1H), 5.52-5.26 (m, 2H), 4.91-4.80 (m, 2H), 4.72-4.57 (m, 2H), 3.63-3.48 (m, 1H), 1.49 (s, 9H).

A-193:

To a solution of tert-butyl N-[[3-(3-fluorophenyl)-1,2,4-oxadiazol-5-yl]-(oxetan-3-yl) methyl] carbamate (200 mg, 0.57 mmol) in DCM (4 mL) was added TFA (1.26 mL, 17.17 mmol) at 0° C. The mixture was then warmed to 25° C. and stirred for 30 mins. The reaction was concentrated to give the crude product (207 mg) as a solid. LCMS Rt=0.68 min in 2.0 min chromatography, 5-95AB, MS ESI calcd. For $C_{12}H_{12}FN_3O_2$ $[M+H]^+$ 249.1, found 249.6.

147:

To a solution of 2-methyl-5-(trifluoromethyl)pyrazole-3-carboxylic acid (165.92 mg, 0.85 mmol) and $Et_3N$ (0.28 mL, 1.99 mmol) in DCM (5 mL) was added HATU (325.01 mg, 0.85 mmol) at 25° C. and the mixture was stirred at 25° C. for 15 mins. Then [3-(3-fluorophenyl)-1,2,4-oxadiazol-5-yl]-(oxetan-3-yl)methanamine 2,2,2-trifluoroacetic acid (207 mg, 0.57 mmol) was added to the solution and the mixture was stirred at 25° C. for 16 hours. The mixture was poured in to water (20 mL) and extracted with DCM (10 mL×2). The combined organic phase was washed with brine (30 mL), dried over $Na_2SO_4$ filtered and concentrated. The crude was purified by prep-HPLC (Waters)(Bridge (150 mm×25 mm x 5 μm), A=$H_2O$ (10 mM $NH_4HCO_3$) and B=$CH_3CN$; 40-70% over 10 min) to give the product (11.84 mg, 0.03 mmol, 5% yield) as a solid. $^1H$ NMR (400 MHz, DMSO-$d_6$) $\delta_H$=7.86 (d, 1H), 7.76 (td, 1H), 7.48 (dt, 1H), 7.26-7.19 (m, 1H), 6.96 (s, 1H), 6.84 (d, 1H), 5.93 (t, 1H), 4.97-4.87 (m, 2H), 4.70-4.64 (m, 2H), 4.25 (s, 3H), 3.70-3.58 (m, 1H). LCMS Rt=1.15 min in 2.0 min chromatography, 10-80AB, MS ESI calcd. For $C_{18}H_{15}F_4N_5O_3$ $[M+H]^+$ 425.1, found 426.1.

Example 106. Synthesis of 148 and 149

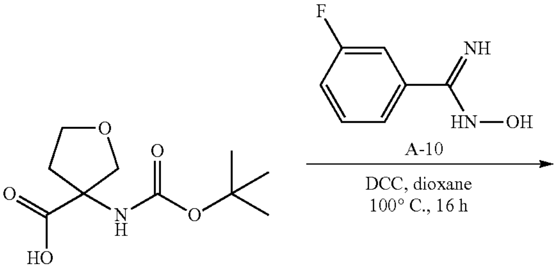

A-194

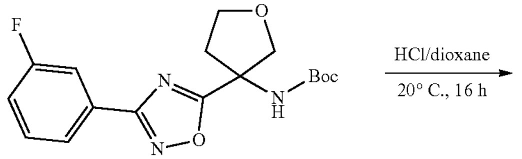

A-195

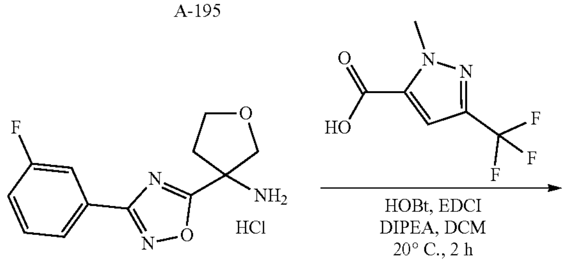

A-196

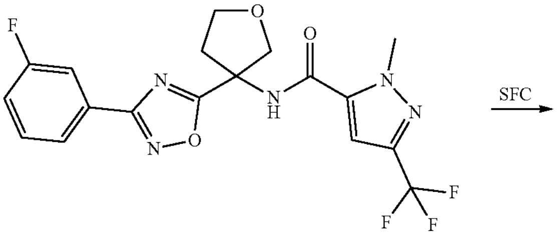

A-197

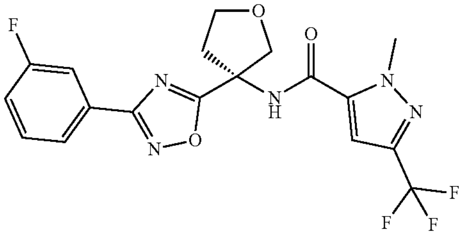

148

-continued

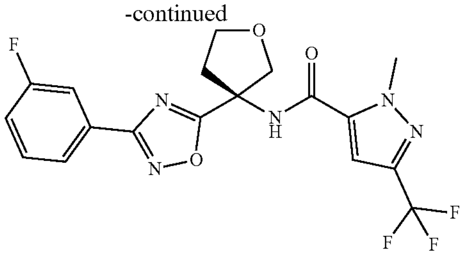

149

A-195:

A mixture of 3-fluoro-N-hydroxy-benzamidine (200 mg, 1.3 mmol), 4-(tert-butoxycarbonylamino)tetrahydrofuran-3-carboxylic acid (302.66 mg, 1.31 mmol) and DCC (534.58 mg, 2.6 mmol) in 1,4-dioxane (15 mL) was stirred at 100° C. for 16 hours. After cooling to room temperature, the mixture was filtered and the solid washed with EtOAc (10 mL). The combined organic layer was diluted with $NH_4Cl$ (30 mL) and extracted with EtOAc (30 mL×2). The combined organic phase was washed with brine (20 mL), dried over $Na_2SO_4$, filtered and concentrated to give the crude product. The crude product was purified by flash column chromatography flash column on silica gel (EtOAc in PE=0% to 10% to 30%) to give the product (370 mg, 1.06 mmol, 81% yield) as a solid. $^1H$ NMR (400 MHz, $CDCl_3$) $\delta_H$=7.92-7.86 (m, 1H), 7.83-7.75 (m, 1H), 7.50-7.41 (m, 1H), 7.25-7.16 (m, 1H), 5.46-5.14 (m, 1H), 4.40-4.28 (m, 1H), 4.22-4.09 (m, 3H), 2.83-2.70 (m, 1H), 2.50 (s, 1H), 1.52-1.35 (m, 9H).

A-196:

A mixture of tert-butyl N-[3-[3-(3-fluorophenyl)-1,2,4-oxadiazol-5-yl]tetrahydrofuran-3-yl]carbamate (370 mg, 1.06 mmol) in 4M HCl in 1,4-dioxane (15 mL, 60 mmol) was stirred at 20° C. for 16 hours. The mixture was concentrated to give the crude product (350 mg) as oil. LCMS $R_t$=0.65 min in 2 min chromatography, 5-95AB, MS ESI calcd. for $C_{12}H_{13}FN_3O_2$ $[M+H]^+$ 250.1, found 249.8.

A-197:

To a mixture of 3-[3-(3-fluorophenyl)-1,2,4-oxadiazol-5-yl]tetrahydrofuran-3-amine hydrochloride (302 mg, 1.06 mmol), 2-methyl-5-(trifluoromethyl)pyrazole-3-carboxylic acid (205.18 mg, 1.06 mmol) in DCM (10 mL) was added EDCI (405.27 mg, 2.11 mmol) and the reaction mixture was stirred at 20° C. for 2 hours. The reaction was quenched with the addition of sat. $NH_4Cl$ (20 mL), then extracted with DCM (15 mL). The combined organic phase was washed brine (15 mL×2), dried over $Na_2SO_4$, filtered and concentrated to give the crude product. The crude product was purified by flash chromatography on silica gel (EtOAc in PE=0% to 40%) to give the give the product (100 mg, 0.23 mmol, 22% yield) as oil. $^1H$ NMR (400 MHz, $CDCl_3$) $\delta_H$=7.90-7.84 (m, 1H), 7.81-7.75 (m, 1H), 7.50-7.42 (m, 1H), 7.25-7.18 (m, 1H), 7.06-7.00 (m, 1H), 6.99 (s, 1H), 4.33 (s, 2H), 4.27-4.17 (m, 2H), 4.15 (s, 3H), 3.03-2.90 (m, 1H), 2.74-2.63 (m, 1H).

148 & 149:

Analytical SFC (Daicel CHIRALCEL OJ-3 (150 mm×4.6 mm I.D., 3 μm), mobile phase: A: $CO_2$ B: ethanol (0.05% DEA), gradient: from 5% to 40% of B in 5 min and from 40% to 5% of B in 0.5 min, hold 5% of B for 1.5 min, flow rate: 2.5 mL/min, column temp: 35° C.) showed two peaks at 2.71 min and 3.02 min. The product was separated by SFC (Daicel CHIRALPAK AD-H (250 mm×30 mm, 5 μm); A=$CO_2$ and B=EtOH; 38° C.; 60 mL/min; 15% B; 9 min run; 10 injections, Rt of peak 1=6.16 min, Rt of peak 2=7.95 min) to give the enantiomer 1, randomly assigned as 148 (10.45 mg, 24.6 μmol, 10% yield) (Rt=2.71 min in analytical SFC) as a solid and the enantiomer 2, randomly assigned as 149 (3.18 mg, 7.50 μmol, 3% yield) (Rt=3.02 min in analytical SFC) as a solid.

148:

$^1H$ NMR (400 MHz, $CDCl_3$) $\delta_H$=7.91-7.85 (m, 1H), 7.82-7.75 (m, 1H), 7.51-7.43 (m, 1H), 7.26-7.19 (m, 1H), 6.95 (s, 1H), 6.70 (s, 1H), 4.38-4.29 (m, 2H), 4.25-4.18 (m, 2H), 4.16 (s, 3H), 3.06-2.89 (m, 1H), 2.74-2.61 (m, 1H). LCMS $R_t$=1.32 min in 2 min chromatography, 10-80AB, MS ESI calcd. for $C_{18}H_{16}F_4N_5O_3$ $[M+H]^+$ 426.1, found 426.2.

149:

$^1H$ NMR (400 MHz, $CDCl_3$) $\delta_H$=7.91-7.84 (m, 1H), 7.83-7.75 (m, 1H), 7.51-7.43 (m, 1H), 7.25-7.18 (m, 1H), 6.95 (s, 1H), 6.73 (s, 1H), 4.39-4.30 (m, 2H), 4.23-4.18 (m, 2H), 4.16 (s, 3H), 3.03-2.93 (m, 1H), 2.73-2.64 (m, 1H). LCMS $R_t$=1.31 min in 2 min chromatography, 10-80AB, MS ESI calcd. for $C_{18}H_{16}F_4N_5O_3$ $[M+H]^+$ 426.1, found 426.1.

Example 107. Synthesis of 150

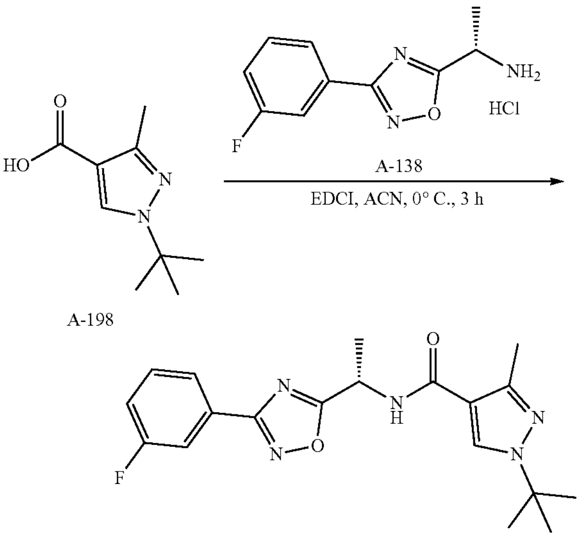

150

To a mixture of 1-tert-butyl-3-methyl-pyrazole-4-carboxylic acid (100 mg, 0.55 mmol) and EDCI (105.2 mg, 0.55 mmol) in $CH_3CN$ (3 mL) was added (1S)-1-[3-(3-fluorophenyl)-1,2,4-oxadiazol-5-yl]ethanamine hydrochloride (133.72 mg, 0.55 mmol) and the mixture was stirred at 0° C. for 3 hours. The reaction was quenched with the addition of 1N HCl (5 mL), extracted with EtOAc (5 mL) and concentrated under reduced pressure to give the crude product. The crude product was purified by prep-HPLC (Welch Xtimate C18 (150 mm×25 mm, 5 μm) A=$H_2O$ (0.075% TFA) and B=$CH_3CN$; 45-70% B over 7.5 min) to give the product (24.1 mg, 65.0 μmol, 12% yield) as a solid. $^1H$ NMR (400 MHz, $CDCl_3$) $\delta_H$=7.93 (s, 1H), 7.88 (d, 1H), 7.81-7.76 (m, 1H), 7.47 (dt, 1H), 7.25-7.19 (m, 1H), 6.32 (br d, 1H), 5.70-5.61 (m, 1H), 2.56 (s, 3H), 1.74 (d, 3H), 1.59 (s, 9H). LCMS $R_t$=1.23 min in 2.0 min chromatography, 10-80AB, MS ESI calcd. for $C_{19}H_{23}FN_5O_2$ $[M+H]^+$ 372.2, found 372.1.

Example 108. Synthesis of 151

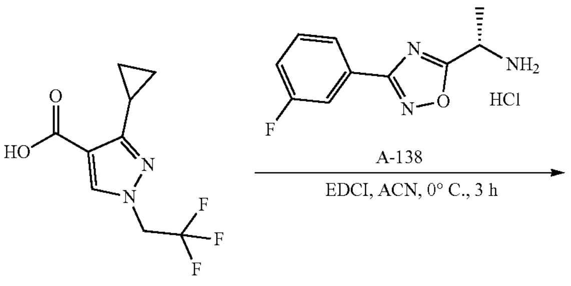

A-199

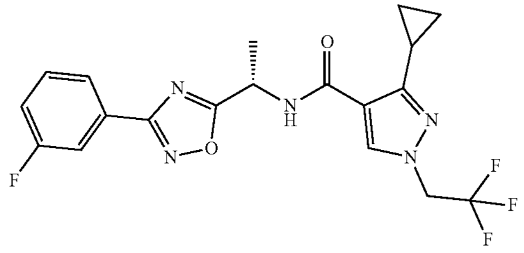

151

To a mixture of 3-cyclopropyl-1-(2,2,2-trifluoroethyl) pyrazole-4-carboxylic acid (100 mg, 0.43 mmol), EDCI (81.86 mg, 0.43 mmol) in $CH_3CN$ (3 mL) was added (1S)-1-[3-(3-fluorophenyl)-1,2,4-oxadiazol-5-yl] ethanamine hydrochloride (104.05 mg, 0.43 mmol) and the mixture was stirred at 0° C. for 3 hours. The reaction was quenched by the addition of 1N HCl (5 mL), then extracted with EtOAc (5 mL), and concentrated to give the crude product. The crude product was purified by prep-HPLC (Welch Xtimate C18 (150 mm×25 mm, 5 μm) A=$H_2O$ (0.075% TFA) and B=$CH_3CN$; 49-79% B over 9 min) to give the product (4.3 mg, 10.1 mmol, 2% yield) as a solid. $^{1}$H NMR (400 MHz, $CDCl_3$) $\delta_H$=7.94 (s, 1H), 7.87 (d, 1H), 7.77 (br d, 1H), 7.51-7.44 (m, 1H), 7.25-7.20 (m, 1H), 6.70 (br d, 1H), 5.71-5.63 (m, 1H), 4.88 (q, 2H), 1.95-1.87 (m, 1H), 1.76 (d, 3H), 1.33-1.26 (m, 2H), 1.00-0.86 (m, 2H). LCMS $R_t$=1.28 min in 2.0 min chromatography, 10-80AB, MS ESI calcd. for $C_{19}H_{18}F_4N_5O_2$ $[M+H]^+$ 424.1, found 424.1.

Example 109. Synthesis of 152

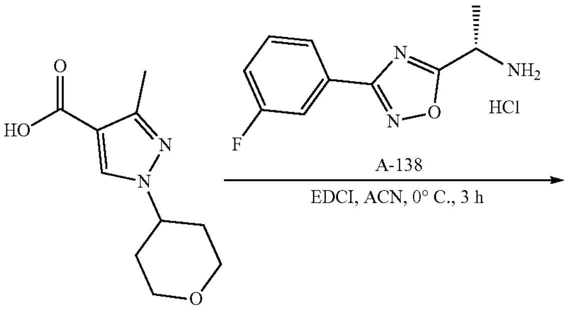

A-200

-continued

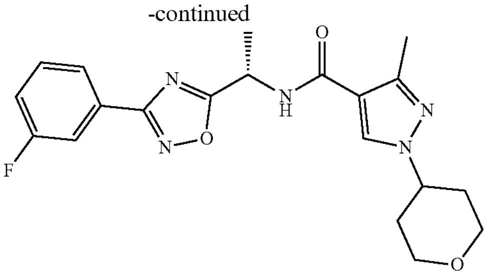

152

To a mixture of methyl 3-methyl-1-tetrahydropyran-4-yl-pyrazole-4-carboxylate (100 mg, 0.45 mmol), EDCI (85.48 mg, 0.45 mmol) in $CH_3CN$ (3 mL) was added (1S)-1-[3-(3-fluorophenyl)-1,2,4-oxadiazol-5-yl]ethanamine hydrochloride (108.66 mg, 0.45 mmol) and the mixture was stirred at 0° C. for 3 hours. The reaction was quenched by the addition of 1N HCl (5 mL), extracted with EtOAc (5 mL) and the organic phase was concentrated to give the crude product. The crude product was purified by prep-HPLC (Welch Xtimate C18 (150 mm×25 mm, 5 μm) A=$H_2O$ (0.075% TFA) and B=$CH_3CN$; 43-68% B over 7.5 min) to give the product (10.1 mg, 25.3 mmol, 5% yield) as a solid. $^{1}$H NMR (400 MHz, $CDCl_3$) $\delta_H$=7.89-7.86 (m, 2H), 7.78 (td, 1H), 7.47 (dt, 1H), 7.25-7.20 (m, 1H), 6.33 (br d, 1H), 5.69-5.61 (m, 1H), 4.34-4.25 (m, 1H), 4.15-4.10 (m, 2H), 3.54 (dt, 2H), 2.55 (s, 3H), 2.16-1.99 (m, 4H), 1.74 (d, 3H). LCMS $R_t$=1.13 min in 2.0 min chromatography, 10-80AB, MS ESI calcd. for $C_{20}H_{23}FN_5O_3$ $[M+H]^+$ 400.2, found 400.1.

Example 110. Synthesis of 153

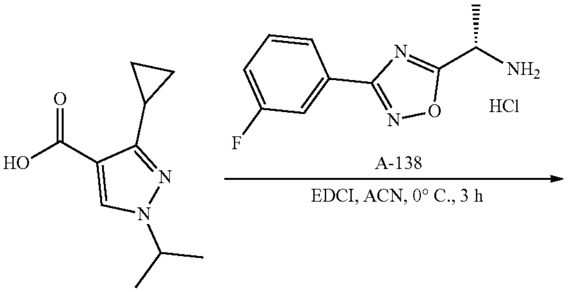

A-201

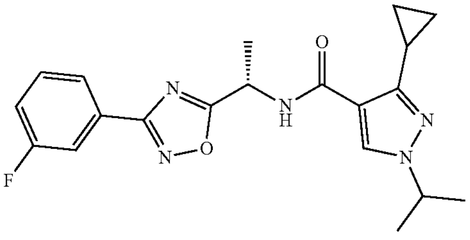

153

To a mixture of 3-cyclopropyl-1-isopropyl-pyrazole-4-carboxylic acid (100 mg, 0.51 mmol), EDCI (98.7 mg, 0.51 mmol) in $CH_3CN$ (3 mL) was added (1S)-1-[3-(3-fluorophenyl)-1,2,4-oxadiazol-5-yl]ethanamine hydrochloride (125.45 mg, 0.51 mmol) and the mixture was stirred at 0° C.

for 3 hours. The reaction was quenched with by the addition of 1N HCl (5 mL), extracted with EtOAc (5 mL) and the organic phase was concentrated to give the crude product. The crude product was purified by prep-HPLC (Welch Xtimate C18 (150 mm×25 mm, 5 μm) A=$H_2O$ (0.075% TFA) and B=$CH_3CN$; 53-78% B over 7.5 min) to give the product (15.4 mg, 39.9 mol, 8% yield) as a solid. $^1H$ NMR (400 MHz, $CDCl_3$) $\delta_H$=7.93 (s, 1H), 7.87 (d, 1H), 7.77 (br d, 1H), 7.50-7.43 (m, 1H), 7.25-7.19 (m, 2H), 5.73-5.65 (m, 1H), 4.48-4.38 (m, 1H), 2.17-2.09 (m, 1H), 1.75 (d, 3H), 1.48 (d, 6H), 1.12-1.00 (m, 4H). LCMS $R_t$=1.28 min in 2.0 min chromatography, 10-80AB, MS ESI calcd. for $C_{20}H_{23}FN_5O_2$ [M+H]$^+$ 384.2, found 384.1.

Example 111. Synthesis of 154

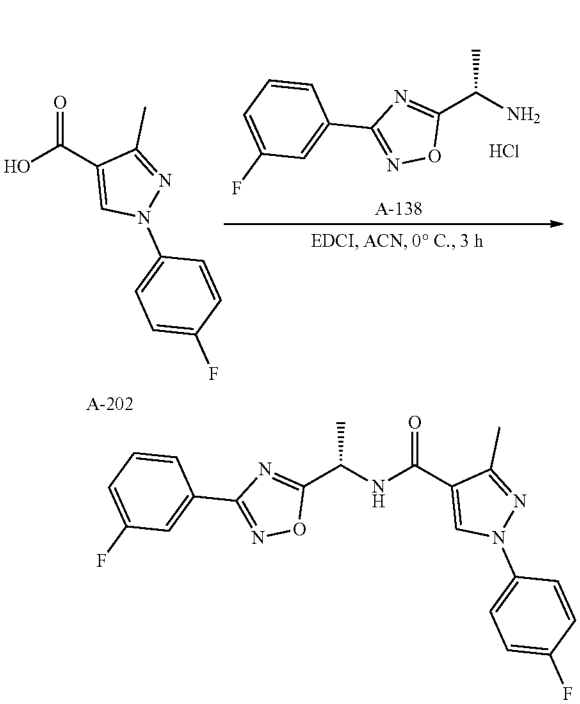

A-202

154

To a mixture of 1-(4-fluorophenyl)-3-methyl-pyrazole-4-carboxylic acid (100 mg, 0.45 mmol), EDCI (87.06 mg, 0.45 mmol) in $CH_3CN$ (3 mL) was added (1S)-1-[3-(3-fluorophenyl)-1,2,4-oxadiazol-5-yl]ethanamine hydrochloride (110.66 mg, 0.45 mmol) and the mixture was stirred at 0° C. for 3 hours. The reaction was quenched with the addition of 1N HCl (5 mL), extracted with EtOAc (5 mL), and the organic phase was concentrated to give the crude product. The crude product was purified by prep-HPLC (Welch Xtimate C18 (150 mm×25 mm, 5 μm), A=$H_2O$ (0.075% TFA) and B=$CH_3CN$; 55-80% B over 7.5 min) to give the product (8.1 mg, 19.7 mol, 4% yield) as a solid. $^1H$ NMR (400 MHz, $CDCl_3$) $\delta_H$=8.26 (s, 1H), 7.88 (td, 1H), 7.81-7.76 (m, 1H), 7.68-7.63 (m, 2H), 7.51-7.44 (m, 1H), 7.26-7.15 (m, 3H), 6.44 (br d, 1H), 5.72-5.63 (m, 1H), 2.64 (s, 3H), 1.77 (d, 3H). LCMS $R_t$=1.32 min in 2.0 min chromatography, 10-80AB, MS ESI calcd. for $C_{21}H_{18}F_2N_5O_2$ [M+H]$^+$ 410.1, found 410.1.

Example 112. Synthesis of 155

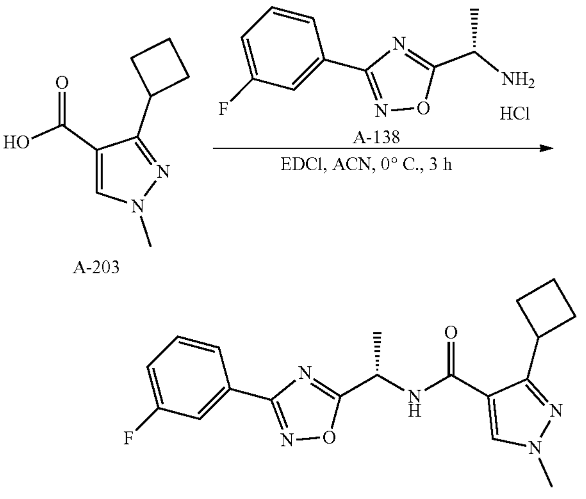

A-203

155

To a mixture of 3-cyclobutyl-1-methyl-pyrazole-4-carboxylic acid (100 mg, 0.55 mmol), EDCI (106.38 mg, 0.55 mmol) in $CH_3CN$ (3 mL) was added (1S)-1-[3-(3-fluorophenyl)-1,2,4-oxadiazol-5-yl]ethanamine hydrochloride (135.22 mg, 0.55 mmol) and the mixture was stirred at 0° C. for 3 hours. The reaction was quenched by the addition of 1N HCl (5 mL), extracted with EtOAc (5 mL) and the organic phase was concentrated to give the crude product. The crude product was purified by prep-HPLC (Welch Xtimate C18 (150 mm×25 mm, 5 μm), A=$H_2O$ (0.075% TFA) and B=$CH_3CN$; 45-70% B over 7.5 min) to give the product (13.5 mg, 6.4 mol, 6% yield) as a solid. $^1H$ NMR (400 MHz, $CDCl_3$) $\delta_H$=7.89 (td, 1H), 7.82-7.77 (m, 2H), 7.48 (dt, 1H), 7.26-7.20 (m, 1H), 6.33 (br d, 1H), 5.66-5.58 (m, 1H), 3.94-3.85 (m, 4H), 2.50-2.40 (m, 4H), 2.17-2.04 (m, 1H), 2.01-1.92 (m, 1H), 1.72 (d, 3H). LCMS $R_t$=1.22 min in 2.0 min chromatography, 10-80AB, MS ESI calcd. for $C_{19}H_{21}FN_5O_2$ [M+H]$^+$ 370.2, found 370.1.

Example 113. Synthesis of 156

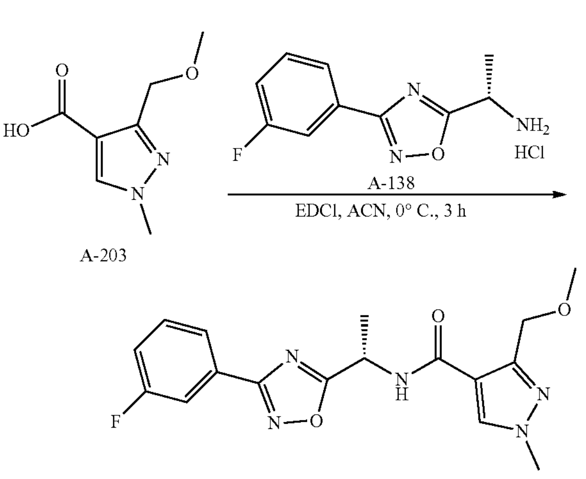

A-203

156

To a mixture of 3-(methoxymethyl)-1-methyl-pyrazole-4-carboxylic acid (100 mg, 0.59 mmol), EDCI (112.65 mg, 0.59 mmol) in $CH_3CN$ (3 mL) was added (1S)-1-[3-(3-fluorophenyl)-1,2,4-oxadiazol-5-yl]ethanamine hydrochloride (143.19 mg, 0.59 mmol) and the mixture was stirred at 0° C. for 3 hours. The reaction was quenched with the addition of 1N HCl (5 mL), extracted with EtOAc (5 mL) and the organic phase was concentrated to give the crude product. The crude product was purified by prep-HPLC (Welch Xtimate C18 (150 mm×25 mm, 5 μm), A=$H_2O$ (0.075% TFA) and B=$CH_3CN$; 39-69% B over 9 min) to give the product (5.3 mg, 14.7 μmol, 2% yield) as a solid. $^1H$ NMR (400 MHz, $CDCl_3$) $\delta_H$=7.90-7.84 (m, 2H), 7.78 (br d, 1H), 7.50-7.43 (m, 1H), 7.25-7.18 (m, 2H), 5.68-5.59 (m, 1H), 4.85-4.76 (m, 2H), 3.95 (s, 3H), 3.45 (s, 3H), 1.73 (d, 3H). LCMS $R_t$=1.12 min in 2.0 min chromatography, 10-80AB, MS ESI calcd. for $C_{17}H_{19}FN_5O_3$ $[M+H]^+$ 360.1, found 360.1.

Example 114. Synthesis of 157

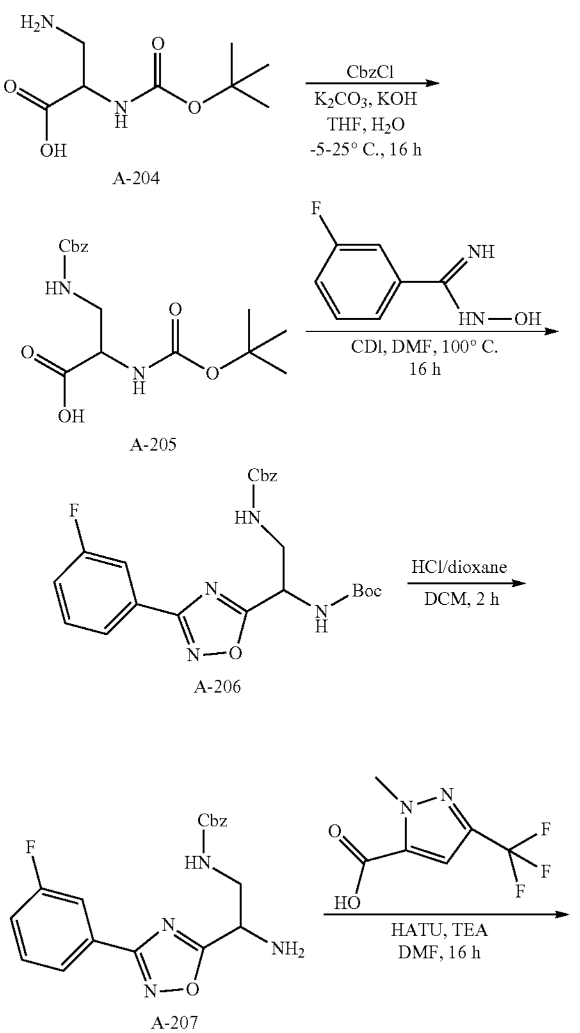

A-204
A-205
A-206
A-207

-continued

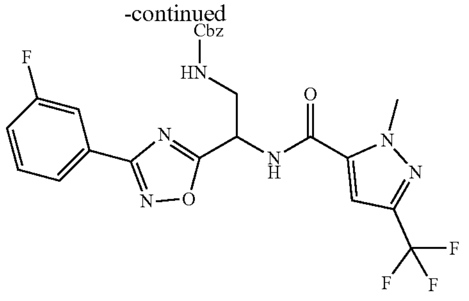
157

A-205:

To the solution of 3-amino-2-(tert-butoxycarbonylamino) propanoic acid (1 g, 4.9 mmol), $K_2CO_3$ (1.35 g, 9.79 mmol), KOH (0.27 g, 4.9 mmol) in THF (15 mL) and water (5 mL) was added benzyl carbonochloridate (1.25 g, 7.35 mmol) in a dropwise manner at −5° C. The suspension was stirred at 25° C. for 16 hours. The mixture was partially concentrated to remove THF. The residue was acidified with solid citric acid to pH~4 and extracted with DCM (20 mL×2). The combined organic phase was dried over $Na_2SO_4$, filtered and concentrated to give product (1 g) as an oil. LCMS $R_t$=0.78 min in 1.5 min chromatography, 5-95AB, MS ESI calcd. for $C_{16}H_{22}N_2O_6$ $[M+Na]^+$361.2, found 360.9.

A-206:

A mixture of 3-(benzyloxycarbonylamino)-2-(tert-butoxycarbonylamino)propanoic acid (900 mg, 2.66 mmol) and CDI (862.6 mg, 5.32 mmol) in DMF (25 mL) was stirred at 25° C. for 30 minutes, then 3-fluoro-N-hydroxy-benzamidine (819.99 mg, 5.32 mmol) was added and the resulting mixture was stirred at 100° C. for 16 hours. After cooling to room temperature, the reaction mixture was diluted with $H_2O$ (50 mL) and then extracted with EtOAc (50 mL×2). The combined organic phase was washed with brine (50 mL), dried over $Na_2SO_4$, filtered and concentrated to give the crude product. The crude product was purified with flash chromatography on silica gel (EtOAc in PE=0/1 to 1/5) to give the product (800 mg, 1.70 mmol, 64% yield). LCMS $R_t$=1.33 min in 2.0 min chromatography, 10-80AB, MS ESI calcd. for $C_{23}H_{25}FN_4O_5$ $[M+Na]^+$479.2, found 479.2.

A-207:

A solution of tert-butyl N-[2-(benzyloxycarbonylamino)-1-[3-(3-fluorophenyl)-1,2,4-oxadiazol-5-yl]ethyl]carbamate (400 mg, 0.88 mmol) and 4M HCl in 1,4-dioxane (5 mL, 20 mmol) in DCM (10 mL) was stirred at 25° C. for 2 hours. The reaction mixture was concentrated to give a crude product (350 mg, 0.89 mmol) as a solid. LCMS $R_t$=0.74 min in 1.5 min chromatography, 10-80AB, MS ESI calcd. for $C_{18}H_{18}FN_4O_3$ $[M+H]^+$ 357.1, found 357.0.

157:

To a solution of benzyl N-[2-amino-2-[3-(3-fluorophenyl)-1,2,4-oxadiazol-5-yl]ethyl]carbamate hydrochloride (336 mg, 0.86 mmol), 2-methyl-5-(trifluoromethyl)pyrazole-3-carboxylic acid (182.64 mg, 0.94 mmol) and HATU (650.5 mg, 1.71 mmol) in DMF (4 mL) was added $Et_3N$ (0.59 mL, 4.28 mmol). The mixture was stirred at 25° C. for 16 hours. The reaction was quenched with the addition of sat. $NH_4Cl$ (20 mL) and the mixture was extracted with EtOAc (30 mL×2). The combined organic phase was washed with brine (20 mL), dried over $Na_2SO_4$, filtered and concentrated to give the crude product. The crude product was purified by prep-HPLC (Phenomenex Gemini-NX (150 mm×30 mm, 5 μm), A=$H_2O$ (0.04% $NH_3H_2O$+10 mM $NH_4HCO_3$) and B=$CH_3CN$; 38-68% B over 8.5 mins) to give the product (216.9 mg, 0.40 mmol, 47% yield) as a solid. $^1$H NMR (400M Hz $CDCl_3$) $\delta_H$=9.46 (d, 1H), 7.87 (d, 1H), 7.76 (br d, 1H), 7.71-7.59 (m, 2H), 7.48 (dt, 1H), 7.42 (s, 1H), 7.28 (s, 5H), 5.44 (q, 1H), 5.06-4.94 (m, 2H), 4.11 (s, 3H), 3.82 (td, 1H), 3.65 (td, 1H). LCMS $R_t$=1.39 min in 2.0 min chromatography, 10-80AB, MS ESI calcd. for $C_{24}H_{21}F_4N_6O_4$ $[M+H]^+$ 533.2, found 533.1.

Example 116. Synthesis of 160

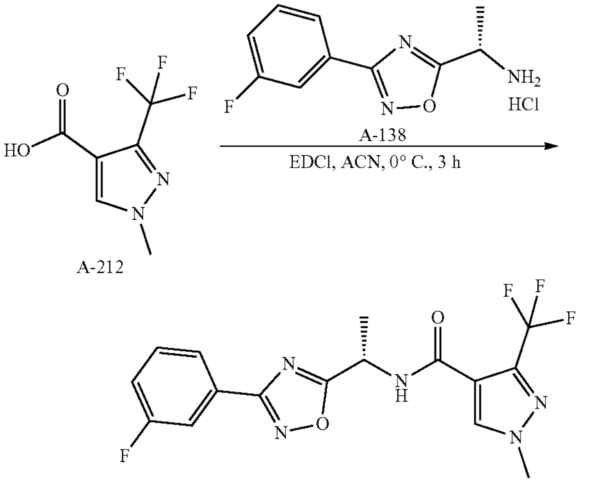

160

To a mixture of 1-methyl-3-(trifluoromethyl)pyrazole-4-carboxylic acid (100 mg, 0.52 mmol), EDCI (98.76 mg, 0.52 mmol) in $CH_3CN$ (3 mL) was added (1S)-1-[3-(3-fluorophenyl)-1,2,4-oxadiazol-5-yl]ethanamine hydrochloride (125.53 mg, 0.52 mmol) and the mixture was stirred at 0° C. for 3 hours. The reaction was quenched with the addition of 1N HCl (5 mL), extracted with EtOAc (5 mL), and concentrated to give the crude product. The crude product was partially purified by prep-HPLC (Boston Green ODS (150 mm×30 mm, 5 μm) A=$H_2O$ (0.075% TFA) and B=$CH_3CN$; 55-75% B over 7 min) to give the impure product. The impure product was triturated with n-hexane:DCM (10:1, 2 mL) to give the product (5.0 mg, 13.0 μmol, 2% yield) as a solid. $^1$H NMR (400 MHz, $CDCl_3$) $\delta_H$=8.00 (s, 1H), 7.88 (br d, 1H), 7.78 (br d, 1H), 7.50-7.44 (m, 1H), 7.25-7.19 (m, 1H), 6.75 (br s, 1H), 5.64-5.55 (m, 1H), 4.00 (s, 3H), 1.74 (d, 3H). LCMS $R_t$=1.18 min in 2.0 min chromatography, 10-80AB, MS ESI calcd. for $C_{16}H_{14}F_4N_5O_2$ $[M+H]^+$ 384.1, found 384.1.

Example 117. Synthesis of 161

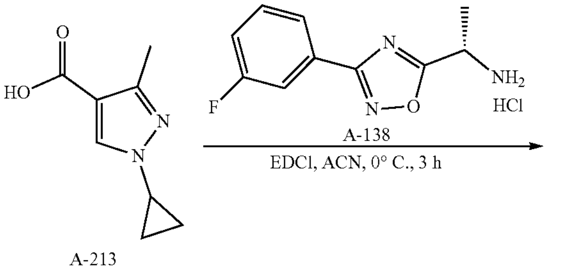

-continued

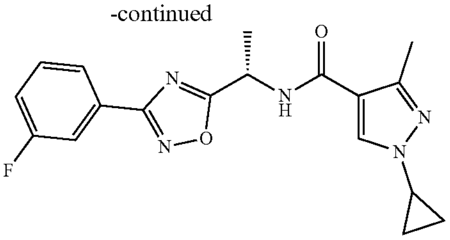

161

To a mixture of 1-cyclopropyl-3-methyl-pyrazole-4-carboxylic acid (100 mg, 0.60 mmol) and EDCI (115.36 mg, 0.60 mmol) in $CH_3CN$ (3 mL) was added (1S)-1-[3-(3-fluorophenyl)-1,2,4-oxadiazol-5-yl]ethanamine hydrochloride (124.68 mg, 0.51 mmol) and the mixture was stirred at 0° C. for 3 hours. The reaction was quenched with the addition of 1N HCl (5 mL), extracted with EtOAc (5 mL) and concentrated to give the crude product. The crude product was purified by prep-HPLC (Waters)(Bridge (150 mm×25 mm, 5 μm), A=$H_2O$ (10 mM $NH_4HCO_3$) and B=$CH_3CN$; 35-65% B over 10 min) to give the product (18.6 mg, 52.3 mol, 8% yield) as a solid. $^1$H NMR (400 MHz, $CDCl_3$) $\delta_H$=7.89-7.84 (m, 2H), 7.81-7.75 (m, 1H), 7.47 (dt, 1H), 7.25-7.19 (m, 1H), 6.30 (br d, 1H), 5.68-5.59 (m, 1H), 3.60-3.53 (m, 1H), 2.53 (s, 3H), 1.73 (d, 3H), 1.15-1.09 (m, 2H), 1.08-1.02 (m, 2H). LCMS $R_t$=1.16 min in 2.0 min chromatography, 10-80AB, MS ESI calcd. for $C_{18}H_{19}FN_5O_2$ $[M+H]^+$ 356.1, found 356.1.

Example 118. Synthesis of 162

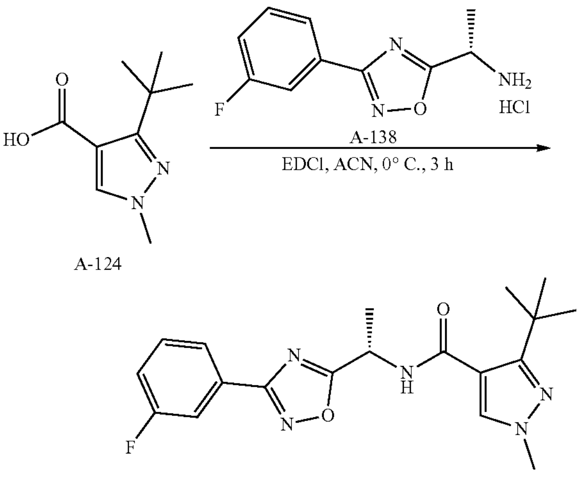

162

To a mixture of 3-tert-butyl-1-methyl-pyrazole-4-carboxylic acid (100 mg, 0.55 mmol) and EDCI (105.2 mg, 0.55 mmol) in $CH_3CN$ (3 mL) was added (1S)-1-[3-(3-fluorophenyl)-1,2,4-oxadiazol-5-yl]ethanamine hydrochloride (113.71 mg, 0.47 mmol) and the mixture was stirred at 0° C. for 3 hours. The reaction was quenched with the addition of 1N HCl (5 mL), extracted with EtOAc (5 mL) and concentrated to give the crude product. The crude product was purified by prep-HPLC (Phenomenex Gemini-NX (150 mm×30 mm, 5 μm), A=$H_2O$ (0.04% $NH_3H_2O$+10 mM $NH_4HCO_3$) and B=$CH_3CN$; 43-73% B over 8.5 mins) to give the product (28.5 mg, 76.6 μmol, 14% yield) as a solid. $^1H$ NMR (400 MHz, $CDCl_3$) $\delta_H$=7.87 (td, 1H), 7.80-7.75 (m, 1H), 7.64 (s, 1H), 7.47 (dt, 1H), 7.25-7.19 (m, 1H), 6.26 (br d, 1H), 5.62-5.54 (m, 1H), 3.87 (s, 3H), 1.72 (d, 3H), 1.42 (s, 9H). LCMS $R_t$=1.26 min in 2.0 min chromatography, 10-80AB, MS ESI calcd. for $C_{19}H_{23}FN_5O_2$ $[M+H]^+$ 372.2, found 372.1.

Example 119. Synthesis of 163

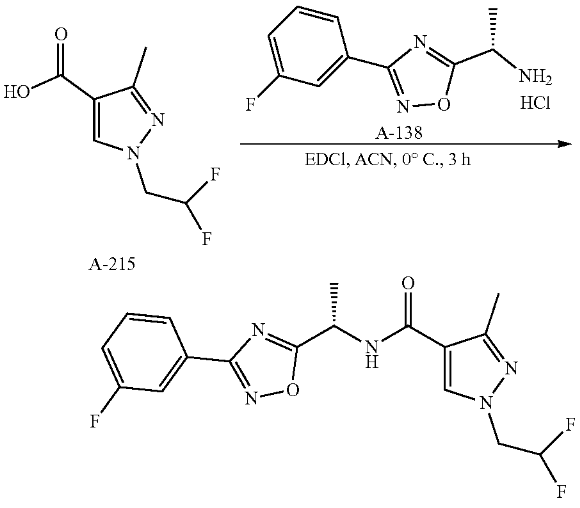

A-215

163

To a mixture of 1-(2,2-difluoroethyl)-3-methyl-pyrazole-4-carboxylic acid (100 mg, 0.53 mmol) and EDCI (100.82 mg, 0.53 mmol) in $CH_3CN$ (3 mL) was added (1S)-1-[3-(3-fluorophenyl)-1,2,4-oxadiazol-5-yl]ethanamine hydrochloride (128.15 mg, 0.53 mmol) and the mixture was stirred at 0° C. for 3 hours. The reaction was quenched with the addition of 1N HCl (5 mL), extracted with EtOAc (5 mL), and concentrated to give the crude product. The crude product was purified by prep-HPLC (Waters)(Bridge (150 mm×25 mm, 5 μm), A=$H_2O$ (10 mM $NH_4HCO_3$) and B=$CH_3CN$; 30-60% B over 10 min) to give the product (16.9 mg, 44.7 mol, 8% yield) as a solid. $^1H$ NMR (400 MHz, $CDCl_3$) $\delta_H$=7.89-7.86 (m, 2H), 7.80-7.76 (m, 1H), 7.47 (dt, 1H), 7.25-7.19 (m, 1H), 6.34 (br d, 1H), 6.26-5.96 (m, 1H), 5.68-5.59 (m, 1H), 4.42 (dt, 2H), 2.54 (s, 3H), 1.74 (d, 3H). LCMS $R_t$=1.18 min in 2.0 min chromatography, 10-80AB, MS ESI calcd. for $C_{17}H_{17}F_3N_5O_2$ $[M+H]^+$ 380.1, found 380.0.

Example 120. Synthesis of 164

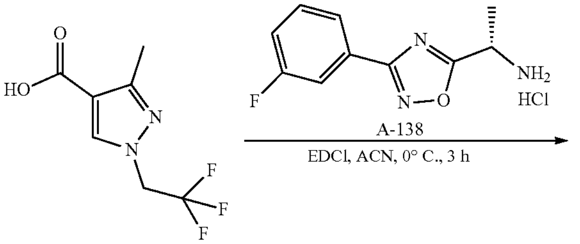

A-216

-continued

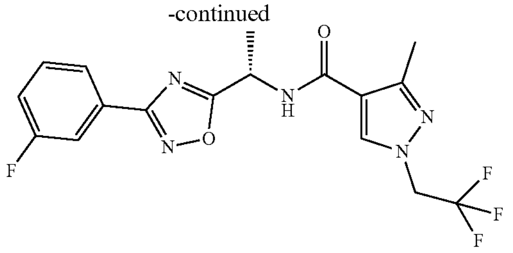

164

To a mixture of 3-methyl-1-(2,2,2-trifluoroethyl)pyrazole-4-carboxylic acid (100 mg, 0.48 mmol), EDCI (92.1 mg, 0.48 mmol) in $CH_3CN$ (3 mL) was added (1S)-1-[3-(3-fluorophenyl)-1,2,4-oxadiazol-5-yl]ethanamine hydrochloride (117.07 mg, 0.48 mmol) and the mixture was stirred at 0° C. for 3 hours. The reaction was quenched with 1N HCl (5 mL) and then extracted with EtOAc (5 mL) and concentrated to give the crude product. The crude product was purified by prep-HPLC (Boston Green ODS (150 mm×30 mm, 5 μm); A=$H_2O$ (0.075% TFA) and B=$CH_3CN$; 53-73% B over 8 min) to give the impure product. The impure product was purified by prep-TLC (PE:EtOAc=3:1) to give the product (8.25 mg, 20.8 mol, 4% yield) as a solid. $^1H$ NMR (400 MHz, $CDCl_3$) $\delta_H$=7.93 (s, 1H), 7.90-7.86 (m, 1H), 7.80-7.76 (m, 1H), 7.48 (dt, 1H), 7.26-7.20 (m, 1H), 6.37 (br d, 1H), 5.68-5.60 (m, 1H), 4.70-4.63 (m, 2H), 2.57-2.53 (m, 3H), 1.75 (d, 3H). LCMS $R_t$=1.21 min in 2.0 min chromatography, 10-80AB, MS ESI calcd. for $C_{17}H_{16}F_4N_5O_2$ $[M+H]^+$ 398.1, found 398.0.

Example 121. Synthesis of 165

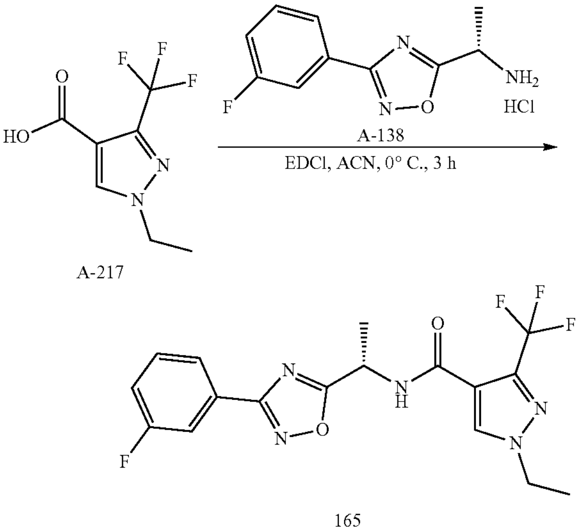

A-217

165

To a mixture of 1-ethyl-3-(trifluoromethyl)pyrazole-4-carboxylic acid (100 mg, 0.48 mmol), EDCI (92.1 mg, 0.48 mmol) in $CH_3CN$ (3 mL) was added (1S)-1-[3-(3-fluorophenyl)-1,2,4-oxadiazol-5-yl]ethanamine hydrochloride (117.07 mg, 0.48 mmol) and the mixture was stirred at 0° C. for 3 hours. The reaction was quenched with 1N HCl (5 mL), extracted with EtOAc (5 mL) and concentrated to give the crude product. The crude product was purified by prep-HPLC (Waters)(Bridge (150 mm×25 mm, 5 μm); A=$H_2O$ (10 mM $NH_4HCO_3$) and B=$CH_3CN$; 40-70% B over 10 min) to give the impure product. The impure product was purified by prep-TLC (PE:EtOAc=3:1) to give the product (4.7 mg, 11.9 μmol, 2% yield) as a solid. $^1H$ NMR (400 MHz, $CDCl_3$) $\delta_H$=8.04 (s, 1H), 7.88 (d, 1H), 7.78 (br d, 1H), 7.47 (dt, 1H), 7.25-7.18 (m, 1H), 6.76 (br s, 1H), 5.65-5.55 (m, 1H), 4.25 (q, 2H), 1.74 (d, 3H), 1.55 (t, 3H). LCMS $R_t$=1.25 min in 2.0 min chromatography, 10-80AB, MS ESI calcd. for $C_{17}H_{16}F_4N_5O_2$ [M+H]$^+$ 398.1, found 398.0.

Example 122. Synthesis of 166

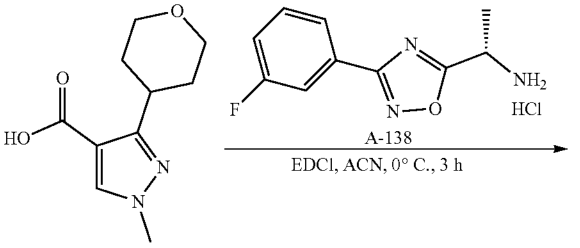

A-218

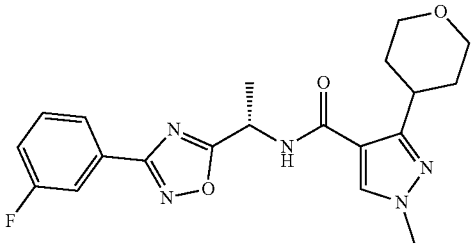

166

To a mixture of 1-methyl-3-tetrahydropyran-4-yl-pyrazole-4-carboxylic acid (100 mg, 0.48 mmol), EDCI (91.19 mg, 0.48 mmol) in $CH_3CN$ (3 mL) was added (1S)-1-[3-(3-fluorophenyl)-1,2,4-oxadiazol-5-yl]ethanamine hydrochloride (115.91 mg, 0.48 mmol) and the mixture was stirred at 0° C. for 3 hours. The reaction was quenched with 1N HCl (5 mL), extracted with EtOAc (5 mL) and concentrated to give the crude product. The crude product was purified by prep-HPLC (Welch Xtimate C18 (150 mm×25 mm, 5 μm); A=$H_2O$ (0.075% TFA) and B=$CH_3CN$; 37-62% B over 7.5 min) then the product was re-dissolved in $CH_2Cl_2$ (5 mL), washed with water (5 mL), brine (5 mL), dried over $Na_2SO_4$, filtered and concentrated to give the product (11.4 mg, 28.5 μmol, 6% yield) as a solid. $^1H$ NMR (400 MHz, $CDCl_3$) $\delta_H$=7.87 (td, 1H), 7.81-7.75 (m, 1H), 7.71 (s, 1H), 7.47 (dt, 1H), 7.25-7.19 (m, 1H), 6.24 (br d, 1H), 5.66-5.57 (m, 1H), 4.08-4.01 (m, 2H), 3.91 (s, 3H), 3.60-3.51 (m, 2H), 3.49-3.40 (m, 1H), 1.99-1.87 (m, 4H), 1.72 (d, 3H). LCMS $R_t$=1.12 min in 2.0 min chromatography, 10-80AB, MS ESI calcd. for $C_{20}H_{23}FN_5O_3$ [M+H]$^+$ 400.2, found 400.1.

Example 123. Synthesis of 167

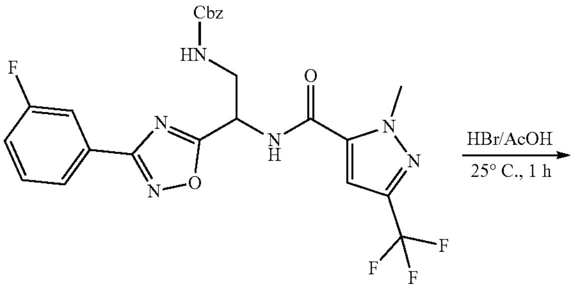

157

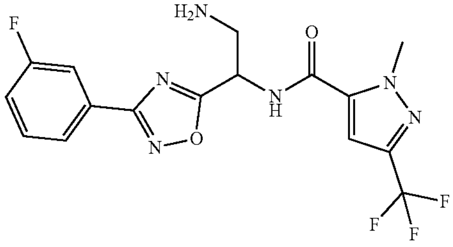

167

To a mixture of benzyl N-[2-[3-(3-fluorophenyl)-1,2,4-oxadiazol-5-yl]-2-[[2-methyl-5-(trifluoromethyl)pyrazole-3-carbonyl]amino]ethyl]carbamate (500 mg, 0.94 mmol) in HBr/AcOH (0.5 mL, 33%), and the mixture was stirred at 25° C. for 1 hour. The mixture was concentrated to give the crude product. The crude product was purified by purified by prep-HPLC (Boston Green ODS (150 mm×30 mm, 5 μm); A=$H_2O$ (0.075% TFA) and B=$CH_3CN$; 33-63% B over 7 min) to give the product (123.9 mg, 0.31 mmol, 33% yield) as a solid. LCMS $R_t$=1.03 min in 2.0 min chromatography, 10-80AB, MS ESI calcd. for $C_{16}H_{15}F_4N_6O_2$ [M+H]$^+$ 399.1, found 399.0. $^1H$ NMR (400 MHz, DMSO-$d_6$) $\delta_H$=7.87 (d, 1H), 7.81-7.71 (m, 1H), 7.64 (dt, 1H), 7.55-7.42 (m, 2H), 5.29 (t, 1H), 4.12 (s, 3H), 3.26-3.08 (m, 2H).

Example 124. Synthesis of 168

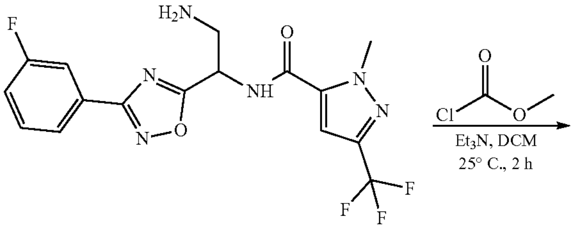

167

-continued

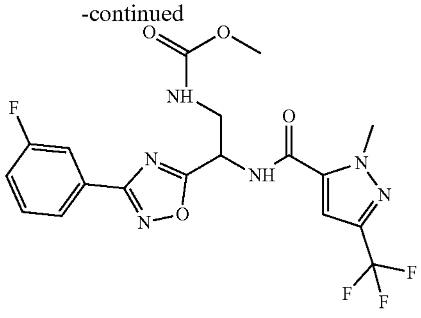

168

To a solution of N-[2-amino-1-[3-(3-fluorophenyl)-1,2,4-oxadiazol-5-yl]ethyl]-2-methyl-5-(trifluoromethyl)pyrazole-3-carboxamide (180 mg, 0.45 mmol) and $Et_3N$ (0.19 mL, 1.36 mmol) in DCM (2 mL) was added methyl carbonochloridate (42.71 mg, 0.45 mmol) and the reaction mixture was stirred at 25° C. for 2 hours. The reaction was quenched with sat. $NH_4Cl$ (10 mL) and then the mixture was extracted with EtOAc (20 mL×2). The combined organic phase was washed with brine (10 mL), dried over $Na_2SO_4$, filtered and concentrated to give the crude product. The crude product was purified by purified by prep-HPLC (Boston Green ODS (150 mm×30 mm, 5 μm); A=$H_2O$ (0.075% TFA) and B=$CH_3CN$; 53-83% B over 9 min) to give the product (10.82 mg, 23.7 μmol, 5% yield) as a solid. LCMS $R_t$=1.26 min in 2.0 min chromatography, 10-80AB, MS ESI calcd. for $C_{18}H_{17}F_4N_6O_4$ $[M+H]^+$ 457.1, found 457.0. $^1H$ NMR (400 MHz, $CDCl_3$) $\delta_H$=8.36 (br d, 1H), 7.87 (d, 1H), 7.78 (td, 1H), 7.47 (dt, 1H), 7.23 (dt, 1H), 7.02 (s, 1H), 5.49 (br d, 1H), 5.24 (br s, 1H), 4.23 (s, 3H), 3.98-3.83 (m, 2H), 3.75 (s, 3H).

Example 125. Synthesis of 169

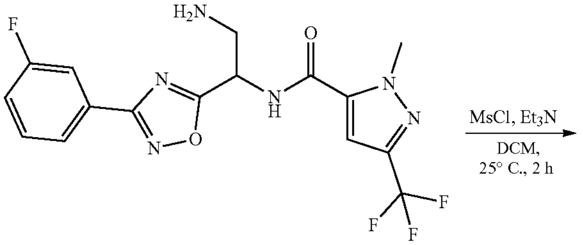

167

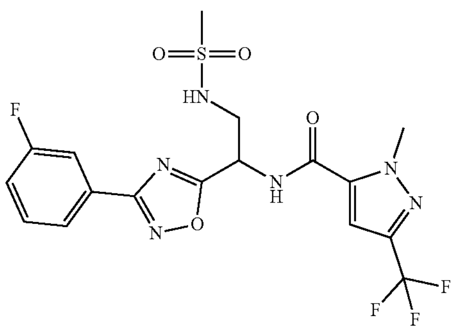

169

To a solution of N-[2-amino-1-[3-(3-fluorophenyl)-1,2,4-oxadiazol-5-yl]ethyl]-2-methyl-5-(trifluoromethyl)pyrazole-3-carboxamide (60 mg, 0.15 mmol) and $Et_3N$ (0.06 mL, 0.45 mmol) in DCM (2 mL) was added methanesulfonyl chloride (34.51 mg, 0.30 mmol) and the reaction mixture was stirred at 25° C. for 2 hours. The reaction was quenched with sat. $NH_4Cl$ (10 mL) and then the mixture was extracted with EtOAc (20 mL×2). The combined organic phase was washed with brine (10 mL), dried over $Na_2SO_4$, filtered and concentrated to give the crude product. The crude product was purified by prep-HPLC (Waters)(Bridge (150 mm×25 mm, 5 μm); A=$H_2O$ (10 mM $NH_4HCO_3$) and B=$CH_3CN$; 40-67% B over 9 min) to give the product (9.54 mg, 19.7 μmol, 13% yield) as a solid. LCMS $R_t$=1.23 min in 2.0 min chromatography, 10-80AB, MS ESI calcd. for $C_{17}H_{17}F_4N_6O_4S$ $[M+H]^+$ 477.1, found 477.0. $^1H$ NMR (400 MHz, $CDCl_3$) $\delta_H$=7.87 (d, 1H), 7.77 (td, 1H), 7.62 (br d, 1H), 7.54-7.44 (m, 1H), 7.26-7.21 (m, 1H), 7.04 (s, 1H), 5.61-5.55 (m, 1H), 5.13 (br t, 1H), 4.24 (s, 3H), 4.00-3.90 (m, 1H), 3.90-3.80 (m, 1H), 3.09 (s, 3H).

Example 126. Synthesis of 170

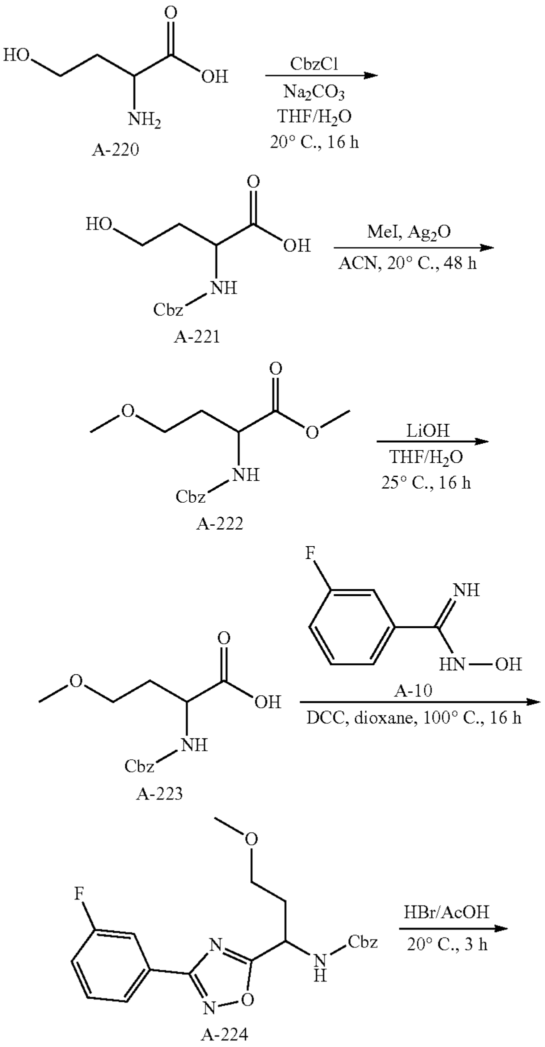

A-220

A-221

A-222

A-223

A-224

-continued

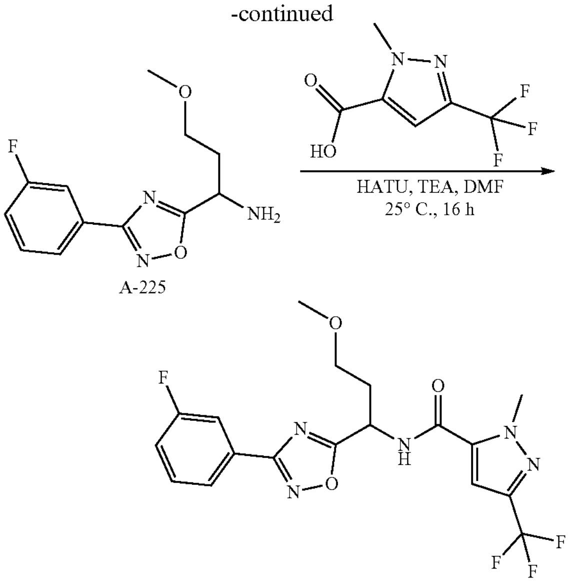

A-225

170

A-221:

To a solution of benzyl carbonochloridate (8.93 g, 52.34 mmol) in 1,4-dioxane (50 mL) at 0° C. was added 2-amino-4-hydroxy-butanoic acid (5 g, 41.97 mmol) in water (200 mL). The mixture was stirred for 0.5 hour then $NaHCO_3$ (9.99 g, 118.95 mmol) was added portionwise and the reaction mixture was stirred at 20° C. for 16 hours. The mixture was washed with EtOAc (50 mL×2). The aqueous layer was acidified to pH 2 with HCl (1N) and extracted with EtOAc (50 mL). The combined organic layers were washed with water (30 mL) and brine (30 mL), dried over anhydrous $Na_2SO_4$, filtered and concentrated to give the crude product (9.68 g) as a an oil. LCMS Rt=0.64 min in 1.5 min chromatography, 5-95AB, MS ESI calcd. $C_{12}H_{16}NO_5$ $[M+H-44]^+$210.1, found 210.1.

A-222:

To a solution of 2-(benzyloxycarbonylamino)-4-hydroxy-butanoic acid (3 g, 10.36 mmol) in MeCN (60 mL) at 0° C. was added $Ag_2O$ (12.01 g, 51.82 mmol) followed by $CH_3I$ (9.68 mL, 155.45 mmol). The reaction mixture was warmed and stirred at 20° C. for 48 hours. The reaction mixture was filtered through Celite, eluted with EtOAc (50 mL×2) and the filtrate was concentrated to give the product. The crude product was purified by flash chromatography on silica gel (DCM in PE=0% to 50%) to give the product (1.25 g, 2 mmol, 22% yield) as an oil. LCMS Rt=2.1 min in 4 min chromatography, 10-80AB, MS ESI calcd. $C_{14}H_{20}NO_5$ $[M+H]^+$ 282.13, found 281.9.

A-223:

To a solution of methyl 2-(benzyloxycarbonylamino)-4-methoxy-butanoate (2.78 g, 9.88 mmol) in THF (28 mL) and water (28 mL) was added $LiOH.H_2O$ (1.24 g, 29.65 mmol). The mixture was stirred at 25° C. for 16 hours. The mixture was washed with EtOAc (10 mL×2). The aqueous layer was acidified to pH ~2 with HCl (1N) and then extracted with EtOAc (50 mL). The combined organic layers were washed with water (30 mL) and brine (20 mL), dried over anhydrous $Na_2SO_4$, filtered and concentrated to give the crude product (780 mg) as a an oil. LCMS Rt=1.76 min in 4 min chromatography, 10-80AB, MS ESI calcd. $C_{13}H_{18}NO_5$ $[M+H]^+$ 268.11, found 267.9.

A-224:

A mixture of 2-(benzyloxycarbonylamino)-4-methoxy-butanoic acid (780 mg, 2.92 mmol), 3-fluoro-N-hydroxy-benzamidine (494.81 mg, 3.21 mmol) and DCC (601.17 mg, 2.92 mmol) in 1,4-dioxane (10 mL) was stirred at 100° C. for 16 hours. After cooling to room temperature, the mixture was concentrated to give the crude product. The crude product was purified by flash chromatography on silica gel (DCM in PE=0% to 40%) to give the product (720 mg, 1.13 mmol, 39% yield) as an oil. LCMS Rt=0.91 min in 1.5 min chromatography, 5-95AB, MS ESI calcd. $C_{20}H_{21}FN_3O_4$ $[M+H]^+$ 386.14, found 386.2.

A-225:

To a solution of benzyl N-[1-[3-(3-fluorophenyl)-1,2,4-oxadiazol-5-yl]-3-methoxy-propyl]carbamate (230 mg, 0.60 mmol) in acetic acid (6 mL) was added HBr/AcOH (0.5 mL, 33%). Then the mixture was stirred at 25° C. for 1 hours. The mixture was concentrated to give the crude product (200 mg, 0.62 mmol) as an oil. LCMS Rt=0.67 min in 1.5 min chromatography, 5-95AB, MS ESI calcd. $C_{12}H_{15}FN_3O_2$ $[M+H]^+$ 252.1, found 252.0.

170:

To a solution of 2-methyl-5-(trifluoromethyl)pyrazole-3-carboxylic acid (265 mg, 0.14 mmol), $Et_3N$ (0.06 mL, 0.46 mmol) and HATU (69.21 mg, 0.18 mmol) in DCM (10 mL) was added 1-[3-(3-fluorophenyl)-1,2,4-oxadiazol-5-yl]-3-methoxy-propan-1-amine (200 mg, 0.09 mmol). Then the mixture was stirred at 25° C. for 16 hours. The mixture was diluted with $H_2O$ (10 mL) and extracted with DCM (10 mL×2). The combined organic phase was washed with brine (10 mL), dried over $Na_2SO_4$, filtered and concentrated to give the crude product. The crude product was purified by prep-HPLC (Waters)(Bridge (150 mm×25 mm, 5 μm); A=$H_2O$ (10 mM $NH_4HCO_3$) and B=$CH_3CN$; 43-73% B over 10 min) to give the product (22.83 mg, 0.05 mmol) as a an oil. $^1H$ NMR (400 MHz $CDCl_3$) $\delta_H$=7.95-7.85 (m, 2H), 7.82-7.75 (m, 1H), 7.47 (dt, 1H), 7.26-7.19 (m, 1H), 6.82 (s, 1H), 5.67-5.58 (m, 1H), 4.23 (s, 3H), 3.71-3.62 (m, 1H), 3.61-3.52 (m, 1H), 3.43 (s, 3H), 2.51-2.39 (m, 1H), 2.38-2.29 (m, 1H). LCMS Rt=1.35 min in 2.0 min chromatography, 10-80AB, MS ESI calcd. $C_{18}H_{18}F_4N_5O_3$ $[M+H]^+$ 428.13, found 428.0.

Example 127. Synthesis of 171

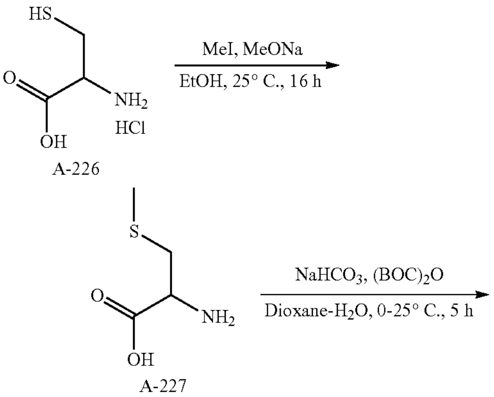

A-226

A-227

-continued

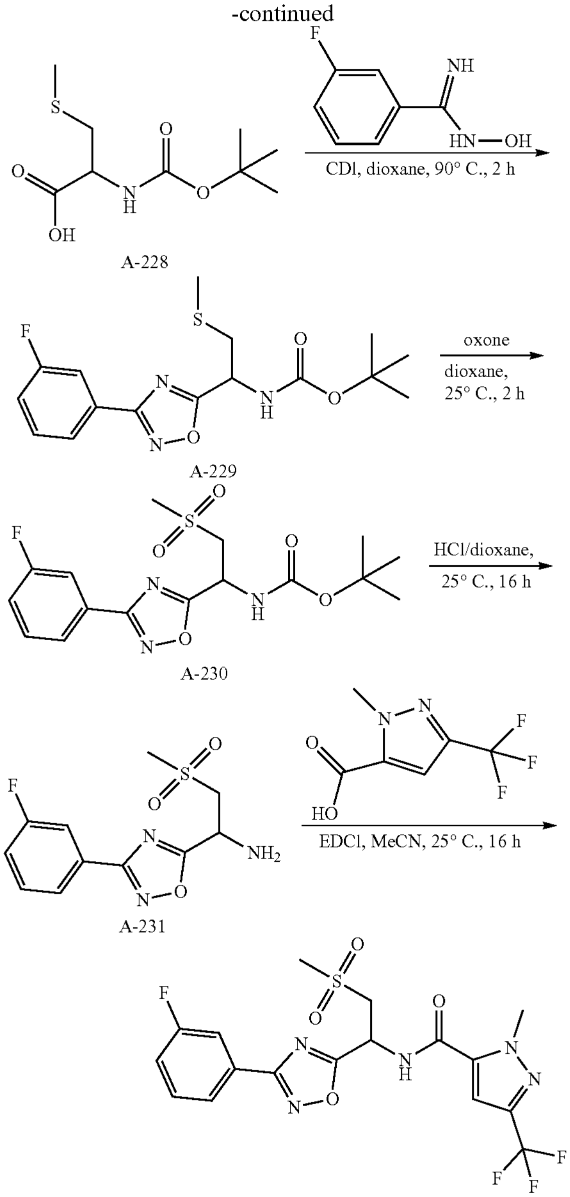

A-228

A-229

A-230

A-231

171

A-227:

To a mixture of 2-amino-3-sulfanyl-propanoic acid hydrochloride (3 g, 19.03 mmol, 1.00 eq) in methanol (20 mL) was added NaOMe (4.11 g, 76.13 mmol, 4.00 eq), and the mixture was stirred at 25° C. for 1 h and then MeI (4.05 g, 28.55 mmol, 1.5 eq) was added. The mixture was stirred at 25° C. for 16 hours under $N_2$. Isopropyl ether (100 mL) was added and the precipitated solid was collected by filtration, washed with cold ethanol and dried to give the product (3 g) as a solid. $^1$HNMR (400 MHz, $D_2O$) 3.93-3.85 (m, 1H), 3.10-2.40 (m, 2H), $\delta_H$=2.13 (s, 3H).

A-228:

To a mixture of 2-amino-3-methylsulfanyl-propanoic acid (2 g, 14.8 mmol, 1 eq) and $NaHCO_3$ (4.97 g, 59.18 mmol, 4 eq) in 1,4-dioxane (20 mL) and $H_2O$ (5 mL) was added di-tert butyl dicarbonate (6.46 g, 29.59 mmol, 1 eq), and the mixture was stirred at 25° C. for 5 hours. The reaction mixture quenched with sat. $NaHCO_3$ and extracted with EtOAc (50 mL×3). The combined organic phrase was washed with brine (20 mL), dried over $Na_2SO_4$, filtered and concentrated to give the product (2.7 g). $^1$HNMR (400 MHz, $CDCl_3$) $\delta_H$=10.42-11.05 (m, 1H) 5.30-5.61 (m, 1H) 4.13-4.64 (m, 1H) 2.69-3.08 (m, 2H) 2.09 (s, 3H) 1.32-1.43 (m, 9H).

A-229:

To a mixture of 2-(tert-butoxycarbonylamino)-3-methyl-sulfanyl-propanoic acid (500 mg, 2.12 mmol, 1 eq) in 1,4-dioxane (5 mL) was added CDI (1.37 g, 8.5 mmol, 4 eq) and the mixture was stirred at 25° C. for 30 min and then 3-fluoro-N-hydroxy-benzamidine (655.08 mg, 4.25 mmol) was added and the mixture was stirred at 25° C. for 2 hours under $N_2$. The mixture was warmed to 90° C. and stirred for 2 hours under N2. After cooling to 25° C., the mixture was extracted with EtOAc (30 mL×2). The combined organic phase was washed with brine (15 mL), dried over $Na_2SO_4$, filtered and concentrated to give the product (290 mg). LCMS $R_t$=1.01 min in 1.5 min chromatography, 5-95AB, MS ESI calcd. for $C_{12}H_{12}FN_3O_3S$ $[M-56+H]^+$297.9, found 297.9.

A-230:

To a mixture of tert-butyl N-[1-[3-(3-fluorophenyl)-1,2,4-oxadiazol-5-yl]-2-methylsulfanyl-ethyl]carbamate (290 mg, 0.82 mmol) in 1,4-dioxane (5 mL) and water (2 mL) was added oxone (1 g, 1.64 mmol), and the mixture was stirred at 25° C. for 2 hours. Then the mixture was concentrated and the residue was extracted with EtOAc (30 mL×3). The combined organic phase was washed with brine (50 mL), dried over $NaSO_4$, filtered and concentrated to give the product (330 mg). LCMS $R_t$=0.92 min in 1.5 min chromatography, 5-95AB, MS ESI calcd. for $C_{16}H_{20}FN_3O_5S$ Na $[M+Na]^+$408.0, found 408.0.

A-231:

A mixture of tert-butyl N-[1-[3-(3-fluorophenyl)-1,2,4-oxadiazol-5-yl]-2-methylsulfonyl-ethyl]carbamate (330 mg, 0.86 mmol) in 4M HCl/1,4-dioxane (3 M, 6 mL) was stirred at 25° C. under $N_2$ for 16 hours to give a mixture. The reaction was quenched with sat. $NaHCO_3$ (20 mL) and then extracted with EtOAc (30 mL×2). The combined organic phase was washed with brine (15 mL), dried over $Na_2SO_4$, filtered and concentrated to give the product (300 mg). $^1$HNMR (400 MHz, $CDCl_3$) $\delta_H$=9.24-9.68 (m, 2H) 7.86-7.92 (m, 1H) 7.75-7.81 (m, 1H) 7.64-7.73 (m, 1H) 7.47-7.55 (m, 1H) 5.31-5.60 (m, 1H) 4.08-4.18 (m, 2H) 3.18-3.27 (m, 3H).

171:

To a mixture of 2-methyl-5-(trifluoromethyl)pyrazole-3-carboxylic acid (150 mg, 0.53 mmol, 1 eq) in MeCN (5 mL) was added EDCI (302.38 mg, 1.58 mmol, 3 eq) and the mixture was stirred at 25° C. for 5 min and then 1-[3-(3-fluorophenyl)-1,2,4-oxadiazol-5-yl]-2-methylsulfonyl-ethanamine (153 mg, 0.79 mmol, 1.5 eq) was added. The mixture was stirred at 25° C. for 16 hours under $N_2$. The reaction mixture was extracted with EtOAc (30 mL×3). The combined organic phrase was washed with brine (20 mL), dried over $Na_2SO_4$, filtered and concentrated to give the crude product, the crude product was purified by flash chromatography on silica gel (EtOAc in PE, 0% to 10%) to give the product (110 mg). The impure product was triturated from n-hexane (5 mL) to give the product (86.28 mg, 0.19 mmol). $^1$H NMR (400 MHz, $CDCl_3$) $\delta_H$=7.84-7.95 (m, 1H) 7.72-7.82 (m, 1H) 7.43-7.66 (m, 2H) 7.23-7.27 (m, 1H) 6.90-7.06 (m, 1H) 5.83-6.09 (m, 1H) 4.19-4.28 (m, 3H) 4.05-4.15 (m, 1H) 3.84-3.96 (m, 1H) 2.98-3.09 (m, 3H). LCMS $R_t$=1.26 min in 2.0 min chromatography, 10-80AB, MS ESI calcd. for $C_{17}H_{16}F_4N_5O_4S$ $[M+H]^+$ 462.0, found 462.0.

Example 128. Synthesis of 172, 173, 174, and 175

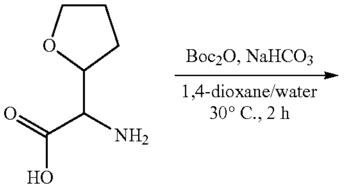

A-232

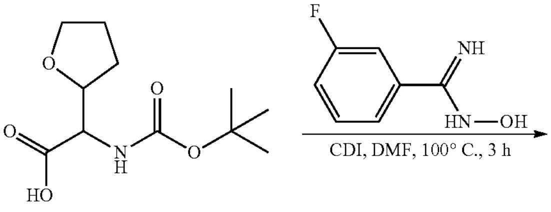

A-233

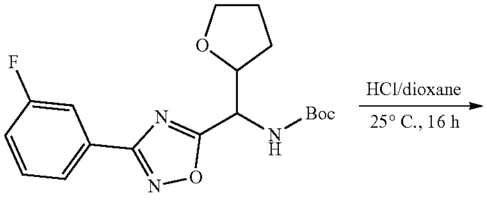

A-234

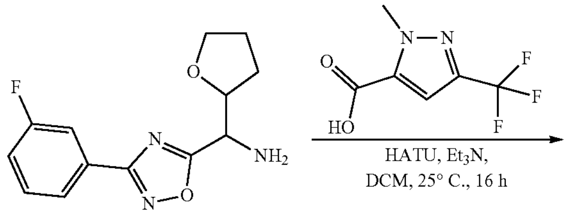

A-235

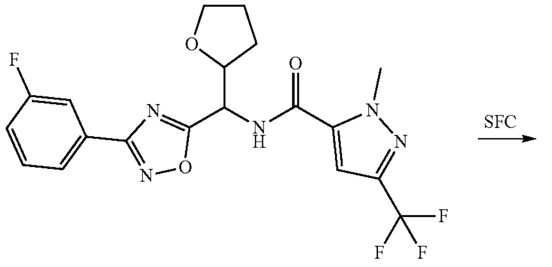

A-236

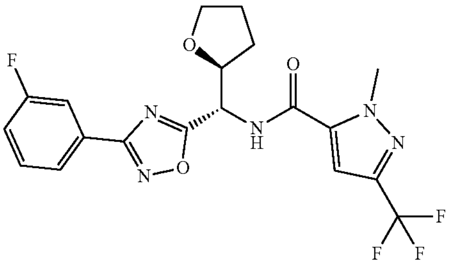

172

-continued

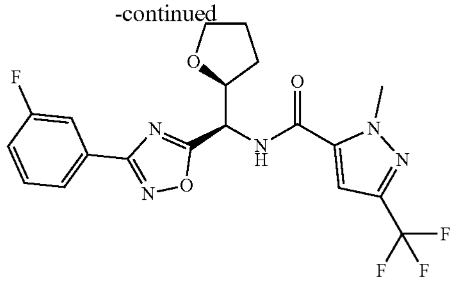

173

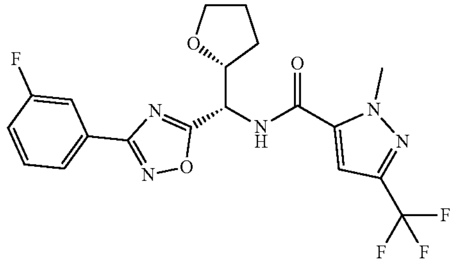

174

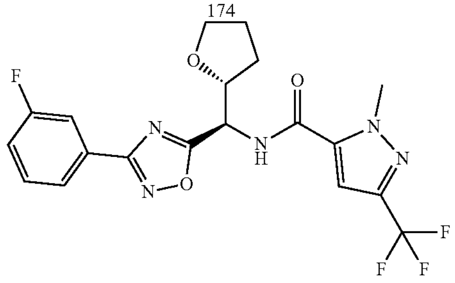

175

A-233:

To a solution of 2-amino-2-tetrahydrofuran-2-yl-acetic acid (300 mg, 2.07 mmol) and $NaHCO_3$ (434.06 mg, 5.17 mmol) in 1,4-dioxane (4 mL) and water (1 mL) was added $Boc_2O$ (676.58 mg, 3.1 mmol) at 25° C. The mixture was stirred at 30° C. for 2 hours. The mixture was poured into water (30 mL) and acidified with 30% citric acid to pH ~2 and extracted with EtOAc (20 mL×2). The combined organic phase was washed with brine (30 mL), dried over $Na_2SO_4$ filtered and concentrated to give crude product (500 mg) as an oil. $^1$H NMR (400 MHz, $CDCl_3$) $\delta_H$=5.24 (d, 1H), 4.47-4.26 (m, 1H), 4.16-4.07 (m, 1H), 4.02-3.91 (m, 1H), 3.89-3.76 (m, 1H), 2.15-1.88 (m, 4H), 1.46 (d, 9H).

A-234:

To a solution of 2-(tert-butoxycarbonylamino)-2-tetrahydrofuran-2-yl-acetic acid (400 mg, 1.63 mmol) in 1,4-dioxane (6 mL) was added CDI (528.89 mg, 3.26 mmol) and the mixture was stirred at 25° C. for 30 mins. Then 3-fluoro-N-hydroxy-benzamidine (301.66 mg, 1.96 mmol) was added to the solution and the mixture was stirred at 25° C. for 3 hours and then stirred at 100° C. for 16 hours. The mixture was cooled to room temperature and poured into water (30 mL) and extracted with EtOAc (20 mL×2). The combined organic phase was washed with brine (30 mL), dried over $Na_2SO_4$ filtered and concentrated to give the crude product. The crude was purified by flash chromatography on silica gel (EtOAc in PE=0% to 20%) to give the product (320 mg, 0.80 mmol, 49% yield) as an oil. LCMS Rt=0.92 min in 1.5 min chromatography, 5-95AB MS ESI calcd. For $C_{14}H_{15}FN_3O_4$ $[M-tBu+H]^+$ 308.16, found 308.2.

A-235:

To tert-butyl N-[[3-(3-fluorophenyl)-1,2,4-oxadiazol-5-yl]-tetrahydrofuran-2-yl-methyl] carbamate (320 mg, 0.88 mmol) was added 4M HCl/1,4 dioxane (5 mL, 20 mmol) at 25° C. The mixture was stirred at 25° C. for 16 hours. The reaction mixture was concentrated to give the crude product (263 mg) as a solid. LCMS Rt=0.75 min in 1.5 min chromatography, 5-95AB, MS ESI calcd. For $C_{13}H_{15}FN_3O_2$ $[M+H]^+$ 264.11, found 263.9.

A-236:

To a solution of 2-methyl-5-(trifluoromethyl)pyrazole-3-carboxylic acid (204.39 mg, 1.05 mmol) and TEA (0.43 mL, 3.07 mmol) in DCM (5 mL) was added HATU (500.47 mg, 1.32 mmol) at 25° C. The mixture was stirred at 25° C. for 15 mins and then [3-(3-fluorophenyl)-1,2,4-oxadiazol-5-yl]-tetrahydrofuran-2-yl-methanamine hydrochloride (263 mg, 0.88 mmol) was added to the solution. The mixture was stirred at 25° C. for 16 hrs. The mixture was poured into water (30 mL) and extracted with DCM (10 mL×2). The combined organic phase was washed with brine (30 mL), dried over $Na_2SO_4$ filtered and concentrated to give the crude product. The crude was purified by flash chromatography on silica gel (EtOAc in PE=0% to 20%) to give the product, a mixture of 4 diastereomers (260 mg, 0.58 mmol, 66% yield) as an oil. LCMS Rt=1.02 min in 1.5 min chromatography, 5-95AB, MS ESI calcd. For $C_{19}H_{18}F_4N_5O_3$ $[M+H]^+$ 440.1, found 440.0.

172, 173, 174, and 175:

Analytical SFC: Analysis by SFC (Phenomenex Cellulose-2 (100 mm×4.6 mm, 3 μm); mobile phase: A: $CO_2$ B: methanol (0.05% DEA); gradient: from 5% to 40% of B in 4 min and hold 40% for 2.5 min, then 5% of B for 1.5 min; flow rate: 2.8 mL/min, column temp: 35° C.; ABPR: 1500 psi). Showed four peaks at =1.56 min, 1.64 min, 2.04 min and 2.27 min). The isomers were partially separated by SFC (Phenomenex Cellulose-2 (250 mm×30 mm, 5 μm); A=$CO_2$ and B=MeOH (0.1% $NH_3H_2O$); 35° C.; 60 mL/min; 15% B; 11 min run; 150 injections, Rt of peak 1=4.4 min, peak 2=5.3 min, peak 3=7.4 min and peak 4=9.2 min) Stereoisomers 1 and 2 were randomly assigned as 172 and 173 (65 mg) (Rt=1.56 and 1.64 min in analytical SFC) as a solid, and the stereoisomer isomer 3, randomly assigned as 174 (32.25 mg, 0.074 mmol) (Rt=2.04 min in analytical SFC) as a solid and the stereoisomer 4, randomly assigned as 175 (50 mg, impure) as a solid. 175 (50 mg, impure) was further purified by SFC (Phenomenex Cellulose-2 (250 mm×30 mm, 5 μm); A=$CO_2$ and B=MeOH (0.1% $NH_3H_2O$); 35° C.; 60 mL/min; 15% B; 11 min run; 80 injections, Rt=9.2 min) to give the isomer 4 (26.86 mg, 0.06 mmol) (Rt=2.27 min in analytical SFC) as a solid. Separation for Stereoisomers 1 and 2 (which were randomly assigned as 172 and 173)

Analysis by SFC (Daicel CHIRALPAK AD-3 (150 mm×4.6 mm, 3 μm) mobile phase: A: $CO_2$ B: ethanol (0.05% DEA); gradient: from 5% to 40% of B in 5 min and from 40% to 5% of B in 0.5 min, hold 5% of B for 1.5 min; flow rate: 2.5 mL/min, column temp: 35° C.). Showed two peaks at =1.94 min and 2.39 min). The mixture of isomers 1 and 2 was separated by SFC (Phenomenex Amylose-1 (250 mm×30 mm, 5 μm); A=$CO_2$ and B=0.1% $NH_3H_2O$ EtOH; 35° C.; 50 mL/min; 15% B; 9 min run; 80 injections, Rt of peak 1=4.7 min and peak 2=6.6 min) to give the isomer 1, randomly assigned as 173 (28.78 mg, 0.065 mmol) (Rt=1.94 min in analytical SFC) as a solid, and isomer 2, randomly assigned as 172 (28.63 mg, 0.065 mmol) (Rt=2.39 min in analytical SFC) as a solid.

172:

$^1$H NMR (400 MHz, $CDCl_3$) $\delta_H$=7.90 (d, 1H), 7.80 (d, 1H), 7.51-7.42 (m, 1H), 7.25-7.21 (m, 1H), 7.09 (d, 1H), 6.98 (s, 1H), 5.58 (dd, 1H), 4.44-4.39 (m, 1H), 4.21 (s, 3H), 3.78 (t, 2H), 2.25-2.13 (m, 1H), 2.12-2.01 (m, 1H), 1.97-1.87 (m, 1H), 1.73-1.62 (m, 1H). LCMS $R_t$=1.36 min in 2.0 min chromatography, 10-80AB, MS ESI calcd. for $C_{19}H_{18}F_4N_5O_3$ $[M+H]^+$ 440.1, found 439.9.

173:

$^1$H NMR (400 MHz, $CDCl_3$) $\delta_H$=7.88 (d, 1H), 7.79 (d, 1H), 7.49-7.44 (m, 1H), 7.25-7.18 (m, 1H), 6.95 (s, 1H), 6.88 (d, 1H), 5.58 (dd, 1H), 4.56-4.52 (m, 1H), 4.24 (s, 3H), 4.04-3.96 (m, 1H), 3.90-3.81 (m, 1H), 2.24-2.14 (m, 1H), 2.07-1.96 (m, 2H), 1.92-1.80 (m, 1H). LCMS $R_t$=1.37 min in 2.0 min chromatography, 10-80AB, MS ESI calcd. for $C_{19}H_{18}F_4N_5O_3$ $[M+H]^+$ 440.1, found 439.9.

174:

$^1$H NMR (400 MHz, $CDCl_3$) $\delta_H$=7.88 (d, 1H), 7.80 (d, 1H), 7.49-7.44 (m, 1H), 7.25-7.18 (m, 1H), 6.96 (s, 1H), 6.89 (d, 1H), 5.59 (dd, 1H), 4.56-4.52 (m, 1H), 4.24 (s, 3H), 4.03-3.96 (m, 1H), 3.90-3.81 (m, 1H), 2.24-2.13 (m, 1H), 2.06-1.95 (m, 2H), 1.91-1.82 (m, 1H). LCMS $R_t$=1.36 min in 2.0 min chromatography, 10-80AB, MS ESI calcd. for $C_{19}H_{18}F_4N_5O_3$ $[M+H]^+$ 440.1, found 439.9.

175:

$^1$H NMR (400 MHz, $CDCl_3$) $\delta_H$=7.90 (d, 1H), 7.80 (d, 1H), 7.51-7.45 (m, 1H), 7.25-7.21 (m, 1H), 7.10 (d, 1H), 6.98 (s, 1H), 5.59 (dd, 1H), 4.44-4.39 (m, 1H), 4.21 (s, 3H), 3.78 (t, 2H), 2.23-2.15 (m, 1H), 2.10-2.03 (m, 1H), 1.97-1.87 (m, 1H), 1.72-1.63 (m, 1H). LCMS $R_t$=1.35 min in 2.0 min chromatography, 10-80AB, MS ESI calcd. for $C_{19}H_{18}F_4N_5O_3$ $[M+H]^+$ 440.1, found 440.0.

Example 129. Synthesis of 176

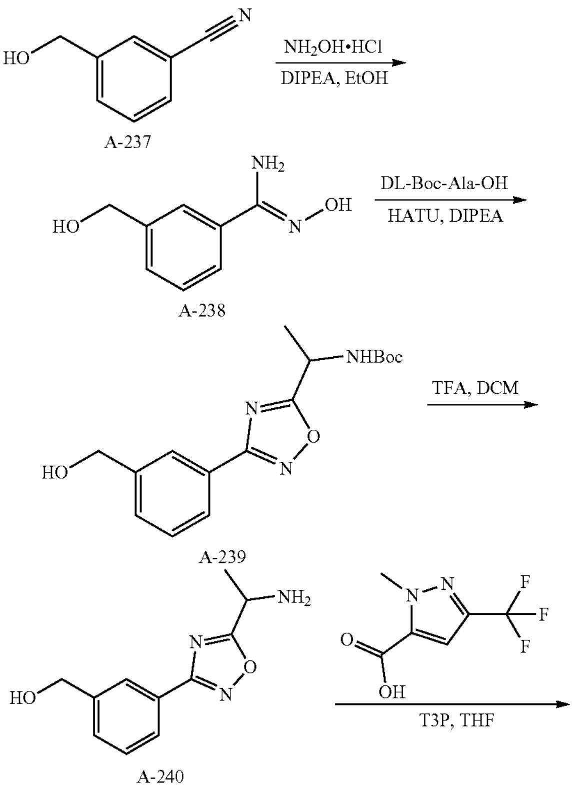

-continued

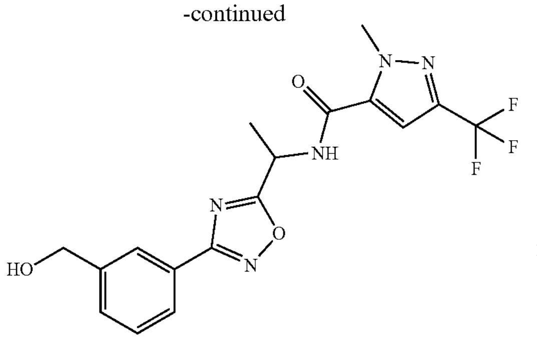

176

Synthesis of N'-hydroxy-3-(hydroxymethyl)benzimidamide (A-238)

To a stirred solution of 3-(hydroxymethyl)benzonitrile (2.0 g, 14.72 mmol) in ethanol (25 mL) was added hydroxylamine hydrochloride (2.56 g, 36.8 mmol) and DIPEA (6.14 mL, 44.16 mmol) at room temperature under nitrogen. The reaction mixture was heated at 100° C. for 16 h. The reaction mixture was cooled to room temperature and concentrated under reduced pressure. The residue was treated with water (25 mL) and extracted with EtOAc (2×25 mL). The organic layer was washed with brine (20 mL), dried over $Na_2SO_4$ and concentrated to afford compound A-238 (1.47 g). The crude compound was used for the next step without further purification.

Synthesis of tert-butyl (1-(3-(3-(hydroxymethyl) phenyl)-1,2,4-oxadiazol-5-yl)ethyl)carbamate (A-239)

To a stirred solution of compound A-238 (1.47 g, 8.86 mmol) in DMF (25 mL) was added DL-Boc-alanine (1.68 g, 8.86 mmol), DIPEA (1.85 mL, 13.29 mmol) and HATU (5.05 g, 13.29 mmol) at 10° C. under nitrogen. The reaction mixture was slowly warmed to room temperature, stirred for 2 h and then heated at 110° C. for 6 h. The reaction mixture was cooled to room temperature, diluted with water (50 mL) and extracted with ethyl acetate (2×25 mL). The organic layer was washed with brine (2×20 mL), dried over $Na_2SO_4$ and concentrated. The crude product was purified by column chromatography on silica gel with 25% EtOAc/PE to afford compound A-239 (1.61 g, 5.05 mmol, 57% yield). $^1$H NMR (400 MHz, DMSO-$d_6$): δ 7.99 (s, 1H), 7.86 (m, 1H), 7.79 (d, 1H), 7.51 (m, 2H), 5.39 (t, 1H), 4.99-4.96 (m, 1H), 4.59 (d, 2H), 1.52 (d, 3H), 1.41 (s, 9H).

Synthesis of (3-(5-(1-aminoethyl)-1,2,4-oxadiazol-3-yl)phenyl)methanol (A-240)

To a stirred solution of compound A-239 (1.61 g, 5.05 mmol) in DCM (30 mL) was added TFA (1.85 mL) at 0° C. under nitrogen. The reaction mixture was slowly warmed to room temperature and stirred for 12 h. The mixture was concentrated under reduced pressure and treated with ice water (20 mL). The mixture was treated with 10% $NaHCO_3$ solution (20 mL) and extracted with DCM (2×30 mL). The organic layer was washed with brine (20 mL), dried over $Na_2SO_4$ and concentrated to afford compound A-240 (0.71 g). The crude compound was used for the next step without further purification.

Synthesis of N-(1-(3-(3-(hydroxymethyl)phenyl)-1,2,4-oxadiazol-5-yl)ethyl)-1-methyl-3-(trifluoromethyl)-1H-pyrazole-5-carboxamide (176)

To a solution of 1-methyl-3-(trifluoromethyl)-1H-pyrazole-5-carboxylic acid (500 mg, 2.52 mmol) in DCM (10 mL) was added compound A-240 (663 mg, 3.03 mmol) followed by TEA (1.05 mL, 7.57 mmol) and T3P (50% in ethyl acetate, 3.0 mL, 5.05 mmol) at 10° C. under nitrogen. The reaction mixture was slowly warmed to room temperature and stirred for 4 h. The reaction mixture was diluted with water (25 mL) and extracted with dichloromethane (2×25 mL). The organic layer was washed with brine (20 mL), dried over $Na_2SO_4$ and concentrated. The crude product was purified by flash column chromatography on silica get with 40% EtOAc/pet ether to afford 176 (430 mg, 1.08 mmol, 43% yield) as a liquid. HPLC: Rt 4.19 min, 99.8%; Column: XBridge C8 (50×4.6) mm, 3.5 μm); Mobile phase: A: 0.1% TFA in water, B: 0.1% TFA in ACN; Flow Rate: 2.0 mL/min. LCMS: 396.2 (M+H), Rt 2.03 min, Column: ZORBAX XDB C-18 (50×4.6 mm), 3.5 μm, Mobile Phase: A: 0.1% HCOOH in water:ACN (95:5), B: ACN; Flow Rate: 1.5 mL/min. $^1$H NMR (400 MHz, DMSO-$d_6$): δ 9.52 (brs, 1H), 8.05 (s, 1H), 7.94-7.90 (m, 1H), 7.57-7.54 (m, 2H), 7.51 (s, 1H), 5.54-5.49 (m, 1H), 5.44 (brs, 1H), 4.64 (s, 2H), 4.19 (s, 3H), 1.73 (d, 3H).

Example 130. Synthesis of 177

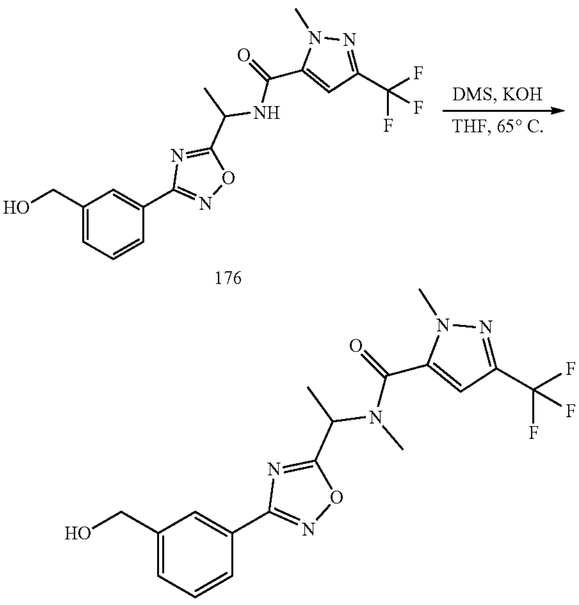

176

177

Synthesis of N-(1-(3-(3-(hydroxymethyl)phenyl)-1,2,4-oxadiazol-5-yl)ethyl)-N,1-dimethyl-3-(trifluoromethyl)-1H-pyrazole-5-carboxamide (177)

To a stirred solution of compound 176 (150 mg, 0.38 mmol) in THF (9.0 mL) was added dimethyl sulphate (95 mg, 0.76 mmol) and KOH (64 mg, 1.14 mmol) under nitrogen atmosphere. The reaction mixture was heated at 65° C. for 3 h. The reaction mixture was cooled to room temperature, treated with water (25 mL) and extracted with ethyl acetate (2×25 mL). The organic layer was washed with brine (20 mL), dried over $Na_2SO_4$ and concentrated. The crude was purified by flash column chromatography on silica get with 50% EtOAc/PE to afford 177 (38 mg, 0.092 mmol, 24% yield) as a liquid. HPLC: Rt 4.31 min, 99.8%; Column: XBridge C8 (50×4.6) mm, 3.5 μm; Mobile phase: A: 0.1% TFA in water, B: 0.1% TFA in ACN; Flow Rate: 2.0 mL/min. LCMS: 410.2 (M+H), Rt 1.96 min; Column: ZORBAX XDB C-18 (50×4.6 mm), 3.5 μm, Mobile Phase: A: 0.1% HCOOH in water:ACN (95:5), B: ACN; Flow Rate: 1.5 mL/min. $^1H$ NMR (400 MHz, DMSO-$d_6$): δ 8.01 (s, 1H), 7.89 (m, 1H), 7.56-7.53 (m, 2H), 7.22 and 7.09 (s, 1H), 5.90 and 5.59 (m, 1H), 5.39 (t, 1H), 4.61-4.57 (m, 2H), 3.98 (s, 3H), 3.08 and 2.93 (s, 3H), 1.76 (d, 3H).

Example 131. Synthesis of 178

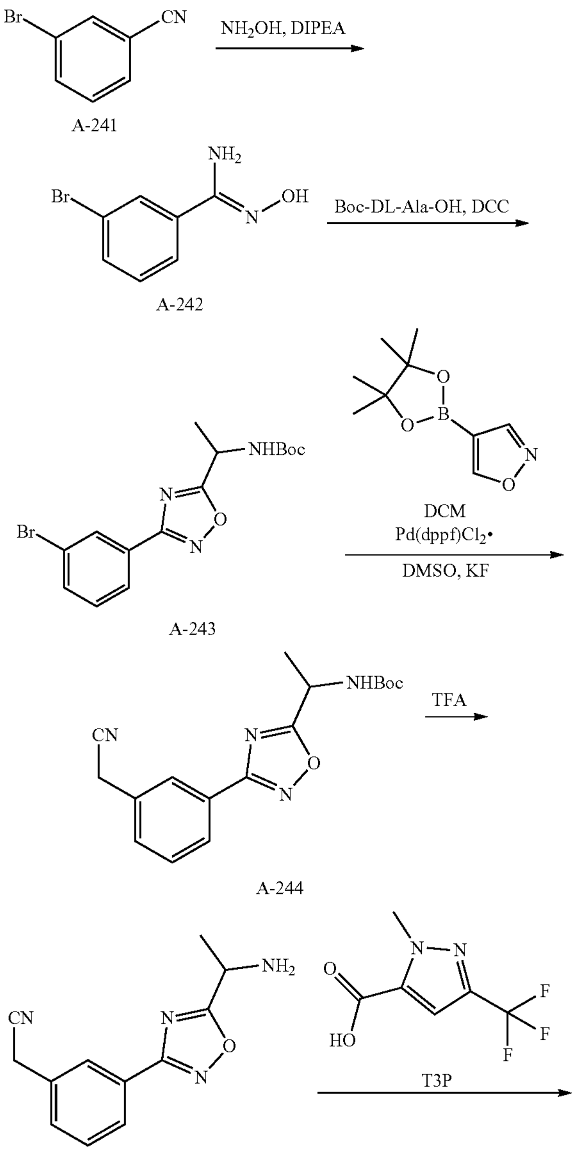

A-241

A-242

A-243

A-244

A-245

-continued

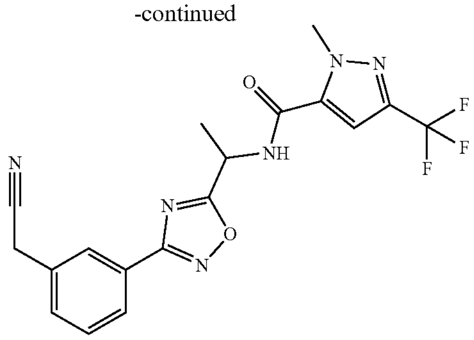

178

Synthesis of 3-bromo-N'-hydroxybenzimidamide (A-242)

To a solution of 3-bromobenzonitrile (10 g, 55.25 mmol) in ethanol (200 mL) was added hydroxylamine hydrochloride (11.45 g, 164.82 mmol) followed by DIPEA (29.25 mL, 164.82 mmol). The reaction mixture was heated at 70° C. for 16 h. The reaction mixture was cooled to room temperature and concentrated. The mixture was treated with water (100 mL) and extracted with ethyl acetate (2×150 mL). The organic layer was washed with brine (40 mL), dried over $Na_2SO_4$ and concentrated to afford compound A-242 (10 g). It was used for the next step without further purification.

Synthesis of tert-butyl (1-(3-(3-bromophenyl)-1,2,4-oxadiazol-5-yl)ethyl)carbamate (A-243)

To a solution of compound A-242 (2.0 g, 9.3 mmol) in 1,4-dioxane (40 mL) was added 2-(tert-butoxycarbonylamino)propanoic acid (1.76 g, 9.3 mmol) followed by DCC (2.1 g, 10.23 mmol). The reaction mixture was heated at 100° C. for 16 h. The reaction mixture was cooled to room temperature and concentrated. The residue was treated with water (30 mL) and extracted with EtOAc (2×50 mL). The organic layer was washed with brine (40 mL), dried over $Na_2SO_4$ and concentrated. The crude was purified by column chromatography on silica gel with 25% EtOAc/PE to afford compound A-243 (1.3 g, 3.54 mmol, 38% yield). LCMS: 366.0 (M−H) and 368.1 (M+2-H). Rt 2.73 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of tert-butyl (1-(3-(3-(cyanomethyl)phenyl)-1,2,4-oxadiazol-5-yl)ethyl)carbamate (A-244)

To a PTFE screw-capped vial containing 4-(4,4,5,5-tetramethyl-1,3,2-dioxaborolan-2-yl)isoxazole (0.83 g, 4.24 mmol) and compound A-243 (1.3 g, 3.54 mmol) in DMSO (20 mL) was added KF (0.62 g, 10.59 mmol) and water (0.19 mL, 10.62 mmol). The reaction mixture was degassed and Pd(dppf)$Cl_2$.DCM (0.29 g, 0.35 mmol) was added under nitrogen. The reaction mixture was heated at 130° C. for 16 h. The reaction mixture was cooled to room temperature and filtered over celite. The filtrate was treated with saturated NaCl solution (25 mL) and extracted with EtOAc (2×25 mL). The organic layer was washed with brine (20 mL), dried over $Na_2SO_4$ and concentrated. The crude was taken up in methanol (10 mL) and KF (0.62 g, 10.59 mmol) was added. The reaction mixture was stirred at room temperature for 3 h. The mixture was concentrated, the residue was treated with water (20 mL) and extracted with EtOAc (2×25 mL). The organic layer was washed with brine (20 mL), dried over $Na_2SO_4$ and concentrated. The crude was purified by column chromatography on silica gel with 20% EtOAc/PE to afford compound A-244 (242 mg, 0.74 mmol, 20% yield). LCMS: 327.1 (M−H), Rt 2.20 min; Column: ZORBAX XDB C-18 (50×4.6 mm), 3.5 μm. Mobile Phase: A: 0.1% HCOOH in water:ACN (95:5), B: ACN; Flow Rate: 1.5 mL/min.

Synthesis of 2-(3-(5-(1-aminoethyl)-1,2,4-oxadiazol-3-yl)phenyl)acetonitrile (A-245)

To a stirred solution of compound A-244 (120 mg, 0.37 mmol) in DCM (4 mL) was added TFA (0.5 mL) at 0° C. The reaction mixture was slowly warmed to room temperature and stirred for 8 h. The mixture was concentrated under reduced pressure and treated with saturated $NaHCO_3$ solution (10.0 mL) and extracted with EtOAc (2×20 mL). The organic layer was washed with brine (10 mL), dried over $Na_2SO_4$ and concentrated to afford compound A-245 (66 mg). It was used for the next step without further purification.

Synthesis of N-(1-(3-(3-(cyanomethyl)phenyl)-1,2,4-oxadiazol-5-yl)ethyl)-1-methyl-3-(trifluoromethyl)-1H-pyrazole-5-carboxamide (178)

To a stirred solution of 1-methyl-3-(trifluoromethyl)-1H-pyrazole-5-carboxylic acid (62 mg, 0.32 mmol) in THF (10 mL) was added T3P (0.35 mL, 0.58 mmol) and TEA (0.12 mL, 0.87 mmol). The reaction mixture was stirred at room temperature for 10 min and compound A-245 (66 mg, 0.27 mmol) was added. The reaction mixture was stirred for 16 h at room temperature. The reaction mixture was concentrated, treated with water (30 mL) and extracted with EtOAc (2×25 mL). The organic layer was washed with brine (20 mL), dried over $Na_2SO_4$ and concentrated. The crude was purified by column chromatography on silica get with 45% EtOAc/PE to afford 178 (26 mg, 0.06 mmol, 21% yield) as a solid. HPLC: Rt 4.78 min, 98.4%; Column: XBridge C8 (50×4.6) mm, 3.5 μm; Mobile phase: A: 0.1% TFA in water, B: 0.1% TFA in ACN; Flow Rate: 2.0 mL/min. LCMS: 405.1 (M+H), Rt 2.41 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, $CDCl_3$): δ 8.09-8.07 (m, 2H), 7.56-7.54 (m, 2H), 6.96 (s, 1H), 6.73 (d, 1H), 5.67-5.59 (m, 1H), 4.25 (s, 3H), 3.86 (s, 2H), 1.79 (d, 3H).

Example 132. Synthesis of 179

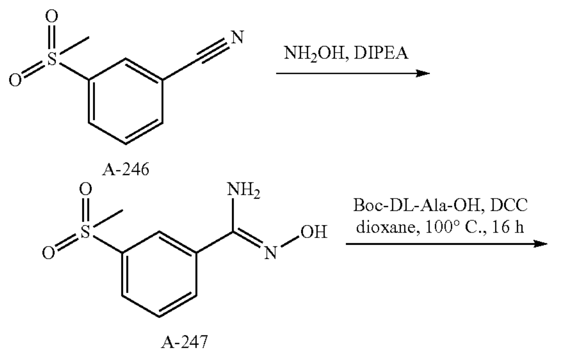

A-246

A-247

-continued

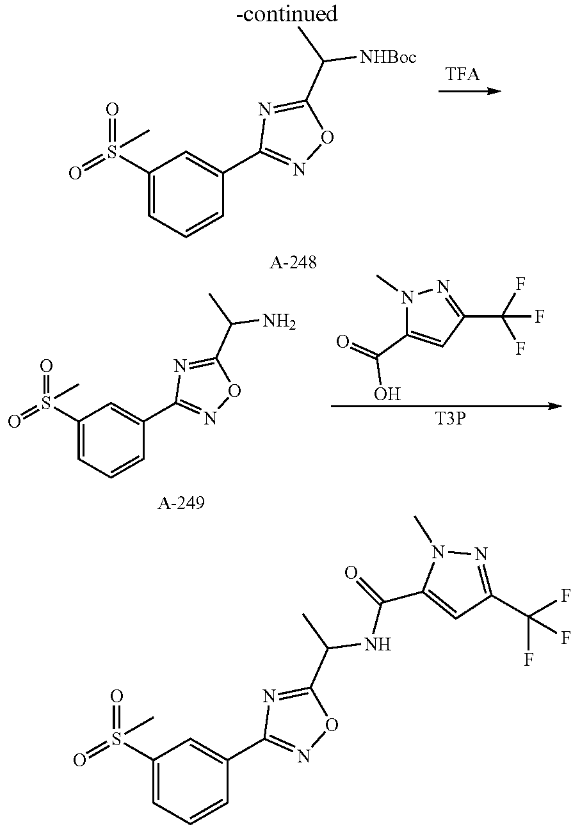

A-248

A-249

179

Synthesis of N'-hydroxy-3-(methylsulfonyl)benzimidamide (A-247)

To a solution of 3-methylsulfonylbenzonitrile (A-246, 1.0 g, 5.52 mmol) n ethanol (20 mL) was added hydroxylamine hydrochloride (1.15 g, 16.56 mmol) and DIPEA (2.94 mL, 16.56 mmol). The reaction mixture was then heated at 70° C. for 16 h. The reaction mixture was cooled to room temperature and concentrated. The mixture was treated with water (25 mL) and extracted with ethyl acetate (2×25 mL). The organic layer was washed with brine (20 mL), dried over anhydrous $Na_2SO_4$ and concentrated to afford compound A-247 (0.6 g). The compound was used for the next step without further purification.

Synthesis of tert-butyl (1-(3-(3-(methylsulfonyl)phenyl)-1,2,4-oxadiazol-5-yl)ethyl)carbamate (A-248)

To a solution of compound A-247 (0.6 g, 2.8 mmol) in 1,4-dioxane (20 mL) was added 2-(tert-butoxycarbonylamino)propanoic acid (0.77 g, 4.05 mmol) and DCC (846.15 mg, 4.11 mmol). The reaction mixture was heated at 100° C. for 16 h. The reaction mixture was cooled to room temperature and concentrated. The mixture was treated with water (20 mL) and extracted with EtOAc (2×25 mL). The organic layer was washed with brine (20 mL), dried over anhydrous $Na_2SO_4$ and concentrated. The crude was purified by column chromatography on silica gel with 20% EtOAc/PE to afford compound A-248 (0.5 g, 1.35 mmol, 48% yield). LCMS: 366.1 (M−H), Rt 2.05 min; Column: ZOR- BAX XDB C-18 (50×4.6 mm), 3.5 μm; Mobile Phase: A: 0.1% HCOOH in water:ACN (95:5), B: ACN; Flow Rate: 1.5 mL/min.

Synthesis of 1-(3-(3-(methylsulfonyl)phenyl)-1,2,4-oxadiazol-5-yl)ethan-1-amine (A-249)

To a stirred solution of compound A-248 (300 mg, 0.81 mmol) in DCM (3 mL) was added TFA (0.5 mL) at 0° C. The reaction mixture was slowly warmed to room temperature and stirred for 8 h. The reaction mixture was concentrated and treated with saturated $NaHCO_3$ solution (20 mL). The mixture was extracted with EtOAc (2×25 mL). The organic layer was washed with brine (20 mL), dried over anhydrous $Na_2SO_4$ and concentrated to afford compound A-249 (200 mg). The compound was used for the next step without further purification.

Synthesis of 1-methyl-N-(1-(3-(3-(methylsulfonyl)phenyl)-1,2,4-oxadiazol-5-yl)ethyl)-3-(trifluoromethyl)-1H-pyrazole-5-carboxamide (179)

To a stirred solution of 1-methyl-3-(trifluoromethyl)-1H-pyrazole-5-carboxylic acid (160 mg, 0.82 mmol) in THF was added T3P (1.33 mL, 2.24 mmol) and triethylamine (0.52 mL, 3.74 mmol) at 0° C. The reaction mixture was stirred for 10 min and compound A-249 (200 mg, 0.75 mmol) was added. The reaction mixture was slowly warmed to room temperature and stirred for 16 h. The reaction mixture was concentrated, and the residue was treated with water (20 mL). The mixture was extracted with EtOAc (2×25 mL) and washed with brine (20 mL). The organic layer was dried over anhydrous $Na_2SO_4$ and concentrated. The crude was purified by column chromatography on silica get with 35% EtOAc/PE to afford 179 (120 mg, 0.27 mmol, 36% yield) as a solid. HPLC: Rt 4.43 min, 99.8%; Column: X-Bridge C8 (50×4.6) mm, 3.5 μm Mobile phase: A: 0.1% TFA in water, B: ACN; Flow Rate: 2.0 mL/min; LCMS: 444.0 (M+H), Rt 2.12 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min; $^1$H NMR (400 MHz, $CDCl_3$): δ 8.67 (t, 1H), 8.39-8.36 (m, 1H), 8.13-8.10 (m, 1H), 7.74 (t, 1H), 6.99 (s, 1H), 6.78 (d, 1H), 5.67-5.60 (m, 1H), 4.25 (s, 3H), 3.13 (s, 3H), 1.80 (d, 3H).

Example 133. Synthesis of 180

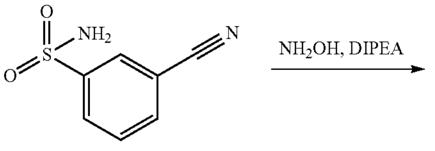

A-250

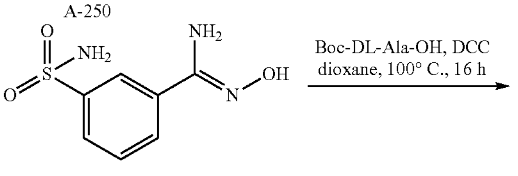

A-251

-continued

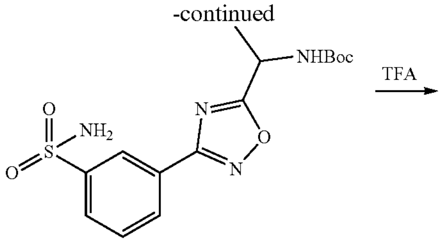

A-252

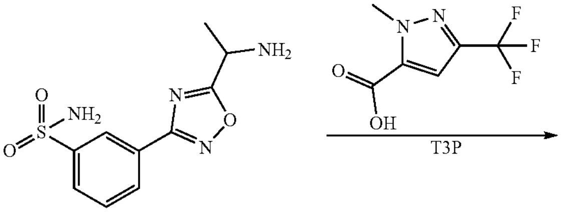

A-253

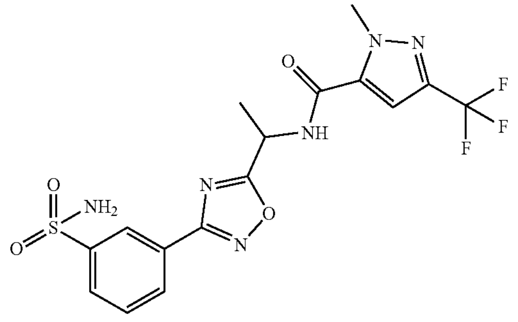

180

Synthesis of N'-hydroxy-3-sulfamoylbenzimidamide (A-251)

To a stirred solution of 3-cyanobenzenesulfonamide (1.0 g, 5.49 mmol) in ethanol (15 mL) at room temperature was added hydroxylamine hydrochloride (572 mg, 8.23 mmol) and N,N-diisopropylethylamine (2.87 mL, 16.47 mmol). The reaction mixture was heated at 77° C. for 2 h. The reaction mixture was cooled to room temperature and concentrated. The mixture was treated with water (20 mL) and extracted with EtOAc (2×25 mL). The organic layer was washed with brine (20 mL), dried over anhydrous $Na_2SO_4$ and concentrated to afford compound A-251 (800 mg). The compound was used for the next step without further purification.

Synthesis of tert-butyl (1-(3-(3-sulfamoylphenyl)-1,2,4-oxadiazol-5-yl)ethyl)carbamate (A-252)

To a stirred solution of compound A-251 (800 mg, 3.72 mmol) in 1,4-dioxane (30 mL) was added 2-(tert-butoxycarbonylamino)propanoic acid (703 mg, 3.72 mmol) and DCC (843 mg, 4.09 mmol). The reaction mixture was heated at 100° C. for 16 h. The reaction mixture was cooled to room temperature and concentrated. The mixture was treated with water (30 mL) and extracted with EtOAc (2×25 mL). The organic layer was washed with brine (20 mL), dried over anhydrous $Na_2SO_4$ and concentrated. The crude was purified by column chromatography on silica get with 60% EtOAc/PE to afford compound A-252 (685 mg, 1.86 mmol, 50% yield) as a solid. LCMS: 367.2 (M−H), Rt 1.91 min; Column: ZORBAX XDB C-18 (50×4.6 mm), 3.5 μm;

Mobile Phase: A: 0.1% HCOOH in water:ACN (95:5), B: ACN; Flow Rate: 1.5 mL/min

Synthesis of 3-(5-(1-aminoethyl)-1,2,4-oxadiazol-3-yl)benzenesulfonamide (A-253)

To a stirred solution of compound A-252 (500 mg, 1.35 mmol) in DCM (12 mL) was added TFA (2.5 mL). The reaction mixture was stirred at room temperature for 2 h. The reaction mixture was concentrated and treated with saturated sodium bicarbonate solution (10 mL). The mixture was extracted with EtOAc (2×20 mL) and washed with brine (10 mL). The organic layer was dried over anhydrous $Na_2SO_4$ and concentrated to afford compound A-253 (260 mg). The compound was used for the next step without further purification.

Synthesis of 1-methyl-N-(1-(3-(3-sulfamoylphenyl)-1,2,4-oxadiazol-5-yl)ethyl)-3-(trifluoromethyl)-1H-pyrazole-5-carboxamide (180)

To a stirred solution of compound A-253 (260 mg, 0.97 mmol) and 1-methyl-3-(trifluoromethyl)-1H-pyrazole-5-carboxylic acid (225 mg, 1.16 mmol) in THF (10 mL) was added T3P (1.73 mL, 2.91 mmol) and DIPEA (0.4 mL, 2.91 mmol). The reaction mixture was stirred at room temperature for 16 h. The reaction mixture was treated with water (30 mL) and extracted with EtOAc (2×30 mL). The organic layer was washed with brine (20 mL), dried over anhydrous $Na_2SO_4$ and concentrated. The crude product was purified by preparative HPLC to afford 180 (80 mg, 0.17 mmol, 18% yield) as a solid. prep-HPLC method: Rt 10.59; Column: XBridge C18 (150×19 mm), 5.0 μm; Mobile phase: 0.1% TFA in water/acetonitrile; Flow Rate: 15.0 mL/min. HPLC: Rt 4.19 min, 99.4%; Column:) (Bridge C8 (50×4.6) mm, 3.5 μm; Mobile phase: A: 0.1% TFA in water, B: 0.1% TFA in ACN; Flow Rate: 2.0 mL/min. LCMS: 445.1 (M+H), Rt 2.03 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, DMSO-$d_6$): δ 9.48 (d, 1H), 8.45 (t, 1H), 8.24-8.22 (m, 1H), 8.05-8.03 (m, 1H), 7.79 (t, 1H), 7.57 (brs, 2H), 7.46 (s, 1H), 5.51-5.47 (m, 1H), 4.14 (s, 3H), 1.70 (d, 3H).

Example 134. Synthesis of 181

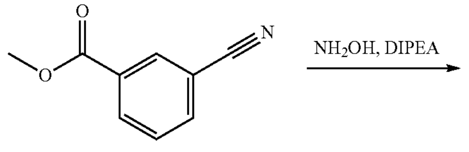

A-254

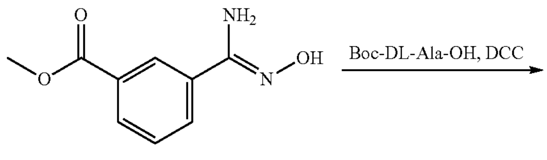

A-255

-continued

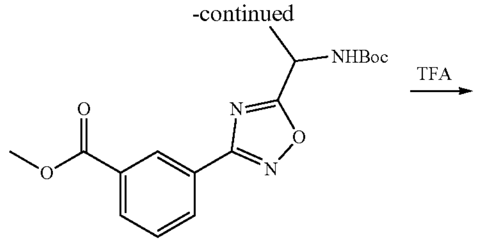

A-256

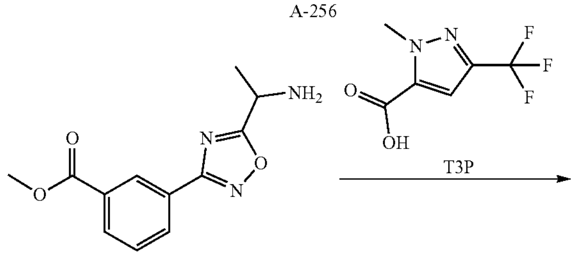

A-257

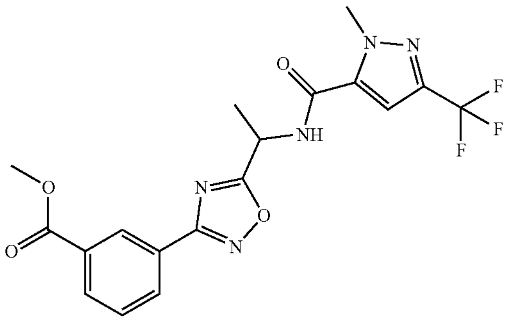

181

Synthesis of methyl 3-(N'-hydroxycarbamimidoyl)benzoate (A-255)

To a solution of methyl 3-cyanobenzoate (10 g, 62.05 mmol) in ethanol (200 mL) was added hydroxylamine hydrochloride (12.94 g, 186.15 mmol) followed by DIPEA (6.28 mL, 62.05 mmol). The reaction mixture was stirred at 70° C. for 16 h. The reaction mixture was cooled to room temperature and concentrated. The mixture was treated with water (100 mL) and extracted with ethyl acetate (2×80 mL). The organic layer was washed with brine (40 mL), dried over anhydrous $Na_2SO_4$ and concentrated to afford compound A-255 (8.47 g). It was used for the next step without further purification.

Synthesis of methyl 3-(5-(1-((tert-butoxycarbonyl)amino)ethyl)-1,2,4-oxadiazol-3-yl)benzoate (A-256)

To a solution of compound A-255 (1.68 g, 8.7 mmol) in 1,4-dioxane (60 mL) was added 2-(tert-butoxycarbonylamino)propanoic acid (2.11 g, 11.17 mmol) and DCC (2.33 g, 11.33 mmol). The reaction mixture heated at 100° C. for 16 h. The reaction mixture was cooled to room temperature and concentrated. The residue was treated with water (30 mL) and extracted with EtOAc (2×40 mL). The organic layer was washed with brine (30 mL), dried over anhydrous $Na_2SO_4$ and concentrated. The crude was purified by column chromatography on silica get with 25% EtOAc/PE to afford compound A-256 (1.2 g, 3.4 mmol, 33% yield). LCMS: 346.1 (M−H), Rt 2.45 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of methyl 3-(5-(1-aminoethyl)-1,2,4-oxadiazol-3-yl)benzoate (A-257)

To a stirred solution of compound A-256 (1.2 g, 3.45 mmol) in DCM (3 mL) was added TFA (2.1 mL) at 0° C. The reaction mixture was slowly warmed to room temperature and concentrated. The mixture was treated with saturated $NaHCO_3$ solution (20 mL) and extracted with EtOAc (2×30 mL). The organic layer was washed with brine (1×10 mL), dried over anhydrous $Na_2SO_4$ and concentrated to afford compound A-257 (524 mg). The compound was used for the next step without further purification.

Synthesis of methyl 3-(5-(1-(1-methyl-3-(trifluoromethyl)-1H-pyrazole-5-carboxamido)ethyl)-1,2,4-oxadiazol-3-yl)benzoate (181)

To a stirred solution of 1-methyl-3-(trifluoromethyl)-1H-pyrazole-5-carboxylic acid (0.5 mL, 2.22 mmol) in THF (10 mL) was added T3P (6.0 mL, 10.11 mmol) and TEA (0.84 mL, 6.07 mmol). The reaction mixture was stirred at room temperature for 10 min and compound A-257 (500 mg, 2.02 mmol) was added. The reaction mixture was stirred at room temperature for 16 h and concentrated. The mixture was treated water (20 mL) and extracted with EtOAc (2×20 mL). The organic layer was washed with brine (1×10 mL), dried over anhydrous $Na_2SO_4$ and concentrated. The crude was purified by column chromatography on silica gel with 25% EtOAc/PE to afford 181 (350 mg, 0.81 mmol, 40% yield). HPLC: Rt 5.04 min, 98.3% Column: XBridge C8 (50×4.6) mm, 3.5 μm; Mobile phase: A: 0.1% TFA in water, B: 0.1% TFA in ACN; Flow Rate: 2.0 mL/min. LCMS: 424.1 (M+H), Rt 2.43 min, Column: ZORBAX XDB C-18 (50×4.6 mm), 3.5 μm, Mobile Phase: A: 0.1% HCOOH in water:ACN (95:5), B: ACN; Flow Rate: 1.5 mL/min. $^1H$ NMR (400 MHz, CDCl3): δ 8.73 (s, 1H), 8.26 (d, 1H), 8.19 (d, 1H), 7.59 (t, 1H), 6.96 (s, 1H), 6.79 (d, 1H), 5.65-5.60 (m, 1H), 4.24 (s, 3H), 3.97 (s, 3H), 1.78 (d, 3H).

Example 135. Synthesis of 182

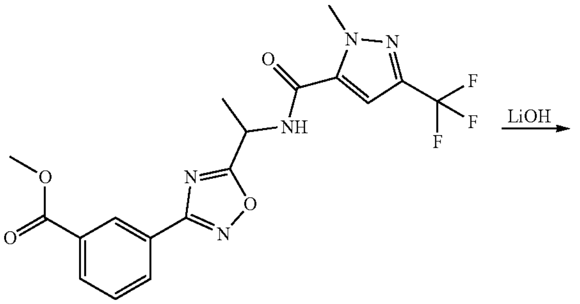

181

-continued

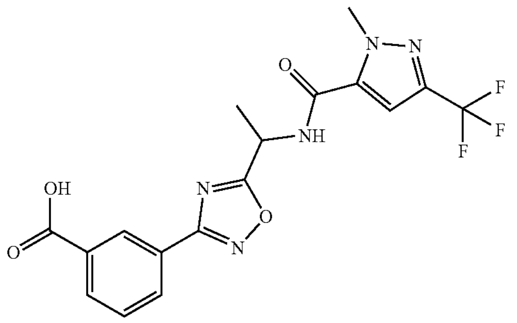

182

Synthesis of 3-(5-(1-(1-methyl-3-(trifluoromethyl)-1H-pyrazole-5-carboxamido)ethyl)-1,2,4-oxadiazol-3-yl)benzoic Acid (182)

To a stirred solution of compound 181 (330 mg, 0.78 mmol) in THF (8 mL), methanol (2 mL) and water (1 mL) was added $LiOH.H_2O$ (170.62 mg, 4.07 mmol) at room temperature. The reaction mixture was stirred at room temperature for 8 h and concentrated. The mixture was treated with 1 N HCl (8 mL) and extracted with EtOAc (2×25 mL). The organic layer was washed with brine (1×20 mL), dried over anhydrous $Na_2SO_4$ and concentrated. The crude was purified by column chromatography on silica gel with 75% EtOAc/PE to afford 182 (250 mg, 0.60 mmol, 78% yield). HPLC: Rt 4.37 min, 98.9%; Column: XBridge C8 (50×4.6) mm, 3.5 μm; Mobile phase: A: 0.1% TFA in water, B: 0.1% TFA in ACN; Flow Rate: 2.0 mL/min. LCMS: 410.1 (M+H), Rt 2.02 min; Column: ZORBAX XDB C-18 (50×4.6 mm), 3.5 μm Mobile Phase: A: 0.1% HCOOH in water:ACN (95:5), B: ACN; Flow Rate: 1.5 mL/min; $^1H$ NMR (400 MHz, DMSO-$d_6$): δ 9.48 (d, 1H), 8.56 (s, 1H), 8.22 (d, 1H), 8.14 (d, 1H), 7.70 (t, 1H), 7.46 (s, 1H), 5.51-5.47 (m, 1H), 4.14 (s, 3H), 1.69 (d, 3H).

Example 136. Synthesis of 183

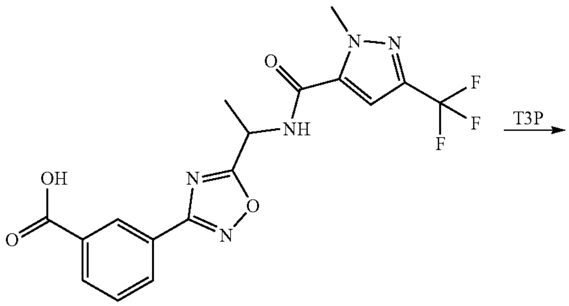

182

-continued

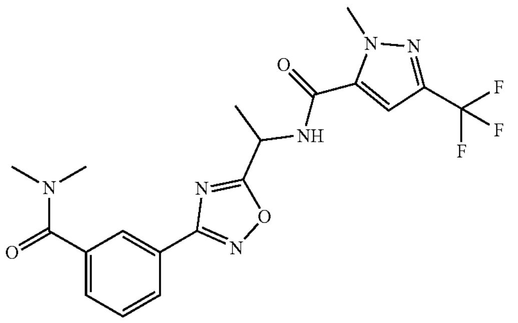

183

Synthesis of N-(1-(3-(3-(dimethylcarbamoyl)phenyl)-1,2,4-oxadiazol-5-yl)ethyl)-1-methyl-3-(trifluoromethyl)-1H-pyrazole-5-carboxamide (183)

To a stirred solution of compound 182 (150 mg, 0.37 mmol) in THF (15 mL) was added T3P (0.43 mL, 0.73 mmol) and TEA (0.15 mL, 1.1 mmol). The reaction mixture was stirred at room temperature for 10 min and dimethylamine (2.0 M in THF, 0.92 mL, 1.83 mmol) was added. The reaction mixture was stirred at room temperature for 16 h and concentrated. The mixture was treated with water (30 mL) and extracted with EtOAc (2×25 mL). The organic layer was washed with brine (1×15 mL), dried over anhydrous $Na_2SO_4$ and concentrated. The crude was purified by column chromatography on silica gel with 75% EtOAc/PE to afford 183 (65 mg, 0.14 mmol, 40% yield). HPLC: Rt 4.19 min, 98.7%; Column: XBridge C8 (50×4.6) mm, 3.5 μm; Mobile phase: A: 0.1% TFA in water, B: 0.1% TFA in ACN; Flow Rate: 2.0 mL/min. LCMS: 437.2 (M+H), Rt 2.03 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1H$ NMR (400 MHz, $CDCl_3$): δ 8.10-8.07 (m, 2H), 7.54-7.52 (m, 2H), 7.45 (d, 1H), 7.06 (s, 1H), 5.62-5.55 (m, 1H), 4.23 (s, 3H), 3.15 (s, 3H), 2.99 (s, 3H), 1.74 (d, 3H).

Example 137. Synthesis of 184

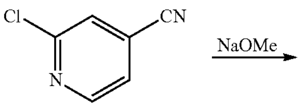

A-258

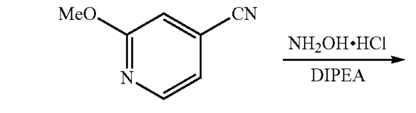

A-259

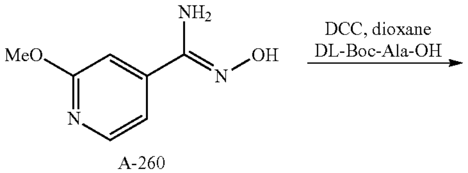

A-260

-continued

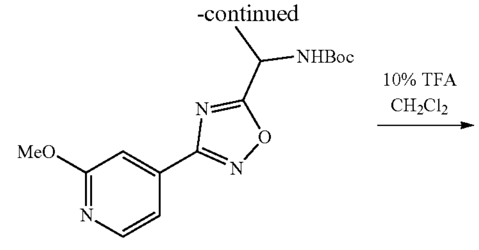

A-261

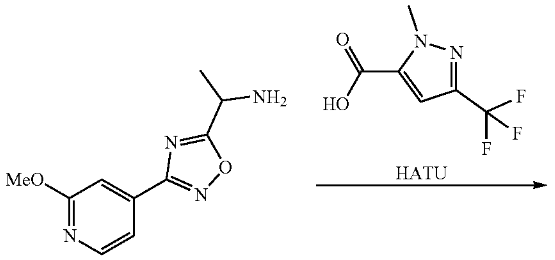

A-262

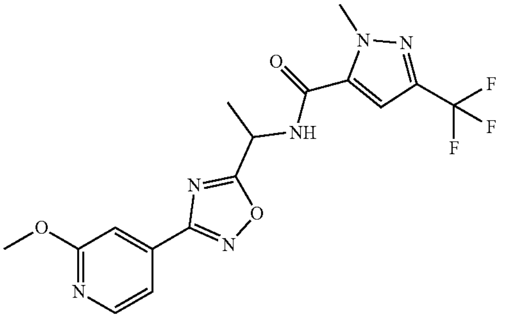

184

Synthesis of 2-methoxyisonicotinonitrile (A-259)

To a solution of 2-chloropyridine-4-carbonitrile (10 g, 72.18 mmol) in 1,4-dioxane (20 mL) was added sodium methoxide (25% in methanol, 16.4 mL, 72.18 mmol) at room temperature. The reaction mixture was heated at 100° C. for 5 h. The reaction mixture was cooled to room temperature and left in the refrigerator at 0° C. for 16 h. The precipitate was filtered and washed with cold methanol (60 mL). The filtrate was concentrated and ice water (50 mL) was added. The precipitate was filtered, washed with water (100 mL) and dried to afford compound A-259 (4.43 g) as a solid. It was used for the next step without further purification.

Synthesis of N'-hydroxy-2-methoxyisonicotinimidamide (A-260)

To a stirred solution of compound A-259 (4.43 g, 33.15 mmol) in ethanol (50 mL) was added DIPEA (9.22 mL, 66.3 mmol) and hydroxylamine hydrochloride (4.6 g, 66.3 mmol). The reaction mixture was heated at 100° C. for 16 h and concentrated. The mixture was treated with water (50 mL) and extracted with ethyl acetate (2×50 mL). The organic layer was washed with brine (1×20 mL), dried over anhydrous $Na_2SO_4$ and concentrated to afford compound A-260 (3.75 g) as a solid. It was used for the next step without further purification.

Synthesis of tert-butyl (1-(3-(2-methoxypyridin-4-yl)-1,2,4-oxadiazol-5-yl)ethyl)carbamate (A-261)

To a solution of compound A-260 (3.75 g, 22.43 mmol) in 1,4-dioxane (40 mL) was added DL-Boc-alanine (4.67 g, 24.68 mmol) and DCC (5.08 g, 24.68 mmol) at room temperature. The reaction mixture was then heated at 100° C. for 16 h. The reaction mixture was cooled to room temperature and concentrated. The mixture was treated with water (20 mL) and extracted with ethyl acetate (2x30 mL). The organic layer was washed with brine (20 mL), dried over $Na_2SO_4$ and concentration. The crude was purified by column chromatography on silica gel with 30% EtOAc/PE to afford compound A-261 (5.3 g, 16.3 mmol, 72% yield) as a solid. LCMS: 321.1 (M+H), Rt 2.33 min; Column: ZORBAX XDB C-18 (50x4.6 mm), 3.5 μm; Mobile Phase: A: 0.1% HCOOH in water:ACN (95:5), B: ACN; Flow Rate: 1.5 mL/min.

Synthesis of 1-(3-(2-methoxypyridin-4-yl)-1,2,4-oxadiazol-5-yl)ethan-1-amine (A-262)

To a stirred solution of compound A-261 (5.3 g, 16.3 mmol) in DCM (50 mL) was added TFA (10.02 mL) at 0° C. The reaction mixture was slowly warmed to room temperature and stirred for 1 h. The reaction mixture was concentrated, treated with 10% $NaHCO_3$ solution (30 mL) and extracted with DCM (2x40 mL). The organic layer was washed with brine (20 mL), dried over anhydrous $Na_2SO_4$ and concentrated to afford compound A-262 (3 g) as a solid. It was used for the next step without further purification.

Synthesis of N-(1-(3-(2-methoxypyridin-4-yl)-1,2,4-oxadiazol-5-yl)ethyl)-1-methyl-3-(trifluoromethyl)-1H-pyrazole-5-carboxamide (184)

To a solution of compound A-262 (250 mg, 1.13 mmol) in DMF (10 mL) was added DIPEA (0.47 mL, 3.4 mmol) and 1-methyl-3-(trifluoromethyl)-1H-pyrazole-5-carboxylic acid (241.7 mg, 1.25 mmol) followed by HATU (861 mg, 2.26 mmol). The reaction mixture was stirred at room temperature for 12 h. The reaction mixture was treated with water (30 mL) and extracted with ethyl acetate (2x25 mL). The organic layer was washed with brine (20 mL), dried over anhydrous $Na_2SO_4$ and concentrated. The crude product was purified by column chromatography on silica gel with 45% EtOAc/PE to afford 184 (122 mg, 0.30 mmol, 27% yield) as a solid. HPLC: Rt 4.65 min, 99.3%; Column:) (Bridge C8 (50x4.6) mm, 3.5 μm; Mobile phase: A: 0.1% TFA in water, B: 0.1% TFA in ACN; Flow Rate: 2.0 mL/min; LCMS: 397.1 (M+H), Rt 2.35 min, Column: ZORBAX XDB C-18 (50x4.6 mm), 3.5 μm, Mobile Phase: A: 0.1% HCOOH in water:ACN (95:5), B: ACN; Flow Rate: 1.5 mL/min; $^1H$ NMR (400 MHz, DMSO-$d_6$): δ 9.47 (d, 1H), 8.39 (d, 1H), 7.54-7.52 (m, 1H), 7.45 (s, 1H), 7.31 (s, 1H), 5.50-5.46 (m, 1H), 4.13 (s, 3H), 3.93 (s, 3H), 1.68 (d, 3H).

Example 138. Synthesis of 145 and 146 a) Synthesis of 145

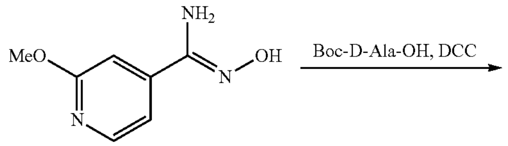

A-341

-continued

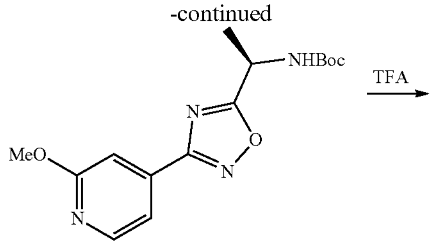

A-342

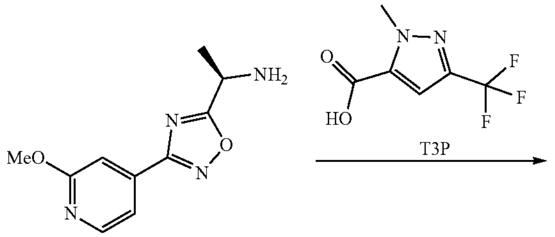

A-343

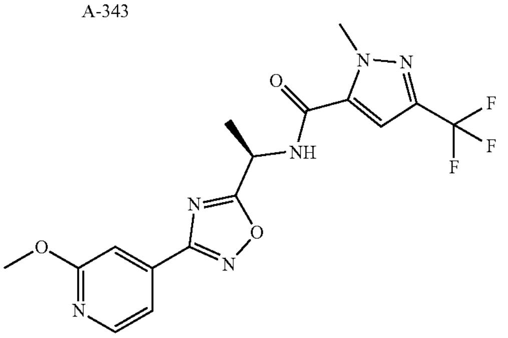

145

Synthesis of tert-butyl N-[(1R)-1-[3-(2-methoxy-4-pyridyl)-1,2,4-oxadiazol-5-yl]ethyl]carbamate (A-342)

To a stirred solution of compound A-341 (320 mg, 1.91 mmol) in 1,4-dioxane (10.0 mL) was added Boc-D-alanine (434 mg, 2.3 mmol) and DCC (591 mg, 2.87 mmol) at room temperature. The reaction mixture was then stirred at 100° C. for 16 h. The reaction mixture was cooled to room temperature and concentrated. The mixture was treated with water (30 mL) and extracted with EtOAc (2x30 mL). The organic layer was washed with brine (20 mL), dried over anhydrous $Na_2SO_4$ and concentrated. The crude was purified by column chromatography on silica gel with 12% EtOAc/PE to afford compound A-342 (592 mg, 1.85 mmol, 96% yield). LCMS: 321.3 (M+H), Rt 2.32 min, Column: ZORBAX XDB C-18 (50x4.6 mm), 3.5 μm m Mobile Phase: A: 0.1% HCOOH in water:ACN (95:5), B: ACN; Flow Rate: 1.5 mL/min Synthesis of (1R)-1-[3-(2-methoxy-4-pyridyl)-1,2,4-oxadiazol-5-yl]ethanamine (A-343)

To a stirred solution of compound A-342 (592 mg, 1.85 mmol) in DCM (7.0 mL) was added TFA (1.43 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (5 mL) and extracted with EtOAc (2x30 mL). The organic layer was washed with brine (20 mL), dried over anhydrous $Na_2SO_4$ and concentrated to afford compound A-343 (340 mg). The compound was used for the next step without further purification.

Synthesis of 2-methyl-N-[(1R)-1-[3-(2-methoxy-4-pyridyl)-1,2,4-oxadiazol-5-yl]ethyl]-5-(trifluoromethyl)pyrazole-3-carboxamide (145)

To a stirred solution of compound A-343 (340 mg, 1.54 mmol) in THF (10.0 mL) was added 2-methyl-5-(trifluoromethyl)pyrazole-3-carboxylic acid (299 mg, 1.54 mmol) followed by T3P (2.76 mL, 4.63 mmol) and $Et_3N$ (0.64 mL, 4.63 mmol). The reaction mixture was stirred at room temperature for 16 h. The reaction mixture was treated with water (30 mL) and extracted with ethyl acetate (2×25 mL). The organic layer was washed with saturated sodium bicarbonate solution (20 mL), washed with brine (20 mL), dried over $Na_2SO_4$ and concentrated. The crude compound was purified by preparative HPLC to afford 145 (346 mg, 0.86 mmol, 55% yield) as a solid. Prep. HPLC method: Rt 13.0; Column: YMC C18 (150×19 mm), 5.0 μm; Mobile phase: 0.1% TFA in water/acetonitrile; Flow Rate: 15.0 mL/min. HPLC: Rt 4.63 min, 99.3%, Column: XBridge C8 (50×4.6) mm, 3.5 μm, Mobile phase: A: 0.1% TFA in water, B: 0.1% TFA in ACN; Flow Rate: 2.0 mL/min; LCMS: 397.1 (M+H), Rt 2.34 min, Column: ZORBAX XDB C-18 (50×4.6) mm, 3.5 μm, Mobile phase: A: A: 0.1% HCOOH in water:ACN (95:5), B: ACN; Flow Rate: 1.5 mL/min Chiral method: Rt 2.54 min, SFC column: CHIRALCEL OJ-H; mobile phase: 80:20 (A:B), A=liquid $CO_2$, B=methanol; flow rate: 3.0 mL/min; wave length: 210 nm. $^1H$ NMR (400 MHz, DMSO-d6): δ 9.47 (d, 1H), 8.39 (d, 1H), 7.54-7.52 (dd, 1H), 7.45 (s, 1H), 7.31 (s, 1H), 5.50-5.45 (m, 1H), 4.13 (s, 3H), 3.92 (s, 3H), 1.67 (d, 3H).

b) Synthesis of 146

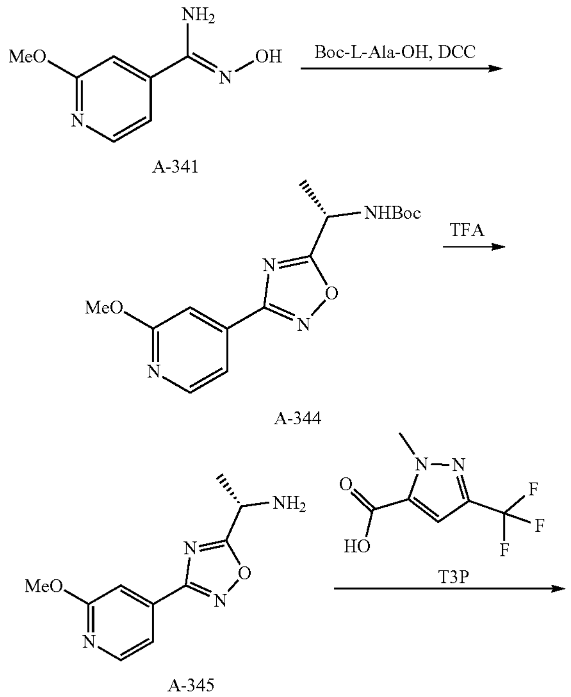

A-341

A-344

A-345

-continued

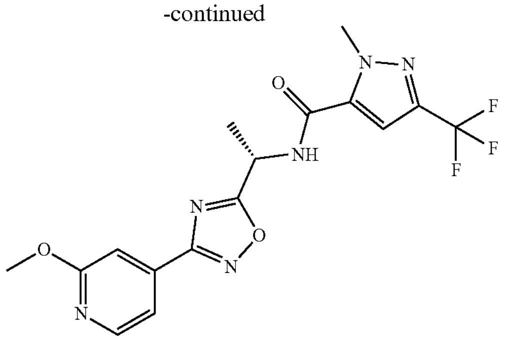

146

Synthesis of tert-butyl N-[(1S)-1-[3-(2-methoxy-4-pyridyl)-1,2,4-oxadiazol-5-yl]ethyl]carbamate (A-344)

To a stirred solution of compound A-341 (320.mg, 1.9 mmol) in 1,4-dioxane (10.0 mL) was added (2S)-2-(tert-butoxycarbonylamino)propanoic acid (359 mg, 1.9 mmol) and DCC (430 mg, 2.09 mmol) at room temperature. The reaction mixture was heated at 100° C. for 16 h. The reaction mixture was cooled to room temperature and concentrated. The mixture was treated with water (30 mL) and extracted with EtOAc (2×30 mL). The organic layer was washed with brine (20 mL), dried over anhydrous $Na_2SO_4$ and concentrated. The crude was purified by column chromatography on silica gel with 12% EtOAc/PE to afford compound A-344 (530 mg, 1.65 mmol, 87% yield). LCMS: 321.1 (M+H), Rt 2.32 min, Column: ZORBAX XDB C-18 (50×4.6 mm), 3.5 μm, Mobile Phase: A: 0.1% HCOOH in water:ACN (95:5), B: ACN; Flow Rate: 1.5 mL/min Synthesis of (1S)-1-[3-(2-methoxy-4-pyridyl)-1,2,4-oxadiazol-5-yl]ethanamine (A-345)

To a stirred solution of compound A-344 (530 mg, 1.65 mmol) in DCM (10.0 mL) was added TFA (1.94 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (5 mL) and extracted with EtOAc (2×30 mL). The organic layer was washed with brine (20 mL), dried over anhydrous $Na_2SO_4$ and concentrated to afford compound A-345 (310 mg). The compound was used for the next step without further purification.

Synthesis of 2-methyl-N-[(1S)-1-[3-(2-methoxy-4-pyridyl)-1,2,4-oxadiazol-5-yl]ethyl]-5-(trifluoromethyl)pyrazole-3-carboxamide (146)

To a stirred solution of compound A-345 (310 mg, 1.4 mmol) in THF (10.0 mL) was added 2-methyl-5-(trifluoromethyl)pyrazole-3-carboxylic acid (273 mg, 1.41 mmol) followed by T3P (2.51 mL, 4.22 mmol) and $Et_3N$ (0.59 mL, 4.22 mmol). The reaction mixture was stirred at room temperature for 16 h. The reaction mixture was treated with water (30 mL) and extracted with ethyl acetate (2×25 mL). The organic layer was washed with saturated sodium bicarbonate solution (20 mL), washed with brine (20 mL), dried over $Na_2SO_4$ and concentrated. The crude compound was purified by preparative HPLC to afford 146 (133 mg, 0.32 mmol, 23% yield) as a solid. Prep. HPLC method: Rt 11.21; Column: Atlantis (150×19 mm), 5.0 μm; Mobile phase: 0.1% TFA in water/acetonitrile; Flow Rate: 15.0 mL/min. HPLC: Rt 4.64 min, 96.8%, Column: XBridge C8 (50×4.6) mm, 3.5 μm, Mobile phase: A: 0.1% TFA in water, B: 0.1% TFA in ACN; Flow Rate: 2.0 mL/min; LCMS: 397.1 (M+H), Rt 2.20 min, Column: XBridge C8 (50×4.6) mm, 3.5 μm, Mobile phase: A: 0.1% TFA in water:ACN (95:5), B: 0.1% TFA in ACN; Flow Rate: 1.5 mL/min. Chiral method: Rt 1.99 min, SFC column: Chiralcel OJ-H; mobile phase: 80:20 (A:B), A=liquid $CO_2$, B=methanol; flow rate: 3.0 mL/min; wave length: 210 nm. $^1H$ NMR (400 MHz, $CD_3OD$): δ 8.32-8.30 (dd, 1H), 7.57-7.55 (dd, 1H), 7.415-7.41 (dd, 1H), 7.25 (s, 1H), 5.53 (q, 1H), 4.19 (s, 3H), 3.98 (s, 3H), 1.77 (d, 3H).

Example 139. Synthesis of 185

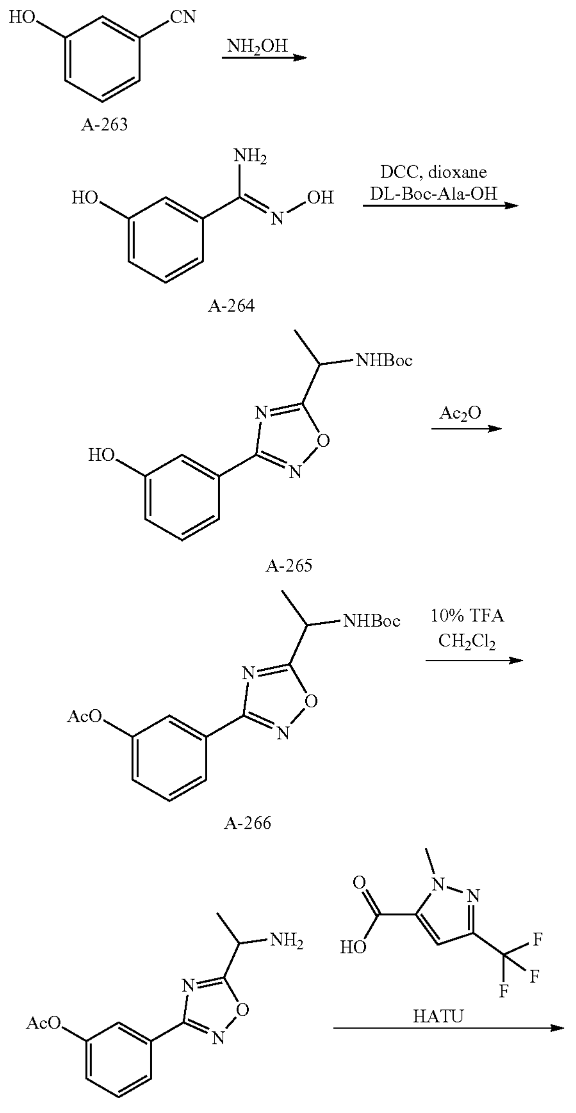

A-263
A-264
A-265
A-266
A-267

-continued

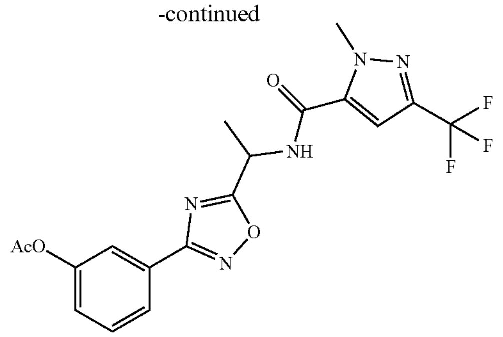

185

Synthesis of N',3-dihydroxybenzimidamide (A-264)

To a stirred solution of 3-hydroxybenzonitrile (5.0 g, 41.97 mmol) in ethanol (50 mL) was added DIPEA (11.67 mL, 83.95 mmol) and hydroxylamine hydrochloride (5.83 g, 83.95 mmol). The reaction mixture was heated at 100° C. for 16 h. The reaction mixture was cooled to room temperature and concentrated. The reaction mixture was treated with water (50 mL) and extracted with ethyl acetate (2×50 mL). The organic layer was washed with brine (30 mL), dried over anhydrous $Na_2SO_4$ and concentrated to afford compound A-264 (4.4 g). The compound was used for the next step without further purification.

Synthesis of tert-butyl (1-(3-(3-hydroxyphenyl)-1,2,4-oxadiazol-5-yl)ethyl)carbamate (A-265)

To a solution of compound A-264 (2.5 g, 16.44 mmol) in 1,4-dioxane (100 mL) was added DL-Boc-alanine (3.11 g, 16.44 mmol) and DCC (3.72 g, 18.08 mmol) and the reaction mixture was heated at 100° C. for 16 h. The reaction mixture was cooled to room temperature and concentrated. The mixture was treated with water (40 mL) and extracted with ethyl acetate (2×50 mL). The organic layer was washed with brine (30 mL), dried over anhydrous $Na_2SO_4$ and concentrated. The crude was purified by column chromatography on silica gel with 15% EtOAc/PE to afford compound A-265 (4.2 g, 13.6 mmol, 82% yield) as a solid. LCMS: 304.2 (M−H), Rt 2.00 min Column: ZORBAX XDB C-18 (50×4.6 mm), 3.5 μm; Mobile Phase: A: 0.1% HCOOH in water:ACN (95:5), B: ACN; Flow Rate: 1.5 mL/min Synthesis of 3-(5-(1-((tert-butoxycarbonyl)amino)ethyl)-1,2,4-oxadiazol-3-yl)phenyl Acetate (A-266)

To a solution of compound A-265 (500 mg, 1.62 mmol) in DCM (15 mL) was added pyridine (0.39 mL, 4.83 mmol), DMAP (19.81 mg, 0.16 mmol) and acetic anhydride (0.17 mL, 1.78 mmol). The reaction mixture was stirred at room temperature for 3 h. The reaction mixture was treated with saturated $NaHCO_3$ solution (20 mL) and extracted with ethyl acetate (2×30 mL). The organic layer was washed with brine (30 mL), dried over anhydrous $Na_2SO_4$ and concentrated. The crude was purified by column chromatography on silica gel with 12% EtOAc/PE to afford compound A-266 (500 mg) as a solid. LCMS: 346.1 (M−H), Rt 2.32 min Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of 3-(5-(1-aminoethyl)-1,2,4-oxadiazol-3-yl)phenyl acetate (A-267)

To a solution of compound A-266 (500 mg, 1.42 mmol) in DCM (10 mL) was added TFA (0.55 mL) at 0° C. The reaction mixture was slowly warmed to room temperature and stirred for 2 h. The reaction mixture was concentrated, treated with 10% $NaHCO_3$ solution (10 mL) and extracted with DCM (2×20 mL). The organic layer was washed with brine (10 mL), dried over anhydrous $Na_2SO_4$ and concentrated to afford compound A-267 (265 mg). The compound was used for the next step without further purification.

Synthesis of 3-(5-(1-(1-methyl-3-(trifluoromethyl)-1H-pyrazole-5-carboxamido)ethyl)-1,2,4-oxadiazol-3-yl)phenyl acetate (185)

To a stirred solution of 1-methyl-3-(trifluoromethyl)-1H-pyrazole-5-carboxylic acid (200 mg, 1.03 mmol) in DMF (10 mL) was added HATU (1.17 g, 3.09 mmol), DIPEA (0.55 mL, 3.09 mmol) and compound A-267 (247 mg, 0.99 mmol). The reaction mixture was stirred at room temperature for 16 h. The reaction mixture was treated with water (30 mL) and extracted with ethyl acetate (2×25 mL). The organic layer was washed with brine (20 mL), dried over anhydrous $Na_2SO_4$ and concentrated. The crude was purified by column chromatography on silica gel with 35% EtOAc/PE to afford 185 (68 mg, 0.16 mmol, 15% yield) as a solid. HPLC: Rt 4.93 min, 99.9%; Column: XBridge C8 (50×4.6) mm, 3.5 μm; Mobile phase: A: 0.1% TFA in water, B: ACN; Flow Rate: 2.0 mL/min. LCMS: 424.1 (M+H), Rt 2.42 min, Column: ZORBAX XDB C-18 (50×4.6 mm), 3.5 μm Mobile Phase: A: 0.1% HCOOH in water:ACN (95:5), B: ACN; Flow Rate: 1.5 mL/min. $^1$H NMR (400 MHz, DMSO-$d_6$): δ 9.46 (d, 1H), 7.90 (d, 1H), 7.77 (s, 1H), 7.63 (t, 1H), 7.46 (s, 1H), 7.38 (d, 1H), 5.50-5.43 (m, 1H), 4.14 (s, 3H), 2.31 (s, 3H), 1.68 (d, 3H).

Example 140. Synthesis of 186

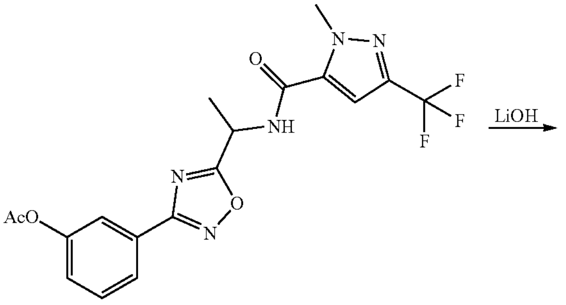

185

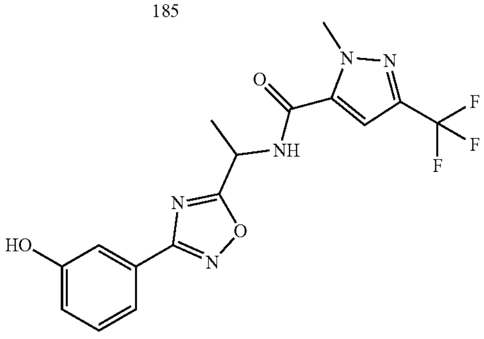

186

Synthesis of N-(1-(3-(3-hydroxyphenyl)-1,2,4-oxadiazol-5-yl)ethyl)-1-methyl-3-(trifluoromethyl)-1H-pyrazole-5-carboxamide (186)

To a stirred solution of compound 185 (60 mg, 0.14 mmol) in methanol (10 mL) and water (10 mL) was added $LiOH.H_2O$ (18 mg, 0.43 mmol) at room temperature. The reaction mixture was heated at 50° C. for 1 h. The reaction mixture was cooled to room temperature, treated with 1.5 N hydrochloric acid (2.0 mL) and extracted with EtOAc (2×15 mL). The organic layer was washed with brine (10 mL), dried over anhydrous $Na_2SO_4$ and concentrated. The crude was purified by column chromatography on silica gel with 5% MeOH/DCM to afford 186 (48 mg, 0.12 mmol, 87% yield) as a solid. HPLC: Rt 4.40 min, 98.0%; Column: XBridge C8 (50×4.6) mm, 3.5 μm; Mobile phase: A: 0.1% TFA in water, B: 0.1% TFA in ACN; Flow Rate: 2.0 mL/min. LCMS: 382.1 (M+H), Rt 2.11 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1$H NMR (400 MHz, DMSO-$d_6$): δ 9.86 (s, 1H), 9.44 (d, 1H), 7.45-7.34 (m, 4H), 6.99-6.97 (m, 1H), 5.47-5.43 (m, 1H), 4.14 (s, 3H), 1.66 (d, 3H).

Example 141. Synthesis of 282 (tert-butyl (R)-(1-(3-(3-fluorophenyl)-1,2,4-oxadiazol-5-yl)ethyl)carbamate)

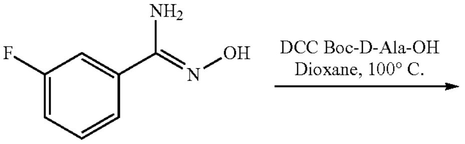

A-10

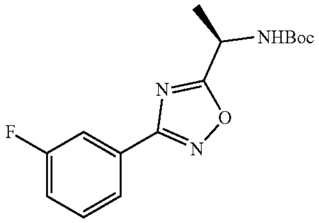

282

To a solution of compound A-10 (0.25 g, 1.62 mmol) in 1,4-dioxane (10.0 mL) was added (2R)-2-(tert-butoxycarbonylamino)propanoic acid (0.33 g, 1.76 mmol) and DCC (0.37 g, 1.78 mmol the reaction mixture was heated at 100° C. for 16 h. The reaction mixture was cooled to room temperature and concentrated. The mixture was treated with water (15 mL) and extracted with ethyl acetate (2×20 mL). The organic layer was washed with brine (10 mL), dried over anhydrous $Na_2SO_4$ and concentrated. The crude was purified by column chromatography on silica gel with 8% EtOAc/PE to afford 282 (270 mg, 0.86 mmol, 53% yield) as a solid. HPLC: Rt 5.02 min, 99.3%; Column: XBridge C8 (50×4.6) mm, 3.5 μm; Mobile phase: A: 0.1% TFA in water, B: 0.1% TFA in ACN; Flow Rate: 2.0 mL/min. LCMS: 306.1 (M−H), Rt 2.51 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.94 min, SFC column: YMC Amylose-C; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CDCl_3$): δ 7.89 (d, 1H), 7.82-7.78 (m, 1H), 7.50-7.45 (m, 1H), 7.25-7.20 (m, 1H), 5.19 (m, 2H), 1.65 (d, 3H), 1.49 (s, 9H).

Example 143. Synthesis of 187

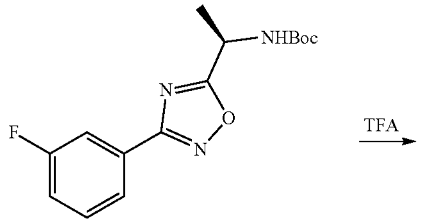

282

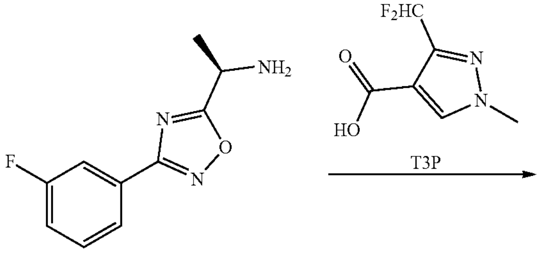

A-210

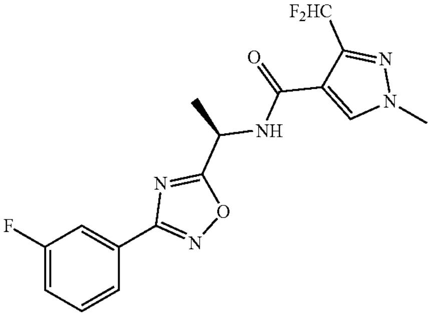

187

Synthesis of (R)-1-(3-(3-fluorophenyl)-1,2,4-oxadiazol-5-yl)ethan-1-amine (A-210)

To a solution of compound 282 (270 mg, 0.88 mmol) in DCM (5 mL) was added TFA (1.3 mL) and the mixture stirred at room temperature for 3 h. The reaction mixture was treated with saturated $NaHCO_3$ solution (10 mL) and extracted with DCM (2×20 mL). The organic layer was washed with brine (10 mL), dried over anhydrous $Na_2SO_4$ and concentrated to afford compound A-210 (170 mg) as a liquid. The compound was used for the next step without further purification.

Synthesis of (R)-3-(difluoromethyl)-N-(1-(3-(3-fluorophenyl)-1,2,4-oxadiazol-5-yl)ethyl)-1-methyl-1H-pyrazole-4-carboxamide (187)

To a solution of compound A-210 (170 mg, 0.82 mmol) in THF (5 mL) was added 3-(difluoromethyl)-1-methyl-pyrazole-4-carboxylic acid (158.95 mg, 0.90 mmol) followed by T3P (50% in ethyl acetate, 1.47 mL, 2.46 mmol) and $Et_3N$ (0.34 mL, 2.46 mmol). The reaction mixture was stirred at room temperature for 16 h. The reaction mixture was treated with water (15 mL) and extracted with EtOAc (2×20 mL). The organic layer was washed with brine (15 mL), dried over anhydrous $Na_2SO_4$ and concentrated. The crude was purified by column chromatography on silica gel with 60% EtOAc/PE to afford 187 (85 mg, 0.23 mmol, 28% yield) as a solid. HPLC: Rt 4.22 min, 98.6%; Column: XBridge C8 (50×4.6) mm, 3.5 μm; Mobile phase: A: 0.1% TFA in water, B: 0.1% TFA in ACN; Flow Rate: 2.0 mL/min. LCMS: 366.1 (M+H), Rt 2.02 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 3.27 min, SFC column: YMC Cellulose-SC; mobile phase: 60:40 (A:B), A=liquid $CO_2$, B=methanol; flow rate: 3.0 mL/min; wave length: 220 nm. $^1H$ NMR (400 MHz, $CDCl_3$): δ 8.00 (s, 1H), 7.91-7.89 (m, 1H), 7.82-7.79 (m, 1H), 7.50-7.45 (m, 1H), 7.25-7.20 (m, 1H), 7.03 (brs, 1H), 6.90 (t, 1H), 5.65-5.58 (m, 1H), 3.97 (s, 3H), 1.75 (d, 3H).

Example 144. Synthesis of 188

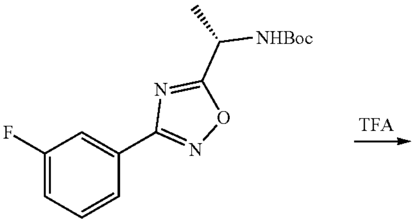

281

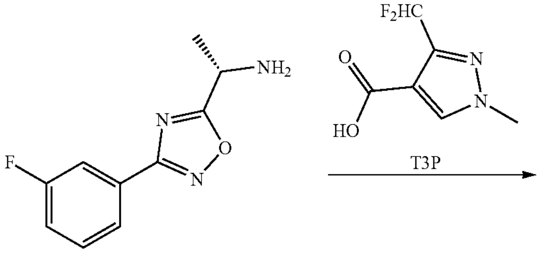

A-138

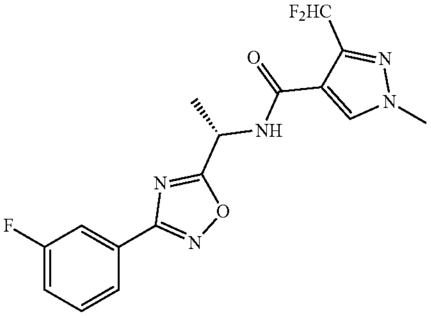

188

Synthesis of (S)-1-(3-(3-fluorophenyl)-1,2,4-oxadiazol-5-yl)ethan-1-amine (A-138)

To a solution of compound 281 (300 mg, 0.98 mmol) in DCM (5 mL) was added TFA (1.45 mL) and the mixture was stirred at room temperature for 3 h. The reaction mixture was treated with saturated $NaHCO_3$ solution (10 mL) and extracted with DCM (2×20 mL). The organic layer was washed with brine (10 mL), dried over anhydrous $Na_2SO_4$ and concentrated to afford compound A-138 (200 mg). The compound was used for the next step without further purification.

Synthesis of (S)-3-(difluoromethyl)-N-(1-(3-(3-fluorophenyl)-1,2,4-oxadiazol-5-yl)ethyl)-1-methyl-1H-pyrazole-4-carboxamide (188)

To a solution of compound A-138 (200 mg, 0.97 mmol) in THF (5.0 mL) was added 3-(difluoromethyl)-1-methyl-pyrazole-4-carboxylic acid (187 mg, 1.06 mmol) followed by T3P (50% in ethyl acetate, 1.73 mL, 2.91 mmol) and $Et_3N$ (0.4 mL, 2.9 mmol). The reaction mixture was stirred at room temperature for 16 h. The reaction mixture was treated with water (15 mL) and extracted with EtOAc (2×20 mL). The organic layer was washed with brine (15 mL), dried over anhydrous $Na_2SO_4$ and concentrated. The crude was purified by column chromatography on silica gel with 60% EtOAc/PE to afford 188 (140 mg, 0.38 mmol, 39% yield) as a solid. HPLC: Rt 4.22 min, 97.9%; Column: XBridge C8 (50×4.6) mm, 3.5 μm; Mobile phase: A: 0.1% TFA in water, B: 0.1% TFA in ACN; Flow Rate: 2.0 mL/min. LCMS: 366.1 (M+H), Rt 2.10 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min; Chiral method: Rt 1.76 min, SFC column: YMC Cellulose-SC; mobile phase: 60:40 (A:B), A=liquid $CO_2$, B=methanol; flow rate: 3.0 mL/min; wave length: 220 nm. $^1H$ NMR (400 MHz, $CDCl_3$): δ 7.99 (s, 1H), 7.90-7.88 (m, 1H), 7.81-7.78 (m, 1H), 7.49-7.44 (m, 1H), 7.24-7.19 (m, 1H), 7.02 (brs, 1H), 6.89 (t, 1H), 5.64-5.56 (m, 1H), 3.96 (s, 3H), 1.74 (d, 3H).

Example 145. Synthesis of 189

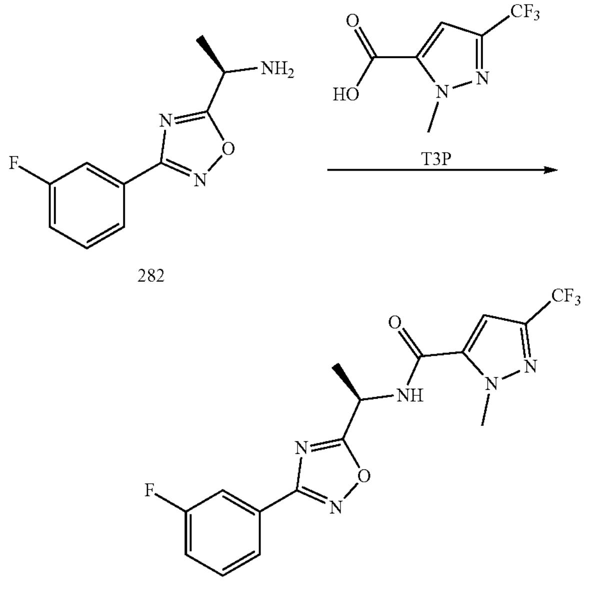

282

189

Synthesis of (R)—N-(1-(3-(3-fluorophenyl)-1,2,4-oxadiazol-5-yl)ethyl)-1-methyl-3-(trifluoromethyl)-1H-pyrazole-5-carboxamide (189)

To a solution of compound 282 (145 mg, 0.70 mmol) in THF (5.0 mL) was added 1-methyl-3-(trifluoromethyl)-1H-pyrazole-5-carboxylic acid (135 mg, 0.70 mmol) followed by T3P (1.25 mL, 2.1 mmol) and $Et_3N$ (0.29 mL, 2.1 mmol). The reaction mixture was stirred at room temperature for 16 h. The reaction mixture was treated with water (20 mL) and extracted with EtOAc (2×20 mL). The organic layer was washed with brine (20 mL), dried over anhydrous $Na_2SO_4$ and concentrated. The crude was purified by column chromatography on silica gel with 60% EtOAc/PE to afford 189 (130 mg, 0.33 mmol, 47% yield) as a solid. HPLC: Rt 5.17 min, 99.0%; Column: XBridge C8 (50×4.6) mm, 3.5 μm; Mobile phase: A: 0.1% TFA in water, B: 0.1% TFA in ACN; Flow Rate: 2.0 mL/min; LCMS: 384.1 (M+H), Rt 2.50 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min; Chiral method: Rt 2.76 min, SFC column: YMC Cellulose-SJ; mobile phase: 85:15 (A:B), A=liquid $CO_2$, B=0.5% isopropyl amine in methanol; flow rate: 3.0 mL/min; wave length: 220 nm. $^1H$ NMR (400 MHz, $CDCl_3$): δ 7.91-7.88 (m, 1H), 7.81-7.78 (m, 1H), 7.52-7.47 (m, 1H), 7.27-7.22 (m, 1H), 6.94 (s, 1H), 6.69 (d, 1H), 5.64-5.60 (m, 1H), 4.25 (s, 3H), 1.79 (d, 3H).

Example 150. Synthesis of 193

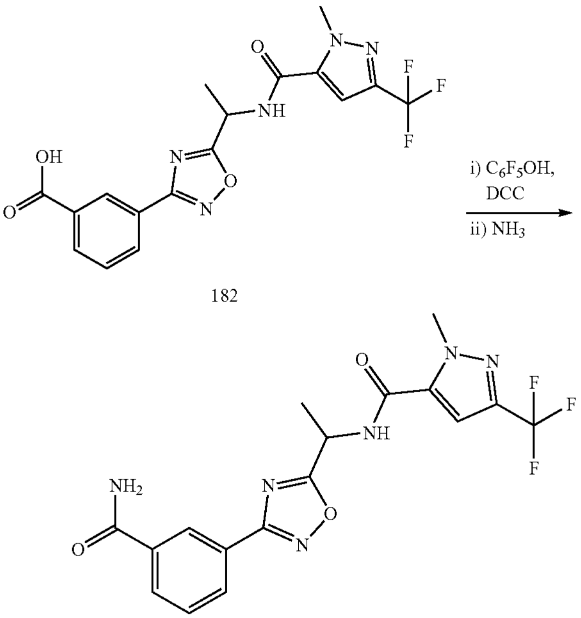

182

193

Synthesis of N-(1-(3-(3-carbamoylphenyl)-1,2,4-oxadiazol-5-yl)ethyl)-1-methyl-3-(trifluoromethyl)-1H-pyrazole-5-carboxamide (193)

To a stirred solution of compound 182 (100 mg, 0.24 mmol) in THF (10.0 mL) was added pentafluorophenol (66 mg, 0.36 mmol) and DCC (74 mg, 0.36 mmol). The reaction mixture was stirred at room temperature for 16 h and $NH_3$ (2.0 M in methanol, 2 mL) was added. The mixture was stirred for 1 h at room temperature and concentrated under reduced pressure. The residue was treated with water (25 mL) and extracted with ethyl acetate (2×30 mL). The organic layer was washed with brine (10 mL), dried over $Na_2SO_4$ and concentrated. The crude was purified by column chromatography on silica gel with 45% EtOAc/PE to afford 193 (13 mg, 0.03 mmol, 13% yield) as a solid. HPLC: Rt 3.84 min, 99.6%; Column: XBridge C8 (50×4.6) mm, 3.5 µm; Mobile phase: A: 0.1% TFA in water, B: 0.1% TFA in ACN; Flow Rate: 2.0 mL/min. LCMS: 409.1 (M+H), Rt 1.88 min, Column: ZORBAX XDB C-18 (50×4.6 mm), 3.5 µm Mobile Phase: A: 0.1% HCOOH in water:ACN (95:5), B: ACN; Flow Rate: 1.5 mL/min. $^1H$ NMR (400 MHz, DMSO-$d_6$): δ 9.47 (d, 1H), 8.51 (s, 1H), 8.21 (s, 1H), 8.14 (d, 1H), 8.09 (d, 1H), 7.66 (t, 1H), 7.55 (s, 1H), 7.46 (s, 1H), 5.50-5.46 (m, 1H), 4.14 (s, 3H), 1.69 (d, 3H).

Example 151. Synthesis of 194 and 195

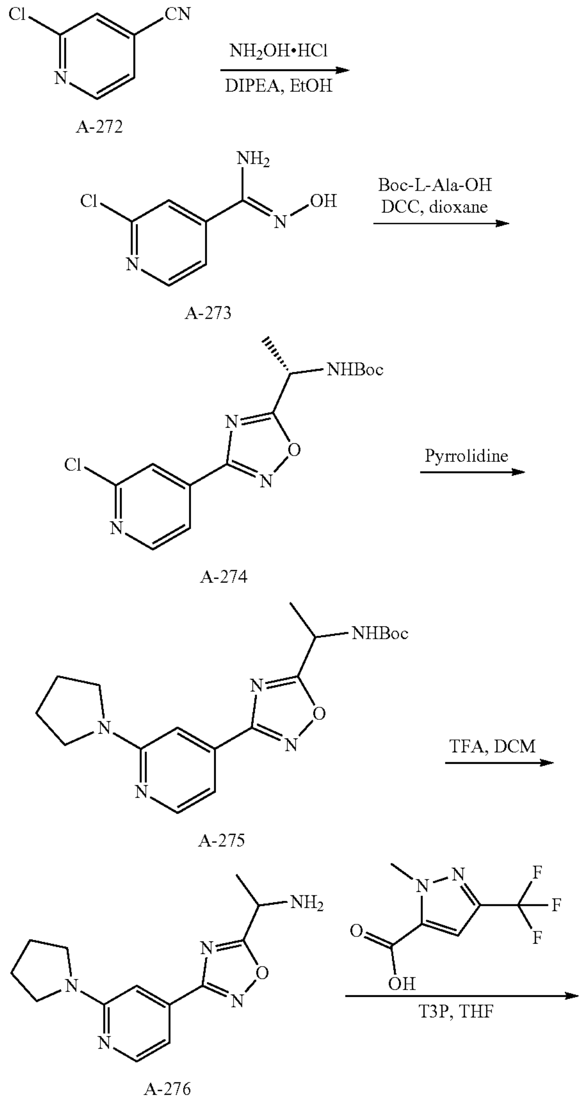

A-272

A-273

A-274

A-275

A-276

-continued

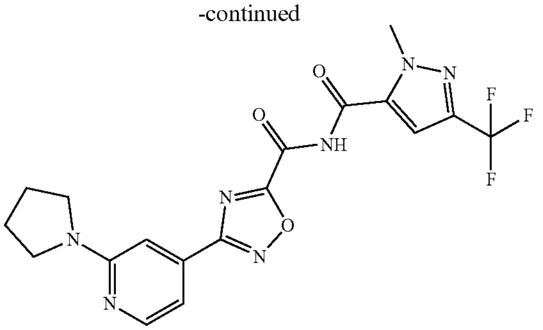

194

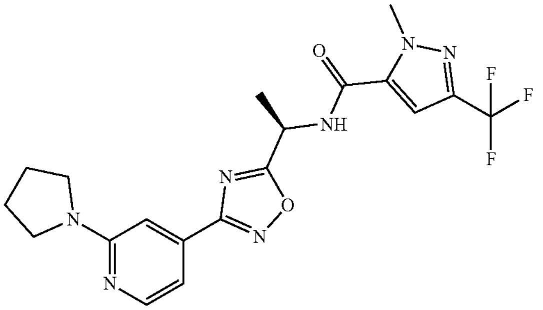

195

Synthesis of (Z)-2-chloro-N'-hydroxyisonicotinimidamide (A-273)

To a solution of 2-chloropyridine-4-carbonitrile (20 g, 144 mmol) in ethanol (200 mL) was added hydroxylamine hydrochloride (15.05 g, 216 mmol) followed by DIPEA (59.6 mL, 360 mmol). The reaction mixture was heated at 75° C. for 12 h. The reaction mixture was cooled to room temperature and concentrated under reduced pressure. The crude was treated with water (100 mL) followed by saturated sodium bicarbonate solution (50 mL) and extracted with ethyl acetate (2×100 mL). The organic layer was washed with brine (50 mL), dried over $Na_2SO_4$ and concentrated to afford compound A-273 (23 g) as a solid. It was used for the next step without further purification.

Synthesis of tert-butyl (S)-(1-(3-(2-chloropyridin-4-yl)-1,2,4-oxadiazol-5-yl)ethyl)carbamate (A-274)

To a solution of compound A-273 (4.0 g, 23.3 mmol) in 1,4-dioxane (50.0 mL) was added (2S)-2-(tert-butoxycarbonylamino)propanoic acid (4.78 g, 25.29 mmol) followed by DCC (5.28 g, 25.64 mmol). The reaction mixture was heated at 100° C. for 16 h. The reaction mixture was cooled to room temperature and concentrated under reduced pressure. The mixture was treated with water (50 mL) and extracted with ethyl acetate (2×50 mL). The organic layer was washed with brine (20 mL), dried over $Na_2SO_4$ and concentrated. The crude was purified by column chromatography on silica gel with 7% ethyl acetate/PE to afford compound A-274 (3.2 g, 9.8 mmol, 42% yield) as a solid. LCMS: 325.1 (M+H), Rt 2.36 min; Column: ZORBAX XDB C-18 (50×4.6 mm), 3.5 µm; Mobile Phase: A: 0.1% HCOOH in water, B: 0.1% HCOOH in ACN; Flow Rate: 1.5 mL/min.

Synthesis of tert-butyl (1-(3-(2-(pyrrolidin-1-yl) pyridin-4-yl)-1,2,4-oxadiazol-5-yl)ethyl)carbamate (A-275)

To a solution of compound A-274 (1.0 g, 3.0 mmol) in NMP (8.0 mL) was added pyrrolidine (429 mg, 6.04 mmol) and irradiated in microwave at 120° C. for 1 h. The reaction mixture was cooled to room temperature and treated with water (30 mL). The mixture was extracted with ethyl acetate (2×25 mL). The organic layer was washed with brine (20 mL), dried over $Na_2SO_4$ and concentrated. The crude was purified by column chromatography on silica gel with 10% EtOAc/PE to afford compound A-275 (720 mg, 2.0 mmol, 66% yield) as a solid. LCMS: 360.2 (M+H), Rt 1.41 min; Column: ZORBAX XDB C-18 (50×4.6 mm), 3.5 μm; Mobile Phase: A: 0.1% HCOOH in water, B: 0.1% HCOOH in ACN; Flow Rate: 1.5 mL/min.

Synthesis of 1-(3-(2-(pyrrolidin-1-yl)pyridin-4-yl)-1,2,4-oxadiazol-5-yl)ethan-1-amine (A-276)

To a solution of compound A-275 (400 mg, 1.11 mmol) in DCM (5.0 mL) was added TFA (1.22 mL) at 0° C. The reaction mixture was slowly warmed to room temperature and stirred for 3 h. The mixture was concentrated under reduced pressure and treated with ice water (20 mL). The mixture was treated with saturated $NaHCO_3$ solution (5 mL) and extracted with EtOAc (2×25 mL). The organic layer was washed with brine (20 mL), dried over anhydrous $Na_2SO_4$ and concentrated to afford compound A-276 (200 mg). The compound was used for the next step without further purification.

Synthesis of (S)-1-methyl-N-(1-(3-(2-(pyrrolidin-1-yl)pyridin-4-yl)-1,2,4-oxadiazol-5-yl)ethyl)-3-(trifluoromethyl)-1H-pyrazole-5-carboxamide (194) and (R)-1-methyl-N-(1-(3-(2-(pyrrolidin-1-yl)pyridin-4-yl)-1,2,4-oxadiazol-5-yl)ethyl)-3-(trifluoromethyl)-1H-pyrazole-5-carboxamide (195)

To a solution of compound A-276 (200 mg, 0.77 mmol) in THF (10.0 mL) was added 2-methyl-5-(trifluoromethyl) pyrazole-3-carboxylic acid (164 mg, 0.85 mmol) followed by T3P (50% in EtOAc, 1.38 mL, 2.31 mmol) and $Et_3N$ (0.32 mL, 2.31 mmol). The reaction mixture was stirred at room temperature for 16 h. The reaction mixture was treated with water (30 mL) and extracted with ethyl acetate (2×25 mL). The organic layer was washed with saturated sodium bicarbonate solution (20 mL), washed with brine (20 mL), dried over $Na_2SO_4$ and concentrated. The crude was purified by column chromatography on silica gel with 30% EtOAc/PE to afford 100 mg of racemic compound. The racemic mixture was separated by SFC purification to afford 194 (35 mg, 0.08 mmol, 10% yield) and 195 (38 mg, 0.09 mmol, 11% yield) as solids. Chiral method: SFC column: CHIRALCEL OX-H; mobile phase: 90:10 (A:B), A=liquid $CO_2$, B=0.5% isopropyl amine in methanol; flow rate: 3.0 mL/min; wave length: 220 nm. The stereochemistry of 194 and 195 was randomly assigned.

194:

HPLC: Rt 3.46 min, 99.1%; Column: XBridge C8 (50×4.6) mm, 3.5 μm; Mobile phase: A: 0.1% TFA in water, B: 0.1% TFA in ACN; Flow Rate: 2.0 mL/min. LCMS: 436.1 (M+H), Rt 1.52 min, Column: ZORBAX XDB C-18 (50×4.6 mm), 3.5 μm; Mobile Phase: A: 0.1% HCOOH in water, B: 0.1% HCOOH in ACN; Flow Rate: 1.5 mL/min. Chiral method: Rt 6.55 min, SFC column: CHIRALCELOX-H; mobile phase: 90:10 (A:B), A=liquid $CO_2$, B=0.5% isopropyl amine in methanol; flow rate: 3.0 mL/min; wave length: 220 nm. $^1H$ NMR (400 MHz, DMSO-$d_6$): δ 9.47 (d, 1H), 8.24 (d, 1H), 7.45 (s, 1H), 7.06-7.04 (m, 1H), 6.91 (s, 1H), 5.51-5.41 (m, 1H), 4.13 (s, 3H), 3.44 (t, 4H), 1.97 (t, 4H), 1.67 (d, 3H).

195:

HPLC: Rt 3.46 min, 99.8%; Column: XBridge C8 (50×4.6) mm, 3.5 μm; Mobile phase: A: 0.1% TFA in water, B: 0.1% TFA in ACN; Flow Rate: 2.0 mL/min. LCMS: 436.2 (M+H), Rt 1.54 min, Column: ZORBAX XDB C-18 (50×4.6 mm), 3.5 μm; Mobile Phase: A: 0.1% HCOOH in water, B: 0.1% HCOOH in ACN; Flow Rate: 1.5 mL/min. Chiral method: Rt 7.16 min, SFC column: Chiralcel OX-H; mobile phase: 90:10 (A:B), A=liquid $CO_2$, B=0.5% isopropyl amine in methanol; flow rate: 3.0 mL/min; wave length: 220 nm. $^1H$ NMR (400 MHz, DMSO-$d_6$): δ 9.47 (s, 1H), 8.24 (d, 1H), 7.45 (s, 1H), 7.05 (d, 1H), 6.91 (s, 1H), 5.47 (m, 1H), 4.13 (s, 3H), 3.44 (m, 4H), 1.97 (m, 4H), 1.67 (d, 3H).

Example 152. Synthesis of 283 & 196

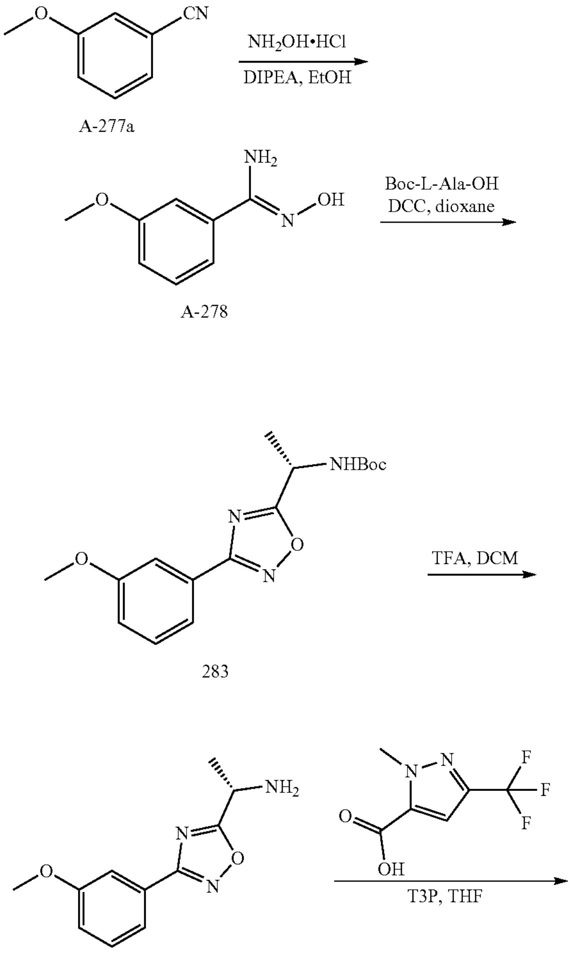

A-277a

A-278

283

A-280

-continued

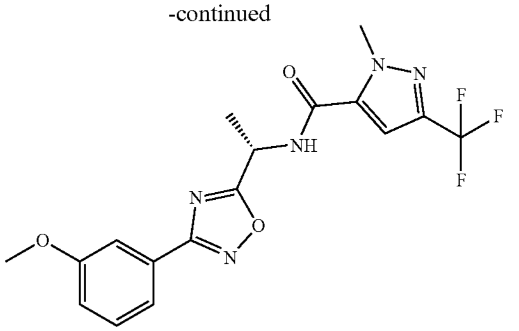

196

Synthesis of (Z)—N'-hydroxy-3-methoxybenzimidamide (A-278)

To a stirred solution of 3-methoxybenzonitrile (5.0 g, 37.5 mmol) in ethanol (50.0 mL) was added hydroxylamine hydrochloride (3.91 g, 56.3 mmol) followed by DIPEA (19.6 mL, 112.6 mmol). The reaction mixture was heated at 80° C. for 2 h. The reaction mixture was cooled to room temperature and concentrated under reduced pressure. The mixture was treated with water (100 mL) followed by saturated sodium bicarbonate solution (20 mL) and extracted with ethyl acetate (2×100 mL). The organic layer was washed with brine (100 mL), dried over $Na_2SO_4$ and concentrated to afford compound A-278 (6.0 g) as a solid. It was used for the next step without further purification.

Synthesis of tert-butyl (S)-(1-(3-(3-methoxyphenyl)-1,2,4-oxadiazol-5-yl)ethyl)carbamate (283)

To a stirred solution of compound A-278 (2.7 g, 16.2 mmol) in 1,4-dioxane (30 mL) was added (2S)-2-(tert-butoxycarbonylamino)propanoic acid (3.06 g, 16.2 mmol) and DCC (3.67 g, 17.8 mmol). The reaction mixture was heated at 100° C. for 16 h. The reaction mixture was cooled to room temperature and concentrated under reduced pressure. The mixture was treated with water (100 mL) and extracted with ethyl acetate (2×70 mL). The organic layer was washed with brine (100 mL), dried over $Na_2SO_4$ and concentrated. The crude compound was purified by column chromatography on silica gel with 9% EtOAc/PE to afford compound 283 (4.6 g, 14.4 mmol, 88% yield) as a solid. LCMS: 318.1 (M−H), Rt 2.45 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (S)-1-(3-(3-methoxyphenyl)-1,2,4-oxadiazol-5-yl)ethan-1-amine (A-280)

To a stirred solution of compound 283 (0.5 g, 1.5 mmol) in DCM (10 mL) was added TFA (1.1 mL) at 0° C. The reaction mixture was slowly warmed to room temperature and stirred for 2 h. The mixture was concentrated under reduced pressure and treated with ice water (20 mL). The mixture was treated with 10% aqueous $NaHCO_3$ solution (5.0 mL) and extracted with ethyl acetate (2×25 mL). The organic layer was washed with brine (50 mL), dried over anhydrous $Na_2SO_4$ and concentrated to afford compound A-280 (320 mg). The compound was used for the next step without further purification.

Synthesis of (S)—N-(1-(3-(3-methoxyphenyl)-1,2,4-oxadiazol-5-yl)ethyl)-1-methyl-3-(trifluoromethyl)-1H-pyrazole-5-carboxamide (196)

To a stirred solution of 2-methyl-5-(trifluoromethyl)pyrazole-3-carboxylic acid (150 mg, 0.77 mmol) in THF (6.0 mL) was added compound A-280 (170 mg, 0.77 mmol). To the reaction mixture TEA (0.32 mL, 2.32 mmol) and T3P (50% in EtOAc, 1.38 mL, 2.32 mmol) were added and the mixture was stirred at RT for 16 h. The reaction mixture was treated with water (30 mL) and extracted with ethyl acetate (2×25 mL). The organic layer was washed with brine (50 mL), dried over anhydrous $Na_2SO_4$ and concentrated. The crude compound was purified by column chromatography on silica gel with 30% EtOAc/PE to afford 196 (95 mg, 0.24 mmol, 30% yield) as a colourless liquid. HPLC: Rt 5.02 min, 99%; Column: XBridge C8 (50×4.6) mm, 3.5 μm; Mobile phase: A: 0.1% TFA in water, B: 0.1% TFA in ACN; Flow Rate: 2.0 mL/min. LCMS: 394.1 (M−H), Rt 2.48 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.41 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1$H NMR (400 MHz, DMSO-$d_6$): δ 9.45 (d, 1H), 7.59 (d, 1H), 7.52-7.45 (m, 3H), 7.19-7.17 (m, 1H), 5.49-5.42 (m, 1H), 4.14 (s, 3H), 3.84 (s, 3H), 1.67 (d, 3H).

Example 153. Synthesis of 197 and 198

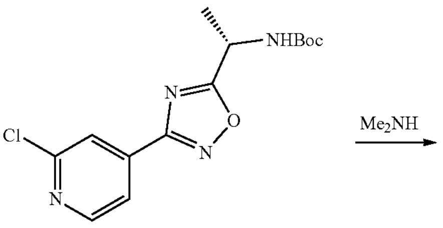

A-274

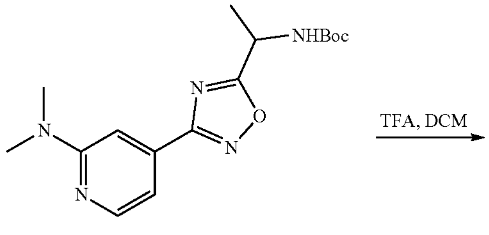

A-281

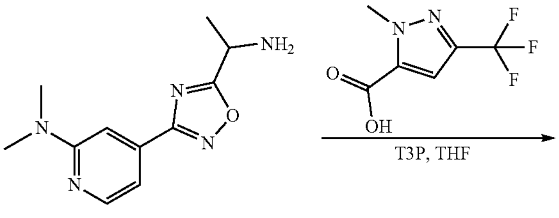

A-282

-continued

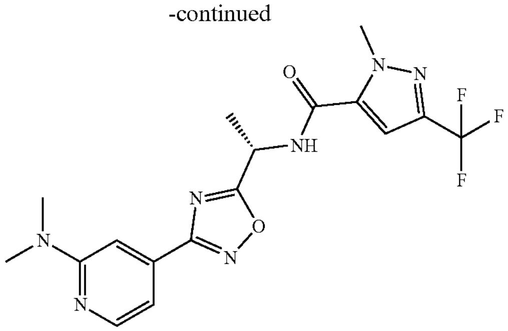

197

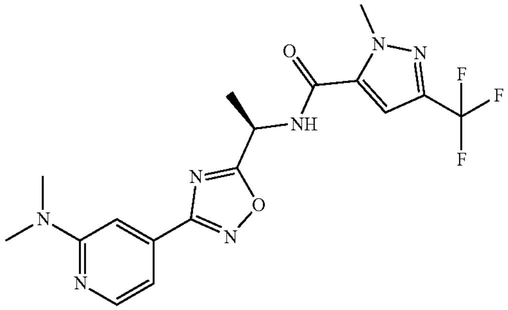

198

Synthesis of tert-butyl (1-(3-(2-(dimethylamino) pyridin-4-yl)-1,2,4-oxadiazol-5-yl)ethyl)carbamate (A-281)

To a solution of compound A-274 (0.5 g, 1.51 mmol) in NMP (2.0 mL) was added dimethylamine solution (2.0 M in THF, 3.77 mL, 7.54 mmol) and irradiated in microwave at 120° C. for 2 h. The reaction mixture was cooled to room temperature and treated with water (30 mL). The mixture was extracted with ethyl acetate (2×25 mL). The organic layer was washed with brine (20 mL), dried over $Na_2SO_4$ and concentrated. The crude was purified by column chromatography on silica gel with 10% EtOAc/PE to afford compound A-281 (220 mg, 0.66 mmol, 43% yield) as a solid. LCMS: 334.3 (M+H), Rt 1.43 min; Column: ZORBAX XDB C-18 (50×4.6 mm), 3.5 µm; Mobile Phase: A: 0.1% HCOOH in water:ACN (95:5), B: ACN; Flow Rate: 1.5 mL/min.

Synthesis of 4-(5-(1-aminoethyl)-1,2,4-oxadiazol-3-yl)-N,N-dimethylpyridin-2-amine (A-282)

To a solution of compound A-281 (220 mg, 0.66 mmol) in DCM (5.0 mL) was added TFA (0.72 mL) at 0° C. The reaction mixture was slowly warmed to room temperature and stirred for 3 h. The mixture was concentrated under reduced pressure and treated with ice water (20 mL). The mixture was treated with 10% aqueous $NaHCO_3$ solution (10 mL) and extracted with EtOAc (2×25 mL). The organic layer was washed with brine (20 mL), dried over anhydrous $Na_2SO_4$ and concentrated to afford compound A-282 (140 mg). The compound was used for the next step without further purification.

Synthesis of (S)—N-(1-(3-(2-(dimethylamino)pyridin-4-yl)-1,2,4-oxadiazol-5-yl)ethyl)-1-methyl-3-(trifluoromethyl)-1H-pyrazole-5-carboxamide (197) and (R)—N-(1-(3-(2-(dimethylamino)pyridin-4-yl)-1,2,4-oxadiazol-5-yl)ethyl)-1-methyl-3-(trifluoromethyl)-1H-pyrazole-5-carboxamide (198)

To a solution of compound A-282 (140 mg, 0.60 mmol) in THF (8.0 mL) was added 2-methyl-5-(trifluoromethyl) pyrazole-3-carboxylic acid (116 mg, 0.60 mmol) followed by $Et_3N$ (0.25 mL, 1.8 mmol) and T3P (50% in EtOAc, 1.07 mL, 1.8 mmol). The reaction mixture was stirred at room temperature for 16 h. The reaction mixture was treated with water (30 mL) and extracted with ethyl acetate (2×25 mL). The organic layer was washed with saturated sodium bicarbonate solution (20 mL), washed with brine (20 mL), dried over $Na_2SO_4$ and concentrated. The crude was purified by column chromatography on silica gel with 32% EtOAc/PE to afford 110 mg of racemic compound. The racemic mixture was separated by SFC purification to afford 1977 (24 mg, 0.06 mmol, 9% yield) and 198 (34 mg, 0.08 mmol, 13% yield) as solids. Chiral method: SFC column: LUX $C_3$; mobile phase: 80:20 (A:B), A=liquid $CO_2$, B=methanol; flow rate: 3.0 mL/min; wave length: 220 nm. The stereochemistry of 197 and 198 was randomly assigned.

197:

HPLC: Rt 3.23 min, 97.1%; Column: X-Bridge C8 (50×4.6) mm, 3.5 µm; Mobile phase: A: 0.1% TFA in water, B: 0.1% TFA in ACN; Flow Rate: 2.0 mL/min. LCMS: 410.1 (M+H), Rt 1.49 min, Column: ZORBAX XDB C-18 (50×4.6 mm), 3.5 µm; Mobile Phase: A: 0.1% HCOOH in water:ACN (95:5), B: ACN; Flow Rate: 1.5 mL/min. Chiral method: Rt 1.88 min, SFC column: LUX $C_3$; mobile phase: 80:20 (A:B), A=liquid $CO_2$, B=methanol; flow rate: 3.0 mL/min; wave length: 220 nm. $^1H$ NMR (400 MHz, $CD_3OD$): δ 8.21 (d, 1H), 7.27 (s, 1H), 7.26 (s, 1H), 7.18 (d, 1H), 5.53 (q, 1H), 4.19 (s, 3H), 3.16 (s, 6H), 1.77 (d, 3H).

198:

HPLC: Rt 3.21 min, 99.2%; Column: XBridge C8 (50×4.6) mm, 3.5 µm; Mobile phase: A: 0.1% TFA in water, B: 0.1% TFA in ACN; Flow Rate: 2.0 mL/min. LCMS: 410.1 (M+H), Rt 1.49 min, Column: ZORBAX XDB C-18 (50×4.6 mm), 3.5 µm; Mobile Phase: A: 0.1% HCOOH in water:ACN (95:5), B: ACN; Flow Rate: 1.5 mL/min. Chiral method: Rt 2.41 min, SFC column: LUX $C_3$; mobile phase: 80:20 (A:B), A=liquid $CO_2$, B=methanol; flow rate: 3.0 mL/min; wave length: 220 nm. $^1H$ NMR (400 MHz, $CD_3OD$): δ 8.21-8.20 (m, 1H), 7.27 (s, 1H), 7.26 (s, 1H), 7.19-7.17 (m, 1H), 5.53 (q, 1H), 4.19 (s, 3H), 3.15 (s, 6H), 1.77 (d, 3H).

Example 154. Synthesis of 199

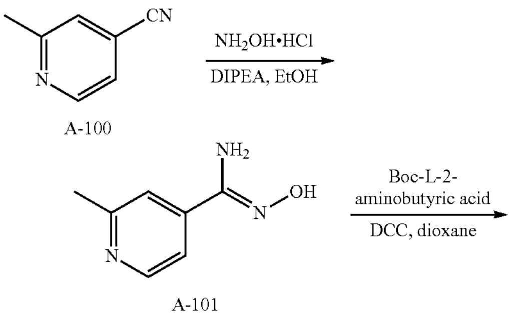

-continued

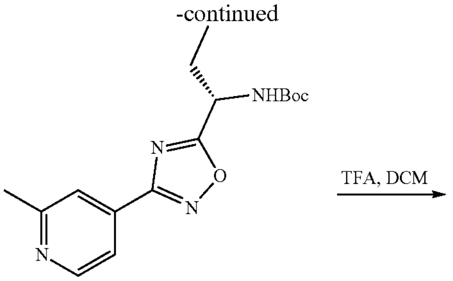

284

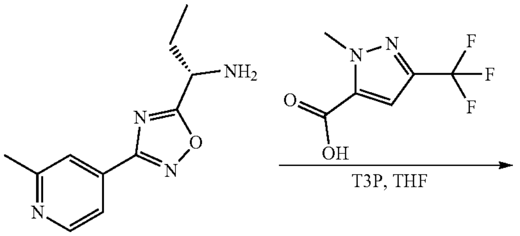

A-284

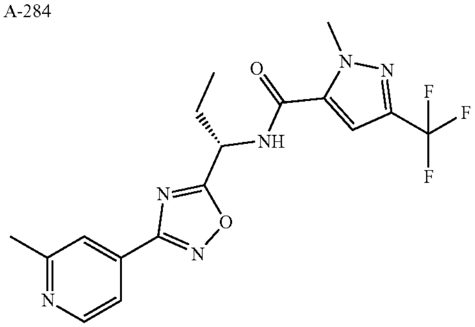

199

Synthesis of (Z)—N'-hydroxy-2-methylisonicotin-imidamide (A-101)

To a stirred solution of 2-methylpyridine-4-carbonitrile (1.0 g, 8.46 mmol) in ethanol (20 mL) was added hydroxylamine hydrochloride (0.88 g, 12.7 mmol) followed by DIPEA (4.41 mL, 25.4 mmol). The reaction mixture was heated at 80° C. for 2 h. The reaction mixture was cooled to room temperature and concentrated under reduced pressure. The mixture was treated with water (20 mL) followed by saturated sodium bicarbonate solution (10 mL) and extracted with ethyl acetate (2×50 mL). The organic layer was washed with brine (50 mL), dried over $Na_2SO_4$ and concentrated to afford compound A-101 (1.1 g) as a liquid. It was used for the next step without further purification.

Synthesis of tert-butyl (S)-(1-(3-(2-methylpyridin-4-yl)-1,2,4-oxadiazol-5-yl)propyl)carbamate (284)

To a stirred solution of compound A-101 (1.1 g, 7.3 mmol) in 1,4-dioxane (20 mL) was added (2S)-2-(tert-butoxycarbonylamino)butanoic acid (1.41 g, 6.9 mmol) followed by DCC (1.57 g, 7.6 mmol). The reaction mixture was heated at 100° C. for 16 h. The reaction mixture was cooled to room temperature and concentrated under reduced pressure. The mixture was treated with water (60 mL) and extracted with ethyl acetate (2×50 mL). The organic layer was washed with brine (50 mL), dried over $Na_2SO_4$ and concentrated. The crude compound was purified by column chromatography on silica gel with 12% EtOAc/PE to afford compound 284 (1.7 g, 5.3 mmol, 76% yield) as a liquid. LCMS: 319.2 (M+H), Rt 1.89 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (S)-1-(3-(2-methylpyridin-4-yl)-1,2,4-oxadiazol-5-yl)propan-1-amine (A-284)

To a stirred solution of compound 284 (700 mg, 2.2 mmol) in DCM (14 mL) was added TFA (2.7 mL) at 0° C. The reaction mixture was slowly warmed to room temperature and stirred for 2 h. The mixture was concentrated under reduced pressure and treated with ice water (30 mL). The mixture was treated with 10% aqueous $Na_2CO_3$ solution (5.0 mL) and extracted with ethyl acetate (2×50 mL). The organic layer was washed with brine (50 mL), dried over anhydrous $Na_2SO_4$ and concentrated to afford compound A-284 (270 mg). The compound was used for the next step without further purification.

Synthesis of (S)-1-methyl-N-(1-(3-(2-methylpyridin-4-yl)-1,2,4-oxadiazol-5-yl)propyl)-3-(trifluoromethyl)-1H-pyrazole-5-carboxamide (199)

To a stirred solution of 2-methyl-5-(trifluoromethyl)pyrazole-3-carboxylic acid (150 mg, 0.77 mmol) in THF (6 mL) was added compound A-284 (170 mg, 0.77 mmol). To the reaction mixture TEA (0.32 mL, 2.32 mmol) and T3P (50% in EtOAc, 1.38 mL, 2.32 mmol) were added and the mixture was stirred at RT for 16 h. The reaction mixture was treated with water (30 mL) and extracted with ethyl acetate (2×25 mL). The organic layer was washed with brine (30 mL), dried over anhydrous $Na_2SO_4$ and concentrated. The crude compound was purified by preparative HPLC to 199 (51 mg, 0.13 mmol, 16% yield) as a colourless liquid. Prep. HPLC method: Rt 9.30; Column: XBridge (150×19 mm), 5.0 μm; Mobile phase: 10 mM $NH_{40}Ac$ in water/acetonitrile; Flow Rate: 15.0 mL/min. HPLC: Rt 5.94 min, 99.8%; Column: XBridge C8 (50×4.6) mm, 3.5 μm; Mobile phase: A: 0.1% TFA in water, B: ACN; Flow Rate: 2.0 mL/min LCMS: 395.2 (M+H), Rt 2.01 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.31 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.61 (d, 1H), 7.96 (s, 1H), 7.86 (d, 1H), 7.28 (s, 1H), 5.40-5.36 (m, 1H), 4.19 (s, 3H), 2.64 (s, 3H), 2.28-2.09 (m, 2H), 1.13 (t, 3H).

Example 155. Synthesis of 200

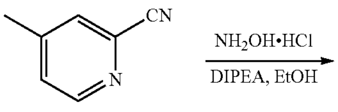

A-285

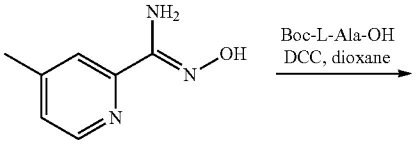

A-286

-continued

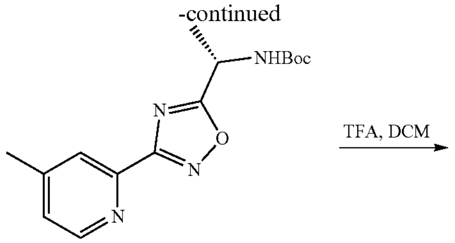

285

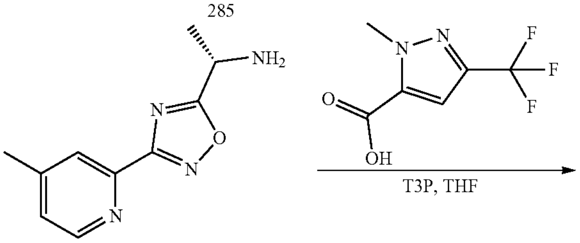

A-288

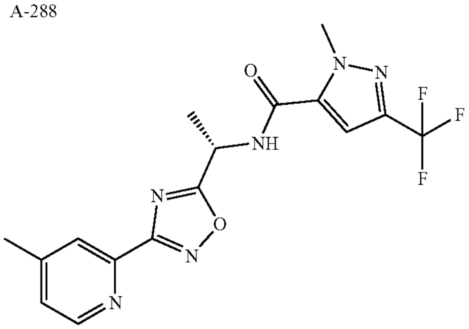

200

Synthesis of (Z)—N'-hydroxy-4-methylpicolinimidamide (A-286)

To a stirred solution of 4-methylpyridine-2-carbonitrile (5.0 g, 42.3 mmol) in ethanol (50.0 mL) was added DIPEA (20.9 mL, 126.7 mmol) followed by hydroxylamine hydrochloride (2.94 g, 42.3 mmol). The reaction heated at 80° C. for 2 h. The reaction mixture was cooled to room temperature and concentrated under reduced pressure. The mixture was treated with water (80 mL) followed by saturated sodium bicarbonate solution (20 mL) and extracted with ethyl acetate (2×100 mL). The organic layer was washed with brine (100 mL), dried over $Na_2SO_4$ and concentrated to afford compound A-286 (5.6 g) as a solid. It was used for the next step without further purification.

Synthesis of tert-butyl (S)-(1-(3-(4-methylpyridin-2-yl)-1,2,4-oxadiazol-5-yl)ethyl)carbamate (285)

To a stirred solution of compound A-286 (3.0 g, 19.8 mmol) in 1,4-dioxane (30 mL) was added (2S)-2-(tert-butoxycarbonylamino)propanoic acid (3.74 g, 19.8 mmol) followed by DCC (4.48 g, 21.7 mmol). The reaction mixture was heated at 100° C. for 16 h. The reaction mixture was cooled to room temperature and concentrated under reduced pressure. The mixture was treated with water (80 mL) and extracted with ethyl acetate (2×100 mL). The organic layer was washed with brine (100 mL), dried over $Na_2SO_4$ and concentrated. The crude compound was purified by column chromatography on silica gel with 18% EtOAc/PE to afford compound 285 (3 g, 9.8 mmol, 49% yield) as a solid. LCMS: 305.2 (M+H), Rt 2.02 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (S)-1-(3-(4-methylpyridin-2-yl)-1,2,4-oxadiazol-5-yl)ethan-1-amine (A-288)

To a stirred solution of compound 285 (700 mg, 2.3 mmol) in DCM (14 mL) was added TFA (1.8 mL) at 0° C. The reaction mixture was slowly warmed to room temperature and stirred for 2 h. The mixture was concentrated under reduced pressure and treated with ice water (30 mL). The mixture was treated with 10% aqueous $NaHCO_3$ solution (5.0 mL) and extracted with ethyl acetate (2×25 mL). The organic layer was washed with brine (30 mL), dried over anhydrous $Na_2SO_4$ and concentrated to afford compound A-288 (230 mg). The compound was used for the next step without further purification.

Synthesis of (S)-1-methyl-N-(1-(3-(4-methylpyridin-2-yl)-1,2,4-oxadiazol-5-yl)ethyl)-3-(trifluoromethyl)-1H-pyrazole-5-carboxamide (200)

To a stirred solution of 2-methyl-5-(trifluoromethyl)pyrazole-3-carboxylic acid (150 mg, 0.77 mmol) in THF (6.0 mL) was added compound A-288 (169 mg, 0.83 mmol). To the reaction mixture TEA (0.32 mL, 2.32 mmol) and T3P (50% in EtOAc, 1.38 mL, 2.32 mmol) were added and the mixture was stirred at RT for 16 h. The reaction mixture was treated with water (30 mL) and extracted with ethyl acetate (2×25 mL). The organic layer was washed with brine (30 mL), dried over anhydrous $Na_2SO_4$ and concentrated. The crude compound was purified by preparative HPLC to obtain 200 (58 mg, 0.15 mmol, 19% yield) as a solid. Prep. HPLC method: Rt 11.04; Column: Sunfire C18 (150×19 mm), 5.0 μm; Mobile phase: 0.1% TFA in water/acetonitrile; Flow Rate: 15.0 mL/min. HPLC: Rt 3.83 min, 99.6%; Column: XBridge C8 (50×4.6) mm, 3.5 μm; Mobile phase: A: 0.1% TFA in water, B: 0.1% TFA in ACN; Flow Rate: 2.0 mL/min. LCMS: 381.2 (M+H), Rt 2.11 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.38 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.56 (d, 1H), 8.05 (s, 1H), 7.45 (d, 1H), 7.28 (s, 1H), 5.59-5.53 (m, 1H), 4.19 (s, 3H), 2.50 (s, 3H), 1.78 (d, 3H).

Example 156. Synthesis of 286 & 201

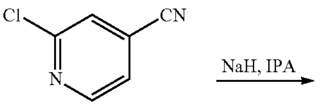

A-272

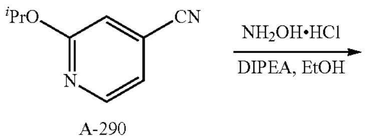

A-290

-continued

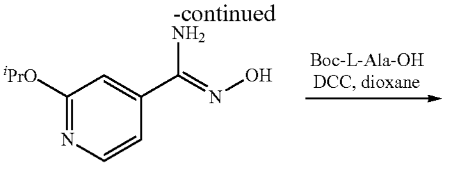

A-291

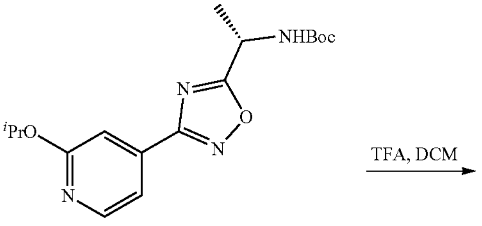

286

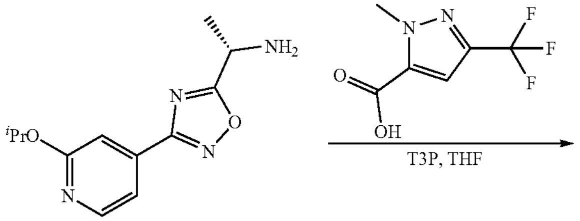

A-293

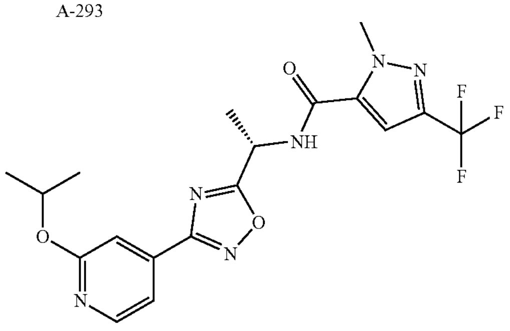

201

Synthesis of 2-isopropoxyisonicotinonitrile (A-290)

To the isopropyl alcohol (45.0 mL) at 0° C. was added NaH (60% in mineral oil, 952 mg, 23.8 mmol) in small portions. The resulting suspension was stirred for 5 min and 2-chloropyridine-4-carbonitrile (3.0 g, 21.65 mmol) was added in small portions. The reaction mixture was heated at 80° C. for 1 h. The reaction mixture was cooled to 10° C. and treated with ice water (50 mL). The mixture was extracted with ethyl acetate (2×50 mL). The organic layer was washed with brine (50 mL), dried over anhydrous $Na_2SO_4$ and concentrated. The crude compound was purified by column chromatography on silica gel with 10% ethyl acetate/PE to afford compound A-290 (980 mg, 6.0 mmol, 27% yield). LCMS: 163.1 (M+H), Rt 2.32 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (Z)—N'-hydroxy-2-isopropoxyisonicotinimidamide (A-291)

To a stirred solution of compound A-290 (0.98 g, 6.0 mmol) in ethanol (20.0 mL) was added hydroxylamine hydrochloride (0.63 g, 9.0 mmol) followed by DIPEA (3.16 mL, 18.13 mmol). The reaction mixture was heated at 80° C. for 2 h. The reaction mixture was cooled to room temperature and treated with water (30 mL). The mixture was treated with 10% sodium carbonate solution (10 mL) and extracted with ethyl acetate (2×50 mL). The organic layer was washed with brine (50 mL), dried over anhydrous $Na_2SO_4$ and concentrated to afford compound A-291 (1.1 g). It was used for next step without further purification.

Synthesis of tert-butyl (S)-(1-(3-(2-isopropoxypyridin-4-yl)-1,2,4-oxadiazol-5-yl)ethyl)carbamate (286)

To a stirred solution of compound A-291 (1.1 g, 5.6 mmol) in 1,4-dioxane (20.0 mL) was added (2S)-2-(tert-butoxycarbonylamino)propanoic acid (1.07 g, 5.6 mmol) and DCC (1.28 g, 6.2 mmol). The reaction mixture was heated to 100° C. for 16 h. The reaction mixture was cooled to room temperature and concentrated under reduced pressure. The mixture was treated with water (30 mL) and extracted with ethyl acetate (2×50 mL). The organic layer was washed with brine (50 mL), dried over anhydrous $Na_2SO_4$ and concentrated. The crude was purified by column chromatography on silica gel with 14% EtOAc/PE to afford compound 286 (1.5 g, 4.3 mmol, 76% yield) as a solid. LCMS: 349.1 (M+H), Rt 2.64 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (S)-1-(3-(2-isopropoxypyridin-4-yl)-1,2,4-oxadiazol-5-yl)ethan-1-amine (A-293)

To a stirred solution of compound 286 (700 mg, 2.01 mmol) in DCM (14.0 mL) was added TFA (0.77 mL) at 0° C. The reaction mixture was slowly warmed to room temperature and stirred for 2 h. The mixture was concentrated under reduced pressure and treated with ice water (10 mL). The mixture was treated with 10% $Na_2CO_3$ solution (5.0 mL) and extracted with ethyl acetate (2×25 mL). The organic layer was washed with brine (25 mL), dried over anhydrous $Na_2SO_4$ and concentrated to afford compound A-293 (280 mg). The compound was used for the next step without further purification.

Synthesis of (S)—N-(1-(3-(2-isopropoxypyridin-4-yl)-1,2,4-oxadiazol-5-yl)ethyl)-1-methyl-3-(trifluoromethyl)-1H-pyrazole-5-carboxamide (201)

To a stirred solution of 2-methyl-5-(trifluoromethyl)pyrazole-3-carboxylic acid (150 mg, 0.77 mmol) in THF (6.0 mL) was added compound A-293 (191 mg, 0.77 mmol) followed by TEA (0.32 mL, 2.32 mmol). To the reaction mixture T3P (50% in EtOAc, 1.38 mL, 2.32 mmol) was added and the mixture was stirred at room temperature for 16 h. The reaction mixture was treated with water (30 mL) and extracted with ethyl acetate (2×25 mL). The organic layer was washed with brine (30 mL), dried over anhydrous $Na_2SO_4$ and concentrated. The crude was purified by preparative HPLC to afford 201 (280 mg, 0.3 mmol, 38% yield) as a solid. Prep. HPLC method: Rt 9.82; Column: XBridge (150×19 mm), 5.0 μm; Mobile phase: 0.1% TFA in water/acetonitrile; Flow Rate: 15.0 mL/min. HPLC: Rt 5.27 min, 99.7%; Column: XBridge C8 (50×4.6) mm, 3.5 μm; Mobile phase: A: 0.1% TFA in water, B: 0.1% TFA in ACN; Flow Rate: 2.0 mL/min; LCMS: 423.1 (M–H), Rt 2.71 min, Column: ZORBAX XDB C-18 (50×4.6 mm), 3.5 μm; Mobile Phase: A: 0.1% HCOOH in water:ACN (95:5), B:

ACN; Flow Rate: 1.5 mL/min. Chiral method: Rt 1.29 min, SFC column: Chiralcel OX-H; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.28 (dd, 1H), 7.52-7.50 (m, 1H), 7.33-7.32 (m, 1H), 7.25 (s, 1H), 5.53 (q, 1H), 5.40-5.31 (m, 1H), 4.19 (s, 3H), 1.77 (d, 3H), 1.37 (d, 6H).

Example 157. Synthesis of 287 & 202

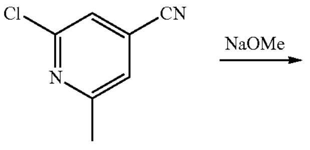

A-294

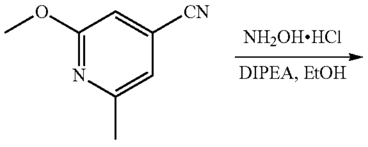

A-295

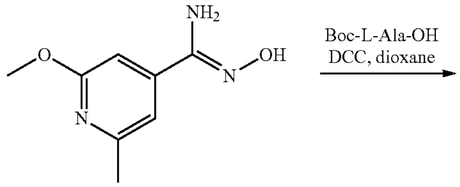

A-296

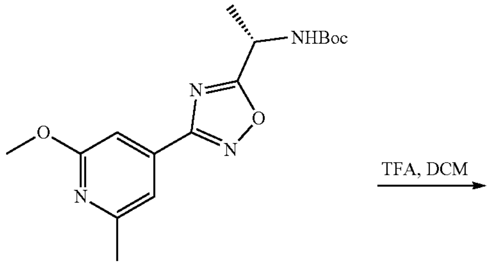

287

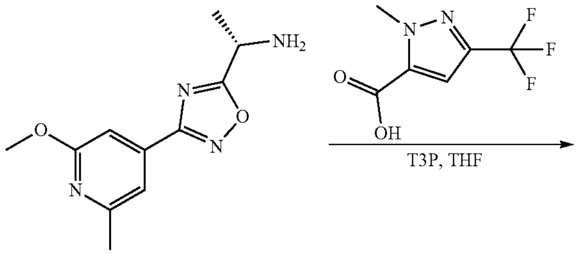

A-298

-continued

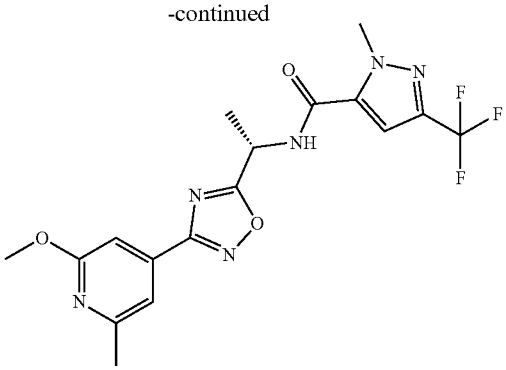

202

Synthesis of 2-methoxy-6-methylisonicotinonitrile (A-295)

To a stirred solution of 2-chloro-6-methyl-pyridine-4-carbonitrile (1.0 g, 6.55 mmol) in 1,4-dioxane (10.0 mL) was added NaOMe (0.39 g, 7.21 mmol) at room temperature. The reaction mixture was heated at 60° C. for 4 h. The reaction mixture was cooled, treated with ice water (30 mL) and extracted with ethyl acetate (2×50 mL). The organic layer was washed with brine (50 mL), dried over anhydrous $Na_2SO_4$ and concentrated. The crude compound was purified by column chromatography on silica gel with 10% ethyl acetate/PE to afford compound A-295 (650 mg, 4.3 mmol, 66% yield) as a solid. LCMS: 149.2 (M+H), Rt 2.05 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (Z)—N'-hydroxy-2-methoxy-6-methylisonicotinimidamide (A-296)

To a stirred solution of compound A-295 (650 mg, 4.3 mmol) in ethanol (20.0 mL) was added hydroxylamine hydrochloride (452 mg, 6.51 mmol) followed by DIPEA (2.26 mL, 13.03 mmol). The reaction mixture was heated at 80° C. for 2 h. The reaction mixture was cooled to room temperature and concentrated under reduced pressure. The mixture was treated with water (20 mL) followed by saturated sodium bicarbonate solution (20 mL) and extracted with ethyl acetate (2×50 mL). The organic layer was washed with brine (50 mL), dried over anhydrous $Na_2SO_4$ and concentrated to afford compound A-296 (680 mg) as a solid. The compound was used for the next step without further purification.

Synthesis of tert-butyl (S)-(1-(3-(2-methoxy-6-methylpyridin-4-yl)-1,2,4-oxadiazol-5-yl)ethyl)carbamate (287)

To a stirred solution of compound A-296 (680 mg, 3.7 mmol) in 1,4-dioxane (15.0 mL) was added (2S)-2-(tert-butoxycarbonylamino)propanoic acid (701 mg, 3.7 mmol) and DCC (840 mg, 4.1 mmol). The reaction mixture was heated at 100° C. for 16 h. The reaction mixture was cooled to room temperature and concentrated under reduced pressure. The mixture was treated with water (30 mL) and extracted with ethyl acetate (2×30 mL). The organic layer was washed with brine (30 mL), dried over anhydrous $Na_2SO_4$ and concentrated. The crude compound was purified by column chromatography on silica gel with 12% EtOAc/PE to afford compound 287 (1.0 g, 3.0 mmol, 80% yield) as a solid. LCMS: 335.2 (M+H), Rt 2.55 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (S)-1-(3-(2-methoxy-6-methylpyridin-4-yl)-1,2,4-oxadiazol-5-yl)ethan-1-amine (A-298)

To a stirred solution of compound 287 (400 mg, 1.2 mmol) in DCM (10 mL) was added TFA (0.88 mL) at 0° C. The reaction mixture was slowly warmed to room temperature and stirred for 2 h. The mixture was concentrated under reduced pressure and treated with ice water (20 mL). The mixture was treated with 10% aqueous $NaHCO_3$ solution (5.0 mL) and extracted with ethyl acetate (2×25 mL). The organic layer was washed with brine (30 mL), dried over anhydrous $Na_2SO_4$ and concentrated to afford compound A-298 (260 mg). The compound was used for the next step without further purification.

Synthesis of (S)—N-(1-(3-(2-methoxy-6-methylpyridin-4-yl)-1,2,4-oxadiazol-5-yl)ethyl)-1-methyl-3-(trifluoromethyl)-1H-pyrazole-5-carboxamide (202)

To a stirred solution of 2-methyl-5-(trifluoromethyl)pyrazole-3-carboxylic acid (150 mg, 0.77 mmol) in THF (6.0 mL) was added compound A-298 (181 mg, 0.77 mmol) followed by TEA (0.32 mL, 2.32 mmol). To the reaction mixture T3P (50% in EtOAc, 1.38 mL, 2.32 mmol) was added and the mixture was stirred at room temperature for 16 h. The reaction mixture was treated with water (30 mL) and extracted with ethyl acetate (2×25 mL). The organic layer was washed with brine (25 mL), dried over anhydrous $Na_2SO_4$ and concentrated. The crude compound was purified by preparative HPLC to afford 202 (135 mg, 0.33 mmol, 42% yield) as a solid. Prep. HPLC method: Rt 10.49; Column: Sunfire C18 (150×19 mm), 5.0 μm; Mobile phase: 0.1% TFA in water/acetonitrile; Flow Rate: 15.0 mL/min. HPLC: Rt 4.82 min, 99.8%; Column: XBridge C8 (50×4.6) mm, 3.5 μm; Mobile phase: A: 0.1% TFA in water, B: 0.1% TFA in ACN; Flow Rate: 2.0 mL/min. LCMS: 411.1 (M+H), Rt 2.54 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.97 min, SFC column: LUX $C_3$; mobile phase: 85:15 (A:B), A=liquid $CO_2$, B=methanol; flow rate: 3.0 mL/min; wave length: 210 nm. $^1H$ NMR (400 MHz, $CD_3OD$): δ 7.42 (d, 1H), 7.25 (s, 1H), 7.19 (d, 1H), 5.52 (q, 1H), 4.19 (s, 3H), 3.96 (s, 3H), 2.51 (s, 3H), 1.76 (d, 3H).

Example 158. Synthesis of 288 & 203

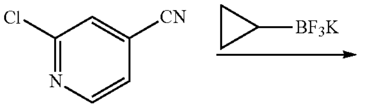

A-272

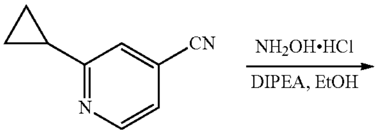

A-300

-continued

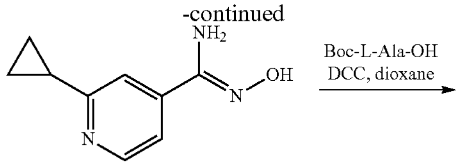

A-301

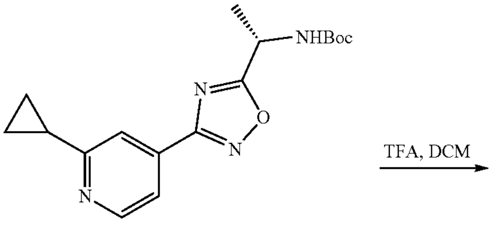

288

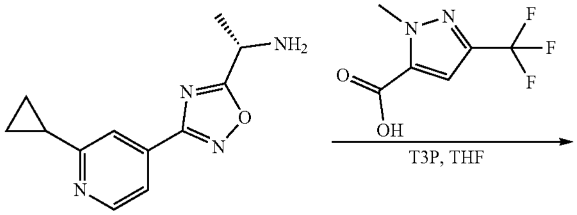

A-303

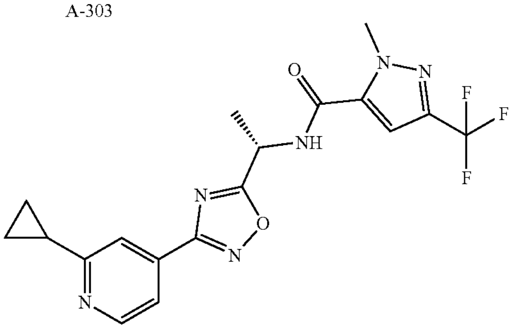

203

Synthesis of 2-cyclopropylisonicotinonitrile (A-300)

To a solution of 2-chloropyridine-4-carbonitrile (2.0 g, 14.4 mmol) in 1,4-dioxane (25 mL) was added potassium cyclopropyltrifluoroborate (6.41 g, 43.3 mmol) followed by $K_2CO_3$ (7.98 g, 57.7 mmol) and RuPhos (1.35 g, 2.89 mmol). The resulting mixture was degassed with $N_2$ gas for 10 min and $Pd(OAc)_2$ (324 mg, 1.44 mmol) was added. The mixture was stirred at 100° C. for 1 h. The reaction mixture was cooled to room temperature and filtered through celite. The filtrate was concentrated under reduced pressure and the crude was purified by column chromatography on silica gel with 15% EtOAc/PE to afford compound A-300 (1.1 g, 7.6 mmol, 50% yield) as a solid. LCMS: 145.1 (M+H), Rt 1.87 min; Column: ZORBAX XDB C-18 (50×4.6 mm), 3.5 μm Mobile Phase: A: 0.1% TFA in water:ACN (95:5), B: 0.1% TFA in ACN; Flow Rate: 1.5 mL/min.

Synthesis of (Z)-2-cyclopropyl-N'-hydroxyisonicotinimidamide (A-301)

To a solution of compound A-300 (450 mg, 3.1 mmol) in ethanol (15.0 mL) was added hydroxylamine hydrochloride (312 mg, 4.4 mmol) followed by DIPEA (1.49 mL, 8.99 mmol) at room temperature. The reaction mixture was heated at 80° C. for 5 h. The reaction mixture was cooled to room temperature and concentrated under reduced pressure. The crude was treated with water (30 mL) followed by saturated sodium bicarbonate solution (20 mL) and extracted with ethyl acetate (2×25 mL). The organic layer was washed with brine (10 mL), dried over $Na_2SO_4$ and concentrated to afford compound A-301 (420 mg) as a solid. It was used for the next step without further purification.

Synthesis of tert-butyl (S)-(1-(3-(2-cyclopropylpyridin-4-yl)-1,2,4-oxadiazol-5-yl)ethyl)carbamate (288)

To a solution of (2S)-2-(tert-butoxycarbonylamino)propanoic acid (0.44 g, 2.31 mmol) in 1,4-dioxane (10.0 mL) was added compound A-301 (0.41 g, 2.31 mmol) followed by DCC (0.52 g, 2.55 mmol). The resulting mixture was stirred at 100° C. for 16 h. The reaction mixture was cooled to room temperature and concentrated under reduced pressure. The mixture was treated with water (30 mL) and extracted with ethyl acetate (2×25 mL). The organic layer was washed with brine (20 mL), dried over $Na_2SO_4$ and concentrated. The crude was purified by column chromatography on silica gel with 15% ethyl acetate/PE to afford compound 288 (570 mg, 1.72 mmol, 74% yield) as a solid. LCMS: 331.3 (M+H), Rt 2.22 min; Column: ZORBAX XDB C-18 (50×4.6 mm), 3.5 μm; Mobile Phase: A: 0.1% TFA in water:ACN (95:5), B: 0.1% TFA in ACN; Flow Rate: 1.5 mL/min.

Synthesis of (S)-1-(3-(2-cyclopropylpyridin-4-yl)-1,2,4-oxadiazol-5-yl)ethan-1-amine (A-303)

To a solution of compound 288 (410 mg, 1.24 mmol) in DCM (5.0 mL) was added TFA (1.36 mL) at 0° C. The reaction mixture was slowly warmed to room temperature and stirred for 3 h. The mixture was concentrated under reduced pressure and treated with ice water (20 mL). The mixture was treated with 10% aqueous $NaHCO_3$ solution (5 mL) and extracted with EtOAc (2×25 mL). The organic layer was washed with brine (20 mL), dried over anhydrous $Na_2SO_4$ and concentrated to afford compound A-303 (240 mg). The compound was used for the next step without further purification.

Synthesis of (S)—N-(1-(3-(2-cyclopropylpyridin-4-yl)-1,2,4-oxadiazol-5-yl)ethyl)-1-methyl-3-(trifluoromethyl)-1H-pyrazole-5-carboxamide (203)

To a solution of compound A-303 (240 mg, 1.04 mmol) in THF (8.0 mL) was added 2-methyl-5-(trifluoromethyl) pyrazole-3-carboxylic acid (202 mg, 1.04 mmol) followed by $Et_3N$ (0.43 mL, 3.13 mmol) and T3P (50% in EtOAc, 1.86 mL, 3.13 mmol). The reaction mixture was stirred at room temperature for 16 h. The reaction mixture was treated with water (30 mL) and extracted with ethyl acetate (2×25 mL). The organic layer was washed with brine (20 mL), dried over $Na_2SO_4$ and concentrated. The crude was purified by column chromatography on silica get with 60% EtOAc/PE to afford 203 (216 mg, 0.53 mmol, 51% yield) as a solid. HPLC: Rt 3.48 min, 97.3%; Column: XBridge C8 (50×4.6) mm, 3.5 μm; Mobile phase: A: 0.1% TFA in water, B: 0.1% TFA in ACN; Flow Rate: 2.0 mL/min. LCMS: 407.1 (M+H), Rt 1.77 min, Column: ZORBAX XDB C-18 (50×4.6 mm), 3.5 μm; Mobile Phase: A: 0.1% TFA in water:ACN (95:5), B: 0.1% TFA in ACN; Flow Rate: 1.5 mL/min. Chiral method: Rt 1.42 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CDCl_3$): δ 8.61 (d, 11H), 7.79 (s, 1H), 7.68 (dd, 1H), 6.95 (s, 1H), 6.70 (d, 1H), 5.67-5.60 (m, 1H), 4.25 (s, 3H), 2.20-2.13 (m, 1H), 1.80 (d, 3H), 1.14-1.10 (m, 4H).

Example 159. Synthesis of 289 & 204

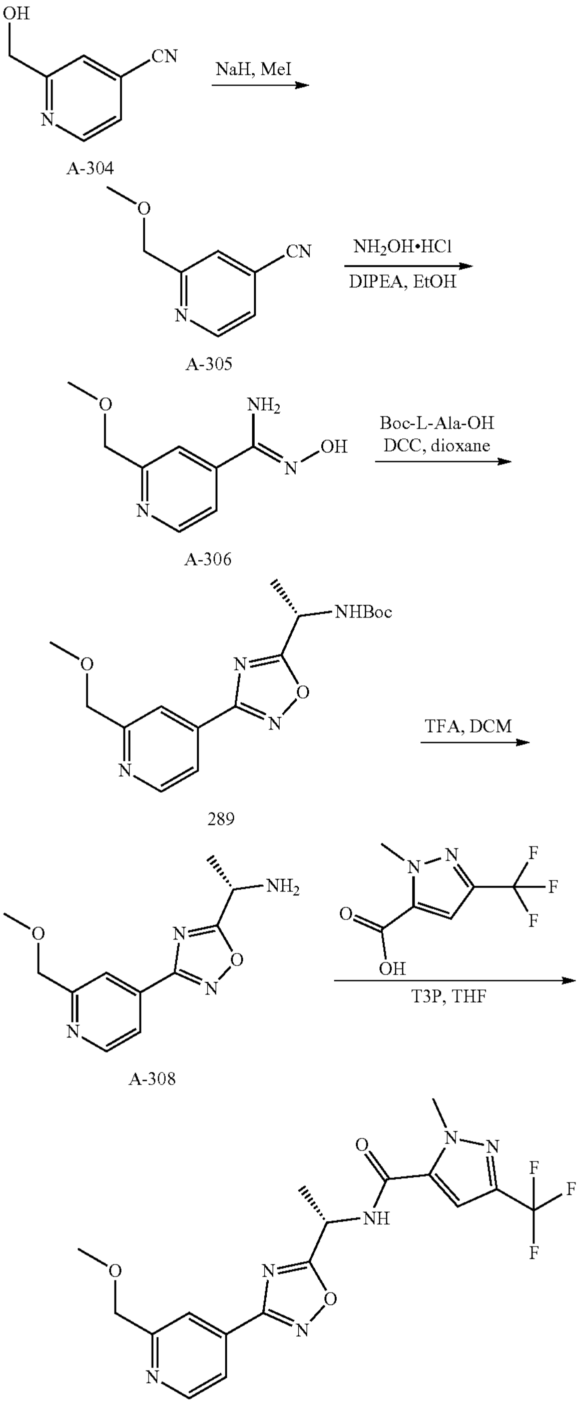

A-304

A-305

A-306

289

A-308

204

Synthesis of 2-(methoxymethyl)isonicotinonitrile (A-305)

To a stirred solution of 2-(hydroxymethyl)pyridine-4-carbonitrile (500 mg, 3.73 mmol) in THF (8.0 mL) was added NaH (60% in mineral oil, 164 mg, 4.1 mmol) at 0° C. in small portions followed by iodomethane (0.23 mL, 3.73 mmol). The reaction temperature was slowly raised to room temperature and stirred for 2 h. The reaction mixture was cooled to 10° C., treated with ice water (20 mL) and extracted with EtOAc (2×25 mL). The organic layer was washed with brine (30 mL), dried over anhydrous $Na_2SO_4$ and concentrated. The crude was purified by column chromatography on silica gel with 10% ethyl acetate/PE to afford compound A-305 (470 mg, 3.17 mmol, 85% yield). LCMS: 149.1 (M+H), Rt 1.31 min; Column: ZORBAX XDB C-18 (50×4.6 mm), 3.5 μm; Mobile Phase: A: 0.1% TFA in water:ACN (95:5), B: ACN; Flow Rate: 1.5 mL/min.

Synthesis of (Z)—N'-hydroxy-2-(methoxymethyl) isonicotinimidamide (A-306)

To a stirred solution of compound A-305 (470 mg, 3.17 mmol) in ethanol (10.0 mL) was added hydroxylamine hydrochloride (330 mg, 4.76 mmol) followed by DIPEA (1.57 mL, 9.52 mmol). The reaction mixture was heated at 80° C. for 2 h. The reaction mixture was cooled to room temperature and concentrated under reduced pressure. The crude was treated with water (30 mL) followed by saturated sodium bicarbonate solution (20 mL) and extracted with ethyl acetate (2×25 mL). The organic layer was washed with brine (20 mL), dried over anhydrous $Na_2SO_4$ and concentrated to afford compound A-306 (420 mg) as a colourless liquid. The compound was used for the next step without further purification.

Synthesis of tert-butyl (S)-(1-(3-(2-(methoxymethyl)pyridin-4-yl)-1,2,4-oxadiazol-5-yl)ethyl)carbamate (289)

To a stirred solution of compound A-306 (420 mg, 2.32 mmol) in 1,4-dioxane (10.0 mL) was added (2S)-2-(tert-butoxycarbonylamino)propanoic acid (438 mg, 2.32 mmol) and DCC (525 mg, 2.55 mmol). The reaction mixture was heated at 100° C. for 16 h. The reaction mixture was cooled to room temperature and concentrated to under reduced pressure. The mixture was treated with water (30 mL) and extracted with ethyl acetate (2×25 mL). The organic layer was washed with brine (30 mL), dried over anhydrous $Na_2SO_4$ and concentrated. The crude was purified by column chromatography on silica gel with 8% ethyl acetate/PE to afford compound 289 (560 mg, 1.6 mmol, 72% yield) as a solid. LCMS: 335.3 (M+H), Rt 2.23 min; Column: X-Bridge C8 (50×4.6 mm), 3.5 μm; Mobile Phase: A: 10 mM $NH_4HCO_3$ in $H_2O$, B: ACN; Flow Rate: 1.5 mL/min.

Synthesis of (S)-1-(3-(2-(methoxymethyl)pyridin-4-yl)-1,2,4-oxadiazol-5-yl)ethan-1-amine (A-308)

To a stirred solution of compound 289 (420 mg, 1.26 mmol) in DCM (8.0 mL) was added TFA (0.96 mL) at 0° C. The reaction mixture was slowly warmed to room temperature and stirred for 2 h. The mixture was concentrated under reduced pressure and treated with ice water (30 mL). The mixture was treated with 10% aqueous $NaHCO_3$ solution (5 mL) and extracted with EtOAc (2×25 mL). The organic layer was washed with brine (30 mL), dried over anhydrous $Na_2SO_4$ and concentrated to afford compound A-308 (210 mg). The compound was used for the next step without further purification.

Synthesis of (S)—N-(1-(3-(2-(methoxymethyl)pyridin-4-yl)-1,2,4-oxadiazol-5-yl)ethyl)-1-methyl-3-(trifluoromethyl)-1H-pyrazole-5-carboxamide (204)

To a stirred solution of 2-methyl-5-(trifluoromethyl)pyrazole-3-carboxylic acid (150 mg, 0.77 mmol) in THF (6.0 mL) was added compound A-308 (168 mg, 0.72 mmol). To the reaction mixture TEA (0.32 mL, 2.32 mmol) and T3P (50% in EtOAc, 1.38 mL, 2.32 mmol) were added and the mixture was stirred at room temperature for 16 h. The reaction mixture was treated with water (30 mL) and extracted with ethyl acetate (2×25 mL). The organic layer was washed with brine (30 mL), dried over anhydrous $Na_2SO_4$ and concentrated. The crude was purified by preparative HPLC to afford 204 (96 mg, 0.23 mmol, 30% yield) as a solid. Prep. HPLC method: Rt 10.75; Column: Atlantis C18 (150×19 mm), 5.0 μm; Mobile phase: 0.1% TFA in water/acetonitrile; Flow Rate: 15.0 mL/min. HPLC: Rt 3.58 min, 99.2%; Column: XBridge C8 (50×4.6) mm, 3.5 μm; Mobile phase: A: 0.1% TFA in water, B: 0.1% TFA in ACN; Flow Rate: 2.0 mL/min. LCMS: 411.0 (M+H), Rt 2.90 min, Column: X-Bridge C8 (50×4.6 mm), 3.5 μm, Mobile Phase: A: 10 mM $NH_4HCO_3$ in $H_2O$, B: ACN; Flow Rate: 0.8 mL/min. Chiral method: Rt 1.81 min, SFC column: LUX $C_3$; mobile phase: 85:15 (A:B), A=liquid $CO_2$, B=methanol; flow rate: 3.0 mL/min; wave length: 210 nm. $^1H$ NMR (400 MHz, $CD_3OD$): δ 8.67 (d, 1H), 8.12 (s, 1H), 7.95-7.93 (m, 1H), 7.25 (s, 1H), 5.54 (q, 1H), 4.64 (s, 2H), 4.18 (s, 3H), 3.51 (s, 3H), 1.77 (d, 3H).

Example 160. Synthesis of 290 & 205

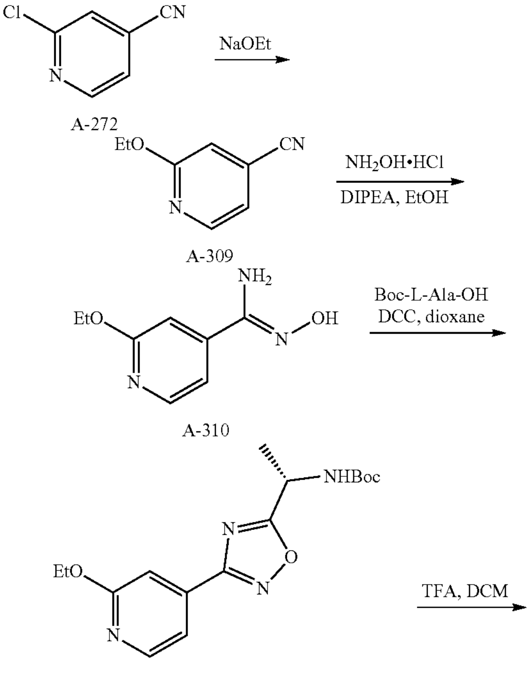

A-272

A-309

A-310

290

-continued

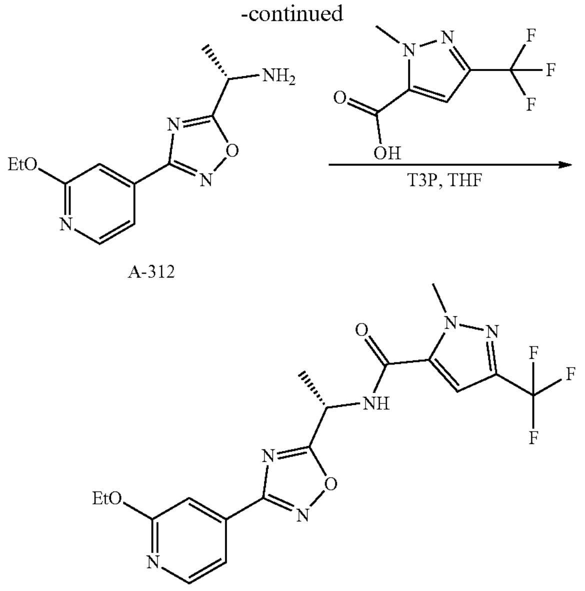

A-312

205

Synthesis of 2-ethoxyisonicotinonitrile (A-309)

To a stirred solution of 2-chloropyridine-4-carbonitrile (5.0 g, 36.1 mmol) in 1,4-dioxane (50.0 mL) was added NaOEt (2.46 g, 36.1 mmol) at one portion. The reaction mixture was heated at 60° C. for 4 h. The reaction mixture was cooled to room temperature, treated with ice cold water (50 mL) and extracted with ethyl acetate (2×100 mL). The organic layer was washed with brine (100 mL), dried over anhydrous $Na_2SO_4$ and concentrated. The crude compound was purified by column chromatography on silica get with 6% EtOAc/PE to afford compound A-309 (3.5 g, 23.5 mmol, 65% yield). LCMS: 149.1 (M+H), Rt 2.06 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (Z)-2-ethoxy-N'-hydroxyisonicotinimidamide (A-310)

To a stirred solution of 2-ethoxypyridine-4-carbonitrile (1.5 g, 10.12 mmol) in ethanol (30.0 mL) was added hydroxylamine hydrochloride (1.06 g, 15.19 mmol) followed by DIPEA (5.29 mL, 30.37 mmol). The reaction mixture was heated at 80° C. for 2 h. The reaction mixture was cooled to room temperature and concentrated under reduced pressure. The crude was treated with water (30 mL) followed by saturated sodium bicarbonate solution (20 mL) and extracted with ethyl acetate (2×50 mL). The organic layer was washed with brine (100 mL), dried over anhydrous $Na_2SO_4$ and concentrated to afford compound A-310 (1.7 g). The compound was used for the next step without further purification.

Synthesis of tert-butyl (S)-(1-(3-(2-ethoxypyridin-4-yl)-1,2,4-oxadiazol-5-yl)ethyl)carbamate (290)

To a stirred solution of (2S)-2-(tert-butoxycarbonylamino)propanoic acid (1.78 g, 9.38 mmol) in 1,4-dioxane (34.0 mL) was added compound A-310 (1.7 g, 9.38 mmol) and DCC (2.13 g, 10.32 mmol). The reaction mixture was heated at 100° C. for 16 h. The reaction mixture was cooled to room temperature and concentrated under reduced pressure. The mixture was treated with water (100 mL) and extracted with ethyl acetate (2×100 mL). The organic layer was washed with brine (100 mL), dried over anhydrous $Na_2SO_4$ and concentrated. The crude was purified by column chromatography on silica gel with 14% EtOAc/PE to afford compound 290 (2.4 g, 7.07 mmol, 75% yield) as a solid. LCMS: 335.1 (M+H), Rt 3.22 min; Column: XBridge C8 (50×4.6 mm), 3.5 μm; Mobile Phase: A: 10 mM $NH_4HCO_3$ in $H_2O$, B: ACN; Flow Rate: 0.8 mL/min.

Synthesis of (S)-1-(3-(2-ethoxypyridin-4-yl)-1,2,4-oxadiazol-5-yl)ethan-1-amine (A-312)

To a stirred solution of compound 290 (400 mg, 1.2 mmol) in DCM (10.0 mL) was added TFA (0.9 mL) at 0° C. The reaction mixture was slowly warmed to room temperature and stirred for 2 h. The mixture was concentrated under reduced pressure and treated with ice water (20 mL). The mixture was treated with 10% aqueous $NaHCO_3$ solution (5 mL) and extracted with EtOAc (2×25 mL). The organic layer was washed with brine (50 mL), dried over anhydrous $Na_2SO_4$ and concentrated to afford compound A-312 (240 mg). The compound was used for the next step without further purification.

Synthesis of (S)—N-(1-(3-(2-ethoxypyridin-4-yl)-1,2,4-oxadiazol-5-yl)ethyl)-1-methyl-3-(trifluoromethyl)-1H-pyrazole-5-carboxamide (205)

To a stirred solution of 2-methyl-5-(trifluoromethyl)pyrazole-3-carboxylic acid (150 mg, 0.77 mmol) in THF (6.0 mL) was added compound A-312 (181 mg, 0.77 mmol) followed by TEA (0.32 mL, 2.32 mmol). To the reaction mixture T3P (50% in EtOAc, 1.38 mL, 2.32 mmol) was added and the mixture was stirred at room temperature for 16 h. The reaction mixture was treated with water (30 mL) and extracted with ethyl acetate (2×25 mL). The organic layer was washed with brine (50 mL), dried over anhydrous $Na_2SO_4$ and concentrated. The crude was purified by preparative HPLC to afford 205 (186 mg, 0.45 mmol, 58% yield) as a solid. Prep. HPLC method: Rt 9.81; Column: Sunfire (150×19 mm), 5.0 μm; Mobile phase: 0.1% TFA in water/acetonitrile; Flow Rate: 15.0 mL/min. HPLC: Rt 4.93 min, 99.1%; Column: XBridge C8 (50×4.6) mm, 3.5 μm; Mobile phase: A: 0.1% TFA in water, B: 0.1% TFA in ACN; Flow Rate: 2.0 mL/min. LCMS: 411.2 (M+H), Rt 3.22 min, Column: XBridge C8 (50×4.6 mm), 3.5 μm Mobile Phase: A: 10 mM $NH_4HCO_3$ in $H_2O$, B: ACN; Flow Rate: 0.8 mL/min. Chiral method: Rt 2.01 min, SFC column: LUX $C_3$; mobile phase: 85:15 (A:B), A=liquid $CO_2$, B=methanol; flow rate: 3.0 mL/min; wave length: 210 nm. $^1$H NMR (400 MHz, $CD_3OD$): δ 8.27 (d, 1H), 7.54-7.53 (m, 1H), 7.37 (s, 1H), 7.25 (s, 1H), 5.53 (q, 1H), 4.40 (q, 2H), 4.19 (s, 3H), 1.77 (d, 3H), 1.42 (t, 3H).

Example 161. Synthesis of 291 & 206

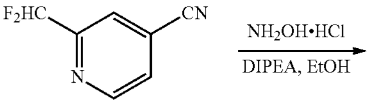

A-277b

-continued

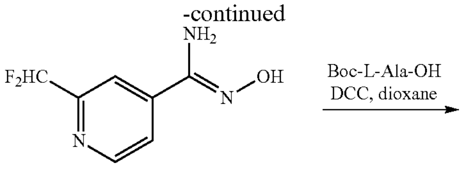

A-313

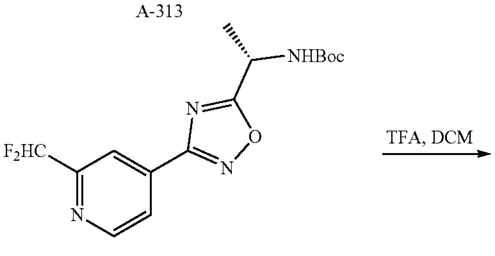

291

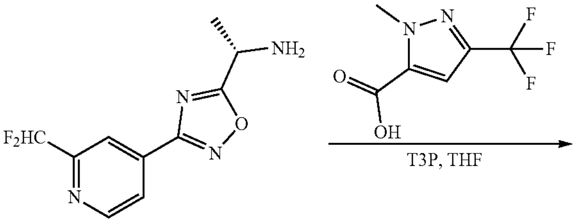

A-315

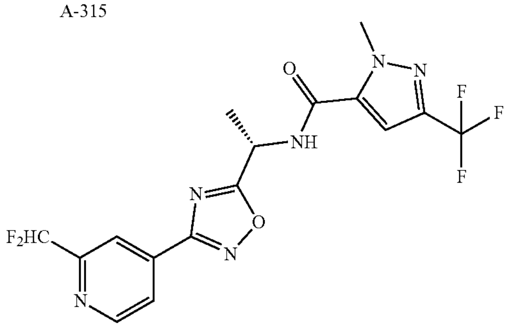

206

Synthesis of (Z)-2-(difluoromethyl)-N'-hydroxyisonicotinimidamide (A-313)

To a stirred solution of 2-(difluoromethyl)pyridine-4-carbonitrile (500 mg, 3.24 mmol) in ethanol (20.0 mL) was added hydroxylamine hydrochloride (338 mg, 4.87 mmol) followed by DIPEA (1.69 mL, 9.73 mmol). The reaction mixture was heated at 80° C. for 2 h. The reaction mixture was cooled to room temperature and concentrated under reduced pressure. The crude was treated with water (20 mL) followed by saturated sodium bicarbonate solution (20 mL) and extracted with ethyl acetate (2×50 mL). The organic layer was washed with brine (50 mL), dried over $Na_2SO_4$ and concentrated to afford compound A-313 (580 mg) as a solid. It was used for the next step without further purification.

Synthesis of tert-butyl (S)-(1-(3-(2-(difluoromethyl)pyridin-4-yl)-1,2,4-oxadiazol-5-yl)ethyl)carbamate (291)

To a stirred solution of compound A-313 (580 mg, 3.05 mmol) in 1,4-dioxane (15 mL) was added (2S)-2-(tert-butoxycarbonylamino)propanoic) acid (586 mg, 3.1 mmol) followed by DCC (702 mg, 3.41 mmol). The reaction mixture was heated at 100° C. for 16 h. The reaction mixture was cooled to room temperature, concentrated and was diluted with ethyl acetate (30 mL). The organics washed with water (2×20 mL) and then with brine (20 mL). The organic layer was dried over $Na_2SO_4$ and concentrated. The crude was purified by column chromatography on silica gel with 8% EtOAc/PE to afford compound 291 (1.0 g, 2.93 mmol, 94% yield) as a solid. LCMS: 341.1 (M+H), Rt 2.24 min; Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of (S)-1-(3-(2-(difluoromethyl)pyridin-4-yl)-1,2,4-oxadiazol-5-yl)ethan-1-amine (A-315)

To a stirred solution of compound 291 (400 mg, 1.18 mmol) in DCM (8.0 mL) was added TFA (0.9 mL) at 0° C. The reaction mixture was slowly warmed to room temperature and stirred for 2 h. The mixture was concentrated under reduced pressure and treated with ice water (30 mL). The mixture was treated with 10% aqueous $NaHCO_3$ solution (5 mL) and extracted with EtOAc (2×25 mL). The organic layer was washed with brine (30 mL), dried over anhydrous $Na_2SO_4$ and concentrated to afford compound A-315 (260 mg). The compound was used for the next step without further purification.

Synthesis of (S)—N-(1-(3-(2-(difluoromethyl)pyridin-4-yl)-1,2,4-oxadiazol-5-yl)ethyl)-1-methyl-3-(trifluoromethyl)-1H-pyrazole-5-carboxamide (206)

To a stirred solution of 2-methyl-5-(trifluoromethyl)pyrazole-3-carboxylic acid (150 mg, 0.77 mmol) in THF (6 mL) was added compound A-315 (200 mg, 0.77 mmol). To the reaction mixture TEA (0.32 mL, 2.32 mmol) and T3P (50% in EtOAc, 1.38 mL, 2.32 mmol) were added and the mixture was stirred at room temperature for 16 h. The reaction mixture was treated with water (30 mL) and extracted with ethyl acetate (2×25 mL). The organic layer was washed with brine (30 mL), dried over anhydrous $Na_2SO_4$ and concentrated. The crude was purified by preparative HPLC to afford 206 (97 mg, 0.23 mmol, 29% yield) as a solid. Prep. HPLC method: Rt 9.60; Column: Sunfire C18 (150×19 mm), 5.0 μm; Mobile phase: 0.1% TFA in water/acetonitrile; Flow Rate: 15.0 mL/min. HPLC: Rt 4.68 min, 99%; Column: XBridge C8 (50×4.6) mm, 3.5 μm; Mobile phase: A: 0.1% TFA in water, B: 0.1% TFA in ACN; Flow Rate: 2.0 mL/min. LCMS: 417.2 (M+H), Rt 2.29 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.74 min; SFC column: LUX $C_3$; mobile phase: 85:15 (A:B), A=liquid $CO_2$, B=methanol; flow rate: 3.0 mL/min; wave length: 210 nm. $^1H$ NMR (400 MHz, $CD_3OD$): δ 8.85 (d, 1H), 8.29 (s, 1H), 8.17 (d, 1H), 7.26 (s, 1H), 6.84 (t, 1H), 5.56 (q, 1H), 4.19 (s, 3H), 1.79 (d, 3H).

Example 162. Synthesis of 292 & 207

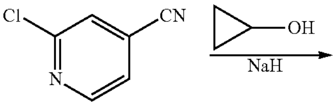

A-272

-continued

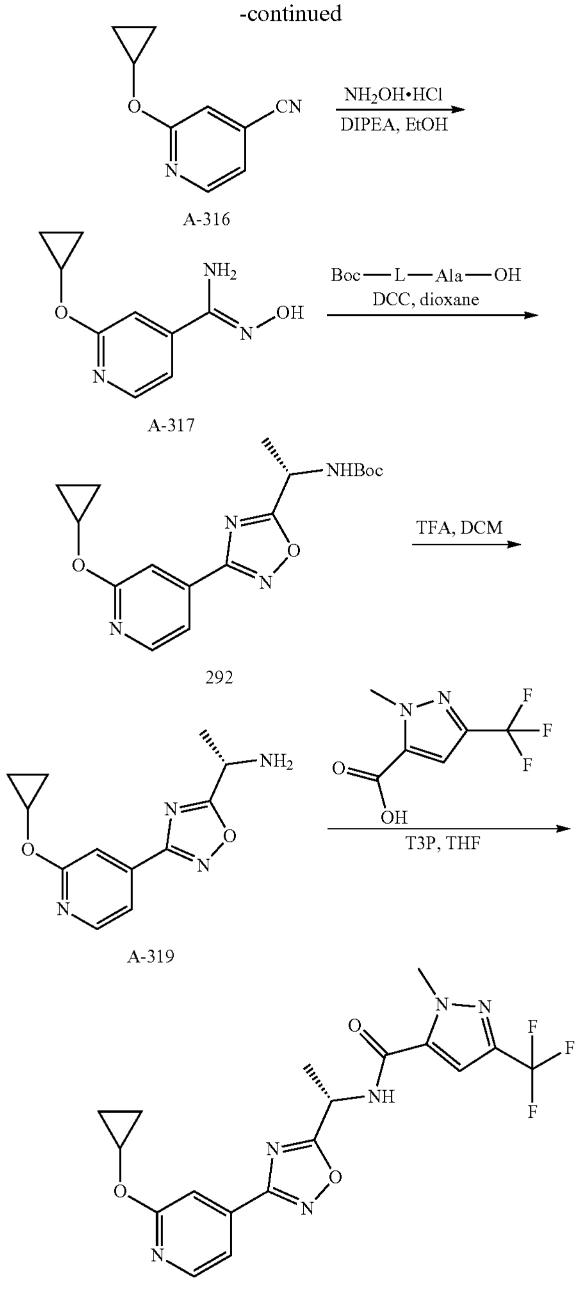

A-316

A-317

292

A-319

207

Synthesis of 2-(methylamino)isonicotinonitrile (A-316)

To a stirred solution of NaH (0.32 g, 7.94 mmol) in THF (20.0 mL) was added cyclopropanol (0.5 g, 8.66 mmol) and 2-chloropyridine-4-carbonitrile (1.0 g, 7.22 mmol) at 0° C. under a nitrogen atmosphere. The reaction mixture was slowly warmed to room temperature and stirred for 4 h. The reaction mixture was cooled to 10° C. and treated with ice water (10 mL). The mixture was extracted with ethyl acetate (2×30 mL). The organic layer was washed with brine (20 mL), dried over anhydrous $Na_2SO_4$ and concentrated. The crude compound was purified by column chromatography on silica gel with 15% ethyl acetate/PE to afford compound A-316 (550 mg, 3.43 mmol, 43% yield). LCMS: 161.1 (M+H), Rt 2.37 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (Z)-2-cyclopropoxy-N'-hydroxyisonicotinimidamide (A-317)

To a stirred solution of compound A-316 (550 mg, 3.43 mmol) in ethanol (15 mL) was added DIPEA (1.7 mL, 10.31 mmol) and hydroxylamine hydrochloride (357 mg, 5.15 mmol) at room temperature under nitrogen atmosphere. The reaction mixture was heated at 80° C. for 2 h. The reaction mixture was cooled to room temperature and concentrated under reduced pressure. The crude was treated with water (15 mL) followed by saturated sodium bicarbonate solution (10 mL) and extracted with ethyl acetate (2×30 mL). The organic layer was washed with brine (20 mL), dried over $Na_2SO_4$ and concentrated to afford compound A-317 (646 mg). It was used for the next step without further purification.

Synthesis of tert-butyl (S)-(1-(3-(2-cyclopropoxypyridin-4-yl)-1,2,4-oxadiazol-5-yl)ethyl)carbamate (292)

To a stirred solution of compound A-317 (646 mg, 3.35 mmol) in 1,4-dioxane (10 mL) was added DCC (937 mg, 4.55 mmol) and (2S)-2-(tert-butoxycarbonylamino)propanoic acid (783 mg, 4.14 mmol) at room temperature. The reaction mixture was heated at 100° C. for 16 h. The reaction mixture was cooled to room temperature and concentrated under reduced pressure. The mixture was treated with water (30 mL) and extracted with ethyl acetate (2×25 mL). The organic layer was washed with brine (20 mL), dried over $Na_2SO_4$ and concentrated. The crude was purified by column chromatography on silica gel with 40% ethyl acetate/PE to afford compound 292 (550 g, 1.58 mmol, 47% yield). LCMS: 347.2 (M+H), Rt 2.38 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min.

Synthesis of (S)-1-(3-(2-cyclopropoxypyridin-4-yl)-1,2,4-oxadiazol-5-yl)ethan-1-amine (A-319)

To a stirred solution of compound 292 (550 mg, 1.58 mmol) in DCM (10 mL) was added TFA (1.1 mL) at 0° C. The reaction mixture was slowly warmed to room temperature and stirred for 4 h. The mixture was concentrated under reduced pressure and treated with ice water (20 mL). The mixture was treated with saturated $NaHCO_3$ solution (10 mL) and extracted with EtOAc (2×25 mL). The organic layer was washed with brine (20 mL), dried over anhydrous $Na_2SO_4$ and concentrated to afford compound A-319 (250 mg). The compound was used for the next step without further purification.

Synthesis of (S)—N-(1-(3-(2-cyclopropoxypyridin-4-yl)-1,2,4-oxadiazol-5-yl)ethyl)-1-methyl-3-(trifluoromethyl)-1H-pyrazole-5-carboxamide (207)

To a stirred solution of 2-methyl-5-(trifluoromethyl)pyrazole-3-carboxylic acid (150 mg, 0.77 mmol) in THF (10.0 mL) was added compound A-319 (190 mg, 0.77 mmol) followed by $Et_3N$ (0.32 mL, 2.32 mmol) and T3P (50% in EtOAc, 1.38 mL, 2.32 mmol). The reaction mixture was stirred at room temperature for 16 h. The reaction mixture was treated with water (30 mL) and extracted with ethyl acetate (2x30 mL). The organic layer was washed with saturated sodium bicarbonate solution (20 mL), washed with brine (20 mL), dried over $Na_2SO_4$ and concentrated. The crude was purified by preparative HPLC to afford 207 (130 mg, 0.30 mmol, 39% yield) as a solid. Prep. HPLC method: Rt 13.48; Column: XBridge (150x19 mm), 5.0 μm; Mobile phase: 0.1% TFA in water/acetonitrile; Flow Rate: 15.0 mL/min. HPLC: Rt 4.80 min, 99.2%; Column: X-Bridge C8 (50x4.6) mm, 3.5 μm; Mobile phase: A: 0.1% TFA in water, B: 0.1% TFA in ACN; Flow Rate: 2.0 mL/min. LCMS: 423.0 (M+H), Rt 3.14 min, Column: XBridge C8 (50x4.6 mm), 3.5 μm; Mobile Phase: A: 10 mM $NH_4HCO_3$ in $H_2O$, B: ACN; Flow Rate: 0.8 mL/min; Chiral method: Rt 1.17 min, SFC column: YMC Cellulose-SJ; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.34-8.32 (m, 1H), 7.63-7.62 (m, 1H), 7.52 (s, 1H), 7.24 (s, 1H), 5.53 (q, 1H), 4.24-4.20 (m, 1H), 4.18 (s, 3H), 1.76 (d, 3H), 0.86-0.83 (m, 2H), 0.79-0.77 (m, 2H).

Example 163. Synthesis of 293 & 208

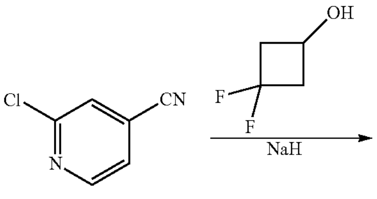

A-272

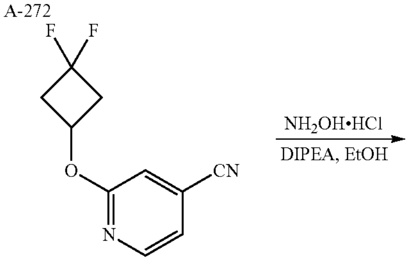

A-320

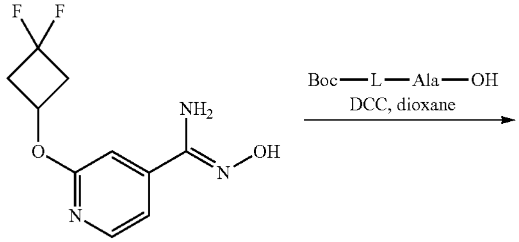

A-321

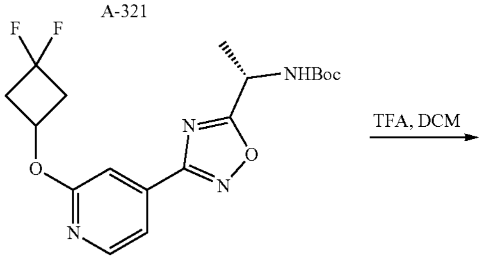

293

-continued

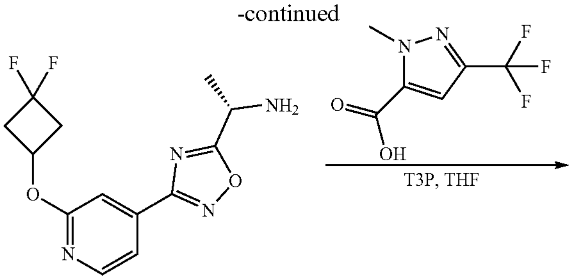

A-323

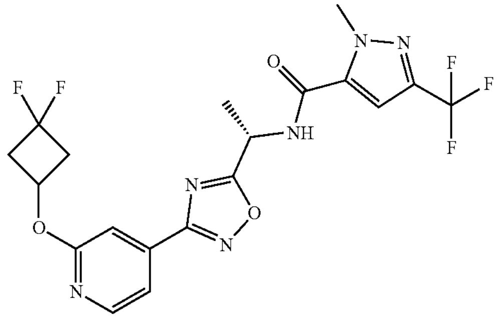

208

Synthesis of 2-(3,3-difluorocyclobutoxy)isonicotinonitrile (A-320)

To a stirred solution of NaH (158 mg, 3.97 mmol) in THF (10.0 mL) was added 3,3-difluorocyclobutanol (468 mg, 4.33 mmol) and 2-chloropyridine-4-carbonitrile (500 mg, 3.61 mmol) at 0° C. under a nitrogen atmosphere. The reaction mixture was slowly warmed to room temperature and stirred for 4 h. The reaction mixture was cooled to 10° C. and treated with ice water (10 mL). The mixture was extracted with ethyl acetate (2x30 mL). The organic layer was washed with brine (20 mL), dried over anhydrous $Na_2SO_4$ and concentrated. The crude compound was purified by column chromatography on silica gel with 20% ethyl acetate/PE to afford compound A-320 (320 mg, 1.5 mmol, 42% yield). $^1H$ NMR (400 MHz, $CD_3OD$): δ 8.30 (dd, 1H), 7.13 (dd, 1H), 7.03 (m, 1H), 5.20-5.15 (m, 1H), 3.20-3.10 (m, 2H), 2.81-2.69 (m, 2H).

Synthesis of (Z)-2-(3,3-difluorocyclobutoxy)-N'-hydroxyisonicotinimidamide (A-321)

To a stirred solution of compound A-320 (320 mg, 1.52 mmol) in ethanol (10.0 mL) was added DIPEA (589 mg, 4.57 mmol) and hydroxylamine hydrochloride (95.27 mg, 3.97 mmol) at room temperature under nitrogen. The reaction mixture was heated at 80° C. for 3 h. The reaction mixture was cooled to room temperature and concentrated under reduced pressure. The crude was treated with water (20 mL) followed by saturated sodium bicarbonate solution (10 mL) and extracted with ethyl acetate (2x40 mL). The organic layer was washed with brine (30 mL), dried over $Na_2SO_4$ and concentrated to afford compound A-321 (326 mg). It was used for the next step without further purification.

Synthesis of tert-butyl (S)-(1-(3-(2-(3,3-difluorocyclobutoxy)pyridin-4-yl)-1,2,4-oxadiazol-5-yl)ethyl) carbamate (293)

To a stirred solution of compound A-321 (320 mg, 1.32 mmol) in 1,4-dioxane (10.0 mL) was added DCC (294 mg, 1.43 mmol) and (2S)-2-(tert-butoxycarbonylamino)propanoic acid_(248 mg, 1.32 mmol) at room temperature under nitrogen. The reaction mixture was heated at 100° C. for 16 h. The reaction mixture was cooled to room temperature and concentrated under reduced pressure. The mixture was treated with water (30 mL) and extracted with ethyl acetate (2x30 mL). The organic layer was washed with brine (20 mL), dried over $Na_2SO_4$ and concentrated. The crude was purified by column chromatography on silica gel with 40% ethyl acetate/PE to afford compound 293 (404 mg, 1.02 mmol, 77% yield). LCMS: 397.2 (M+H), Rt 2.64 min; Column: ZORBAX XDB C-18 (50x4.6 mm), 3.5 μm; Mobile Phase: A: 0.1% HCOOH in water:ACN (95:5), B: ACN; Flow Rate: 1.5 mL/min.

Synthesis of (S)-1-(3-(2-(3,3-difluorocyclobutoxy)pyridin-4-yl)-1,2,4-oxadiazol-5-yl)ethan-1-amine (A-323)

To a stirred solution of compound 293 (350 mg, 0.88 mmol) in DCM (10.0 mL) was added TFA (1.5 mL) at 0° C. under nitrogen. The reaction mixture was slowly warmed to room temperature and stirred for 4 h. The mixture was concentrated under reduced pressure and treated with ice water (20 mL). The mixture was treated with saturated $NaHCO_3$ solution (10 mL) and extracted with EtOAc (2x30 mL). The organic layer was washed with brine (20 mL), dried over anhydrous $Na_2SO_4$ and concentrated to afford compound A-323 (245 mg). The compound was used for the next step without further purification.

Synthesis of (S)—N-(1-(3-(2-(3,3-difluorocyclobutoxy)pyridin-4-yl)-1,2,4-oxadiazol-5-yl)ethyl)-1-methyl-3-(trifluoromethyl)-1H-pyrazole-5-carboxamide (208)

To a stirred solution of 2-methyl-5-(trifluoromethyl)pyrazole-3-carboxylic acid (150 mg, 0.77 mmol) in THF (10.0 mL) was added compound A-323 (230.mg, 0.77 mmol) followed by $Et_3N$ (0.32 mL, 2.32 mmol) and T3P (50% in EtOAc, 1.38 mL, 2.32 mmol). The reaction mixture was stirred at room temperature for 16 h. The reaction mixture was treated with water (30 mL) and extracted with ethyl acetate (2x30 mL). The organic layer was washed with saturated sodium bicarbonate solution (20 mL), washed with brine (20 mL), dried over $Na_2SO_4$ and concentrated. The crude was purified by column chromatography on silica gel with 40% ethyl acetate/PE to afford 208 (160 mg, 0.33 mmol, 44% yield) as a solid. HPLC: Rt 5.46 min, 99.2%; Column: XBridge C8 (50x4.6) mm, 3.5 μm; Mobile phase: A: 0.1% TFA in water, B: 0.1% TFA in ACN; Flow Rate: 2.0 mL/min. LCMS: 473.1 (M+H), Rt 2.49 min, Column: X-Bridge C8 (50x4.6 mm), 3.5 μm; Mobile Phase: A: 0.1% TFA in water:ACN (95:5), B: 0.1% TFA in ACN; Flow Rate: 1.5 mL/min. Chiral method: Rt 1.15 min, SFC column: YMC Cellulose-SJ; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.30 (d, 1H), 7.58 (dd, 1H), 7.43 (s, 1H), 7.24

(s, 1H), 5.52 (q, 1H), 5.21-5.17 (m, 1H), 4.18 (s, 3H), 3.19-3.09 (m, 2H), 2.80-2.68 (m, 2H), 1.76 (d, 3H).

Example 164. Synthesis of 209 and 210

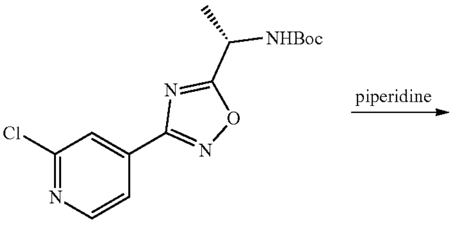

A-274

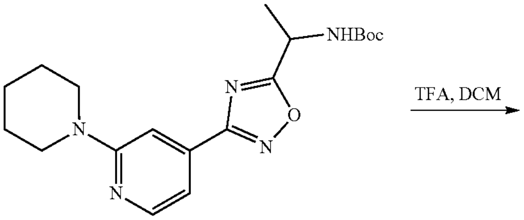

A-324

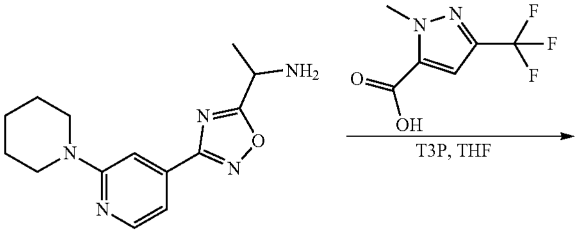

A-325

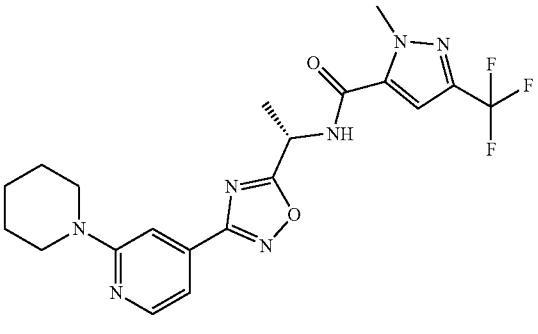

209

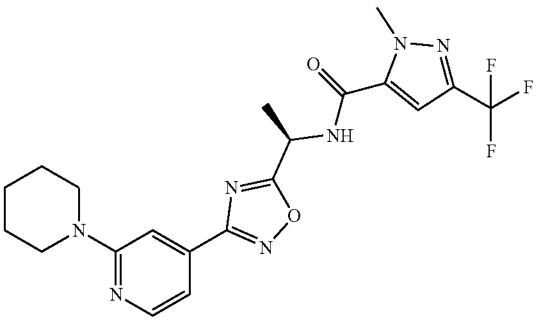

210

Synthesis of tert-butyl (1-(3-(2-(piperidin-1-yl)pyridin-4-yl)-1,2,4-oxadiazol-5-yl)ethyl)carbamate (A-324)

To a solution of compound A-274 (1.2 g, 3.7 mmol) in NMP (10.0 mL) was added piperidine (629 mg, 7.39 mmol), and the mixture was irradiation in microwave at 120° C. for 2 h. The reaction mixture was cooled to room temperature and treated with water (30 mL). The mixture was extracted with ethyl acetate (2×25 mL). The organic layer was washed with brine (20 mL), dried over $Na_2SO_4$ and concentrated. The crude was purified by column chromatography on silica gel with 10% EtOAc/PE to afford compound A-324 (962 mg, 2.58 mmol, 69% yield) as a solid. LCMS: 374.3 (M+H), Rt 2.00 min; Column: ZORBAX XDB C-18 (50×4.6 mm), 3.5 μm Mobile Phase: A: 0.1% HCOOH in water:ACN (95:5), B: ACN; Flow Rate: 1.5 mL/min Synthesis of 1-(3-(2-(piperidin-1-yl)pyridin-4-yl)-1,2,4-oxadiazol-5-yl)ethan-1-amine (A-325)

To a stirred solution of compound A-324 (887 mg, 2.38 mmol) in DCM (10.0 mL) was added TFA (1.0 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (10 mL) and extracted with EtOAc (2×25 mL). The organic layer was washed with brine (20 mL), dried over $Na_2SO_4$ and concentrated to afford compound A-325 (316 mg). The compound was used for the next step without further purification.

Synthesis of (S)-1-methyl-N-(1-(3-(2-(piperidin-1-yl)pyridin-4-yl)-1,2,4-oxadiazol-5-yl)ethyl)-3-(trifluoromethyl)-1H-pyrazole-5-carboxamide (209) and (R)-1-methyl-N-(1-(3-(2-(piperidin-1-yl)pyridin-4-yl)-1,2,4-oxadiazol-5-yl)ethyl)-3-(trifluoromethyl)-1H-pyrazole-5-carboxamide (210)

To a solution of A-325 (210 mg, 0.77 mmol) in THF (5.0 mL) was added 2-methyl-5-(trifluoromethyl)pyrazole-3-carboxylic acid (150 mg, 0.77 mmol) followed by $Et_3N$ (0.5 mL, 3.58 mmol) and T3P (50% in EtOAc, 1.38 mL, 2.32 mmol). The reaction mixture was stirred at room temperature for 16 h. The reaction mixture was treated with water (30 mL) and extracted with ethyl acetate (2×25 mL). The organic layer was washed with saturated sodium bicarbonate solution (20 mL), washed with brine (20 mL), dried over $Na_2SO_4$ and concentrated. The racemic mixture was separated by SFC purification to afford 209 (19.0 mg, 0.04 mmol, 5% yield) and 210 (20.0 mg, 0.05 mmol, 5% yield) as solids. Chiral method: SFC column: CHIRALCEL OX-H; mobile phase: 90:10 (A:B), A=liquid $CO_2$, B=0.5% isopropyl amine in methanol; flow rate: 3.0 mL/min; wave length: 220 nm. The stereochemistry of 209 and 210 was randomly assigned.

209:

HPLC: Rt 3.68 min, 99.2%; Column: XBridge C8 (50×4.6) mm, 3.5 μm; Mobile phase: A: 0.1% TFA in water, B: 0.1% TFA in ACN; Flow Rate: 2.0 mL/min. LCMS: 450.3 (M+H), Rt 2.05 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 4.8 min, SFC column: CHIRALCEL OX-H; mobile phase: 90:10 (A:B), A=liquid $CO_2$, B=0.5% isopropyl amine in methanol; flow rate: 3.0 mL/min; wave length: 220 nm. $^1$H NMR (400 MHz, $CD_3OD$): δ 8.21 (d, 1H), 7.40 (s, 1H), 7.26 (s, 1H), 7.19-7.18 (m, 1H), 5.53 (q, 1H), 4.19 (s, 3H), 3.64-3.61 (m, 4H), 1.77 (d, 3H), 1.73-1.67 (m, 6H).

210:

HPLC: Rt 3.67 min, 99.1%; Column: XBridge C8 (50×4.6) mm, 3.5 μm; Mobile phase: A: 0.1% TFA in water, B: 0.1% TFA in ACN; Flow Rate: 2.0 mL/min. LCMS: 450.2 (M+H), Rt 2.05 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 5.05 min, SFC column: CHIRALCEL OX-H; mobile phase: 90:10 (A: B), A=liquid $CO_2$, B=0.5% isopropyl amine in methanol; flow rate: 3.0 mL/min; wave length: 220 nm. $^1$H NMR (400 MHz, $CD_3OD$): δ 8.21-8.20 (m, 1H), 7.39 (s, 1H), 7.25 (s, 1H), 7.18-7.17 (m, 1H), 5.52 (q, 1H), 4.18 (s, 3H), 3.63-3.60 (m, 4H), 1.76 (d, 3H), 1.72-1.67 (m, 6H).

Example 165. Synthesis of 294 & 211

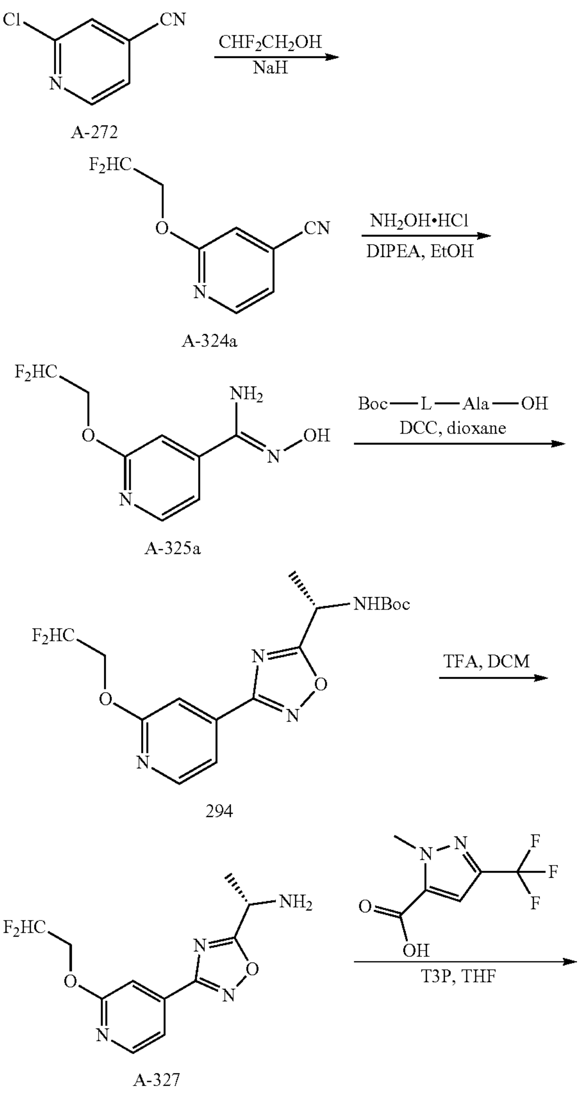

A-272

A-324a

A-325a

294

A-327

-continued

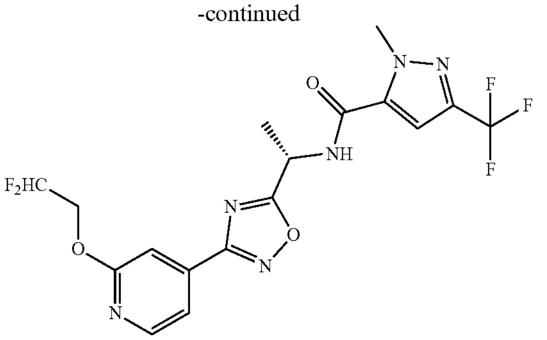

211

Synthesis of 2-(2,2-difluoroethoxy)isonicotinonitrile (A-324a)

NaH (60% in mineral oil, 866 mg, 21.65 mmol) was added in small portions to a solution of 2,2-difluoroethanol (2.13 g, 25.98 mmol) in THF (35 mL) at 0° C. The resulting suspension was stirred for 5 min and 2-chloropyridine-4-carbonitrile (3.0 g, 21.65 mmol) was added to the mixture in small portions. The mixture was stirred at room temperature for 3 h. The reaction mixture was cooled to 10° C. and treated with ice water (50 mL). The mixture was extracted with ethyl acetate (2×50 mL). The organic layer was washed with brine (50 mL), dried over anhydrous $Na_2SO_4$ and concentrated. The crude compound was purified by column chromatography on silica gel with 10% ethyl acetate/PE to afford compound A-324a (2.9 g, 15.7 mmol, 72% yield). LCMS: 185.1 (M+H), Rt 2.46 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min Synthesis of (Z)-2-(2,2-difluoroethoxy)-N'-hydroxyisonicotinimidamide (A-325a)

To a stirred solution of compound A-324a (2.9 g, 15.7 mmol) in ethanol (20 mL) was added hydroxylamine hydrochloride (1.63 g, 23.44 mmol) and DIPEA (8.16 mL, 46.87 mmol). The reaction mixture was heated at 80° C. for 3 h. The reaction mixture was cooled to room temperature and concentrated under reduced pressure. The crude was treated with water (30 mL) followed by saturated sodium bicarbonate solution (10 mL) and extracted with ethyl acetate (2×50 mL). The organic layer was washed with brine (20 mL), dried over $Na_2SO_4$ and concentrated to afford compound A-325a (3.4 g) as a solid. It was used for the next step without further purification.

Synthesis of tert-butyl (S)-(1-(3-(2-(2,2-difluoroethoxy)pyridin-4-yl)-1,2,4-oxadiazol-5-yl)ethyl)carbamate (294)

To a solution of compound A-325a (3.3 g, 15.3 mmol) in 1,4-dioxane (30 mL) was added (2S)-2-(tert-butoxycarbonylamino)propanoic acid (2.9 g, 15.3 mmol) followed by DCC (3.48 g, 16.88 mmol). The reaction mixture was heated at 100° C. for 16 h. The reaction mixture was cooled to room temperature and concentrated under reduced pressure. The mixture was treated with water (50 mL) and extracted with ethyl acetate (2×50 mL). The organic layer was washed with brine (20 mL), dried over $Na_2SO_4$ and concentrated. The crude was purified by column chromatography on silica gel with 7% ethyl acetate/PE to afford compound 294 (5.2 g, 14.0 mmol, 91% yield) as a solid. LCMS: 371.1 (M+H), Rt 2.48 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min Synthesis of (S)-1-(3-(2-(2,2-difluoroethoxy)pyridin-4-yl)-1,2,4-oxadiazol-5-yl)ethan-1-amine (A-327)

To a stirred solution of compound 294 (0.9 g, 2.43 mmol) in DCM (15.0 mL) was added TFA (2.0 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (10 mL) and extracted with EtOAc (2×25 mL). The organic layer was washed with brine (20 mL), dried over anhydrous $Na_2SO_4$ and concentrated to afford compound A-327 (297 mg). The compound was used for the next step without further purification.

Synthesis of (S)—N-(1-(3-(2-(2,2-difluoroethoxy)pyridin-4-yl)-1,2,4-oxadiazol-5-yl)ethyl)-1-methyl-3-(trifluoromethyl)-1H-pyrazole-5-carboxamide (211)

To a solution of 2-methyl-5-(trifluoromethyl)pyrazole-3-carboxylic acid (150 mg, 0.77 mmol) in THF (8.0 mL) was added compound A-327 (240 mg, 0.88 mmol) followed by $Et_3N$ (0.32 mL, 2.32 mmol) and T3P (50% in EtOAc, 1.38 mL, 2.32 mmol). The reaction mixture was stirred at room temperature for 16 h. The reaction mixture was treated with water (30 mL) and extracted with ethyl acetate (2×25 mL). The organic layer was washed with saturated sodium bicarbonate solution (20 mL), washed with brine (20 mL), dried over $Na_2SO_4$ and concentrated. The crude was purified by preparative HPLC to afford 211 (146 mg, 0.32 mmol, 42% yield) as a solid. Prep. HPLC method: Rt 9.18; Column:) (Bridge (150×19 mm), 5.0 μm; Mobile phase: 10 mM $NH_4HCO_3$ in water/acetonitrile; Flow Rate: 15.0 mL/min. HPLC: Rt 5.16 min, 99.2%; Column: XBridge C8 (50×4.6) mm, 3.5 μm; Mobile phase: A: 0.1% TFA in water, B: 0.1% TFA in ACN; Flow Rate: 2.0 mL/min. LCMS: 447.1 (M+H), Rt 2.48 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.35 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.34-8.33 (m, 1H), 7.64-7.63 (m, 1H), 7.48 (s, 1H), 7.25 (s, 1H), 6.24 (tt, 1H), 5.54 (q, 1H), 4.60 (dt, 2H), 4.19 (s, 3H), 1.77 (d, 3H).

Example 166. Synthesis of 212

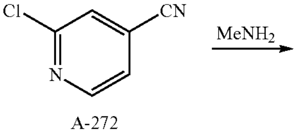

A-272

-continued

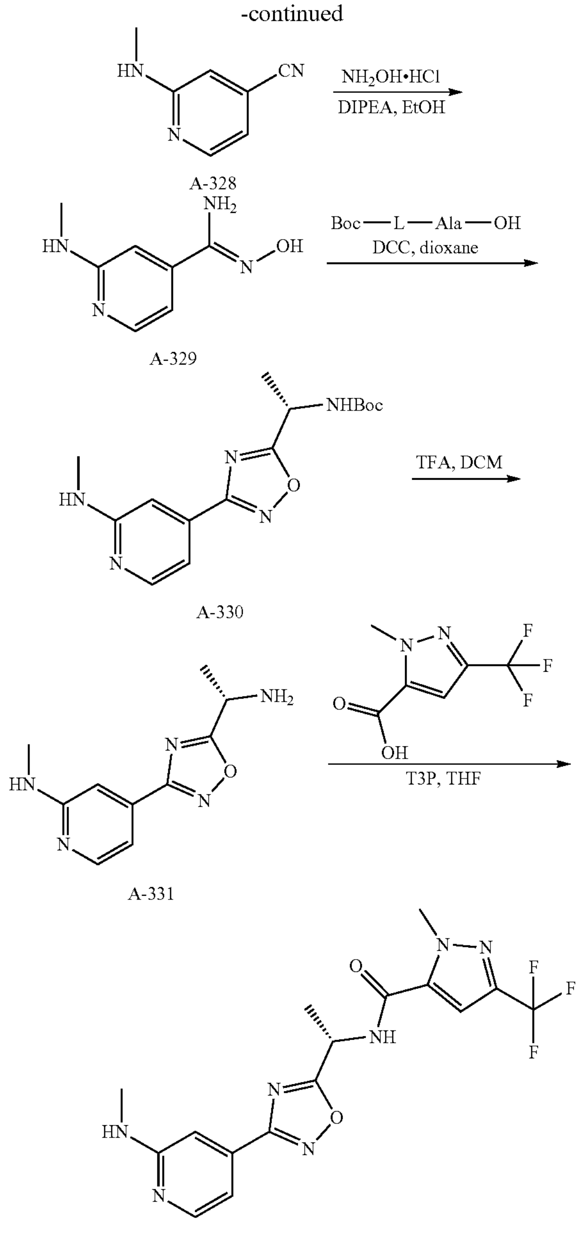

A-328

A-329

A-330

A-331

212

Synthesis of 2-(methylamino)isonicotinonitrile (A-328)

To a stirred solution of 2-chloropyridine-4-carbonitrile (800 mg, 5.77 mmol) in NMP (8.0 mL) at room temperature was added methylamine (2.0 M in THF, 3.4 mL, 6.8 mmol). The reaction mixture was irradiated in microwave at 120° C. for 2 h. The reaction mixture was cooled to room temperature and treated with water (30 mL). The mixture was extracted with ethyl acetate (2×30 mL). The organic layer was washed with brine (20 mL), dried over $Na_2SO_4$ and concentrated. The crude was purified by column chromatography on silica gel with 12% EtOAc/PE to afford compound A-328 (720 mg, 5.4 mmol, 93% yield). LCMS: 134.2 (M+H), Rt 1.71 min; Column: ZORBAX Extend C-18 (50×4.6 mm), 5 μm; Mobile Phase: A: 10 mM Ammonium acetate in water, B: ACN; Flow Rate: 1.2 mL/min Synthesis of (Z)—N'-hydroxy-2-(methylamino) isonicotinimidamide (A-329)

To a stirred solution of compound A-328 (700 mg, 5.26 mmol) in ethanol (10.0 mL) was added DIPEA (2.75 mL, 15.77 mmol) and hydroxylamine hydrochloride (547 mg, 7.89 mmol) at room temperature. The reaction mixture was heated at 80° C. for 3 h. The reaction mixture was cooled to room temperature and concentrated under reduced pressure. The crude was treated with water (20 mL) followed by saturated sodium bicarbonate solution (10 mL) and extracted with ethyl acetate (2×30 mL). The organic layer was washed with brine (20 mL), dried over $Na_2SO_4$ and concentrated to afford compound A-329 (860 mg). It was used for the next step without further purification.

Synthesis of tert-butyl (S)-(1-(3-(2-(methylamino) pyridin-4-yl)-1,2,4-oxadiazol-5-yl)ethyl)carbamate (A-330)

To a stirred solution of compound A-329 (860 g, 5.2 mmol) in 1,4-dioxane (20 mL) was added DCC (1.64 g, 7.94 mmol) and (2S)-2-(tert-butoxycarbonylamino)propanoic acid (1.37 g, 7.22 mmol) at room temperature. The reaction heated at 100° C. for 16 h. The reaction mixture was cooled to room temperature and concentrated under reduced pressure. The mixture was treated with water (40 mL) and extracted with ethyl acetate (2×50 mL). The organic layer was washed with brine (20 mL), dried over $Na_2SO_4$ and concentrated. The crude was purified by column chromatography on silica gel with 40% ethyl acetate/PE to afford compound A-330 (600 mg, 1.87 mmol, 36% yield). LCMS: 320.2 (M+H), Rt 1.24 min; Column: ZORBAX XDB C-18 (50×4.6 mm), 3.5 μm; Mobile Phase: A: 0.1% HCOOH in water, B: ACN; Flow Rate: 1.5 mL/min Synthesis of (S)-4-(5-(1-aminoethyl)-1,2,4-oxadiazol-3-yl)-N-methylpyridin-2-amine (A-331)

To a stirred solution of compound A-330 (600 mg, 1.87 mmol) in DCM (15 mL) was added TFA (1.5 mL) at 0° C. under nitrogen. The reaction mixture was slowly warmed to room temperature and stirred for 3 h. The mixture was concentrated under reduced pressure and treated with ice water (20 mL). The mixture was treated with saturated $NaHCO_3$ solution (10 mL) and extracted with EtOAc (2×30 mL). The organic layer was washed with brine (20 mL), dried over anhydrous $Na_2SO_4$ and concentrated to afford compound A-331 (270 mg). The compound was used for the next step without further purification.

Synthesis of (S)-1-methyl-N-(1-(3-(2-(methylamino) pyridin-4-yl)-1,2,4-oxadiazol-5-yl)ethyl)-3-(trifluoromethyl)-1H-pyrazole-5-carboxamide (212)

To a stirred solution of 2-methyl-5-(trifluoromethyl)pyrazole-3-carboxylic acid (239 mg, 1.23 mmol) in THF (10 mL) was added compound A-331 (270 mg, 1.23 mmol) followed by TEA (0.51 mL, 3.69 mmol) and T3P (50% in EtOAc, 2.2 mL, 3.69 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 212 (178 mg, 0.44 mmol, 36% yield) as a solid. Prep. HPLC method: Rt 11.39; Column:

Sunfire (150×19 mm), 5.0 µm; Mobile phase: 0.1% TFA in water/acetonitrile; Flow Rate: 15.0 mL/min. HPLC: Rt 3.16 min, 99.8%; Column: XBridge C8 (50×4.6) mm, 3.5 µm; Mobile phase: A: 0.1% TFA in water, B: 0.1% TFA in ACN; Flow Rate: 2.0 mL/min. LCMS: 396.3 (M+H), Rt 1.45 min, Column: ZORBAX XDB C-18 (50×4.6 mm), 3.5 µm; Mobile Phase: A: 0.1% HCOOH in water, B: ACN; Flow Rate: 1.5 mL/min. Chiral method: Rt 1.4 min, SFC column: YMC Amylose-SA; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.10-8.09 (m, 1H), 7.26 (s, 1H), 7.17-7.16 (m, 1H), 7.14-7.12 (m, 1H), 5.52 (q, 1H), 4.19 (s, 3H), 2.92 (s, 3H), 1.76 (d, 3H).

Example 167. Synthesis of 213

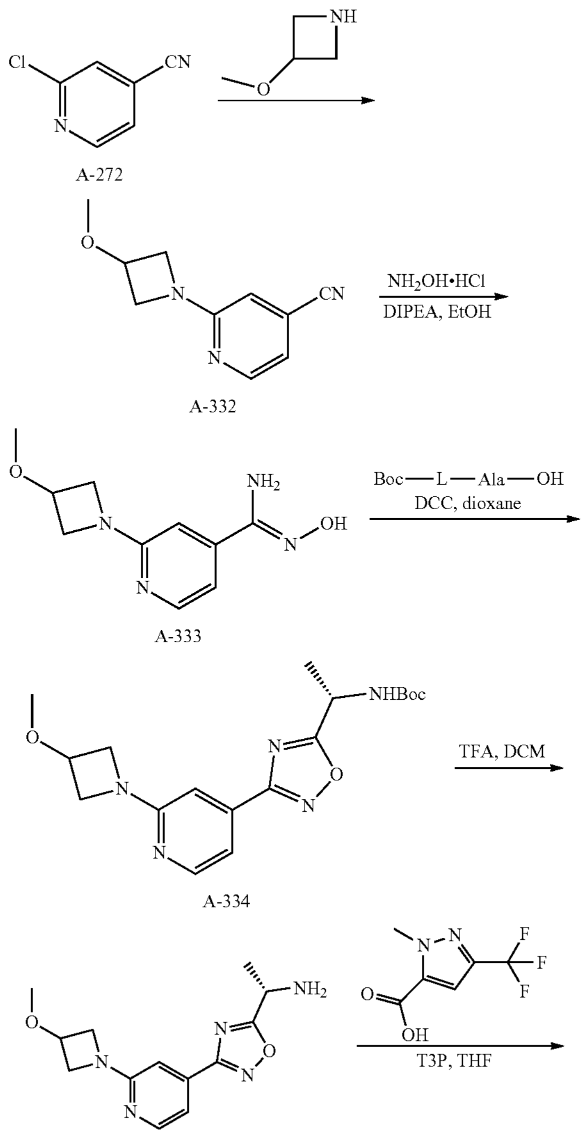

-continued

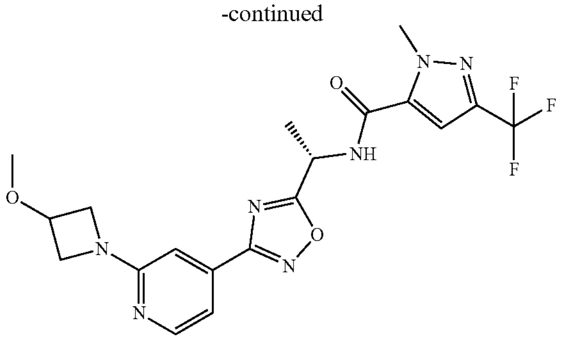

213

Synthesis of 2-(3-methoxyazetidin-1-yl)isonicotinonitrile (A-332)

To a stirred solution of 2-chloropyridine-4-carbonitrile (500 mg, 3.61 mmol) in NMP (5.0 mL) was added DIPEA (1.89 mL, 10.83 mmol) and 3-methoxyazetidine hydrochloride (0.54 g, 4.33 mmol) at room temperature under nitrogen and the reaction mixture was irradiated in microwave at 120° C. for 2 h. The reaction mixture was cooled to room temperature and treated with water (30 mL). The mixture was extracted with ethyl acetate (2×25 mL). The organic layer was washed with brine (20 mL), dried over $Na_2SO_4$ and concentrated. The crude was purified by column chromatography on silica gel with 10% EtOAc/PE to afford compound A-332 (650 mg, 3.43 mmol, 95% yield). LCMS: 190.2 (M+H), Rt 1.29 min; Column: ZORBAX XDB C-18 (50×4.6 mm), 3.5 µm; Mobile Phase: A: 0.1% HCOOH in water, B: ACN; Flow Rate: 1.5 mL/min Synthesis of (Z)—N'-hydroxy-2-(3-methoxyazetidin-1-yl)isonicotinimidamide (A-333)

To a stirred solution of compound A-332 (650 mg, 3.43 mmol) in ethanol (10.0 mL) was added DIPEA (1.73 mL, 10.46 mmol) and hydroxylamine hydrochloride (363 mg, 5.23 mmol) at room temperature. The reaction mixture was heated at 80° C. for 3 h. The reaction mixture was cooled to room temperature and concentrated under reduced pressure. The crude was treated with water (20 mL) followed by saturated sodium bicarbonate solution (10 mL) and extracted with ethyl acetate (2×30 mL). The organic layer was washed with brine (20 mL), dried over $Na_2SO_4$ and concentrated to afford compound A-333 (760 mg). It was used for the next step without further purification.

Synthesis of tert-butyl (S)-(1-(3-(2-(3-methoxyazetidin-1-yl)pyridin-4-yl)-1,2,4-oxadiazol-5-yl)ethyl) carbamate (A-334)

To a stirred solution of compound A-333 (760 mg, 3.43 mmol) in 1,4-dioxane (20 mL) was added DCC (866 mg, 4.21 mmol) and (2S)-2-(tert-butoxycarbonylamino)propanoic acid_(723 mg, 3.82 mmol) at room temperature. The reaction heated at 100° C. for 16 h. The reaction mixture was cooled to room temperature and concentrated under reduced pressure. The mixture was treated with water (40 mL) and extracted with ethyl acetate (2×40 mL). The organic layer was washed with brine (20 mL), dried over $Na_2SO_4$ and concentrated. The crude was purified by column chromatography on silica gel with 60% ethyl acetate/PE to afford compound A-334 (671 mg, 1.78 mmol, 51% yield). LCMS: 376.2 (M+H), Rt 1.49 min; Column: ZORBAX XDB C-18 (50×4.6 mm), 3.5 μm; Mobile Phase: A: 0.1% HCOOH in water, B: ACN; Flow Rate: 1.5 mL/min

Synthesis of (S)-1-(3-(2-(3-methoxyazetidin-1-yl)pyridin-4-yl)-1,2,4-oxadiazol-5-yl)ethan-1-amine (A-335)

To a stirred solution of compound A-334 (671 mg, 1.78 mmol) in DCM (20 mL) was added TFA (1.5 mL) at 0° C. The reaction mixture was slowly warmed to room temperature and stirred for 6 h. The mixture was concentrated under reduced pressure and treated with ice water (20 mL). The mixture was treated with saturated $NaHCO_3$ solution (10 mL) and extracted with EtOAc (2×30 mL). The organic layer was washed with brine (20 mL), dried over anhydrous $Na_2SO_4$ and concentrated to afford compound A-335 (290 mg). The compound was used for the next step without further purification.

Synthesis of (S)—N-(1-(3-(2-(3-methoxyazetidin-1-yl)pyridin-4-yl)-1,2,4-oxadiazol-5-yl)ethyl)-1-methyl-3-(trifluoromethyl)-1H-pyrazole-5-carboxamide (213)

To a stirred solution of 2-methyl-5-(trifluoromethyl)pyrazole-3-carboxylic acid (183 mg, 0.94 mmol) in THF (10.0 mL) was added compound A-335 (260 mg, 0.94 mmol) followed by TEA (0.39 mL, 2.83 mmol) and T3P (50% in EtOAc, 1.69 mL, 2.83 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 213 (186 mg, 0.41 mmol, 43% yield) as a solid. Prep. HPLC method: Rt 9.32; Column: Sunfire C18 (150×19 mm), 5.0 μm; Mobile phase: 0.1% TFA in water/acetonitrile; Flow Rate: 15.0 mL/min. HPLC: Rt 3.38 min, 99.5%; Column: XBridge C8 (50×4.6) mm, 3.5 μm; Mobile phase: A: 0.1% TFA in water, B: 0.1% TFA in ACN; Flow Rate: 2.0 mL/min. LCMS: 452.2 (M+H), Rt 1.67 min, Column: ZORBAX XDB C-18 (50×4.6 mm), 3.5 μm; Mobile Phase: A: 0.1% HCOOH in water, B: ACN; Flow Rate: 1.5 mL/min. Chiral method: Rt 1.45 min, SFC column: YMC Amylose-SA; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.18-8.16 (m, 1H), 7.26-7.24 (m, 2H), 7.02 (s, 1H), 5.52 (q, 1H), 4.42-4.38 (m, 1H), 4.30-4.26 (m, 2H), 4.18 (s, 3H), 3.92-3.89 (m, 2H), 3.36 (s, 3H), 1.76 (d, 3H).

Example 168. Synthesis of 214

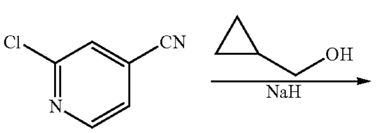

A-272

-continued

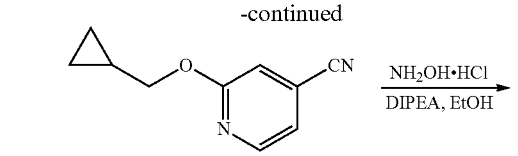

A-346

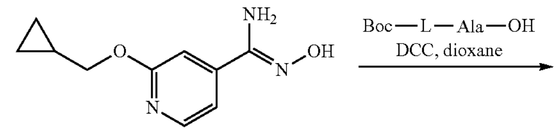

A-347

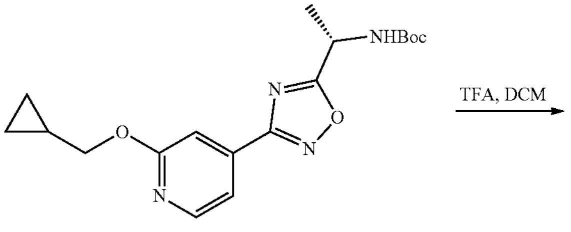

A-348

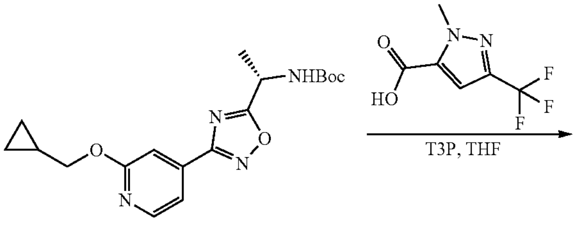

A-349

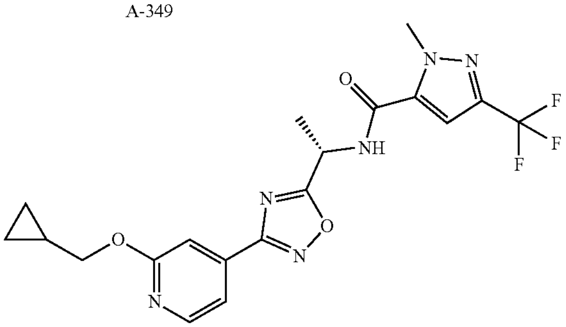

214

Synthesis of 2-(cyclopropylmethoxy)isonicotinonitrile (A-346)

To a solution of cyclopropylmethanol (0.58 g, 8.0 mmol) in THF (15.0 mL) was added NaH (60% in mineral oil, 290 mg, 7.26 mmol) and stirred at room temperature for 15 min. 2-chloropyridine-4-carbonitrile (1.0 g, 7.22 mmol) was added to the reaction mixture and stirred for 3 h at room temperature. The reaction mixture was cooled to 10° C. and treated with ice water (30 mL). The mixture was extracted with ethyl acetate (2×30 mL). The organic layer was washed with brine (30 mL), dried over anhydrous $Na_2SO_4$ and concentrated. The crude compound was purified by column chromatography on silica gel with 10% ethyl acetate/PE to afford A-346 (900 mg, 5.17 mmol, 71% yield). LCMS: 175.2 (M+H), Rt 2.28 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min Synthesis of 2-(cyclopropylmethoxy)-N'-hydroxyisonicotinimidamide (A-347)

To a stirred solution of compound A-346 (900 mg, 5.17 mmol) in ethanol (20 mL) was added hydroxylamine hydrochloride (0.54 g, 7.74 mmol) and DIPEA (2.7 mL, 15.5 mmol). The reaction mixture was heated at 80° C. for 3 h. The reaction mixture was cooled to room temperature and treated with water (20 mL). The mixture was treated with 10% sodium carbonate solution (10 mL) and extracted with ethyl acetate (2×30 mL). The organic layer was washed with brine (30 mL), dried over anhydrous $Na_2SO_4$ and concentrated to afford compound A-347 (1.05 g). It was used for next step without further purification.

Synthesis of tert-butyl (S)-(1-(3-(2-(cyclopropylmethoxy)pyridin-4-yl)-1,2,4-oxadiazol-5-yl)ethyl) carbamate (A-348)

To a solution of compound A-347 (1.05 g, 5.1 mmol) in 1,4-dioxane (30 mL) was added (2S)-2-(tert-butoxycarbonylamino)propanoic acid (1.22 g, 6.47 mmol) and DCC (1.47 g, 7.11 mmol). The reaction mixture was heated to 100° C. for 16 h. The reaction mixture was cooled to room temperature and concentrated under reduced pressure. The mixture was treated with water (30 mL) and extracted with ethyl acetate (2×50 mL). The organic layer was washed with brine (50 mL), dried over anhydrous $Na_2SO_4$ and concentrated. The crude was purified by column chromatography on silica gel with 14% EtOAc/PE to afford compound A-348 (1.47 g, 4.1 mmol, 80% yield) as a solid. LCMS: 361.2 (M+H), Rt 2.71 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min Synthesis of (S)-1-(3-(2-(cyclopropylmethoxy)pyridin-4-yl)-1,2,4-oxadiazol-5-yl)ethan-1-amine (A-349)

To a stirred solution of compound A-348 (1.2 g, 3.33 mmol) in DCM (12 mL) was added TFA (3.9 mL) at 0° C. The reaction mixture was slowly warmed to room temperature and stirred for 2 h. The mixture was concentrated under reduced pressure and THF (20 mL) was added. The mixture was treated with silicon carbonate (3.0 g), stirred for 30 min. and filtered over celite. The filtrate was concentrated to afford compound A-349 (720 mg). It was used for the next step without further purification.

Synthesis of (S)—N-(1-(3-(2-(cyclopropylmethoxy) pyridin-4-yl)-1,2,4-oxadiazol-5-yl)ethyl)-1-methyl-3-(trifluoromethyl)-1H-pyrazole-5-carboxamide (214)

To a stirred solution of 2-methyl-5-(trifluoromethyl)pyrazole-3-carboxylic acid (150 mg, 0.77 mmol) in THF (6.0 mL) was added A-349 (201 mg, 0.77 mmol) followed by $Et_3N$ (0.32 mL, 2.32 mmol) and T3P (1.38 mL, 2.32 mmol). The reaction mixture stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 214 (111 mg, 0.25 mmol, 32% yield) as a solid. Prep. HPLC method: Rt 11.55; Column: X-Select C-18 (150×19 mm), 5.0 μm; Mobile phase: 0.1% TFA in water/acetonitrile; Flow Rate: 15.0 mL/min. HPLC: Rt 5.45 min, 99.1%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 437.2 (M+H), Rt 2.67 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.44 min, SFC column: Lux $C_3$; mobile phase: 85:15 (A:B), A=liquid $CO_2$, B=methanol; flow rate: 3.0 mL/min; wave length: 210 nm. $^1H$ NMR (400 MHz, $CD_3OD$): δ 8.27 (d, 1H), 7.53 (dd, 1H), 7.39 (d, 1H), 7.26 (s, 1H), 5.53 (q, 1H), 4.20-4.18 (m, 5H), 1.77 (d, 3H), 1.35-1.29 (m, 1H), 0.65-0.60 (m, 2H), 0.40-0.36 (m, 2H).

Example 169. Synthesis of 215

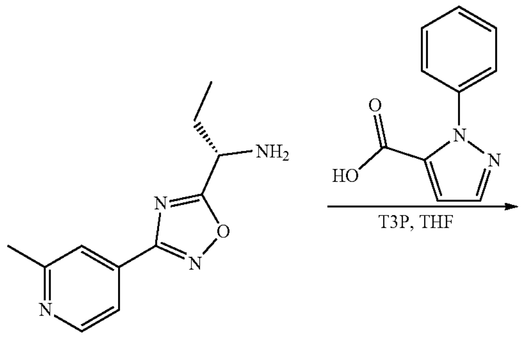

A-284

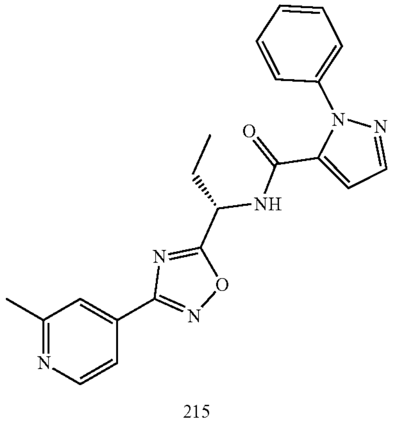

215

Synthesis of (S)—N-(1-(3-(2-methylpyridin-4-yl)-1,2,4-oxadiazol-5-yl)propyl)-1-phenyl-1H-pyrazole-5-carboxamide (215)

To a stirred solution of compound A-284 (120 mg, 0.55 mmol) in THF (8.0 mL) was added 2-phenylpyrazole-3-carboxylic acid (106 mg, 0.57 mmol) followed by $Et_3N$ (0.23 mL, 1.65 mmol) and T3P (50% in EtOAc, 0.98 mL, 1.65 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 215 (56 mg, 0.14 mmol, 25% yield) as a solid. Prep. HPLC method: Rt 5.85; Column: YMC C-18 (150×19 mm), 5.0 μm; Mobile phase: 0.1% TFA in water/acetonitrile; Flow Rate: 15.0 mL/min. HPLC: Rt 2.80 min, 97.6%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 389.3 (M+H), Rt 1.63 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.76 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1$H NMR (400 MHz, $CD_3OD$): δ 8.62 (d, 1H), 7.96 (s, 1H), 7.88 (d, 1H), 7.77 (d, 1H), 7.48-7.38 (m, 5H), 6.97 (d, 1H), 7.26 (dd, 1H), 2.65 (s, 3H), 2.23-2.03 (m, 2H), 1.09 (t, 3H).

Example 169. Synthesis of 216

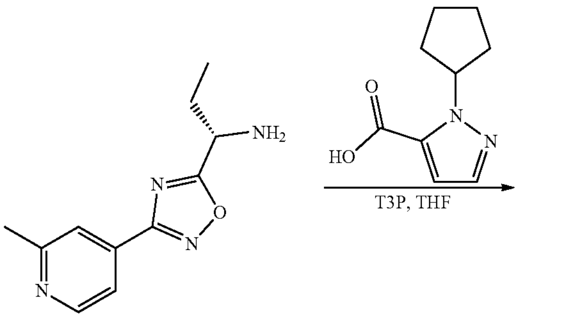

A-284

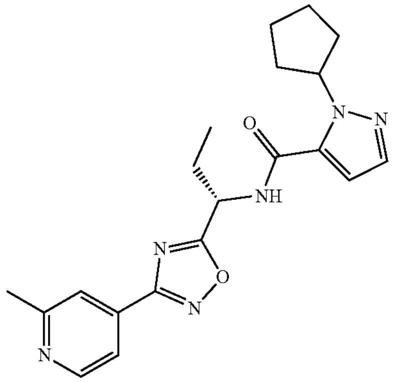

216

Synthesis of (S)-1-cyclopentyl-N-(1-(3-(2-methylpyridin-4-yl)-1,2,4-oxadiazol-5-yl)propyl)-1H-pyrazole-5-carboxamide (216)

To a stirred solution of compound A-284 (120 mg, 0.55 mmol) in THF (8.0 mL) was added 2-cyclopentylpyrazole-3-carboxylic acid (106 mg, 0.59 mmol) followed by $Et_3N$ (0.23 mL, 1.65 mmol) and T3P (50% in EtOAc, 0.98 mL, 1.65 mmol). The reaction mixture was stirred at room temperature for 16 h. The reaction mixture was treated with water (20 mL) and extracted with ethyl acetate (2×20 mL). The organic layer was washed with saturated sodium bicarbonate solution (20 mL), washed with brine (20 mL), dried over $Na_2SO_4$ and concentrated. The crude was purified by preparative HPLC to afford 216 (72 mg, 0.18 mmol, 34% yield) as a solid. Prep. HPLC method: Rt 8.05; Column: X-Bridge (150×19 mm), 5.0 μm; Mobile phase: 0.1% TFA in water/acetonitrile; Flow Rate: 15.0 mL/min. HPLC: Rt 3.30 min, 99.7%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 381.3 (M+H), Rt 2.00 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min Chiral method: Rt 1.6 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1$H NMR (400 MHz, $CD_3OD$): δ 8.60 (d, 1H), 7.96 (s, 1H), 7.86 (d, 1H), 7.53 (d, 1H), 6.86 (d, 1H), 5.58-5.50 (m, 1H), 5.35 (dd, 1H), 2.64 (s, 3H), 2.28-1.88 (m, 8H), 1.71-1.65 (m, 2H), 1.13 (t, 3H).

Example 170. Synthesis of 217

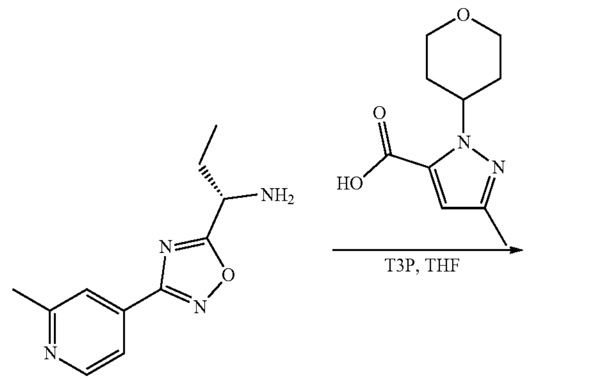

A-284

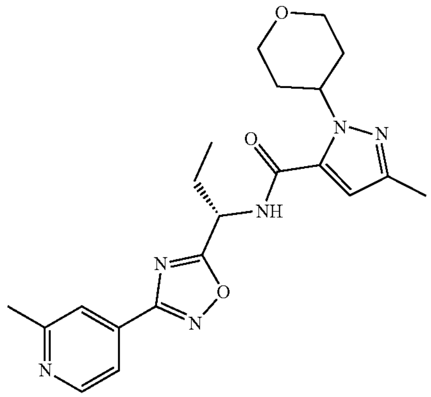

217

Synthesis of (S)-3-methyl-N-(1-(3-(2-methylpyridin-4-yl)-1,2,4-oxadiazol-5-yl)propyl)-1-(tetrahydro-2H-pyran-4-yl)-1H-pyrazole-5-carboxamide (217)

To a stirred solution of compound A-284 (123 mg, 0.57 mmol) in THF (6.0 mL) was added 5-methyl-2-tetrahydropyran-4-yl-pyrazole-3-carboxylic acid (120 mg, 0.57 mmol) followed by $Et_3N$ (0.24 mL, 1.7 mmol) and T3P (50% in EtOAc, 1.01 mL, 1.7 mmol). The reaction mixture was stirred at room temperature for 16 h. The reaction mixture was treated with water (30 mL) and extracted with ethyl acetate (2×50 mL). The organic layer was washed with brine (30 mL), dried over $Na_2SO_4$ and concentrated. The crude was purified by preparative HPLC to afford 217 (68 mg, 0.16 mmol, 29% yield) as a solid. Prep. HPLC method: Rt 12.65;

Column: X-Select (150×19 mm), 5.0 μm; Mobile phase: 0.1% HCOOH in water/acetonitrile; Flow Rate: 15.0 mL/min. HPLC: Rt 2.68 min, 98.3%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 411.2 (M+H), Rt 1.47 min, Column: ZORBAX XDB C-18 (50×4.6 mm), 3.5 μm Mobile Phase: A: 0.1% HCOOH in water:ACN (95:5), B: ACN; Flow Rate: 1.5 mL/min; Chiral method: Rt 1.53 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.61 (d, 1H), 7.95 (s, 1H), 7.86 (d, 1H), 6.66 (s, 1H), 5.34 (dd, 1H), 5.23-5.19 (m, 1H), 4.05-4.00 (m, 2H), 3.55-3.46 (m, 2H), 2.64 (s, 3H), 2.29 (s, 3H), 2.26-2.09 (m, 4H), 1.90-1.86 (m, 2H), 1.13 (t, 3H).

Example 171. Synthesis of 218

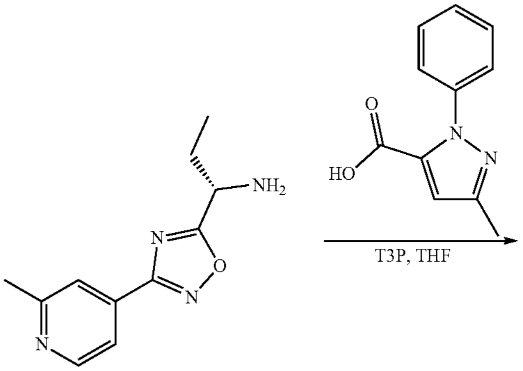

A-284

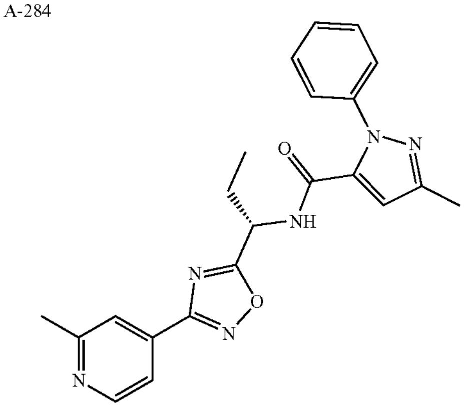

218

Synthesis of (S)-3-methyl-N-(1-(3-(2-methylpyridin-4-yl)-1,2,4-oxadiazol-5-yl)propyl)-1-phenyl-1H-pyrazole-5-carboxamide (218)

To a stirred solution of compound A-284 (120 mg, 0.55 mmol) in THF (5.0 mL) was added 5-methyl-2-phenyl-pyrazole-3-carboxylic acid (122 mg, 0.60 mmol) followed by $Et_3N$ (0.23 mL, 1.65 mmol) and T3P (50% in EtOAc, 1.5 mL, 2.52 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (30 mL), dried over $Na_2SO_4$ and concentrated. The crude was purified by preparative HPLC to afford 218 (20 mg, 0.05 mmol, 8% yield) as a solid. Prep. HPLC method: Rt 6.95; Column: X-Bridge (150×19 mm), 5.0 μm; Mobile phase: 10 mM $NH_{40}Ac$ in water/acetonitrile; Flow Rate: 15.0 mL/min. HPLC: Rt 2.95 min, 97.1% Column: X-Bridge C8 (50×4.6) mm, 3.5 μm; Mobile phase: A: 0.1% TFA in water, B: 0.1% TFA in ACN; Flow Rate: 2.0 mL/min. LCMS: 403.1 (M+H), Rt 1.54 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.62 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1H$ NMR (400 MHz, DMSO-$d_6$): δ 9.44 (d, 1H), 8.68 (d, 1H), 7.82 (s, 1H), 7.73 (d, 1H), 7.38-7.30 (m, 5H), 6.78 (s, 1H), 5.19-5.13 (m, 1H), 2.58 (s, 3H), 2.28 (s, 3H), 2.07-2.00 (m, 2H), 0.99 (t, 3H).

Example 172. Synthesis of 219

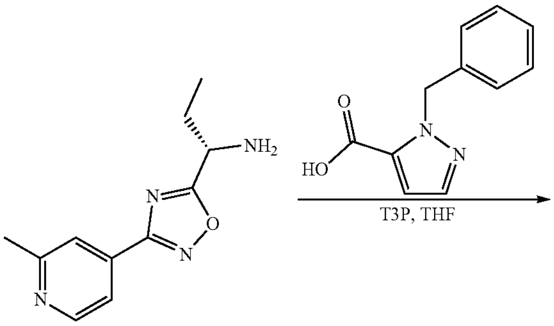

A-284

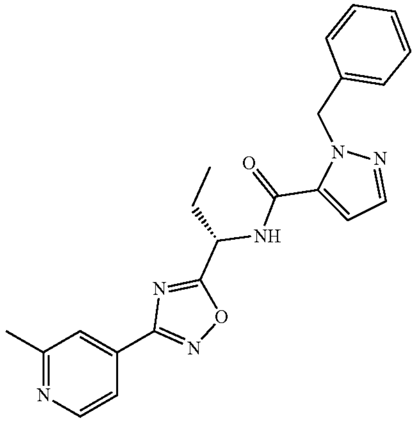

219

Synthesis of (S)-1-benzyl-N-(1-(3-(2-methylpyridin-4-yl)-1,2,4-oxadiazol-5-yl)propyl)-1H-pyrazole-5-carboxamide (219)

To a stirred solution of compound A-284 (120 mg, 0.55 mmol) in THF (5.0 mL) was added 2-benzylpyrazole-3-carboxylic acid (122 mg, 0.60 mmol) followed by $Et_3N$ (0.23 mL, 1.65 mmol) and T3P (50% in EtOAc, 1.5 mL, 2.52 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (30 mL), dried over $Na_2SO_4$ and concentrated. The crude was purified by preparative HPLC to afford 219 (95 mg, 0.23 mmol, 42% yield) as a solid. Prep. HPLC method: Rt 7.46; Column: YMC C-18 (150×19 mm), 5.0 μm; Mobile phase: 0.1% TFA in water/acetonitrile; Flow Rate: 15.0 mL/min. HPLC: Rt 3.29 min, 98.3%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 403.1 (M+H), Rt 1.66 min, Column: X-Bridge C8 (50×4.6 mm), 3.5 μm; Mobile Phase: A: 0.1% TFA in water:ACN (95:5), B: 0.1% TFA in ACN; Flow Rate: 1.5 mL/min. Chiral method: Rt 1.81 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.60 (d, 1H), 7.93 (s, 1H), 7.84 (d, 1H), 7.59 (d, 1H), 7.26-7.15 (m, 5H), 6.96 (d, 1H), 5.74 (d, 2H), 5.32 (q, 1H), 2.64 (s, 3H), 2.24-2.17 (m, 1H), 2.11-2.03 (m, 1H), 1.06 (t, 3H).

Example 173. Synthesis of 220

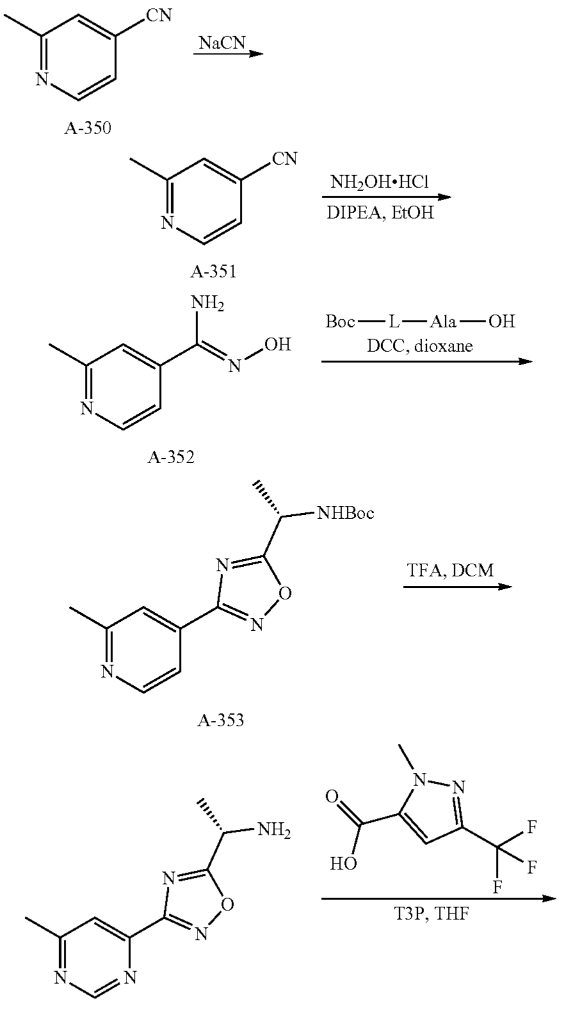

A-350

A-351

A-352

A-353

A-354

-continued

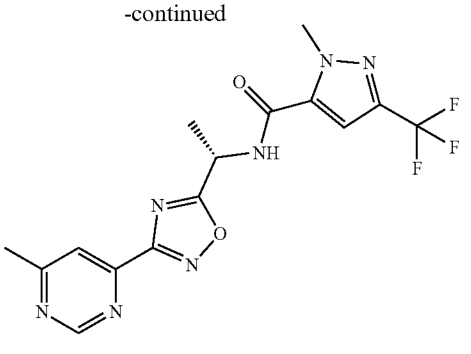

220

Synthesis of 6-methylpyrimidine-4-carbonitrile (A-351)

To a stirred solution of 4-chloro-6-methyl-pyrimidine (A-350, 2.0 g, 15.56 mmol) in DMSO (25.0 mL) and water (7.0 mL) was added DABCO (0.87 g, 7.78 mmol) and NaCN (1.68 g, 34.23 mol) at 0° C. The reaction mixture was slowly warmed to room temperature and stirred for 7 h. The reaction mixture was treated with water (80 mL) and extracted with EtOAc (2×80 mL). The organic layer was washed with saturated sodium bicarbonate solution (60 mL), washed with brine (60 mL), dried over $Na_2SO_4$ and concentrated. The crude was purified by column chromatography on silica gel with 10% ethyl acetate/PE to afford A-351 (850 mg, 7.13 mmol, 45% yield). LCMS: 120.2 (M+H), Rt 1.01 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min Synthesis of N'-hydroxy-6-methylpyrimidine-4-carboximidamide (A-352)

To a stirred solution of compound A-351 (830 mg, 6.97 mmol) in ethanol (10.0 mL) was added hydroxylamine hydrochloride (726 mg, 10.45 mmol) and DIPEA (3.45 mL, 20.9 mmol). The reaction mixture was heated at 80° C. for 2 h. The reaction mixture was cooled to room temperature and concentrated under reduced pressure. The crude was treated with water (20 mL) followed by saturated sodium bicarbonate solution (20 mL) and extracted with ethyl acetate (2×30 mL). The organic layer was washed with brine (20 mL), dried over anhydrous $Na_2SO_4$ and concentrated to afford A-352 (850 mg). The compound was used for the next step without further purification.

Synthesis of tert-butyl (S)-(1-(3-(6-methylpyrimidin-4-yl)-1,2,4-oxadiazol-5-yl)ethyl)carbamate (A-353)

To a stirred solution of compound A-352 (530 mg, 3.47 mmol) in 1, 4-dioxane (20 mL) was added DCC (859 mg, 4.16 mmol) and (2S)-2-(tert-butoxycarbonylamino)propanoic acid (984 mg, 5.21 mmol). The reaction mixture was heated at 100° C. for 16 h. The reaction mixture was cooled to room temperature and concentrated under reduced pressure. The mixture was treated with water (30 mL) and extracted with ethyl acetate (2×30 mL). The organic layer was washed with brine (20 mL), dried over $Na_2SO_4$ and concentrated. The crude compound was purified by column chromatography on silica gel with 29% EtOAc/PE to afford A-353 (520 mg, 1.7 mmol, 49% yield). LCMS: 306.1 (M+H), Rt 2.04 min; Column: X-Bridge C8 (50×4.6 mm), 3.5 μm; Mobile Phase: A: 10 mM $NH_4HCO_3$ in water, B: ACN; Flow Rate: 1.5 mL/min Synthesis of (S)-1-(3-(6-methylpyrimidin-4-yl)-1,2,4-oxadiazol-5-yl)ethan-1-amine (A-354)

To a stirred solution of compound A-353 (520 mg, 1.71 mmol) in DCM (10.0 mL) was added TFA (1.25 mL) at 0° C. The reaction mixture was slowly warmed to room temperature and stirred for 4 h. The mixture was concentrated under reduced pressure and treated with ice water (20 mL). The mixture was treated with 10% $NaHCO_3$ solution (10 mL) and extracted with DCM (2×30 mL). The organic layer was washed with brine (20 mL), dried over $Na_2SO_4$ and concentrated to afford compound A-354 (225 mg). The crude compound was used for the next step without further purification.

Synthesis of (S)-1-methyl-N-(1-(3-(6-methylpyrimidin-4-yl)-1,2,4-oxadiazol-5-yl)ethyl)-3-(trifluoromethyl)-1H-pyrazole-5-carboxamide (220)

To a stirred solution of 2-methyl-5-(trifluoromethyl)pyrazole-3-carboxylic acid (213 mg, 1.1 mmol) and compound A-354 (280 mg, 1.1 mmol) in THF (10.0 mL) was added $Et_3N$ (0.46 mL, 3.3 mmol) followed by T3P (50% in EtOAc, 0.98 mL, 3.3 mmol) at 0° C. The reaction mixture was slowly warmed to room temperature and stirred for 16 h. The reaction mixture was treated with water (30 mL) and extracted with ethyl acetate (2×30 mL). The organic layer was washed with brine (30 mL), dried over anhydrous $Na_2SO_4$ and concentrated. The crude compound was purified by preparative HPLC to afford 220 (220 mg, 0.57 mmol, 52% yield) as a solid. Prep. HPLC method: Rt 11.40; Column: X-Bridge (150×19 mm), 5.0 μm; Mobile phase: 10 mM $NH_{40}Ac$ in water/acetonitrile; Flow Rate: 15.0 mL/min. HPLC: Rt 3.75 min, 99.2% Column: X-Bridge C8 (50×4.6) mm, 3.5 μm; Mobile phase: A: 0.1% TFA in water, B: 0.1% TFA in ACN; Flow Rate: 2.0 mL/min; LCMS: 382.2 (M+H), Rt 1.89 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.21 min, SFC column: YMC Cellulose-C; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 9.17 (s, 1H), 8.10 (s, 1H), 7.26 (s, 1H), 5.55 (q, 1H), 4.18 (s, 3H), 2.66 (s, 3H), 1.77 (d, 3H).

Example 174. Synthesis of 221

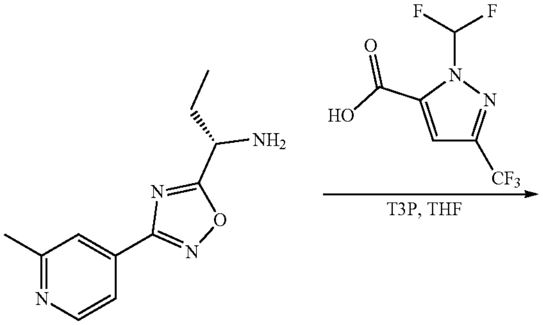

A-284

-continued

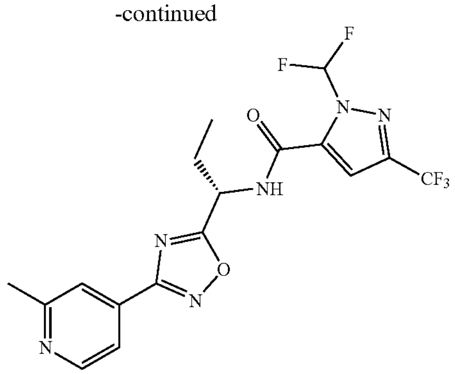

221

Synthesis of (S)-1-(difluoromethyl)-N-(1-(3-(2-methylpyridin-4-yl)-1,2,4-oxadiazol-5-yl)propyl)-3-(trifluoromethyl)-1H-pyrazole-5-carboxamide (221)

To a stirred solution of 2-(difluoromethyl)-5-trifluoromethyl-pyrazole-3-carboxylic acid (100 mg, 0.57 mmol) and compound A-284 (123 mg, 0.57 mmol) in THF (6.0 mL) was added $Et_3N$ (0.24 mL, 1.7 mmol) and T3P (50% in EtOAc, 1.01 mL, 1.7 mmol). The reaction mixture was stirred at room temperature for 16 h. The reaction mixture was treated with water (30 mL) and extracted with ethyl acetate (2×50 mL). The organic layer was washed with brine (30 mL), dried over $Na_2SO_4$ and concentrated. The crude was purified by preparative HPLC to afford 221 (125 mg, 0.33 mmol, 58% yield) as a solid. Prep. HPLC method: Rt 12.23; Column: X-Bridge (150×19 mm), 5.0 μm; Mobile phase: 10 mM $NH_4OAc$ in water/acetonitrile; Flow Rate: 15.0 mL/min. HPLC: Rt 2.84 min, 99.6%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 377.2 (M+H), Rt 1.67 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.4 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.60 (d, 1H), 8.13 (t, 1H), 7.95 (s, 1H), 7.86 (d, 1H), 6.94 (s, 1H), 5.38 (dd, 1H), 2.64 (s, 3H), 2.36 (s, 3H), 2.28-2.20 (m, 1H), 2.16-2.05 (m, 1H), 1.12 (t, 3H).

Example 175. Synthesis of 222

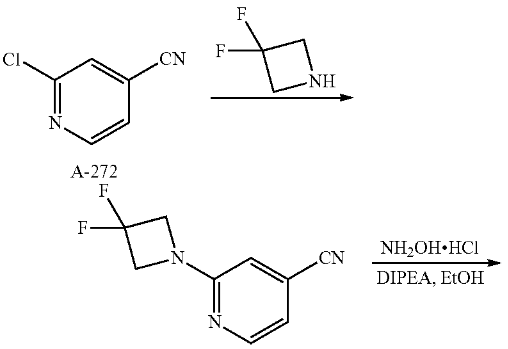

A-272

A-355

-continued

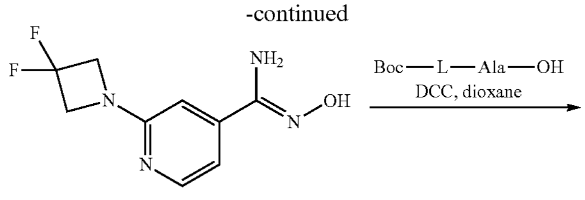

A-356

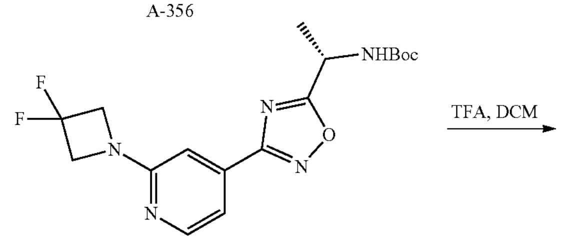

A-357

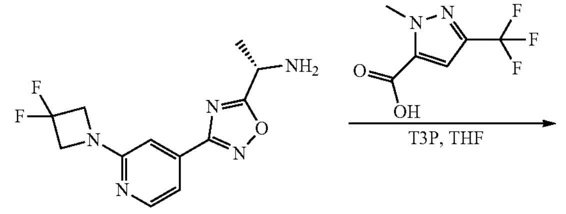

A-358

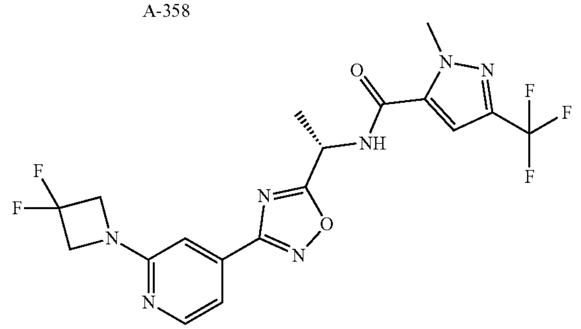

222

Synthesis of 2-(3,3-difluoroazetidin-1-yl)isonicotinonitrile (A-355)

To a stirred solution of 3,3-difluoroazetidine (A-272, 1.4 g, 10.86 mmol) in NMP (8.0 mL) was added DIPEA (1.9 mL, 10.86 mmol) and 2-chloropyridine-4-carbonitrile (750 mg, 5.4 mmol). The reaction mixture was heated in a microwave at 120° C. for 2 h. The reaction mixture was cooled to room temperature and treated with water (50 mL). The mixture was extracted with ethyl acetate (2×40 mL). The organic layer was washed with brine (20 mL), dried over $Na_2SO_4$ and concentrated. The crude was purified by column chromatography on silica gel with 20% EtOAc/PE to afford A-355 (750 mg, 3.84 mmol, 71% yield). LCMS: 196.1 (M+H), Rt 1.86 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min

Synthesis of 2-(3,3-difluoroazetidin-1-yl)-N'-hydroxyisonicotinimidamide (A-356)

To a stirred solution of compound A-355 (750 mg, 3.84 mmol) in ethanol (10.0 mL) was added hydroxylamine hydrochloride (0.4 g, 5.81 mmol) and DIPEA (2.0 mL, 11.52 mmol). The reaction mixture was heated at 80° C. for 4 h. The reaction mixture was cooled to room temperature and concentrated under reduced pressure. The crude was treated with water (20 mL) followed by saturated sodium bicarbonate solution (20 mL) and extracted with ethyl acetate (2×30 mL). The organic layer was washed with brine (20 mL), dried over anhydrous $Na_2SO_4$ and concentrated to afford compound A-356 (840 mg). The compound was used for the next step without further purification.

Synthesis of tert-butyl (S)-(1-(3-(2-(3,3-difluoroazetidin-1-yl)pyridin-4-yl)-1,2,4-oxadiazol-5-yl)ethyl) carbamate (A-357)

To a stirred solution of compound A-356 (840 mg, 3.68 mmol) in 1,4-dioxane (30 mL) was added (2S)-2-(tert-butoxycarbonylamino)propanoic acid (0.7 g, 3.68 mmol) followed by DCC (0.83 g, 4.05 mmol). The reaction mixture was heated at 100° C. for 16 h. The reaction mixture was cooled to room temperature and concentrated under reduced pressure. The mixture was treated with water (30 mL) and extracted with ethyl acetate (2×30 mL). The organic layer was washed with brine (20 mL), dried over $Na_2SO_4$ and concentrated. The crude compound was purified by column chromatography on silica gel with 40% EtOAc/PE to afford compound A-357 (1.25 g, 3.3 mmol, 90% yield) as a solid. LCMS: 382.3 (M+H), Rt 2.29 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min

Synthesis of (S)-1-(3-(2-(3,3-difluoroazetidin-1-yl) pyridin-4-yl)-1,2,4-oxadiazol-5-yl)ethan-1-amine (A-358)

To a stirred solution of compound A-357 (680 mg, 1.78 mmol) in DCM (8.0 mL) was added TFA (2.0 mL) at 0° C. The reaction mixture was slowly warmed to room temperature and stirred for 2 h. The mixture was concentrated under reduced pressure and treated with ice water (20 mL). The mixture was treated with 10% $NaHCO_3$ solution (10.0 mL) and extracted with ethyl acetate (2×30 mL). The organic layer was washed with brine (20 mL), dried over $Na_2SO_4$ and concentrated to afford compound A-358 (465 mg). The crude compound was used for the next step without further purification.

Synthesis of (S)—N-(1-(3-(2-(3,3-difluoroazetidin-1-yl)pyridin-4-yl)-1,2,4-oxadiazol-5-yl)ethyl)-1-methyl-3-(trifluoromethyl)-1H-pyrazole-5-carboxamide (222)

To a stirred solution of 2-methyl-5-(trifluoromethyl)pyrazole-3-carboxylic acid (150 mg, 0.77 mmol) in THF (8.0 mL) was added compound A-358 (260 mg, 0.92 mmol) followed by T3P (50% in EtOAc, 1.38 mL, 2.32 mmol) and $Et_3N$ (0.32 mL, 2.32 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 222 (23 mg, 0.05 mmol, 6% yield) as a solid. Prep. HPLC method: Rt 10.23; Column: Atlantis C-18 (150×19 mm), 5.0 μm; Mobile phase: 0.1% TFA in water/acetonitrile; Flow Rate:

15.0 mL/min. HPLC: Rt 3.87 min, 99.9%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 458.2 (M+H), Rt 2.33 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.06 min, SFC column: LUX $C_3$; mobile phase: 85:15 (A:B), A=liquid $CO_2$, B=methanol; flow rate: 3.0 mL/min; wave length: 210 nm. $^1H$ NMR (400 MHz, $CD_3OD$): δ 8.28 (dd, 1H), 7.40 (dd, 1H), 7.25 (s, 1H), 7.18-7.17 (m, 1H), 5.53 (q, 1H), 4.45 (t, 4H), 4.19 (s, 3H), 1.77 (d, 3H).

Example 176. Synthesis of 223

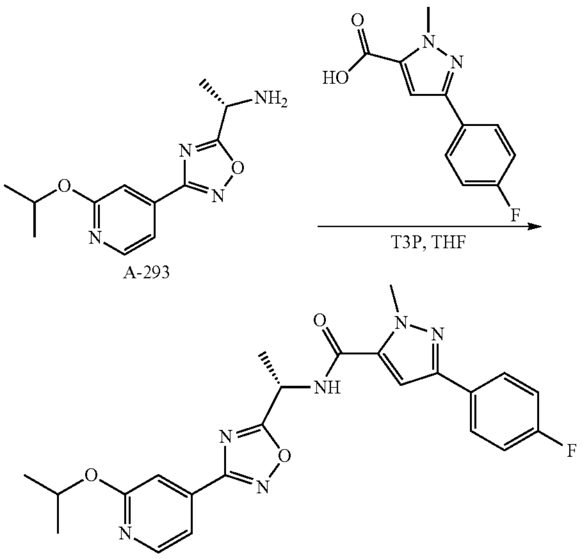

A-293

223

Synthesis of (S)-3-(4-fluorophenyl)-N-(1-(3-(2-isopropoxypyridin-4-yl)-1,2,4-oxadiazol-5-yl)ethyl)-1-methyl-1H-pyrazole-5-carboxamide (223)

To a stirred solution of compound A-293 (120 mg, 0.48 mmol) in THF (6.0 mL) was added 5-(4-fluorophenyl)-2-methyl-pyrazole-3-carboxylic acid (106 mg, 0.48 mmol) followed by $Et_3N$ (0.2 mL, 1.45 mmol) and T3P (50% in EtOAc, 0.86 mL, 1.45 mmol). The reaction mixture was stirred at room temperature for 16 h. The reaction mixture was treated with water (30 mL) and extracted with ethyl acetate (2×25 mL). The organic layer was washed with brine (20 mL), dried over $Na_2SO_4$ and concentrated. The crude was purified by preparative HPLC to afford 223 (80 mg, 0.17 mmol, 36% yield) as a solid. Prep. HPLC method: Rt 12.41; Column: YMC C-18 (150×19 mm), 5.0 μm; Mobile phase: 0.1% TFA in water/acetonitrile; Flow Rate: 15.0 mL/min. HPLC: Rt 5.38 min, 98.5%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 451.1 (M+H), Rt 2.44 min, Column: X-Bridge C8 (50×4.6 mm), 3.5 μm, Mobile Phase: A: 0.1% TFA in water:ACN (95:5), B: 0.1% TFA in ACN; Flow Rate: 1.5 mL/min. Chiral method: Rt 1.94 min, SFC column: YMC Cellulose-SC; mobile phase: 70:30 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.28 (d, 1H), 7.85-7.82 (m, 2H), 7.52 (d, 1H), 7.33 (s, 1H), 7.23 (s, 1H), 7.17 (t, 2H), 5.55 (q, 1H), 5.36-5.29 (m, 1H), 4.16 (s, 3H), 1.79 (d, 3H), 1.37 (d, 6H).

Example 177. Synthesis of 224

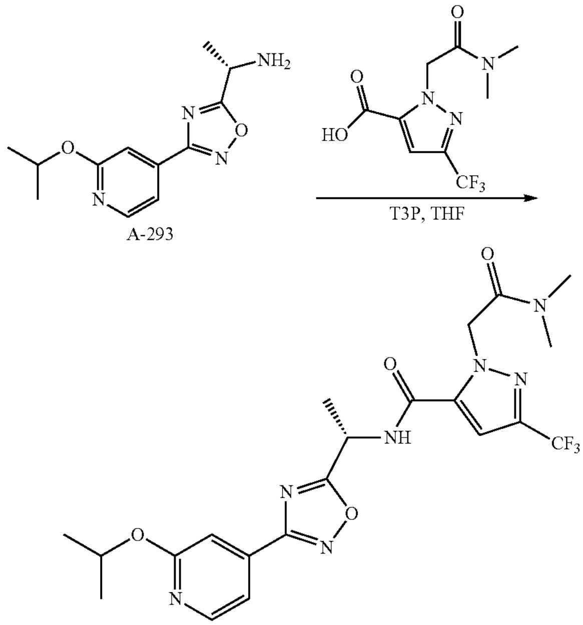

A-293

224

Synthesis of (S)-1-(2-(dimethylamino)-2-oxoethyl)-N-(1-(3-(2-isopropoxypyridin-4-yl)-1,2,4-oxadiazol-5-yl)ethyl)-3-(trifluoromethyl)-1H-pyrazole-5-carboxamide (224)

To a stirred solution of 2-[2-(dimethylamino)-2-oxo-ethyl]-5-(trifluoromethyl)pyrazole-3-carboxylic acid (128 mg, 0.48 mmol) and compound A-293 (120 mg, 0.48 mmol) in THF (6.0 mL) was added $Et_3N$ (0.2 mL, 1.45 mmol) and T3P (50% in EtOAc, 0.86 mL, 1.45 mmol). The reaction mixture was stirred at room temperature for 16 h. The reaction mixture was treated with water (30 mL) and extracted with ethyl acetate (2×30 mL). The organic layer was washed with brine (20 mL), dried over $Na_2SO_4$ and concentrated. The crude was purified by preparative HPLC to afford 224 (143 mg, 0.28 mmol, 59% yield) as a solid. Prep. HPLC method: Rt 15.01; Column: X-Select (150×19 mm), 5.0 μm; Mobile phase: 0.1% TFA in water/acetonitrile; Flow Rate: 15.0 mL/min. HPLC: Rt 4.82 min, 99.3%; Column: X-Bridge C8 (50×4.6) mm, 3.5 μm Mobile phase: A: 0.1% TFA in water, B: 0.1% TFA in ACN; Flow Rate: 2.0 mL/min. LCMS: 496.1 (M+H), Rt 2.23 min, Column: X-Bridge C8 (50×4.6 mm), 3.5 μm; Mobile Phase: A: 0.1% TFA in water:ACN (95:5), B: 0.1% TFA in ACN; Flow Rate: 1.5 mL/min. Chiral method: Rt 1.52 min, SFC column: YMC Cellulose-SB; mobile phase: 70:30 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.27 (d, 1H), 7.50 (d, 1H), 7.35-7.33 (m, 2H), 5.61-5.46 (m, 3H), 5.35-5.31 (m, 1H), 3.12 (s, 3H), 2.94 (s, 3H), 1.75 (d, 3H), 1.37 (d, 6H).

Example 178. Synthesis of 295 & 225

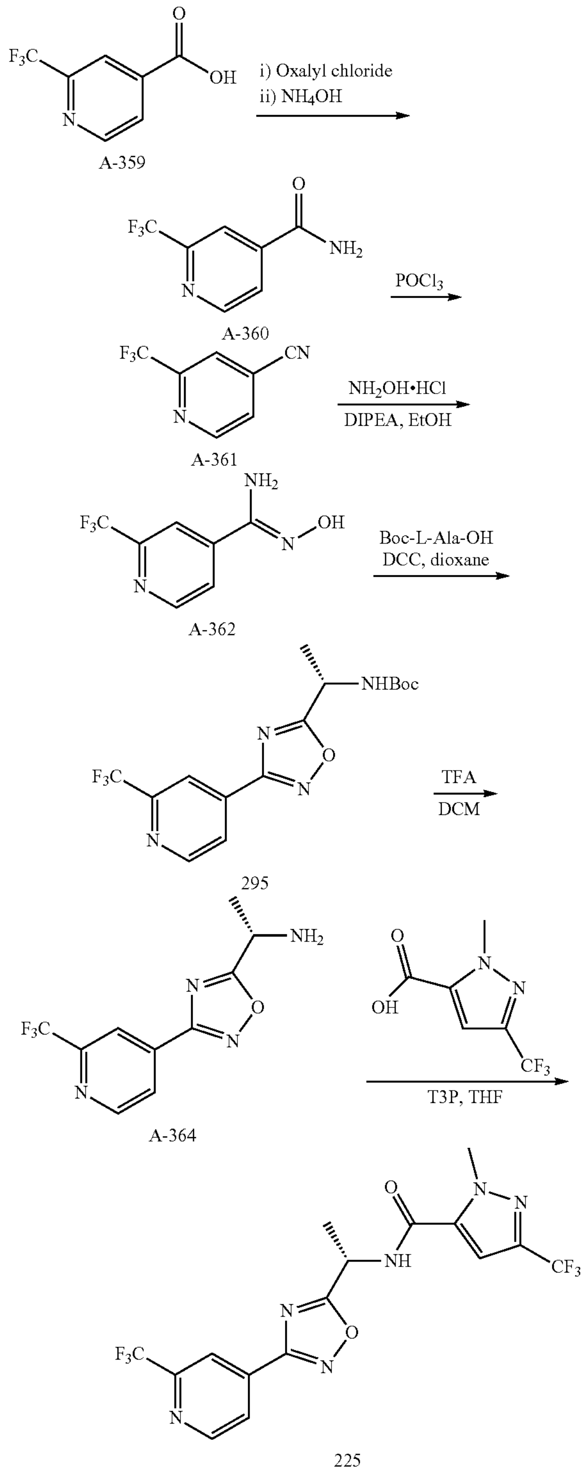

A-359

A-360

A-361

A-362

295

A-364

225

Synthesis of 2-(trifluoromethyl)isonicotinamide (A-360)

To a stirred solution of 2-(trifluoromethyl)pyridine-4-carboxylic acid (A-359, 2.0 g, 10.47 mmol) in DCM (20.0 mL) was added oxalyl chloride (1.39 g, 10.99 mmol) and catalytic amount of DMF (0.05 mL) at 0° C. The reaction mixture was warmed to room temperature and stirred for 2 h. The reaction mixture was concentrated under reduced pressure and aqueous $NH_4OH$ (2.0 mL) was added at 0° C. dropwise followed by MeCN (10.0 mL). The reaction mixture was stirred at room temperature for 30 min and diluted with ethylacetate (100 mL). The organic layer was washed with water (2×50 mL), washed with brine (20 mL), dried over $Na_2SO_4$ and concentrated to afford compound A-360 (1.3 g). The compound was used for the next step without further purification.

Synthesis of 2-(trifluoromethyl)pyridine-4-carbonitrile (A-361)

$POCl_3$ (3.04 mL, 32.61 mmol) was added dropwise to the compound A-360 (1.3 g, 6.84 mmol) at 0° C. The reaction mixture heated at 100° C. for 3 h. The reaction mixture was cooled to room temperature and treated with 50% NaOH solution (10 mL). The reaction mixture was diluted with water (50 mL) and extracted with ethylacetate (2×70 mL). The organic layer was washed with brine (40 mL), dried over $Na_2SO_4$ and concentrated. The crude was purified by column chromatography on silica gel with 8% ethyl acetate/PE to afford compound A-361 (520 mg, 3.0 mmol, 44% yield). LCMS: 173.1 (M+H), Rt 1.84 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min

Synthesis of N'-hydroxy-2-(trifluoromethyl)pyridine-4-carboxamidine (A-362)

To a stirred solution of compound A-361 (520 mg, 3.02 mmol) in ethanol (10.0 mL) was added hydroxylamine hydrochloride (314 mg, 4.53 mmol) and DIPEA (1.58 mL, 9.05 mmol) at room temperature under nitrogen atmosphere. The reaction mixture was heated at 80° C. for 2 h. The reaction mixture was cooled to room temperature and concentrated under reduced pressure. The crude was treated with water (15 mL) followed by saturated sodium bicarbonate solution (10 mL) and extracted with ethyl acetate (2×30 mL). The organic layer was washed with brine (20 mL), dried over $Na_2SO_4$ and concentrated to afford compound A-362 (580 mg). It was used for the next step without further purification.

Synthesis of tert-butyl (S)-(1-(3-(2-(trifluoromethyl)pyridin-4-yl)-1,2,4-oxadiazol-5-yl)ethyl)carbamate (295)

To a stirred solution of compound A-362 (580 mg, 2.83 mmol) in 1,4-dioxane (20.0 mL) was added (2S)-2-(tert-butoxycarbonylamino)propanoic acid (534 mg, 2.83 mmol) and DCC (640 mg, 3.11 mmol). The reaction mixture was stirred at 100° C. for 16 h. The reaction mixture was cooled to room temperature and concentrated under reduced pressure. The mixture was treated with water (30 mL) and extracted with ethyl acetate (2×30 mL). The organic layer was washed with brine (20 mL), dried over $Na_2SO_4$ and concentrated. The crude was purified by column chromatography on silica gel with 12% ethyl acetate/PE to afford compound 295 (840 mg, 2.34 mmol, 82% yield). LCMS: 359.2 (M+H), Rt 2.42 min; Column: ZORBAX XDB C-18

(50×4.6 mm), 3.5 μm; Mobile Phase: A: 0.1% HCOOH in water:ACN (95:5), B: ACN; Flow Rate: 1.5 mL/min Synthesis of (1S)-1-[3-[2-(trifluoromethyl)-4-pyridyl]-1,2,4-oxadiazol-5-yl]ethanamine (A-364)

To a stirred solution of compound 295 (400 mg, 1.12 mmol) in DCM (8.0 mL) was added TFA (1.5 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (10 mL) and extracted with EtOAc (2×25 mL). The organic layer was washed with brine (20 mL), dried over anhydrous $Na_2SO_4$ and concentrated to afford compound A-364 (260 mg). The compound was used for the next step without further purification.

Synthesis of (S)-1-methyl-3-(trifluoromethyl)-N-(1-(3-(2-(trifluoromethyl)pyridin-4-yl)-1,2,4-oxadiazol-5-yl)ethyl)-1H-pyrazole-5-carboxamide (225)

To a stirred solution of compound A-364 (260 mg, 1.01 mmol) in THF (10.0 mL) was added 2-methyl-5-(trifluoromethyl)pyrazole-3-carboxylic acid (195 mg, 1.01 mmol) followed by $Et_3N$ (0.42 mL, 3.02 mmol) and T3P (50% in EtOAc, 1.8 mL, 3.02 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 225 (130 mg, 0.3 mmol, 29% yield) as a solid. Prep. HPLC method: Rt 7.15; Column: X-Bridge (150×19 mm), 5.0 μm; Mobile phase: 0.1% TFA in water/acetonitrile; Flow Rate: 15.0 mL/min. HPLC: Rt 5.10 min, 99.5%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 435.0 (M+H), Rt 2.56 min, Column: Atlantis dc-18 (50×4.6 mm), 5.0 μm; Mobile Phase: A: 0.1% HCOOH in water: ACN (95:5), B: ACN; Flow Rate: 1.5 mL/min. Chiral method: Rt 1.73 min, SFC column: LUX $C_3$; mobile phase: 85:15 (A:B), A=liquid $CO_2$, B=methanol; flow rate: 3.0 mL/min; wave length: 210 nm. $^1H$ NMR (400 MHz, $CD_3OD$): δ 8.92 (d, 1H), 8.38 (s, 1H), 8.28 (dd, 1H), 7.25 (s, 1H), 5.55 (q, 1H), 4.18 (s, 3H), 1.78 (d, 3H).

Example 179. Synthesis of 226

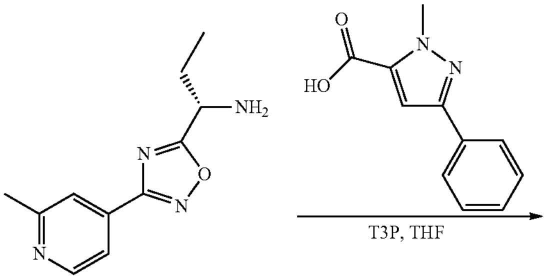

A-284

-continued

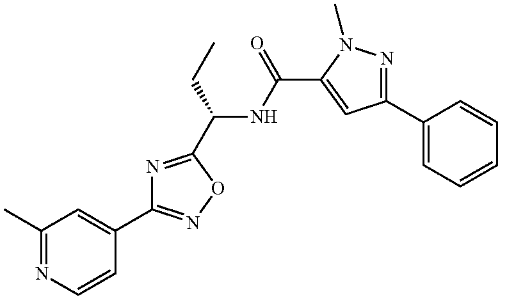

226

Synthesis of (S)-1-methyl-N-(1-(3-(2-methylpyridin-4-yl)-1,2,4-oxadiazol-5-yl)propyl)-3-phenyl-1H-pyrazole-5-carboxamide (226)

To a stirred solution of compound A-284 (120 mg, 0.55 mmol) in THF (5.0 mL) was added 2-methyl-5-phenyl-pyrazole-3-carboxylic acid (122 mg, 0.60 mmol) followed by $Et_3N$ (0.23 mL, 1.65 mmol) and T3P (50% in EtOAc, 1.5 mL, 2.52 mmol). The reaction mixture was stirred at room temperature for 16 h. The reaction mixture was treated with water (40 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 226 (85 mg, 0.21 mmol, 38% yield) as a solid. Prep. HPLC method: Rt 7.65; Column: X-Bridge (150×19 mm), 5.0 μm; Mobile phase: 0.1% TFA in water/acetonitrile; Flow Rate: 15.0 mL/min. HPLC: Rt 3.53 min, 99.8%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 403.1 (M+H), Rt 1.75 min, Column: X-Bridge C8 (50×4.6) mm, 3.5 μm; Mobile phase: A: 0.1% TFA in water:ACN (95:5), B: 0.1% TFA in ACN; Flow Rate: 1.5 mL/min. Chiral method: Rt 2.47 min, SFC column: YMC Cellulose-SB; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.61 (d, 1H), 7.96 (s, 1H), 7.88-7.87 (m, 1H), 7.84-7.81 (m, 2H), 7.45-7.42 (m, 2H), 7.36-7.31 (m, 1H), 7.30 (s, 1H), 5.40 (dd, 1H), 4.17 (s, 3H), 2.64 (s, 3H), 2.31-2.12 (m, 2H), 1.15 (t, 3H).

Example 180. Synthesis of 227

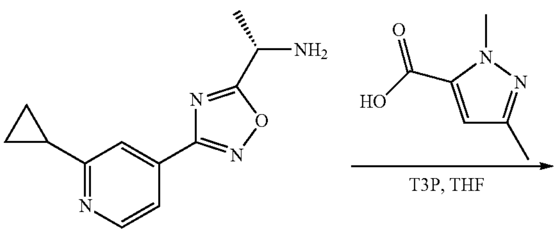

A-303

-continued

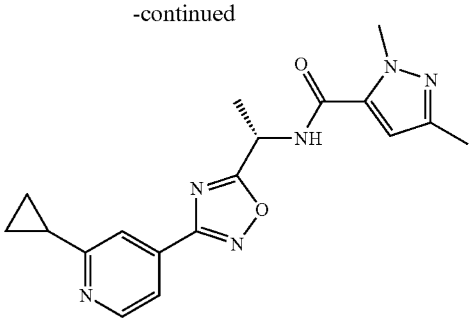

227

Synthesis of (S)—N-(1-(3-(2-cyclopropylpyridin-4-yl)-1,2,4-oxadiazol-5-yl)ethyl)-1,3-dimethyl-1H-pyrazole-5-carboxamide (227)

To a solution of compound A-303 (100 mg, 0.43 mmol) in THF (8.0 mL) was added 2,5-dimethylpyrazole-3-carboxylic acid (84 mg, 0.60 mmol) followed by $Et_3N$ (0.18 mL, 1.3 mmol) and T3P (50% in EtOAc, 0.78 mL, 1.3 mmol). The reaction mixture was stirred at room temperature for 16 h. The reaction mixture was treated with water (30 mL) and extracted with ethyl acetate (2×50 mL). The organic layer was washed with saturated sodium bicarbonate solution (20 mL), washed with brine (30 mL), dried over $Na_2SO_4$ and concentrated. The crude was purified by preparative HPLC to afford 227 (75 mg, 0.21 mmol, 48% yield) as a solid. Prep. HPLC method: Rt 10.61; Column: X-Bridge (150×19 mm), 5.0 μm; Mobile phase: 10 mM $NH_{40}Ac$ in water/acetonitrile; Flow Rate: 15.0 mL/min. HPLC: Rt 2.42 min, 99.8%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 353.2 (M+H), Rt 1.66 min, Column: Zorbax XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.48 min, SFC column: YMC Amylose-C; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.53 (d, 1H), 7.85 (s, 1H), 7.76 (dd, 1H), 6.69 (s, 1H), 5.51 (q, 1H), 4.04 (s, 3H), 2.27 (s, 3H), 2.23-2.19 (m, 1H), 1.76 (d, 3H), 1.12-1.02 (m, 4H).

Example 181. Synthesis of 228

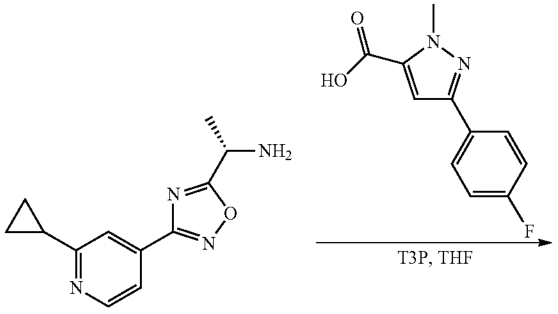

A-303

-continued

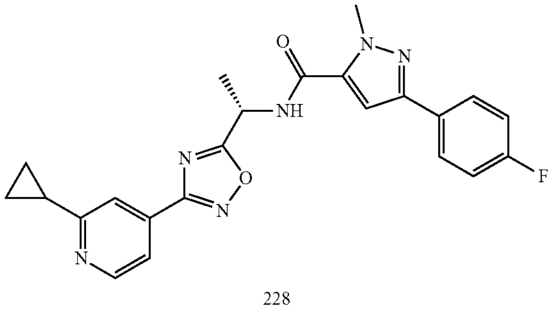

228

Synthesis of (S)—N-(1-(3-(2-cyclopropylpyridin-4-yl)-1,2,4-oxadiazol-5-yl)ethyl)-3-(4-fluorophenyl)-1-methyl-1H-pyrazole-5-carboxamide (228)

To a solution of compound A-303 (100 mg, 0.43 mmol) in THF (8.0 mL) was added 5-(4-fluorophenyl)-2-methyl-pyrazole-3-carboxylic acid (105 mg, 0.48 mmol) followed by $Et_3N$ (0.18 mL, 1.3 mmol) and T3P (50% in EtOAc, 0.78 mL, 1.3 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (30 mL), dried over $Na_2SO_4$ and concentrated. The crude was purified by preparative HPLC to afford 228 (60 mg, 0.13 mmol, 31% yield) as a solid. Prep. HPLC method: Rt 11.15; Column: X-Bridge (150×19 mm), 5.0 μm; Mobile phase: 0.1% TFA in water/acetonitrile; Flow Rate: 15.0 mL/min. HPLC: Rt 3.73 min, 98.4%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 433.1 (M+H), Rt 1.82 min, Column: X-Bridge C8 (50×4.6 mm), 3.5 μm; Mobile Phase: A: 0.1% TFA in water:ACN (95:5), B: 0.1% TFA in ACN; Flow Rate: 1.5 mL/min. Chiral method: Rt 2.56 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.53 (d, 1H), 7.85-7.81 (m, 3H), 7.77-7.75 (m, 1H), 7.23 (s, 1H), 7.18-7.14 (m, 2H), 5.55 (q, 1H), 4.16 (s, 3H), 2.23-2.16 (m, 1H), 1.79 (d, 3H), 1.11-1.04 (m, 4H).

Example 181. Synthesis of 229

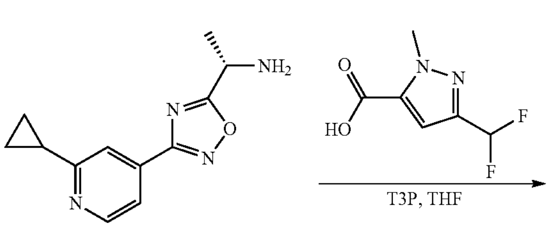

A-303

-continued

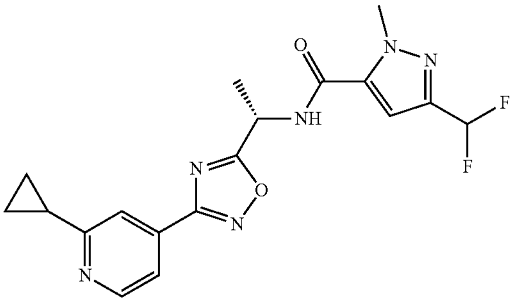

229

Synthesis of (S)—N-(1-(3-(2-cyclopropylpyridin-4-yl)-1,2,4-oxadiazol-5-yl)ethyl)-3-(difluoromethyl)-1-methyl-1H-pyrazole-5-carboxamide (229)

To a stirred solution of compound A-303 (120 mg, 0.52 mmol) in THF (6.0 mL) was added 5-(difluoromethyl)-2-methyl-pyrazole-3-carboxylic acid (91 mg, 0.52 mmol) followed by $Et_3N$ (0.22 mL, 1.56 mmol) and T3P (50% in EtOAc, 0.93 mL, 1.56 mmol). The reaction mixture was stirred at room temperature for 16 h. The reaction mixture was treated with water (30 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 229 (47 mg, 0.12 mmol, 23% yield) as colourless liquid. Prep. HPLC method: Rt 8.38; Column: X-Select (150×19 mm), 5.0 μm; Mobile phase: 0.1% TFA in water/acetonitrile; Flow Rate: 15.0 mL/min. HPLC: Rt 2.94 min, 99.4%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 389.2 (M+H), Rt 2.06 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.55 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.54 (dd, 1H), 8.86 (dd, 1H), 7.76 (dd, 1H), 7.16 (s, 1H), 6.78 (t, 1H), 5.53 (q, 1H), 4.15 (s, 3H), 2.23-2.18 (m, 1H), 1.77 (d, 3H), 1.12-1.05 (m, 4H).

Example 182. Synthesis of 230

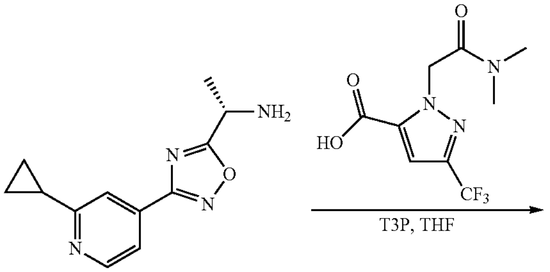

A-303

-continued

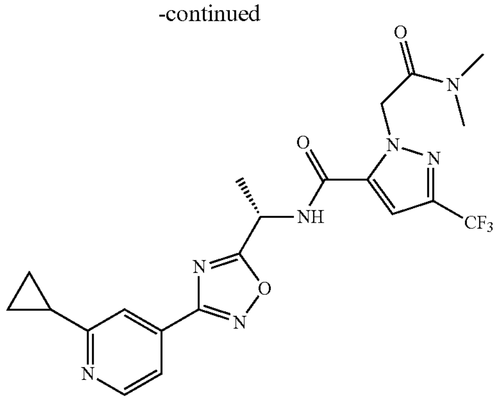

230

Synthesis of (S)—N-(1-(3-(2-cyclopropylpyridin-4-yl)-1,2,4-oxadiazol-5-yl)ethyl)-1-(2-(dimethylamino)-2-oxoethyl)-3-(trifluoromethyl)-1H-pyrazole-5-carboxamide (230)

To a stirred solution of compound A-303 (100 mg, 0.43 mmol) in THF (8.0 mL) was added 2-[2-(dimethylamino)-2-oxo-ethyl]-5-(trifluoromethyl)pyrazole-3-carboxylic acid (126 mg, 0.48 mmol) followed by $Et_3N$ (0.18 mL, 1.3 mmol) and T3P (50% in EtOAc, 0.78 mL, 1.3 mmol). The reaction mixture was stirred at room temperature for 16 h. The reaction mixture was treated with water (25 mL) and extracted with ethyl acetate (2×30 mL). The organic layer was washed with saturated sodium bicarbonate solution (20 mL), washed with brine (20 mL), dried over $Na_2SO_4$ and concentrated. The crude was purified by preparative HPLC to afford 230 (85 mg, 0.17 mmol, 40% yield) as a solid. Prep. HPLC method: Rt 8.51; Column: X-Bridge (150×19 mm), 5.0 μm; Mobile phase: 0.1% TFA in water/acetonitrile; Flow Rate: 15.0 mL/min. HPLC: Rt 3.11 min, 99.5%; Column: X-Bridge $C_8$ (50×4.6) mm, 3.5 μm; Mobile phase: A: 0.1% TFA in water, B: 0.1% TFA in ACN; Flow Rate: 2.0 mL/min. LCMS: 478.1 (M+H), Rt 2.04 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.51 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CD_3OD$): δ 8.53 (d, 1H), 7.92 (s, 1H), 7.86 (d, 1H), 7.35 (s, 1H), 5.61-5.45 (m, 3H), 3.12 (s, 3H), 2.93 (s, 3H), 2.23-2.18 (m, 1H), 1.76 (d, 3H), 1.12-1.04 (m, 4H), Example 183. Synthesis of 231

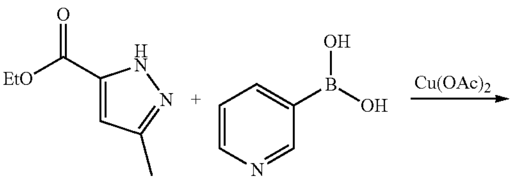

A-365 A-366

-continued

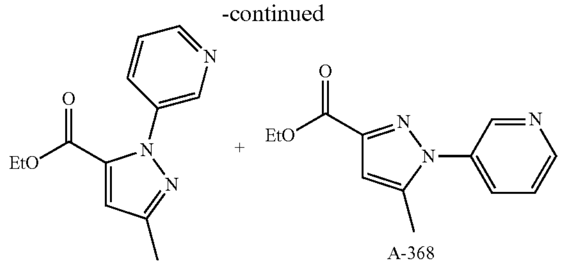

A-367

A-368

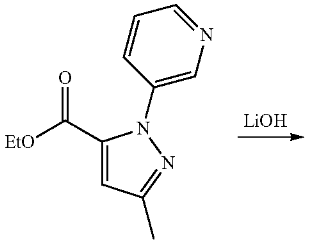

A-367

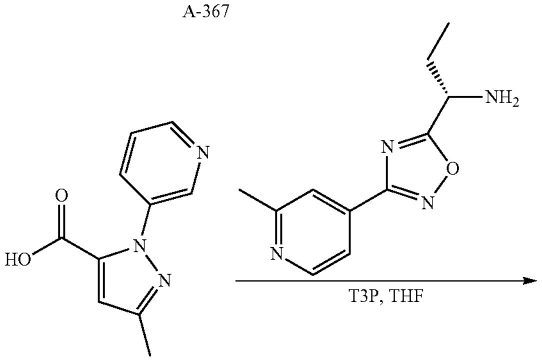

A-369

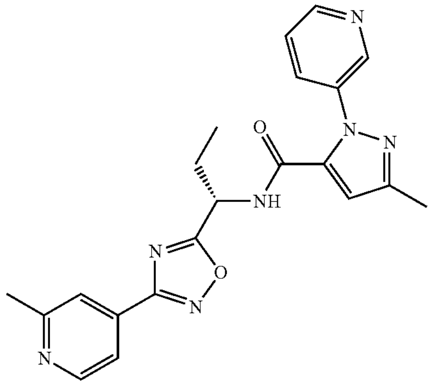

231

Synthesis of ethyl 3-methyl-1-(pyridin-3-yl)-1H-pyrazole-5-carboxylate (A-367) and Ethyl 5-methyl-1-(pyridin-3-yl)-1H-pyrazole-3-carboxylate (A-368)

To a stirred solution of ethyl 3-methyl-1H-pyrazole-5-carboxylate (2.0 g, 12.97 mmol) in DCM (25.0 mL) was added 3-pyridylboronic acid (3.18 g, 25.95 mmol) followed by pyridine (2.09 mL, 25.95 mmol), copper (II) acetate (3.53 g, 19.46 mmol) and molecular sieves. The reaction mixture was stirred for at room temperature for 36 h. The reaction mixture was filtered through sintered funnel and washed with DCM (50 mL). The organic layer was washed with water (2×30 mL), washed with brine (20 mL), dried over $Na_2SO_4$ and concentrated. The crude was purified by preparative HPLC to afford A-367 (320 mg, 1.3 mmol, 10% yield) and A-368 (150 mg, 0.65 mmol, 5% yield). Prep. HPLC method: Rt 12.0 (A-368) and 13.1 (A-367); Column: X-Bridge (150×19 mm), 5.0 μm; Mobile phase: 0.1% TFA in water/acetonitrile; Flow Rate: 15.0 mL/min. LCMS: 232.3 (M+H), Rt 1.68 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. $^1$H NMR (400 MHz, $CD_3OD$): δ 8.66-8.63 (m, 2H), 7.97-7.94 (m, 1H), 7.59 (dd, 1H), 6.96 (s, 1H), 4.25 (q, 2H), 2.36 (s, 3H), 1.26 (t, 3H). LCMS: 232.1 (M+H), Rt 1.49 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min; $^1$H NMR (400 MHz, $CD_3OD$): δ 8.81 (s, 1H), 8.69 (d, 1H), 8.09-8.07 (m, 1H), 7.66 (dd, 1H), 6.81 (s, 1H), 4.39 (q, 2H), 2.41 (s, 3H), 1.40 (t, 3H).

Synthesis of 3-methyl-1-(pyridin-3-yl)-1H-pyrazole-5-carboxylic Acid (A-369)

To a stirred solution of compound A-367 (50 mg, 0.22 mmol) in methanol (2 mL), THF (2 mL) and water (2 mL) was added lithium hydroxide monohydrate (18 mg, 0.43 mmol). The reaction mixture was stirred at room temperature for 2 h. The reaction mixture was concentrated under reduced pressure and treated with ice water (10 mL). The mixture was treated with 1N HCl (1.0 mL) and extracted with ethyl acetate (2×30 mL). The organic layer was washed with brine (20 mL), dried over $Na_2SO_4$ and concentrated to afford compound A-369 (38 mg). The crude compound was used for the next step without further purification.

Synthesis of (S)-3-methyl-N-(1-(3-(2-methylpyridin-4-yl)-1,2,4-oxadiazol-5-yl)propyl)-1-(pyridin-3-yl)-1H-pyrazole-5-carboxamide (231)

To a stirred solution of compound A-369 (38 mg, 0.19 mmol) in THF (2.0 mL) was added (1S)-1-[3-(2-methyl-4-pyridyl)-1,2,4-oxadiazol-5-yl]propan-1-amine (41 mg, 0.19 mmol) followed by $Et_3N$ (0.08 mL, 0.56 mmol) and T3P (50% in EtOAc, 0.33 mL, 0.56 mmol). The reaction mixture was stirred at room temperature for 16 h. The reaction mixture was treated with water (10 mL) and extracted with ethyl acetate (2×20 mL). The organic layer was washed with saturated sodium bicarbonate solution (20 mL), washed with brine (20 mL), dried over $Na_2SO_4$ and concentrated. The crude was purified by preparative HPLC to afford 231 (7 mg, 0.02 mmol, 9% yield) as an solid. Prep. HPLC method: Rt 9.69; Column: X-Select C-18 (150×19 mm), 5.0 μm; Mobile phase: 0.1% TFA in water/acetonitrile; Flow Rate: 15.0 mL/min. HPLC: Rt 2.10 min, 98.5%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 404.1 (M+H), Rt 1.11 min, Column: X-Bridge C8 (50×4.6 mm), 3.5 μm; Mobile Phase: A: 0.1% TFA in water:ACN (95:5), B: 0.1% TFA in ACN; Flow Rate: 1.5 mL/min. Chiral method: Rt 1.53 min, SFC column: Chiralcel OD-H; mobile phase: 60:40 (A:B), A=liquid $CO_2$, B=0.5% isopropyl amine in methanol; flow rate: 3.0 mL/min; wave length: 210 nm. $^1$H NMR (400 MHz, $CD_3OD$): δ 8.65 (d, 1H), 8.61 (d, 1H), 8.53 (dd, 1H), 7.96-7.92 (m, 2H), 7.88-7.86 (m, 1H), 7.51-7.47 (m, 1H), 6.89 (s, 1H), 5.27 (dd, 1H), 2.65 (s, 3H), 2.39 (s, 3H), 2.25-2.04 (m, 2H), 1.09 (t, 3H).

Example 184. Synthesis of 232

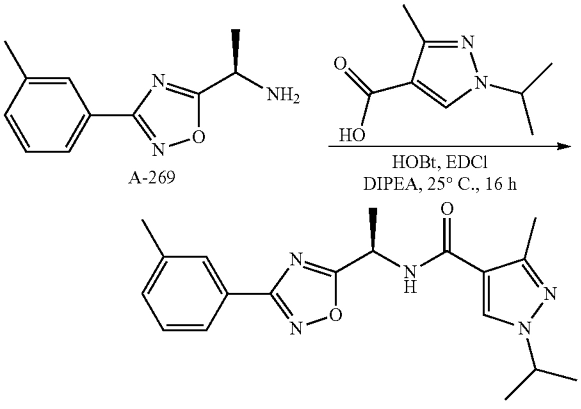

A-269

232

To a mixture of 1-isopropyl-3-methyl-pyrazole-4-carboxylic acid (100 mg, 0.59 mmol) in DCM (10 mL) was added HOBt (160.69 mg, 1.19 mmol), EDCI (227.96 mg, 1.19 mmol), DIPEA (0.33 mL, 2.38 mmol) and (1R)-1-[3-(m-tolyl)-1,2,4-oxadiazol-5-yl]ethanamine (120.84 mg, 0.59 mmol), the mixture was stirred at 25° C. for 16 hours. The reaction was quenched with $H_2O$ (10 mL), then extracted with DCM (20 mL×3). The combined organic phase was washed with brine (30 mL), dried over $Na_2SO_4$, filtered and concentrated to give the crude product. The crude product was purified from Prep-HPLC ((Boston Prime C18 150×30 mm, 5 μm) A=$H_2O$ (0.05% $NH_4OH$) and B=$CH_3CN$; 17-47% B over 8 minutes) to give the product as an oil. Analytical SFC (Column: Chiralpak AS-3 150 mm×4.6 mm I.D., 3 μm Mobile phase: A: $CO_2$ B: ethanol (0.05% DEA) Gradient: from 5% to 40% of B in 5 min and from 40% to 5% of B in 0.5 min, hold 5% of B for 1.5 min Flow rate: 2.5 mL/min Column temp.: 35° C. ABPR: 1500 psi) showed 2 peaks at 2.39 min (main peak) and 2.55 min. Then the product was purified by SFC (DAICEL Chiralpak AS-H 250 mm×30 mm, 5 μm); A=$CO_2$ and B=EtOH (0.1% $NH_3H_2O$); 38° C.; 65 mL/min; 20% B; 8.60 min run; 50 injections, Rt of peak 1=5.57 min, Rt of Peak 2=6.60 min) to give the product of 1-isopropyl-3-methyl-N-[(1R)-1-[3-(m-tolyl)-1,2,4-oxadiazol-5-yl]ethyl]pyrazole-4-carboxamide (66.75 mg, 0.19 mmol, 32% yield). (Rt=2.39 min in analytical SFC) as a an oil. $^1H$ NMR (400 MHz, $CD_3CN$) 400 MHz δ=8.00 (s, 1H), 7.89 (s, 1H), 7.86 (d, 1H), 7.48-7.38 (m, 2H), 7.06 (br d, 1H), 5.50-5.40 (m, 1H), 4.46 (quin, 1H), 2.44 (s, 3H), 2.39 (s, 3H), 1.69 (d, 3H), 1.48 (d, 6H). LCMS $R_t$=1.13 min in in 2.0 min chromatography, 10-80AB, MS ESI calcd. for $C_{19}H_{24}N_5O_2$ $[M+H]^+$ 354.2, found 354.0.

Example 185. Synthesis of 233

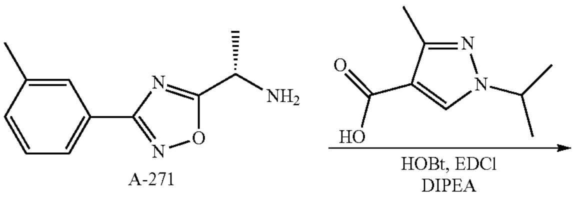

A-271

-continued

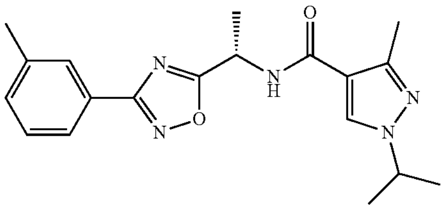

233

A mixture of 1-isopropyl-3-methyl-pyrazole-4-carboxylic acid (100 mg, 0.59 mmol), HOBt (160.69 mg, 1.19 mmol), EDCI (227.96 mg, 1.19 mmol), DIPEA (0.33 mL, 2.38 mmol) and (1S)-1-[3-(m-tolyl)-1,2,4-oxadiazol-5-yl] ethanamine (120.84 mg, 0.59 mmol) in DCM (10 mL), the mixture was stirred at 25° C. for 16 hours. The mixture was concentrated to give the residue. The residue was diluted with $H_2O$ (20 mL), and the mixture was extracted with EtOAc (20 mL×2). The combined organic phase was washed with water (20 mL) and brine (20 mL), dried over $Na_2SO_4$, filtered and concentrated to give the crude product. The crude product was purified by prep-HPLC (Boston Prime (150 mm×30 mm, 5 μm) A=$H_2O$ (0.05% $NH_4OH$) and B=$CH_3CN$; 40-60% B over 9 minutes) to give the crude product. Analytical SFC (Column: Chiralpak AS-3 150 mm×4.6 mm I.D., 3 μm, Mobile phase: A: $CO_2$ B: ethanol (0.05% DEA), Gradient: from 5% to 40% of B in 5 min and from 40% to 5% of B in 0.5 min, hold 5% of B for 1.5 min, Flow rate: 2.5 mL/min, Column temp.: 35° C., ABPR: 1500 psi.) showed two peaks at 2.37 min and 2.55 min (main peak). The product was purified by SFC (DAICEL CHIRALPAK AS-H (250 mm×30 mm, 5 μm); A=$CO_2$ and B=EtOH (0.1% $NH_3H_2O$); 38° C.; 60 mL/min; 20% B; 8 min run; 10 injections, Rt of peak 1=4.8 min, Rt of Peak 2=6 min) to give the product (50.77 mg, 0.14 mmol, 24% yield) (Rt=2.55 min in analytical SFC) as a solid. $^1H$ NMR (400 MHz, $CD_3CN$) $\delta_H$=7.96 (s, 1H), 7.86 (s, 1H), 7.83 (br d, 1H), 7.44-7.36 (m, 2H), 7.04 (br d, 1H), 5.46-5.37 (m, 1H), 4.47-4.36 (m, 1H), 2.41 (s, 3H), 2.36 (s, 3H), 1.66 (d, 3H), 1.44 (d, 6H). LCMS Rt=1.20 min in 2.0 min chromatography, 10-80AB, MS ESI calcd. $C_{19}H_{24}N_5O_2$ $[M+H]^+$ 354.2, found 354.1.

Example 186. Synthesis of 296 & 234

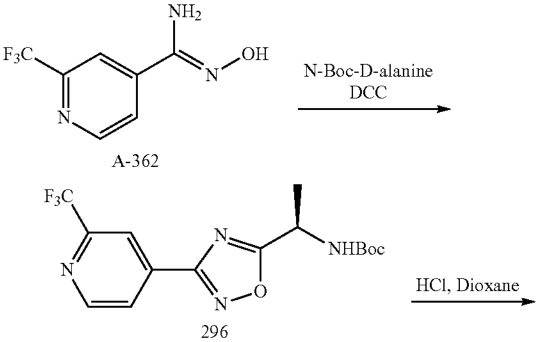

A-362

296

-continued

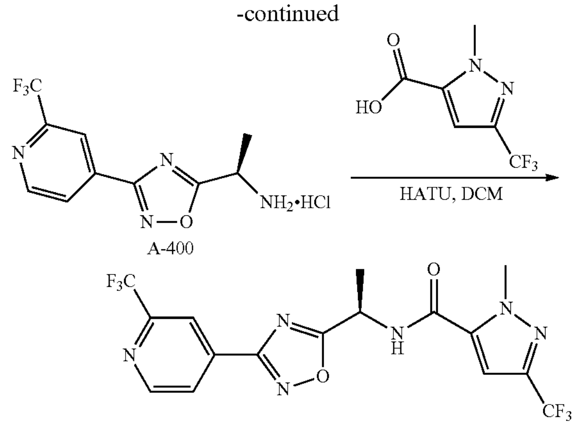

A-400

234

Synthesis of tert-butyl (R)-(1-(3-(2-(trifluoromethyl) pyridin-4-yl)-1,2,4-oxadiazol-5-yl)ethyl)carbamate (296)

To a stirred solution of A-362 (1.5 g, 7.31 mmol) in 1,4-dioxane (20 mL) was added N-Boc-D-alanine (1.52 g, 8.04 mmol), followed by DCC (1.66 g, 8.04 mmol). The reaction was heated at 100° C. for 16 h. The mixture was concentrated to dryness and was diluted with ethyl acetate (100 mL). The organic layer was washed with water (2×30 mL) and then with saturated brine solution (1×50 mL). The organic layer was dried over magnesium sulphate and concentrated. The crude compound was purified by flash column chromatography eluting 50% EtOAc in hexane. The desired fractions were concentrated to dryness under reduced pressure to afford 1.5 g of desired compound that was used as it is in next step. 300 mg of the compound was purified by prep HPLC to afford 296, tert-butyl N-[(1R)-1-[3-[2-(trifluoromethyl)-4-pyridyl]-1,2,4-oxadiazol-5-yl] ethyl]carbamate as a solid (153 mg). HPLC: Rt 7.71 min, 99.80%; Column: HPLC-X-Bridge C18 (4.6×150) mm, 5 μm; Mobile phase: A: 0.1% $NH_3$ in water B: ACN; Flow Rate: 1.2 mL/min. LCMS: 359.15 (M+H), Rt 2.03 min; Column: X-select CSH C18 (3×50) mm, 2.5 μm. Chiral method: Rt 3.90 min; SFC column: DIACEL CHIRALPAK-IG (150×4.6 mm, 5 μm), —Mobile Phase: A) $CO_2$ B) MTBE:IPA (60:40 Gradient: 10-40% B in 5 min, hold 40% B till 9 min, 40-10% B at 10 min, hold 10% B till 12 Min., Wavelength: 270 nm; Flow: 3 mL/min. $^1$H NMR (400 MHz, DMSO): $\delta_H$=9.02 (d, 1H), 8.3-8.24 (m, 2H), 7.84 (d, 1H), 5.05-5.00 (m, 1H), 1.53 (d, 3H), 1.40 (s, 9H).

Synthesis of (1R)-1-[3-[2-(trifluoromethyl)-4-pyridyl]-1,2,4-oxadiazol-5-yl]ethanamine Hydrochloride (A-400)

To a stirred solution of compound 296 (1.2 g, 3.35 mmol) in 1,4-dioxane (3 mL) was added 4 M HCl in dioxane (15 mL) at 0° C. The reaction was slowly brought to room temperature and stirred for 6 h. After completion, the reaction mass was concentrated to dryness to afford compound A-400 (0.80 g, 2.69 mmol, 80% yield) as a solid. The compound A-400 was used for the next step without further purification.

Synthesis of 2-methyl-5-(trifluoromethyl)-N-[(1R)-1-[3-[2-(trifluoromethyl)-4-pyridyl]-1,2,4-oxadiazol-5-yl]ethyl]pyrazole-3-carboxamide (234)

To a stirred solution of 2-methyl-5-(trifluoromethyl)pyrazole-3-carboxylic acid (150 mg, 0.77 mmol) in DCM (10 mL) was added compound A-400 (273.24 mg, 0.93 mmol). To this reaction was added HATU (323.21 mg, 0.85 mmol), and DIPEA (0.27 mL, 1.55 mmol) and the mixture was stirred at room temperature for 6 h. The reaction was treated with water (10 mL) and extracted with DCM (10 mL) The organic layer was washed with brine solution and dried over anhydrous $Na_2SO_4$ and concentrated. The crude compound was purified by flash column chromatography. eluting 50% EtOAc in hexane. The desired fractions were concentrated to dryness under reduced pressure to afford 234 as a solid (53 mg, 0.12 mmol, 15% yield). HPLC: Rt 9.16 min, 99.8%; Column: X-select CSH C18 (4.6*150) mm, 5 μm; Mobile phase: A: 0.1% Formic acid in water:ACN (95:05), B: ACN; Flow Rate: 1.0 mL/min. LCMS: 435 (M+H), Rt 2.15 min; Column: X-select CSH C18 (3×50) mm, 2.5 μm; Chiral method: Rt 3.61 min; SFC column: DIACEL CHIRALPAK-IG (150×4.6 mm, 5 μm), —Mobile Phase: A) $CO_2$ B) MTBE:IPA (60:40) Gradient: 10-40% B in 5 min, hold 40% B till 9 min, 40-10% B at 10 min, hold 10% B till 12 Min., Wavelength: 270 nm; Flow: 3 mL/min. $^1$H NMR (400 MHz, DMSO): $\delta_H$=9.49 (d, 1H), 9.01 (d, 1H), 8.32-8.24 (m, 2H), 7.45 (s, 1H), 5.52-5.48 (m, 1H), 4.12 (s, 3H), 1.69 (d, 3H).

Example 187. Synthesis of 235

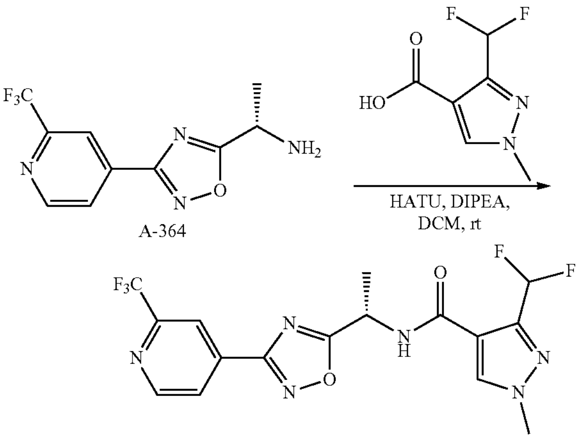

A-364

235

To a stirred solution 3-(difluoromethyl)-1-methyl-1H-pyrazole-4-carboxylic acid (90.73 mg, 0.52 mmol) in DCM (5 mL) was added DIPEA (0.27 mL, 1.55 mmol) and HATU (293.83 mg, 0.77 mmol) at 0° C. To the resulting reaction mixture was added A-364 (166.98 mg, 0.57 mmol) at 0° C. and stirred at RT for 12 h. The reaction was diluted with water and extracted with DCM (3×10 mL). The combined organic layer was dried over sodium sulphate and concentrated to obtain the crude compound. The crude compound was purified by prep HPLC to afford 235 (82 mg, 0.19 mmol, 38% yield) as a solid. HPLC: Rt 8.13 min, 99.8%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 417.20 (M+H), Rt 1.85 min; Column: X-select CSH C18 (3×50) mm, 2.5 μm. $^1$H NMR (400 MHz, DMSO): $\delta_H$=9.07 (d, 1H), 9.01 (d, 1H), 8.38 (s, 1H), 8.29-8.26 (m, 2H), 7.26 (t, 1H), 5.54-5.45 (m, 1H), 3.94 (s, 3H), 1.65 (d, 3H). Chiral HPLC: Rt 3.27 min, 100%; SFC column: DIACEL CHIRALPAK-IG (250×4.6 mm, 5 μm), —Mobile Phase: A) $CO_2$ B) MeOH+0.1% $NH_3$, Gradient: 20-40% B in 5 min, hold 40% B till 9 min, 40-20% B in 10 min, hold 20% B till 12 min. Wavelength: 270 nm, Flow: 3 mL/min.

Example 188. Synthesis of 236

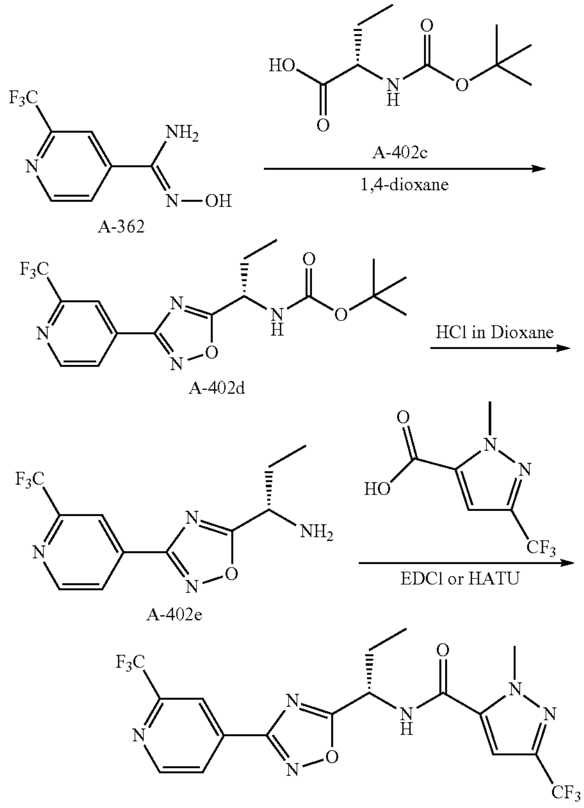

236

Synthesis of tert-butyl (S)-(1-(3-(2-(trifluoromethyl) pyridin-4-yl)-1,2,4-oxadiazol-5-yl)propyl)carbamate (A-402d)

To a stirred solution of A-362 (0.6 g, 2.92 mmol) in 1,4-dioxane (15 mL) was added A-402c (0.59 g, 2.92 mmol), DCC (0.6 g, 2.92) mmol and stirred at 100° C. for 16 h. The reaction mixture was evaporated under reduced pressure and the residue was diluted with EtOAc (50 ml). The organic material was washed with (2×15 mL) water and (1×15 mL) saturated brine solution, dried over $MgSO_4$ and evaporated to afford the crude product. The product was purified by flash column chromatography eluting 50% EtOAc in hexane to afford desired A-402d (0.60 g, 1.29 mmol, 44% yield) as a solid.

Synthesis of (S)-1-(3-(2-(trifluoromethyl)pyridin-4-yl)-1,2,4-oxadiazol-5-yl)propan-1-amine (A-402e)

To a stirred solution of A-402d (0.6 g, 1.61 mmol) in 1, 4-Dioxane (2 mL) was added 4 M HCl in Dioxane (10 mL, 1.61 mmol) at 0° C. and stirred at RT for 6 h. After completion, the reaction mixture was evaporated to dryness to afford A-402e (0.48 g, 1.49 mmol, 92% yield) as a solid.

Synthesis of (S)-1-methyl-3-(trifluoromethyl)-N-(1-(3-(2-(trifluoromethyl)pyridin-4-yl)-1,2,4-oxadiazol-5-yl)propyl)-1H-pyrazole-5-carboxamide (236)

To a stirred solution of A-402e (0.32 g, 1.03 mmol) and 1-methyl-3-(trifluoromethyl)-1H-pyrazole-5-carboxylic acid (0.2 g, 1.03 mmol) in DCM (15 ml) was added HATU (0.47 g, 1.24 mmol) followed by DIPEA (0.18 mL, 1.03 mmol) and stirred at RT for 6 h. The reaction mixture was quenched with water (10 mL) and diluted with DCM (10 mL). The organic layer was separated, washed with brine solution (1×10 mL) and dried over $MgSO_4$ and evaporated to afford the crude product. The crude product was purified by flash column chromatography using 50% EtOAc in hexane as an eluent to afford 236 (58 mg, 0.12 mmol, 12% yield) as a solid. HPLC: Rt 7.95 min, 99.7%; Column: X-Bridge C18 (4.6×150) mm, 5 μm; Mobile phase: A: 0.1% $NH_3$ in water B: ACN; Flow Rate: 1.2 mL/min. LCMS: 449.04 (M+H), Rt 2.21 min; Column: X-select CSH C18 (3×50) mm, 2.5 μm. $^1H$ NMR (400 MHz, DMSO-$d_6$) $\delta_H$=9.43 (d, 1H), 9.02 (d, 1H), 8.28-8.27 (m, 2H), 7.49 (s, 1H), 5.38-5.28 (m, 1H), 4.12 (s, 3H), 2.21-2.00 (m, 2H), 1.03 (t, 3H).

Example 189. Synthesis of 237

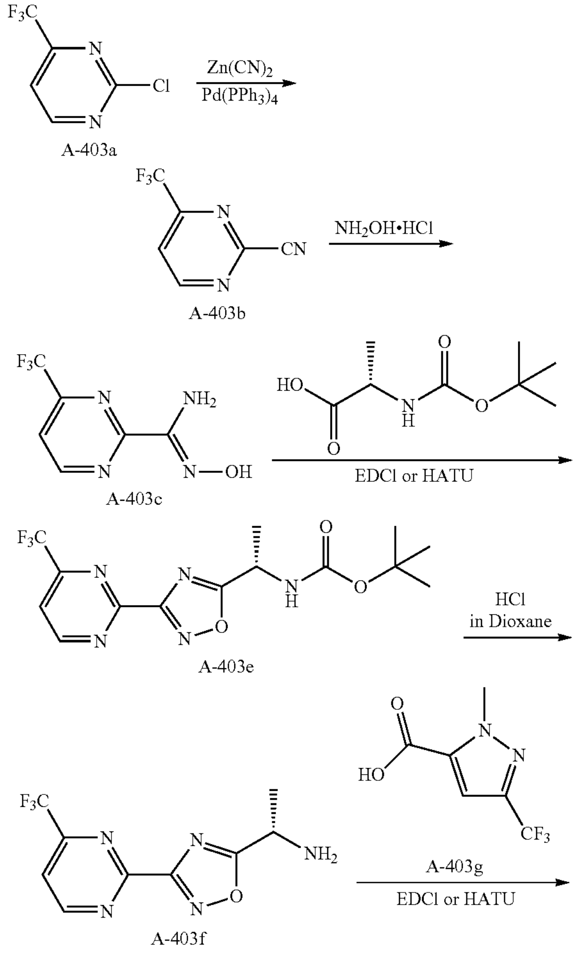

-continued

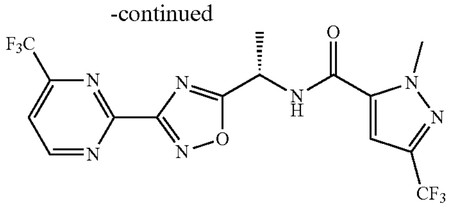

237

Synthesis of 4-(trifluoromethyl)pyrimidine-2-carbonitrile (A-403b)

To a stirred solution of A-403a (2 g, 10.96 mmol)) and Zinc cyanide (769.19 mg, 6.57 mmol) in DMF (20 mL) was added $Pd(PPh_3)_4$ (1.3 g, 1.1 mmol) at RT and stirred at 110° C. for 16 h. The reaction mixture was quenched using water (50 mL) and diluted with EtOAc (100 mL×2). The organic layer was separated, dried over $Na_2SO_4$ and evaporated to afford crude product. The crude product was purified by column chromatography using 100-200 silica and 5-10% EtOAc/Hexane as an eluent to afford A-403b (1.8 g, 10.39 mmol, 94% yield).

Synthesis of (Z)—N'-hydroxy-4-(trifluoromethyl) pyrimidine-2-carboximidamide (A-403c)

To a stirred solution of A-403b (1 g, 5.78 mmol) in ethanol (20 mL) was added hydroxylamine hydrochloride (602.17 mg, 8.67 mmol) and TEA (1.61 mL, 11.55 mmol) at RT and stirred at 70° C. for 16 h. The reaction was quenched with water (100 mL) and diluted with EtOAc (50 mL×2). The combined organic layer was separated, dried with $Na_2SO_4$ and evaporated to afford the crude product. The crude product was purified by column chromatography using 100-200 silica and 10-20% EtOAc/Hexane as an eluent to afford A-403c (1 g, 4.75 mmol, 82% yield).

Synthesis of tert-butyl (S)-(1-(3-(4-(trifluoromethyl) pyrimidin-2-yl)-1,2,4-oxadiazol-5-yl)ethyl)carbamate (A-403e)

To a stirred solution of A-403c (1 g, 4.85 mmol) and (tert-butoxycarbonyl)-L-alanine (917.92 mg, 4.85 mmol) in 1,4-dioxane (20 mL) was added DCC (1089.31 mg, 5.29 mmol) and stirred at 75° C. for 16 h. The reaction mixture was quenched with water (100 mL) and diluted with EtOAc (50 mL×2). The combined organic layer was separated, dried over $Na_2SO_4$ and evaporated to afford the crude product. The crude product was purified by column chromatography using 100-200 silica and 20-30% EtOAc/ Hexane as eluent to afford A403-e (1 g, 2.42 mmol, 49% yield).

Synthesis of (S)-1-(3-(4-(trifluoromethyl)pyrimidin-2-yl)-1,2,4-oxadiazol-5-yl)ethan-1-amine (A403-1)

To a stirred solution of A403-e (1 g, 2.78 mmol) in 1,4-dioxane (10 mL) was added 4 M hydrochloric acid in dioxane (10 mL, 2.78 mmol) at 0° C. and stirred for 2 h. The reaction mixture was evaporated to afford the crude product. The crude product was then washed with diethyl ether to afford A-403f (300 mg, 0.81 mmol, 29% yield) as a solid.

(S)-1-methyl-3-(trifluoromethyl)-N-(1-(3-(4-(trifluoromethyl)pyrimidin-2-yl)-1,2,4-oxadiazol-5-yl) ethyl)-1H-pyrazole-5-carboxamide (237)

To a stirred solution of A-403f (0.15 g, 0.51 mmol) and A-403 g (118.18 mg, 0.61 mmol) in DCM (10 mL) were added HATU (289.37 mg, 0.76 mmol) followed by DIPEA (0.18 mL, 1.01 mmol) at RT and stirred at RT for 2 h. The reaction mixture was diluted with water (100 mL) and DCM (100 mL×2). The organic layer was separated, dried over $Na_2SO_4$ and evaporated to afford the crude product. The crude product was purified by column chromatography using 100-200 silica and 30-80% 50% EtOAc in hexane as an eluent to afford 237 (152.86 mg, 0.35 mmol, 69% yield) as a solid. HPLC: Rt 8.36 min, 99.7%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 435.95 (M+H), Rt 1.99 min; Column: X-select CSH C18 (3×50) mm, 2.5 μm. $^1H$ NMR (400 MHz, DMSO-$d_6$) $\delta_H$=9.47 (d, 1H), 9.38 (d, 1H), 8.23 (d, 1H), 7.42 (s, 1H), 5.52-5.44 (m, 1H), 4.10 (s, 3H), 1.67 (d, 3H).

Example 190. Synthesis of 238

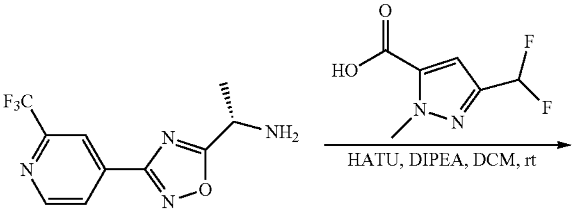

A-364

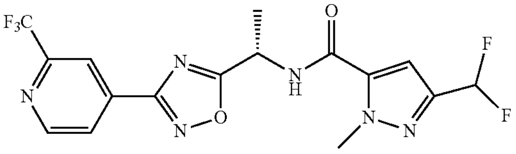

238

To a stirred solution of 3-(difluoromethyl)-1-methyl-1H-pyrazole-5-carboxylic acid (59.77 mg, 0.34 mmol) in DCM (4 mL) was added DIPEA (0.15 mL, 0.85 mmol) and HATU (193.56 mg, 0.51 mmol) at 0° C. To the resulting reaction mixture A-364 (100 mg, 0.34 mmol) was added at 0° C. and was stirred at RT for 3 h. After completion, the reaction was diluted with water and extracted with DCM (3×10 mL). Combined organic layer was dried over sodium sulphate and concentrated to obtain the crude product. The crude product was purified by prep HPLC to afford 238 (55 mg, 0.13 mmol, 39% yield) as a solid. HPLC: Rt 8.68 min, 99.9%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 417.15 (M+H), Rt 2.11 min, Column: X-select CSH C18 (3×50) mm, 2.5 μm. $^1H$ NMR (400 MHz, DMSO): $\delta_H$=9.43 (d, 1H), 9.02 (d, 1H), 8.29 (s, 2H), 7.27 (s, 1H), 7.05 (t, 1H), 5.51-5.47 (m, 1H), 4.08 (s, 3H), 1.69 (d, 3H).

Example 191. Synthesis of 239

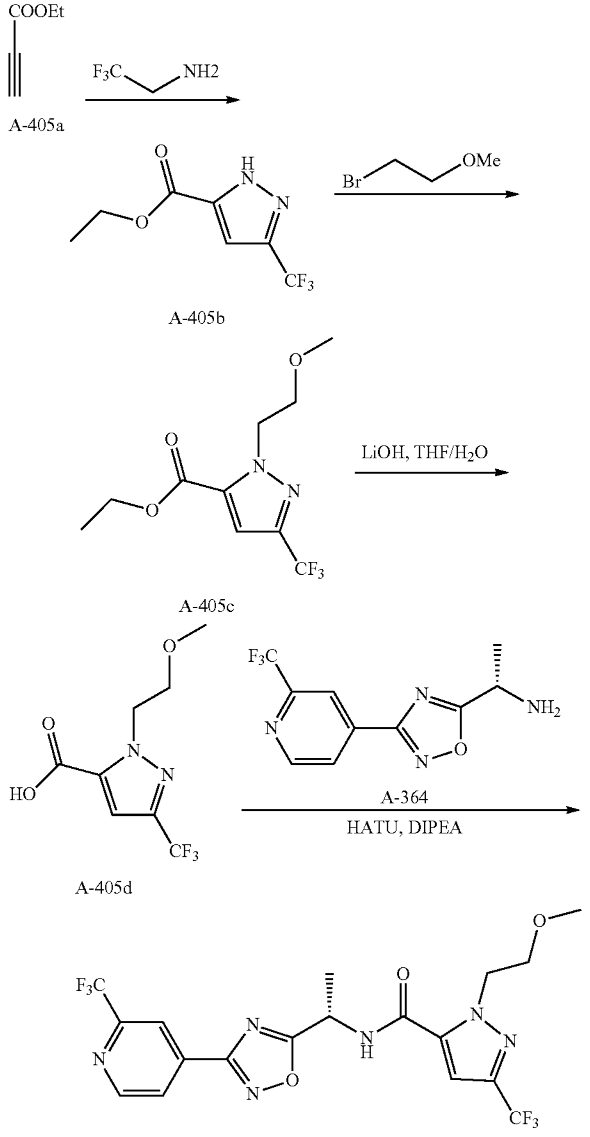

239

Synthesis of ethyl 3-(trifluoromethyl)-1H-pyrazole-5-carboxylate (A-405b)

To a stirred solution of sodium nitrite (3.52 g, 50.97 mmol) in toluene: water (80:40 mL) was added 2,2,2-trifluoroethanamine hydrochloride (6.91 g, 50.97 mmol) at 0° C. and stirred at 0° C. for 30 min. The resulting reaction mixture was charged with A-405a (5 g, 50.97 mmol) and stirred at 100° C. for 6 h. The reaction mixture was quenched with distilled water (50 mL) and extracted with EtOAc (3x50 mL). The combined organic phase was washed with brine solution (150 mL), dried over anhydrous $Na_2SO_4$, filtered and evaporated under reduced pressure to afford the crude product. The crude product was then purified by column chromatography (100-200 mesh silica; 5-8% EtOAc in hexane as an eluent) to afford A-405b (6.1 g, 29.19 mmol, 57% yield) as a solid.

Synthesis of ethyl 2-(2-methoxyethyl)-5-(trifluoromethyl)pyrazole-3-carboxylate (A-405c)

To a stirred solution of A-405b (1 g, 4.8 mmol) in DMF (10 mL) were added potassium carbonate (1.33 g, 9.61 mmol) followed by 1-bromo-2-methoxy-ethane (0.8 g, 5.77 mmol) at 0° C. and stirred at RT for 6 h. The reaction mixture was diluted with EtOAc (100 mL) and washed with cold water (5x25 mL), brine solution (50 mL). The organic layer was separated, dried over anhydrous sodium sulfate, filtered and evaporated under reduced pressure to afford the crude product. The crude product was purified by column chromatography (100-200 mesh silica, 10-12% EtOAc in hexane as an eluent) to afford A-405c (600 mg, 2.18 mmol, 45% yield) as an oil.

Synthesis of 1-(2-methoxyethyl)-3-(trifluoromethyl)-1H-pyrazole-5-carboxylic Acid (A-405d)

To a stirred solution of A-405c (250 mg, 0.94 mmol) in THF (10 mL) was added a solution of Lithium hydroxide (44.98 mg, 1.88 mmol) in water (3 mL) at 0° C. and stirred at RT for 2 h. The reaction mixture was evaporated to afford the crude product. The crude product was diluted with water (5 mL), acidified with 1 N HCl solution to pH 4 and extracted with EtOAc (3x15 mL). The combined organic phase was dried and evaporated under reduced pressure to afford A-405d (200 mg, 0.83 mmol, 89% yield) as a solid.

Synthesis of (S)-1-(2-methoxyethyl)-3-(trifluoromethyl)-N-(1-(3-(2-(trifluoromethyl)pyridin-4-yl)-1,2,4-oxadiazol-5-yl)ethyl)-1H-pyrazole-5-carboxamide (239)

To a stirred solution of A-405d (100 mg, 0.42 mmol) in DCM (10 mL) was added A-364 (148.47 mg, 0.50 mmol), HATU (239.48 mg, 0.63 mmol) and DIPEA (0.15 mL, 0.84 mmol) at 0° C. and stirred at RT for 3 h. The reaction mixture was diluted with DCM (10 mL) and washed with water (3x15 mL) followed by saturated sodium bicarbonate solution (3x15 mL). The organic layer was dried over anhydrous sodium sulphate, filtered and evaporated to afford the crude product. The crude compound was purified by flash column chromatography (100-200 mesh silica, 2-4% EtOAc in hexane as an eluent) to afford 239 (35 mg, 0.07 mmol, 17% yield,) as a solid. HPLC: Rt 9.67 min, 99.9%; Column: X-select CSH C18 (4.6*150) mm, 5 µm; Mobile phase: 10 mM ammonium bicarbonate in water, B: ACN; Flow Rate: 1.0 mL/min. LCMS: 479.04 (M+H), Rt 2.10 min, Column: X-select CSH C18 (3.0*50) mm, 2.5 µm. $^1H$ NMR (400 MHz, DMSO-$d_6$) $\delta_H$=9.55 (d, 1H), 9.05-8.99 (m, 1H), 8.29 (d, 2H), 7.40 (s, 1H), 5.52-5.46 (m, 1H), 4.81-4.64 (m, 2H), 3.68-3.62 (m, 2H), 3.15 (s, 3H), 1.69 (d, 3H). Chiral method: Rt 3.12 min, 100%; SFC column: DIACEL CHIRALPAK-IG (250x4.6 mm, 5 µm), —Mobile Phase: A) $CO_2$ B) MeOH+0.1% $NH_3$, Gradient: 10-40% B in 5 min, hold 40% B till 9 min, 40-10% B at 10 min, hold 10% B till 12 min. Wavelength: 270 nm, Flow: 3 mL/min.

Example 192. Synthesis of 240

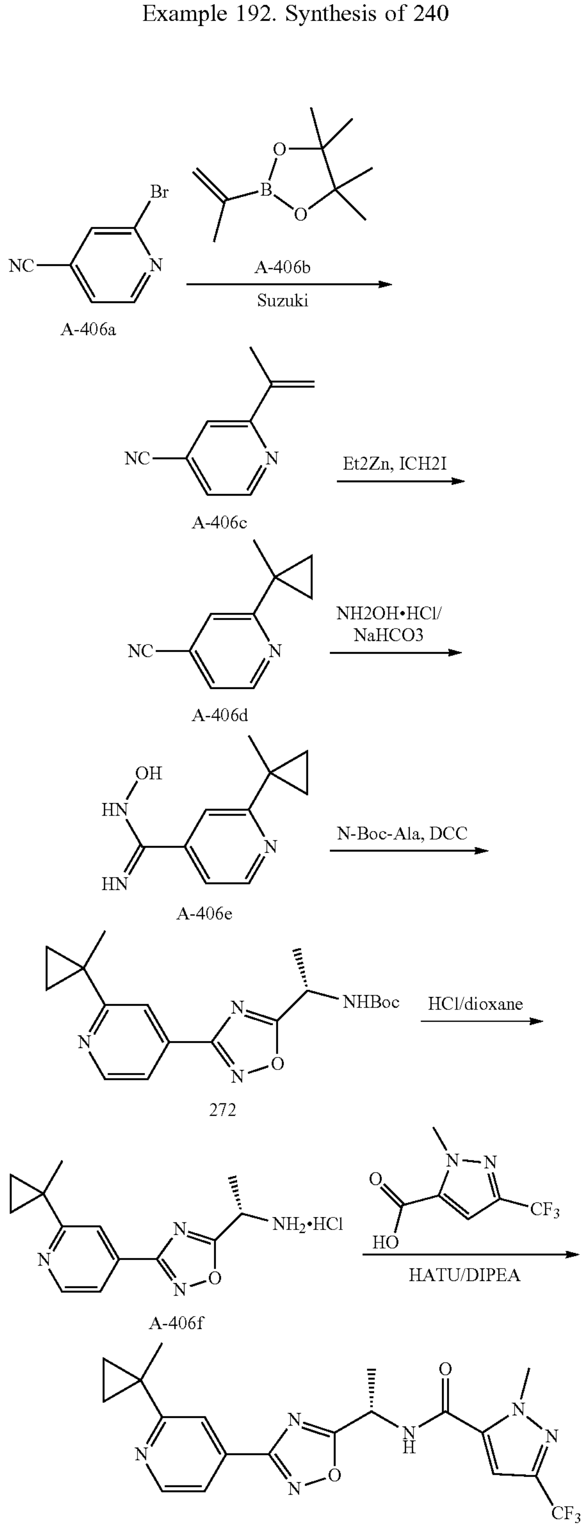

A-406a
A-406c
A-406d
A-406e
272
A-406f
240

Synthesis of 2-(prop-1-en-2-yl)isonicotinonitrile (A-406c)

To a stirred solution of A-406a (5 g, 27.32 mmol) in 1,4 dioxane (50 mL) and water (50 mL) was added A-406b (6.89 g, 40.98 mmol) and sodium carbonate (8.69 g, 81.96 mmol) and degassed with argon for 30 minute. The reaction was concentrated and the residue was diluted with water (30 mL) and EtOAc (100 mL) and the organics were washed with saturated brine solution (1×30 mL). The organic layer was separated, dried over $MgSO_4$ and concentrated to dryness. The crude was then purified by flash column chromatography eluting 50% EtOAc in hexane. The desired fractions were concentrated to dryness to afford desired product A-406c (3 g, 20.241 mmol, 74% yield) as a solid product.

Synthesis of 2-(1-methylcyclopropyl)isonicotinonitrile (A-406d)

A stirred solution of Diethyl zinc solution 1.0 M in hexanes (41.61 mL, 41.62 mmol) was added to DCM (100 mL) at 0° C. followed by Diiodomethane (3.36 mL, 41.62 mmol) drop wise and the reaction mixture was stirred at the same temperature for 30 min. After that A-406c (1.5 g, 10.4 mmol) in DCM (20 mL) was added to the reaction mixture at 0° C. drop wise and stirred at RT for 1.5 h. The reaction was quenched with sat. $NH_4Cl$ at 0° C. and diluted with DCM (100 mL). The organic layer was separated and washed with 1×30 ml saturated brine solution, dried over $MgSO_4$ and concentrated to obtain the crude product. The crude compound was purified by flash column chromatography eluting 20% EtOAc in hexane to afford desired product A-406d (0.40 g, 1.22 mmol, 11% yield) as a solid.

Synthesis of N-hydroxy-2-(1-methylcyclopropyl) isonicotinimidamide (A-406e)

To a stirred solution of A-406d (0.4 g, 2.53 mmol) in ethanol (20 mL) was added Hydroxyl amine hydrochloride (0.31 g, 3.79 mmol) and triethyl amine (0.51 g, 5.06 mmol) and heated to 80° C. for 12 hours. The reaction mixture was concentrated to dryness and the residue was taken up in EtOAc (60 mL). The organic layer was washed with water (2×30 mL) then saturated brine solution (1×30 mL). The organic layer was then separated, dried over $MgSO_4$ and concentrated to afford the desired product A-406e (0.48 g, 2.04 mmol, 80% yield) as an oil.

Synthesis of tert-butyl (S)-(1-(3-(2-(1-methylcyclopropyl)pyridin-4-yl)-1,2,4-oxadiazol-5-yl)ethyl)carbamate (272)

To a stirred solution of A-406e (0.48 g, 2.51 mmol) in 1,4-dioxane (15 mL) was added N-Boc-L-alanine (0.52 g, 2.76 mmol) and DCC (0.57 g, 2.76 mmol) and reaction mixture was stirred at 100° C. for 16 hour. After completion, the reaction was concentrated under reduced pressure and the residue was taken up in EtOAc (30 mL). The organics was washed with water (2×10 mL) and saturated brine solution (1×10 mL). The organic layer was then separated and dried over $MgSO_4$ before concentration to obtain crude. The crude compound was purified by flash column chromatography eluting 30% EtOAc in hexane to afford the desired compound (0.80 g, 2.28 mmol, 91% yield). From this material was purified 200 mg by prep-HPLC to afford (35 mg) of 272. HPLC: Rt 8.00 min, 98.4%; Column: X-Bridge C18 (4.6×150) mm, 5 μm; Mobile phase: A: 0.1 $NH_3$ in water, B: Acetonitrile; Flow Rate: 1.2 mL/min. LCMS: 345.15 (M+H), Rt 2.27 min; Column: X-select CSH C18 (3×50) mm, 2.5 μm. $^1H$ NMR (400 MHz, DMSO-$d_6$) $\delta_H$=8.65 (d, 1H), 7.84-7.75 (m, 2H), 7.67 (d, 1H), 5.04-4.96 (m, 1H), 1.55-1.48 (m, 6H), 1.42-1.34 (m, 9H), 1.25-1.20 (m, 2H), 0.92-0.85 (m, 2H). Chiral method: Rt 4.91 min, 99.2%; SFC column: DIACEL CHIRALPAK-IG (250×4.6 mm, 5 μm), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 290 nm, Flow: 3 mL/min.

Synthesis of (S)-1-(3-(2-(1-methylcyclopropyl)pyridin-4-yl)-1,2,4-oxadiazol-5-yl)ethan-1-amine hydrochloride (A-406f)

To a stirred solution of 272 (0.6 g, 1.74 mmol) in 1,4-dioxane (2 mL) was added 4 M hydrochloric acid in dioxane (6 mL) at 0° C. and stirred for 6 h. After completion, the reaction was concentrated to afford the desired product A-406f (0.40 g, 1.32 mmol, 76% yield).

Synthesis of (S)-1-methyl-N-(1-(3-(2-(1-methylcyclopropyl)pyridin-4-yl)-1,2,4-oxadiazol-5-yl)ethyl)-3-(trifluoromethyl)-1H-pyrazole-5-carboxamide (240)

To a stirred solution of A-406f (0.22 g, 0.77 mmol) and 1-methyl-3-(trifluoromethyl)-1H-pyrazole-5-carboxylic acid (0.15 g, 0.77 mmol) in DCM (15 mL) was added HATU (0.32 g, 0.85 mmol) followed by DIPEA (0.27 mL, 1.55 mmol) at 0° C. and stirred at RT for 6 h. After completion, the reaction mixture was diluted with water (20 mL) and DCM (30 mL). The organic layer was separated, washed with (1×20 mL) saturated brine solution and dried over $MgSO_4$ and concentrated to obtain the crude product. The crude material was purified by flash column chromatography eluting 30% EtOAc in hexane and concentrated to afford compound 240 (110 mg, 0.25 mmol, 33% yield) as a solid. HPLC: Rt 9.20 min, 98.4%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 421.20 (M+H), Rt 2.13 min; Column: X-select CSH (3×50) mm, 2.5 μm. $^1H$ NMR (400 MHz, DMSO-$d_6$) $\delta_H$=9.46 (d, 1H), 8.65 (d, 1H), 7.82 (s, 1H), 7.67 (d, 1H), 7.44 (s, 1H), 5.52-5.44 (m, 1H), 4.12 (s, 3H), 1.68 (d, 3H), 1.52 (s, 3H), 1.22 (d, 2H), 0.92-0.86 (m, 2H). Chiral method: Rt 3.71 min, 100%; SFC column: DIACEL CHIRALPAK-IG (250×4.6 mm, 5 μm), —Mobile Phase: A) $CO_2$ B) MeOH+0.1% $NH_3$, Gradient: 10-25% B in 5 min, hold 25% B till 9 min, 25-10% B in 10 min, hold 10% B till 12 min. Wavelength: 290 nm, Flow: 3 mL/min.

Example 193. Synthesis of 241

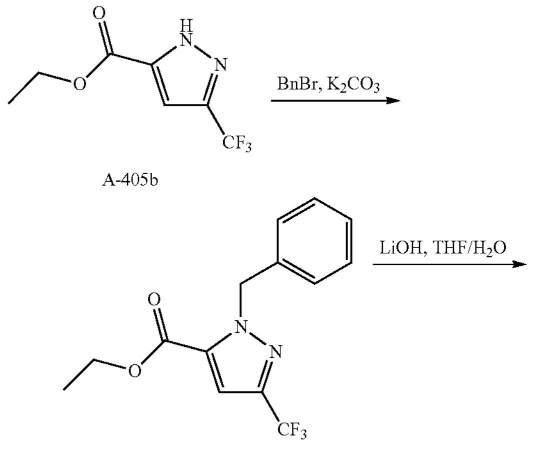

A-405b

A-406g

-continued

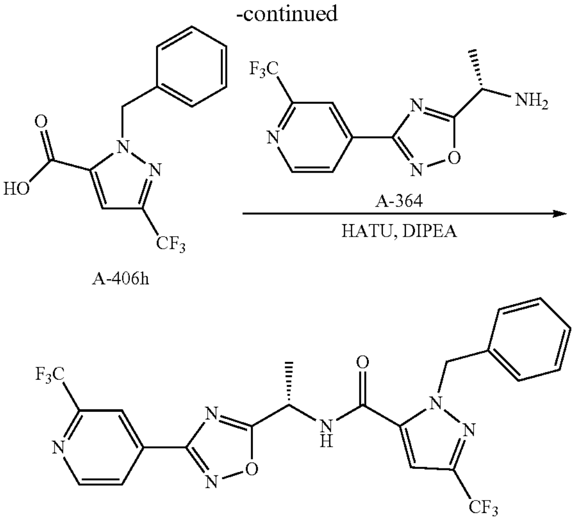

A-406h

A-364

241

Synthesis of ethyl 1-benzyl-3-(trifluoromethyl)-1H-pyrazole-5-carboxylate (A-406 g)

To a stirred solution of A-405b (0.5 g, 2.4 mmol) in DMF (10 mL) was added potassium carbonate (663.88 mg, 4.8 mmol) followed by addition of benzyl bromide (0.34 mL, 2.88 mmol) at 0° C. and stirred at RT for 6 h under nitrogen. The reaction mixture was diluted with EtOAc (100 mL) and washed with cold water (20 mL) then brine solution. The organic layer was dried over anhydrous sodium sulfate, filtered and evaporated under reduced pressure to afford A-406 g (500 mg, 1.55 mmol, 64% yield) as an oil.

Synthesis of 1-benzyl-3-(trifluoromethyl)-1H-pyrazole-5-carboxylic Acid (A-406h)

To a stirred solution of A-406 g (500 mg, 1.68 mmol) in THF (5 mL) was added a solution of Lithium hydroxide.$H_2O$ (140.7 mg, 3.35 mmol) in water (5 mL) at 0° C. and stirred at RT for 2 h. The reaction mixture was evaporated to afford the crude product. The crude product was acidified with 2 N HCl (5 mL) leading to precipitation. The precipitate formed was filtered and dried under reduced pressure to afford A-406h (300 mg, 1.08 mmol, 64% yield) as a solid.

Synthesis of (S)-1-benzyl-3-(trifluoromethyl)-N-(1-(3-(2-(trifluoromethyl)pyridin-4-yl)-1,2,4-oxadiazol-5-yl)ethyl)-1H-pyrazole-5-carboxamide (241)

To a stirred solution of A-406h (200 mg, 0.74 mmol) in DCM (10 mL) was added A-364 (229.3 mg, 0.890 mmol), HATU (337.7 mg, 0.89 mmol) and DIPEA (0.26 mL, 1.48 mmol) under nitrogen and stirred at RT for 3 h. The reaction mixture was diluted with DCM (25 mL), washed with water (20 mL) and brine. The aqueous layer was again extracted with DCM (25 mL) and washed with brine. The combined organic layer was dried over anhydrous sodium sulphate, filtered and evaporated to afford the crude product. The crude compound was purified by flash column chromatography using 100-200 mesh silica and 15% EtOAc in hexane as an eluent to afford 241 (35 mg, 0.06 mmol, 9% yield) as a solid. HPLC: Rt 9.93 min, 95.4%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 511.15 (M+H), Rt 2.25 min, Column: X-select CSH C18 (3×50) mm, 2.5 μm. $^1$H NMR (400 MHz, DMSO-$d_6$) $\delta_H$=9.57 (d, 1H), 9.02 (d, 1H), 8.30-8.24 (m, 2H), 7.48 (s, 1H), 7.30-7.14 (m, 5H), 5.82-5.72 (m, 2H), 5.51-5.72 (m, 1H), 1.68 (d, 3H). Chiral method: Rt 3.61 min, 100%; SFC column: DIACEL CHIRALPAK-IG (250×4.6 mm, 5 μm), —Mobile Phase: A) $CO_2$ B) Iso-propyl alcohol, Gradient: 10-15% B in 5 min, hold 15% B till 9 min, 15-10% B in 10 min, hold 10% B till 12 min. Wavelength: 280 nm, Flow: 3 mL/min.

Example 194. Synthesis of 242

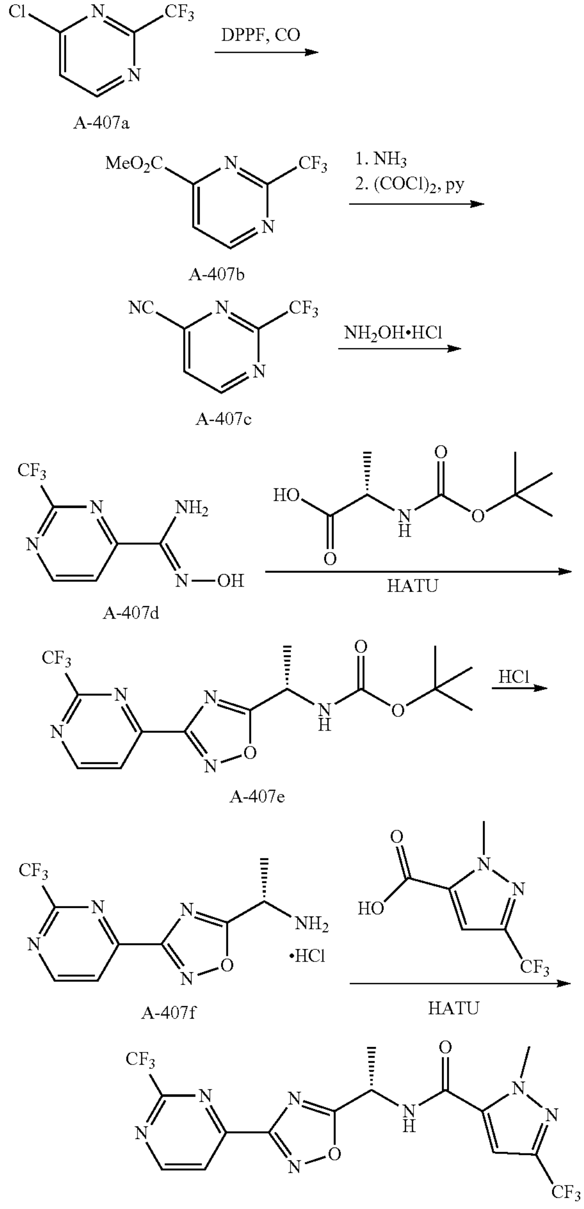

A-407a

A-407b

A-407c

A-407d

A-407e

A-407f

242

Synthesis of methyl 2-(trifluoromethyl)pyrimidine-4-carboxylate (A-407b)

To a solution of A-407a (1 g, 5.48 mmol) in methanol (15 mL) was added triethyl amine (0.57 mL, 4.11 mmol), 1,1'-ferrocenediyl-bis(diphenylphosphine) (303.72 mg, 0.55 mmol) and palladium (II) acetate (0.06 g, 0.27 mmol) The reaction mixture was heated at 60° C. under carbon monoxide (60 psi) for 16 h. The reaction mixture was filtered through celite and washed with EtOAc (3×20 mL). The combined organic phase was dried over anhydrous sodium sulphate, filtered and dried under reduced pressure to afford the crude product which was purified by column chromatography using 100-200 mesh silica and 15-18% EtOAc in hexane as an eluent to afford A-407b (700 mg, 3.4 mmol, 62% yield) as a solid.

Synthesis of 2-(trifluoromethyl)pyrimidine-4-carbonitrile (A-407c)

To a solution of A-407b (600 mg, 2.91 mmol) in methanol (5 mL) was added 7 M ammonia in methanol (1.27 mL, 58.22 mmol) and was stirred at 50° C. for 6 h. The reaction mixture was evaporated under reduced pressure to afford a solid which was washed with pentane (20 mL) and dried under reduced pressure to afford the product (500 mg, 2.52 mmol, 87% yield) as a solid. To a solution of oxalyl chloride (166.04 mg, 1.31 mmol) in DMF (15 mL) were added pyridine (0.63 mL, 7.85 mmol) and a solution of 2-(trifluoromethyl)pyrimidine-4-carboxamide (500.mg, 2.62 mmol) in DMF (5 mL) at 0° C. The reaction mixture was stirred at the 0° C. for 3 h. and then stirred at RT for 16 h. The reaction mixture was evaporated under reduced pressure to afford the crude product which was diluted with EtOAc (200 mL) and washed with cold water (5×30 mL). The organic layer was dried over anhydrous sodium sulphate, filtered and evaporated under reduced pressure to afford A-407c (400 mg, 2.03 mmol, 78% yield) as a liquid Synthesis of (Z)—N'-hydroxy-2-(trifluoromethyl)pyrimidine-4-carboximidamide (A-407d)

To a solution of A-407c (400 mg, 2.31 mmol) in ethanol (10 mL) was added hydroxyl amine hydrochloride (284.33 mg, 3.47 mmol) followed by triethyl amine (0.64 mL, 4.62 mmol) and then reaction mixture was stirred at 70° C. for 5 h. The solvent was removed under reduced pressure to afford the crude product which was diluted with water (10 mL) and extracted with EtOAc (3×15 mL). The combined organic layer was dried over anhydrous sodium sulphate, filtered and evaporated under reduced pressure to afford A-407d (520 mg, 2.47 mmol, quantitative) as a solid.

Synthesis of (tert-butyl (S)-(1-(3-(2-(trifluoromethyl)pyrimidin-4-yl)-1,2,4-oxadiazol-5-yl)ethyl)carbamate (A-407e)

To a solution of A-407d (515 mg, 2.5 mmol) and (2S)-2-(tert-butoxycarbonylamino)propanoic acid (520 mg, 2.75 mmol) in 1,4-dioxane (10 mL) was added DCC (566.14 mg, 2.75 mmol) and stirred at 100° C. for 16 h. The reaction mixture was diluted with EtOAc (50 mL), washed with water (3×25 mL), followed by brine (25 mL) and organic layer separated. The organic layer was dried over anhydrous sodium sulphate, filtered and evaporated under reduced pressure to afford the crude product which was purified by column chromatography using 100-200 mesh silica and 12-14% of EtOAc in hexane as an eluent to afford A-407e (150 mg, 0.38 mmol, 15% yield) as a solid.

Synthesis of (S)-1-(3-(2-(trifluoromethyl)pyrimidin-4-yl)-1,2,4-oxadiazol-5-yl)ethan-1-amine hydrochloride (A-407f)

To a solution of A-407e (150.41 mg, 0.42 mmol) in 1,4-dioxane (10 mL) was added 4.0 M Hydrogen chloride solution in dioxane (0.74 mL, 20.93 mmol) in a dropwise manner at 0° C. and stirred at RT for 3 h. The solvent was removed under reduced pressure to afford the crude product which was washed with ether (3×20 mL) and dried to afford A-407f (80 mg, 0.22 mmol, 53% yield) as a solid.

Synthesis of ((S)-1-methyl-3-(trifluoromethyl)-N-(1-(3-(2-(trifluoromethyl)pyrimidin-4-yl)-1,2,4-oxadiazol-5-yl)ethyl)-1H-pyrazole-5-carboxamide (242)

To a solution of 2-methyl-5-(trifluoromethyl)pyrazole-3-carboxylic acid (50.mg, 0.26 mmol), A-407f (83.77 mg, 0.28 mmol) and HATU (146.91 mg, 0.39 mmol) in DCM (1 0 mL) was added DIPEA (0.13 mL, 0.77 mmol) at 0° C. and stirred at RT for 3 h. The reaction mixture was diluted with DCM (15 mL), washed with water (3×15 mL), saturated sodium bicarbonate solution (3×15 mL) and brine solution (25 mL) and the organic layer was separated. The organic phase was dried over anhydrous sodium sulphate, filtered and evaporated under reduced pressure to afford the crude product which was purified by column chromatography using 100-200-mesh silica and 25-30% of EtOAc in hexane as an eluent to afford a solid, which was further purified by prep HPLC purification to afford 242 (10 mg, 0.023 mmol, 9% yield) as a solid. HPLC: Rt 9.01 min, 98.5%; Column: X-Select CSH C18 (4.6×150) mm, 5 μm; Mobile phase: A: 10 mM Ammonium Bicarbonate in water, B: ACN; Flow Rate: 1.0 mL/min. LCMS: 434.10 (M−H), Rt 2.02 min, Column: X-select CSH C18 (3×50) mm, 2.5 μm. $^1H$ NMR (400 MHz, DMSO-$d_6$) $\delta_H$=9.52 (d, 1H), 9.32 (d, 1H), 8.42 (d, 1H), 7.46 (s, 1H), 5.55-5.50 (m, 1H), 4.13 (s, 3H), 1.70 (d, 3H). Chiral method: Rt 3.09 min, 100%; SFC column: DIACEL CHIRALPAK-IG (250×4.6 mm, 5 μm), —Mobile Phase: A) $CO_2$ B) Iso-propyl-alcohol, Gradient: 10-15% B in 5 min, hold 15% B till 9 min, 15-10% B in 10 min, hold 10% B till 12 min. Wavelength: 270 nm, Flow: 3 mL/min.

Example 195. Synthesis of 243

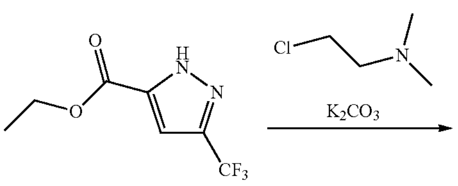

A-405b

-continued

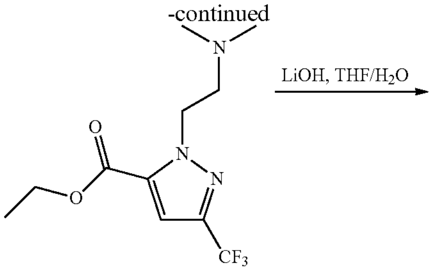

A-408c

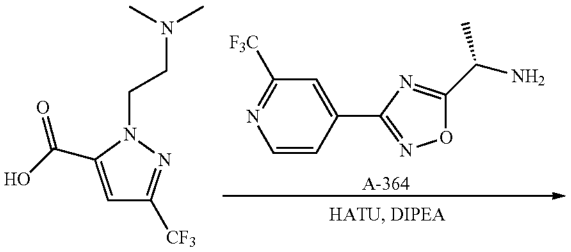

A-408d

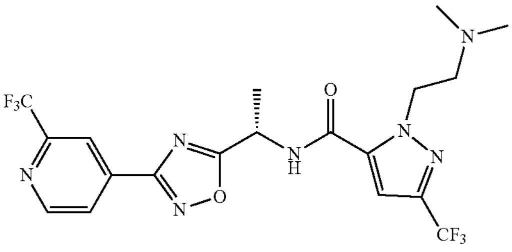

243

Synthesis of ethyl 1-(2-(dimethylamino)ethyl)-3-(trifluoromethyl)-1H-pyrazole-5-carboxylate (A-408c)

To a stirred solution of A-405b (0.5 g, 2.4 mmol) in DMF (5 mL) was added potassium carbonate (663.88 mg, 4.8 mmol) followed by the addition of 2-chloro-N,N-dimethyl-ethanamine hydrochloride (415.2 mg, 2.9 mmol) at 0° C. and stirred at RT for 16 h. The reaction mixture was diluted with water and extracted with EtOAc. The organic layer thus separated treated with brine and dried over anhydrous sodium sulfate, filtered and evaporated under reduced pressure to afford the crude product which was purified by combiflash chromatography in MeOH: DCM as an eluent to afford A-408c (300 mg, 1.07 mmol, 45% yield) as an oil.

Synthesis of 1-(2-(dimethylamino)ethyl)-3-(trifluoromethyl)-1H-pyrazole-5-carboxylic Acid (A-408d)

To a stirred solution of A-408c (300 mg, 1.07 mmol) in THF (3 mL) was added a solution of lithium hydroxide.$H_2O$ (90.15 mg, 2.15 mmol) in THF (3 mL) at 0° C. and stirred at RT for 3 h. The reaction mixture was evaporated to afford the crude product. The crude product was acidified with 2 N HCl and was lyophilised to afford A-408d (280 mg, 1.06 mmol, 99% yield) as a solid.

(S)-1-(2-(dimethylamino)ethyl)-3-(trifluoromethyl)-N-(1-(3-(2-(trifluoromethyl)pyridin-4-yl)-1,2,4-oxadiazol-5-yl)ethyl)-1H-pyrazole-5-carboxamide (243)

To a stirred solution of A-408d (153.46 mg, 0.61 mmol) in DCM (10 mL) were added HATU (290.34 mg, 0.76 mmol) and DIPEA (0.27 mL, 1.53 mmol) at 0° C. for 10 min and added A-364 (150.mg, 0.51 mmol), and stirred at RT for 3 h. The reaction mixture was washed with water (20 mL) and extracted with ethyl acetate (3 times). The combined organic layer obtained was dried over anhydrous sodium sulphate, filtered and evaporated to afford the crude product. The crude compound was purified by flash column chromatography and then further purified using prep HPLC to afford 243 (60 mg, 0.12 mmol, 24% yield) as a solid. HPLC: Rt 5.91 min, 99.63%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 492.20 (M+H), Rt 1.49 min, Column: X-select CSH C18 (3×50) mm, 2.5 μm. $^1H$ NMR (400 MHz, DMSO-$d_6$) $\delta_H$=9.59 (d, 1H), 9.02 (d, 1H), 8.31-8.25 (m, 2H), 7.37 (s, 1H), 5.51-5.46 (m, 1H), 4.69-4.58 (m, 2H), 2.61 (t, 2H), 2.09 (s, 6H), 1.69 (d, 3H). Chiral method: Rt 4.89 min, 100%; SFC column: DIACEL CHIRALPAK-IG (250×4.6 mm, 5 um), —Mobile Phase: A) $CO_2$ B) Iso-propyl-alcohol, Gradient: 10-40% B in 5 min, hold 40% B till 9 min, 40-10% B in 10 min, hold 10% B till 12 min. Wavelength: 280 nm, Flow: 3 mL/min.

Example 196. Synthesis of 244

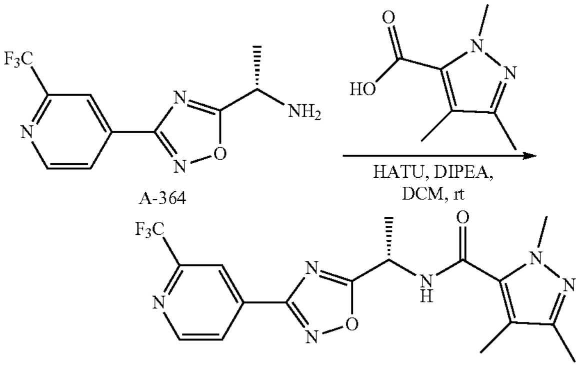

A-364

244

To a stirred solution of 1,3,4-trimethyl-1H-pyrazole-5-carboxylic acid (125.6 mg, 0.81 mmol) in DCM (10 mL) was added A-364 (0.2 g, 0.68 mmol), HATU (387.12 mg, 1.02 mmol) and DIPEA (0.24 mL, 1.36 mmol) at RT and stirred at RT for 2 h. The reaction mixture was quenched with water (100 mL), diluted with DCM (2×100 mL), The combined organic layer was dried over anhydrous sodium sulphate, filtered and evaporated to afford the crude product. The crude compound was purified by flash column chromatography using 100-200 mesh silica and 30-80% EtOAc in hexane as an eluent to afford 244 (96 mg, 0.24 mmol, 36% yield) as a solid. HPLC: Rt 8.14 min, 99.9%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 395 (M+H), Rt 1.91 min; Column: X-select CSH C18 (3×50) mm, 2.5 μm. $^1H$ NMR (400 MHz, DMSO-$d_6$) $\delta_H$=9.08 (d, 1H), 9.03 (d, 1H), 8.30-8.24 (m, 2H), 5.51-5.45 (m, 1H), 3.78 (s, 3H), 2.09-2.06 (m, 6H), 1.67 (d, 3H). Chiral method: Rt 4.24 min, 100%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 250 nm, Flow: 3 mL/min.

Example 197. Synthesis of 245

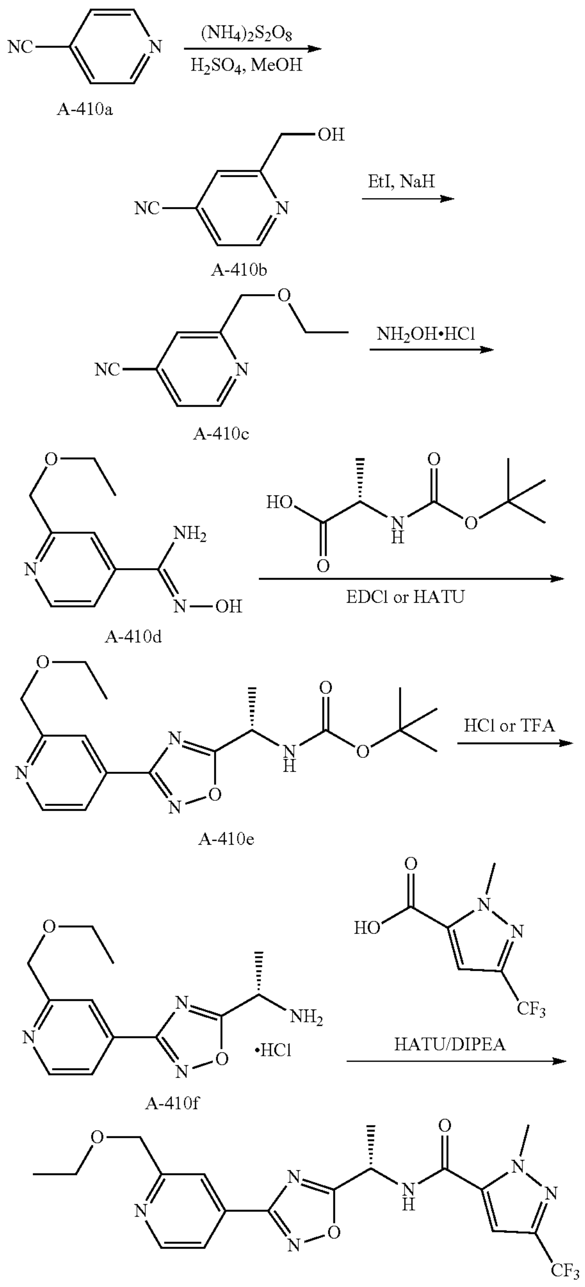

A-410a

A-410b

A-410c

A-410d

A-410e

A-410f

245

Synthesis of 2-(hydroxymethyl)isonicotinonitrile (A-410b)

To the stirred solution of A-410a (10 g, 96.05 mmol) in methanol (130 mL) was added sulfuric acid (2.57 mL, 48.03 mmol) at RT and stirred for 30 min at reflux. To the reaction mixture ammonium persulphate (35.07 g, 153.68 mmol) in water (70 mL) was slowly added over 30 min under reflux. The reaction mass was stirred for 4 h at reflux. The reaction mixture was evaporated under reduced pressure to afford a liquid which was treated with saturated solution of sodium bicarbonate to pH 9. The resulting aqueous layer was extracted with DCM (3×15 mL). The combined organic layer was separated, dried over sodium sulfate to afford the crude product which was purified using column chromatography, product using 40% of ethyl acetate in hexane as an eluent to afford A-410b (3.4 g, 23.06 mmol, 24% yield).

Synthesis of 2-(ethoxymethyl)isonicotinonitrile (A-410c)

To the stirred solution of A-410b (1.g, 7.45 mmol) in THF (15 mL) was added sodium hydride (0.75 g, 18.64 mmol) at 0-5° C. and the reaction mixture was stirred for 30 min at 0-5° C. To the resulting reaction mixture was added dropwise iodoethane (1.2 mL, 14.91 mmol) and stirred for 3 h at RT. The reaction mixture was diluted with ethylacetate (2 mL) and the reaction quenched with water at 0-5° C. and the aqueous layer extracted with ethyl acetate. The organic layer was dried over sodium sulphate and evaporated to afford A-410c (500 mg, 2.59 mmol, 35% yield) as a liquid.

Synthesis of (Z)-2-(ethoxymethyl)-N'-hydroxyisonicotinimidamide (A-410d)

To a stirred solution of A-410c (500.mg, 3.08 mmol) in ethanol (5 mL) was added triethylamine (0.86 mL, 6.17 mmol) and hydroxylamine hydrochloride (321.34 mg, 4.62 mmol) at RT and refluxed for 4 h. The reaction mixture was evaporated to afford the crude product which was diluted with ethyl acetate and washed with water. The organic layer separated and the aqueous layer was extracted with ethyl acetate (4×10 mL). The combined organic layer was dried over sodium sulphate evaporated under reduced pressure to afford A-410d (400 mg, 1.97 mmol, 64% yield).

Synthesis of tert-butyl (S)-(1-(3-(2-(ethoxymethyl)pyridin-4-yl)-1,2,4-oxadiazol-5-yl)ethyl)carbamate (A-410e)

To a stirred solution of A-410d (400 mg, 2.05 mmol) in 1,4-dioxane (5 mL) was added N,N'-Dicyclohexylcarbodiimide (422.76 mg, 2.05 mmol) and N-Boc-L-alanine (387.69 mg, 2.05 mmol) at RT then was refluxed for 4 h. The reaction mixture was filtered and the mother liquor was diluted with ethyl acetate and washed with water (3×10 mL). The organic layer was dried over sodium sulphate and evaporated under reduced pressure to obtain the crude product which was purified by column chromatography using 25-30% of ethyl acetate in hexane to afford A-410e (370 mg, 1.06 mmol, 52% yield) as a solid.

Synthesis of (S)-1-(3-(2-(ethoxymethyl)pyridin-4-yl)-1,2,4-oxadiazol-5-yl)ethan-1-amine (A-410f)

To the stirred solution of A-410e (270 mg, 0.77 mmol) in 1,4-dioxane (2 mL) was added 4 M HCl in 1,4 dioxane (2 mL) at 0-5° C. and stirred for 2 h at RT. The reaction mixture was evaporated completely under reduced pressure to afford A-410f (200 mg, 0.68 mmol, 88% yield) as the hydrochloride salt.

Synthesis of (S)—N-(1-(3-(2-(ethoxymethyl)pyridin-4-yl)-1,2,4-oxadiazol-5-yl)ethyl)-1-methyl-3-(trifluoromethyl)-1H-pyrazole-5-carboxamide (245)

To a stirred solution of 2-methyl-5-(trifluoromethyl)pyrazole-3-carboxylic acid (156.36 mg, 0.81 mmol) in DCM (2 mL) was added DIPEA (0.42 mL, 2.42 mmol), HATU (459.44 mg, 1.21 mmol) and A-410f (200.mg, 0.8100 mmol) at RT and stirred for 2 h at RT. The reaction mixture was diluted with DCM and washed with water. The organic layer was dried over sodium sulphate and evaporated under reduced pressure to afford the crude product which was purified by column chromatography using 30-35% of ethyl acetate in hexane as an eluent to afford 245 (40 mg, 0.09 mmol, 11% yield,) as a solid. HPLC: Rt 8.41 min, 99.6%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 425.15 (M+H), Rt 1.95 min; Column: X-select CSH C18 (3×50) mm, 2.5 μm. $^1H$ NMR (400 MHz, DMSO-$d_6$) $\delta_H$=9.46 (d, 1H), 8.73 (d, 1H), 7.95 (s, 1H), 7.85-7.82 (m, 1H), 7.45 (s, 1H), 5.52-5.44 (m, 1H), 4.63 (s, 2H), 4.13 (s, 3H), 3.60 (q, 2H), 1.68 (d, 3H), 1.20 (t, 3H). Chiral method: Rt 3.57 min, 99.5%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 280 nm, Flow: 3 mL/min.

Example 198. Synthesis of 246

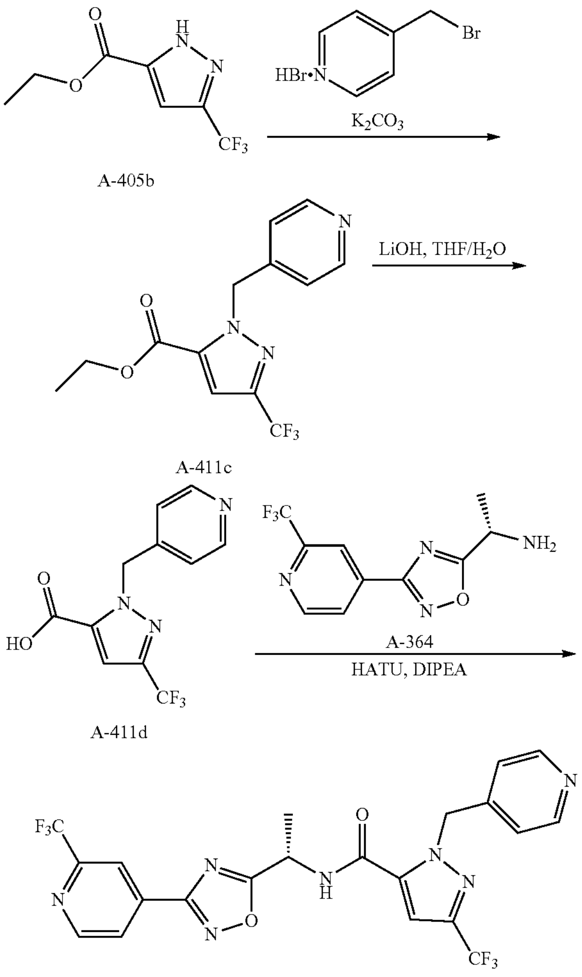

A-405b

A-411c

A-411d

246

Synthesis of ethyl 1-(pyridin-4-ylmethyl)-3-(trifluoromethyl)-1H-pyrazole-5-carboxylate (A-411c)

To a stirred solution of A-405b (500 mg, 2.4 mmol) and 4-(bromomethyl)pyridine, hydrobromide (729.12 mg, 2.88 mmol) at RT in DMF (5 mL) were added K2CO$_3$ (274.21 mg, 3.6 mmol) at RT and stirred at RT for 4 h. The reaction mixture was diluted with water and extracted with ethyl acetate. The organic layer was separated, dried over $Na_2SO_4$ and evaporated to afford crude product which was purified by column chromatography using 30-35% ethyl acetate in hexane as an eluent to afford A-411c (250 mg, 0.79 mmol, 32% yield).

Synthesis of 1-(pyridin-4-ylmethyl)-3-(trifluoromethyl)-1H-pyrazole-5-carboxylic Acid (A-411d)

To a stirred solution of A-411c (200 mg, 0.67 mmol) in THF (2 mL) was added a solution of lithium hydroxide (84.13 mg, 2.01 mmol) in water (0.2000 mL) at RT and stirred at RT for 2 h. The reaction mixture was evaporated to afford crude product. The crude product was acidified with 6 M HCl. Aqueous layer was lyophilized to afford A-411d (180 mg, 0.54 mmol, 81% yield) as a solid.

Synthesis of (S)-1-(pyridin-4-ylmethyl)-3-(trifluoromethyl)-N-(1-(3-(2-(trifluoromethyl)pyridin-4-yl)-1,2,4-oxadiazol-5-yl)ethyl)-1H-pyrazole-5-carboxamide (246)

To a stirred solution of A-411d (126.04 mg, 0.46 mmol) and A-364 (100 mg, 0.39 mmol) in DCM (2 mL) was added HATU (147.26 mg, 0.39 mmol), DIPEA (0.2 mL, 1.16 mmol) and stirred at RT for 2 h. The reaction mixture was diluted with water and DCM. The organic layer was separated, washed with brine solution, dried over $Na_2SO_4$ and evaporated to afford the crude product. The crude product was purified by column chromatography using silica gel 100-200 mesh and 30-35% EA in Hexane eluent to afford 246 (40 mg, 0.07 mmol, 19% yield) as a solid. HPLC: Rt 7.71 min, 98%; Column: X-Select CSH C18 (4.6×150) mm, 3.5 μm; Mobile phase: A: 0.1% Formic acid in water: Acetonitrile (95:05), B: Acetonitrile; Flow Rate: 1.0 mL/min. LCMS: 512.10 (M+H), Rt 1.81 min, Column: X-select CSH C18 (3×50) mm, 2.5 μm. $^1$H NMR (400 MHz, DMSO-d$_6$) $\delta_H$=9.60 (d, 1H), 9.01 (d, 1H), 8.48 (d, 2H), 8.28-8.20 (m, 2H), 7.57 (s, 1H), 7.04 (d, 2H), 5.83 (s, 2H), 5.49-5.42 (m, 1H), 1.66 (d, 3H). Chiral method: Rt 3.50 min, 99.3%; SFC column: DIACEL CHIRALPAK-IG (250×4.6 mm, 5 um), —Mobile Phase: A) $CO_2$ B) MEOH+0.1% $NH_3$, Gradient: 10-40% B in 5 min, hold 40% B till 9 min, 40-10% B at 10 min, hold 10% B till 12 min, Wavelength: 280 nm, Flow: 3 mL/min.

Example 199. Synthesis of 247 and 248

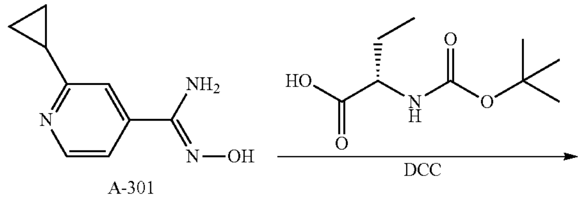

A-301

-continued

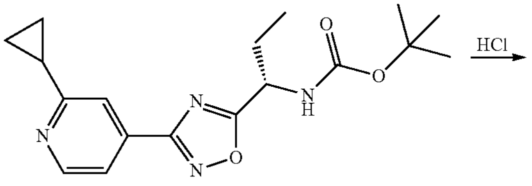

247

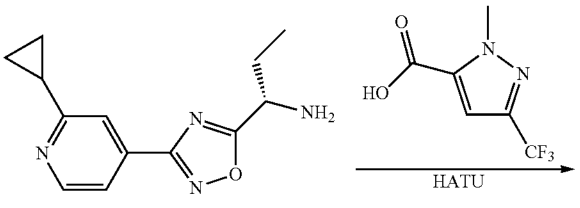

A-412f

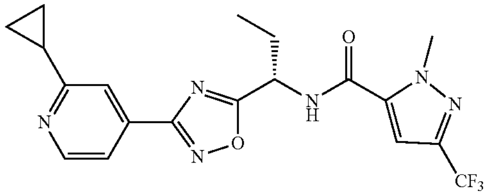

248

Synthesis of tert-butyl (S)-(1-(3-(2-cyclopropylpyridin-4-yl)-1,2,4-oxadiazol-5-yl)propyl)carbamate (247)

To a stirred solution of A-301 (500 mg, 2.82 mmol) in 1, 4-Dioxane (10 mL) was added (S)-2-((tert-butoxycarbonyl) amino)butanoic acid (630.82 mg, 3.1 mmol) followed by DCC (639.39 mg, 3.1 mmol) and stirred at 70° C. for 5 h. The solvent was removed under reduced pressure and residue was diluted with water (10 mL) and extracted with EtOAc (3×15 mL). The combined organic phase was dried and evaporated to afford crude compound, which was purified by column chromatography (15-22% EtOAc in hexane as an eluent) followed by prep HPLC purification to afford 247 (510 mg, 1.47 mmol, 52% yield) as a semi solid. HPLC: Rt 9.23 min, 99.8%; Column: X-Select C18 (4.6×150) mm, 5 μm; Mobile phase: A: 0.1% Formic acid in water B: Acetonitrile (95:05); Flow Rate: 1.0 mL/min. LCMS: 345.20 (M+H), Rt 2.16 min; Column: X-select CSH C18 (3×50) mm, 2.5 μm. $^1$H NMR (400 MHz, DMSO-d$_6$) $\delta_H$=8.60 (d, 1H), 7.84-7.78 (m, 2H), 7.64 (d, 1H), 4.82-4.80 (m, 1H), 2.32-2.28 (m, 1H), 1.97-1.85 (m, 2H), 1.40 (s, 9H), 1.22-1.21 (m, 2H), 1.22-0.94 (m, 5H). Chiral method: Rt 6.21 min, 99.1%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B at 10 min, hold 10% B till 12 min, Wavelength: 292 nm, Flow: 3 mL/min.

Synthesis of (S)-1-(3-(2-cyclopropylpyridin-4-yl)-1,2,4-oxadiazol-5-yl)propan-1-amine (A-412f)

To a stirred solution of 247 (400 mg, 1.16 mmol) in 1, 4-dioxane (10 ml) was added HCl solution 4.0 M in dioxane (0.41 mL, 11.61 mmol) at 0° C. and the reaction mixture was stirred at RT for 3 h. The solvent was evaporated under reduced pressure, resulting crude product was washed with n-pentane (3×20 mL) and dried under reduced pressure to afford A-412f (390 mg, 0.96 mmol, 82% yield) as a solid.

Synthesis of (S)—N-(1-(3-(2-cyclopropylpyridin-4-yl)-1,2,4-oxadiazol-5-yl)propyl)-1-methyl-3-(trifluoromethyl)-1H-pyrazole-5-carboxamide (248)

To a stirred solution of A-412f (100 mg, 0.36 mmol) and 1-methyl-3-(trifluoromethyl)-1H-pyrazole-5-carboxylic acid (76.05 mg, 0.39 mmol) in DCM (10 ml) were added HATU (203.15 mg, 0.53 mmol) followed by DIPEA (0.12 mL, 0.71 mmol) at 0° C. and stirred at RT for 3 h. The reaction mixture was diluted with DCM (30 mL), washed with water (3×25 mL) and sodium bicarbonate solution (3×25 mL). The organic phase was separated, dried over anhydrous sodium sulfate, filtered and evaporated to afford the crude product, which was purified by column chromatography (100-200 mesh silica, 8-9.5% of EtOAc in hexane as an eluent) followed by prep HPLC to afford 248 (50 mg, 0.11 mmol, 33% yield) as a solid. HPLC: Rt 9.64 min, 99.7%; Column: X-Select C18 (4.6×150) mm, 5 μm; Mobile phase: A: 10 mM ammonium bicarbonate in water B: Acetonitrile; Flow Rate: 1.0 mL/min. LCMS: 421.50 (M+H), Rt 2.14 min, Column: X-select CSH C18 (3×50) mm, 2.5 μm. $^1H$ NMR (400 MHz, DMSO-$d_6$) $\delta_H$=9.41 (d, 1H), 8.60 (d, 1H), 7.85 (d, 1H), 7.68-7.62 (m, 1H), 7.49 (s, 1H), 5.32-5.26 (m, 1H), 4.13 (s, 3H), 2.34-2.22 (m, 1H), 2.21-1.97 (m, 2H), 1.06-0.92 (m, 7H). Chiral method: Rt 3.24 min, 100%; SFC column: DIACEL CHIRALPAK-IG (250×4.6 mm, 5 um), —Mobile Phase: A) $CO_2$ B) MeOH+0.1% $NH_3$, Gradient: 10-40 B in 5 min, hold 40% B till 9 min, 40-10% B at 10 min, hold 10% B till 12 min, Wavelength: 292 nm, Flow: 3 mL/min.

Example 200. Synthesis of 249

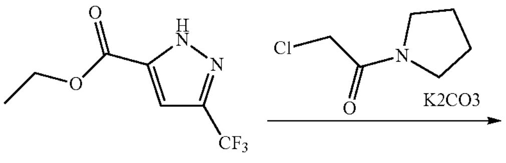

A-405b

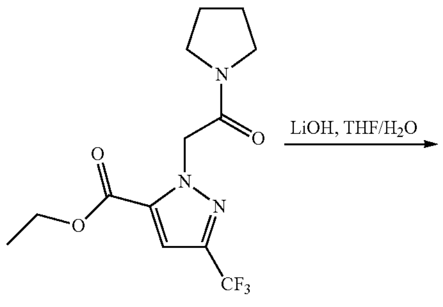

A-413c

-continued

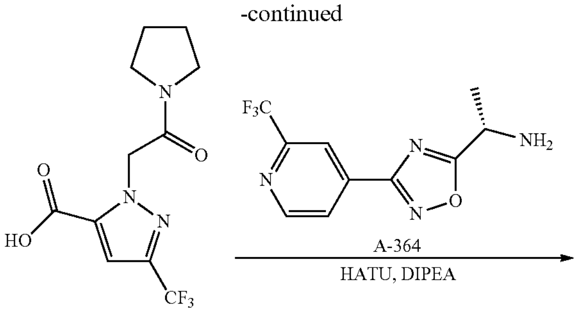

A-413d

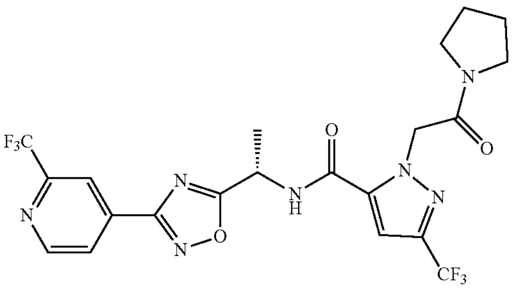

249

Synthesis of ethyl 1-(2-oxo-2-(pyrrolidin-1-yl)ethyl)-3-(trifluoromethyl)-1H-pyrazole-5-carboxylate (A-413c)

To a stirred solution of A-405b (500 mg, 2.4 mmol) and 2-chloro-1-pyrrolidin-1-yl-ethanone (390.03 mg, 2.64 mmol) in DMF (5 mL) were added $K_2CO_3$ (663.88 mg, 4.8 mmol) at 0° C. and stirred at RT for 16 h. The reaction mixture was diluted with ethyl acetate (50 mL) and the organic layer was washed with water (3×25 mL) followed by brine (25 mL). The organic phase was dried over anhydrous sodium sulfate, filtered and evaporated to afford crude product which was purified by column chromatography (100-200 mesh silica, 10-1% EtOAc in hexane as an eluent) to afford A-413c (480 mg, 1.46 mmol, 61% yield) as a solid.

Synthesis of 1-(2-oxo-2-(pyrrolidin-1-yl)ethyl)-3-(trifluoromethyl)-1H-pyrazole-5-carboxylic Acid (A-413d)

To a stirred solution of A-413c (481.49 mg, 1.51 mmol) in THF (10 mL) was added a solution of lithium hydroxide (54.18 mg, 2.26 mmol) in water (3 mL) at 0° C. and stirred at RT for 3 h. The reaction mixture was evaporated to afford the crude product. The crude product was diluted with water (15 mL), acidified with 5 N HCl to pH 4, precipitate collected by filtration and dried to afford A-413d (320 mg, 1.09 mmol, 72% yield) as a solid.

Synthesis of (S)-1-(2-oxo-2-(pyrrolidin-1-yl)ethyl)-3-(trifluoromethyl)-N-(1-(3-(2-(trifluoromethyl)pyridin-4-yl)-1,2,4-oxadiazol-5-yl)ethyl)-1H-pyrazole-5-carboxamide (249)

To a stirred solution of A-413d (100 mg, 0.34 mmol) and A-364 (121.41 mg, 0.41 mmol) in DCM (10 mL) were added HATU (195.84 mg, 0.52 mmol) followed by DIPEA (0.18 mL, 1.03 mmol) at 0° C. and stirred at RT for 3 h. The reaction mixture was diluted with DCM (25 mL). The organic layer was separated, washed with sodium bicarbonate solution (3×25 mL), brine solution (30 mL) then dried ($Na_2SO_4$) and concentrated to afford the crude product. The crude product was purified by column chromatography using silica gel 100-200 mesh and 35-40% EA in hexane as an eluent to afford 249 (30 mg, 0.05 mmol, 16% yield) as a solid. HPLC: Rt 9.12 min, 99.9%; Column: X-Select CSH C18 (4.6×150) mm, 5 μm; Mobile phase: A: 10 mM ammonium bicarbonate in water B: Acetonitrile; Flow Rate: 1.0 mL/min. LCMS: 531.90 (M+H), Rt 2.04 min; Column: X-select CSH (3×50) mm, 2.5 μm. $^1H$ NMR (400 MHz, DMSO-$d_6$) $\delta_H$=9.50 (d, 1H), 9.02 (d, 1H), 8.28-8.24 (m, 2H), 7.49 (s, 1H), 5.52-5.40 (m, 3H), 3.50-3.40 (m, 2H), 3.26-3.18 (m, 2H), 1.90-1.80 (m, 2H), 1.78-1.62 (m, 5H). Chiral method: Rt 3.86 min, 100%; SFC column: DIACEL CHIRALPAK-IG (250×4.6 mm, 5 um), —Mobile Phase: A) $CO_2$ B) MEOH+0.1% $NH_3$, Gradient: 10-40% B in 5 min, hold 40% B till 9 min, 40-10% B at 10 min, hold 10% B till 12 min, Wavelength: 280 nm, Flow: 3 mL/min.

Example 201. Synthesis of 250

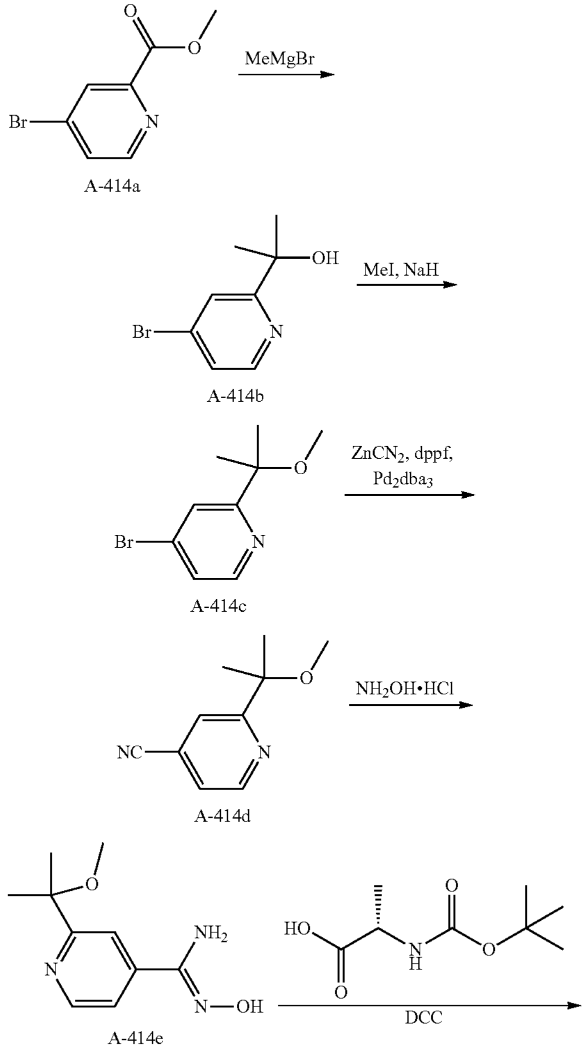

A-414a
A-414b
A-414c
A-414d
A-414e

-continued

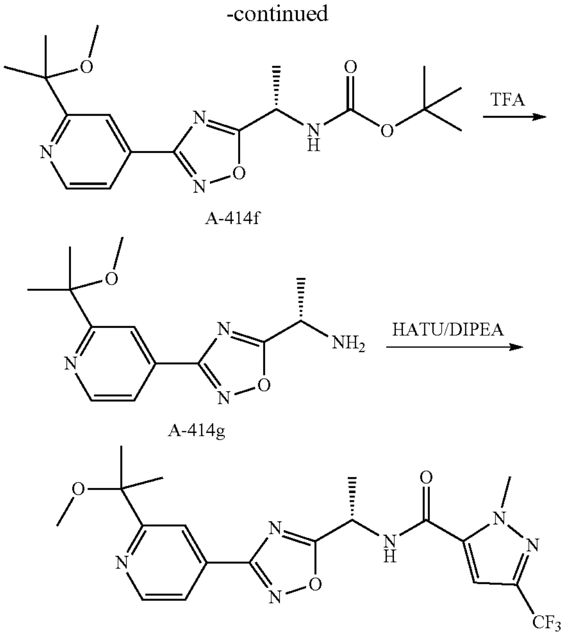

A-414f
A-414g

250

Synthesis of 2-(4-bromopyridin-2-yl)propan-2-ol (A-414b)

To a stirred solution of A-414a (5 g, 23.14 mmol) in THF (50 mL) was added MeMgBr (8.28 g, 69.43 mmol) at 0° C. in dropwise manner and stirred at RT for 2 h. The reaction mixture was diluted with saturated $NH_4Cl$ solution and extracted with EtOAc. The organic layer was dried over $Na_2SO_4$ filtered and evaporated to afford the crude product which was purified by combiflash using 15% EtOAc/hexane as an eluent to afford A-414b (1.9 g, 7.12 mmol, 31% yield) as an oil.

Synthesis of 4-bromo-2-(2-methoxypropan-2-yl) pyridine (A-414c)

To a stirred solution of A-414b (1.9 g, 8.83 mmol) in THF (20 mL), was added NaH (0.42 g, 17.67 mmol) at 0° C. portion-wise and stirred at 0° C. for 20 min. To the resulting reaction mixture was added Methyl iodide (1.25 g, 8.83 mmol) and stirred at RT for 2 h. The reaction mixture was diluted with water and extracted with EtOAc. The organic layer was dried over $Na_2SO_4$, filtered and evaporated to afford A-414c (1.6 g, 6.9835 mmol, 79% yield) as an oil.

Synthesis of 2-(2-methoxypropan-2-yl)isonicotinonitrile (A-414d)

To a stirred solution of A-414c (1 g, 4.35 mmol) in 1,4-dioxane (10 mL), was added. $ZnCN_2$ (1.53 g, 13.04 mmol) and the reaction mixture was purged with $N_2$ gas for 20 min followed by the addition of DPPF (0.24 g, 0.43 mmol), $Pd_2dba_3$ (398.09 mg, 0.43 mmol). The reaction mixture was stirred at 100° C. for 16 h. The reaction mixture was filtered through a celite bed, diluted with water and extracted with EtOAc. The organic layer was dried over $Na_2SO_4$, filtered and evaporated to afford A-414d which was used for next step without further purification.

Synthesis of (Z)—N'-hydroxy-2-(2-methoxypropan-2-yl)isonicotinimidamide (A-414e)

To a stirred solution of A-414d (700 mg, 3.97 mmol) in ethanol (5 mL) were added $NH_2OH.HCl$ (1.16 g, 11.92 mmol), TEA (0.55 mL, 3.97 mmol) and heated 70° C. for 1 h. The reaction mixture was evaporated to afford the crude product which was diluted in water and extracted with EtOAc. The organic layer was dried over $Na_2SO_4$ filtered and evaporated to afford A-414e (600 mg, 2.87 mmol, 72% yield) as an oil.

Synthesis of tert-butyl (S)-(1-(3-(2-(2-methoxypropan-2-yl)pyridin-4-yl)-1,2,4-oxadiazol-5-yl)ethyl) carbamate (A-414f)

To a solution of A-414e (500 mg, 2.39 mmol) in 1,4-dioxane (10 mL) was added (2S)-2-(tert-butoxycarbonylamino)propanoic acid (452.14 mg, 2.39 mmol), DCC (492.26 mg, 2.39 mmol) and heated to 100° C. for 16 h. The reaction mixture was diluted with water and extracted with ethyl acetate. The organic layer was dried with $Na_2SO_4$, filtered and evaporated to afford the crude product which was purified by column chromatography using 100-200 mesh silica and 15% EtOAc/hexane as eluents to afford A-414f (320 mg, 0.88 mmol, 37% yield) as an oil.

Synthesis of (S)-1-(3-(2-(2-methoxypropan-2-yl) pyridin-4-yl)-1,2,4-oxadiazol-5-yl)ethan-1-amine (A-414 g)

To a solution of A-414f (300 mg, 0.83 mmol) in DCM (5 mL) was added TFA (0.19 mL, 2.48 mmol) in a dropwise manner and stirred at RT for 4 h. The reaction mixture was diluted with saturated $NaHCO_3$ solution and extracted with EtOAc. The organic layer was dried over $Na_2SO_4$ filtered and evaporated to afford A-414 g (75 mg, 0.28 mmol, 34% yield) as an oil.

Synthesis of (S)—N-(1-(3-(2-(2-methoxypropan-2-yl)pyridin-4-yl)-1,2,4-oxadiazol-5-yl)ethyl)-1-methyl-3-(trifluoromethyl)-1H-pyrazole-5-carboxamide (250)

To a stirred solution of 2-methyl-5-(trifluoromethyl)pyrazole-3-carboxylic acid (53.28 mg, 0.27 mmol) in DCM (3 mL) was added A-414 g (72.mg, 0.27 mmol), HATU (130.46 mg, 0.34 mmol), DIPEA (0.05 mL, 0.27 mmol) and stirred at RT for 16 h. The reaction mixture was diluted with water and extracted with EtOAc. The organic layer was dried over $Na_2SO_4$ filtered and evaporated to afford the crude product which was purified by prep HPLC to afford 250 (25 mg, 0.057 mmol, 21% yield) as an oil. HPLC: Rt 8.90 min, 99.67%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 439.15 (M+H), Rt 2.02 min; Column: X-select CSH C18 (3×50) mm, 2.5 μm. $^1H$ NMR (400 MHz, DMSO-d6) $\delta_H$=9.47 (d, 1H), 8.75 (d, 1H), 8.06 (s, 1H), 7.84-7.80 (m, 1H), 7.45 (s, 1H), 5.52-5.46 (m, 1H), 4.13 (s, 3H), 3.15 (s, 3H), 1.68 (d, 3H), 1.50 (s, 6H). Chiral method: Rt 3.06 min, 100%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 280 nm, Flow: 3 mL/min.

Example 202. Synthesis of 251

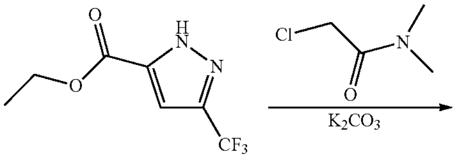

A-415b

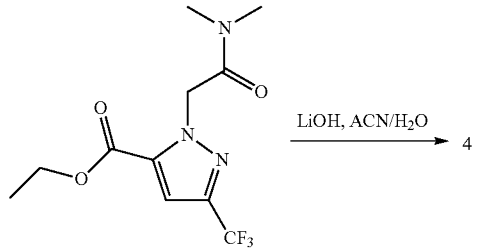

A-415c

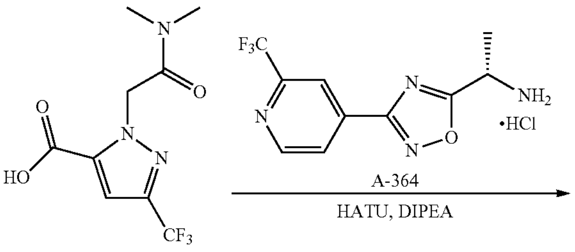

A-415d

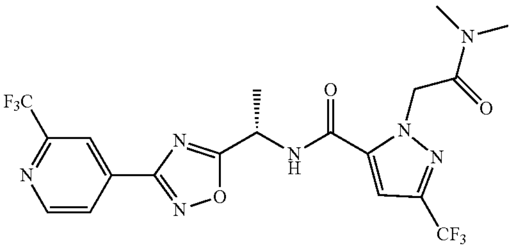

251

Synthesis of ethyl 1-(2-(dimethylamino)-2-oxo-ethyl)-3-(trifluoromethyl)-1H-pyrazole-5-carboxylate (A-415c)

To a solution of A-405b (400.mg, 1.92 mmol) in DMF (5 mL) was added K2$CO_3$ (0.33 mL, 3.84 mmol) at 0° C. and stirred for 10 min at 0° C. To a reaction mixture was added 2-chloro-N,N-dimethylacetamide (0.22 mL, 2.11 mmol) and stirred at RT for 4 h. The reaction mixture was diluted with EtOAc (100 mL) and washed with cold water (5×25 mL), organic layer separated. The organic layer was dried over anhydrous sodium sulphate, filtered and evaporated to afford the crude product which was purified by column chromatography using 100-200 mesh silica and 18-22% of EtOAc in hexane as an eluent to afford A-415c (355 mg, 1.19 mmol, 62% yield) as an oil.

Synthesis of 2-[2-(dimethylamino)-2-oxo-ethyl]-5-(trifluoromethyl)pyrazole-3-carboxylic Acid (A-415d)

To a solution of A-415c (350 mg, 1.19 mmol) in MeCN (10 mL) was added a solution of lithium hydroxide (42.88 mg, 1.79 mmol) in water (3 mL) at 0° C. and stirred at RT for 3 h. The solvent was removed under reduced pressure and the crude product was diluted with water (15 mL) and acidified with 5 N aq. HCl solution to pH 5. The obtained precipitate was filtered, washed with water (10 mL) followed by hexane (10 mL) and dried under reduced pressure to afford A-415d (130 mg, 0.49 mmol, 41% yield) as a solid.

Synthesis of (S)-1-(2-(dimethylamino)-2-oxoethyl)-3-(trifluoromethyl)-N-(1-(3-(2-(trifluoromethyl)pyridin-4-yl)-1,2,4-oxadiazol-5-yl)ethyl)-1H-pyrazole-5-carboxamide (251)

To a suspension of A-415d (95.mg, 0.36 mmol) and A-364 hydrochloride salt (126.67 mg, 0.43 mmol) in DCM (10 mL) were added HATU (204.32 mg, 0.54 mmol) followed by DIPEA (0.19 mL, 1.07 mmol) at 0° C. and reaction mixture was stirred at RT for 3 h. The reaction mixture was diluted with DCM (25 mL), washed with water (3×20 mL), saturated sodium bicarbonate solution (3×20 mL) followed by brine solution (30 mL). The organic phase was dried over anhydrous sodium sulphate, filtered and evaporated under reduced pressure to afford the crude product, which was purified by column chromatography using 100-200 mesh silica and 25-28% EtOAc in hexane as an eluent to afford 251 (35 mg, 0.069 mmol, 19% yield) as a solid. HPLC: Rt 8.86 min, 99.9%; Column: X-Select CSH C18 (4.6×150) mm, 5 μm; Mobile phase: A: 10 mM Ammonium Bicarbonate in water, B: ACN; Flow Rate: 1.0 mL/min. LCMS: 506.11 (M+H), Rt 2.04 min, Column: X-select CSH C18 (3×50) mm, 2.5 μm. $^1$H NMR (400 MHz, DMSO-$d_6$) $\delta_H$=9.52-9.48 (m, 1H), 9.02 (d, 1H), 8.30-8.26 (m, 2H), 7.50 (s, 1H), 5.53 (s, 2H), 5.48-5.45 (m, 1H), 3.00 (s, 3H), 2.78 (s, 3H), 1.66 (d, 3H). Chiral method: Rt 4.35 min, 99.7%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 270 nm, Flow: 3 mL/min.

Example 203. Synthesis of 252

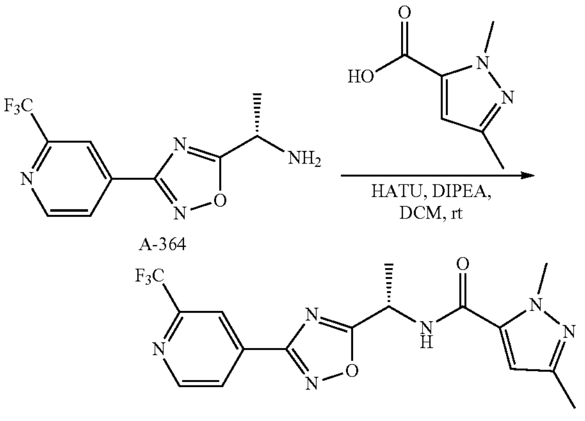

A-364

252

To a stirred solution of 1,3-dimethyl-1H-pyrazole-5-carboxylic acid (57.07 mg, 0.41 mmol) in DCM (2 mL) was added A-364 (0.1 g, 0.34 mmol), HATU (193.56 mg, 0.51 mmol) and DIPEA (0.18 mL, 1.02 mmol) at RT and stirred at RT for 2 h. The reaction mixture was diluted with DCM and washed with water (3×3 mL). The organic layer was dried over anhydrous sodium sulphate, filtered and evaporated to afford the crude product. The crude compound was purified by flash column chromatography using 100-200 mesh silica and 20-25% EtOAc in hexane as an eluent to afford 252 (65 mg, 0.1665 mmol, 49% yield) as a solid. HPLC: Rt 8.14 min, 97.43%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 381.50 (M+H), Rt 1.79 min, Column: X-select CSH C18 (3×50) mm, 2.5 μm. $^1$H NMR (400 MHz, DMSO-$d_6$) $\delta_H$=9.18 (d, 1H), 9.02 (d, 1H), 8.30-8.26 (m, 2H), 6.75 (s, 1H), 5.48-5.42 (m, 1H), 3.95 (s, 3H), 2.17 (s, 3H), 1.67 (d, 3H). Chiral method: Rt 3.96 min, 100%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 240 nm, Flow: 3 mL/min.

Example 204. Synthesis of 253

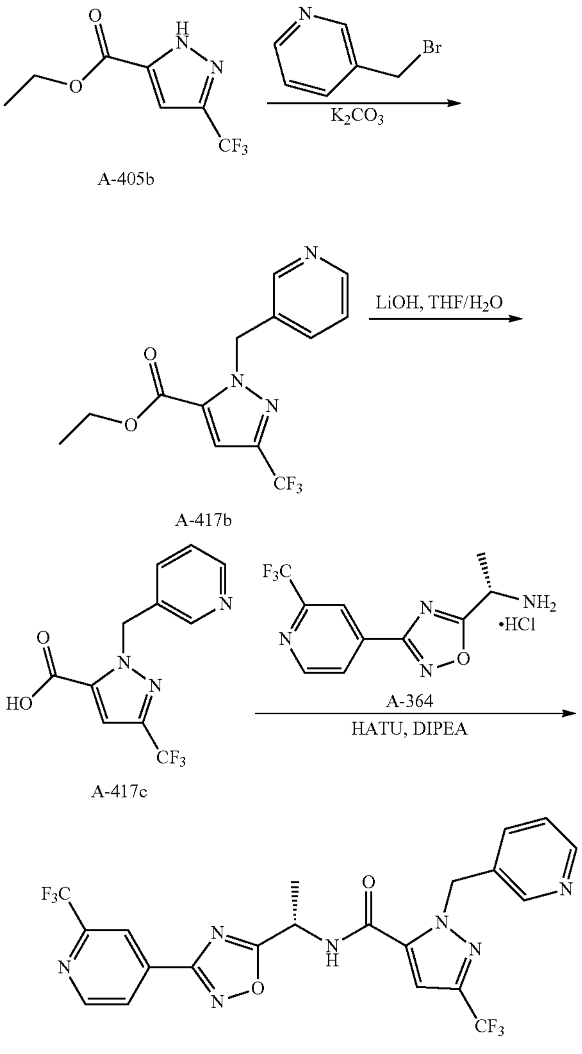

A-405b

A-417b

A-417c

253

Synthesis of ethyl 1-(pyridin-3-ylmethyl)-3-(trifluoromethyl)-1H-pyrazole-5-carboxylate (A-417b)

To a stirred solution of A-405b (300 mg, 1.44 mmol) and 3-(bromomethyl)pyridine (297.53 mg, 1.73 mmol) in DMF (10 mL) were added $K_2CO_3$ (398.33 mg, 2.88 mmol) and stirred at RT for 10 h. The reaction mixture was diluted by ethyl acetate (20 mL) and water (20 mL) and the organic layer was separated. The aqueous layer was treated with ethylacetate (20 mL). The combined organic layer was washed with cold water (20 mL), brine, dried over $Na_2SO_4$ and evaporated to afford the crude product which was purified by column chromatography using silica gel 100-200 mesh and 40% EA in Hexane as an eluent to afford A-417b (300 mg, 0.91 mmol, 63% yield) as a solid.

Synthesis of 1-(pyridin-3-ylmethyl)-3-(trifluoromethyl)-1H-pyrazole-5-carboxylic Acid (A-417c)

To a stirred solution of A-417b (300 mg, 1 mmol) in THF (5 mL) was added lithium hydroxide (48.02 mg, 2.01 mmol) and stirred at 0° C. for 3 h. The solvent was evaporated under reduced pressure and reaction mixture was cooled to 0° C. and acidified using 2 N HCl (5 mL) leading to precipitation. The precipitate was collected by filtration and dried to afford A-417c (150 mg, 0.36 mmol, 36% yield).

Synthesis of (S)-1-(pyridin-3-ylmethyl)-3-(trifluoromethyl)-N-(1-(3-(2-(trifluoromethyl)pyridin-4-yl)-1,2,4-oxadiazol-5-yl)ethyl)-1H-pyrazole-5-carboxamide (253)

To a stirred solution of A-417c (150 mg, 0.55 mmol) and A-364 (195.57 mg, 0.66 mmol) in DCM (10 mL) was added HATU (252.37 mg, 0.66 mmol) and DIPEA (0.19 mL, 1.11 mmol) at 0° C. and stirred at RT for 3 h. The reaction mixture was diluted with DCM (25 mL) and water (25 mL) and the organic layer was separated. The aqueous layer was washed with DCM (20 mL). The combined organic layer was washed with brine (30 ml), dried over $Na_2SO_4$ then evaporated to dryness to afford the crude product which was purified by column chromatography using silica gel 100-200 mesh and 30% EA in Hexane as an eluent to afford 253 (22 mg, 0.043 mmol, 8% yield). HPLC: Rt 8.23 min, 99.2%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 512.20 (M+H), Rt 2.00 min, 99.8%; Column: X-select CSH C18 (3×50) mm, 2.5 μm. $^1H$ NMR (400 MHz, DMSO-$d_6$) $\delta_H$=9.60 (d, 1H), 9.01 (d, 1H), 8.45-8.42 (m, 2H), 8.28-8.24 (m, 2H), 7.59-7.56 (m, 1H), 7.50 (s, 1H), 7.33-7.30 (m, 1H), 5.81 (s, 2H), 5.51-5.45 (m, 1H), 1.66 (d, 3H). Chiral method: Rt 4.55 min, 99.3%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 250 nm, Flow: 3 mL/min.

Example 205. Synthesis of 254

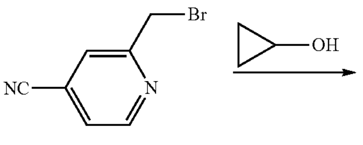

A-418b

-continued

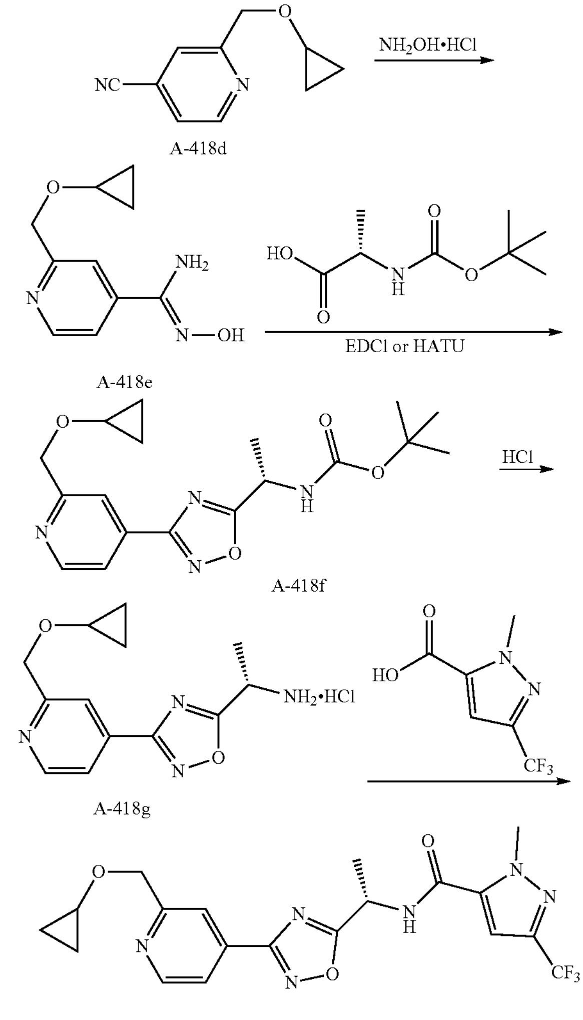

A-418d

A-418e

A-418f

A-418g

254

Synthesis of 2-(bromomethyl)isonicotinonitrile (A-418c)

To the stirred solution of A-410b (3 g, 22.36 mmol) in THF (30 mL) was added triphenylphosphine (8.8 g, 33.55 mmol) at RT. Reaction mixture was cooled to 0° C. and carbon-tetrabromide (11.12 g, 33.55 mmol) was added and stirred for 5 h at RT. The reaction mixture was diluted with ethyl acetate and washed with water. The organic layer was dried over sodium sulphate and evaporated under reduced pressure to afford a liquid which was purified by column chromatography using 30% ethyl acetate in hexane as an eluent to afford A-418c (1.27 g, 6 mmol, 27% yield) as a solid.

Synthesis of 2-(cyclopropoxymethyl)isonicotinonitrile (A-418d)

To a stirred solution of cyclopropanol (0.74 g, 12.69 mmol) in THF (10 mL), maintained 0-5° C. was added sodium hydride (1.01 g, 25.38 mmol) and stirred for 30 min. To the resultant reaction mixture was added A-418c (1 g, 5.08 mmol) in THF (10 mL) dropwise. The reaction mixture was stirred for 5 h at RT. The reaction mixture was quenched with ice cold water and extracted with ethyl acetate (2×20 mL) and the organic layer was separated. The combined organic layer was dried over sodium sulphate, evaporated to afford the crude product which was purified by column chromatography using 10-15% of ethyl acetate in hexane as an eluent to afford A-418d (350 mg, 1.98 mmol, 39% yield).

Synthesis of (Z)-2-(cyclopropoxymethyl)-N'-hydroxyisonicotinimidamide (A-418e)

To the stirred solution of A-418d (500 mg, 2.87 mmol) in ethanol (5 mL) was added triethylamine (0.8 mL, 5.74 mmol) and hydroxylamine hydrochloride (299.18 mg, 4.31 mmol) at RT. The reaction was stirred for 4 h at reflux. The reaction mixture was evaporated to afford a liquid which was diluted with ethyl acetate and washed with water and separated. The aqueous layer was extracted with ethyl acetate (4×10 mL). The combined organic layer was dried over sodium sulphate and evaporated to afford A-418e (400 mg, 1.88 mmol, 66% yield).

Synthesis of tert-butyl (S)-(1-(3-(2-(cyclopropoxymethyl)pyridin-4-yl)-1,2,4-oxadiazol-5-yl) ethyl)carbamate (A-418f)

To the stirred solution of A-418e (600 mg, 2.9 mmol) in 1,4-dioxane (6 mL) was added DCC (656.08 mg, 3.18 mmol) and N-Boc-L-alanine (602.61 mg, 3.18 mmol) at RT and stirred for 4 h at reflux. The reaction mixture was filtered and diluted with ethyl acetate, washed with water (3×10 mL), dried over sodium sulphate and evaporated under reduced pressure to afford the crude product which was purified by column chromatography using 25-30% of ethyl acetated in hexane as an eluent to afford A-418f (660 mg, 1.82 mmol, 63% yield).

Synthesis of (S)-1-(3-(2-(cyclopropoxymethyl)pyridin-4-yl)-1,2,4-oxadiazol-5-yl)ethan-1-amine (A-418 g)

To a solution of A-418f (500 mg, 1.39 mmol) in 1,4-dioxane (5 mL) was added 4 M HCl/dioxane (5 mL) and stirred for 2 h at RT. The reaction mixture was evaporated to afford A-418 g (238 mg, 0.79 mmol, 57% yield).

Synthesis of (S)—N-(1-(3-(2-(cyclopropoxymethyl) pyridin-4-yl)-1,2,4-oxadiazol-5-yl)ethyl)-1-methyl-3-(trifluoromethyl)-1H-pyrazole-5-carboxamide (254)

To a stirred solution of 2-methyl-5-(trifluoromethyl)pyrazole-3-carboxylic acid (130.82 mg, 0.67 mmol) in DCM (3 mL) was added DIPEA (0.35 mL, 2.02 mmol), HATU (384.39 mg, 1.01 mmol) and A-418 g (200 mg, 0.67 mmol) and stirred for 2 h at RT. The reaction mixture was diluted with DCM and washed with water (2×5 mL). The organic layer was dried over sodium sulphate and evaporated to afford the crude product which was purified by column chromatography with 20-25% ethyl acetate in hexane as an eluent to afford 254 (60 mg, 0.13 mmol, 20% yield) as a solid. HPLC: Rt 8.78 min, 97.7%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 437.25 (M+H), Rt 2.02 min, Column: X-select CSH C18 (3×50) mm, 2.5 μm. $^1$H NMR (400 MHz, DMSO-$d_6$) $\delta_H$=9.47 (d, 1H), 8.74 (d, 1H), 7.92 (s, 1H), 7.86-7.84 (m, 1H), 7.45 (s, 1H), 5.51-5.46 (m, 1H), 4.69 (s, 2H), 4.13 (s, 3H), 3.51-3.45 (m, 1H), 1.68 (d, 3H), 0.62-0.58 (m, 2H), 0.52-0.46 (m, 2H). Chiral method: Rt 5.14 min, 99.5%; SFC column: DIACEL CHIRALPAK-IG (250×4.6 mm, 5 um), —Mobile Phase: A) $CO_2$ B) MeOH+0.1% $NH_3$, Gradient: 10-40% B in 5 min, hold 40% B till 9 min, 40-10% B in 10 min, hold 10% B till 12 min. Wavelength: 278 nm, Flow: 3 mL/min.

Example 206. Synthesis of 255 and 256

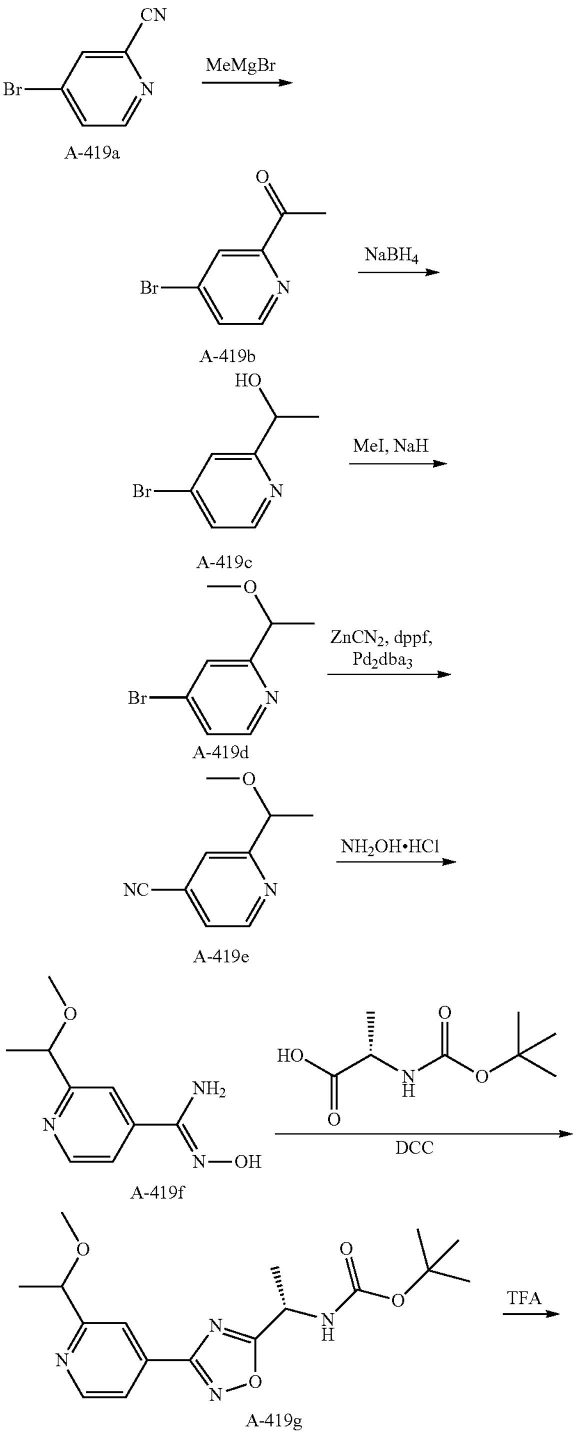

-continued

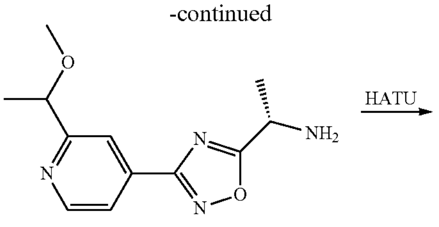

A-419h

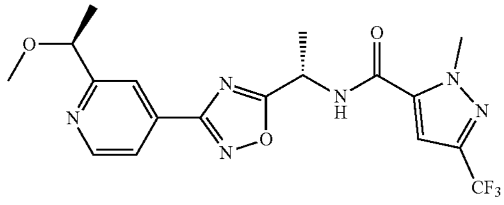

255

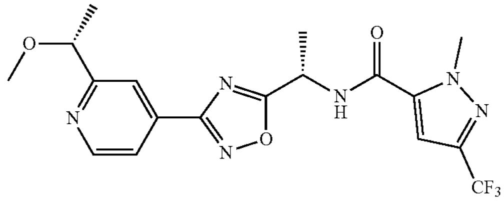

256

Synthesis of 1-(4-bromopyridin-2-yl)ethan-1-one (A-419b)

To a stirred solution of A-419a (8.g, 43.71 mmol) in THF (50 mL) was added MeMgBr (6.25 g, 52.46 mmol) in dropwise manner at 0° C. and stirred at RT for 1 h. The reaction mixture was diluted with saturated $NH_4Cl$ solution and extracted with EtOAc. The organic layer dried over $Na_2SO_4$ filtered and evaporated to afford crude product which was. purified by column chromatography using 100% hexane as an eluent to afford A-419b (4 g, 19.4 mmol, 44% yield) as an oil.

Synthesis of 1-(4-bromo-2-pyridyl)ethanol (A-419c)

To as stirred solution of A-419b (2 g, 10 mmol) in methanol (15 mL) was added $NaBH_4$ (758.89 mg, 20 mmol) in a portion-wise manner and stirred at RT for 1 h. The reaction mixture was evaporated to afford the crude product which was diluted with water and extracted with EtOAc. The organic layer was dried over $Na_2SO_4$ filtered and evaporated to afford A-419c (2 g, 6.23 mmol, 62% yield) as a semi solid. This material was used in the next step without purification.

Synthesis of 4-bromo-2-(1-methoxyethyl)pyridine (A-419d)

To a stirred solution of A-419c (2 g, 9.9 mmol) in THF (20 mL) was added 60% NaH (0.64 mL, 19.8 mmol) in one portion and was stirred at RT for 30 min. To the reaction mixture was added methyl iodide (2.8 g, 19.8 mmol) and stirred at RT for 1 h. The reaction mixture was diluted with water, extracted with EtOAc and the organic layer separated. The organic layer was dried over $Na_2SO_4$, filtered and evaporated to afford A-419d (2.2 g, 10.2 mmol) as an oil.

Synthesis of 2-(1-methoxyethyl)pyridine-4-carbonitrile (A-419e)

To a stirred solution of A-419d (2 g, 9.26 mmol) in DMF (7 mL) was added ZnCN (3.26 g, 27.77 mmol) and the reaction was purged with $N_2$ for 20 min. To the reaction mixture was added DPPF (0.51 g, 0.93 mmol), $Pd_2dba_3$ (0.85 g, 0.93 mmol) and heated at 100° C. for 16 h. The reaction was cooled, diluted with water, extracted with EtOAc and the organic layer separated. The organic layer was dried over $Na_2SO_4$, filtered and evaporated to afford the crude product which was purified by column chromatography using 100-200 mesh silica and 3% EtOAc/hexane as an eluent to afford A-419e (1 g, 4.62 mmol, 50% yield).

Synthesis of N-hydroxy-2-(1-methoxyethyl)pyridine-4-carboxamidine (A-419f)

To a stirred solution of A-419e (900 mg, 5.55 mmol) in ethanol (10 mL) was added $NH_2OH{\cdot}HCl$ (3.43 g, 16.65 mmol), TEA (2.32 mL, 16.65 mmol) and heated at 70° C. for 1 h. The reaction mixture was evaporated and crude product was diluted in water, extracted with EtOAc and the organic layer separated. The organic layer was dried over $Na_2SO_4$, filtered and evaporated to afford A-419f (920 mg, 3.9 mmol, 71% yield) as a solid.

Synthesis of tert-butyl N-[(1S)-1-[3-[2-(1-methoxyethyl)-4-pyridyl]-1,2,4-oxadiazol-5-yl]ethyl]carbamate (A-419 g)

To a stirred solution of A-419f (900 mg, 4.61 mmol) in 1,4-dioxane (10 mL) was added (2R)-2-(tert-butoxycarbonylamino)propanoic acid (872.29 mg, 4.61 mmol), DCC (949.7 mg, 4.61 mmol) and stirred at 100° C. for 16 h. The reaction mixture was diluted in water and extracted with ethyl acetate. The organic layer was dried over $Na_2SO_4$, filtered and evaporated to afford crude product which was purified by column chromatography using 100-200 mesh silica 9% EtOAC/hexane as an eluent to afford A-419 g (700 mg, 1.99 mmol, 43% yield)

Synthesis of (1S)-1-[3-[2-(1-methoxyethyl)-4-pyridyl]-1,2,4-oxadiazol-5-yl]ethanamine (A-419h)

To a stirred solution of A-419 g (350 mg, 1 mmol) in DCM (5 mL) was added TFA (0.23 mL, 3.01 mmol) in a dropwise manner and stirred at RT for 3 h. The reaction mixture was diluted with saturated $NaHCO_3$ solution and extracted with ethyl acetate. The organic layer was dried over $Na_2SO_4$, filtered and evaporated to afford A-419h (180 mg, 0.72 mmol, 72% yield) as an oil.

Synthesis of N—((S)-1-(3-(2-((S)-1-methoxyethyl)pyridin-4-yl)-1,2,4-oxadiazol-5-yl)ethyl)-1-methyl-3-(trifluoromethyl)-1H-pyrazole-5-carboxamide (255) and N—((S)-1-(3-(2-((R)-1-methoxyethyl)pyridin-4-yl)-1,2,4-oxadiazol-5-yl)ethyl)-1-methyl-3-(trifluoromethyl)-1H-pyrazole-5-carboxamide (256). Note that the Stereochemistry of the Ether is Randomly Assigned To a stirred solution of A-419h (180 mg, 0.72 mmol) in DCM (5 mL) was added 2-methyl-5-(trifluoromethyl)pyrazole-3-carboxylic acid (168.87 mg, 0.87 mmol), DIPEA (0.38 mL, 2.17 mmol) and HATU (413.49 mg, 1.09 mmol) and the reaction was stirred at RT for 16 h. The reaction mixture was diluted with water and extracted with DCM and separated. The organic layer was dried over $Na_2SO_4$, filtered and evaporated to afford the crude product which was purified by column chromatography using 100-200 mesh silica and 30% EtOAc/hexane as an eluent to afford racemic mixture which was purified by chiral chromatography to afford 255 (24 mg, 0.056 mmol, 8% yield) and 256 (20 mg, 0.046 mmol, 6.4% yield).

The chiral separation was carried out using SFC: Mobile Phase: A) $CO_2$ B) MeOH+0.1% $NH_3$ Gradient: 10-20% B in 5 min, hold 20-20% B till 4 min, 20-40% B at 2 min, hold 40-50% B till 2 Min. Column: DIACEL CHIRALPAK-IG (250×30 mm, 5 um) Wavelength: 280 nm Flow: 80/min. Note: Stereochemistry has been arbitrarily assigned at one chiral centre.

255:

HPLC: Rt 8.30 min, 98.6%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 425.05 (M+H), Rt 1.90 min, Column: X-select CSH C18 (3×50) mm, 2.5 μm. $^1$H NMR (400 MHz, DMSO-$d_6$) $\delta_H$=9.47 (d, 1H), 8.75 (d, 1H), 7.93 (s, 1H), 7.86-7.84 (m, 1H), 7.45 (s, 1H), 5.50-5.45 (m, 1H), 4.50 (q, 1H), 4.13 (s, 3H), 3.26 (s, 3H), 1.68 (d, 3H), 1.40 (d, 3H). Chiral method: Rt 4.15 min, 100%; SFC column: DIACEL CHIRALPAK-IG (250×4.6 mm, 5 um), —Mobile Phase: A) $CO_2$ B) MeOH+0.1% $NH_3$, Gradient: 10-25% B in 5 min, hold 25% B till 9 min, 25-10% B in 10 min, hold 10% B till 12 min. Wavelength: 280 nm, Flow: 3 mL/min.

256:

HPLC: Rt 8.29 min, 99.2%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 425.05 (M+H), Rt 1.89 min, Column: X-select CSH C18 (3×50) mm, 2.5 μm. $^1$H NMR (400 MHz, DMSO-$d_6$) $\delta_H$=9.47 (d, 1H), 8.75 (d, 1H), 7.93 (s, 1H), 7.86-7.84 (m, 1H), 7.45 (s, 1H), 5.54-5.44 (m, 1H), 4.50 (q, 1H), 4.13 (s, 3H), 3.27 (s, 3H), 1.68 (d, 3H), 1.40 (d, 3H). Chiral method: Rt 4.62 min, 99.6%; SFC column: DIACEL CHIRALPAK-IG (250×4.6 mm, 5 um), —Mobile Phase: A) $CO_2$ B) MeOH+0.1% $NH_3$, Gradient: 10-25% B in 5 min, hold 25% B till 9 min, 25-10% B in 10 min, hold 10% B till 12 min. Wavelength: 280 nm, Flow: 3 mL/min.

Example 207. Synthesis of 257

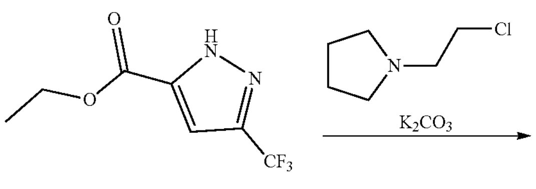

A-405b

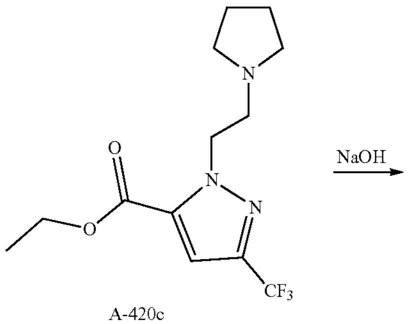

A-420c

-continued

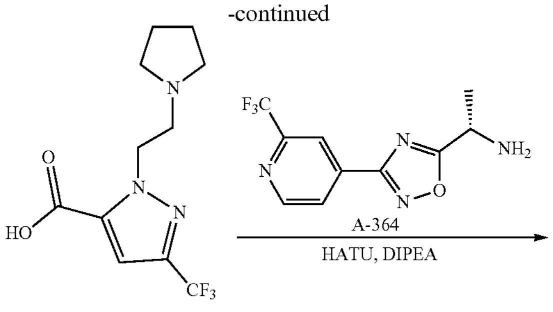

A-420d

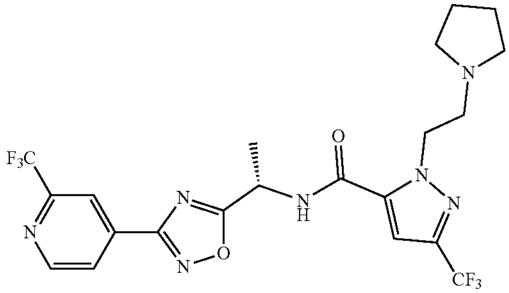

257

Synthesis of 2-(2-pyrrolidin-1-ylethyl)-5-(trifluoromethyl)pyrazole-3-carboxylate (A-420c)

To a stirred solution of A-405b (300 mg, 1.44 mmol) in DMF (5 mL) was added 1-(2-chloroethyl)pyrrolidine (385.18 mg, 2.88 mmol), $K_2CO_3$ (597.49 mg, 4.32 mmol) and stirred at RT for 2 h. The reaction mixture was diluted with water and extracted with EtOAc. The organic layer was dried with $Na_2SO_4$, filtered and concentrated to afford the crude product which was purified by column chromatography using 100-200 mesh silica and 6% EtOAc/hexane as eluent to afford A-420c (200 mg, 0.6551 mmol, 45% yield).

Synthesis of 2-(2-pyrrolidin-1-ylethyl)-5-(trifluoromethyl)pyrazole-3-carboxylic Acid (A-420d)

To a stirred solution of A-420c (130 mg, 0.43 mmol) in THF (2 mL) and water (2 mL) was added sodium hydroxide solution (51.1 mg of NaOH in 2 mL water). The reaction mixture was stirred at RT for 3 h and concentrated to afford the crude product which was diluted with water and extracted with EtOAc. The aqueous layer was acidified with 2 N HCl then extracted with EtOAc. The combined organic layer was dried over $Na_2SO_4$, filtered and concentrated to afford A-420d (80 mg, 0.29 mmol, 68% yield) as an oil.

Synthesis of (S)-1-(2-(pyrrolidin-1-yl)ethyl)-3-(trifluoromethyl)-N-(1-(3-(2-(trifluoromethyl)pyridin-4-yl)-1,2,4-oxadiazol-5-yl)ethyl)-1H-pyrazole-5-carboxamide (257)

To a stirred solution A-420d (107.37 mg, 0.39 mmol) and (1S)-1-[3-[2-(trifluoromethyl)-4-pyridyl]-1,2,4-oxadiazol-5-yl]ethanamine (100 mg, 0.39 mmol) in DCM (3 mL) was added DIPEA (0.2 mL, 1.16 mmol), HATU (220.89 mg, 0.58 mmol) and stirred at RT for 16 h. The reaction mixture was diluted with water and extracted with EtOAc. The organic layer was dried ($NaSO_4$), filtered and concentrated to afford the crude product which was purified by prep HPLC to afford 257 (10 mg, 0.018 mmol, 5% yield). HPLC: Rt 6.37 min, 94.4%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 518.10 (M+H), Rt 1.53 min, 99.3%; Column: X-select CSH C18 (3×50) mm, 2.5 μm. $^1$H NMR (400 MHz, DMSO-$d_6$) $\delta_H$=9.59 (d, 1H), 9.02 (d, 1H), 8.30-8.26 (m, 2H), 7.39 (s, 1H), 5.51-5.46 (m, 1H), 4.71-4.63 (m, 2H), 2.85-2.75 (m, 2H), 2.49-2.42 (m, 4H), 1.69 (d, 3H), 1.62-1.56 (m, 4H). Chiral method: Rt 7.99 min, 95.6%; column: DIACEL CHIRALPAK-IG (250×4.6 mm, 5 um), —Mobile Phase: A) n-Hexane+0.1% Iso-propyl-amine B) DCM:MeOH (90:10), Isocratic: 20% B; Wavelength: 250 nm, Flow: 1.0 mL/min.

Example 208. Synthesis of 258

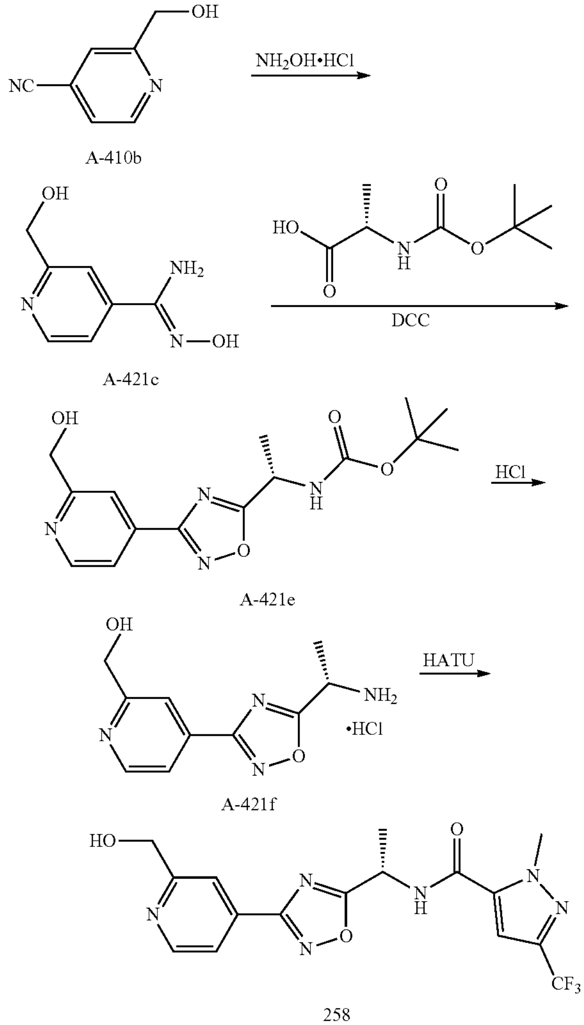

A-410b

A-421c

A-421e

A-421f

258

Synthesis of N'-hydroxy-2-(hydroxymethyl)pyridine-4-carboxamidine (A-421c)

To a stirred solution of A-410b (0.5 g, 3.73 mmol) in ethanol (10 mL) was added hydroxylamine hydrochloride (388.53 mg, 5.59 mmol), TEA (1.04 mL, 7.45 mmol) and stirred for 6 h at 80° C. The reaction mixture was quenched with water (10 mL) and diluted with EtOAc (100 mL×2).

The organic layer was separated, dried over $Na_2SO_4$, filtered and evaporated to afford the crude product which was purified by column chromatography using 100-200 silica at 30-80% EtOAc/Hexane as an eluent to afford A-421c (0.5 g, 1.49 mmol, 40% yield).

Synthesis of tert-butyl N-[(1S)-1-[3-[2-(hydroxymethyl)-4-pyridyl]-1,2,4-oxadiazol-5-yl]ethyl]carbamate (A-421e)

To a stirred solution of A-421c (0.5 g, 2.99 mmol) and (2S)-2-(tert-butoxycarbonylamino)propanoic acid (565.92 mg, 2.99 mmol) in 1,4-dioxane (10 mL) was added DCC (616.14 mg, 2.99 mmol) and the reaction was stirred for 12 h at 100° C. The reaction mixture was quenched with water (10 mL) and diluted with EtOAc (100 mL×2). The combined organic layer was separated, dried over $Na_2SO_4$, filtered, evaporated under reduced pressure and purified by column chromatography using 100-200 silica and 30-80% EtOAc/Hexane as an eluent to afford A-421e (0.4 g, 1.07 mmol, 36% yield) as a solid.

Synthesis of tert-butyl N-[(1S)-1-[3-[2-(hydroxymethyl)-4-pyridyl]-1,2,4-oxadiazol-5-yl]ethyl]carbamate (A-421f) hydrochloride salt To a stirred solution of A-421e (0.4 g, 1.25 mmol) in 1,4-dioxane (5 mL) was added 4 M HCl in 1,4 dioxane (6 mL, 1.25 mmol) and stirred at 0° C. for 2 h. The reaction mixture was evaporated to afford the crude product which was washed using diethyl ether to afford A-421f (0.3 g, 1.05 mmol, 84% yield).

Synthesis of N-[(1S)-1-[3-[2-(hydroxymethyl)-4-pyridyl]-1,2,4-oxadiazol-5-yl]ethyl]-2-methyl-5-(trifluoromethyl)pyrazole-3-carboxamide (258)

To a stirred solution of A-421f (0.3 g, 1.17 mmol) and 2-methyl-5-(trifluoromethyl)pyrazole-3-carboxylic acid (249.55 mg, 1.29 mmol) in DCM (10 mL) was added HATU (666.58 mg, 1.75 mmol) and DIPEA (0.41 mL, 2.34 mmol) and stirred for 2 h at RT. The reaction mixture was quenched with water (100 mL) and DCM (100 mL×2) was added. The organic layer was separated, dried over $Na_2SO_4$, then filtered and evaporated to afford the crude product. Purification by column chromatography using 100-200 silica and 30-80% EtOAc/Hexane as an eluent afforded 258 (15 mg, 0.037 mmol, 3% yield). HPLC: Rt 7.20 min, 99.6%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 397.05 (M+H), Rt 1.70 min, Column: X-select CSH C18 (3×50) mm, 2.5 μm. $^1$H NMR (400 MHz, DMSO-$d_6$) $\delta_H$=9.48 (d, 1H), 8.70 (d, 1H), 8.04 (s, 1H), 7.82-7.78 (m, 1H), 7.45 (s, 1H), 5.65-5.55 (m, 1H), 5.51-5.46 (m, 1H), 4.66 (s, 2H), 4.13 (s, 3H), 1.69 (d, 3H). Chiral method: Rt 5.38 min, 100%; column: DIACEL CHIRALPAK-IG (250×4.6 mm, 5 um), —Mobile Phase: A) n-Hexane+0.1% Iso-propyl-amine B) DCM: MeOH (1:1), Isocratic: 50% B; Wavelength: 230 nm, Flow: 1.0 mL/min.

Example 209. Synthesis of 259

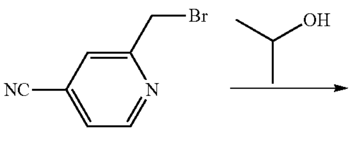

A-418c

-continued

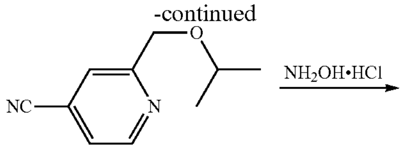

A-422d

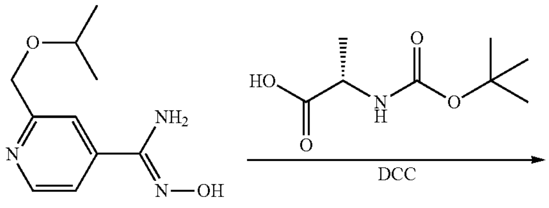

A-422e

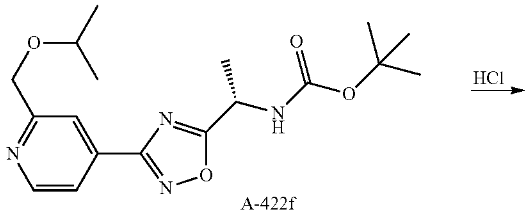

A-422f

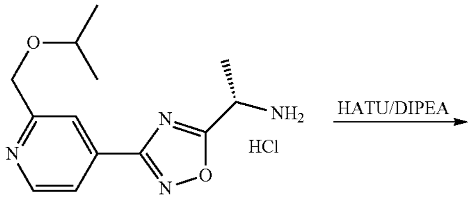

A-422g

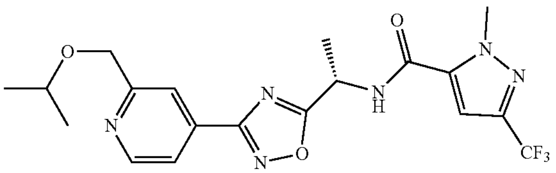

259

Synthesis of 2-(isopropoxymethyl)pyridine-4-carbonitrile (A-422d)

To a stirred solution of 2-propanol (1.13 g, 18.77 mmol) in THF (20 mL) was added NaH (0.68 g, 28.16 mmol) at 0-5° C. and stirred for 30 min at 0-5° C. To the resulting reaction was added A-418c (1.85 g, 9.39 mmol) in THF (20 mL) in a dropwise manner. The reaction mixture was stirred for 5 h at RT. The reaction mixture was quenched with ice cold water and extracted with ethyl acetate (2×20 mL). The combined organic layer was dried over sodium sulphate and concentrated. The crude product was purified by column chromatography, using 10-15% of ethyl acetate in hexane as an eluent to afford A-422d (830 mg, 4.39 mmol, 47% yield).

Synthesis of N'-hydroxy-2-(isopropoxymethyl)pyridine-4-carboxamidine (A-422e)

To a stirred solution of A-422d (800 mg, 4.54 mmol) in ethanol (8 mL) was added TEA (1.27 mL, 9.08 mmol) and hydroxylamine hydrochloride (473.2 mg, 6.81 mmol) and stirred for 3 h at reflux. The reaction mixture was concentrated under reduced pressure and diluted with ethyl acetate (20 mL). The organic layer was washed with water (10 mL×2) and the organic layer was evaporated to afford A-422e (800 mg, 3.77 mmol, 83% yield).

Synthesis of tert-butyl (S)-(1-(3-(2-(cyclopropoxymethyl)pyridin-4-yl)-1,2,4-oxadiazol-5-yl) ethyl)carbamate (A-422f)

To a stirred solution of A-422e (700 mg, 3.35 mmol) in 1,4-dioxane (7 mL) was added N,N'-dicyclohexylcarbodiimide (DCC) (759.29 mg, 3.68 mmol) and N-Boc-L-alanine (696.29 mg, 3.68 mmol) at RT and the reaction mixture was stirred for 4 h at reflux. The reaction mixture was filtered and diluted with ethyl acetate and washed with water (3×10 mL). The organic layer was dried over sodium sulphate and concentrated to afford the crude product which was purified by column chromatography. using 25-30% of ethyl acetated in hexane as eluent to afford A-422f (700 mg, 1.84 mmol, 55% yield).

Synthesis of (1S)-1-[3-[2-(isopropoxymethyl)-4-pyridyl]-1,2,4-oxadiazol-5-yl]ethanamine Hydrochloride (A-422 g)

To a stirred solution of A-422f (0.7 g, 1.93 mmol) in 1,4-dioxane (5 mL) was added 4 M HCl/dioxane (5 mL) and stirred for 2 h at RT. The reaction mixture was evaporated under reduced pressure to afford A-422 g (450 mg, 1.48 mmol, 77% yield) as a hydrochloride salt.

Synthesis of N-[(1S)-1-[3-[2-(isopropoxymethyl)-4-pyridyl]-1,2,4-oxadiazol-5-yl]ethyl]-2-methyl-5-(trifluoromethyl)pyrazole-3-carboxamide (259)

To a stirred solution of 2-methyl-5-(trifluoromethyl)pyrazole-3-carboxylic acid (116.95 mg, 0.6 mmol) in DCM (2 mL) was added DIPEA (0.09 mL, 0.5 mmol), HATU (286.35 mg, 0.7500 mmol) and A-422 g (150.mg, 0.5 mmol) and stirred for 2 h at RT. The reaction mixture was diluted with DCM and washed with water (2×5 mL). The organic layer was dried over sodium sulphate and concentrated to afford the crude product which was purified by column chromatography using at 30% ethyl acetate in hexane as an eluent to afford 259 (75 mg, 0.16 mmol, 33% yield) as a solid. HPLC: Rt 8.73 min, 96.3%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 439.25 (M+H), Rt 2.02 min, Column: X-select CSH C18 (3×50) mm, 2.5 μm. $^1$H NMR (400 MHz, DMSO-$d_6$) $\delta_H$=9.47 (d, 1H), 8.72 (d, 1H), 7.96 (s, 1H), 7.84-7.80 (m, 1H), 7.44 (s, 1H), 5.52-5.45 (m, 1H), 4.64 (s, 2H), 4.13 (s, 3H), 3.80-3.72 (m, 1H), 1.68 (d, 3H), 1.18 (d, 6H). Chiral method: Rt 8.94 min, 100%; column: DIACEL CHIRALPAK-IG (250×4.6 mm, 5 um), —Mobile Phase: A) n-Hexane+0.1% Iso-propyl-amine B) DCM: MeOH (90:10), Isocratic: 20% B; Wavelength: 280 nm, Flow: 1.0 mL/min.

Example 210. Synthesis of 260 and 261

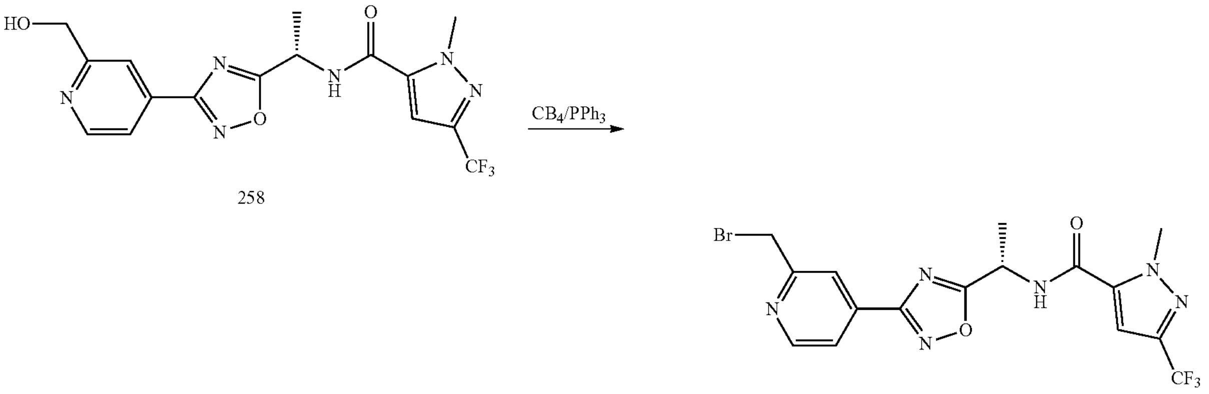

258

A-423a

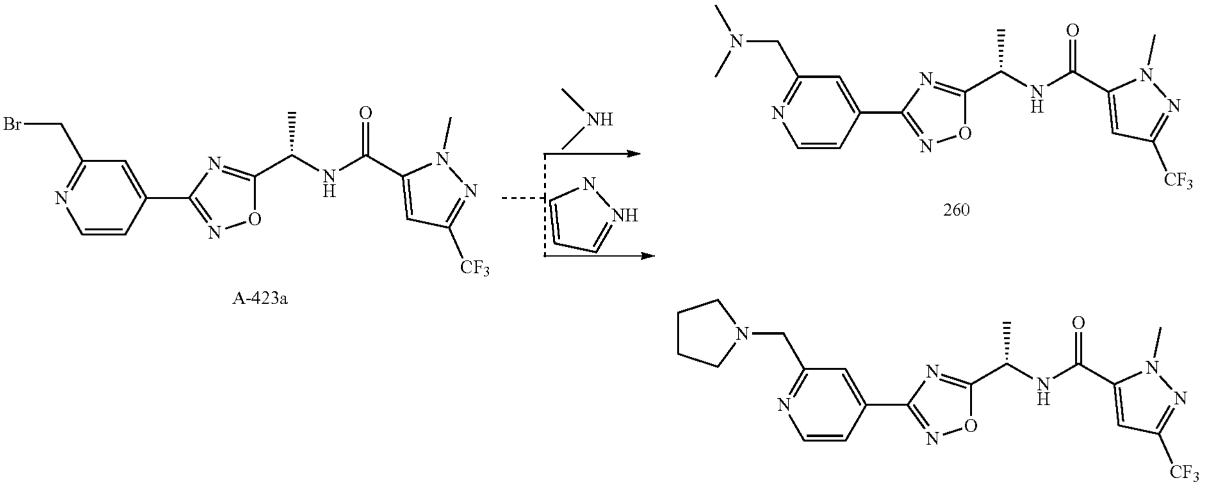

260

A-423a

261

Synthesis of N-[(1S)-1-[3-[2-(bromomethyl)-4-pyridyl]-1,2,4-oxadiazol-5-yl]ethyl]-2-methyl-5-(trifluoromethyl)pyrazole-3-carboxamide (A-423a)

To a stirred solution of 258 (600 mg, 1.51 mmol) in DCM (3 mL) was added $CBr_4$ (1 g, 3.03 mmol) and $PPh_3$ (794.18 mg, 3.03 mmol) in portions at 0° C. and stirred at 0° C. for 30 min. The reaction mixture was evaporated to afford the crude product which was purified by column chromatography using 100-200 mesh silica and 30% EtOAc:hexane as an eluent to afford A-423a (250 mg, 0.45 mmol, 30% yield) as an oil.

Synthesis of (S)-1-methyl-N-(1-(3-(2-(pyrrolidin-1-ylmethyl)pyridin-4-yl)-1,2,4-oxadiazol-5-yl)ethyl)-3-(trifluoromethyl)-1H-pyrazole-5-carboxamide (261)

To a stirred solution of A-423a (100 mg, 0.22 mmol) in THF (3 mL) was added pyrrolidine (0.04 mL, 0.44 mmol) and DIPEA (0.11 mL, 0.65 mmol) at RT and stirred for 2 h. The reaction mixture was diluted with water and extracted with ethylacetate and the organic layer was dried over $Na_2SO_4$, filtered and evaporated to afford crude product which was purified by prep HPLC to afford 261 (10 mg, 0.02 mmol, 10% yield) as an oil. HPLC: Rt 5.90 min, 98.8%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 450.15 (M+H), Rt 1.39 min; Column: X-select CSH C18 (3×50) mm, 2.5 μm. $^1$H NMR (400 MHz, DMSO-$d_6$) $\delta_H$=9.46 (d, 1H), 8.69 (d, 1H), 8.16 (s, 1H), 7.97 (s, 1H), 7.81-7.78 (m, 1H), 7.44 (s, 1H), 5.50-5.45 (m, 1H), 4.13 (s, 3H), 3.82 (s, 2H), 1.75-1.65 (m, 6H), 4H merged in solvent peak. Chiral method: Rt 5.79 min, 99.6%; column: DIACEL CHIRALPAK-IG (250×4.6 mm, 5 um), —Mobile Phase: A) n-Hexane+0.1% Iso-propyl-amine B) EtOH, Isocratic: 15% B; Wavelength: 278 nm, Flow: 1.0 mL/min.

Synthesis of (S)—N-(1-(3-(2-((dimethylamino)methyl)pyridin-4-yl)-1,2,4-oxadiazol-5-yl)ethyl)-1-methyl-3-(trifluoromethyl)-1H-pyrazole-5-carboxamide (260)

To a stirred solution A-423a (100 mg, 0.2200 mmol) in THF (3 mL) was added dimethylamine (0.03 mL, 0.65 mmol) and stirred at RT for 1 h. The reaction mixture was diluted with water and extracted with EtOAc. The organic layer was dried over $Na_2SO_4$ filtered and concentrated to afford the crude product which was purified using prep HPLC to afford 260 (6 mg, 0.014 mmol, 6% yield) as an oil. HPLC: Rt 5.76 min, 96.2%; Column: X-Select CSH C18

(4.6×150) mm, 5 μm; Mobile phase: A: 0.1% Formic acid in water: ACN (95:05), B: ACN; Flow Rate: 1.0 mL/min. LCMS: 424.10 (M+H), Rt 1.40 min, Column: X-select CSH C18 (3×50) mm, 2.5 μm. $^1$H NMR (400 MHz, DMSO-$d_6$) $\delta_H$=9.47 (d, 1H), 8.69 (d, 1H), 7.99 (s, 1H), 7.82-7.80 (m, 1H), 7.45 (s, 1H), 5.50-5.45 (m, 1H), 4.13 (s, 3H), 3.62 (s, 2H), 2.22 (s, 6H), 1.68 (d, 3H). Chiral method: Rt 5.83 min, 99.6%; column: DIACEL CHIRALPAK-IG (250×4.6 mm, 5 um), —Mobile Phase: A) n-Hexane+0.1% Iso-propyl-amine B) EtOH, Isocratic: 15% B; Wavelength: 278 nm, Flow: 1.0 mL/min.

Example 211. Synthesis of 262 and 263

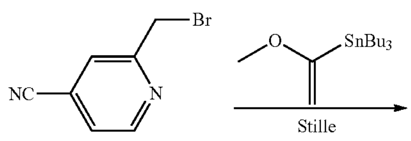

A-424a

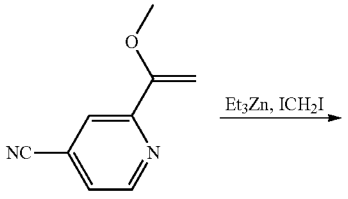

A-424b

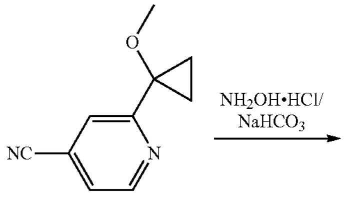

A-424c

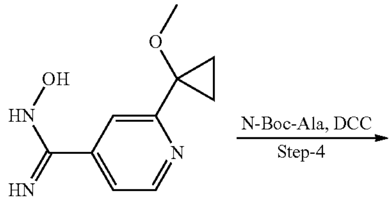

A-424d

262

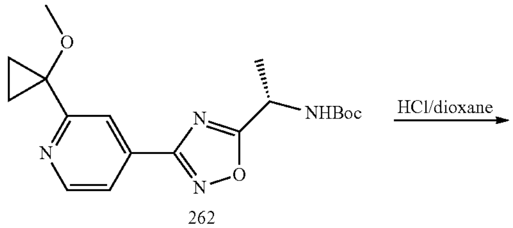

262

-continued

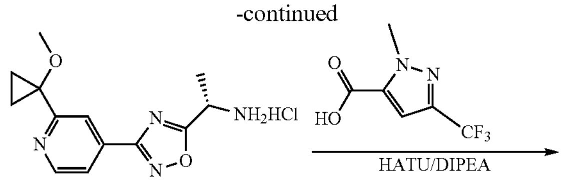

A-424f

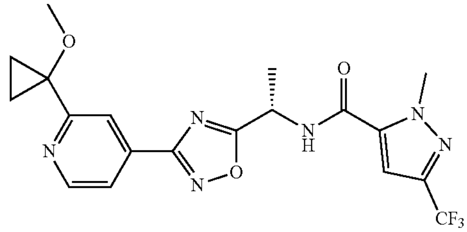

263

Synthesis of 2-(1-methoxyvinyl)isonicotinonitrile (A-424b)

To a stirred solution of A-424a (1.2 g, 6.56 mmol) in ACN (10 mL) was added tributyl(1-methoxyvinyl)stannane (1.8 g, 5.25 mmol), L-Proline (20.83 mg, 0.18 mmol) and sodium hydroxide (7.24 mg, 0.18 mmol) and stirred at 90° C. for 16 h. The reaction mixture was quenched with water (100 mL) and diluted with EtOAc (50 mL). The organic layer was separated, and dried with $Na_2SO_4$, filtered and evaporated to afford crude reaction product. The crude product was purified by column chromatography using 100-200 silica and 30-80% EtOAc/Hexane as an eluent to afford A-424b (1 g, 3.12 mmol, 48% yield) as a solid.

Synthesis of 2-(1-methoxycyclopropyl)isonicotinonitrile (A-424c)

To a solution of diethyl zinc (1.5 g, 12.46 mmol) in DCM was added di-iodo methane (1.01 mL, 12.49 mmol) and stirred for 1 hr 0° C. To the resulting reaction mixture was added A-424b (0.5 g, 3.12 mmol) at 0° C. and stirred at RT for 2 h. The reaction mixture was quenched with water and diluted with ethyl acetate. The organic layer was separated and dried over $Na_2SO_4$ and evaporated to afford the crude product which was purified by column chromatography using 100-200 silica and 10-30% EtOAc/hexane as an eluent to afford A-424c (300 mg, 0.86 mmol, 28% yield).

Synthesis of N-hydroxy-2-(1-methoxycyclopropyl) isonicotinimidamide (A-424d)

To a mixture of A-424c (300 mg, 1.72 mmol) and hydroxylamine hydrochloride (143.61 mg, 2.07 mmol) in ethanol (5 mL) was added TEA (0.48 mL, 3.44 mmol) and heated at 80° C. for 16 h. The reaction mixture was diluted with water and extracted with ethyl acetate. The organic layer was washed with water and brine, dried over sodium sulphate and evaporated to afford the crude product which was further purified by column chromatography using 100-200 silica and 20-50% EtOAc/hexane as an eluent to afford A-424d (100 mg, 0.24 mmol, 14% yield).

Synthesis of tert-butyl (S)-(1-(3-(2-(1-methoxycyclopropyl)pyridin-4-yl)-1,2,4-oxadiazol-5-yl)ethyl) carbamate (262)

To a mixture of A-424d (0.1 g, 0.48 mmol) and (2S)-2-(tert-butoxycarbonylamino)propanoic acid (109.6 mg, 0.58 mmol) in 1,4-dioxane (10 mL) was added DCC (198.8 mg, 0.97 mmol) and heated at 100° C. for 16 h. The reaction mixture was diluted with water and extracted with ethyl acetate. The combined organic layer was washed with water and brine, dried over sodium sulphate and evaporated to afford the crude product which was purified by combi-flash chromatography using ethyl acetate: hexane as an eluent, to afford 200 mg crude product which was further purified by prep HPLC to afford 262 as a solid (10 mg, 0.027 mmol, 6% yield). HPLC: Rt 8.96 min, 99.8%; Column: X-Select CSH C18 (4.6×150) mm, 5 μm; Mobile phase: A: 0.1% Formic acid in water, B: ACN (95:5); Flow Rate: 1 mL/min. LCMS: 360.95 (M+H), Rt 2.05 min, Column: X-select CSH C18 (3×50) mm, 2.5 μm. $^1H$ NMR (400 MHz, DMSO-$d_6$) $\delta_H$=8.65 (d, 1H), 7.82-7.79 (m, 2H), 7.67 (d, 1H), 5.05-4.95 (m, 1H), 1.54-1.51 (m, 6H), 1.40-1.36 (m, 9H), 1.24-1.22 (m, 2H), 0.89-0.87 (m, 2H). Chiral method: Rt 5.36 min, 100%; SFC column: DIACEL CHIRALPAK-IG (250×4.6 mm, 5 um), —Mobile Phase: A) n-hexane+0.1% isopropyl amine B) DCM: MeOH (1:1), Isocratic: 50% B. Wavelength: 290 nm, Flow: 3 mL/min.

Synthesis of (S)-1-(3-(2-(1-methoxycyclopropyl) pyridin-4-yl)-1,2,4-oxadiazol-5-yl)ethan-1-amine Hydrochloride (A-424f)

To a stirred solution of 262 (60 mg, 0.17 mmol) in 1,4-dioxane (10 mL) was added 4 M HCl in 1,4-dioxane (10 mL) at 0° C. and stirred at RT for 6 h. The reaction mixture was concentrated to afford A-424f (40 mg, 0.14 mmol, 83% yield) as a solid.

Synthesis of (S)—N-(1-(3-(2-(1-methoxycyclopropyl)pyridin-4-yl)-1,2,4-oxadiazol-5-yl)ethyl)-1-methyl-3-(trifluoromethyl)-1H-pyrazole-5-carboxamide (263)

To a stirred solution 2-methyl-5-(trifluoromethyl)pyrazole-3-carboxylic acid (31.4 g, 0.16 mmol) in DCM (5 mL) was added A-424f (31.6 g, 0.16 mmol), HATU (77 mg, 0.2 mmol), DIPEA (0.05 mL, 0.27 mmol) in water (1 mL) and stirred at RT 2 h. The reaction mixture was diluted with water nd DCM. The organic layer was separated, washed with saturated brine solution (20 mL), separated and dried over $MgSO_4$, The solution was evaporated to dryness and the crude product was then purified using prep HPLC to afford 263 (10 mg, 0.023 mmol, 17% yield) as a solid. HPLC: Rt 4.71 min, 99%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 437.20 (M+H), Rt 2.06 min; Column: X-select CSH C18 (3×50) mm, 2.5 μm. $^1H$ NMR (400 MHz, DMSO-$d_6$) $\delta_H$=9.46 (d, 1H), 8.61 (d, 1H), 7.87 (s, 1H), 7.69-7.66 (m, 1H), 7.45 (s, 1H), 5.50-5.45 (m, 1H), 4.13 (s, 3H), 1.68 (d, 3H), 1.04-0.97 (m, 4H), 3H merged in solvent peak. Chiral method: Rt 6.92 min, 99.66%; column: DIACEL CHIRALPAK-IG (250×4.6 mm, 5 um), —Mobile Phase: A) n-Hexane+0.1% TFA B) DCM: MeOH (50:50), Isocratic: 25% B; Wavelength: 254 nm, Flow: 1.0 mL/min.

Example 212. Synthesis of 264

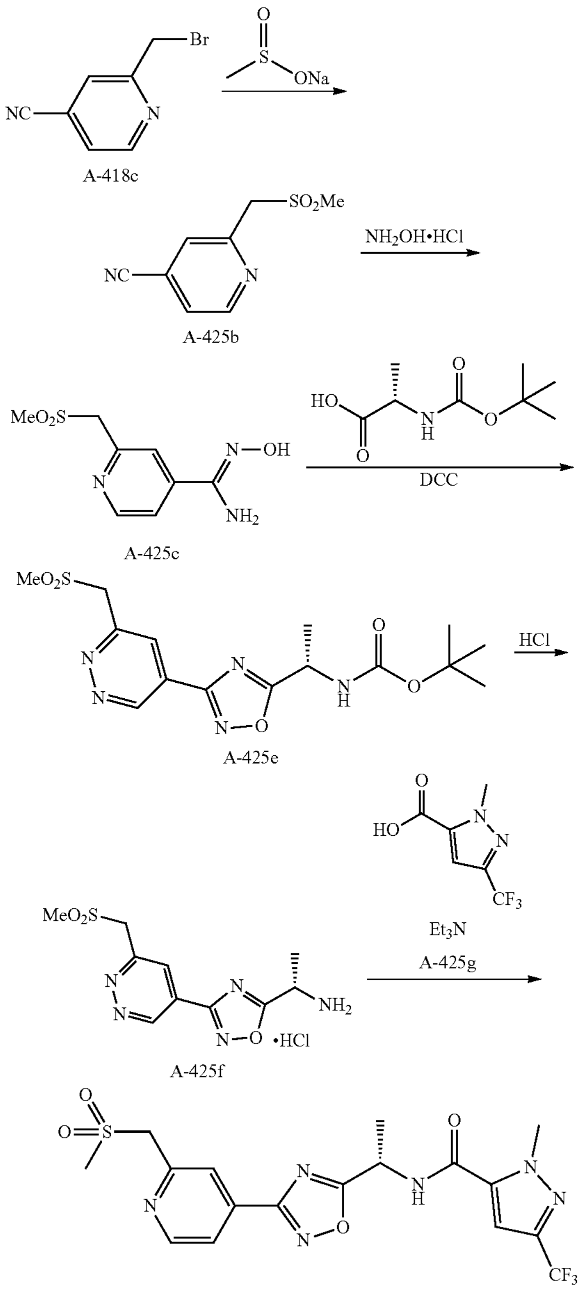

264

Synthesis of 2-((methylsulfonyl)methyl)isonicotinonitrile (A-425b)

To a stirred solution of A-418c (1 mg, 0.01 mmol) in DMF (10 mL) was added sodium methanesulfinate (0.78 mg, 0.01 mmol) and TBAI (0.37 mg) at RT and stirred for 7h. The reaction mixture was quenched with ice cold water and extracted with ethyl acetate and the organic layer separated. The organic layer was washed with water (1×5 mL), dried over sodium sulphate and evaporated to afford A-425b (0.55 mg, 0.0026 mmol, 51% yield).

Synthesis of (Z)—N'-hydroxy-2-((methylsulfonyl) methyl)isonicotinimidamide (A-425c)

To a stirred solution of A-425b (350 mg, 1.78 mmol) in ethanol (4 mL) was added TEA (0.5 mL, 3.57 mmol) and hydroxylamine hydrochloride (185.92 mg, 2.68 mmol) at RT and the reaction mixture was stirred for 3 h at reflux. The reaction mixture was evaporated and the residue diluted with ethyl acetate (20 mL). The organic layer was washed with water (2×10 mL), brine, dried over sodium sulphate and evaporated to afford A-425c (550 mg, 1.33 mmol, 75% yield) as a solid.

Synthesis of tert-butyl (S)-(1-(3-(6-((methylsulfonyl)methyl)pyridazin-4-yl)-1,2,4-oxadiazol-5-yl) ethyl)carbamate (A-425e)

To a stirred solution of A-425c (0.5 g, 1.21 mmol) in 1,4-dioxane (5 mL) was added N,N'-dicyclohexylcarbodiimide (DCC) (0.27 g, 1.33 mmol) and N-Boc-L-alanine (0.25 g, 1.33 mmol) at RT and stirred for 12 h at reflux. The reaction mixture was filtered then diluted with ethyl acetate and washed with water (3×5 mL). The organic layer was dried over sodium sulphate and evaporated to afford the crude product which was purified by column chromatography using silica gel and 25-30% of ethyl acetated in hexane as an eluent to afford A-425e (165 mg, 0.35 mmol, 29% yield) as a solid.

Synthesis of (1R)-1-[3-[2-(methylsulfonylmethyl)-4-pyridyl]-1,2,4-oxadiazol-5-yl]ethanamine hydrochloride (A-425f)

To a stirred solution of A-425e (150 mg, 0.39 mmol) in 1,4-dioxane (3 mL) was added 4 M HCl in dioxane (3 mL) at RT and stirred for 2h. The reaction mixture was evaporated under reduced pressure to afford A-425f (165 mg, 0.37 mmol, 97% yield).

Synthesis of 2-methyl-N-[(1S)-1-[3-[2-(methylsulfonylmethyl)-4-pyridyl]-1,2,4-oxadiazol-5-yl]ethyl]-5-(trifluoromethyl)pyrazole-3-carboxamide (264)

To a stirred solution of 2-methyl-5-(trifluoromethyl)pyrazole-3-carboxylic acid (95 mg, 0.49 mmol) in DCM (2 mL) was added DIPEA (0.39 mL, 2.25 mmol) and HATU (232.6 mg, 0.6100 mmol) and stirred for 15 min at RT. To the resulting reaction mixture was added A-425f (130 mg, 0.41 mmol) and the reaction was stirred for 3 h. The reaction mixture was diluted with DCM. The organic layer was washed with water (3×5 mL), dried over sodium sulphate and evaporated to afford a crude product which was purified using column chromatography to afford 264 (25 mg, 0.05 mmol, 13% yield) as a solid. HPLC: Rt 7.76 min, 99.8%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 459.85 (M+H), Rt 1.71 min; Column: X-select CSH C18 (3×50) mm, 2.5 μm. $^1H$ NMR (400 MHz, DMSO-$d_6$) $\delta_H$=9.50-9.47 (m, 1H), 8.81 (d, 1H), 8.10 (s, 1H), 7.96-7.94 (m, 1H), 7.45 (s, 1H), 5.50-5.46 (m, 1H), 4.82 (s, 2H), 4.13 (s, 3H), 3.05 (s, 3H), 1.68 (d, 3H). Chiral method: Rt 6.06 min, 99.4%; column: DIACEL CHIRALPAK-IG (250×4.6 mm, 5 um), —Mobile Phase: A) n-Hexane+0.1% Iso propyl amine B) EtOH:MeOH (50:50), Isocratic: 25% B; Wavelength: 279 nm, Flow: 1.0 mL/min.

Example 213. Synthesis of 265

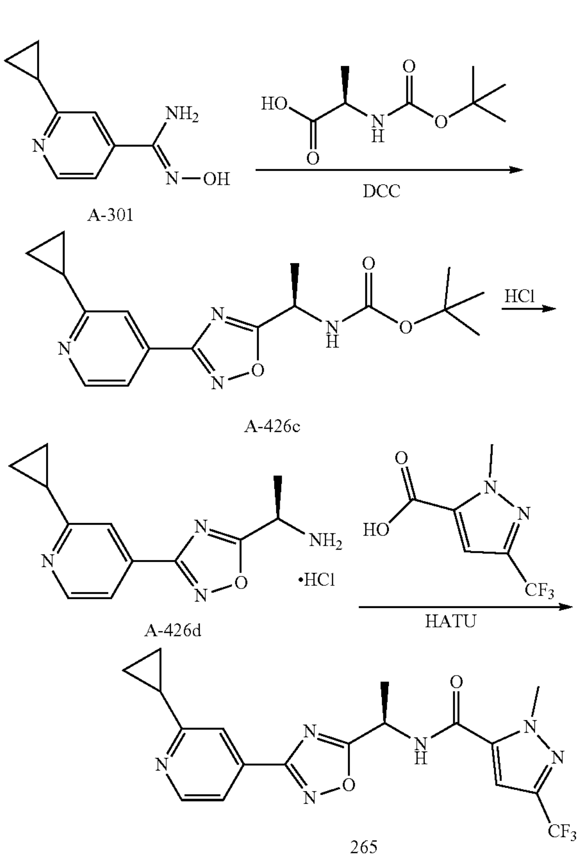

Synthesis of tert-butyl N-[(1R)-1-[3-(2-cyclopropyl-4-pyridyl)-1,2,4-oxadiazol-5-yl]ethyl]carbamate (A-426c)

To a stirred solution of A-301 (0.5 g, 2.82 mmol) in 1,4-dioxane (5 mL) was added N,N'-dicyclohexylcarbodiimide (DCC) (0.64 g, 3.1 mmol) and N-Boc-D-alanine (0.59 g, 3.1 mmol) at RT and stirred for 12 h at reflux. The reaction mixture was filtered, diluted with ethyl acetate, washed with water (3×5 mL) and separated. The organic layer was dried over sodium sulphate and evaporated under reduced pressure to afford the crude product which was purified by column chromatography using silica and 25-30% of ethyl acetated in hexane as an eluent to afford A-426c (0.63 g, 1.79 mmol, 63% yield) as a solid.

Synthesis of (R)-1-(3-(2-cyclopropylpyridin-4-yl)-1,2,4-oxadiazol-5-yl)ethan-1-amine hydrochloride (A-426d)

To the stirred solution of A-426c (500 mg, 1.51 mmol) in 1,4-dioxane (5 mL) was added 4 M HCl/dioxane (3 mL) at RT and stirred for 2 h. The reaction mixture was evaporated under to afford A-426d (350 mg, 0.81 mmol, 53% yield).

Synthesis of N-[(1R)-1-[3-(2-cyclopropyl-4-pyridyl)-1,2,4-oxadiazol-5-yl]ethyl]-2-methyl-5-(trifluoromethyl)pyrazole-3-carboxamide (265)

To a stirred solution of 2-methyl-5-(trifluoromethyl)pyrazole-3-carboxylic acid (174.66 mg, 0.9 mmol) in DCM (2 mL) was added DIPEA (0.39 mL, 2.25 mmol) and HATU (427.66 mg, 1.12 mmol) and stirred for 15 min at RT. To the resulting reaction was added A-426d (200 mg, 0.75 mmol) and stirred for 3 h at RT. The reaction was diluted with DCM and the organic layer was washed with water (3×5 mL), dried over sodium sulphate and evaporated to afford the crude product which was purified using column chromatography to afford 265 (50 mg, 0.13 mmol, 16% yield) as a solid. HPLC: Rt 9.28 min, 99.9%; Column: X-Select CSH C18 (4.6×150) mm, 5 μm; Mobile phase: A: 10 mM Ammonium Bicarbonate in water; B: ACN; Flow Rate: 1.0 mL/min. LCMS: 407.06 (M+H), Rt 2.09 min; Column: X-select CSH C18 (3×50) mm, 2.5 μm. $^1$H NMR (400 MHz, DMSO-$d_6$) $\delta_H$=9.47 (d, 1H), 8.61 (d, 1H), 7.87 (s, 1H), 7.68-7.66 (m, 1H), 7.45 (s, 1H), 5.50-5.45 (m, 1H), 4.13 (s, 3H), 2.34-2.28 (m, 1H), 1.68 (d, 3H), 1.05-0.98 (m, 4H). Chiral method: Rt 9.37 min, 99.7%; column: DIACEL CHIRALPAK-IG (250×4.6 mm, 5 um), —Mobile Phase: A) n-Hexane+0.1% TFA B) Iso propyl Alcohol, Isocratic: 10% B; Wavelength: 210-240 nm, Flow: 1.0 mL/min.

Example 214. Synthesis of 266

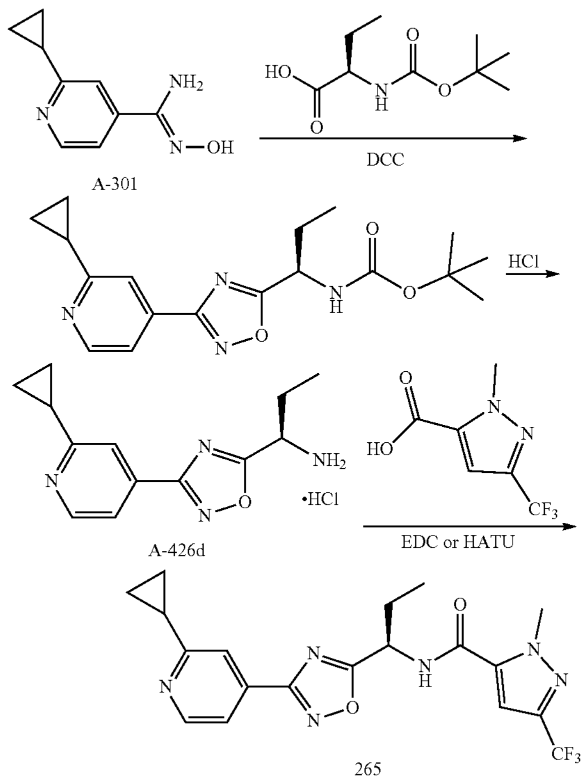

Synthesis of tert-butyl N-[(1R)-1-[3-(2-cyclopropyl-4-pyridyl)-1,2,4-oxadiazol-5-yl]propyl]carbamate (A-427d)

To a stirred solution of A-301 (200 mg, 1.13 mmol) in 1,4-dioxane (4 mL) was added (2R)-2-(tert-butoxycarbonylamino)butanoic acid (275.27 mg, 1.35 mmol) and DCC (279.01 mg, 1.35 mmol) and the reaction mixture was heated at 100° C. for 16 h. The reaction mixture was cooled then diluted with water and extracted with EtOAc. The organic was dried over $Na_2SO_4$, filtered and evaporated to afford the crude product which was purified by combiflash chromatography using 100-200 mesh silica and 6% EtOAc/hexane as an eluent to afford A-427d (210 mg, 0.58 mmol, 51% yield) as an oil.

Synthesis of (1R)-1-[3-(2-cyclopropyl-4-pyridyl)-1,2,4-oxadiazol-5-yl]propan-1-amine hydrochloride (A-427e)

To a stirred solution of A-427d (200 mg, 0.58 mmol) in 1,4-dioxane (2 mL) was added 4 M HCl in 1,4 dioxane (1.12 mL, 2.9 mmol) in a dropwise manner. The reaction mixture was stirred at RT for 16 h then the reaction mixture was evaporated to afford A-427e (120 mg, 0.38 mmol, 66% yield) as a solid.

Synthesis of N-[(1R)-1-[3-(2-cyclopropyl-4-pyridyl)-1,2,4-oxadiazol-5-yl]propyl]-2-methyl-5-(trifluoromethyl)pyrazole-3-carboxamide (266)

To a stirred solution of A-427e (150 mg, 0.53 mmol) in DCM (5 mL) was added 2-methyl-5-(trifluoromethyl)pyrazole-3-carboxylic acid (103.71 mg, 0.53 mmol), DIPEA (0.19 mL, 1.07 mmol) and HATU (203.15 mg, 0.5300 mmol) and stirred at RT for 16 h. The reaction mixture was diluted with water and extracted with EtOAC. The organic layer was dried over $Na_2SO_4$ and evaporated to afford the crude product which was purified by column chromatography using 100-200 mesh silica and 20% EtOAc/hexane as an eluent to afford 266 (40 mg, 0.092 mmol, 17% yield) as an oil. HPLC: Rt 8.99 min, 96.3%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 421.4 (M+H), Rt 2.09 min, Column: X-select CSH C18 (3×50) mm, 2.5 μm. $^1$H NMR (400 MHz, DMSO-$d_6$) $\delta_H$=9.40 (d, 1H), 8.60 (d, 1H), 7.85 (s, 1H), 7.68-7.62 (m, 1H), 7.49 (s, 1H), 5.34-5.28 (m, 1H), 4.13 (s, 3H), 2.30-2.25 (m, 1H), 2.10-2.02 (m, 2H), 1.10-0.95 (m, 7H). Chiral method: Rt 5.25 min, 99.1%; column: DIACEL CHIRALPAK-IG (250×4.6 mm, 5 um), —Mobile Phase: A) n-Hexane+0.1% Iso propyl amine B) DCM:MeOH (50:50), Isocratic: 20% B; Wavelength: 295 nm, Flow: 1.0 mL/min.

Example 215. Synthesis of 267, 268, and 269

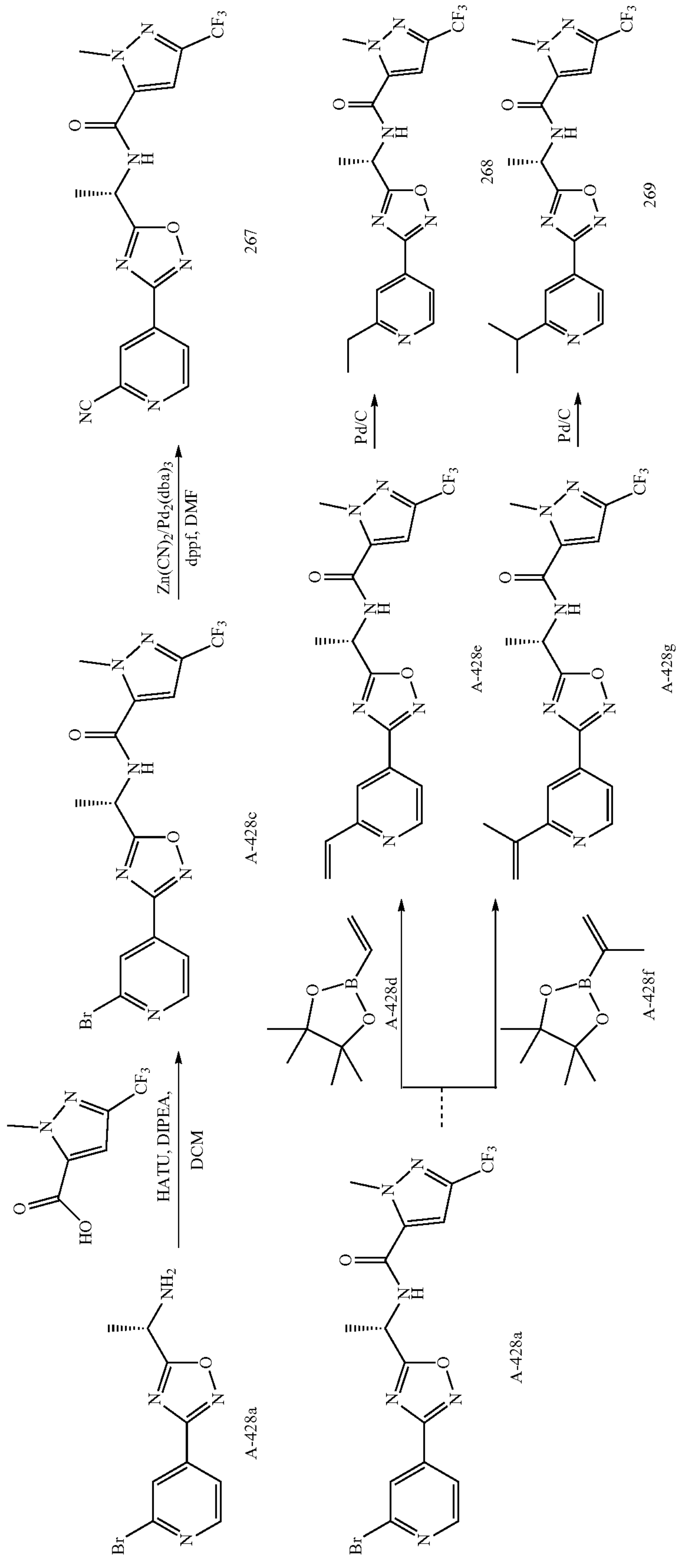
A-428a A-428c 267 A-428a A-428d A-428f A-428e A-428g 268 269

Synthesis of (S)—N-(1-(3-(2-bromopyridin-4-yl)-1,2,4-oxadiazol-5-yl)ethyl)-1-methyl-3-(trifluoromethyl)-1H-pyrazole-5-carboxamide (A-428c)

To a stirred solution of 1-methyl-3-(trifluoromethyl)-1H-pyrazole-5-carboxylic acid (1.27 g, 6.55 mmol) in DCM (10 mL) was added A-428a (2 g, 6.55 mmol), DIPEA (1.14 mL, 6.55 mmol) and HATU (2 0.5 g, 6.55 mmol) at RT and stirred for 16 h. The reaction mixture was diluted with EtOAc (2×100 mL) and washed with water (100 mL). The organic layer was dried over anhydrous sodium sulphate, filtered and evaporated to afford the crude product. The crude compound was purified by combiflash column chromatography and 10-15% EtOAc in hexane to afford A-428c (0.9 g, 1.88 mmol, 29% yield) as a solid.

Synthesis of (S)—N-(1-(3-(2-cyanopyridin-4-yl)-1,2,4-oxadiazol-5-yl)ethyl)-1-methyl-3-(trifluoromethyl)-1H-pyrazole-5-carboxamide (267)

To a stirred solution of A-428c (200 mg, 0.4 mmol) in DMF (3 mL) was added $Zn(CN)_2$ (158.22 mg, 1.35 mmol) and purged with $N_2$ gas for 20 min. To the solution was then added $Pd_2(dba)_3$ (4.12 mg, 0.0045 mmol) and dppf (2.49 mg, 0.0045 mmol). The reaction mixture was stirred at 100° C. for 16 h. The reaction mixture was diluted with EtOAc and washed with water. The organic layer was dried over anhydrous sodium sulphate, filtered and evaporated to afford the crude product. The crude compound was purified by combiflash column chromatography and 10-15% EtOAc in hexane to afford 267 (18 mg, 0.046 mmol, 10% yield) as a solid. HPLC: Rt 8.31 min, 99.7%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 391.8 (M+H), Rt 1.96 min; Column: X-select CSH C18 (3×50) mm, 2.5 μm. $^1H$ NMR (400 MHz, DMSO-$d_6$) $\delta_H$=9.49 (d, 1H), 8.97 (d, 1H), 8.53 (s, 1H), 8.28-8.24 (m, 1H), 7.45 (s, 1H), 5.52-5.45 (m, 1H), 4.12 (s, 3H), 1.68 (d, 3H). Chiral method: Rt 8.72 min, 84.2%; column: DIACEL CHIRALPAK-IG (250×4.6 mm, 5 um), —Mobile Phase: A) n-Hexane+0.1% Iso-propyl-amine B) DCM: MeOH (1:1), Isocratic: 20% B; Wavelength: 220 nm, Flow: 1.0 mL/min.

Synthesis of (S)-1-methyl-3-(trifluoromethyl)-N-(1-(3-(2-vinylpyridin-4-yl)-1,2,4-oxadiazol-5-yl)ethyl)-1H-pyrazole-5-carboxamide (A-428e)

To a stirred solution of A-428c (300 mg, 0.67 mmol) in 1,4-dioxane (4 mL):water (3 mL) was added $Na_2CO_3$ (214.27 mg, 2.02 mmol) and the reaction mixture was purged with $N_2$ gas for 20 min. To this solution was added A-428d (207.57 mg, 1.35 mmol) and tetrakis(triphenylphosphine)palladium (77.87 mg, 0.07 mmol). The reaction mixture was stirred at 100° C. for 3 h. The reaction mixture was cooled then diluted with DCM and washed with water. The organic layer was dried over anhydrous sodium sulphate, filtered and evaporated to afford the crude product. The crude compound was purified by flash column chromatography using 100-200 mesh silica and 10-15% EtOAc in hexane to afford A-428e (120 mg, 0.24 mmol, 36% yield).

Synthesis of (S)—N-(1-(3-(2-ethylpyridin-4-yl)-1,2,4-oxadiazol-5-yl)ethyl)-1-methyl-3-(trifluoromethyl)-1H-pyrazole-5-carboxamide (268)

To a stirred solution of A-428e (100 mg, 0.25 mmol) in methanol (4 mL) was added 10% Pd/C (27.12 mg, 0.25 mmol). The reaction mixture was stirred at RT under $H_2$ atmosphere for 30 min. The reaction was filtered through a celite pad and the filtrate was concentrated under reduced pressure. The crude compound was purified by combiflash column chromatography and 20-25% EtOAc in hexane to afford 268 (17 mg, 0.042 mmol, 16% yield) as a solid. HPLC: Rt 7.96 min, 97.5%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 395 (M+H), Rt 1.90 min; Column: X-select CSH C18 (3×50) mm, 2.5 μm. $^1H$ NMR (400 MHz, DMSO-$d_6$) $\delta_H$=9.46 (d, 1H), 8.68 (d, 1H), 7.80 (s, 1H), 7.75-7.72 (m, 1H), 7.45 (s, 1H), 5.50-5.44 (m, 1H), 4.13 (s, 3H), 2.86 (q, 2H), 1.68 (d, 3H), 1.26 (t, 3H). Chiral method: Rt 5.81 min, 100%; column: DIACEL CHIRALPAK-IG (250×4.6 mm, 5 um), —Mobile Phase: A) n-Hexane+0.1% Iso-propyl-amine B) DCM: MeOH (1:1), Isocratic: 20% B; Wavelength: 227 nm, Flow: 1.0 mL/min.

Synthesis of (S)-1-methyl-N-(1-(3-(2-(prop-1-en-2-yl)pyridin-4-yl)-1,2,4-oxadiazol-5-yl)ethyl)-3-(trifluoromethyl)-1H-pyrazole-5-carboxamide (A-428 g)

To a stirred solution of A-428c (302.69 mg, 0.68 mmol) in 1,4-dioxane (4 mL) and water (2 mL) was added $Na_2CO_3$ (216.19 mg, 2.04 mmol) and the reaction mixture was purged with $N_2$ gas for 20 min. Then $Pd(PPh_3)_4$ (7.86 mg, 0.01 mmol) and A-428f (228.51 mg, 1.36 mmol) were added. The reaction mixture was stirred at 100° C. for 3 h. The reaction mixture was diluted with EtOAc and washed with water. The organic layer was dried over anhydrous sodium sulphate, filtered and evaporated to afford the crude product. The crude compound was purified by combiflash column chromatography and 10-15% EtOAc in hexane to afford A-428 g (18 mg, 0.046 mmol, 11% yield) as a solid.

Synthesis of (S)—N-(1-(3-(2-isopropylpyridin-4-yl)-1,2,4-oxadiazol-5-yl)ethyl)-1-methyl-3-(trifluoromethyl)-1H-pyrazole-5-carboxamide (269)

To a stirred solution of A-428 g (144.12 mg, 0.35 mmol) in EtOAc (5 mL) was added 10% Pd/C (37.74 mg, 0.35 mmol). The reaction mixture was stirred under hydrogen atmosphere for 30 min. The reaction was filtered through a celite pad and the filtrate was concentrated under reduced pressure. The crude compound was purified by combiflash column chromatography and 20-25% EtOAc in hexane to afford 269 (13 mg, 0.031 mmol, 9% yield) as a solid. HPLC: Rt 8.68 min, 95.94%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 409.4 (M+H), Rt 2.05 min, Column: X-select CSH C18 (3×50) mm, 2.5 μm. $^1H$ NMR (400 MHz, DMSO-$d_6$) $\delta_H$=9.46 (d, 1H), 8.68 (d, 1H), 7.79 (s, 1H), 7.75-7.72 (m, 1H), 7.45 (s, 1H), 5.50-5.44 (m, 1H), 4.12 (s, 3H), 3.20-3.11 (m, 1H), 1.68 (d, 3H), 1.27 (d, 6H). Chiral method: Rt 5.08 min, 100%; column: DIACEL CHIRALPAK-IG (250×4.6 mm, 5 um), —Mobile Phase: A) n-Hexane+0.1% Iso-propyl-amine B) DCM: MeOH (1:1), Isocratic: 20% B; Wavelength: 225 nm, Flow: 1.0 mL/min.

Example 216. Synthesis of 270

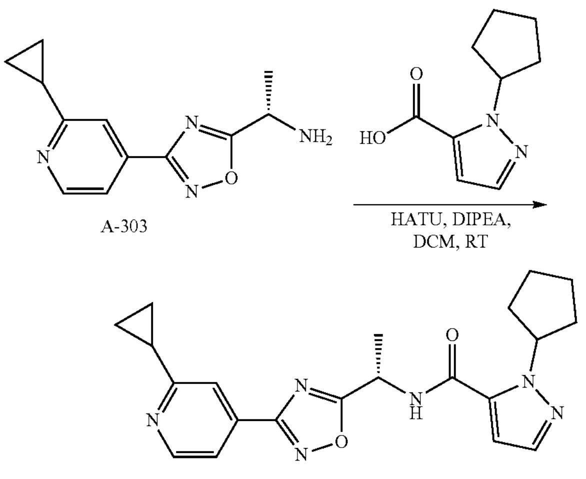

A-303

270

To a stirred solution of A-303 (100.mg, 0.43 mmol) and 1-cyclopentyl-1H-pyrazole-5-carboxylic acid (93.91 mg, 0.52 mmol) in DCM (10 mL) were added HATU (247.69 mg, 0.65 mmol) and DIPEA (0.15 mL, 0.87 mmol) at RT and stirred for 2 h at RT. The reaction mixture was quenched with water (100 mL) diluted with DCM (100 mL×2) and the organic layer separated. The organic layer was dried over $Na_2SO_4$, filtered and evaporated. The reaction mixture was purified by column chromatography using 100-200 silica and 30-80% EtOAc/Hexane as an eluent to afford 270 (15 mg, 0.037 mmol, 8% yield). HPLC: Rt 8.041 min, 97.7%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 393.10 (M+H), Rt 2.083 min; Column: X-select CSH C18 (3×50) mm, 2.5 μm. $^1H$ NMR (400 MHz, DMSO-$d_6$) $\delta_H$=9.23 (d, 1H), 8.60 (d, 1H), 7.85 (s, 1H), 7.66-7.64 (m, 1H), 7.52 (d, 1H), 6.90 (d, 1H), 5.58-5.50 (m, 1H), 5.46-5.42 (m, 1H), 2.31-2.24 (m, 1H), 2.05-1.85 (m, 4H), 1.80-1.78 (m, 2H), 1.67 (d, 3H), 1.60-1.57 (m, 2H), 1.03-0.94 (m, 4H). Chiral method: Rt 11.51 min, 98.4%; column: DIACEL CHIRALPAK-IG (250×4.6 mm, 5 um), —Mobile Phase: A) n-Hexane+0.1% Iso-propyl-amine B) DCM: MeOH (1:1), Isocratic: 20% B; Wavelength: 292 nm, Flow: 1.0 mL/min.

Example 217. Synthesis of 271

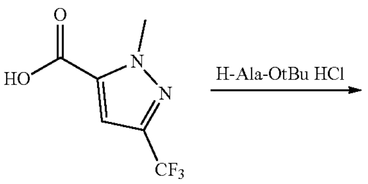

A-430aa

-continued

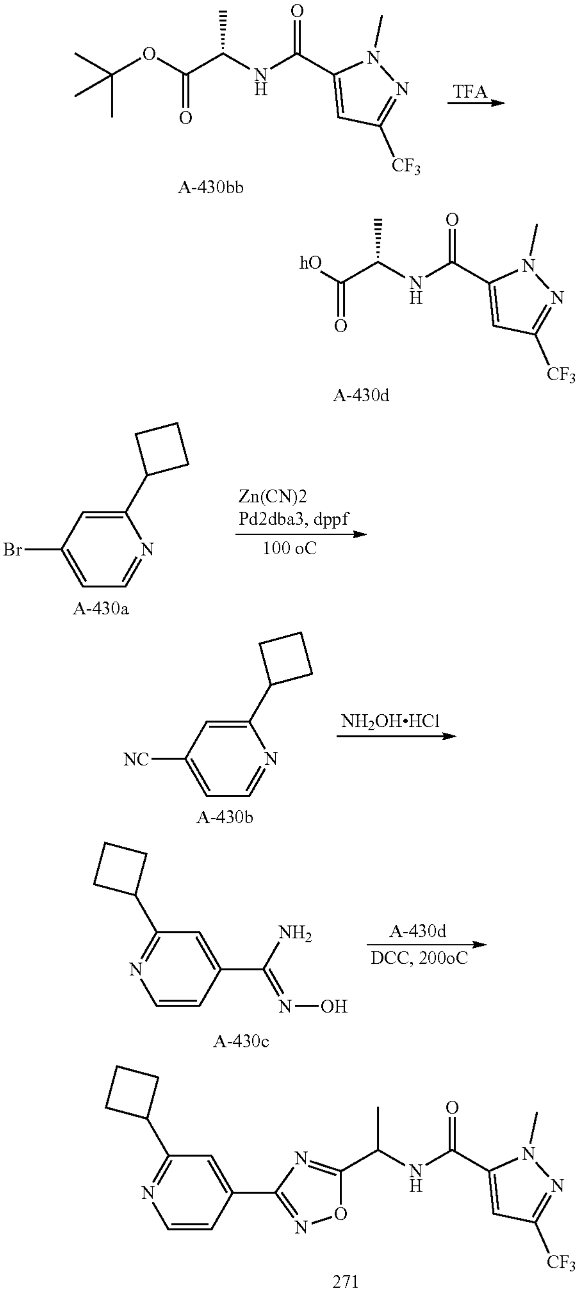

A-430bb

A-430d

A-430a

A-430b

A-430c

271

Synthesis of (25)-2-[[2-methyl-5-(trifluoromethyl) pyrazole-3-carbonyl]amino]propanoate (A-430bb)

To a stirred solution of A-430aa (1 g, 5.15 mmol) in DCM (2 mL) was added DIPEA (2.69 mL, 15.46 mmol) and HATU (2.94 g, 7.7 3 mmol) and stirred for 10 min. To resulting reaction mixture was added H-Ala-OtBu HCl (0.94 g, 5.15 mmol) and stirred for 2 h at RT. The reaction mixture was diluted with DCM, washed with water and the organic layer separated. The organic layer was dried over sodium sulphate and evaporated to afford the crude product. The crude product was purified by column chromatography to afford A-430bb (1.5 g, 4.2073 mmol, 82% yield) as a solid.

Synthesis of (2S)-2-[[2-methyl-5-(trifluoromethyl) pyrazole-3-carbonyl]amino]propanoic Acid (A-430d)

To a stirred solution of A-430bb (500 mg, 1.56 mmol) in DCM (10 mL) was added TFA (3 mL, 40.96 mmol) at 0-5° C. in dropwise manner and stirred at RT for 5 h. The reaction mixture was concentrated to afford the crude product as a liquid. The crude product was dissolved in ethyl acetate, washed with water, dried over sodium sulphate and concentrated to afford A-430d (400 mg, 1.39 mmol, 89% yield) as an oil.

Synthesis of 2-cyclobutylpyridine-4-carbonitrile (A-430b)

To a stirred solution of A-430a (500 mg, 2.36 mmol) in DMF (4 mL) was added zinc cyanide (827.48 mg, 7.07 mmol) and purged with $N_2$ gas for 10 min. To the resulting reaction mixture was added $Pd_2dba_3$ (215.95 mg, 0.24 mmol), dppf (130.69 mg, 0.24 mmol) and heated at 100° C. for 16 h. The reaction mixture was diluted with water and extracted with EtOAc and the organic layer separated. The organic layer was dried over $Na_2SO_4$, filtered and evaporated to afford the crude product which was purified by combi-flash using 10% EA/hexane as an eluent to afford A-430b (90 mg, 0.57 mmol, 24% yield) as an oil.

Synthesis of 2-cyclobutyl-N'-hydroxy-pyridine-4-carboxamidine (A-430c)

To a stirred solution of A-430b (140 mg, 0.88 mmol) in ethanol (3 mL) was added hydroxylamine hydrochloride (184.49 mg, 2.65 mmol), TEA (0.37 mL, 2.65 mmol) and stirred at 100° C. for 16 h. The reaction mixture was diluted with water and extracted using EtOAc and the organic layer separated. The organic layer was dried over $Na_2SO_4$, filtered and evaporated to afford A-430c (160 mg, 0.84 mmol, 95% yield). The crude product was used in the next step without purification.

Synthesis of (S)—N-(1-(3-(2-cyclobutylpyridin-4-yl)-1,2,4-oxadiazol-5-yl)ethyl)-1-methyl-3-(trifluoromethyl)-1H-pyrazole-5-carboxamide (271)

To a stirred solution of A-430c (150 mg, 0.78 mmol) and A-430d (208.01 mg, 0.78 mmol) in 1,4-dioxane (4 mL) was added DCC (242.38 mg, 1.18 mmol) and stirred at 100° C. for 16 h. The reaction mixture was diluted with water, extracted with EtOAc, and the organic layer separated. The organic layer was dried over $Na_2SO_4$ filtered and concentrated to afford the crude product which was purified by column chromatography using 15% EA/hexane as an eluent to afford 271 (28 mg, 0.064 mmol, 8% yield). HPLC: Rt: 8.88 min, 96.5%; Column: X-Select CSH C18 (4.6×150) mm, 5 μm; Mobile phase: A: 0.1% Formic acid in water: ACN (95:05), B: ACN; Flow Rate: 1.0 mL/min. LCMS: 420.9 (M+H), Rt 2.101 min, Column: X-select CSH C18 (3×50) mm, 2.5 μm. $^1H$ NMR (400 MHz, DMSO-d6) $\delta_H$=9.46 (d, 1H), 8.74 (d, 1H), 7.76-7.72 (m, 2H), 7.45 (s, 1H), 5.50-5.43 (m, 1H), 4.13 (s, 3H), 3.80-3.72 (m, 1H), 2.33-2.27 (m, 4H), 2.06-1.96 (m, 1H), 1.88-1.66 (m, 1H), 1.67 (d, 3H). Chiral method: Rt 5.574 min, 97.6%; column: DIACEL CHIRALPAK-IG (250×4.6 mm, 5 um), —Mobile Phase: A) n-Hexane+0.1% Iso-propyl amine B) DCM: MeOH (1:1), Isocratic: 20% B; Wavelength: 284 nm, Flow: 1.0 mL/min. Note that under the reaction conditions racemization was observed Example 218. (S)—N-(1-(3-(2-cyclobutylpyridin-4-yl)-1,2,4-oxadiazol-5-yl)ethyl)-1-methyl-3-(trifluoromethyl)-1H-pyrazole-5-carboxamide (278) and (R)—N-(1-(3-(2-cyclobutylpyridin-4-yl)-1,2,4-oxadiazol-5-yl)ethyl)-1-methyl-3-(trifluoromethyl)-1H-pyrazole-5-carboxamide (279). Note that Stereochemistry has been Randomly Assigned

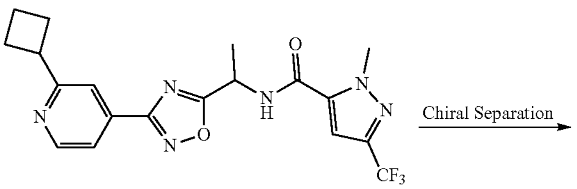

271

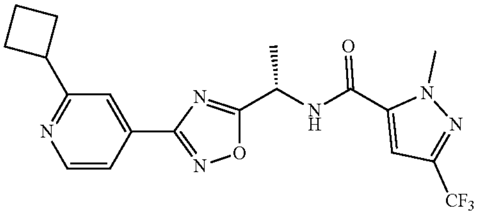

278

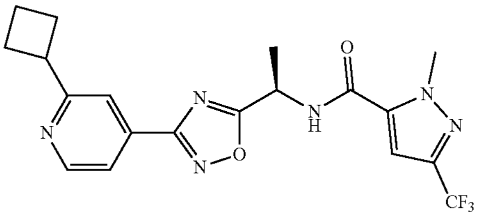

279

Racemic 271 (60.0 mg, 0.14 mmol) was separated by chiral HPLC to give the two pure enantiomers. The separation carried out 60 mg of 271 using prep-HPLC SFC giving 278 (Rt 9.046 min, 10 mg, 0.0238 mmol, 20% yield) as a solid and 279 (Rt 9.920 min, 10 mg, 0.0238 mmol, 20% yield) as a solid. Prep-HPLC conditions were: column: DIACEL CHIRALPAK-IG (250×4.6 mm, 5 um), —Mobile Phase: A) n-Hexane+0.1% Iso-propyl-amine B) EtOH: MeOH (50:50), Isocratic: 10% B; Wavelength: 283 nm, Flow: 1.0 mL/min.

278:

LCMS: 421.0 (M+H), Rt 2.087 min, Column: X-select CSH C18 (3*50) mm, 2.5 μm. $^1H$ NMR (400 MHz, DMSO-$d_6$) δ 9.47 (d, 1H), 8.75 (d, 1H), 7.78 (s, 2H), 7.45 (s, 1H), 5.46-5.56 (m, 1H), 4.13 (s, 3H), 3.76-3.84 (m, 1H), 2.20-2.44 (m, 4H), 1.94-2.16 (m, 1H), 1.82-1.92 (m, 1H), 1.68 (d, 3H). Chiral method: Rt 9.046 min, 99.6%; column: DIACEL CHIRALPAK-IG (250 mm×4.6 mm, 5 um), —Mobile Phase: A) n-Hexane+0.1% Iso-propyl-amine B) EtOH: MeOH (50:50), Isocratic: 10% B; Wavelength: 283 nm, Flow: 1.0 mL/min.

279:

HPLC: Rt 8.892 min, 94.4%; Column: X-Select CSH C18 (4.6×150) mm, 3.5 μm; Mobile phase: A: 0.1% Formic acid in water: ACN (95:05), B: ACN; Flow Rate: 1.0 mL/min.

LCMS: 421.3 (M+H), Rt 2.092 min, Column: X-select CSH C18 (3*50) mm, 2.5 μm; $^1$H NMR (400 MHz, DMSO-$d_6$) δ 9.47 (d, 1H), 8.75 (d, 1H), 7.80 (s, 2H), 7.45 (s, 1H), 5.46-5.56 (m, 1H), 4.13 (s, 3H), 3.68-3.86 (m, 1H), 2.26-2.38 (m, 4H), 1.94-2.19 (m, 1H), 1.82-1.92 (m, 1H), 1.68 (d, 3H). Chiral method: Rt 9.920 min, 99%; column: DIACEL CHIRALPAK-IG (250 mm x4.6 mm, 5 um), —Mobile Phase: A) n-Hexane+0.1% Iso-propyl-amine B) EtOH: MeOH (50:50), Isocratic: 10% B; Wavelength: 283 nm, Flow: 1.0 mL/min.

Example 219. (S)-1-benzyl-N-(1-(3-(2-cyclopropylpyridin-4-yl)-1,2,4-oxadiazol-5-yl)ethyl)-1H-pyrazole-5-carboxamide (280)

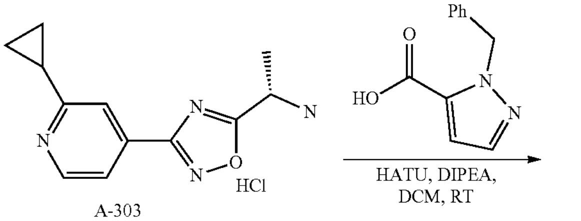

A-303

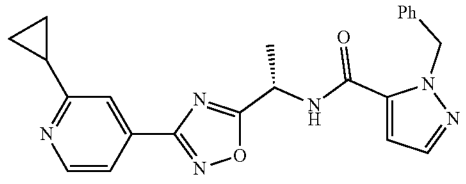

280

To a stirred solution of A-303 (201.5 mg, 0.76 mmol) and 1-benzyl-1H-pyrazole-5-carboxylic acid (203.67 mg, 0.91 mmol) in DCM (10 mL) was added HATU (430.86 mg, 1.13 mmol) and DIPEA (0.26 mL, 1.51 mmol) at RT. The reaction mixture was stirred at RT for 2 h. The reaction mixture was quenched with water (10 mL) and diluted with DCM (2×50 mL). The organic layer was dried over anhydrous sodium sulphate, filtered and evaporated to give the crude product. The crude compound was purified by column chromatography using 100-200 silica and 30-80% EtOAc/hexane as an eluent to give 280 (42 mg, 0.099 mmol, 13% yield) as a solid. HPLC: Rt 8.358 min, 97.9%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 415.6 (M+H), Rt 2.042 min, Column: X-select CSH (3*50) mm, 2.5 μm. $^1$H NMR (400 MHz, DMSO-$d_6$) δ 9.31 (d, 1H), 8.60 (d, 1H), 7.84 (s, 1H), 7.54-7.72 (m, 2H), 7.17-7.33 (m, 3H), 7.13 (d, 2H), 7.01 (s, 1H), 5.70-5.84 (m, 2H), 5.40-5.50 (m, 1H), 2.20-2.45 (m, 1H), 1.65 (d, 3H), 0.93-1.05 (m, 4H). Chiral method: Rt 5.372 min, 98%; column: DIACEL CHIRALPAK-IA (250 mm×4.6 mm, 5 um), —Mobile Phase: A) n-Hexane+0.1% Iso-propyl-amine B) EtOH: MeOH (1:1), Isocratic: 40% B; Wavelength: 292 nm, Flow: 1.0 mL/min.

Example 220. Synthesis of 273

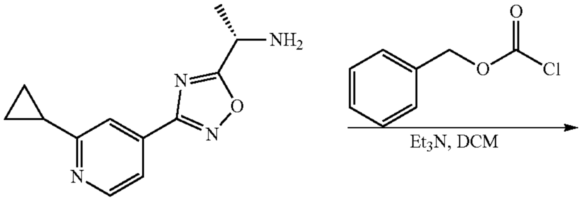

A-303

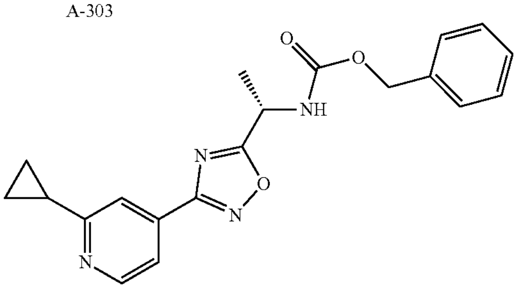

273

To a stirred solution of (S)-1-(3-(2-cyclopropylpyridin-4-yl)-1,2,4-oxadiazol-5-yl)ethan-1-amine (100 mg, 0.43 mmol) in DCM (5.0 mL) at 0° C. was added $Et_3N$ (0.18 mL, 1.3 mmol) followed by benzyl carbonochloridate (111 mg, 0.65 mmol). The reaction mixture was slowly warmed to room temperature and stirred for 4 h. The reaction mixture was treated with saturated $NaHCO_3$ solution (20 mL) and extracted with DCM (2×25 mL). The organic layer was washed with brine (20 mL), dried over $Na_2SO_4$ and concentrated. The crude was purified by preparative HPLC to afford 273 (35 mg, 0.09 mmol, 21% yield) as a solid. Prep. HPLC method: Rt 12.6; Column: X-Bridge (150×19 mm), 5.0 μm; Mobile phase: 0.1% TFA in water/acetonitrile; Flow Rate: 15.0 mL/min. HPLC: Rt 3.37 min, 97.6%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 365.2 (M+H), Rt 2.38 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 5.0 min, SFC column: YMC Amylose-C; mobile phase: 60:40 (A:B), A=liquid $CO_2$, B=0.5% isopropyl amine in methanol; flow rate: 3.0 mL/min; wave length: 210 nm. $^1$H NMR (400 MHz, $CD_3OD$): δ 8.54 (d, 1H), 7.85 (s, 1H), 7.76-7.71 (m, 1H), 7.40-7.20 (m, 5H), 5.14 (m, 3H), 2.23-2.19 (m, 1H), 1.66 (d, 3H), 1.13-1.05 (m, 4H).

Example 221. Synthesis of 274

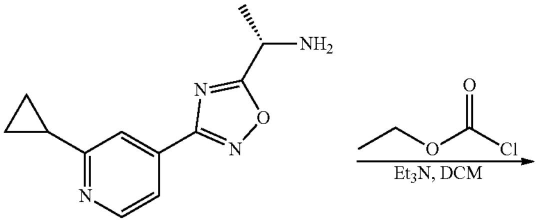

A-303

-continued

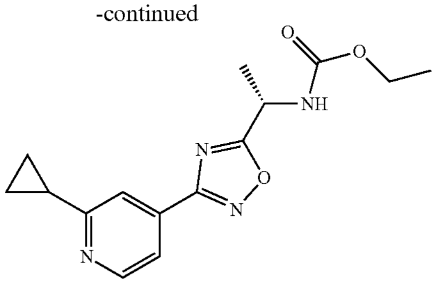

274

To a stirred solution of (S)-1-(3-(2-cyclopropylpyridin-4-yl)-1,2,4-oxadiazol-5-yl)ethan-1-amine (100 mg, 0.43 mmol) in DCM (5.0 mL) at 0° C. was added $Et_3N$ (0.18 mL, 1.3 mmol) followed by ethyl carbonochloridate (70 mg, 0.65 mmol). The reaction mixture was slowly warmed to room temperature and stirred for 4 h. The reaction mixture was treated with saturated $NaHCO_3$ solution (20 mL) and extracted with DCM (2×25 mL). The organic layer was washed with brine (20 mL), dried over $Na_2SO_4$ and concentrated. The crude was purified by preparative HPLC to afford 274 (30 mg, 0.09 mmol, 22% yield) as a solid. Prep. HPLC method: Rt 10.5; Column: X-Bridge (150×19 mm), 5.0 μm; Mobile phase: 0.1% TFA in water/acetonitrile; Flow Rate: 15.0 mL/min. HPLC: Rt 2.89 min, 98.7%; Column: X-Bridge C8 (50×4.6) mm, 3.5 μm; Mobile phase: A: 0.1% HCOOH in water, B: ACN; Flow Rate: 2.0 mL/min. LCMS: 303.1 (M+H), Rt 1.80 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.73 min, SFC column: YMC Amylose-C; mobile phase: 60:40 (A:B), A=liquid $CO_2$, B=0.5% isopropyl amine in methanol; flow rate: 3.0 mL/min; wave length: 210 nm. $^1H$ NMR (400 MHz, DMSO-$d_6$): δ 8.60 (d, 1H), 8.09 (d, 1H), 7.85 (s, 1H), 7.65 (d, 1H), 5.08-5.04 (m, 1H), 4.03 (q, 2H), 2.33-2.27 (m, 1H), 1.55 (d, 3H), 1.18 (t, 3H), 1.11-1.01 (m, 4H).

Example 222. Synthesis of 275

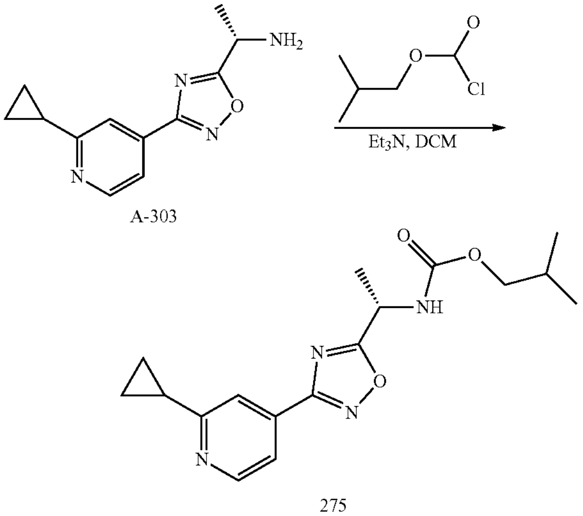

A-303

275

To a stirred solution of (S)-1-(3-(2-cyclopropylpyridin-4-yl)-1,2,4-oxadiazol-5-yl)ethan-1-amine (100 mg, 0.43 mmol) in DCM (5.0 mL) at 0° C. was added $Et_3N$ (0.18 mL, 1.3 mmol) followed by isobutyl carbonochloridate (110 mg, 0.81 mmol). The reaction mixture was slowly warmed to room temperature and stirred for 4 h. The reaction mixture was treated with saturated $NaHCO_3$ solution (20 mL) and extracted with DCM (2×25 mL). The organic layer was washed with brine (20 mL), dried over $Na_2SO_4$ and concentrated. The crude was purified by preparative HPLC to afford 275 (40 mg, 0.11 mmol, 26% yield) as a solid. Prep. HPLC method: Rt 12.1; Column: X-Bridge (150×19 mm), 5.0 μm; Mobile phase: 0.1% TFA in water/acetonitrile; Flow Rate: 15.0 mL/min. HPLC: Rt 3.19 min, 96.6%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 331.2 (M+H), Rt 2.36 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.42 min, SFC column: YMC Amylose-SA; mobile phase: 60:40 (A:B), A=liquid $CO_2$, B=0.5% isopropyl amine in methanol; flow rate: 4.0 mL/min; wave length: 210 nm. $^1H$ NMR (400 MHz, $CD_3OD$): δ 8.54 (d, 1H), 7.85 (s, 1H), 7.76-7.75 (m, 1H), 5.13-5.11 (m, 1H), 3.88 (d, 2H), 2.23-2.19 (m, 1H), 1.95-1.93 (m, 1H), 1.66 (d, 3H), 1.13-0.97 (m, 10H).

Example 223. Synthesis of 276

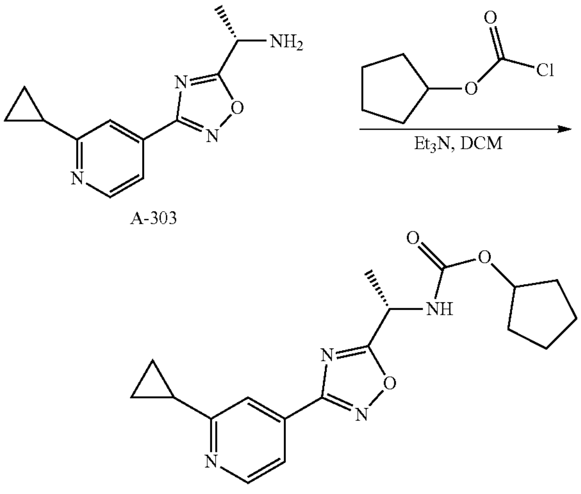

A-303

276

To a stirred solution of A-432e (100 mg, 0.43 mmol) in DCM (5.0 mL) at 0° C. was added $Et_3N$ (0.18 mL, 1.3 mmol) followed by cyclopentyl carbonochloridate (0.08 mL, 0.65 mmol). The reaction mixture was slowly warmed to room temperature and stirred for 4 h. The reaction mixture was treated with saturated $NaHCO_3$ solution (20 mL) and extracted with DCM (2×25 mL). The organic layer was washed with brine (20 mL), dried over $Na_2SO_4$ and concentrated. The crude was purified by preparative HPLC to afford 276 (14 mg, 0.04 mmol, 9% yield) as a solid. Prep. HPLC method: Rt 10.1; Column: X-Bridge (150×19 mm), 5.0 μm; Mobile phase: 0.1% TFA in water/acetonitrile; Flow Rate: 15.0 mL/min. HPLC: Rt 5.66 min, 99.4%; Column: X-Bridge C8 (50×4.6) mm, 3.5 μm; Mobile phase: A: 10 mM ammonium acetate, B: ACN; Flow Rate: 1.0 mL/min;

LCMS: 343.2 (M+H), Rt 2.22 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.02 min, SFC column: Chiralcel OX-H; mobile phase: 70:30 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.54 (d, 1H), 7.85 (s, 1H), 7.76-7.75 (m, 1H), 5.12-5.07 (m, 2H), 2.23-2.19 (m, 1H), 1.87-1.31 (m, 11H), 1.12-1.06 (m, 4H).

Example 224. Synthesis of 277

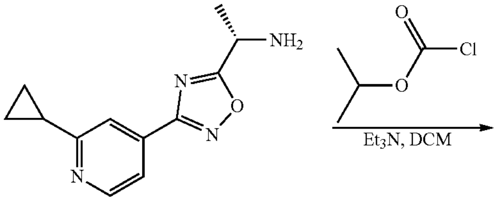

A-303

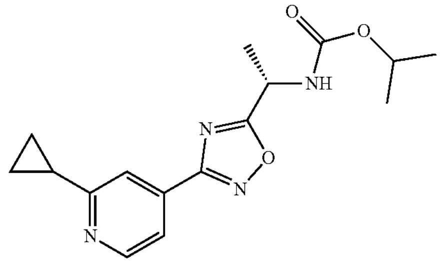

277

To a stirred solution of (S)-1-(3-(2-cyclopropylpyridin-4-yl)-1,2,4-oxadiazol-5-yl)ethan-1-amine (100 mg, 0.43 mmol) in DCM (5.0 mL) at 0° C. was added $Et_3N$ (0.18 mL, 1.3 mmol) followed by isopropyl carbonochloridate (80 mg, 0.65 mmol). The reaction mixture was slowly warmed to room temperature and stirred for 4 h. The reaction mixture was treated with saturated $NaHCO_3$ solution (20 mL) and extracted with DCM (2×25 mL). The organic layer was washed with brine (20 mL), dried over $Na_2SO_4$ and concentrated. The crude was purified by preparative HPLC to afford 277 (15 mg, 0.04 mmol, 10% yield) as a solid. Prep. HPLC method: Rt 11.3; Column: X-Bridge (150×19 mm), 5.0 μm; Mobile phase: 0.1% TFA in water/acetonitrile; Flow Rate: 15.0 mL/min. HPLC: Rt 2.75 min, 94.5%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 317.2 (M+H), Rt 2.15 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.2 min, SFC column: Chiral Pak AD-H; mobile phase: 60:40 (A:B), A=liquid $CO_2$, B=0.5% isopropyl amine in methanol; flow rate: 3.0 mL/min; wave length: 210 nm. $^1H$ NMR (400 MHz, $CD_3OD$): δ 8.54 (d, 1H), 7.85 (s, 1H), 7.76 (dd, 1H), 5.14-5.11 (m, 1H), 2.23-2.19 (m, 1H), 1.65 (d, 3H), 1.27 (d, 6H), 1.13-1.05 (m, 4H).

Example 225. Synthesis of 297

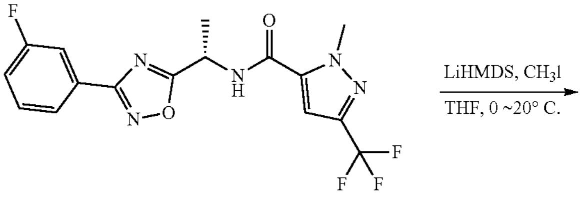

117

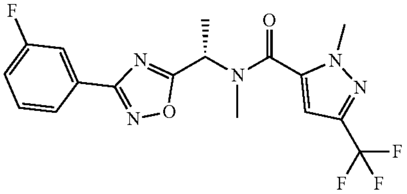

297

To a solution of 2-methyl-N-[(1S)-1-[3-(3-fluorophenyl)-1,2,4-oxadiazol-5-yl]ethyl]-5-(trifluoromethyl)pyrazole-3-carboxamide (800 mg, 2.09 mmol) in THF (10 mL) was added LiHMDS (2.3 mL, 2.3 mmol) at 0° C. The mixture was stirred at 0° C. for 30 minutes and at 20° C. for 30 minutes. Then to the mixture was added $CH_3I$ (1.39 mL, 22.33 mmol) at 0° C. The mixture was stirred at 20° C. for 5 hours. The reaction mixture was quenched with sat. $NH_4Cl$ (20 mL). The layers were separated, the aqueous phase extracted twice with EtOAc (15 mL×2), the combined organic phases washed with brine (30 mL), and dried over $Na_2SO_4$ and concentrated to give the crude product. The crude product was purified by flash chromatography on silica gel (EtOAc in PE=0% to 10% to 15%) to give the product (80 mg, 164.4 μmol, 7% yield) as an oil. LCMS $R_t$=0.93 min in 1.5 min chromatography, 5-95AB, MS ESI calcd. $C_{17}H_{16}F_4N_5O_2$ $[M+H]^+$ 398.12, found 397.8. Analytical SFC: (column (S,S) Whelk-01 100 mm×4.6 mm I.D., 5 μm, Mobile phase: A: $CO_2$ B: IPA (0.05% DEA), Gradient: from 5% to 40% of B in 5.5 min, then 5% of B for 1.5 min. Flow rate: 2.5 mL/min Column temp.: 40° C., ABPR: 100 bar) showed two peaks at 2.82 min (22.5%) and 3.02 min (77.5%). The product was purified by SFC (REGIS (s,$) WHELK-01 (250 mm×30 mm, 5 μm); A=$CO_2$ and B=Neu-IPA; 38° C.; 60 mL/min; 20% B; 10 min run; 10 injections, Rt of Peak 1=6.9 min, Rt of Peak 2=8.0 min) to give the product (30.52 mg, 75.8 μmol, 28% yield) (Rt=3.02 min in analytical SFC) as an oil. $^1H$ NMR (400 MHz DMSO-$d_6$/D20, 80° C.) $\delta_H$=7.83 (br d, 1H), 7.70 (br d, 1H), 7.65-7.54 (m, 1H), 7.39 (dt, 1H), 6.98 (s, 1H), 5.80-5.60 (m, 1H), 3.92 (s, 3H), 3.01 (s, 3H), 1.74 (d, 3H). LCMS $R_t$=1.32 min in 2.0 min chromatography, 10-80AB, MS ESI calcd. $C_{17}H_{16}F_4N_5O_2$ $[M+H]^+$ 398.1, found 398.1.

Example 226. Synthesis of 299

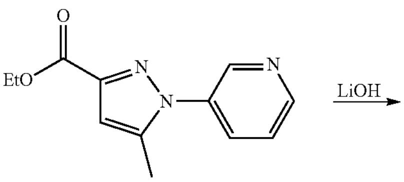

A-368

-continued

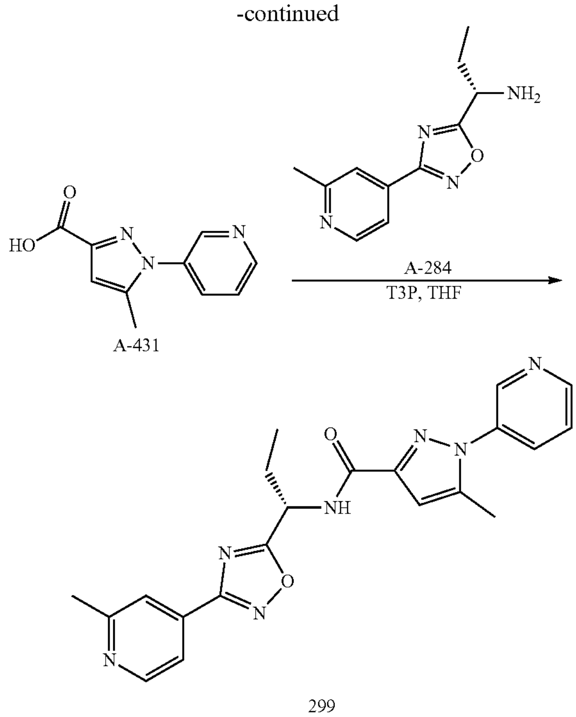

A-431

299

Synthesis of 5-methyl-1-(pyridin-3-yl)-1H-pyrazole-3-carboxylic Acid (A-431)

To a stirred solution of ethyl 5-methyl-1-(pyridin-3-yl)-1H-pyrazole-3-carboxylate (30 mg, 0.13 mmol) in methanol (1.0 mL), THF (1.0 mL) and water (1.0 mL) was added lithium hydroxide monohydrate (11 mg, 0.26 mmol). The reaction mixture was stirred at room temperature for 2 h. The reaction mixture was concentrated under reduced pressure and treated with ice water (10 mL). The mixture was treated with 1N HCl (1.0 mL) and extracted with ethyl acetate (2×20 mL). The organic layer was washed with brine (15 mL), dried over $Na_2SO_4$ and concentrated to afford A-431 (22 mg) as a solid. The crude compound was used for the next step without further purification.

Synthesis of (S)-5-methyl-N-(1-(3-(2-methylpyridin-4-yl)-1,2,4-oxadiazol-5-yl)propyl)-1-(pyridin-3-yl)-1H-pyrazole-3-carboxamide (299)

To a stirred solution of A-431 (22 mg, 0.11 mmol) in THF (3.0 mL) was added (S)-1-(3-(2-methylpyridin-4-yl)-1,2,4-oxadiazol-5-yl)propan-1-amine (23 mg, 0.11 mmol) followed by $Et_3N$ (0.03 mL, 0.21 mmol) and T3P (50% in EtOAc, 0.12 mL, 0.21 mmol). The reaction mixture was stirred at room temperature for 16 h. The reaction mixture was treated with water (10 mL) and extracted with ethyl acetate (2×20 mL). The organic layer was washed with saturated sodium bicarbonate solution (10 mL), washed with brine (10 mL), dried over $Na_2SO_4$ and concentrated. The crude was purified by column chromatography on silica to afford 299 (3.6 mg, 0.009 mmol, 12% yield) as a solid. HPLC: Rt 2.27 min; Column: X-Bridge C8 (50×4.6) mm, 3.5 μm; Mobile phase: A: 0.1% TFA in water, B: 0.1% TFA in ACN; Flow Rate: 2.0 mL/min. LCMS: 404.2 (M+H), Rt 1.39 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.37 min, SFC column: YMC Cellulose-SB; mobile phase: 60:40 (A:B), A=liquid $CO_2$, B=methanol; flow rate: 3.0 mL/min; wavelength: 220 nm. $^1H$ NMR (400 MHz, $CD_3OD$): δ 8.87 (d, 1H), 8.68 (dd, 1H), 8.59 (d, 1H), 8.15-8.11 (m, 1H), 7.95 (s, 1H), 7.86 (d, 1H), 7.66 (dd, 1H), 6.80 (s, 1H), 5.43-5.39 (m, 1H), 3.65 (m, 1H), 2.63 (s, 3H), 2.44 (s, 3H), 2.29-2.24 (m, 1H), 2.19-2.13 (m, 1H), 1.12 (t, 3H).

Example 227. Synthesis of 300

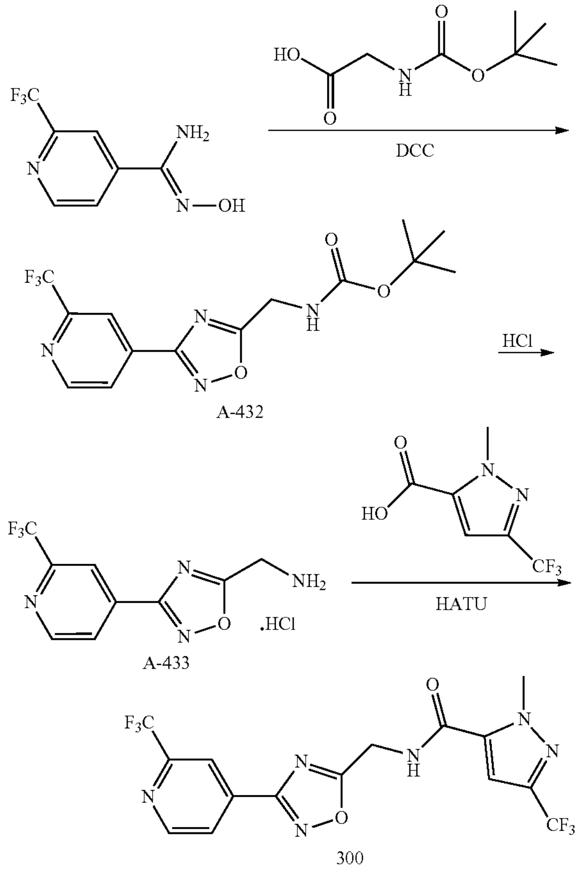

A-432

A-433

300

Synthesis of tert-butyl N-[[3-[2-(trifluoromethyl)-4-pyridyl]-1,2,4-oxadiazol-5-yl]methyl]carbamate (A-432)

To a stirred solution of A-362 (0.3 g, 1.46 mmol) in 1,4-Dioxane (10 mL) was added N-Boc-glycine (0.28 g, 1.61 mmol), DCC (0.33 g, 1.61 mmol) and the reaction mixture was stirred at 100° C. for 16 h. The reaction mixture was evaporated under reduced pressure to afford a residue which was diluted using EtOAc (30 mL). The organic layer was washed with water (2×10 mL), saturated brine solution (10 mL), dried over $MgSO_4$ and evaporated to dryness to afford the crude product, which was purified by flash column chromatography using 20% EtOAc in hexane as an eluent. The eluent fractions were evaporated to dryness under reduced pressure to afford 0.38 g of A-432. Note: 100 mg A-432 was further purified by prep HPLC to afford 30 mg of A-432 as a solid.

Synthesis of [3-[2-(trifluoromethyl)-4-pyridyl]-1,2,4-oxadiazol-5-yl]methanamine (A-433)

To a stirred solution of A-432 (0.25 g, 0.73 mmol) in 1,4-dioxane (2 mL) was added 4M HCl in dioxane (5 mL) at 0° C. and stirred at RT 6 h. The reaction mixture was evaporated to afford A-433 (180 mg, 0.5832 mmol, 80% yield) as a solid.

Synthesis of 2-methyl-5-(trifluoromethyl)-N-[[3-[2-(trifluoromethyl)-4-pyridyl]-1,2,4-oxadiazol-5-yl]methyl]pyrazole-3-carboxamide (300)

To a stirred solution of 1-methyl-3-(trifluoromethyl)-1H-pyrazole-5-carboxylic acid (0.11 g, 0.57 mmol) in DCM (10 mL) was added A-433 (0.16 g, 0.57 mmol), HATU (258.57 mg, 0.68 mmol), and DIPEA (0.2 mL, 1.13 mmol) and stirred at RT 6 h. The reaction mixture was diluted with water (10 mL) and DCM (10 mL) and organic layer separated. The organic layer was washed with saturated brine solution (10 mL), separated, dried over $MgSO_4$ and evaporated to dryness to afford crude product which was then purified by flash column chromatography using 30% EtOAc in hexane as an eluent to afford the product which was again purified by prep HPLC to afford 300 (45 mg, 0.1025 mmol, 18% yield) as a solid. HPLC: Rt 8.858 min, 95.7%; Column: X-Select CSH C18 (4.6x150) mm, 5 μm; Mobile phase: A: 0.1% formic acid in water:ACN (95:05), B: ACN; Flow Rate: 1.0 mL/min; LCMS: 421.15 (M+H), Rt 2.024 min, Column: X-Select CSH (3*50) mm, 2.5 μm. $^1H$ NMR (400 MHz, DMSO-$d_6$) δ 9.68 (s, 1H), 9.02 (d, 1H), 8.29-8.27 (m, 2H), 7.43 (s, 1H), 5.0-4.9 (m, 2H), 4.13 (s, 3H).

Example 228. Synthesis N-[[3-(2-cyclopropyl-4-pyridyl)-1,2,4-oxadiazol-5-yl]methyl]-2-methyl-5-(trifluoromethyl)pyrazole-3-carboxamide (301) and Synthesis of N-[[3-(2-cyclopropyl-4-pyridyl)-1,2,4-oxadiazol-5-yl]methyl]-N,2-dimethyl-5-(trifluoromethyl)pyrazole-3-carboxamide (302)

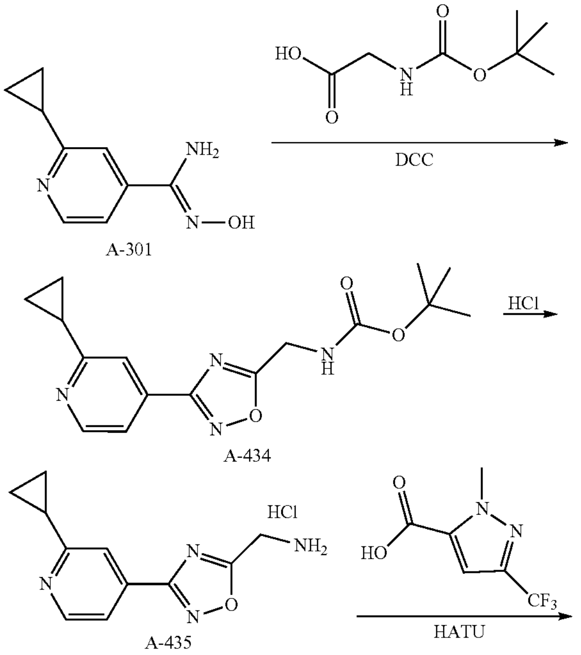

A-301

A-434

A-435

-continued

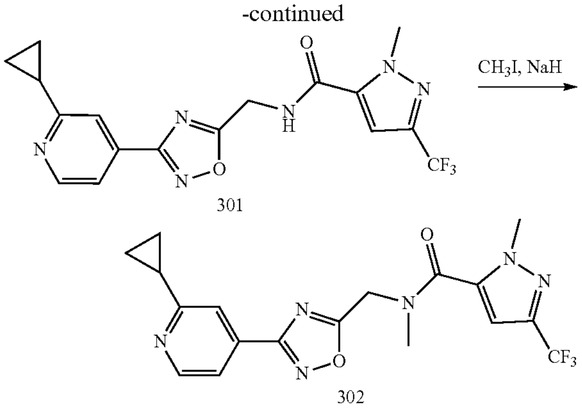

301

302

Synthesis of tert-butyl N-[[3-(2-cyclopropyl-4-pyridyl)-1,2,4-oxadiazol-5-yl]methyl]carbamate (A-434)

To a solution of A-301 (400 mg, 2.26 mmol) and N-Boc-glycine (434.98 mg, 2.48 mmol) in 1,4-dioxane (10 mL) was added N,N'-dicyclohexylcarbodiimide (512.33 mg, 2.48 mmol) at RT. The reaction mixture was heated at 100° C. for 16 h. The reaction mixture was concentrated under reduced pressure to afford the crude product. The crude product was diluted with water and extracted with EtOAc (3x25 mL). The combined organic phase was dried over anhydrous sodium sulfate, filtered and concentrated under reduced pressure to afford the crude product. The residue was further purified by column chromatography (100-200 mesh silica, 22-25% of EtOAc in hexane as an eluent) to afford A-434 (350 mg, 1.09 mmol, 48% yield) as an oil.

Synthesis of [3-(2-cyclopropyl-4-pyridyl)-1,2,4-oxadiazol-5-yl]methanamine (A-435)

To a solution of A-434 (350.mg, 1.11 mmol) in 1,4-dioxane (5 mL) was added hydrogen chloride solution 4.0 M in dioxane (0.78 mL, 22.13 mmol) dropwise at 0° C. The reaction mixture was allowed stirred at RT for 3 h. The volatile solvent was removed under reduced pressure to afford the crude product. The crude product was washed with hexane (3x5 mL) and dried under reduced pressure to afford A-435 (290 mg, 1.09 mmol, 98% yield) as a solid.

Synthesis N-[[3-(2-cyclopropyl-4-pyridyl)-1,2,4-oxadiazol-5-yl]methyl]-2-methyl-5-(trifluoromethyl)pyrazole-3-carboxamide (301)

To a stirred solution of 1-methyl-3-(trifluoromethyl)-1H-pyrazole-5-carboxylic acid (180.mg, 0.93 mmol) and A-435 (281.2 mg, 1.11 mmol) in DCM (15 mL) was added HATU (528.89 mg, 1.39 mmol) and DIPEA (0.48 mL, 2.78 mmol) at 0° C. and reaction mixture was stirred at RT for 3 h. The reaction mixture was diluted with DCM (25 mL) and washed with water (3x20 mL), saturated sodium bicarbonate solution (3x20 mL) followed by brine solution (25 mL). The organic phase was dried over anhydrous sodium sulfate, filtered and concentrated under reduced pressure to afford the crude product, which was purified by column chromatography (22-25% EtOAc in hexane as an eluent) followed by prep HPLC purification to afford 301 (15 mg, 0.0382 mmol, 4% yield) as a solid. HPLC: Rt 8.911 min; Column: X-Select CSH C18 (4.6x150) mm, 5 μm; Mobile phase: A:

10 mM ammonium bicarbonate in water, B: ACN; Flow Rate: 1.0 mL/min. LCMS: 392.9 (M+H), Rt 1.997 min; Column: X-Select CSH (3*50) mm, 2.5 μm. $^1$H NMR (400 MHz, DMSO-$d_6$) δ 9.65 (s, 1H), 8.59 (d, 1H), 7.85 (s, 1H), 7.65-7.64 (m, 1H), 7.42 (s, 1H), 4.86 (s, 1H), 4.13 (s, 3H), 2.3-2.24 (m, 1H), 1.02-0.94 (m, 4H)

Synthesis of N-[[3-(2-cyclopropyl-4-pyridyl)-1,2,4-oxadiazol-5-yl]methyl]-N,2-dimethyl-5-(trifluoromethyl)pyrazole-3-carboxamide (302)

To a suspension of sodium hydride (1.83 mg, 0.08 mmol) in THF (1 mL) was added 301 (25 mg, 0.06 mmol) in THF (1 mL) at 0° C. and stirred for 10 min. at 0° C. To the resulting reaction mixture was added iodomethane (5 mL, 0.08 mmol) and reaction mixture was stirred at RT for 2 h. Then reaction mixture was quenched with cold water (10 mL) and extracted with EtOAc (3×20 mL). The combined organic phase was dried over anhydrous sodium sulfate, filtered and concentrated under reduced pressure to afford crude product, which was purified by column chromatography (100-200 mesh silica, 15-18% EtOAc in hexane as an eluent to afford product which was re-purified by prep HPLC purification to afford 302 (25 mg, 0.061 mmol, 96% yield) as a solid. HPLC: Rt 8.353 min; Column: X-Select CSH C18 (4.6×150) mm, 3.5 μm; Mobile phase: A: 0.1% formic acid in water:ACN (95:05), B: ACN; Flow Rate: 1.0 mL/min. LCMS: 407.20 (M+H), Rt 1.94 min, Column: X-Select CSH (3*50) mm, 2.5 μm. $^1$H NMR (400 MHz, DMSO-$d_6$) δ 8.62 (d, 1H), 7.85 (s, 1H), 7.67 (d, 1H), 7.23-7.04 (m, 1H), 5.12 (s, 2H), 3.97-3.90 (m, 3H), 3.37-3.52 (m, 2H), 3.12 (s, 1H), 2.32-2.25 (m, 1H), 1.0-0.97 (m, 4H)

Example 229. Synthesis of N-[(1S)-1-[3-(6-cyclopropylpyridazin-4-yl)-1,2,4-oxadiazol-5-yl]ethyl]-2-methyl-5-(trifluoromethyl)pyrazole-3-carboxamide (303)

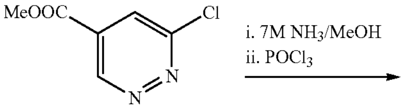

A-436

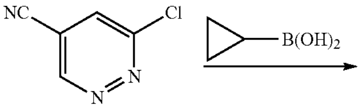

A-437

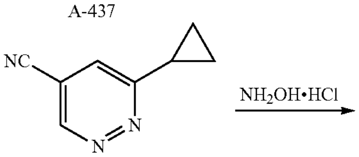

A-438

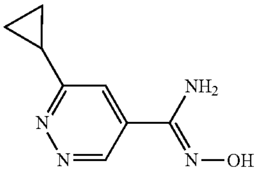

A-439

-continued

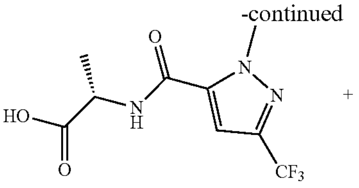

A-430d

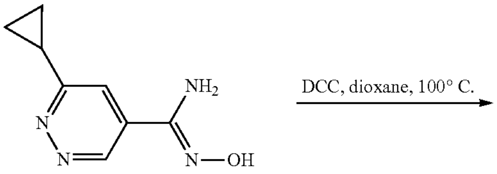

A-439

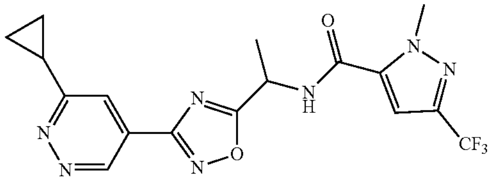

303

Synthesis of 6-chloropyridazine-4-carbonitrile (A-437)

A solution of A-436 (1 g, 5.79 mmol) in 7M ammonia methanol (10 mL) was stirred for 3 h at 80-85° C. The reaction mixture was cooled to RT and evaporated under reduced pressure to afford a solid. The crude solid was dissolved in $POCl_3$ (3 mL, 32.19 mmol) and stirred for 7 h at reflux temperature. The reaction mixture concentrated under reduced pressure to afford crude product, which was diluted using ethyl acetate and washed with water. The organic layer was dried over sodium sulfate and concentrated under reduced pressure to afford A-437 (120 mg, 0.8079 mmol, 14% yield).

Synthesis of 6-cyclopropylpyridazine-4-carbonitrile (A-438)

To the stirred solution of A-437 (40.mg, 0.29 mmol) in 1,4-dioxane (2 mL) was added cesium carbonate (140.1 mg, 0.43 mmol) and cyclopropylboronic acid (41.86 mg, 0.49 mmol) at RT. Reaction mixture was purged under argon for 20 min and treated with $Pd(dppf)Cl_2$ DCM (11.7 mg, 0.01 mmol) at RT and purged with argon for 10 min. The reaction mixture was stirred for 5 h at 100° C. The reaction mixture was diluted with ethyl acetate and filtered through celite. The organic layer was washed with water (10 mL×3), concentrated under reduced pressure to afford the crude product which was purified by column chromatography using 20-25% of ethyl acetate in hexane as an eluent to afford A-438 (35 mg, 0.228 mmol, 80% yield).

Synthesis of 6-cyclopropyl-N'-hydroxy-pyridazine-4-carboxamidine (A-439)

To a stirred solution of A-437 7 (120 mg, 0.83 mmol) in ethanol (2 mL) was added hydroxylamine hydrochloride (86.17 mg, 1.24 mmol) at RT. The reaction mixture was stirred for 2 h at reflux temperature. The reaction mixture was cooled to RT and evaporated under reduced pressure to afford A-439 (120 mg, 0.635 mmol, 77% yield).

Synthesis of N-[1-[3-(6-cyclopropylpyridazin-4-yl)-1,2,4-oxadiazol-5-yl]ethyl]-2-methyl-5-(trifluoromethyl)pyrazole-3-carboxamide (303)

To a stirred solution of A-430d (229.19 mg, 0.86 mmol) in 1,4-dioxane (2 mL) was added A-439 (140.mg, 0.79 mmol) and DCC (178.03 mg, 0.86 mmol) and stirred for 16 h at reflux temperature. The reaction mixture was filtered and mother liquor was diluted with ethyl acetate and washed with water (3 mL×2), and separated. The organic layer was dried over sodium sulfate and concentrated under reduced pressure to afford the crude product which was purified using prep-HPLC to afford 303 (45 mg, 0.11 mmol, 14% yield). HPLC: Rt 8.209 min; Column: X-Select CSH C18 (4.6×150) mm, 5 μm; Mobile phase: A: 0.1% Formic acid in water: Acetonitrile (95:05), B: ACN; Flow Rate: 1.0 mL/min. LCMS: 408 (M+H), Rt 2.05 min, Column: X-Select CSH C18 (3*50) mm, 2.5 μm. $^1$H NMR (400 MHz, DMSO-$d_6$) δ 9.49 (d, 1H), 8.05 (d, 1H), (7.45 (s, 1H), 5.57-5.49 (m, 1H), 4.027 (s, 3H), 2.45-2.42 (m, 1H), 1.69 (d, 3H), 1.29-1.26 (m, 1H), 1.17 (d, 4H). Chiral method: Rt 5.847 min, 35%+6.795 (65%); column: PHENOMENE CELLULOSE I (250×4.6 mm, 5 um), —Mobile Phase: A) n-Hexane+0.1% TFA B) Isopropyl alcohol IPA, Isocratic: 30% B; Wavelength: 254 nm, Flow: 1.0 mL/min. (NOTE: Chiral HPLC shows partial racemization)

Example 230. Synthesis of 2-cyclobutyl-N-[(1S)-1-[3-(2-cyclopropyl-4-pyridyl)-1,2,4-oxadiazol-5-yl]ethyl]pyrazole-3-carboxamide (304)

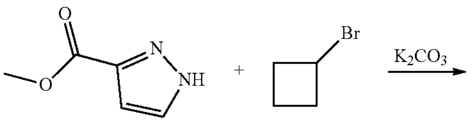

A-440 A-441

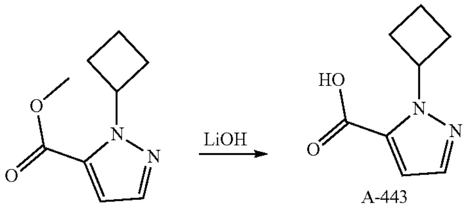

A-442 A-443

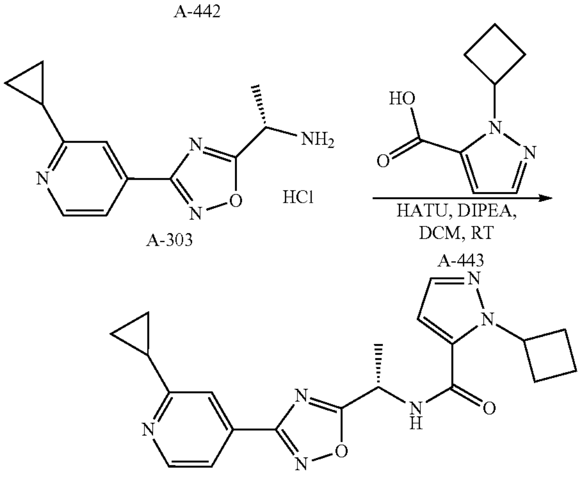

A-303

A-304

Synthesis of methyl 1-cyclobutyl-1H-pyrazole-5-carboxylate (A-442)

To a stirred solution of A-440 (2 g, 14.27 mmol) and A-441 (1.93 mg, 14.27 mmol) in DMF (20 mL) was added $K_2CO_3$ (3944.63 mg, 28.54 mmol) at RT. The reaction mixture was stirred at 80° C. for 24 h. The reaction mixture was quenched using water (10 mL) and diluted with EtOAc (50 mL×2). The organic layer was separated, dried over $Na_2SO_4$, filtered, evaporated under reduced pressure to afford crude product. The crude product was purified by column chromatography using 100-200 silica and 30-80% EtOAc/Hexane as an eluent to afford A-442. (0.40 g, 2.039 mmol, 14% yield) and ethyl 1-cyclobutylpyrazole-3-carboxylate (0.6 g, 3.058 mmol, 21% yield).

Synthesis of 1-cyclobutyl-1H-pyrazole-5-carboxylic Acid (A-443)

To a stirred solution of A-442 (0.3 g, 1.54 mmol) in THF (10 mL) and water (5 mL) was added $LiOH.H_2O$ (97.21 mg, 2.32 mmol) at RT. The reaction mixture was for 2 h at RT. The reaction mixture was quenched using water (100 mL) and diluted with EtOAc (50 mL×2). The organic layer was separated, then the aqueous layer was acidified with 1N HCl leading to precipitation. The precipitate was filtered to afford a solid which was separated and dried under reduced pressure to afford A-443 (100 mg, 0.5957 mmol, 38% yield) as a solid.

Synthesis of 2-cyclobutyl-N-[(1S)-1-[3-(2-cyclopropyl-4-pyridyl)-1,2,4-oxadiazol-5-yl]ethyl]pyrazole-3-carboxamide (304)

To a stirred solution of A-303 (100 mg, 0.37 mmol) and A-443 (74.76 mg, 0.45 mmol) in DCM (10 mL) was added HATU (213.83 mg, 0.56 mmol) and DIPEA (0.1 3 mL, 0.75 mmol) at RT. The reaction mixture was stirred at RT for 2 h. The reaction mixture was quenched with water (10 mL) and diluted with DCM (50 mL×2). The organic layer was dried over anhydrous sodium sulphate, filtered and evaporated to afford the crude product. The crude product was purified by column chromatography using 100-200 silica and 30-80% EtOAc/hexane as an eluent to afford 304 (15 mg, 0.0388 mmol, 10% yield) as a solid. HPLC: Rt 8.176 min, 95.2%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 379 (M+H), Rt 2.143 min, Column: X-select CSH (3*50) mm, 2.5 μm. $^1$H NMR (400 MHz, DMSO-$d_6$) δ 9.23 (d, 1H), 8.63 (d, 1H), 7.88 (s, 1H), 7.72 (d, 1H), 7.58 (s, 1H), 6.93 (s, 1H), 5.60-5.56 (m, 1H), 5.45-5.41 (m, 1H), 2.53-2.50 (m, 2H), 2.31-2.29 (m, 3H), 1.78-1.71 (m, 2H), 1.67 (d, 3H), 1.05-1.01 (m, 4H). Chiral method: Rt 8.967 min, 98.7%; column: DIACEL CHIRALPAK-IG (250×4.6 mm, 5 um), —Mobile Phase: A) n-Hexane+0.1% Iso-propyl amine B) DCM: MeOH (1:1), Isocratic: 20% B; Wavelength: 292 nm, Flow: 1.0 mL/min.

Example 231. Synthesis of 2-cyclopropyl-N-[(1S)-1-[3-(2-cyclopropyl-4-pyridyl)-1,2,4-oxadiazol-5-yl]ethyl]pyrazole-3-carboxamide (305)

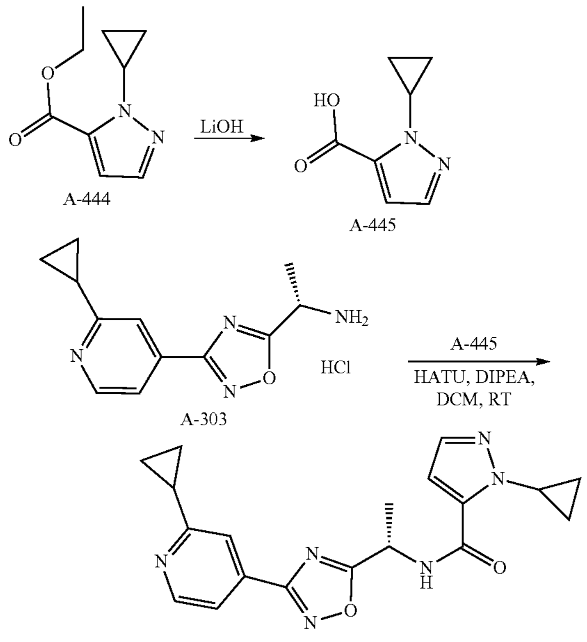

305

Synthesis of 2-cyclopropylpyrazole-3-carboxylic Acid (A-445)

To a stirred solution of A-444 (0.26 g, 1.44 mmol) in THF (2 mL) and water (0.5 mL) was added lithium hydroxide (0.12 g, 2.89 mmol) at 0° C. and stirred at RT 6 h. The reaction mixture was concentrated under reduced pressure and the residue was acidified with 1N HCl leading to precipitation which was collected by filtration to afford A-445 (0.13 g, 0.819 mmol, 57% yield) as a solid.

Synthesis of 2-cyclopropyl-N-[(1S)-1-[3-(2-cyclopropyl-4-pyridyl)-1,2,4-oxadiazol-5-yl]ethyl]pyrazole-3-carboxamide (305)

To a stirred solution of A-445 (0.13 g, 0.85 mmol) in DCM (10 mL) was added HATU (0.32 g, 0.85 mmol), A-303 (0.23 g, 0.850 mmol), and DIPEA (0.3 mL, 1.71 mmol) and stirred at RT for 6 h. The reaction mixture was diluted with DCM (20 mL) and water (10 mL), and the organic layer was separated. The organic layer was washed with water (2×10 mL), saturated brine solution (10 mL), dried over $MgSO_4$, and evaporated to dryness to afford the crude product which was purified by flash column chromatography, eluting 30% EtOAc in hexane to afford 305 (60 mg, 0.1593 mmol, 19% yield) as an oil. HPLC: Rt 7.532 min, 96.8%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 365.45 (M+H), Rt 1.624 min, Column: X-select CSH (3*50) mm, 2.5 μm. $^1H$ NMR (400 MHz, DMSO-$d_6$) δ 9.25 (d, 1H), 8.60 (d, 1H), 7.85 (s, 1H), 7.66 (d, 1H), 7.45 (s, 1H), 6.92 (s, 1H), 5.48-5.45 (m, 1H), 4.43-4.41 (m, 1H), 2.29-2.27 (m, 1H), 1.68 (d, 3H), 1.07-0.92 (m, 8H). Chiral method: Rt 12.941 min, 96.7%; column: DIACEL CHIRALPAK-IG (250×4.6 mm, 5 um), —Mobile Phase: A) n-Hexane+0.1% Iso-propyl amine B) DCM: MeOH (1:1), Isocratic: 20% B; Wavelength: 292 nm, Flow: 1.0 mL/min.

Example 232. Synthesis of 1-benzyl-N-[(1S)-1-[3-(2-cyclopropyl-4-pyridyl)-1,2,4-oxadiazol-5-yl]ethyl]pyrazole-3-carboxamide (306)

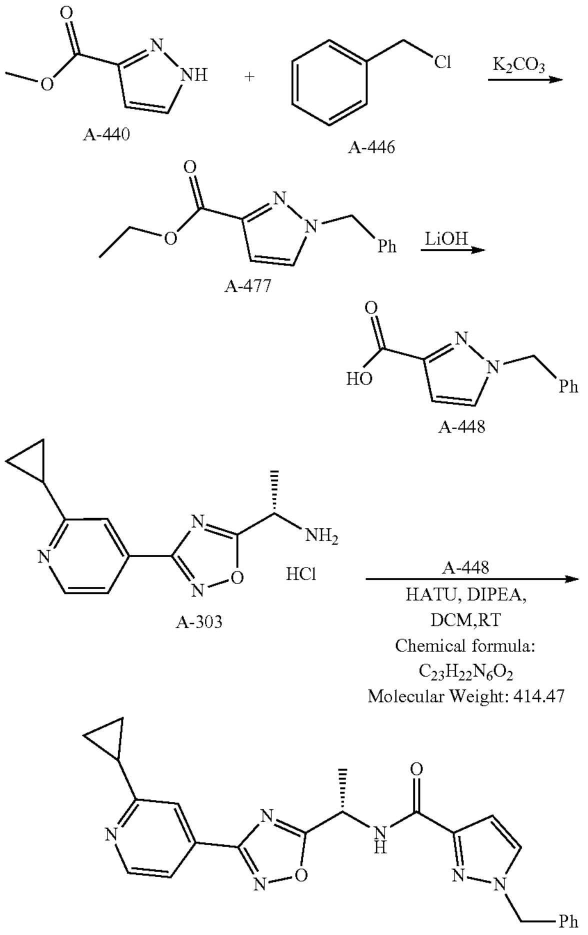

306

Synthesis of ethyl 1-benzylpyrazole-3-carboxylate (A-447)

To a stirred solution of A-440 (5.g, 35.68 mmol) and benzyl chloride (4.14 mL, 35.68 mmol) in ACN (10 mL) was added $K_2CO_3$ (9.86 g, 71.36 mmol) at RT and stirred for 16 h. The reaction mixture was quenched using water (10 mL) and diluted with EtOAc (50 mL×2). The organic layer was separated, dried over $Na_2SO_4$, then filtered. The organic layer was evaporated under reduced pressure. The crude reaction mass was purified by column chromatography using 100-200 silica and 30-80% EtOAc/Hexane as an eluent to afford A-447 (4.2 g, 16.412 mmol, 46% yield) and ethyl 2-benzylpyrazole-3-carboxylate (1.6 g, 16.115 mmol, 17% yield).

Synthesis of 1-benzylpyrazole-3-carboxylic Acid (A-448)

To a stirred solution of A-447 (4.4 g, 19.11 mmol) in THF (20 mL) and water (10 mL) was added $LiOH.H_2O$ (1202.71 mg, 28.66 mmol) at RT and stirred for 2 h. The reaction mixture was quenched using water (100 mL) and diluted with EtOAc (50 mL×2). The combined organic layer was separated, then the aqueous layer was acidified with 1N HCl to form a precipitate which was collected by filtration. The solid was separated and dried under reduced pressure to afford A-448 (2 g, 8.902 mmol, 46% yield).

Synthesis of compound 1-benzyl-N-[(1S)-1-[3-(2-cyclopropyl-4-pyridyl)-1,2,4-oxadiazol-5-yl]ethyl]pyrazole-3-carboxamide (306)

To a stirred solution of A-303 (200 mg, 0.75 mmol) and A-448 (49.31 mg, 0.31 mmol) in DCM (10 mL) was added HATU (427.66 mg, 1.12 mmol) and DIPEA (0.26 mL, 1.5 mmol) at RT. The reaction mixture was stirred at RT for 2 h. The reaction mixture was quenched with water (10 mL) and diluted with DCM (50 mL). The organic layer was dried over anhydrous sodium sulphate, filtered and evaporated to afford the crude product. The crude compound was purified by column chromatography using 100-200 silica and 30-80% EtOAc/hexane as eluent to afford 306 (10 mg, 0.0234 mmol, 3% yield) as a solid. HPLC: Rt 8.433 min; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 415.1 (M+H), Rt 1.966 min, Column: X-select CSH (3*50) mm, 2.5 μm. $^1H$ NMR (400 MHz, DMSO-$d_6$) δ 8.95 (d, 1H), 8.59 (d, 1H), 7.97 (d, 1H), 7.84 (s, 1H), 7.64-7.63 (m, 1H), 7.38-7.30 (m, 3H), 7.26-7.24 (m, 2H), 6.73 (d, 1H), 5.45-5.41 (m, 3H), 2.29-2.26 (m, 1H), 1.66 (d, 3H), 1.00-0.96 (m, 4H). Chiral method: Rt 7.372 min, 86%; column: YMC CHIRAL AMYLOSE-SA (250×4.6 mm, 5 um), —Mobile Phase: A) n-Hexane+0.1% Iso-propyl-amine B) DCM: MeOH (1:1), Isocratic: 15% B; Wavelength: 292 nm, Flow: 1.0 mL/min.

Example 233. Synthesis of (S)—N-(1-(3-(2-cyclopentylpyridin-4-yl)-1,2,4-oxadiazol-5-yl)ethyl)-1-methyl-3-(trifluoromethyl)-1H-pyrazole-5-carboxamide (307), (S)—N-(1-(3-(2-cyclopentylpyridin-4-yl)-1,2,4-oxadiazol-5-yl)ethyl)-3-(difluoromethyl)-1-methyl-1H-pyrazole-5-carboxamide (308) and (S)—N-(1-(3-(2-cyclopentylpyridin-4-yl)-1,2,4-oxadiazol-5-yl)ethyl)-1-(cyclopropylmethyl)-1H-pyrazole-5-carboxamide (309)

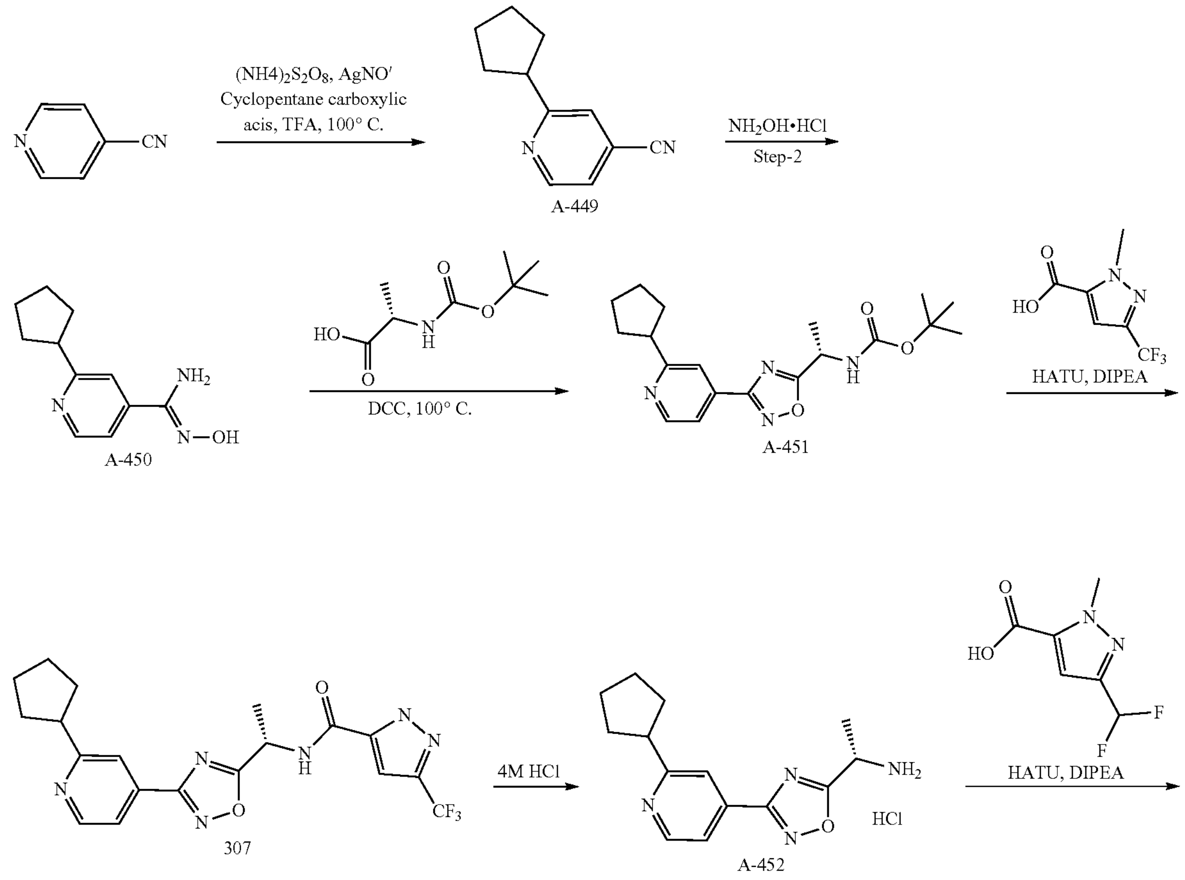

A-449

A-450

A-451

307

A-452

-continued

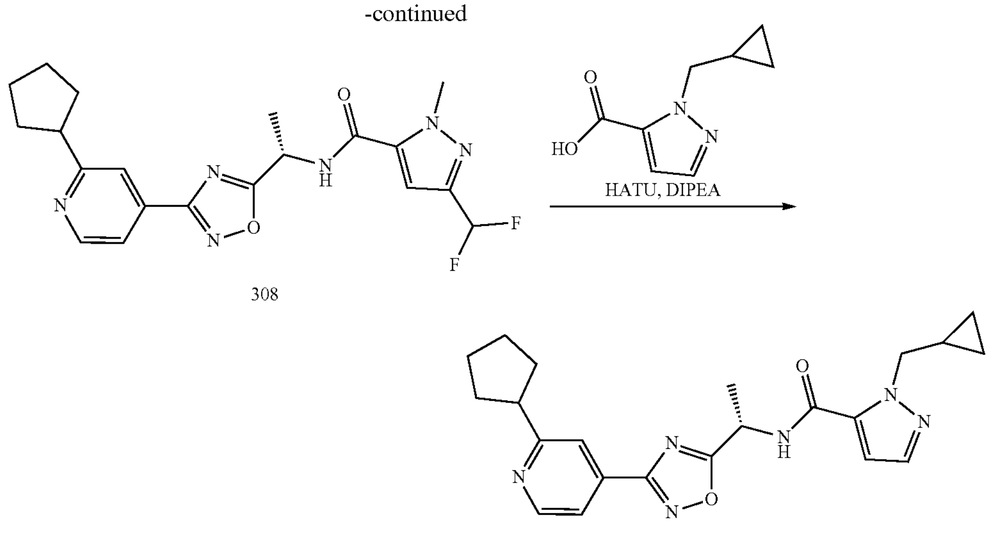

308

309

Synthesis 2-cyclopentylpyridine-4-carbonitrile (A-449)

To a stirred solution of isonicotinonitrile (1.5 g, 14.41 mmol) in water (20 mL) and chlorobenzene (20 mL) was added cyclopentanecarboxylic acid (4.93 g, 43.22 mmol), ammonium persulfate (6.58 g, 28.82 mmol), TFA (1.06 mL, 14.41 mmol), silver nitrate (0.24 g, 1.44 mmol). The reaction mixture was stirred at 120° C. for 3 h. The reaction mixture was diluted with water and extracted with EtOAc. The organic layer was dried over $Na_2SO_4$ filtered and evaporated to afford crude product which was purified by combiflash using 100-200 mesh silica and 8% ethyl acetate/hexane as an eluent to afford A-449 (2 g, 11.61 mmol, 80% yield) as an oil.

Synthesis of 2-cyclopentyl-N-hydroxy-pyridine-4-carboxamidine (A-450)

To a stirred solution of A-449 (2 g, 13.87 mmol) was added hydroxylamine hydrochloride (3.83 g, 55.49 mmol) and TEA (5.81 mL, 41.62 mmol) and stirred for 3 h at 70° C. The reaction mixture was evaporated and diluted using water and EtOAc. The organic layer was separated, dried over $Na_2SO_4$, filtered and evaporated to afford A-450 (2.1 g, 11.85 mmol, 85% yield) as an oil.

Synthesis of tert-butyl N-[(1S)-1-[3-(2-cyclopentyl-4-pyridyl)-1,2,4-oxadiazol-5-yl]ethyl]carbamate (A-451)

To a stirred solution of A-450 (1.2 g, 5.85 mmol) and (2S)-2-(tert-butoxycarbonylamino)propanoic acid (1.33 g, 7.02 mmol) in 1,4-Dioxane (8 mL) was added DCC (1.45 g, 7.02 mmol) and stirred for 16 h at 100° C. The reaction was quenched with water (10 mL) and diluted with EtOAc. The organic layer was separated, dried over $Na_2SO_4$, then filtered and evaporated under reduced pressure to afford crude product. The crude product was purified by column chromatography using 100-200 silica and 22% EtOAc/Hexane as an eluent to afford A-451 (610 mg, 1.702 mmol, 29% yield) as an oil Synthesis of (1S)-1-[3-(2-cyclopentyl-4-pyridyl)-1,2,4-oxadiazol-5-yl]ethanamine Hydrochloride (A-452)

To a stirred solution of A-451 (600.mg, 1.67 mmol) in 1,4-Dioxane (3 mL) was added 4M HCl in 1,4-Dioxane (2 mL, 14.33 mmol) and stirred at RT for 16 h. The reaction mixture was evaporated under reduced pressure and the crude solid was washed with diethyl ether to afford A-452 (410 mg, 1.391 mmol, 83% yield) as a solid.

Synthesis of (S)—N-(1-(3-(2-cyclopentylpyridin-4-yl)-1,2,4-oxadiazol-5-yl)ethyl)-1-(cyclopropylm-ethyl)-1H-pyrazole-5-carboxamide (309)

To a stirred solution of A-452 (70 mg, 0.27 mmol) and 1-(cyclopropylmethyl)-1H-pyrazole-5-carboxylic acid (47.35 mg, 0.28 mmol) in DCM (10 mL) was added HATU (135.44 mg, 0.36 mmol) and DIPEA (0.08 mL, 0.47 mmol) at RT and stirred for 2 h at RT. The reaction was quenched using water (10 mL), diluted with DCM (50 mL), and organic layer was separated. The organic layer was dried over $Na_2SO_4$, filtered and evaporated under reduced pressure to afford the crude product which was purified by column chromatography using 100-200 silica and 30-80% EtOAc/Hexane as an eluent to afford 309 (15 mg, 0.0368 mmol, 15% yield) as a solid. HPLC: Rt 8.756 min; Column: X-Select CSH C18 (4.6×150) mm, 5 μm; Mobile phase: A: 0.1% Formic acid in water: ACN (95:05), B: ACN; Flow Rate: 1.0 mL/min. LCMS: 407.03 (M+H), Rt 2.074 min, Column: X-select CSH C18 (3*50) mm, 2.5 μm. $^1H$ NMR (400 MHz, DMSO-$d_6$) δ 9.29 (d, 1H), 8.70 (d, 1H), 7.77 (s, 1H), 7.71 (d, 1H), 7.53-7.52 (m, 1H), 6.95-6.94 (m, 1H), 5.44-5.41 (m, 1H), 4.32 (d, 2H), 3.29-3.27 (m, 1H), 2.04-1.99 (m, 2H), 1.77-1.71 (m, 4H), 1.68-1.66 (m, 5H), 1.22-1.17 (m, 1H), 0.40-0.34 (m, 2H), 0.30-0.29 (m, 2H). Chiral method: Rt 11.397 min, 96.4% min; column: DIACEL CHIRALPAK-IG (250×4.6 mm, 5 um), —Mobile Phase: A) n-Hexane+0.1% Iso-propyl-amine B) DCM: MeOH (1:1), Isocratic: 20% B; Wavelength: 228 nm, Flow: 1.0 mL/min.

Synthesis of (S)—N-(1-(3-(2-cyclopentylpyridin-4-yl)-1,2,4-oxadiazol-5-yl)ethyl)-1-methyl-3-(trifluoromethyl)-1H-pyrazole-5-carboxamide (307)

To a stirred solution of A-452 (57.06 mg, 0.19 mmol) and 1-methyl-3-(trifluoromethyl)-1H-pyrazole-5-carboxylic acid (56.36 mg, 0.29 mmol) in DCM (3 mL) was added HATU (110.4 mg, 0.29 mmol) and DIPEA (0.08 mL, 0.48 mmol) at RT and stirred for 16 h. The reaction was quenched using water, extracted with DCM, and the organic layer was separated. The organic layer was dried over $Na_2SO_4$, filtered and evaporated under reduced pressure to afford the crude product which was purified by column chromatography using 100-200 silica and 23% EtOAc/Hexane as an eluent to afford 307 (5 mg, 0.0097 mmol, 5% yield) as a solid. HPLC: Rt 9.074 min; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 435.05 (M+H), Rt 2.171 min, Column: X-select CSH C18 (3*50) mm, 2.5 μm. $^1H$ NMR (400 MHz, DMSO-$d_6$) δ 9.47 (d, 1H), 8.70 (d, 1H), 7.78-7.72 (m, 2H), 7.45 (s, 1H), 5.49-5.46 (m, 1H), 4.12 (s, 3H), 2.02-2.00 (m, 2H), 1.77-1.67 (m, 9H). Chiral method: Rt 5.287 min, 99.4% min; column: DIACEL CHIRALPAK-IG (250×4.6 mm, 5 um), —Mobile Phase: A) n-Hexane+0.1% Iso-propyl-amine B) DCM: MeOH (1:1), Isocratic: 20% B; Wavelength: 282 nm, Flow: 1.0 mL/min.

(S)—N-(1-(3-(2-cyclopentylpyridin-4-yl)-1,2,4-oxadiazol-5-yl)ethyl)-3-(difluoromethyl)-1-methyl-1H-pyrazole-5-carboxamide (308)

To a stirred solution of A-452 (100 mg, 0.34 mmol) and 3-(difluoromethyl)-1-methyl-1H-pyrazole-5-carboxylic acid (71.7 mg, 0.41 mmol) in DCM (10 mL) was added HATU (193.48 mg, 0.51 mmol) and DIPEA (0.12 mL, 0.68 mmol) at RT and stirred for 2 h at RT. The reaction was quenched using water (10 mL), extracted with DCM (50 mL), and the organic layer was separated. The organic layer was dried over $Na_2SO_4$, filtered and evaporated under reduced pressure to afford the crude product which was purified by column chromatography using 100-200 silica and 30-80% EtOAc/Hexane as an eluent to afford 308 (12.17 mg, 0.029 mmol, 8% yield) as a solid. HPLC: Rt 8.686 min; Column: X-Select CSH C18 (4.6×150) mm, 5 μm; Mobile phase: A: 0.1% Formic acid in water: ACN (95:05), B: ACN; Flow Rate: 1.0 mL/min. LCMS: 417.1 (M+H), Rt 2.1 min, Column: X-select CSH C18 (3*50) mm, 2.5 μm. $^1H$ NMR (400 MHz, DMSO-$d_6$) δ 9.40 (d, 1H), 8.72 (d, 1H), 7.83 (s, 1H), 7.78 (d, 1H), 7.26 (s, 1H), 7.19-6.91 (m, 1H), 5.48-5.44 (m, 1H), 4.08 (s, 3H), 3.34-3.30 (m, 1H), 2.04-2.02 (m, 2H), 1.78-1.71 (m, 4H), 1.68-1.66 (m, 5H). Chiral method: Rt 7.701 min, 98.4% min; column: DIACEL CHIRALPAK-IG (250×4.6 mm, 5 um), —Mobile Phase: A) n-Hexane+0.1% Iso-propyl-amine B) DCM: MeOH (1:1), Isocratic: 20% B; Wavelength: 227 nm, Flow: 1.0 mL/min.

Example 234. Synthesis of 2-(cyclopropylmethyl)-N-[(1S)-1-[3-(2-cyclopropyl-4-pyridyl)-1,2,4-oxadiazol-5-yl]ethyl]pyrazole-3-carboxamide (310)

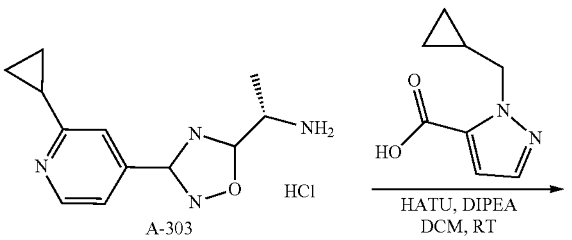

A-303

-continued

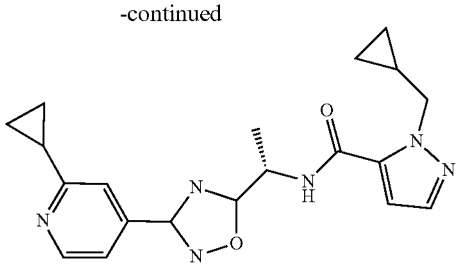

A-310

To a stirred solution of A-303 (100 mg, 0.37 mmol) and 1-(cyclopropylmethyl)-1H-pyrazole-5-carboxylic acid (83.07 mg, 0.45 mmol) in DCM (10 mL) was added HATU (213.83 mg, 0.56 mmol) and DIPEA (0.13 mL, 0.75 mmol) at RT. The reaction mixture was stirred at RT for 2 h. The reaction mixture was quenched with water (10 mL) and diluted with DCM (50 mL×2). The organic layer was dried over anhydrous sodium sulphate, filtered and concentrated under reduced pressure. The crude compound was purified by column chromatography using 100-200 silica and 30 to 80% EtOAc in hexane as an eluent to afford 310 (20 mg, 0.0525 mmol, 14% yield) as a solid. HPLC: Rt 7.97 min; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 379.4 (M+H), Rt 1.801 min, Column: X-select CSH (3*50) mm, 2.5 μm. $^1H$ NMR (400 MHz, DMSO-$d_6$) δ 9.28 (d, 1H), 8.60 (d, 1H), 7.85 (s, 1H), 7.65 (dd, 1H), 7.53 (d, 1H), 6.95 (d, 1H), 5.44 (quin, 1H), 4.27-4.39 (m, 2H), 2.28-2.46 (m, 1H), 1.68 (d, 3H), 1.10-1.30 (m, 1H), 0.90-1.08 (m, 4H), 0.23-0.47 (m, 4H). Chiral method: Rt 6.523 min, 96%: DIACEL CHIRALPAK-IG (250×4.6 mm, 5 um), —Mobile Phase: A) n-Hexane+0.1% Iso-propyl-amine B) EtOH: MeOH (50:50), Isocratic: 30% B; Wavelength: 293 nm, Flow: 1.0 mL/min.

Example 235. Efficacy of Exemplary Compounds in the Inhibition of KCNT1

KCNT1—Patch Clamp Assay

Inhibition of KCNT1 (KNa1.1, Slack) was evaluated using a tetracycline inducible cell line (HEK-TREX). Currents were recorded using the SyncroPatch 384PE automated, patch clamp system. Pulse generation and data collection were performed with PatchController384 V1.3.0 and DataController384 V1.2.1 (Nanion Technologies). The access resistance and apparent membrane capacitance were estimated using built-in protocols. Current were recorded in perforated patch mode (10 μM escin) from a population of cells. The cells were lifted, triturated, and resuspended at 800,000 cells/ml. The cells were allowed to recover in the cell hotel prior to experimentation. Currents were recorded at room temperature. The external solution contained the following (in mM): NaCl 105, NMDG 40, KCl 4, $MgCl_2$ 1, $CaCl_2$ 5 and HEPES 10 (pH=7.4, Osmolarity ~300 mOsm). The extracellular solution was used as the wash, reference and compound delivery solution. The internal solution contained the following (in mM): NaCl 70, KF 70, KCl 10, EGTA 5, HEPES 5 and Escin 0.01 (pH=7.2, Osmolarity ~295 mOsm). Escin is made at a 5 mM stock in water, aliquoted, and stored at −20° C. The compound plate was created at 2× concentrated in the extracellular solution. The compound was diluted to 1:2 when added to the recording well. The amount of DMSO in the extracellular solution was held constant at the level used for the highest tested concentration. A holding potential of −80 mV with a 100 ms step to 0 mV was used. Mean current was measured during the step to 0 mV. 100 μM Bepridil was used to completely inhibit KCNT1 current to allow for offline subtraction of non-KCNT1 current. The average mean current from 3 sweeps was calculated and the % inhibition of each compound was calculated. The % Inhibition as a function of the compound concentration was fit with a Hill equation to derive $IC_{50}$, slope, min and max parameters. If KCNT1 inhibition was less than 50% at the highest tested concentration or if an $IC_{50}$ could not be calculated, then a percent inhibition was reported in place of the $IC_{50}$.

Results from this assay are summarized in Table 1 below. In this table, "A" indicates $IC_{50}$ of less than or equal to 1 μM; "B" indicates inhibition of between 1 μM to 20 μM; and "C" indicates inhibition of greater than or equal to 20 μM.

TABLE 1

| Patent Compound No. | KCNT1-WT $IC_{50}$ (μM) |
|---|---|
| 192 | A |
| 191 | B |
| 3 | C |
| 4 | C |
| 5 | A |
| 6 | A |
| 7 | C |
| 8 | B |
| 9 | A |
| 10 | A |
| 11 | B |
| 12 | A |
| 13 | A |
| 14 | B |
| 15 | B |
| 16 | A |
| 17 | B |
| 19 | A |
| 20 | B |
| 21 | A |
| 22 | A |
| 23 | B |
| 24 | A |
| 25 | B |
| 26 | A |
| 29 | A |
| 30 | A |
| 31 | A |
| 32 | B |
| 33 | A |
| 34 | A |
| 35 | B |
| 36 | A |
| 37 | B |
| 38 | A |
| 39 | B |
| 40 | B |
| 41 | B |
| 42 | A |
| 43 | B |
| 44 | C |
| 45 | A |
| 46 | B |
| 47 | A |
| 48 | A |
| 49 | B |
| 50 | B |
| 51 | B |
| 52 | A |
| 54 | C |
| 55 | B |
| 56 | A |
| 57 | B |
| 58 | B |
| 59 | C |
| 60 | A |
| 61 | A |
| 62 | B |
| 63 | A |
| 64 | A |
| 65 | B |
| 66 | A |
| 67 | A |
| 68 | B |
| 69 | A |
| 70 | A |
| 71 | C |
| 72 | A |
| 73 | A |
| 74 | A |
| 75 | A |
| 76 | A |
| 77 | A |
| 78 | B |
| 79 | B |
| 80 | A |
| 81 | A |
| 82 | A |
| 83 | B |
| 84 | A |
| 85 | C |
| 86 | A |
| 87 | B |
| 88 | B |
| 89 | A |
| 90 | B |
| 91 | A |
| 92 | A |
| 93 | B |
| 94 | C |
| 95 | B |
| 96 | A |
| 97 | A |
| 98 | B |
| 99 | B |
| 100 | B |
| 101 | B |
| 102 | A |
| 103 | A |
| 104 | B |
| 105 | A |
| 106 | B |
| 107 | A |
| 108 | A |
| 109 | A |
| 110 | A |
| 111 | A |
| 112 | A |
| 113 | A |
| 114 | C |
| 115 | C |
| 116 | A |
| 117 | A |
| 118 | B |
| 119 | A |
| 120 | A |
| 121 | C |
| 122 | C |
| 123 | C |
| 124 | C |
| 125 | A |
| 126 | A |
| 127 | A |
| 128 | C |
| 129 | C |
| 130 | A |
| 131 | B |
| 132 | A |
| 133 | B |
| 134 | C |
| 135 | B |

TABLE 1-continued

| Patent Compound No. | KCNT1-WT $IC_{50}$ (μM) |
|---|---|
| 136 | B |
| 137 | B |
| 138 | A |
| 139 | A |
| 140 | B |
| 141 | B |
| 142 | B |
| 143 | C |
| 144 | B |
| 145 | A |
| 146 | A |
| 147 | B |
| 148 | B |
| 149 | A |
| 150 | A |
| 151 | B |
| 152 | B |
| 153 | A |
| 154 | A |
| 155 | B |
| 156 | C |
| 157 | B |
| 160 | B |
| 161 | B |
| 162 | B |
| 163 | B |
| 164 | B |
| 165 | A |
| 166 | B |
| 167 | B |
| 168 | B |
| 169 | B |
| 170 | A |
| 171 | B |
| 172 | B |
| 173 | B |
| 174 | A |
| 175 | A |
| 176 | B |
| 177 | C |
| 178 | B |
| 179 | B |
| 180 | C |
| 181 | A |
| 182 | C |
| 183 | C |
| 184 | A |
| 185 | B |
| 186 | B |
| 187 | C |
| 188 | B |
| 189 | B |
| 193 | C |
| 194 | A |
| 195 | B |
| 196 | A |
| 197 | A |
| 198 | A |
| 199 | A |
| 200 | B |
| 201 | A |
| 202 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | B |
| 214 | A |
| 215 | B |
| 216 | A |

TABLE 1-continued

| Patent Compound No. | KCNT1-WT $IC_{50}$ (μM) |
|---|---|
| 217 | B |
| 218 | A |
| 219 | A |
| 220 | B |
| 221 | A |
| 222 | A |
| 223 | A |
| 224 | A |
| 225 | A |
| 226 | A |
| 227 | A |
| 228 | A |
| 229 | A |
| 230 | A |
| 231 | B |
| 232 | C |
| 233 | A |
| 234 | A |
| 235 | A |
| 236 | A |
| 237 | C |
| 238 | A |
| 239 | A |
| 240 | A |
| 241 | A |
| 242 | B |
| 243 | A |
| 244 | B |
| 245 | B |
| 246 | A |
| 248 | A |
| 249 | A |
| 250 | B |
| 251 | B |
| 252 | B |
| 253 | A |
| 254 | B |
| 255 | A |
| 256 | A |
| 257 | A |
| 258 | B |
| 259 | B |
| 260 | C |
| 261 | C |
| 263 | B |
| 264 | C |
| 265 | A |
| 266 | A |
| 267 | B |
| 268 | A |
| 269 | A |
| 270 | A |
| 271 | A |
| 278 | A |
| 279 | A |
| 280 | A |
| 272 | B |
| 247 | A |
| 262 | B |
| 273 | A |
| 274 | A |
| 275 | A |
| 276 | A |
| 277 | B |
| 281 | B |
| 282 | B |
| 283 | B |
| 284 | B |
| 285 | C |
| 286 | A |
| 287 | A |
| 288 | A |
| 289 | C |
| 290 | A |
| 291 | B |
| 292 | B |

TABLE 1-continued

| Patent Compound No. | KCNT1-WT $IC_{50}$ (μM) |
|---|---|
| 293 | C |
| 294 | B |
| 295 | A |
| 296 | B |
| 297 | B |
| 299 | C |
| 300 | A |
| 301 | A |
| 302 | A |
| 303 | A |
| 304 | A |
| 305 | A |
| 306 | A |
| 307 | A |
| 308 | A |
| 309 | A |
| 310 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A pharmaceutical composition comprising a compound of Formula I:

(I)

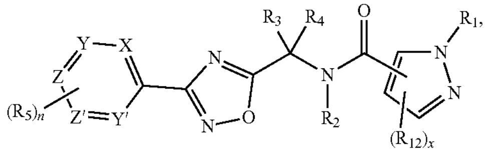

or a pharmaceutically acceptable salt thereof, wherein

X, Y, Z, Y', and Z' each independently are selected from CH and N, wherein the hydrogen of CH optionally is substituted with R5, wherein at least 3 selected from X, Y, Z, Y', and Z' are CH;

$R_1$ is selected from the group consisting of $C_{1-6}$alkyl, $C_{3-10}$cycloalkyl, 3-10 membered heterocyclyl, 3-10 membered heteroaryl, and phenyl, wherein each of the $C_{1-6}$alkyl, $C_{3-10}$cycloalkyl, 3-10 membered heterocyclyl, 3-10 membered heteroaryl, or phenyl optionally is substituted with one or more substituents each independently selected from the group consisting of halogen, $C(O)N(R_9)_2$, $N(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein each of the $C_{1-6}$alkyl, $C_{3-10}$cycloalkyl, 3-10 membered heterocyclyl, 3-10 membered heteroaryl, or phenyl optionally is substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons optionally are taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ optionally are taken together with the carbon attached to $R_3$ and $R_4$ to form a $C_{3-7}$cycloalkylene or 3-7 membered heterocyclene; wherein each of the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene optionally is substituted with one or more $R_7$;

each $R_5$ independently is selected from the group consisting of halogen; $C_{1-6}$alkyl; $C_{1-6}$haloalkyl; $C_{1-6}$alkylene-N$(R_9)_2$; $C_{1-6}$alkylene-O—$C_{3-10}$cycloalkyl; $C_{1-6}$alkoxy, wherein the $C_{1-6}$alkoxy optionally is substituted with $C_{3-10}$cycloalkyl, and wherein the $C_{3-10}$cycloalkyl optionally is substituted with one or more halogens; $C_{1-6}$haloalkoxy; 3-10 membered heterocyclyl, wherein the 3-10 membered heterocyclyl optionally is substituted with one or more halogens or $C_{1-6}$alkoxy; 3-10 membered heteroaryl; $C_{1-6}$alkylene-OH; $C_{1-6}$alkylene-$C_{1-6}$alkoxy; OH; N$(R_9)_2$; —C(O)$OR_8$; C(O)N$(R_9)_2$; $C_{1-6}$alkylene-CN; —CN; —$S(O)_2$-$C_{1-6}$alkyl; $C_{1-6}$alkylene-$S(O)_2$—$C_{1-6}$alkyl; —$S(O)_2$—N$(R_9)_2$; —OC(O)$C_{1-6}$alkyl; and —O—$C_{3-10}$cycloalkyl, wherein the —O—$C_{3-10}$cycloalkyl optionally is substituted with one or more halogen or $C_{1-6}$alkyl;

n is selected from the group consisting of 0, 1, 2, and 3;

each $R_7$ independently is selected from the group consisting of phenyl, $C_{1-6}$alkoxy, —OH, —N$(R_9)_2$, —$NR_9$—$SO_2$—$C_{1-6}$alkyl, —O—($C_{1-6}$alkylene)-phenyl, $C_{3-10}$cycloalkyl, —C(O)$OR_8$, —C(O)N$(R_9)_2$, —$NR_{10}$C(O)—$R_{11}$, —CN, —$S(O)_2$—$C_{1-6}$alkyl, —$S(O)_2$— N$(R_9)_2$, 3-10 membered heterocyclyl, and 3-10 membered heteroaryl, wherein each of the phenyl, $C_{3-10}$cycloalkyl, 3-10 membered heterocyclyl, or 3-10 membered heteroaryl optionally is substituted with one or more substituents each independently selected from the group consisting of $C_{1-6}$alkyl, halogen, —OH, $C_{1-6}$alkoxy, and —N$(R_9)_2$;

$R_8$ is selected from the group consisting of hydrogen, $C_{1-6}$alkyl, and $C_{3-10}$cycloalkyl;

each $R_9$ independently is selected from the group consisting of hydrogen, $C_{1-6}$alkyl, and —($C_{1-6}$alkylene)-OH, or the two $R_9$ optionally are taken together with the nitrogen atom attached to the two $R_9$ to form a heterocycle optionally substituted with one or more substituents each independently selected from halogen and —OH;

each $R_{10}$ independently is hydrogen or $C_{1-6}$alkyl;

$R_{11}$ is selected from the group consisting of $C_{1-6}$alkyl, $C_{1-6}$alkoxy, and —O—($C_{1-6}$alkylene)-phenyl; and when $R_3$ and $R_4$ are both hydrogen, at least one selected from X, Y, Z, Y', and Z' is N;

and a pharmaceutically acceptable excipient.

2. The pharmaceutical composition of claim 1, wherein one of X, Y, Z, Y', and Z' is N and the other four are CH.

3. The pharmaceutical composition of claim 1, wherein the compound is selected from the group consisting of:

a compound of Formula I-a:

(I-a)

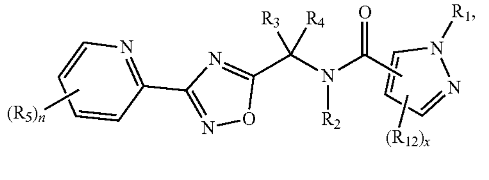

a compound of Formula I-b:

(I-b)

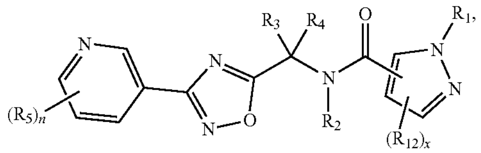

a compound of Formula I-c:

(I-c)

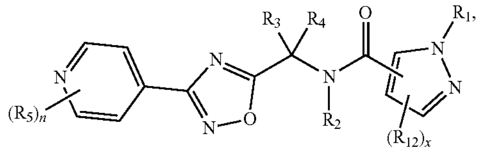

a compound of Formula I-d:

(I-d)

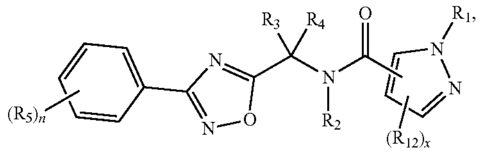

a compound of Formula I-e:

(I-e)

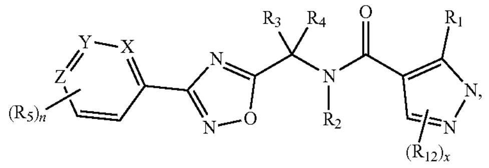

a compound of Formula I-f:

(I-f)

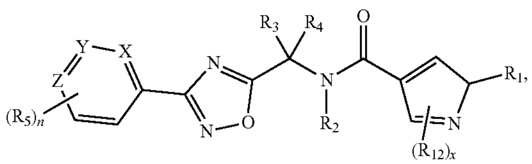

a compound of Formula I-g:

(I-g)

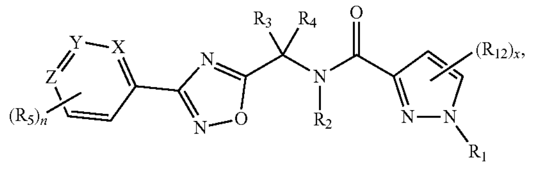

a compound of Formula I-h:
(I-h)
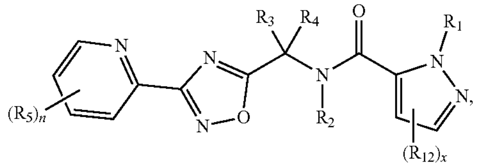
a compound of Formula I-i:
(I-i)
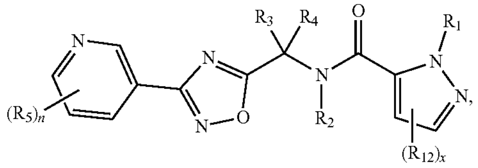
a compound of Formula I-j:
(I-j)
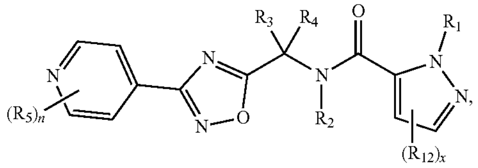
a compound of Formula I-k:
(I-k)
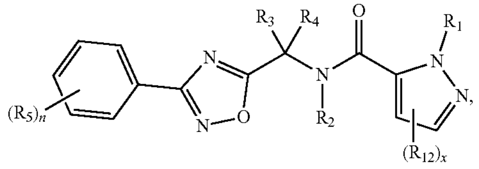
a compound of Formula I-I:
(I-l)
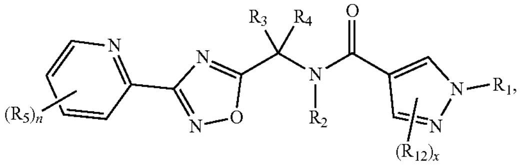
a compound of Formula I-m:
(I-m)
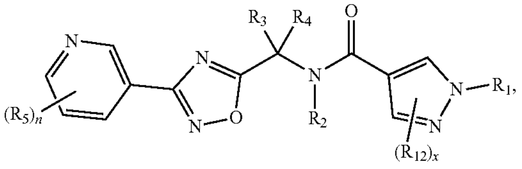
a compound of Formula I-n:
(I-n)
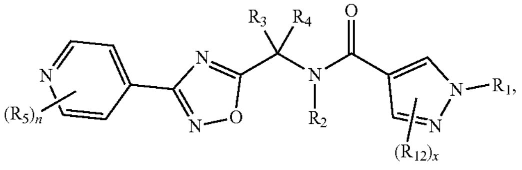
a compound of Formula I-o:
(I-o)
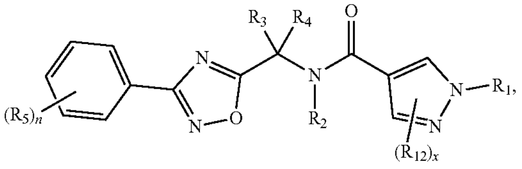
a compound of Formula I-p
(I-p)
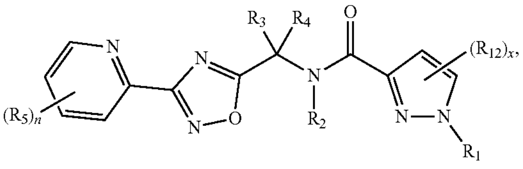
a compound of Formula I-q:
(I-q)
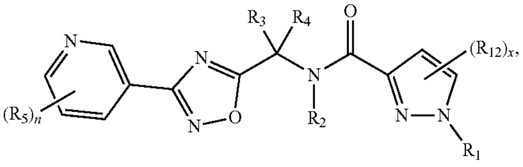

a compound of Formula I-r:

(I-r)

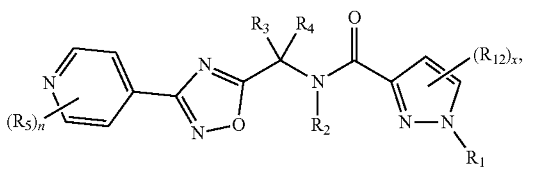

and a compound of Formula I-s:

(I-s)

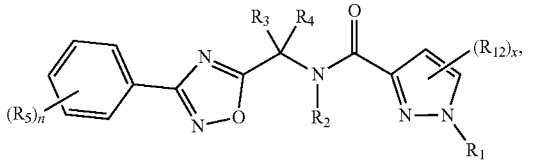

or a pharmaceutically acceptable salt thereof, wherein $R_1$, $R_2$, $R_3$, $R_4$, $R_5$, $R_{12}$, n, and x are as defined in claim 1.

4. The pharmaceutical composition of claim 1, wherein $R_2$ is hydrogen or methyl.

5. The pharmaceutical composition of claim 1, wherein $R_3$ is hydrogen or a $C_{1-6}$alkyl, wherein the $C_{1-6}$alkyl optionally is substituted with $C_{1-6}$alkoxy, —OH, or —C(O)$OR_8$.

6. The pharmaceutical composition of claim 1, wherein $R_4$ is hydrogen.

7. The pharmaceutical composition of claim 1, wherein $R_3$ and $R_4$ are taken together with the carbon attached to $R_3$ and $R_4$ to form a $C_{3-7}$cycloalkylene or 3-7 membered heterocyclene.

8. The pharmaceutical composition of claim 1, wherein each $R_5$ independently is selected from the group consisting of halogen, $C_{1-6}$alkyl, $C_{1-6}$haloalkyl, $C_{1-6}$alkoxy, $C_{1-6}$haloalkoxy, O—$C_{3-10}$cycloalkyl, —OH, —CN, $N(R_9)_2$, and —C(O)$OR_8$.

9. The pharmaceutical composition of claim 1, wherein n is 1 and $R_5$ is attached at either Y or Z'.

10. The pharmaceutical composition of claim 1, wherein n is 2, thereby providing two independent $R_5$ substituents; wherein X and Y' are each at an ortho-position, Y and Z' are each at a meta-position, and Z is at a para-position; and wherein the two independent $R_5$ substituents are attached at the ortho- and para-positions, the meta-and para-positions, or at the meta-positions.

11. The pharmaceutical composition of claim 1, wherein $R_1$ is selected from the group consisting of $C_{1-6}$alkyl, wherein the $C_{1-6}$alkyl optionally is substituted with $C_{1-6}$alkoxy, $N(R_9)_2$, C(O)$N(R_9)_2$, $C_{3-7}$cycloalkyl, pyridyl, tetrahydropyranyl, or phenyl; $C_{1-6}$haloalkyl; $C_{3-7}$cycloalkyl; phenyl, wherein the phenyl optionally is substituted with halogen; and pyridyl, wherein the pyridyl optionally is substituted with halogen.

12. The pharmaceutical composition of claim 1, wherein $R_{12}$ is selected from the group consisting of $C_{1-6}$alkyl, $C_{1-6}$haloalkyl, $C_{3-7}$cycloalkyl, and phenyl, wherein the phenyl optionally is substituted with halogen.

13. A compound of Formula II:

(II)

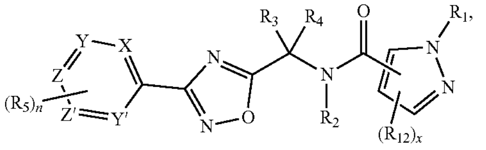

or a pharmaceutically acceptable salt thereof, wherein one or two selected from X, Y, Z, Y', and Z' are N, and the others are CH, wherein the hydrogen of one, two, or three CH is substituted with $R_5$;

$R_1$ is selected from the group consisting of $C_{1-6}$alkyl, $C_{3-10}$cycloalkyl, 3-10 membered heterocyclyl, 3-10 membered heteroaryl, and phenyl, wherein each of the $C_{1-6}$alkyl, $C_{3-10}$cycloalkyl, 3-10 membered heterocyclyl, 3-10 membered heteroaryl, or phenyl optionally is substituted with one or more substituents each independently selected from the group consisting of halogen, C(O)$N(R_9)_2$, $N(R_9)_2$, $C_{3-7}$cycloalkyl, phenyl, 3-10 membered heteroaryl, and $C_{1-6}$alkoxy;

$R_{12}$ is selected from the group consisting of $C_{1-6}$alkyl, $C_{3-10}$cycloalkyl, 3-10 membered heterocyclyl, 3-10 membered heteroaryl, and phenyl, wherein each of the $C_{1-6}$alkyl, $C_{3-10}$cycloalkyl, 3-10 membered heterocyclyl, 3-10 membered heteroaryl, or phenyl optionally is substituted with one or more substituents each independently selected from the group consisting of halogen, —OH, —CN, $C_{1-6}$alkyl, $C_{1-6}$haloalkyl, and $C_{1-6}$alkoxy; or two $R_{12}$ on adjacent carbons optionally are taken together with the two carbons where $R_{12}$ are attached to form a carbocyclic ring;

x is 0, 1 or 2;

$R_2$ is hydrogen or $C_{1-4}$alkyl;

$R_3$ is selected from the group consisting of hydrogen, $C_{1-6}$alkyl, $C_{3-10}$ cycloalkyl, 3-10 membered heterocyclyl, 3-10 membered heteroaryl, and phenyl; and $R_4$ is selected from $C_{1-6}$alkyl and hydrogen; or $R_3$ and $R_4$ optionally are taken together with the carbon attached to $R_3$ and $R_4$ to form a $C_{3-7}$cycloalkylene or 3-7 membered heterocyclene; wherein each of the $C_{1-6}$alkyl, $C_{3-10}$ cycloalkyl, 3-10 membered heterocyclyl, 3-10 membered heteroaryl, phenyl, $C_{3-7}$cycloalkylene, or 3-7 membered heterocyclene optionally is substituted with one or more $R_7$;

each $R_5$ independently is selected from the group consisting of halogen; $C_{1-6}$alkyl; $C_{1-6}$haloalkyl; $C_{1-6}$alkylene-$N(R_9)_2$; $C_{1-6}$alkylene-O—$C_{3-10}$cycloalkyl; $C_{1-6}$alkoxy, wherein the $C_{1-6}$alkoxy optionally is substituted with $C_{3-7}$cycloalkyl; $C_{1-6}$haloalkoxy; 3-10 membered heterocyclyl, wherein the 3-10 membered heterocyclyl optionally is substituted with one or more halogens or $C_{1-6}$alkoxy; 3-10 membered heteroaryl; —$C_{1-6}$alkylene-OH; $C_{1-6}$alkylene-$C_{1-6}$alkoxy; OH, —$N(R_9)_2$;

—C(O)$OR_8$; —C(O)$N(R_9)_2$; —$C_{1-6}$alkylene-CN; —CN; —$S(O)_2$—$C_{1-6}$alkyl; $C_{1-6}$alkylene-$S(O)_2$—$C_{1-6}$alkyl; —$S(O)_2$—$N(R_9)_2$; —OC(O)$C_{1-6}$alkyl; and —O—$C_{3-10}$cycloalkyl, wherein the —O—$C_{3-10}$cycloalkyl optionally is substituted with one or more halogen or $C_{1-6}$alkyl;

n is selected from the group consisting of 1, 2, and 3;

$R_7$ each independently is selected from the group consisting of phenyl, $C_{1-6}$alkoxy, —OH, —$N(R_9)_2$, —$NR_9$—$SO_2$—$C_{1-6}$alkyl, —O—($C_{1-6}$alkylene)-phenyl, $C_3$-iocycloalkyl, —C(O)$OR_8$, —C(O)$N(R_9)_2$, —$NR_{10}$C(O)—$R_{11}$, —CN, —$S(O)_2$—$C_{1-6}$alkyl, —$S(O)_2$—$N(R_9)_2$, 3-10 membered heterocyclyl, and 3-10 membered heteroaryl, wherein each of the phenyl, $C_{3-10}$cycloalkyl, 3-10 membered heterocyclyl, or 3-10 membered heteroaryl optionally is substituted with one or more substituents each independently selected from the group consisting of $C_{1-6}$alkyl, halogen, —OH, $C_{1-6}$alkoxy, and —$N(R_9)_2$;

$R_8$ is selected from the group consisting of hydrogen, $C_{1-6}$alkyl, and $C_{3-10}$cycloalkyl;

each $R_9$ independently is selected from the group consisting of hydrogen, $C_{1-6}$alkyl, and —($C_{1-6}$alkylene)—OH, or the two $R_9$ optionally are taken together with the nitrogen atom attached to the two $R_9$ to form a heterocycle optionally substituted with one or more substituents each independently selected from halogen and —OH;

each $R_{10}$ independently is hydrogen or $C_{1-6}$alkyl; and $R_{11}$ is selected from the group consisting of $C_{1-6}$alkyl, $C_{1-6}$alkoxy, and —O—($C_{1-6}$alkylene)-phenyl.

14. The compound of claim 13, wherein the compound is selected from the group consisting of:

(II-a)

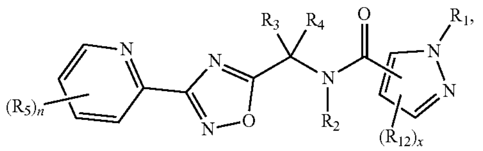

a compound of Formula II-b:

(II-b)

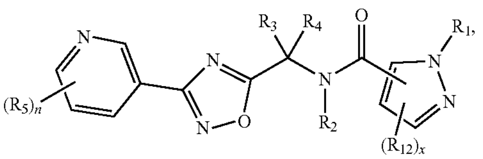

a compound of Formula II-c:

(II-c)

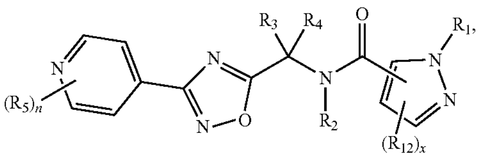

a compound of Formula II-d:

(II-d)

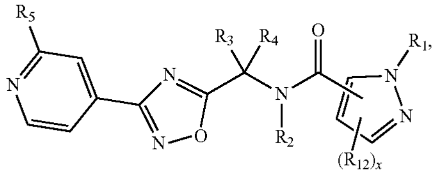

a compound of Formula II-e:

(II-e)

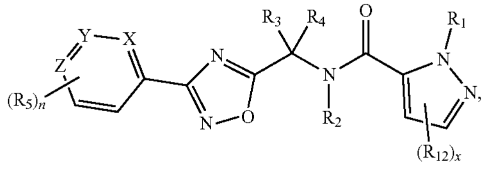

a compound of Formula II-f:

(II-f)

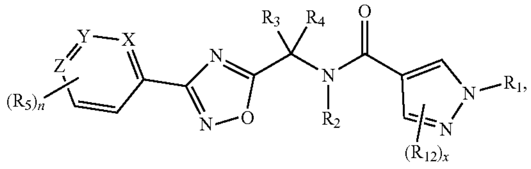

a compound of Formula II-g:

(II-g)

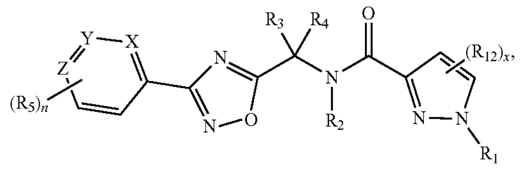

a compound of Formula II-h:

(II-h)

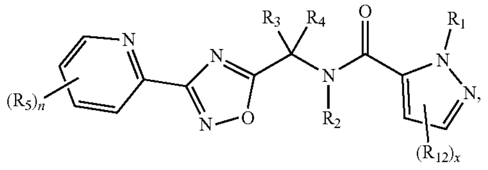

a compound of Formula II-i:

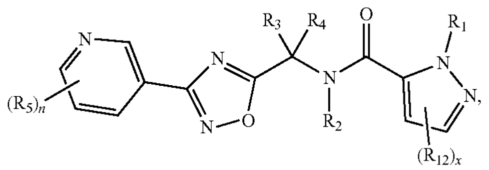

(II-i)

a compound of Formula II-j:

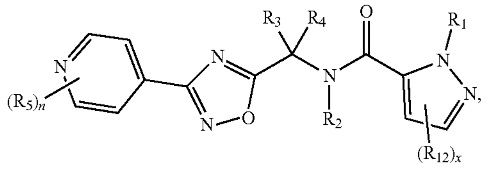

(II-j)

a compound of Formula II-k:

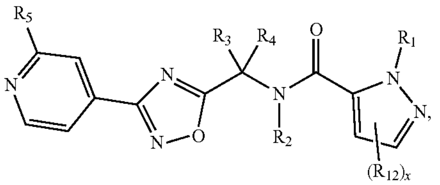

(II-k)

a compound of Formula II-l:

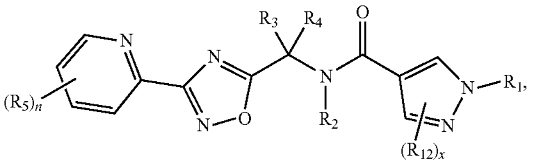

(II-l)

a compound of Formula II-m:

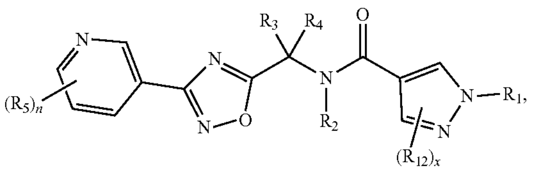

(II-m)

a compound of Formula II-n:

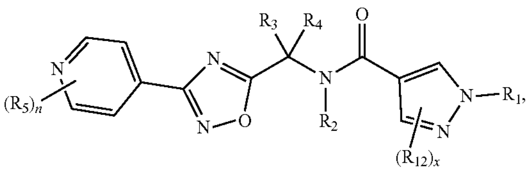

(II-n)

a compound of Formula II-p:

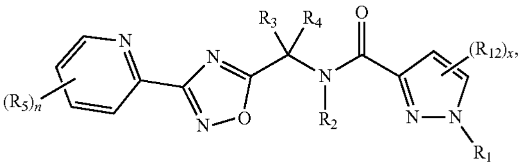

(II-p)

a compound of Formula II-q:

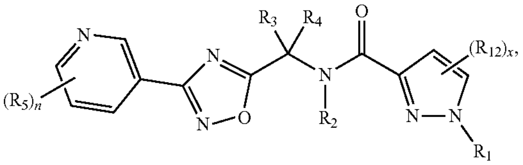

(II-q)

and a compound of Formula II-r:

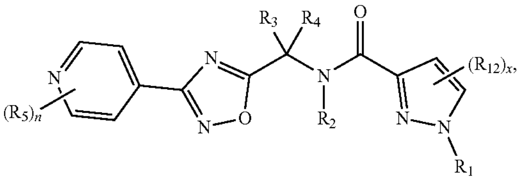

(II-r)

or a pharmaceutically acceptable salt thereof, wherein $R_1$, $R_2$, $R_3$, $R_4$, $R_5$, $R_{12}$, n and x are as defined in claim 13.

15. The compound of claim 13, wherein the compound is a compound of Formula II-k1 or Formula II-k2:

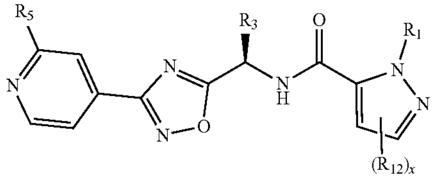

(II-k1)

-continued (II-k2)

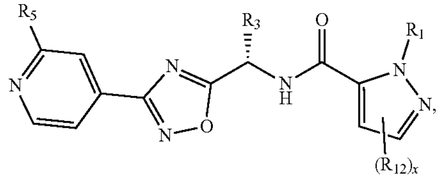

or a pharmaceutically acceptable salt thereof, wherein $R_1$, $R_3$, $R_5$, $R_{12}$, and x are as defined in claim 13.

16. A pharmaceutical composition comprising a compound of claim 13 or a pharmaceutically acceptable salt thereof, and a pharmaceutically acceptable excipient.

17. A method of treating a neurological disease or disorder, wherein:

the neurological disease or disorder is associated with excessive neuronal excitability, or associated with a gain-of-function mutation of a gene which is KCNT1, which comprises administering a pharmaceutical composition of claim 1 to a subject in need thereof.

18. The method of claim 17, wherein the neurological disease or disorder is associated with excessive neuronal excitability, or associated with a gain-of-function mutation of a gene which is KCNT1 is selected from: epilepsy, an epilepsy syndrome, an encephalopathy, a cardiac dysfunction, pain and related conditions, a muscle disorder, itch and pruritis, ataxia and cerebellar ataxias, psychiatric disorders, learning disorders, Fragile X, neuronal plasticity or autism spectrum disorders.

19. The method of claim 17, wherein the neurological disease or disorder is associated with excessive neuronal excitability, or associated with a gain-of-function mutation of a gene which is KCNT1 is selected from the group consisting of epilepsy of infancy with migrating focal seizures, autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox Gastaut syndrome, seizures, leukodystrophy, leukoencephalopathy, intellectual disability, Multifocal Epilepsy, Drug resistant epilepsy, Temporal lobe epilepsy, and cerebellar ataxia.

20. The method of claim 17, wherein the neurological disease or disorder is associated with excessive neuronal excitability, or associated with a gain-of-function mutation of a gene which is KCNT1 is selected from the group consisting of epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

21. The pharmaceutical composition of claim 3, wherein the compound is a compound of Formula I-c and wherein $R_1$ is $CH_3$, $R_2$ is H, $R_3$ is $CH_3$, $R_4$ is H, $R_5$ is $CF_3$, $R_{12}$ is $CF_3$, n is 1, and x is 1.

22. The pharmaceutical composition of claim 1, wherein one or more hydrogen is deuterium.

* * * * *